United States Patent
Jones et al.

(10) Patent No.: US 11,104,916 B2
(45) Date of Patent: Aug. 31, 2021

(54) COMPOSITIONS AND METHODS FOR ALPHAVIRUS VACCINATION

(71) Applicant: ETUBICS CORPORATION, Seattle, WA (US)

(72) Inventors: Frank R. Jones, Seattle, WA (US); Joseph Balint, Seattle, WA (US); Adrian Rice, Seattle, WA (US); Yvette Latchman, Seattle, WA (US); Elizabeth Gabitzsch, Seattle, WA (US)

(73) Assignee: Etubics Corporation, Seattle, WA (US)

( * ) Notice: Subject to any disclaimer, the term of this patent is extended or adjusted under 35 U.S.C. 154(b) by 0 days.

(21) Appl. No.: 16/317,747

(22) PCT Filed: Jul. 14, 2017

(86) PCT No.: PCT/US2017/042272
§ 371 (c)(1),
(2) Date: Jan. 14, 2019

(87) PCT Pub. No.: WO2018/014008
PCT Pub. Date: Jan. 18, 2018

(65) Prior Publication Data
US 2020/0172925 A1    Jun. 4, 2020

Related U.S. Application Data

(60) Provisional application No. 62/363,136, filed on Jul. 15, 2016.

(51) Int. Cl.
| | | |
|---|---|---|
| *A61P 31/14* | (2006.01) | |
| *C12N 15/86* | (2006.01) | |
| *A61K 39/12* | (2006.01) | |
| *C12N 7/00* | (2006.01) | |
| *A61K 39/00* | (2006.01) | |

(52) U.S. Cl.
CPC ............. *C12N 15/86* (2013.01); *A61K 39/12* (2013.01); *A61P 31/14* (2018.01); *C12N 7/00* (2013.01); *A61K 2039/53* (2013.01); *A61K 2039/545* (2013.01); *C12N 2770/36122* (2013.01)

(58) Field of Classification Search
CPC ............ A61K 39/12; A61K 2039/5256; A61K 2039/53; A61K 39/00; A61K 39/235; A61K 39/145; C12N 15/86; C12N 2770/36134; C12N 2770/36143; C12N 2710/10043; C12N 2799/022; C12N 2760/16111; Y02A 50/387; Y02A 50/30; C07K 16/1081; G01N 2333/18
See application file for complete search history.

(56) References Cited

U.S. PATENT DOCUMENTS

| | | | | |
|---|---|---|---|---|
| 6,565,853 | B1 * | 5/2003 | Jacobs ................. | A61K 39/193 424/202.1 |
| 8,298,549 | B2 * | 10/2012 | Balint ................. | A61K 38/204 424/233.1 |
| 10,166,281 | B2 * | 1/2019 | Akahata ................. | A61K 39/12 |
| 2007/0249043 | A1 | 10/2007 | Mayall | |
| 2013/0224144 | A1 | 8/2013 | Balint et al. | |

FOREIGN PATENT DOCUMENTS

| | | |
|---|---|---|
| CA | 2945736 | 11/2015 |
| JP | 2009-529868 | 8/2009 |
| JP | 2015-532090 | 11/2015 |
| WO | WO 2007/105111 | 9/2007 |
| WO | WO 2009/006479 | 1/2009 |
| WO | WO 2014/031178 | 2/2014 |
| WO | WO2014/049094 * | 4/2014 |
| WO | WO 2014/049094 | 4/2014 |
| WO | WO 2014/093602 | 6/2014 |
| WO | WO 2015/142963 | 9/2015 |
| WO | WO 2016/086980 | 6/2016 |
| WO | WO 2016/112188 | 7/2016 |
| WO | WO 2016/112195 | 7/2016 |

OTHER PUBLICATIONS

Phillpotts et al. Vaccine, 2004, vol. 23, Iss. 13, (Feb. 18, 2005): 1615-1623. DOI:10.1016/j.vaccine.2004.06.056.*
O' Brien et al. Journal of General Virology, 2009, 90(4), 874-882.*
Perkins et al. Viral Immunology (2008), 21(4), 451-457.*
Bett et al. Journal of Virology, 1985, vol. 67, No. 19, pp. 5911-5921.*
International Search Report and Written Opinion prepared by the U.S. Patent and Trademark Office dated Sep. 12, 2017, for International Application No. PCT/US2017/042272.
International Preliminary Report on Patentability for International (PCT) Patent Application No. PCT/US2017/042272 dated Jan. 15, 2019, 6 pages.
Official Action for Canadian Patent Application No. 3,030,451 dated Dec. 10, 2019, 6 pages.
Wang et al., "2A self-cleaving peptide-based multi-gene expression system in the silkworm *Bombyx mori*," Scientific Reports, 2015, Iss. 5, Article 16273, 10 pages.
Official Action for Australian Patent Application No. 2017297610 dated Aug. 28, 2019, 3 pages.

(Continued)

*Primary Examiner* — Bao Q Li
(74) *Attorney, Agent, or Firm* — Sheridan Ross P.C.

(57) ABSTRACT

Compositions of a recombinant adenovirus based vector vaccine containing one or more alphavirus antigen genes are disclosed herein. Methods for constructing and producing such vaccines and methods of using these vaccines to generate broad based immune responses against alphaviruses are also described. Compositions described herein allow for vaccinations in individuals with preexisting immunity to adenovirus.

17 Claims, 8 Drawing Sheets

Specification includes a Sequence Listing.

(56) References Cited

OTHER PUBLICATIONS

Amalfitano et al., "Production and Characterization of Improved Adenovirus Vectors with the E1, E2b, and E3 Genes Deleted", Journal of Virology, 1998, vol. 72, Iss. 2, pp. 926-933.
Barabé et al., "Single-dose, fast-acting vaccine candidate against western equine encephalitis virus completely protects mice from intranasal challenge with different strains of the virus", Vaccine, 2007, vol. 25, Iss. 33, pp. 6271-6276.
Gabitzsch et al., "A preliminary and comparative evaluation of a novel Ad5 [E1-, E2b-] recombinant-based vaccine used to induce cell mediated immune responses", Immunology Letters, 2009, vol. 122, Iss. 1, pp. 44-51.
Extended European Search Report for European Patent Application No. 17828595.3 dated Feb. 26, 2020, 13 pages.
Schwameis et al., "Chikungunya vaccines in development", Human Vaccines & Immunotherapeutics, 2016, vol. 12, Iss. 3, pp. 716-731.
Wang et al., "A complex adenovirus vaccine against chikungunya virus provides complete protection against viraemia and arthritis", Vaccine, 2011, vol. 29, Iss. 15, pp. 2803-2809.
Official Action (with English translation) for South Korean Patent Application No. 10-2019-7004334 dated Jul. 28, 2020, 16 pages.
"Chikungunya virus strain S27-African prototype, complete genome," GenBank: AF369024.2, retrieved from www.ncbi.nlm.nih.gov/nuccore/af369024, Jan. 14, 2003, 4 pages.
"Chikungunya virus strain 37997, complete genome," GenBank: AY726732.1, retrieved from www.ncbi.nlm.nih.gov/nucleotide/AY726732.1, Jun. 7, 2005, 4 pages.
"Mayaro virus strain MAYLC from French Guianna, complete genome," GenBank: DQ001069.1, retrieved from www.ncbi.nlm.nih.gov/nucleotide/DQ001069.1, May 12, 2006, 4 pages.
"Ross River virus strain 2982," GenBank, GQ433355.1, retrieved from www.ncbi.nlm.nih.gov/nucleotide/GQ433355.1, Dec. 24, 2009, 5 pages.
"Venezuelan equine encephalitis virus strain VEEV/*Homo sapiens*/PER/FSE507/2000/ID, complete genome," GenBank: KC344522.1, retrieved from www.ncbi.nlm.nih.gov/nucleotide/KC344522.1, Feb. 17, 2013, 5 pages.
"Eastern equine encephalitis virus strain EEEV/*H. sapiens*/USA/V105-00210/2005, complete genome," GenBank: KP282670.1, retrieved from www.nchi.nlm.nih.gov/nuccore/kp282670, Jun. 2, 2015, 5 pages.
"Western equine encephalitis virus strain R0PV00384A, complete genome," GenBank: KJ554991.1, retrieved from www.ncbi.nlm.nih.gov/nuccore/kj554991, Jun. 17, 2014, 4 pages.
Final Action (with English translation) for Japanese Patent Application No. 2019-501689 dated Oct. 6, 2020, 10 pages.
Official Action for Canadian Patent Application No. 3,030,451 dated Nov. 2, 2020, 4 pages.
Final Action (with English machine translation) for South Korean Patent Application No. 10-2019-7004334 dated Jan. 25, 2021, 11 pages.
Official Action for Canadian Patent Application No. 3,030,451 dated Jun. 11, 2021, 4 pages.

* cited by examiner

|      | Non-structural proteins |
|------|-------------------------|
| nsP1 | Replicase complex |
| nsP2 | Replicase complex/protease |
| nsP3 | Replicase complex |
| nsP4 | Replicase complex |

|    | Structural proteins |
|----|---------------------|
| C  | Capsid protein |
| E3 | Removed from E2 by proteolytic cleavage in Golgi |
| E2 | Envelope glycoprotein |
| 6K | Removed from E1 by signal peptidase; role in virus budding |
| E1 | Envelope glycoprotein |

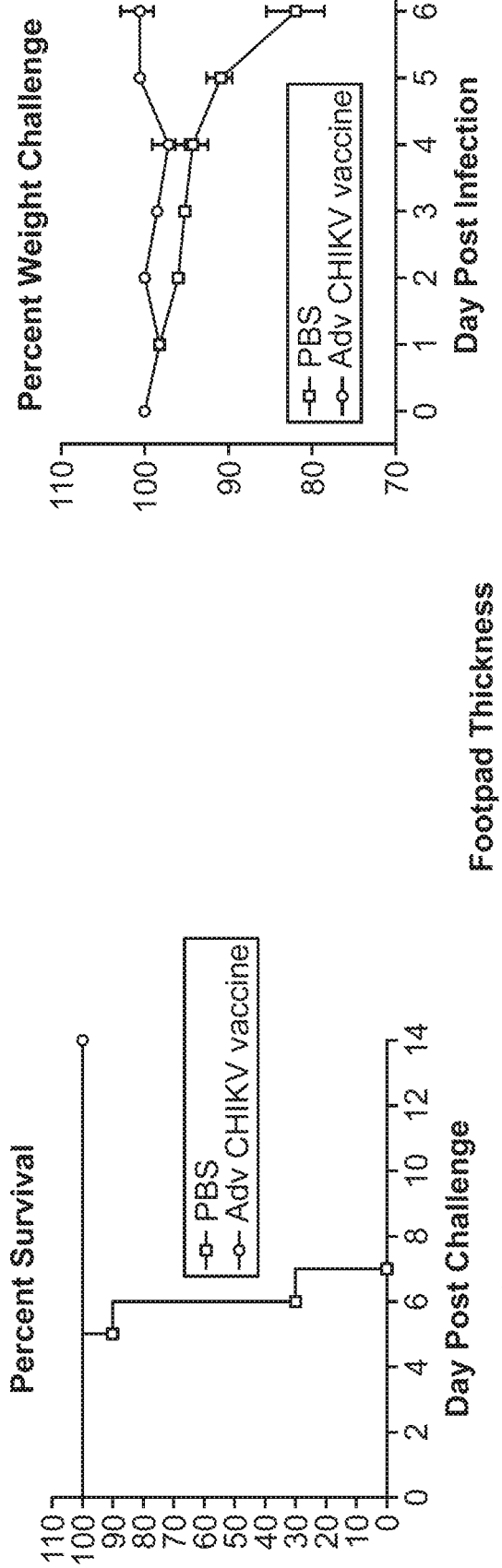
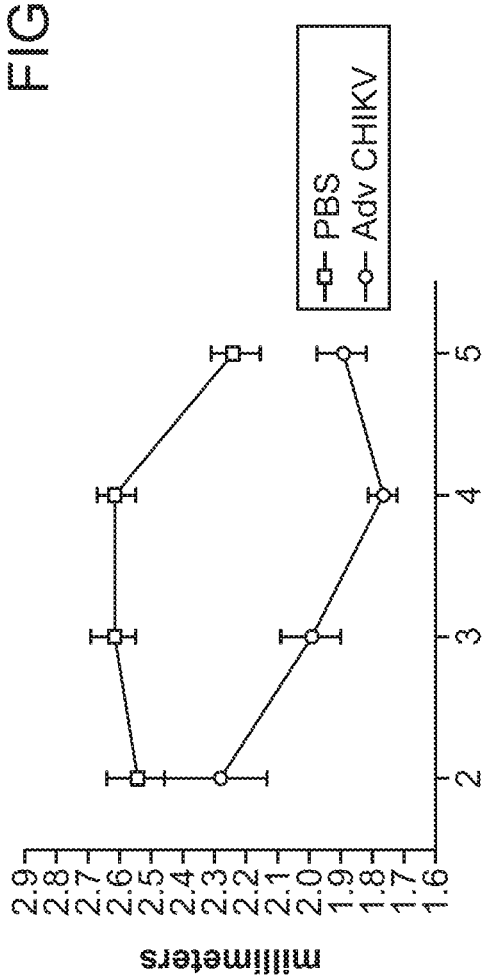
FIG. 4A
FIG. 4B
FIG. 4C

COMPOSITIONS AND METHODS FOR ALPHAVIRUS VACCINATION

CROSS REFERENCE TO RELATED APPLICATIONS

This application is a national stage application under 35 U.S.C. 371 and claims the benefit of PCT Application No. PCT/US2017/042272 having an international filing date of 14 Jul. 2017, which designated the United States, which PCT application claimed the benefit of U.S. Provisional Application No. 62/363,136, filed Jul. 15, 2016, the disclosures of each of which are herein incorporated by reference in their entireties.

SEQUENCE LISTING

The instant application contains a Sequence Listing which has been submitted electronically in ASCII format and is hereby incorporated by reference in its entirety. Said ASCII copy, created on Jul. 7, 2017, is named 39891-725_601_SL.txt and is 460,196 bytes in size.

BACKGROUND

Vaccines help the body fight disease by training the immune system to recognize and destroy harmful substances and diseased cells.

Viral vaccines are currently being developed to prevent infectious diseases and treat existing cancers. These viral vaccines work by inducing expression of a small fraction of genes or complete genes associated with a disease within the host's cells, which in turn, enhance the host's immune system to identify and destroy diseased cells. As such, clinical response due to a viral vaccine can depend on the ability of the vaccine to induce a high-level immunogenicity and have sustained long-term expression.

Therefore, there remains a need to discover novel compositions and methods for enhanced protective or cancer therapeutic responses to complex diseases and especially for newly emerging disease threats.

SUMMARY

In various aspects, the present disclosure provides composition comprising a replication defective virus vector comprising a sequence encoding an alphavirus target antigen. In some aspects, the sequence encoding the alphavirus target antigen comprises a sequence encoding a plurality of alphavirus target antigens. In some aspects, the sequence encoding a plurality of alphavirus target antigens comprises a plurality of gene inserts each corresponding to a target antigen and wherein each gene insert is separated by a nucleic acid sequence encoding a self-cleaving 2A peptide. In some aspects, the self-cleaving 2A peptide is derived from *Porcine teschovirus*-1 or *Thosea asigna* virus.

In some aspects, the replication defective virus vector is an adenovirus vector. In further aspects, the replication defective virus vector is an adenovirus 5 (Ad5) vector. In some aspects, the replication defective virus vector comprises an adenovirus vector with a deletion in an E1 gene region, an E2b gene region, an E3 gene region, E4 gene region, or any combination thereof. In further aspects, the deletion in the E2b gene region comprises a plurality of deletions in the E2b region. In some aspects, the deletion in the E1 gene region, the E2b gene region, the E3 gene region, the E4 gene region, or any combination thereof each comprises at least one base pair.

In other aspects, the deletion in the E1 gene region, the E2b gene region, the E3 gene region, the E4 gene region, or any combination thereof results from a translocation of two or more base pairs. In some aspects, the deletion in the E1 gene region, the E2b gene region, the E3 gene region, the E4 gene region, or any combination thereof each comprises at least 20, at least 30, at least 40, at least 50, at least 60, at least 70, at least 80, at least 90, at least 100, at least 110, at least 120, at least 130, at least 140, or at least 150 base pairs.

In other aspects, the deletion in the E1 gene region, the E2b gene region, the E3 gene region, the E4 gene region, or any combination thereof each comprises more than 150, more than 160, more than 170, more than 180, more than 190, more than 200, more than 250, or more than 300 base pairs.

In some aspects, the alphavirus target antigen comprises an antigen of a virus selected from the group consisting of Chikungunya virus (CHIKV), o'nyong-nyong virus (ONNV), Ross River virus (RRV), Mayaro fever virus (MAYV), Venezuelan equine encephalitis virus (VEEV), Western equine encephalomyelitis virus (WEEV), and Eastern equine encephalitis virus (EEEV), or any combination thereof. In some aspects, the alphavirus target antigen comprises an antigen of a virus selected from the group consisting of CHIKV, ONNV, RRV, and MAYV, or any combination thereof. In further aspects, the alphavirus target antigen comprises an antigen of CHIKV.

In some aspects, the alphavirus target antigen comprises an antigen selected from the group consisting of C, $E3_{ALPHA}$, $E2_{ALPHA}$, 6K, $E1_{ALPHA}$, nsP1, nsP2, nsP3, and nsP4, or any combination thereof. In some aspects, the alphavirus target antigen comprises an antigen selected from the group consisting of C, $E3_{ALPHA}$, $E2_{ALPHA}$, and 6K, $E1_{ALPHA}$, or any combination thereof. In some aspects, the alphavirus target antigen comprises an antigen selected from the group consisting of $E1_{ALPHA}$ and $E2_{ALPHA}$, or any combination thereof.

In some aspects, the sequence encoding an alphavirus target antigen comprises at least 70%, at least 75%, at least 80%, at least 85%, at least 90%, at least 92%, at least 95%, at least 97%, or at least 99% sequence identity to a sequence selected from the group consisting of SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, and SEQ ID NO: 21, or any combination thereof.

In other aspects, the sequence encoding an alphavirus target antigen is an amino acid sequence, and wherein the amino acid sequence comprises at least 70%, at least 75%, at least 80%, at least 85%, at least 90%, at least 92%, at least 95%, at least 97%, or at least 99% sequence identity to a sequence selected from the group consisting of SEQ ID NO: 2, SEQ ID NO: 3, SEQ ID NO: 5, SEQ ID NO: 6, SEQ ID NO: 8, SEQ ID NO: 9, SEQ ID NO: 11, and SEQ ID NO: 12, SEQ ID NO: 14, SEQ ID NO: 15, SEQ ID NO: 17, SEQ ID NO: 18, SEQ ID NO: 20, and SEQ ID NO: 21 or any combination thereof.

In some aspects, the sequence encoding an alphavirus target antigen is a nucleotide sequence, and wherein the nucleotide sequence comprises at least 70%, at least 75%, at least 80%, at least 85%, at least 90%, at least 92%, at least 95%, at least 97%, or at least 99% sequence identity to a sequence selected from the group consisting of SEQ ID NO: 1, SEQ ID NO: 4, SEQ ID NO: 7, SEQ ID NO: 10, SEQ ID NO: 13, SEQ ID NO: 16, and SEQ ID NO: 19, or any combination thereof. In some aspects, the sequence encoding an alphavirus target antigen comprises at least 70%, at least 75%, at least 80%, at least 85%, at least 90%, at least 92%, at least 95%, at least 97%, or at least 99% sequence identity to a sequence selected from the group consisting of SEQ ID NO: 1, SEQ ID NO: 2, and SEQ ID NO: 3, or any combination thereof.

In some aspects, the replication defective virus vector further comprises an element to increase an expression of the alphavirus target antigen. In some aspects, the element comprises at least one element, at least 2 elements, at least 3 elements, at least 4 elements, or at least 5 elements.

In other aspects, the element comprises an internal ribosome binding site. In still other aspects, the element comprises a constitutive promoter. In some aspects, the element comprises an inducible promoter. In some aspects, the element comprises a transcription enhancer. In further aspects, the transcription enhancer is a Rous sarcoma virus (RSV) enhancer. In some aspects, the element does not contain a palindromic sequence.

In some aspects, the replication defective virus vector further comprises a nucleic acid sequence encoding a protein that increases alphavirus target antigen immunogenicity. In some aspects, the replication defective virus vector is not a gutted vector. In some aspects, the composition or the replication defective virus vector further comprises a sequence encoding a costimulatory molecule or an immunological fusion partner. In some aspects, the costimulatory molecule comprises B7, ICAM-1, LFA-3, or any combination thereof.

In various aspects, the present disclosure provides a pharmaceutical composition comprising the composition disclosed herein and a pharmaceutically acceptable carrier.

In various aspects, the present disclosure provides a cell comprising any one of the above compositions. In some aspects, the cell is a host cell. In further aspects, the cell is a dendritic cell (DC).

In various aspects, the present disclosure provides a method of preparing a vaccine, comprising preparing any one of the above compositions or the above described pharmaceutical composition.

In various aspects, the present disclosure provides a method of generating an immune response against an alphavirus target antigen in a subject, comprising: administering to the subject any one of the above compositions or the above described pharmaceutical composition. In some aspects, the subject has not been infected with an alphavirus.

In some aspects, the alphavirus target antigen is from an alphavirus, wherein the alphavirus comprises Chikungunya virus (CHIKV), o'nyong-nyong virus (ONNV), Ross River virus (RRV), Mayaro fever virus (MAYV), Venezuelan equine encephalitis virus (VEEV), Western equine encephalomyelitis virus (WEEV), Eastern equine encephalitis virus (EEEV), or any combination thereof.

In various aspects, the present disclosure provides a method of preventing a Chikungunya virus infection in a subject, the method comprising administering to the subject a composition comprising: a replication defective virus vector comprising a deletion in an E2b gene region; and a nucleic acid sequence encoding at least one Chikungunya target antigen.

In some aspects, the subject has preexisting immunity to an adenovirus or an adenovirus vector. In some aspects, the subject is a human or a non-human animal. In some aspects, the administering is intravenously, subcutaneously, intralymphatically, intratumorally, intradermally, intramuscularly, intraperitoneally, intrarectally, intravaginally, intranasally, orally, via bladder instillation, or via scarification.

In some aspects, the administering of the composition to the subject is at least one time, is repeated at least twice, or is repeated at least three times. In some aspects, the administering to the subject comprises $1 \times 10^9$ to $5 \times 10^{12}$ virus particles per dose. In some aspects, the administering to the subject comprises at least $10^9$ virus particles, at least $10^{10}$ virus particles, or at least $10^{11}$ virus particles per dose. In some aspects, the replication defective virus vector is an adenovirus vector. In further aspects, the replication defective virus vector is an adenovirus 5 (Ad5) vector.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 4 exemplifies results of a challenge study performed using Ad5 [E1-, E2b-]-CHIKV$_{str}$ vaccine. Mice were vaccinated 2 times at days −14 and −7 and then challenged on day 0 with a lethal amount of CHIKV injected into the footpad.

FIG. 4A exemplifies mice vaccinated with Ad5 [E1-, E2b-]-CHIKV$_{str}$ vaccine survive CHIKV infection.

FIG. 4B exemplifies mice vaccinated with Ad5 [E1-, E2b-]-CHIKV$_{tr}$ vaccine maintain their pre-challenge weight.

FIG. 4C exemplifies mice vaccinated with Ad5 [E1-, E2b-]-CHIKV$_{str}$ vaccine resolved CHIKV-induced footpad inflammation faster than the unvaccinated control mice.

FIG. 5 illustrates exemplary gene constructs for Chikungunya vaccines of the present disclosure.

FIG. 6 illustrates cell-mediated immune (CMI) responses (IFN-γ) and cytolytic T lymphocyte (CTL) responses and Granzyme B responses in splenocytes from immunized or control mice using an ELISpot assay. C57BL/6 mice were immunized two times at two-week intervals with $1 \times 10^{10}$ virus particles (VPs) Ad5 [E1-, E2b-]-CHIK vaccine comprising SEQ ID NO: 1 or with $1 \times 10^{10}$ VPs Ad5 [E1-, E2b-]-null (empty vector control). One week after the final immunization, splenocytes from individual mice were tested for induction of immune responses after exposure of cells to Chikungunya virus peptides. The data show the cumulative number of spot forming cells (SFCs) per $10^6$ splenocytes after exposure to three separate pools of Chikungunya virus peptides (peptide numbers for Chikungunya were large enough to merit division into three separate pools to use in assays—CHIKV peptide pool 1 comprised peptides 1-103, CHIKV peptide pool 2 comprising peptides 104-207, and peptide pool 3 comprising peptides 208-310). Additional splenocytes were separately exposed to an SIV-nef peptide pools as a negative control prior to assay measurements.

FIG. 7 illustrates lymphocyte activation in splenocytes from immunized or control C57BL/6 mice as measured by intracellular expression of IFN-γ or IFN-γ/TNF-α analyzed by flow cytometry. C57BL/6 mice were immunized two times at two-week intervals with $1\times10^{10}$ VPs Ad5 [E1-, E2b-]-CHIK vaccine comprising SEQ ID NO: 1 or with $1\times10^{10}$ VPs Ad5 [E1-, E2b-]-null (empty vector controls). One week after the final immunization, splenocytes from individual mice were exposed to three separate pools of Chikungunya virus peptides (peptide numbers for Chikungunya were large enough to merit division into three separate pools to use in assays—CHIKV peptide pool 1 comprised peptides 1-103, CHIKV peptide pool 2 comprising peptides 104-207, and peptide pool 3 comprising peptides 208-310) and analyzed by flow cytometry for induction of intracellular cytokine expression.

DETAILED DESCRIPTION

Figure 1:
FIG. 1 exemplifies one structure of an alphavirus genome.

The following passages describe different aspects in greater detail. Each aspect can be combined with any other aspect or aspects unless clearly indicated to the contrary. In particular, any feature indicated as being preferred or advantageous can be combined with any other feature indicated as being preferred or advantageous.

In certain embodiments, alphavirus antigens such as capsid, $E3_{ALPHA}$, $E2_{ALPHA}$, 6K, and $E1_{ALPHA}$ and nonstructural proteins such as, nsP1, nsP2, nsP3, and nsP4 can be used, for example, in a vaccine composition or a composition comprising an adenovirus vector.

For example, $E2_{ALPHA}$ and $E1_{ALPHA}$ antigens can be used. Clinical correlates of protection have not been established for alphavirus vaccines, however there are data supporting a correlation between neutralizing antibody titers and protection. (Smalley, L., et al. Vaccine. (2016): 34(26): 2976-2981; Garcia-Arriaza, J. et al. Journal of Virology (2014): 88(6): 3527-47).

Non-structural alphavirus antigens can also be used in certain aspects. Studies have shown that the non-structural proteins involved in replication of the genome contain conserved regions that can provide a wider range of alphavirus protection when used in experimental vaccines, including those employing Ad5 vectors.

As used herein, unless otherwise indicated, the article "a" means one or more unless explicitly otherwise provided for.

As used herein, unless otherwise indicated, terms such as "contain," "containing," "include," "including," and the like mean "comprising."

As used herein, unless otherwise indicated, the term "or" can be conjunctive or disjunctive.

As used herein, unless otherwise indicated, any embodiment can be combined with any other embodiment.

As used herein, unless otherwise indicated, some inventive embodiments herein contemplate numerical ranges. A variety of aspects of this invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range as if explicitly written out. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. When ranges are present, the ranges include the range endpoints.

The term "adenovirus" or "Ad" can refer to a group of non-enveloped DNA viruses from the family Adenoviridae. In addition to human hosts, these viruses can be found in, but are not limited to, avian, bovine, porcine and canine species. The use of any adenovirus from any of the four genera of the family Adenoviridae (e.g., Aviadenovirus, Mastadenovirus, Atadenovirus and Siadenovirus) can be contemplated as the basis of an E2b deleted virus vector, or vector containing other deletions as described herein. In addition, several serotypes are found in each species. Ad also pertains to genetic derivatives of any of these viral serotypes, including but not limited to, genetic mutation, deletion or transposition of homologous or heterologous DNA sequences.

A "helper adenovirus" or "helper virus" can refer to an Ad that can supply viral functions that a particular host cell cannot (the host can provide Ad gene products such as E1 proteins). This virus can be used to supply, in trans, functions (e.g., proteins) that are lacking in a second virus, or helper dependent virus (e.g., a gutted or gutless virus, or a virus deleted for a particular region such as E2b or other region as described herein); the first replication-incompetent virus can be said to "help" the second, helper dependent virus thereby permitting the production of the second viral genome in a cell.

The term "Adenovirus5 null (AdSnull)," as used herein, can refer to a non-replicating Ad that does not contain any heterologous nucleic acid sequences for expression.

The term "First Generation adenovirus," as used herein, can refer to an Ad that has the early region 1 (E1) deleted. In additional cases, the nonessential early region 3 (E3) can also be deleted.

The term "gutted" or "gutless," as used herein, can refer to an adenovirus vector that has been deleted of all viral coding regions.

The term "transfection" as used herein can refer to the introduction of foreign nucleic acid into eukaryotic cells. Transfection can be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "stable transfection" or "stably transfected" can refer to the introduction and integration of foreign nucleic acid, DNA or RNA, into the genome of the transfected cell. The term "stable transfectant" can refer to a cell which has stably integrated foreign DNA into the genomic DNA.

The term "reporter gene" can indicate a nucleotide sequence that encodes a reporter molecule (including an enzyme). A "reporter molecule" can be detectable in any of a variety of detection systems, including, but not limited to enzyme-based detection assays (e.g., ELISA, as well as enzyme-based histochemical assays), fluorescent, radioactive, and luminescent systems.

In one embodiment, the *E. coli* β-galactosidase gene (available from Pharmacia Biotech, Pistacataway, N.J.), green fluorescent protein (GFP) (commercially available from Clontech, Palo Alto, Calif.), the human placental alkaline phosphatase gene, the chloramphenicol acetyltransferase (CAT) gene or other reporter genes that are known to the art can be employed.

As used herein, the terms "nucleic acid molecule encoding," "DNA sequence encoding," and "DNA encoding" can refer to the order or sequence of deoxyribonucleotides along a strand of deoxyribonucleic acid. The order of these deoxyribonucleotides can determine the order of amino acids along the polypeptide (protein) chain. The nucleic acid sequence thus can code for the amino acid sequence.

The term "heterologous nucleic acid sequence," as used herein, can refer to a nucleotide sequence that is ligated to, or is manipulated to become ligated to, a nucleic acid sequence to which it is not ligated in nature, or to which it is ligated at a different location in nature. Heterologous nucleic acid can include a nucleotide sequence that is naturally found in the cell into which it is introduced or the heterologous nucleic acid can contain some modification relative to the naturally occurring sequence.

The term "transgene" can refer to any gene coding region, either natural or heterologous nucleic acid sequences or fused homologous or heterologous nucleic acid sequences, introduced into the cells or genome of a test subject. In the current invention, transgenes are carried on any viral vector that is used to introduce the transgenes to the cells of the subject.

The term "Second Generation Adenovirus," as used herein, can refer to an Ad that has all or parts of the E1, E2, E3, and, in certain embodiments, E4 DNA gene sequences deleted (removed) from the virus.

The term "subject," or "individual," as used herein, can refer to any animal, e.g., a mammal or marsupial. Subjects include but are not limited to humans, non-human primates (e.g., rhesus or other types of macaques), mice, pigs, horses, donkeys, cows, sheep, rats and fowl of any kind.

In certain aspects, there can be provided compositions and methods for producing a vaccine that generates immune responses against various alphaviruses using an adenovirus vector that allows for vaccinations to generate broadly reactive immune responses against alphaviruses.

One aspect provides a method of generating an immune response against one or more alphavirus target antigens in an individual comprising administering to the individual an adenovirus vector comprising: a) a replication defective adenovirus vector, wherein the adenovirus vector has a deletion in the E2b region, and b) nucleic acids encoding one or more alphavirus target antigens; and readministering the adenovirus vector at least once or more to the individual; thereby generating an immune response against the alphavirus target antigens.

Another aspect provides a method for generating an immune response against several alphavirus target antigens in an individual, wherein the individual has preexisting immunity to adenovirus, comprising: administering to the individual an adenovirus vector comprising: a) a replication defective adenovirus vector, wherein the adenovirus vector has a deletion in the E2b region, and b) nucleic acids encoding multiple alphavirus target antigens; and readministering the adenovirus vector at least once or more to the individual; thereby generating an immune response against the alphavirus target antigens.

I. Target Antigens

In certain aspects, the target antigens are comprised of antigens derived from various alphavirus proteins. In this regard, the alphavirus proteins can be derived from any alphavirus, including but not limited to Chikungunya virus (CHIKV), o'nyong-nyong virus (ONNV), Ross River virus (RRV), Mayaro fever virus (MAYV), Venezuelan equine encephalitis virus (VEEV), Western equine encephalomyelitis virus (WEEV), and Eastern equine encephalitis virus (EEEV). In certain embodiments, the at least one alphavirus virus protein can be an alphavirus protein comprising $E3_{ALPHA}$, $E2_{ALPHA}$, 6K, $E1_{ALPHA}$, nsP1, nsP2, nsP3, or nsP4, or any combination thereof. In certain embodiments, the at least one alphavirus virus protein can comprise structural proteins from the group comprising $E3_{ALPHA}$, $E2_{ALPHA}$, 6K, or $E1_{ALPHA}$, or any combination thereof. In certain embodiments, the at least one alphavirus virus protein can comprise non-structural proteins from the group comprising nsP1, nsP2, nsP3, or nsP4, or any combination thereof. In certain embodiments, the at least one alphavirus virus protein can comprise structural proteins from the group comprising $E3_{ALPHA}$, $E2_{ALPHA}$, 6K, or $E1_{ALPHA}$, non-structural proteins from the group comprising nsP1, nsP2, nsP3, or nsP4, or combinations thereof. In certain embodiments, the at least one alphavirus virus protein can be an alphavirus protein selected from the group consisting of $E3_{ALPHA}$, $E2_{ALPHA}$, 6K, $E1_{ALPHA}$, nsP1, nsP2, nsP3, and nsP4. In certain embodiments, the at least one alphavirus virus protein can comprise structural proteins selected from the group consisting of $E3_{ALPHA}$, $E2_{ALPHA}$, 6K, and $E1_{ALPHA}$. In certain embodiments, the at least one alphavirus virus protein can comprise non-structural proteins selected from the group consisting of nsP1, nsP2, nsP3, and nsP4. In certain embodiments, the at least one alphavirus virus protein can comprise structural proteins selected from the group consisting of $E3_{ALPHA}$, $E2_{ALPHA}$, 6K, or $E1_{ALPHA}$, non-structural proteins selected from the group consisting of nsP1, nsP2, nsP3, and nsP4, or combinations thereof.

The envelope glycoproteins $E1_{ALPHA}$ and $E2_{ALPHA}$ can form heterodimers that associate to form trimeric spikes on surface of the virion. The alphavirus replicative cycle can begin when the trimeric spikes bind host-cell receptors and can cause the endocytosis of virions. The low pH of the endosomes can induce fusion of the viral and endosomal membranes thereby releasing the viral genome into the cytosol of the cell.

The genomic RNA of alphaviruses can serve as an mRNA which, like cellular mRNAs, can be capped with 7-methylguanosine and can be polyadenylated. The first approximately 7 kB of the genome can encode the non-structural proteins that comprise the viral replicase and transcriptase. The final approximately 5 kB of the genome can encode the structural proteins. The viral replicase proteins, nsP1, nsP2, nsP3, and nsP4, produce anti-genome which then can serve as a template for production of genome and two mRNAs, one for the non-structural proteins and one for the structural proteins.

The non-structural proteins can be translated as a polyprotein that can be subsequently processed by nsP2. It is believed that differential processing of the polyprotein can be necessary for the switch between anti-genome and genome synthesis/sub-genomic mRNA synthesis.

The structural proteins can be translated as a polyprotein that can be processed by a combination of a serine protease activity on the capsid protein and cellular enzymes in the secretory system (e.g., signal peptidase and furin). The envelope glycoproteins, $E1_{ALPHA}$ and $E2_{ALPHA}$, can transit from the secretory system to the plasma membrane where they can be found in the fully processed, mature form. $E1_{ALPHA}$ and $E2_{ALPHA}$ recruit nucleocapsids (capsid protein shells with genomic RNA inside), and virions can be formed by budding from the plasma membrane.

Target antigens can include proteins, or variants or fragments thereof, associated with alphaviruses, such as C, $E3_{ALPHA}$, $E2_{ALPHA}$, 6K, $E1_{ALPHA}$, nsP1, nsP2, nsP3, and nsP4. In some embodiments, the at least one target antigen is structural and/or non-structural antigen of an alphavirus. In certain embodiments, the at least one target antigen is any fragment of a protein or a polyprotein of an alphavirus. For example, the at least one target antigen used herein is a CHIKV structural antigen having an amino acid sequence set forth in SEQ ID NO: 2, a CHIKV non-structural antigen having an amino acid sequence set forth in SEQ ID NO: 3, or a combination thereof. In some embodiments, the at least one target antigen is a CHIKV antigen encoded by the nucleotide sequence set forth in SEQ ID NO: 1. In some embodiments, the nucleic acid sequence in the composition described herein comprises the CHIKV gene (nucleotides 7567-11313 of SEQ ID NO: 1) with a gene ID 956308, which has a gene symbol CHIKVgp2 and encodes a polyprotein containing C, E3, E2, 6K, and E1 proteins. In some embodiments, the nucleic acid sequence in the composition described herein comprises the CHIKV gene (nucleotides 77-7501 of SEQ ID NO: 1) with a gene ID 953609 which has a gene symbol CHIKVgp1 (encoding a polyprotein containing nsp1, nsp2, nsp3, and nsp4 proteins). In some embodiments, the nucleic acid sequence in the composition described herein comprises a nucleic acid sequence encoding a Chikungunya virus structural polyprotein (e.g., NP_690589) or fragments thereof. In some embodiments, the nucleic acid sequence in the composition described herein comprises a nucleic acid sequence encoding a Chikungunya virus nonstructural polyprotein (e.g., NP_690588) or fragments thereof. In some embodiments, the at least one target antigen is a CHIKV antigen that is encoded by a sequence that has at least 70%, at least 75%, at least 80%, at least 85%, at least 90%, at least 92%, at least 95%, at least 97%, or at least 99% sequence identity to SEQ ID NO: 1. In some embodiments, the at least one target antigen is a CHIKV antigen that is encoded by a sequence that has at least 70%, at least 75%, at least 80%, at least 85%, at least 90%, at least 92%, at least 95%, at least 97%, or at least 99% sequence identity to SEQ ID NO: 2, SEQ ID NO: 3, or any combination thereof.

For example, in some embodiments, the at least one target antigen is an ONNV antigen encoded by the nucleotide sequence set forth in SEQ ID NO: 4. In some embodiments, the at least one target antigen used herein is an ONNV structural antigen having an amino acid sequence set forth in SEQ ID NO: 5, an ONNV non-structural antigen having an amino acid sequence set forth in SEQ ID NO: 6, or a combination thereof. In some embodiments, the at least one target antigen is an ONNV antigen that is encoded by a sequence that has at least 70%, at least 75%, at least 80%, at least 85%, at least 90%, at least 92%, at least 95%, at least 97%, or at least 99% sequence identity to SEQ ID NO: 4. In some embodiments, the at least one target antigen is a ONNV antigen that is encoded by a sequence that has at least 70%, at least 75%, at least 80%, at least 85%, at least 90%, at least 92%, at least 95%, at least 97%, or at least 99% sequence identity to SEQ ID NO: 5, SEQ ID NO: 6, or any combination thereof. In some embodiments, the at least one target antigen is a MAYV antigen that is encoded by a sequence set forth in SEQ ID NO: 7. In other embodiments, the at least one target antigen used herein is a MAYV structural antigen having an amino acid sequence set forth in SEQ ID NO: 8, a MAYV non-structural antigen having an amino acid sequence set forth in SEQ ID NO: 9, or a combination thereof. In some embodiments, the at least one target antigen is a MAYV antigen that is encoded by a sequence that has at least 70%, at least 75%, at least 80%, at least 85%, at least 90%, at least 92%, at least 95%, at least 97%, or at least 99% sequence identity to SEQ ID NO: 7. In some embodiments, the at least one target antigen is a MAYV antigen that is encoded by a sequence that has at least 70%, at least 75%, at least 80%, at least 85%, at least 90%, at least 92%, at least 95%, at least 97%, or at least 99% sequence identity to SEQ ID NO: 8, SEQ ID NO: 9, or any combination thereof. In other embodiments, the at least one target antigen is a RRV antigen that is encoded by a sequence set forth in SEQ ID NO: 10. In some embodiments, the at least one target antigen used herein is a RRV structural antigen having an amino acid sequence set forth in SEQ ID NO: 11, a RRV non-structural antigen having an amino acid sequence set forth in SEQ ID NO: 12, or a combination thereof. In some embodiments, the at least one target antigen is a RRV antigen that is encoded by a sequence that has at least 70%, at least 75%, at least 80%, at least 85%, at least 90%, at least 92%, at least 95%, at least 97%, or at least 99% sequence identity to SEQ ID NO: 10. In some embodiments, the at least one target antigen is a RRV antigen that is encoded by a sequence that has at least 70%, at least 75%, at least 80%, at least 85%, at least 90%, at least 92%, at least 95%, at least 97%, or at least 99% sequence identity to SEQ ID NO: 11, SEQ ID NO: 12, or any combination thereof. In other embodiments, the at least one target antigen is a VEEV antigen that is encoded by a sequence set forth in SEQ ID NO: 13. In other embodiments, the at least one target antigen used herein is a VEEV structural antigen having an amino acid sequence set forth in SEQ ID NO: 14, a VEEV non-structural antigen having an amino acid sequence set forth in SEQ ID NO: 15, or a combination thereof. In some embodiments, the at least one target antigen is a VEEV antigen that is encoded by a sequence that has at least 70%, at least 75%, at least 80%, at least 85%, at least 90%, at least 92%, at least 95%, at least 97%, or at least 99% sequence identity to SEQ ID NO: 13. In some embodiments, the at least one target antigen is a VEEV antigen that is encoded by a sequence that has at least 70%, at least 75%, at least 80%, at least 85%, at least 90%, at least 92%, at least 95%, at least 97%, or at least 99% sequence identity to SEQ ID NO: 14, SEQ ID NO: 15, or any combination thereof. In other embodiments, the at least one target antigen is an EEEV antigen that is encoded by a sequence set forth in SEQ ID NO: 16. In some embodiments, the at least one target antigen used herein is an EEEV structural antigen having an amino acid sequence set forth in SEQ ID NO: 17, an EEEV non-structural antigen having an amino acid sequence set forth in SEQ ID NO: 18, or a combination thereof. In some embodiments, the at least one target antigen is a EEEV antigen that is encoded by a sequence that has at least 70%, at least 75%, at least 80%, at least 85%, at least 90%, at least 92%, at least 95%, at least 97%, or at least 99% sequence identity to SEQ ID NO: 16. In some embodiments, the at least one target antigen is a EEEV antigen that is encoded by a sequence that has at least 70%, at least 75%, at least 80%, at least 85%, at least 90%, at least 92%, at least 95%, at least 97%, or at least 99% sequence identity to SEQ ID NO: 17, SEQ ID NO: 18, or any combination thereof. In some embodiments, the at least one target antigen is a WEEV antigen that is encoded by a sequence set forth in SEQ ID NO: 19. In other embodiments, the at least one target antigen used herein is a WEEV structural antigen having an amino acid sequence set forth in SEQ ID NO: 20, a WEEV non-structural antigen having an amino acid sequence set forth in SEQ ID NO: 21, or a combination thereof. In some embodiments, the at least one target antigen is a WEEV antigen that is encoded by a sequence that has at least 70%, at least 75%, at least 80%, at least 85%, at least 90%, at least 92%, at least 95%, at least 97%, or at least 99% sequence identity to SEQ ID NO: 19. In some embodiments, the at least one target antigen is a WEEV antigen that is encoded by a sequence that has at least 70%, at least 75%, at least 80%, at least 85%, at least 90%, at least 92%, at least 95%, at least 97%, or at least 99% sequence identity to SEQ ID NO: 20, SEQ ID NO: 21, or any combination thereof.

II. Adenovirus Vectors

In certain aspects, adenovirus vectors can be used in compositions and methods for the delivery of alphavirus antigens.

The recombinant Ad5 [E1-, E2b-] vector vaccine platform can have additional deletions in the early gene 2b (E2b) region that remove the viral DNA polymerase (pol) and/or the pre-terminal protein (pTP) genes, and can be propagated in the E.C7 human cell line (Amalfitano A, Begy C R, Chamberlain J S Proc Natl Acad Sci USA. 1996 93:3352-6; Amalfitano A, Chamberlain J S Gene Ther. 1997 4:258-63; Amalfitano A et al. J Virol. 1998 72:926-33; Seregin S S and Amalfitano A Expert Opin Biol Ther. 2009 9:1521-31). The vector can be an expanded gene-carrying/cloning capacity of up to 12 kb, compared to the 7 kb capacity of current Ad5 [E1-] vectors, which can be sufficient to allow inclusion of multiple genes (Amalfitano A et al. J Virol. 1998 72:926-33; Seregin S S and Amalfitano A Expert Opin Biol Ther. 2009 9:1521-31). Additional deletions of the E2b region can confer advantageous immune properties such as eliciting potent immune responses to specific antigens while minimizing immune responses to Ad5 viral proteins.

Pre-clinical studies in animals and clinical studies in cancer demonstrate that Ad5 [E1-, E2b-]-based vectors can induce potent CMI and antibody (Ab) responses against a vectored antigen, even in the presence of Ad5 immunity.

The advanced recombinant adenovirus serotype 5 (Ad5) vector platforms can give the opportunity to develop a novel broadly cross-reactive vaccine for alphavirus. This vector can be delivered directly by subcutaneous injection for exposure of defined alphavirus antigens to antigen-presenting cells (APCs) that induce potent immune responses. Importantly, the Ad5 recombinant vector can replicate episomally and may not insert the genome into the host cell genome, thereby ensuring that there is no gene integration or disruption of vital cellular gene functions (Imler J L Vaccine. 1995 13:1143-51; Ertl H C, Xiang Z J Immunol. 1996 156:3579-82; Amalfitano, A Curr Opin Mol Ther. 2003 5:362-6).

Unfortunately, a major challenge facing current Ad5-based vectors is the presence of pre-existing immunity to Ad5. Most people exhibit neutralizing Abs against Ad5, the most widely used subtype for human vaccines, with two-thirds of people studied having lympho-proliferative responses against Ad5 (Chirmule N et al. Gene Ther. 1999 6:1574-83). This immunity can prevent the use of current early gene 1 (E1) region-deleted Ad5 vectors (Ad5 [E1-]) as a platform for an alphavirus vaccine. Ad5 immunity inhibits immunization, and especially re-immunization with recombinant Ad5 vectors, and can preclude immunization of a 15ittere against a second disease antigen as well. Overcoming the problem of pre-existing Ad5 vector immunity has been the subject of intense investigation. However, use of other Ad serotypes or even non-human forms of Ad can lead directly to altered production of important chemokines and cytokines, gene dysregulation, and can have significantly different biodistribution and tissue toxicities (Appledorn D M et al. Gene Ther. 2008 15:885-901; Hartman Z C et al. Virus Res. 2008 132:1-14). Even if these approaches succeed in an initial immunization, subsequent vaccinations can be problematic due to induced immune responses to the Ad subtype. To help avoid the Ad immunization barrier and circumvent the adverse conditions for current Ad5 [E1-] vectors, an improved Ad5 vector platform was constructed, described above.

Further, the Ad5 [E1-, E2b-] vectors can display reduced inflammation during the first 24 to 72 hours after injection compared to current Ad5 [E1-] vectors (Nazir S A, Metcalf J P J Investig Med. 2005 53:292-304; Schaack J Proc Natl Acad Sci USA. 2004 101:3124-9; Schaack J Viral Immunol. 2005 18:79-88). The lack of Ad5 [E1-, E2b-] late gene expression can render infected cells less vulnerable to anti-Ad5 activity and can permit them to produce and express the transgene for extended periods of time (Gabitzsch E S, Jones F R J Clin Cell Immunol. 2011 S4:001. Doi:10.4172/2155-9899. S4-001; Hodges B L J Gene Med. 2000 2:250-9). Reduced inflammatory responses against Ad5 [E1-, E2b-]

viral proteins and the resulting evasion of pre-existing Ad5 immunity can increase the ability of Ad5 [E1-, E2b-] to infect APC cells, resulting in greater immunization of the inoculee. In addition, increased infection of other cell types can provide the high levels of antigen presentation needed for potent CD4$^+$ and CD8$^+$ T cell responses, leading to memory T cell development. Thus it appears that deletion of the E2b region can confer advantageous immune properties, such as eliciting potent immune responses to specific antigens, while minimizing immune responses to Ad5 proteins even in the presence of pre-existing Ad5 immunity.

Results demonstrated the ability of recombinant Ad5 [E1-, E2b-] platform-based vaccines to overcome pre-existing and/or Ad5 vector-induced immunity and induce significant protective immune responses. These studies established that new Ad5 [E1-, E2b-] vector-based vaccines 1) can induce significantly higher CMI responses compared to current Ad5 [E1-] vectors, 2) can be utilized for multiple immunization regimens designed to induce potent CMI responses, 3) can induce significant antigen-specific CMI responses in animals with pre-existing Ad5 immunity, and 4) can induce significant anti-tumor responses or protect against infectious disease in animals with high levels of pre-existing Ad5 immunity.

Certain aspects relate to methods and adenovirus vectors for generating immune responses against alphavirus target antigens. In particular, certain aspects can provide an improved Ad-based vaccine such that multiple vaccinations against more than one antigenic target entity can be achieved. Importantly, vaccination can be performed in the presence of preexisting immunity to the Ad and/or administered to subjects previously immunized multiple times with the adenovirus vector as described herein or other adenovirus vectors. The adenovirus vector can be administered to subjects multiple times to induce an immune response against a variety of alphavirus antigens, including but not limited to, the production of broad based antibody and cell-mediated immune responses against alphaviruses that cause polyarthralgias or encephalitis.

Certain aspects provide the use of E2b deleted adenovirus vectors, such as those described in U.S. Pat. Nos. 6,063,622; 6,451,596; 6,057,158: and 6,083,750 (all incorporated herein in their entirety by reference). As described in the '622 patent, in order to further cripple viral protein expression, and also to decrease the frequency of generating replication competent Ad (RCA), adenovirus vectors containing deletions in the E2b region can be provided in certain aspects. Propagation of these E2b deleted adenovirus vectors requires cell lines that can express the deleted E2b gene products.

In further aspects, there can be provided packaging cell lines; for example E.C7 (formally called C-7), derived from the HEK-203 cell line (Amalfitano A et al. Proc Natl Acad Sci USA 1996 93:3352-56; Amalfitano A et al. Gene Ther 1997 4:258-63).

Further, the E2b gene products, DNA polymerase and preterminal protein, can be constitutively expressed in E.C7, or similar cells along with the E1 gene products. Transfer of gene segments from the Ad genome to the production cell line can have immediate benefits: (1) increased carrying capacity of the recombinant DNA polymerase and preterminal protein-deleted adenovirus vector, since the combined coding sequences of the DNA polymerase and preterminal proteins that can be theoretically deleted approaches 4.6 kb; and, (2) a decreased potential of RCA generation, since two or more independent recombination events would be required to generate RCA.

Therefore, the E1, Ad DNA polymerase and preterminal protein expressing cell lines can enable the propagation of adenovirus vectors with a carrying capacity approaching 13 kb, without the need for a contaminating helper virus (Mitani et al. Proc. Natl. Acad. Sci. USA 1995 92:3854; Hodges et al. J Gene Med 2000 2:250-259; Amalfitano and Parks Curr Gene Ther 2002 2:111-133).

In addition, when genes critical to the viral life cycle are deleted (e.g., the E2b genes), a further crippling of Ad to replicate or express other viral gene proteins can occur. This can decrease immune recognition of virally infected cells, and can allow for extended durations of foreign transgene expression.

Important attributes of E1, DNA polymerase, and preterminal protein deleted vectors, however, include their inability to express the respective proteins from the E1 and E2b regions, as well as a predicted lack of expression of most of the viral structural proteins. For example, the major late promoter (MLP) of Ad is responsible for transcription of the late structural proteins L1 through L5 (Doerfler, In Adenovirus DNA, The Viral Genome and Its Expression (Martinus Nijhoff Publishing Boston, 1986)). Though the MLP is minimally active prior to Ad genome replication, the highly toxic Ad late genes are primarily transcribed and translated from the MLP only after viral genome replication has occurred (Thomas and Mathews Cell 1980 22:523). This cis-dependent activation of late gene transcription is a feature of DNA viruses in general, such as in the growth of polyoma and SV-40. The DNA polymerase and preterminal proteins are absolutely required for Ad replication (unlike the E4 or protein IX proteins) and thus their deletion is extremely detrimental to adenovirus vector late gene expression, and the toxic effects of that expression in cells such as APCs.

In certain embodiments, the adenovirus vectors contemplated for use include E2b deleted adenovirus vectors that have a deletion in the E2b region of the Ad genome and the E1 region but do not have any other regions of the Ad genome deleted. In another embodiment, the adenovirus vectors contemplated for use can include E2b deleted adenovirus vectors that have a deletion in the E2b region of the Ad genome and deletions in the E1 and E3 regions, but no other regions deleted. In a further embodiment, the adenovirus vectors contemplated for use can include adenovirus vectors that have a deletion in the E2b region of the Ad genome and deletions in the E1, E3 and partial or complete removal of the E4 regions but no other deletions.

In another embodiment, the adenovirus vectors contemplated for use include adenovirus vectors that have a deletion in the E2b region of the Ad genome and deletions in the E1 and E4 regions but no other deletions. In an additional embodiment, the adenovirus vectors contemplated for use can include adenovirus vectors that have a deletion in the E2a, E2b, and E4 regions of the Ad genome but no other deletions.

In one embodiment, the adenovirus vectors for use herein comprise vectors having the E1 and DNA polymerase functions of the E2b region deleted but no other deletions. In a further embodiment, the adenovirus vectors for use herein have the E1 and the preterminal protein functions of the E2b region deleted and no other deletions.

In another embodiment, the adenovirus vectors for use herein have the E1, DNA polymerase and the preterminal protein functions deleted, and no other deletions. In one particular embodiment, the adenovirus vectors contemplated for use herein are deleted for at least a portion of the E2b region and the E1 region, but are not "gutted" adenovirus vectors. In this regard, the vectors can be deleted for both the DNA polymerase and the preterminal protein functions of the E2b region.

The term "E2b deleted," as used herein, can refer to a specific DNA sequence that is mutated in such a way so as to prevent expression and/or function of at least one E2b gene product. Thus, in certain embodiments, "E2b deleted" can refer to a specific DNA sequence that is deleted (removed) from the Ad genome. E2b deleted or "containing a deletion within the E2b region" can refer to a deletion of at least one base pair within the E2b region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted. In another embodiment, the deletion is of more than 150, 160, 170, 180, 190, 200, 250, or 300 base pairs within the E2b region of the Ad genome. An E2b deletion can be a deletion that prevents expression and/or function of at least one E2b gene product and therefore, can encompass deletions within exons encoding portions of E2b-specific proteins as well as deletions within promoter and leader sequences. In certain embodiments, an E2b deletion is a deletion that prevents expression and/or function of one or both of the DNA polymerase and the preterminal protein of the E2b region. In a further embodiment, "E2b deleted" can refer to one or more point mutations in the DNA sequence of this region of an Ad genome such that one or more encoded proteins is non-functional. Such mutations can include residues that are replaced with a different residue leading to a change in the amino acid sequence that result in a nonfunctional protein.

As would be understood by the skilled artisan upon reading the present disclosure, other regions of the Ad genome can be deleted. Thus to be "deleted" in a particular region of the Ad genome, as used herein, can refer to a specific DNA sequence that is mutated in such a way so as to prevent expression and/or function of at least one gene product encoded by that region. In certain embodiments, to be "deleted" in a particular region can refer to a specific DNA sequence that is deleted (removed) from the Ad genome in such a way so as to prevent the expression and/or the function encoded by that region (e.g., E2b functions of DNA polymerase or preterminal protein function). "Deleted" or "containing a deletion" within a particular region can refer to a deletion of at least one base pair within that region of the Ad genome. Thus, in certain embodiments, more than one base pair is deleted and in further embodiments, at least 20, 30, 40, 50, 60, 70, 80, 90, 100, 110, 120, 130, 140, or 150 base pairs are deleted from a particular region. In another embodiment, the deletion is more than 150, 160, 170, 180, 190, 200, 250, or 300 base pairs within a particular region of the Ad genome. In some embodiments, any one of the above described deletions can also be a result of translocation of two or more base pairs.

These deletions are such that expression and/or function of the gene product encoded by the region can be prevented. Thus deletions can encompass deletions within exons encoding portions of proteins as well as deletions within promoter and leader sequences. In a further embodiment, "deleted" in a particular region of the Ad genome can refer to one or more point mutations in the DNA sequence of this region of an Ad genome such that one or more encoded proteins is non-functional. Such mutations can include residues that are replaced with a different residue leading to a change in the amino acid sequence that result in a nonfunctional protein.

The adenovirus vectors comprising one or more deletions can be generated using recombinant techniques known in the art (see e.g., Amalfitano et al. J. Virol. 1998 72:926-33; Hodges, et al., J Gene Med 2000 2:250-59). As would be recognized by the skilled artisan, the adenovirus vectors for use can be successfully grown to high titers using an appropriate packaging cell line that constitutively expresses E2b gene products and products of any of the necessary genes that can have been deleted. In certain embodiments, HEK-293-derived cells that not only constitutively express the E1 and DNA polymerase proteins, but also the Ad-preterminal protein, can be used. In one embodiment, E.C7 cells are used to successfully grow high titer stocks of the adenovirus vectors (see e.g., Amalfitano et al. J. Virol. 1998 72:926-33; Hodges et al. J Gene Med 2000 2:250-59)

In order to delete critical genes from self-propagating adenovirus vectors, the proteins encoded by the targeted genes have to first be coexpressed in HEK-293 cells, or similar, along with the E1 proteins. Therefore, only those proteins which are non-toxic when coexpressed constitutively (or toxic proteins inducibly-expressed) can be utilized. Coexpression in HEK-293 cells of the E1 and E4 genes has been demonstrated (utilizing inducible, not constitutive, promoters) (Yeh et al. J. Virol. 1996 70:559; Wang et al. Gene Therapy 1995 2:775; and Gorziglia et al. J. Virol. 1996 70:4173). The E1 and protein IX genes (a virion structural protein) have been coexpressed (Caravokyri and Leppard J. Virol. 1995 69:6627), and coexpression of the E1, E4, and protein IX genes has also been described (Krougliak and Graham Hum. Gene Ther. 1995 6:1575). The E1 and 100 k genes have been successfully expressed in trans-complementing cell lines, as have E1 and protease genes (Oualikene et al. Hum Gene Ther 2000 11:1341-53; Hodges et al. J. Virol 2001 75:5913-20).

Cell lines coexpressing E1 and E2b gene products for use in growing high titers of E2b deleted Ad particles are described in U.S. Pat. No. 6,063,622. The E2b region can encode the viral replication proteins which are absolutely required for Ad genome replication (Doerfler, supra and Pronk et al. Chromosoma 1992 102:S39-S45). Useful cell lines constitutively express the approximately 140 kDa Ad-DNA polymerase and/or the approximately 90 kDa preterminal protein. In particular, cell lines that have high-level, constitutive coexpression of the E1, DNA polymerase, and preterminal proteins, without toxicity (e.g., E.C7), can be desirable for use in propagating Ad for use in multiple vaccinations. These cell lines can permit the propagation of adenovirus vectors deleted for the E1, DNA polymerase, and preterminal proteins.

The recombinant Ad can be propagated using techniques known in the art. For example, in certain embodiments, tissue culture plates containing E.C7 cells are infected with the adenovirus vector virus stocks at an appropriate MOI (e.g., 5) and incubated at 37.0° C. for 40-96 h. The infected cells can be harvested, resuspended in 10 mM Tris-Cl (pH 8.0), and sonicated, and the virus can be purified by two rounds of cesium chloride density centrifugation. In certain techniques, the virus containing band is desalted over a Sephadex CL-6B column (Pharmacia Biotech, Piscataway, N.J.), sucrose or glycerol is added, and aliquots are stored at −80° C. In some embodiments, the virus can be placed in a solution designed to enhance its stability, such as A195 (Evans et al. J Pharm Sci 2004 93:2458-75). The titer of the stock can be measured (e.g., by measurement of the optical density at 260 nm of an aliquot of the virus after SDS lysis). In another embodiment, plasmid DNA, either linear or circular, encompassing the entire recombinant E2b deleted adenovirus vector can be transfected into E.C7, or similar cells, and can be incubated at 37.0° C. until evidence of viral production is present (e.g., the cytopathic effect). The conditioned media from these cells can then be used to infect more E.C7, or similar cells, to expand the amount of virus produced, before purification.

Purification can be accomplished by two rounds of cesium chloride density centrifugation or selective filtration. In certain embodiments, the virus can be purified by column chromatography, using commercially available products (e.g., Adenopure from Puresyn, Inc., Malvem, Pa.) or custom made chromatographic columns.

In certain embodiments, the recombinant Ad can comprise enough of the virus to ensure that the cells to be infected are confronted with a certain number of viruses. Thus, there can be provided a stock of recombinant Ad, particularly, an RCA-free stock of recombinant Ad. The preparation and analysis of Ad stocks is well known in the art. Viral stocks can vary considerably in titer, depending largely on viral genotype and the protocol and cell lines used to prepare them. The viral stocks can have a titer of at least about $10^6$, $10^7$, or $10^8$ virus particles (VPs)/ml, and many such stocks can have higher titers, such as at least about $10^9$, $10^{10}$, $10^{11}$, or $10^{12}$ VPs/ml.

III. Heterologous Nucleic Acids

In certain embodiments, the adenovirus vectors described herein comprise heterologous nucleic acid sequences that encode one or more target antigens of interest such as alphavirus target antigens, fragments or fusions thereof, against which it is desired to generate an immune response. In some embodiments, the adenovirus vectors comprise heterologous nucleic acid sequences that encode several proteins, fusions thereof or fragments thereof, which can modulate the immune response. Certain aspects provide the Second Generation E2b deleted adenovirus vectors that comprise a heterologous nucleic acid sequence such as an alphavirus target antigen.

As such, certain aspects provide nucleic acid sequences, which can also be referred to herein as polynucleotides that encode several alphavirus target antigens of interest. As such, certain aspects provide polynucleotides that encode target antigens from any source as described further herein, vectors comprising such polynucleotides and host cells transformed or transfected with such expression vectors. The terms "nucleic acid" and "polynucleotide" are used essentially interchangeably herein. As will be also recognized by the skilled artisan, polynucleotides can be single-stranded (coding or antisense) or double-stranded, and can be DNA (genomic, cDNA or synthetic) or RNA molecules. RNA molecules can include hnRNA molecules, which contain introns and correspond to a DNA molecule in a one-to-one manner, and mRNA molecules, which do not contain introns. Additional coding or non-coding sequences can, but need not, be present within a polynucleotide, and a polynucleotide can, but need not, be linked to other molecules and/or support materials. An isolated polynucleotide, as used herein, can mean that a polynucleotide is substantially away from other coding sequences. For example, an isolated DNA molecule as used herein does not contain large portions of unrelated coding DNA, such as large chromosomal fragments or other functional genes or polypeptide coding regions. Of course, this can refer to the DNA molecule as originally isolated, and does not exclude genes or coding regions later added to the segment recombinantly in the laboratory.

As will be understood by those skilled in the art, the polynucleotides can include genomic sequences, extra-genomic and plasmid-encoded sequences and smaller engineered gene segments that express, or can be adapted to express target antigens as described herein, fragments of antigens, peptides and the like. Such segments can be naturally isolated, or modified synthetically by the hand of man.

Polynucleotides can comprise a native sequence (i.e., an endogenous sequence that encodes a target antigen polypeptide/protein/epitope or a portion thereof) or can comprise a sequence that encodes a variant or derivative of such a sequence. In certain embodiments, the polynucleotide sequences set forth herein encode target antigen proteins as described herein. In some embodiments, polynucleotides represent a novel gene sequence that has been optimized for expression in specific cell types (i.e., human cell lines) that can substantially vary from the native nucleotide sequence or variant but encode a similar protein antigen.

In other related embodiments, there can be provided polynucleotide variants having substantial identity to native sequences encoding proteins (e.g., target antigens of interest) as described herein, for example those comprising at least 70% sequence identity, particularly at least 75% up to 99% or higher, sequence identity compared to a native polynucleotide sequence encoding the polypeptides using the methods described herein (e.g., BLAST analysis using standard parameters, as described below). One skilled in this art will recognize that these values can be appropriately adjusted to determine corresponding identity of proteins encoded by two nucleotide sequences by taking into account codon degeneracy, amino acid similarity, reading frame positioning and the like.

In certain aspects, polynucleotide variants can contain one or more substitutions, additions, deletions and/or insertions, particularly such that the immunogenicity of the epitope of the polypeptide encoded by the variant polynucleotide or such that the immunogenicity of the heterologous target protein may not be substantially diminished relative to a polypeptide encoded by the native polynucleotide sequence. As described elsewhere herein, the polynucleotide variants can encode a variant of the target antigen, or a fragment (e.g., an epitope) thereof wherein the propensity of the variant polypeptide or fragment (e.g., epitope) thereof to react with antigen-specific antisera and/or T-cell lines or clones may not be substantially diminished relative to the native polypeptide. The term "variants" can also encompass homologous genes of xenogeneic origin.

Certain aspects provide polynucleotides that comprise or consist of at least about 5 up to a 1000 or more contiguous nucleotides encoding a polypeptide, including target protein antigens, as described herein, as well as all intermediate lengths there between. It will be readily understood that "intermediate lengths," in this context, can mean any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through 200-500; 500-1,000, and the like. A polynucleotide sequence as described herein can be extended at one or both ends by additional nucleotides not found in the native sequence encoding a polypeptide as described herein, such as an epitope or heterologous target protein. This additional sequence can consist of 1 up 20 nucleotides or more, at either end of the disclosed sequence or at both ends of the disclosed sequence.

In certain embodiments, the polynucleotides, or fragments thereof, regardless of the length of the coding sequence itself, can be combined with other DNA sequences, such as promoters, expression control sequences, polyadenylation signals, additional restriction enzyme sites, multiple cloning sites, other coding segments, and the like, such that their overall length can vary considerably. It is therefore contemplated that a nucleic acid fragment of almost any length can be employed, and the total length that can be limited by the ease of preparation and use in the intended recombinant DNA protocol. For example, illustrative polynucleotide segments with total lengths of about 1000, 2000, 3000, 4000, 5000, 6000, 7000, 8000, 9000, 10,000, about 500, about 200, about 100, about 50 base pairs in length, and the like, (including all intermediate lengths) are contemplated to be useful in many implementations.

When comparing polynucleotide sequences, two sequences can be said to be "identical" if the sequence of nucleotides in the two sequences is the same when aligned for maximum correspondence, as described below. Comparisons between two sequences can be performed by comparing the sequences over a comparison window to identify and compare local regions of sequence similarity. A "comparison window" as used herein, refers to a segment of at least about 20 contiguous positions, usually 30 to about 75, 40 to about 50, in which a sequence can be compared to a reference sequence of the same number of contiguous positions after the two sequences are optimally aligned.

Optimal alignment of sequences for comparison can be conducted using the Megalign program in the Lasergene suite of bioinformatics software (DNASTAR, Inc., Madison, Wis.), using default parameters. This program embodies several alignment schemes described in the following references: Dayhoff M O (1978) A model of evolutionary change in proteins—Matrices for detecting distant relationships. In Dayhoff M O (ed.) Atlas of Protein Sequence and Structure, National Biomedical Research Foundation, Washington D.C. Vol. 5, Suppl. 3, pp. 345-358; Hein J Unified Approach to Alignment and Phylogenes, pp. 626-645 (1990); Methods in Enzymology vol. 183, Academic Press, Inc., San Diego, Calif.; Higgins D G and Sharp P M CABIOS 1989 5:151-53; Myers E W and Muller W CABIOS 1988 4:11-17; Robinson E D Comb. Theor 1971 11A 05; Saitou N, Nei M Mol. Biol. Evol. 1987 4:406-25; Sneath P H A and Sokal R R Numerical Taxonomy—the Principles and Practice of Numerical Taxonomy, Freeman Press, San Francisco, Calif. (1973); Wilbur W J and Lipman D J Proc. Natl. Acad., Sci. USA 1983 80:726-30).

Alternatively, optimal alignment of sequences for comparison can be conducted by the local identity algorithm of Smith and Waterman, Add. APL. Math 1981 2:482, by the identity alignment algorithm of Needleman and Wunsch J. Mol. Biol. 1970 48:443, by the search for similarity methods of Pearson and Lipman, Proc. Natl. Acad. Sci. USA 1988 85:2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One example of algorithms that are suitable for determining percent sequence identity and sequence similarity are the BLAST and BLAST 2.0 algorithms, which are described in Altschul et al., Nucl. Acids Res. 1977 25:3389-3402, and Altschul et al. J. Mol. Biol. 1990 215:403-10, respectively. BLAST and BLAST 2.0 can be used, for example with the parameters described herein, to determine percent sequence identity for the polynucleotides. Software for performing BLAST analyses is publicly available through the National Center for Biotechnology Information. In one illustrative example, cumulative scores can be calculated using, for nucleotide sequences, the parameters M (reward score for a pair of matching residues; always >0) and N (penalty score for mismatching residues; always <0). Extension of the word hits in each direction can be halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation I of 10, and the BLOSUM62 scoring matrix (see Henikoff and Henikoff, Proc. Natl. Acad. Sci. USA 1989 89:10915) alignments, (B) of 50, expectation I of 10, M=5, N=-4 and a comparison of both strands.

In certain aspects, the "percentage of sequence identity" is determined by comparing two optimally aligned sequences over a window of comparison of at least 20 positions, wherein the portion of the polynucleotide sequence in the comparison window can comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage can be calculated by determining the number of positions at which the identical nucleic acid bases occurs in both sequences to yield the number of matched positions, dividing the number of matched positions by the total number of positions in the reference sequence (i.e., the window size) and multiplying the results by 100 to yield the percentage of sequence identity.

It will be appreciated by those of ordinary skill in the art that, as a result of the degeneracy of the genetic code, there can be many nucleotide sequences that encode a particular antigen of interest, or fragment thereof, as described herein. Some of these polynucleotides can bear minimal homology to the nucleotide sequence of any native gene. Nonetheless, polynucleotides that vary due to differences in codon usage are specifically contemplated in certain aspects. Further, alleles of the genes comprising the polynucleotide sequences provided herein are also contemplated. Alleles can be endogenous genes that can be altered as a result of one or more mutations, such as deletions, additions and/or substitutions of nucleotides. The resulting mRNA and protein can, but need not, have an altered structure or function. Alleles can be identified using standard techniques (such as hybridization, amplification and/or database sequence comparison).

Therefore, in another embodiment, a mutagenesis approach, such as site-specific mutagenesis, is employed for the preparation of variants and/or derivatives of the target antigen sequences, or fragments thereof, as described herein. By this approach, specific modifications in a polypeptide sequence can be made through mutagenesis of the underlying polynucleotides that encode them. These techniques can provide a straightforward approach to prepare and test sequence variants, for example, incorporating one or more of the foregoing considerations, by introducing one or more nucleotide sequence changes into the polynucleotide.

Site-specific mutagenesis can allow the production of mutants through the use of specific oligonucleotide sequences which can encode the DNA sequence of the desired mutation, as well as a sufficient number of adjacent nucleotides, to provide a primer sequence of sufficient size and sequence complexity to form a stable duplex on both sides of the deletion junction being traversed. Mutations can be employed in a selected polynucleotide sequence to improve, alter, decrease, modify, or otherwise change the properties of the polynucleotide itself, and/or alter the properties, activity, composition, stability, or primary sequence of the encoded polypeptide.

Polynucleotide segments or fragments encoding the polypeptides can be readily prepared by, for example, directly synthesizing the fragment by chemical means, as is commonly practiced using an automated oligonucleotide synthesizer. Also, fragments can be obtained by application of nucleic acid reproduction technology, such as the PCR™ technology of U.S. Pat. No. 4,683,202, by introducing selected sequences into recombinant vectors for recombinant production, and by other recombinant DNA techniques generally known to those of skill in the art of molecular biology (see for example, Current Protocols in Molecular Biology, John Wiley and Sons, NY, NY).

In order to express a desired target antigen polypeptide or fragment thereof, or fusion protein comprising any of the above, as described herein, the nucleotide sequences encoding the polypeptide, or functional equivalents, can be inserted into an appropriate Ad as described elsewhere herein using recombinant techniques known in the art. The appropriate adenovirus vector can contain the necessary elements for the transcription and translation of the inserted coding sequence and any desired linkers. Methods that are well known to those skilled in the art can be used to construct these adenovirus vectors containing sequences encoding a polypeptide of interest and appropriate transcriptional and translational control elements. These methods can include in vitro recombinant DNA techniques, synthetic techniques, and in vivo genetic recombination. Such techniques are described, for example, in Amalfitano et al. J. Virol. 1998 72:926-33; Hodges et al. J Gene Med 2000 2:250-259; Sambrook J et al. (1989) Molecular Cloning, A Laboratory Manual, Cold Spring Harbor Press, Plainview, N.Y., and Ausubel F M et al. (1989) Current Protocols in Molecular Biology, John Wiley & Sons, New York. N.Y.

A variety of vector/host systems can be utilized to contain and produce polynucleotide sequences. These can include, but are not limited to, microorganisms such as bacteria transformed with recombinant bacteriophage, plasmid, or cosmid DNA vectors; yeast transformed with yeast vectors; insect cell systems infected with virus vectors (e.g., baculovirus); plant cell systems transformed with virus vectors (e.g., cauliflower mosaic virus, CaMV; tobacco mosaic virus, TMV) or with bacterial vectors (e.g., Ti or pBR322 plasmids); or animal cell systems.

The "control elements" or "regulatory sequences" present in an adenovirus vector can be those non-translated regions of the vector—enhancers, promoters, 5' and 3' untranslated regions—which can interact with host cellular proteins to carry out transcription and translation. Such elements can vary in their strength and specificity. Depending on the vector system and host utilized, any number of suitable transcription and translation elements, including constitutive and inducible promoters, can be used. For example, sequences encoding a polypeptide of interest can be ligated into an Ad transcription/translation complex consisting of the late promoter and tripartite leader sequence. Insertion in a non-essential E1 or E3 region of the viral genome can be used to obtain a viable virus that is capable of expressing the polypeptide in infected host cells (Logan J and Shenk T (1984) Proc. Natl. Acad. Sci 1984 87:3655-59). In addition, transcription enhancers, such as the Rous sarcoma virus (RSV) enhancer, can be used to increase expression in mammalian host cells. Transcriptional enhancers can comprise one element, at least two elements, at least three elements, at least four elements, at least five elements, or at least six elements.

Specific initiation signals can also be used to achieve more efficient translation of sequences encoding a polypeptide of interest. Such signals can include the ATG initiation codon and adjacent sequences. In cases where sequences encoding the polypeptide, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon can be provided. Furthermore, the initiation codon can be in the correct reading frame to ensure translation of the entire insert. Exogenous translational elements and initiation codons can be of various origins, both natural and synthetic. The efficiency of expression can be enhanced by the inclusion of enhancers that are appropriate for the particular cell system which is used, such as those described in the literature (Scharf D. et al. Results Probl. Cell Differ. 1994 20:125-62). Specific termination sequences, either for transcription or translation, can also be incorporated in order to achieve efficient translation of the sequence encoding the polypeptide of choice.

A variety of protocols for detecting and measuring the expression ofpolynucleotide-encoded products (e.g., target antigens of interest), using either polyclonal or monoclonal antibodies specific for the product are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on a given polypeptide can be used for some applications, but a competitive binding assay can also be employed. These and other assays are described, among other places, in Hampton R et al. (1990; Serological Methods, a Laboratory Manual, APS Press, St Paul. Minn.) and Maddox D E et al. J. Exp. Med. 1983 758:1211-16). The adenovirus vectors can comprise nucleic acid sequences encoding several alphavirus antigens of interest.

In certain embodiments, elements that increase the expression of the desired target antigen are incorporated into the nucleic acid sequence of the adenovirus vectors described herein. Such elements include internal ribosome binding sites (IRES; Wang and Siddiqui Curr. Top. Microbiol. Immunol 1995 203:99; Ehrenfeld and Semler Curr. Top. Microbiol. Immunol. 1995 203:65; Rees et al., Biotechniques 1996 20:102; Sugimoto et al. Biotechnology 1994 2:694). IRES can increase translation efficiency. Other sequences can also enhance expression. For some genes, sequences especially at the 5' end can inhibit transcription and/or translation. These sequences can be palindromes that can form hairpin structures. Any such sequences in the nucleic acid to be delivered can be deleted or not deleted.

Expression levels of the transcript or translated product can be assayed to confirm or ascertain which sequences affect expression. Transcript levels can be assayed by any known method, including Northern blot hybridization, Rnase probe protection and the like. Protein levels can be assayed by any known method, including ELISA. As would be recognized by the skilled artisan, the adenovirus vectors comprising heterologous nucleic acid sequences can be generated using recombinant techniques known in the art, such as those described in Maione et al. Proc Natl Acad Sci USA 2001 98:5986-91; Maione et al. Hum Gene Ther 2000 1:859-68; Sandig et al. Proc Natl Acad Sci USA, 2000

97:1002-07; Harui et al. Gene Therapy 2004 11:1617-26; Parks et al. Proc Natl Acad Sci USA 1996 93:13565-570; Dello Russo et al. Proc Natl Acad Sci USA 2002 99:12979-984; Current Protocols in Molecular Biology, John Wiley and Sons, NY, NY).

As noted above, the adenovirus vectors can comprise nucleic acid sequences that can encode several alphavirus target proteins or antigens of interest. In this regard, the vectors can contain nucleic acid encoding 1 to 4 or more different target antigens of interest. The target antigens can be a full length protein or can be a fragment (e.g., an epitope) thereof. The adenovirus vectors can contain nucleic acid sequences encoding multiple fragments or epitopes from one target protein of interest or can contain one or more fragments or epitopes from numerous different target alphavirus antigen proteins of interest.

In some aspects, the nucleic acid sequences encode a plurality of alphavirus target antigens. The nucleic acid sequence encoding the plurality of alphavirus target antigens can comprise a plurality of gene inserts each corresponding to a target antigen and wherein each gene insert is separated by a nucleic acid sequence encoding a self-cleaving 2A peptide. In some aspects, the self-cleaving 2A peptide (i.e., the cleavable linker) is derived from *Porcine teschovirus*-1 or *Thosea asigna* virus or the like.

Examples of cleavable linkers can include 2A linkers (e.g., T2A), 2A-like linkers, or functional equivalents thereof and combinations thereof. In some embodiments, the linkers include the picornaviral 2A-like linker, CHYSEL sequences of *Porcine teschovirus* (P2A), *Thosea asigna* virus (T2A) or combinations, variants and functional equivalents thereof.

In certain embodiments, immunogenic fragments bind to an MHC class I or class II molecule. As used herein, an immunogenic fragment can "bind to" an MHC class I or class II molecule if such binding is detectable using any assay known in the art. For example, the ability of a polypeptide to bind to MHC class I can be evaluated indirectly by monitoring the ability to promote incorporation of $^{125}I$ labeled 32-microglobulin (02m) into MHC class V/32m/peptide heterotrimeric complexes (see Parker et al., J. Immunol. 752:163, 1994). Alternatively, functional peptide competition assays that are known in the art can be employed. Immunogenic fragments of polypeptides can generally be identified using well known techniques, such as those summarized in Paul, Fundamental Immunology, $3^{rd}$ ed., 243-247 (Raven Press, 1993) and references cited therein. Representative techniques for identifying immunogenic fragments can include screening polypeptides for the ability to react with antigen-specific antisera and/or T-cell lines or clones. An immunogenic fragment of a particular target polypeptide can be a fragment that can react with such antisera and/or T-cells at a level that is not substantially less than the reactivity of the full length target polypeptide (e.g., in an ELISA and/or T-cell reactivity assay). In other words, an immunogenic fragment can react within such assays at a level that is similar to or greater than the reactivity of the full length polypeptide. Such screens can generally be performed using methods well known to those of ordinary skill in the art, such as those described in Harlow and Lane, Antibodies: A Laboratory Manual, Cold Spring Harbor Laboratory, 1988.

Target antigens can include but are not limited to antigens derived from any of the alphaviruses. Target antigens can include proteins produced by any of the infectious alphaviruses described herein, such as, C, $E3_{ALPHA}$, $E2_{ALPHA}$, 6K, $E1_{ALPHA}$, nsP1, nsP2, nsP3, and nsP4. As used herein, an "infectious agent" can be any species capable of infecting a host. Infectious agents can include, for example, any virus within the alphavirus genus.

The adenovirus vector can also include nucleic acid sequences that encode proteins that increase the immunogenicity of the target antigen. In this regard, the protein produced following immunization with the adenovirus vector containing such a protein can be a fusion protein comprising the target antigen of interest fused to a protein that increases the immunogenicity of the target antigen of interest.

IV. Combination Therapies

Certain embodiments provide a combination immunotherapy and vaccine composition for the treatment and prevention infectious diseases. Some embodiments provide combination multi-targeted vaccines, immunotherapies, and methods for enhanced therapeutic response to complex diseases such as infectious diseases. Each component of the combination therapy can be independently included in a vaccine composition for prevention of Chikungunya infection or infection by any alphavirus.

"Treatment" can refer to administration of a therapeutically effective dose of a vaccine of this disclosure to a subject. The treatment can be administered in a pharmaceutical composition to a subject. The subject can also be healthy and disease free at the time of treatment and, in this case, the treatment can be referred to as a preventative vaccination. The subject can be suffering from a disease condition at the time of treatment and, in this case, the treatment can be referred to as therapeutic vaccination.

A "subject" can refer to any animal, including, but not limited to, humans, non-human primates (e.g., rhesus or other types of macaques), mice, pigs, horses, donkeys, cows, sheep, rats and fowls. A "subject" can be used herein interchangeably with "individual" or "patient."

In some aspects, the vector comprises at least one antigen. In some aspects, the vector comprises at least two antigens. In some aspects, the vaccine formulation comprises 1:1 ratio of vector to antigen. In some aspects, the vaccine comprises 1:2 ratio of vector to antigen. In some aspects, the vaccine comprises 1:3 ratio of vector to antigen. In some aspects, the vaccine comprises 1:4 ratio of vector to antigen. In some aspects, the vaccine comprises 1:5 ratio of vector to antigen. In some aspects, the vaccine comprises 1:6 ratio of vector to antigen. In some aspects, the vaccine comprises 1:7 ratio of vector to antigen. In some aspects, the vaccine comprises 1:8 ratio of vector to antigen. In some aspects, the vaccine comprises 1:9 ratio of vector to antigen. In some aspects, the vaccine comprises 1:10 ratio of vector to antigen.

In some aspects, the vaccine is a combination vaccine, wherein the vaccine comprises at least two vectors each containing at least a single antigen.

When a mixture of different antigens are simultaneously administered or expressed from a same or different vector in a subject, they can compete with one another. As a result the formulations comprising different concentration and ratios of expressed antigens in a combination immunotherapy or vaccine must be evaluated and tailored to the subject or group of subjects to ensure that effective and sustained immune responses occur after administration.

Composition that comprises multiple antigens can be present at various ratios. For example, formulations with more than one vector can have various ratios. For example, immunotherapies or vaccines can have two different vectors in a stoichiometry of 1:1, 1:2, 1:3, 1:4, 1:5, 1:6, 1:7, 1:8, 1:9, 1:10, 1:15, 1:20, 1:30, 2:1, 2:3, 2:4, 2:5, 2:6, 2:7, 2:8, 3:1, 3:3, 3:4, 3:5, 3:6, 3:7, 3:8, 3:1, 3:3, 3:4, 3:5, 3:6, 3:7, 3:8, 4:1, 4:3, 4:5, 4:6, 4:7, 4:8, 5:1, 5:3, 5:4, 5:6, 5:7, 5:8, 6:1, 6:3, 6:4, 6:5, 6:7, 6:8, 7:1, 7:3, 7:4, 7:5, 7:6, 7:8, 8:1, 8:3, 8:4, 8:5, 8:6, or 8:7.

In some embodiments, at least one of the recombinant nucleic acid vectors is a replication defective virus vector that comprises a replication defective adenovirus 5 vector comprising a first identity value. In some embodiments, the replication defective adenovirus vector comprises a deletion in the E2b gene region. In some embodiments, the replication defective adenovirus vector further comprises a deletion in the E1 gene region. In some embodiments, the replication defective adenovirus vector comprises a deletion in an E1 gene region, and E2b gene region, an E3 gene region, an E4 gene region, or any combination thereof.

Specific therapies that can be used in combination with any Ad5 [E1-, E2b-] vaccine of the present disclosure are described in further detail below.

A. Costimulatory Molecules

In addition to the use of a recombinant adenovirus-based vector vaccine containing target antigens such as alphavirus target antigens, particularly Chikungunya antigens, co-stimulatory molecules can be incorporated into said the vaccine to increase immunogenicity.

Initiation of an immune response can require at least two signals for the activation of I T cells by APCs (Damle, et al. J Immunol 148:1985-92 (1992); Guinan, et al. Blood 84:3261-82 (1994); Hellstrom, et al. Cancer Chemother Pharmacol 38:S40-44 (1996); Hodge, et al. Cancer Res 39:5800-07 (1999). An antigen specific first signal can be delivered through the T cell receptor (TCR) via the peptide/major histocompatibility complex (MHC) and can cause the T cell to enter the cell cycle. A second, or costimulatory, signal can be delivered for cytokine production and proliferation.

At least three distinct molecules normally found on the surface of professional antigen presenting cells (APCs) can be capable of providing the second signal critical for T cell activation: B7-1 (CD80), ICAM-1 (CD54), and LFA-3 (human CD58) (Damle, et al. J Immunol 148:1985-92 (1992); Guinan, et al. Blood 84: 3261-82 (1994); Wingren, et al. Crit Rev Immunol 15: 235-53 (1995); Parra, et al. Scand. J Immunol 38: 508-14 (1993); Hellstrom, et al. Ann NY Acad Sci 690: 225-30 (1993); Parra, et al. J Immunol 158: 637-42 (1997); Sperling, et al. J Immunol 157: 3909-17 (1996); Dubey, et al. J Immunol 155: 45-57 (1995); Cavallo, et al. Eur J Immunol 25: 1154-62 (1995).

These costimulatory molecules can have distinct T cell ligands. B7-1 can interact with the CD28 and CTLA-4 molecules, ICAM-1 can interact with the CD11a/CD18 (LFA-1/beta-2 integrin) complex, and LFA-3 can interact with the CD2 (LFA-2) molecules. Therefore, in a certain embodiment, it would be desirable to have a recombinant adenovirus vector that contains B7-1, ICAM-1, and LFA-3, respectively, that, when combined with a recombinant adenovirus-based vector vaccine containing one or more nucleic acids encoding target antigens such as alphavirus antigens, can further increase/enhance anti-alphavirus immune responses directed to specific target antigens.

V. Immunological Fusion Partners

The viral vector or composition described herein can further comprise nucleic acid sequences that encode proteins, or an "immunological fusion partner," that can increase the immunogenicity of the target antigen such as Chikungunya virus antigens, or any target antigen of the present disclosure. In this regard, the protein produced following immunization with the viral vector containing such a protein can be a fusion protein comprising the target antigen of interest fused to a protein that increases the immunogenicity of the target antigen of interest. Furthermore, combination therapy with Ad5[E1-, E2b-] vectors encoding for a Chikungunya virus antigen and an immunological fusion partner can result in boosting the immune response, such that the combination of both therapeutic moieties acts to synergistically boost the immune response more than either the Ad5[E1-, E2b-] vector encoding for a Chikungunya virus antigen alone, or the immunological fusion partner alone. For example, combination therapy with an Ad5[E1-, E2b-] vector encoding for a Chikungunya virus antigen and an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with an Ad5[E1-, E2b-] vector encoding for a Chikungunya virus antigen and an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5[E1-, E2b-] vector encoding for a Chikungunya virus antigen and an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the Ad5[E1-, E2b-] vectors encoding for a Chikungunya virus antigen and an immunological fusion partner as described herein as compared to an appropriate control. In another embodiment, generating an immune response comprises an increase in target-specific antibody production of about 1.5 to 20, or more fold in a subject administered the adenovirus vector as compared to a control.

As an additional example, combination therapy with an Ad5[E1-, E2b-] vector encoding for target epitope antigens and an immunological fusion partner can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), antibody dependent cellular phagocytosis (ADCP) mechanisms, or any combination thereof. This synergistic boost can vastly improve survival outcomes after administration to a subject in need thereof. In certain embodiments, combination therapy with Ad5[E1-, E2b-] vectors encoding for a target epitope antigen and an immunological fusion partner can result in generating an immune response comprises an increase in target antigen-specific CTL activity of about 1.5 to 20, or more fold in a subject administered the adenovirus vectors as compared to a control. In another embodiment, generating an immune response comprises an increase in target-specific CTL activity of about 1.5 to 20, or more fold in a subject administered the Ad5[E1-, E2b-] vector encoding for target epitope antigen and an immunological fusion partner as compared to a control. In a further embodiment, generating an immune response that comprises an increase in target antigen-specific cell-mediated immunity activity as measured by ELISpot assays measuring cytokine secretion, such as interferon-gamma (IFN-γ), interleukin-2 (IL-2), tumor necrosis factor-alpha (TNF-α), or other cytokines, of about 1.5 to 20, or more fold as compared to a control. In a further embodiment, generating an immune response comprises an increase in target-specific antibody production of between 1.5 and 5 fold in a subject administered the adenovirus vectors as described herein as compared to an appropriate control. In another embodiment, generating an immune response comprises an increase in target-specific antibody production of about 1.5 to 20, or more fold in a subject administered the adenovirus vector as compared to a control.

In one embodiment, such an immunological fusion partner is derived from a *Mycobacterium* sp., such as a *Mycobacterium tuberculosis*-derived Ra12 fragment. The immunological fusion partner derived from *Mycobacterium* sp. can be any one of the sequences set forth in SEQ ID NO: 22-SEQ ID NO: 30 and SEQ ID NO: 93-SEQ ID NO: 98. Oligonucleotides, Met-His tags, and enterokinase recognition sites, which can be used to construct these *Mycobacterium* sp.-derived Ra12 sequences are set forth in any one of SEQ ID NO: 99-SEQ ID NO: 106 as shown in TABLE 2. Ra12 compositions and methods for their use in enhancing the expression and/or immunogenicity of heterologous polynucleotide/polypeptide sequences are described in U.S. Pat. No. 7,009,042, which is herein incorporated by reference in its entirety. Briefly, Ra12 refers to a polynucleotide region that is a subsequence of a *Mycobacterium tuberculosis* MTB32A nucleic acid. MTB32A is a serine protease of 32 kDa encoded by a gene in virulent and avirulent strains of *M. tuberculosis*. The nucleotide sequence and amino acid sequence of MTB32A have been described (see, e.g., U.S. Pat. No. 7,009,042; Skeiky et al., Infection and Immun. 67:3998-4007 (1999), incorporated herein by reference in their entirety). C-terminal fragments of the MTB32A coding sequence can be expressed at high levels and remain as soluble polypeptides throughout the purification process. Moreover, Ra12 can enhance the immunogenicity of heterologous immunogenic polypeptides with which it is fused. A Ra12 fusion polypeptide can comprise a 14 kDa C-terminal fragment corresponding to amino acid residues 192 to 323 of MTB32A. Other Ra12 polynucleotides generally can comprise at least about 15, 30, 60, 100, 200, 300, or more nucleotides that encode a portion of a Ra12 polypeptide. Ra12 polynucleotides can comprise a native sequence (i.e., an endogenous sequence that encodes a Ra12 polypeptide or a portion thereof) or can comprise a variant of such a sequence. Ra12 polynucleotide variants can contain one or more substitutions, additions, deletions and/or insertions such that the biological activity of the encoded fusion polypeptide is not substantially diminished, relative to a fusion polypeptide comprising a native Ra12 polypeptide. Variants can have at least about 70%, 80%, or 90% identity, or more, to a polynucleotide sequence that encodes a native Ra12 polypeptide or a portion thereof.

In certain aspects, an immunological fusion partner can be derived from protein D, a surface protein of the gram-negative bacterium *Haemophilus* 34ittered34 B. The immunological fusion partner derived from protein D can be the sequence set forth in SEQ ID NO: 31. In some cases, a protein D derivative comprises approximately the first third of the protein (e.g., the first N-terminal 100-110 amino acids). A protein D derivative can be 34ittered34. Within certain embodiments, the first 109 residues of a Lipoprotein D fusion partner is included on the N-terminus to provide the polypeptide with additional exogenous T-cell epitopes, which can increase the expression level in *E. coli* and can function as an expression enhancer. The lipid tail can ensure optimal presentation of the antigen to antigen presenting cells. Other fusion partners can include the non-structural protein from influenza virus, NS1 (hemagglutinin). Typically, the N-terminal 81 amino acids are used, although different fragments that include T-helper epitopes can be used.

In certain aspects, the immunological fusion partner can be the protein known as LYTA, or a portion thereof (particularly a C-terminal portion). The immunological fusion partner derived from LYTA can the sequence set forth in SEQ ID NO: 32. LYTA is derived from *Streptococcus pneumoniae*, which synthesizes an N-acetyl-L-alanine amidase known as amidase LYTA (encoded by the LytA gene). LYTA is an autolysin that specifically degrades certain bonds in the peptidoglycan backbone. The C-terminal domain of the LYTA protein can be responsible for the affinity to the choline or to some choline analogues such as DEAE. This property can be exploited for the development of *E. coli* C-LYTA expressing plasmids useful for expression of fusion proteins. Purification of hybrid proteins containing the C-LYTA fragment at the amino terminus can be employed. Within another embodiment, a repeat portion of LYTA can be incorporated into a fusion polypeptide. A repeat portion can, for example, be found in the C-terminal region starting at residue 178. One particular repeat portion can incorporate residues 188-305.

In some embodiments, the target antigen is fused to an immunological fusion partner, which can also be referred to herein as an "immunogenic component," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can produce a protein with substantial identity to one or more of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The target antigen fusion can encode a nucleic acid encoding a protein with substantial identity to one or more of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-3, IL-1α, IL-β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen fusion further comprises one or more immunological fusion partner, which can also be referred to herein as an "immunogenic components," comprising a cytokine selected from the group of IFN-γ, TNFα, IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. The sequence of IFN-γ can be, but is not limited to, a sequence as set forth in SEQ ID NO: 33. The sequence of TNFα can be, but is not limited to, a sequence as set forth in SEQ ID NO: 34. The sequence of IL-2 can be, but is not limited to, a sequence as set forth in SEQ ID NO: 35. The sequence of IL-8 can be, but is not limited to, a sequence as set forth in SEQ ID NO: 36. The sequence of IL-12 can be, but is not limited to, a sequence as set forth in SEQ ID NO: 37. The sequence of IL-18 can be, but is not limited to, a sequence as set forth in SEQ ID NO: 38. The sequence of IL-7 can be, but is not limited to, a sequence as set forth in SEQ ID NO: 39. The sequence of IL-3 can be, but is not limited to, a sequence as set forth in SEQ ID NO: 40. The sequence of IL-4 can be, but is not limited to, a sequence as set forth in SEQ ID NO: 41. The sequence of IL-5 can be, but is not limited to, a sequence as set forth in SEQ ID NO: 42. The sequence of IL-6 can be, but is not limited to, a sequence as set forth in SEQ ID NO: 43. The sequence of IL-9 can be, but is not limited to, a sequence as set forth in SEQ ID NO: 44. The sequence of IL-10 can be, but is not limited to, a sequence as set forth in SEQ ID NO: 45. The sequence of IL-13 can be, but is not limited to, a sequence as set forth in SEQ ID NO: 46. The sequence of IL-15 can be, but is not limited to, a sequence as set forth in SEQ ID NO: 47. The sequence of IL-16 can be, but is not limited to, a sequence as set forth in SEQ ID NO: 74. The sequence of IL-17 can be, but is not limited to, a sequence as set forth in SEQ ID NO: 75. The sequence of IL-23 can be, but is not limited to, a sequence as set forth in SEQ ID NO: 76. The sequence of IL-32 can be, but is not limited to, a sequence as set forth in SEQ ID NO: 77.

In some embodiments, the target antigen is fused or linked to an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β3, IL-1α, IL-β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF. In some embodiments, the target antigen is co-expressed in a cell with an immunological fusion partner, also referred to herein as an "immunogenic component," comprising a cytokine selected from the group of IFN-γ, TNFα IL-2, IL-8, IL-12, IL-18, IL-7, IL-3, IL-4, IL-5, IL-6, IL-9, IL-10, IL-13, IL-15, IL-16, IL-17, IL-23, IL-32, M-CSF (CSF-1), IFN-α, IFN-β, IL-1α, IL-1β, IL-1RA, IL-11, IL-17A, IL-17F, IL-19, IL-20, IL-21, IL-22, IL-24, IL-25, IL-26, IL-27, IL-28A, B, IL-29, IL-30, IL-31, IL-33, IL-34, IL-35, IL-36α,β,λ, IL-36Ra, IL-37, TSLP, LIF, OSM, LT-α, LT-β, CD40 ligand, Fas ligand, CD27 ligand, CD30 ligand, 4-1BBL, Trail, OPG-L, APRIL, LIGHT, TWEAK, BAFF, TGF-β1, and MIF.

In some embodiments, the target antigen is fused or linked to an immunological fusion partner, comprising CpG ODN (e.g., Class A, B, or C CpG ODNs; non-limiting examples sequences are shown in SEQ ID NO: 108-SEQ ID NO: 119 in which phosphodiester bases are in capital letters, phosphorothioate bases are in lower case letters, and palindromes are underlined and the colon denotes the reflection point), cholera toxin (a non-limiting example sequence is shown in SEQ ID NO: 49), a truncated A subunit coding region derived from a bacterial ADP-ribosylating exotoxin (a non-limiting example sequence is shown in (a non-limiting example sequence is shown in SEQ ID NO: 50), a truncated B subunit coding region derived from a bacterial ADP-ribosylating exotoxin (a non-limiting example sequence is shown in SEQ ID NO: 51), Hp91 (a non-limiting example sequence is shown in SEQ ID NO: 52), CCL20 (a non-limiting example sequence is shown in SEQ ID NO: 53 and SEQ ID NO: 107), CCL3 (a non-limiting example sequence is shown in SEQ ID NO: 54), GM-CSF (a non-limiting example sequence is shown in SEQ ID NO: 55), G-CSF (a non-limiting example sequence is shown in SEQ ID NO: 56), LPS peptide mimic (non-limiting example sequences are shown in SEQ ID NO: 57-SEQ ID NO: 68), shiga toxin (a non-limiting example sequence is shown in SEQ ID NO: 69), diphtheria toxin (a non-limiting example sequence is shown in SEQ ID NO: 70), or $CRM_{197}$ (a non-limiting example sequence is shown in SEQ ID NO: 73).

In some embodiments, the target antigen is fused or linked to an immunological fusion partner, comprising an IL-15 superagonist. Interleukin 15 (IL-15) is a naturally occurring inflammatory cytokine secreted after viral infections. Secreted IL-15 can carry out its function by signaling via its cognate receptor on effector immune cells, and thus, can lead to overall enhancement of effector immune cell activity.

Based on IL-15's broad ability to stimulate and maintain cellular immune responses, it is believed to be a promising immunotherapeutic drug. However, major limitations in clinical development of IL-15 can include low production yields in standard mammalian cell expression systems and short serum half-life. Moreover, the IL-15:IL-15Rα complex, comprising proteins co-expressed by the same cell, rather than the free IL-15 cytokine, can be responsible for stimulating immune effector cells bearing IL-15 βγc receptor.

To contend with these shortcomings, a novel IL-15 super-agonist mutant (IL-15N72D) was identified that has increased ability to bind IL-15Rβγc and enhanced biological activity. Addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/Fc super-agonist complex exhibits a median effective concentration (EC50) for supporting IL-15-dependent cell growth that was greater than 10-fold lower than that of free IL-15 cytokine.

In some embodiments, the IL-15 superagonist can be a novel IL-15 superagonist mutant (IL-15N72D). In certain embodiments, addition of either mouse or human IL-15Rα and Fc fusion protein (the Fc region of immunoglobulin) to equal molar concentrations of IL-15N72D can provide a further increase in IL-15 biologic activity, such that IL-15N72D:IL-15Rα/Fc super-agonist complex exhibits a median effective concentration ($EC_{50}$) for supporting IL-15- dependent cell growth that can be greater than 10-fold lower than that of free IL-15 cytokine Thus, in some embodiments, the present disclosure provides a IL-15N72D:IL-15Rα/Fc super-agonist complex with an EC50 for supporting IL-15-dependent cell growth that is greater than 2-fold lower, greater than 3-fold lower, greater than 4-fold lower, greater than 5-fold lower, greater than 6-fold lower, greater than 7-fold lower, greater than 8-fold lower, greater than 9-fold lower, greater than 10-fold lower, greater than 15-fold lower, greater than 20-fold lower, greater than 25-fold lower, greater than 30-fold lower, greater than 35-fold lower, greater than 40-fold lower, greater than 45-fold lower, greater than 50-fold lower, greater than 55-fold lower, greater than 60-fold lower, greater than 65-fold lower, greater than 70-fold lower, greater than 75-fold lower, greater than 80-fold lower, greater than 85-fold lower, greater than 90-fold lower, greater than 95-fold lower, or greater than 100-fold lower than that of free IL-15 cytokine.

In some embodiments, the IL-15 super agonist is a biologically active protein complex of two IL-15N72D molecules and a dimer of soluble IL-15Rα/Fc fusion protein, also known as ALT-803. The composition of ALT-803 and methods of producing and using ALT-803 are described in U.S. Patent Application Publication 2015/0374790, which is herein incorporated by reference. It is known that a soluble IL-15Rα fragment, containing the so-called "sushi" domain at the N terminus (Su), can bear most of the structural elements responsible for high affinity cytokine binding. A soluble fusion protein can be generated by linking the human IL-15RαSu domain (amino acids 1-65 of the mature human IL-15Rα protein) with the human IgG1 CH2-CH3 region containing the Fc domain (232 amino acids). This IL-15RSu/IgG 1 Fc fusion protein can have the advantages of dimer formation through disulfide bonding via IgG1 domains and ease of purification using standard Protein A affinity chromatography methods.

In some embodiments, ALT-803 can have a soluble complex consisting of 2 protein subunits of a human IL-15 variant associated with high affinity to a dimeric IL-15Rα sushi domain/human IgG1 Fc fusion protein. The IL-15 variant is a 114 amino acid polypeptide comprising the mature human IL-15 cytokine sequence with an Asn to Asp substitution at position 72 of helix C N72D). The human IL-15R sushi domain/human IgG1 Fc fusion protein comprises the sushi domain of the IL-15R subunit (amino acids 1-65 of the mature human IL-15Rα protein) linked with the human IgG1 CH2-CH3 region containing the Fc domain (232 amino acids). Aside from the N72D substitution, all of the protein sequences are human. Based on the amino acid sequence of the subunits, the calculated molecular weight of the complex comprising two IL-15N72D polypeptides (an example IL-15N72D sequence is shown in SEQ ID NO: 71) and a disulfide linked homodimeric IL-15RαSu/IgG1 Fc protein (an example IL-15RαSu/Fc domain is shown in SEQ ID NO: 72) is 92.4 kDa. In some embodiments, a recombinant vector encoding for a target antigen and for ALT-803 can have any sequence described herein to encode for the target antigen and can have SEQ ID NO: 71, SEQ ID NO: 71, SEQ ID NO: 72, and SEQ ID NO: 72, in any order, to encode for ALT-803.

Each IL-15N720 polypeptide can have a calculated molecular weight of approximately 12.8 kDa and the IL-15RαSu/IgG 1 Fc fusion protein can have a calculated molecular weight of approximately 33.4 kDa. Both the IL-15N72D and IL-15RαSu/IgG 1 Fc proteins can be glycosylated resulting in an apparent molecular weight of ALT-803 of approximately 114 kDa by size exclusion chromatography. The isoelectric point (pI) determined for ALT-803 can range from approximately 5.6 to 6.5. Thus, the fusion protein can be negatively charged at pH 7.

Combination therapy with Ad5[E1-, E2b-] vectors encoding for a Chikungunya virus antigen and ALT-803 can result in boosting the immune response, such that the combination of both therapeutic moieties acts to synergistically boost the immune response more than either therapy alone. For example, combination therapy with an Ad5[E1-, E2b-] vector encoding for a Chikungunya virus antigen and ALT-803 can result in synergistic enhancement of stimulation of antigen-specific effector CD4+ and CD8+ T cells, stimulation of NK cell response directed towards killing infected cells, stimulation of neutrophils or monocyte cell responses directed towards killing infected cells via antibody dependent cell-mediated cytotoxicity (ADCC), or antibody dependent cellular phagocytosis (ADCP) mechanisms. Combination therapy with an Ad5[E1-, E2b-] vector encoding for a Chikungunya virus antigen and ALT-803 can synergistically boost any one of the above responses, or a combination of the above responses, to vastly improve survival outcomes after administration to a subject in need thereof.

Any of the immunogenicity enhancing agents described herein can be fused or linked to a target antigen by expressing the immunogenicity enhancing agents and the target antigen in the same recombinant vector, using any recombinant vector described herein.

Nucleic acid sequences that encode for such immunogenicity enhancing agents can be any one of SEQ ID NO: 22-SEQ ID NO: 47, SEQ ID NO: 49-SEQ ID NO: 77, and SEQ ID NO: 93-SEQ ID NO: 119 and are summarized in TABLE 1.

TABLE 1

Sequences of Immunological Fusion Partners

| SEQ ID NO | Sequence |
|---|---|
| SEQ ID NO: 22 | TAASDNFQLSQGGQGFAIPIGQAMAIAGQIRSGGGSPTVHIGPTAFLGL GVVDNNGNGARVQRVVGSAPAASLGISTGDVITAVDGAPINSATAM ADALNGHFPGDVISVTWQTKSGGTRTGNVTLAEGPPA |
| SEQ ID NO: 23 | MHHHHHHTAASDNFQLSQGGQGFAIPIGQAMAIAGQIRSGGGSPTVHI GPTAFLGLGVVDNNGNGARVQRVVGSAPAASLGISTGDVITAVDGAP INSATAMADALNGHRPGDVISVTWQTKSGGTRTGNVTLAEGPPAEFD DDDKDPPDPHQPDMTKGYCPGGRWGFGDLAVCDGEKYPDGSFWHQ WMQTWFTGPQFYFDCVSGGEPLPGPPPPGGCGGAIPSEQPNAP |
| SEQ ID NO: 24 | MHHHHHHTAASDNFQLSQGGQGFAIPIGQAMAIAGQIRSGGGSPTVHI GPTAFLGLGVVDNNGNGARVQRVVGSAPAASLGISTGDVITAVDGAP INSATAMADALNGHHPGDVISVTWQTKSGGTRTGNVTLAEGPPAEFP |

TABLE 1-continued Sequences of Immunological Fusion Partners

| SEQ ID NO | Sequence |
|---|---|
|  | LVPRGSPMGSDVRDLNALLPAVPSLGGGGGCALPVSGAAQWAPVLD<br>FAPPGASAYGSLGGPAPPPAPPPPPPPPPHSFIKQEPSWGGAEPHEEQC<br>LSAFTVHFSGQFTGTAGACRYGPFGPPPPSQASSGQARMFPNAPYLPS<br>CLESQPAIRNQGYSTVTFDGTPSYGHTPSHHAAQFPNHSFKHEDPMG<br>QQGSLGEQQYSVPPPVYGCHTPTDSCTGSQALLLRTPYSSDNLYQMT<br>SQLECMTWNQMNLGATLKGHSTGYESDNHTTPILCGAQYRIHTHGV<br>FRGIQDVRRVPGVAPTLVRSASETSEKRPFMCAYSGCNKRYFKLSHL<br>QMHSRKHTGEKPYQCDFKDCERRFFRSDQLKRHQRRHTGVKPFQCK<br>TCQRKFSRSDHLKTHTRTHTGEKPFSCRWPSCQKKFARSDELVRHHN<br>MHQRNMTKLQLAL |
| SEQ ID NO: 25 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEFI<br>EGRGSGCPLLENVISKTINPQVSKTEYKELLQEFIDDNATTNAIDELKE<br>CFLNQTDETLSNVEVFMQLIYDSSLCDLF |
| SEQ ID NO: 26 | MHHHHHHTAASDNFQLSQGGQGFAIPIGQAMAIAGQIRSGGGSPTVHI<br>GPTAFLGLGVVDNNGNGARVQRVVGSAPAASLGISTGDVITAVDGAP<br>INSATAMADALNGHHPGDVISVTWQTKSGGTRTGNVTLAEGPPAEF<br>MVDFGALPPEINSARMYAGPGSASLVAAAQMWDSVASDLFSAASAF<br>QSVVWGLTVGSWIGSSAGLMVAAASPYVAWMSVTAGQAELTAAQV<br>RVAAAAYETAYGLTVPPPVIAENRAELMILIATNLLGQNTPAIAVNEA<br>EYGEMWAQDAAAMFGYAAATATATATLLPFEEAPEMTSAGGLLEQ<br>AAAVEEASDTAAANQLMNNVPQALQQLAQPTQGTTPSSKLGGLWKT<br>VSPHRSPISNMVSMANNHMSMTNSGVSMTNTLSSMLKGFAPAAAAQ<br>AVQTAAQNGVRAMSSLGSSLGSSGLGGGVAANLGRAASVGSLSVPQ<br>AWAAANQAVTPAARALPLTSLTSAAERGPGQMLGGLPVGQMGARA<br>GGGLSGVLRVPPRPYVMPHSPAAGDIAPPALSQDRFADFPALPLDPSA<br>MVAQVGPQVVNINTKLGYNNAVGAGTGIVIDPNGVVLTNNHVIAGA<br>TDINAFSVGSGQTYGVDVVGYDRTQDVAVLQLRGAGGLPSAAIGGG<br>VAVGEPVVAMGNSGGQGGTPRAVPGRVVALGQTVQASDSLTGAEET<br>LNGLIQFDAAIQPGDSGGPVVNGLGQVVGMNTAAS |
| SEQ ID NO: 27 | TAASDNFQLSQGGQGFAIPIGQAMAIAGQI |
| SEQ ID NO: 28 | TAASDNFQLSQGGQGFAIPIGQAMAIAGQIKLPTVHIGPTAFLGLGVV<br>DNNGNGARVQRVVGSAPAASLGISTGDVITAVDGAPINSATAMADAL<br>NGHHPGDVISVTWQTKSGGTRTGNVTLAEGPPA |
| SEQ ID NO: 29 | TAASDNFQLSQGGQGFAIPIGQAMAIAGQIRSGGGSPTVHIGPTAFLGL<br>GVVDNNGNGARVQRVVGSAPAASLGISTGDVITAVDGAPINSATAM<br>ADALNGHHPGDVISVTWQTKSGGTRTGNVTLAE |
| SEQ ID NO: 30 | MSNSRRRSLRWSWLLSVLAAVGLGLATAPAQAAPPALSQDRFADFP<br>ALPLDPSAMVAQVGPQVVNINTKLGYNNAVGAGTGIVIDPNGVVLTN<br>NHVIAGATDINAFSVGSGQTYGVDVVGYDRTQDVAVLQLRGAGGLP<br>SAAIGGGVAVGEPVVAMGNSGGQGGTPRAVPGRVVALGQTVQASDS<br>LTGAEETLNGLIQFDAAIQPGDSGGPVVNGLGQVVGMNTAASDNFQL<br>SQGGQGFAIPIGQAMAIAGQIRSGGGSPTVHIGPTAFLGLGVVDNNGN<br>GARVQRVVGSAPAASLGISTGDVITAVDGAPINSATAMADALNGHHP<br>GDVISVTWQTKSGGTRTGNVTLAEGPPA |
| SEQ ID NO: 31 | MKLKTLALSLLAAGVLAGCSSHSSNMANTQMKSDKIIIAHRGASYL<br>PEHTLESKALAFAQQADYLEQDLAMTKDGRLVVIHDHELDGLTDVA<br>KKFPHRHRKDGRYYVIDFTLKEIQSLEMTENFETKDGKQAVYPNRF<br>PLWKSHFRIHTFEDEIEFIQGLEKSTGKKVGIYPEIKAPWFHHQNGKDI<br>AAETLKVLKKYGYDKKTDMVYLQTFDFNELKRIKTELLPQMGMDLK<br>LVQLIAYTDWKETQEKDPKGYWVNYNYDWMFKPGAMAEVVKYAD<br>GVGPGWYMLVNKEESKPDNIVYTPLVKELAQYNVEVHPYTVRKDAL<br>PAFFTDVNQMYDVLLNKSGATGVFTDFPDTGVEFLKGIK |
| SEQ ID NO: 32 | MEINVSKLRTDLPQVGVQPYRQVHAHSTGNPHSTVQNEADYHWRKD<br>PELGFFSHIVGNGCIMQVGPVDNGAWDVGGGWNAETYAAVELIESH<br>STKEEFMTDYRLYIELLRNLADEAGLPKTLDTGSLAGIKTHEYCTNNQ<br>PNNHSDHVDPYPYLAKWGISREQFKHDIENGLTIETGWQKNDTGYW<br>YVHSDGSYPKDKFEKINGTWYYFDSSGYMLADRWRKHTDGNWYWF<br>DNSGEMATGWKIGADKWYYFNEEGAMKTGWVKYKDTWYYLDAK<br>EGAMVSNAFIQSADGTGWYYLKPDGTLADRPEFRMSQMA |
| SEQ ID NO: 33 | MKYTSYILAFQLCIVLGSLGCYCQDPYVKEAENLKKYFNAGHSDVAD<br>NGTLFLGILKNWKEESDRKIMQSQIVSFYFKLFKNFKDDQSIQKSVETI<br>KEDMNVKFFNSNKKKRDDFEKLTNYSVTDLNVQRKAIHELIQVMAE<br>LSPAAKTGKRKRSQMLFRGRRASQ |

TABLE 1-continued

Sequences of Immunological Fusion Partners

| SEQ ID NO | Sequence |
|---|---|
| SEQ ID NO: 34 | MSTESMIRDVELAEEALPKKTGGPQGSRRCLFLSLFSFLIVAGATTLFC<br>LLHEGVIGPQREEFPRDLSLISPLAQAVRSSSRTPSDKPVAHVVANPQA<br>EGQLQWLNRRANALLANGVELRDNQLVVPSEGLYLIYSQVLFKGQG<br>CPSTHVLLTHTISRIAVSYQTKVNLLSAIKSPCQRETPEGAEAKPWYEP<br>IYLGGVFQLEKGDRLSAEINRPDYLDFAESGQVYFGIIAL |
| SEQ ID NO: 35 | MYRMQLLSCIALSLALVTNSAPTSSSTKKTQLQLEHLLLDLQMILNGI<br>NNYKNPKLTRMLTFKFYMPKKATELKHLQCLEEELKPLEEVLNLAQS<br>KNFHLRPRDLISNINVIVLELKGSETTFMCEYADETATIVEFLNRWITF<br>CQSIISTLT |
| SEQ ID NO: 36 | MTSKLAVALLAAFLISAALCEGAVLPRSAKELRCQCIKTYSKPFHPKFI<br>KELRVIESGPHCANTEIIVKLSDGRELCLDPKENWVQRVVEKFLKRAE<br>NS |
| SEQ ID NO: 37 | MEPLVTWVVPLLFLFLLSRQGAACRTSECCFQDPPYPDADSGSASGPR<br>DLRCYRISSDRYECSWQYEGPTAGVSHFLRCCLSSGRCCYFAAGSAT<br>RLQFSDQAGVSVLYTVTLWVESWARNQTEKSPEVTLQLYNSVKYEPP<br>LGDIKVSKLAGQLRMEWETPDNQVGAEVQFRHRTPSSPWKLGDCGP<br>QDDDTESCLCPLEMNVAQEFQLRRRQLGSQGSSWSKWSSPVCVPPEN<br>PPQPQVRFSVEQLGQDGRRRLTLKEQPTQLELPEGCQGLAPGTEVTYR<br>LQLHMLSCPCKAKATRTLHLGKMPYLSGAAYNVAVISSNQFGPGLN<br>QTWHIPADTHTEPVALNISVGTNGTTMYWPARAQSMTYCIEWQPVG<br>QDGGLATCSLTAPQDPDPAGMATYSWSRESGAMGQEKCYYITIFASA<br>HPEKLTLWSTVLSTYHFGGNASAAGTPHHVSVKNHSLDSVSVDWAP<br>SLLSTCPGVLKEYVVRCRDEDSKQVSEHPVQPTETQVTLSGLRAGVA<br>YTVQVRADTAWLRGVWSQPQRFSIEVQVSDWLIFFASLGSFLSILLVG<br>VLGYLGLNRAARHLCPPLPTPCASSAIEFPGGKETWQWINPVDFQEEA<br>SLQEALVVEMSWDKGERTEPLEKTELPEGAPELALDTELSLEDGDRC<br>KAKM |
| SEQ ID NO: 38 | MAAEPVEDNCINFVAMKFIDNTLYFIAEDDENLESDYFGKLESKLSVI<br>RNLNDQVLFIDQGNRPLFEDMTDSDCRDNAPRTIFIISMYKDSQPRGM<br>AVTISVKCEKISTLSCENKIISFKEMNPPDNIKDTKSDIIFFQRSVPGHDN<br>KMQFESSSYEGYFLACEKERDLFKLILKKEDELGDRSIMFTVQNED |
| SEQ ID NO: 39 | MFHVSFRYIFGLPPLILVLLPVASSDCDIEGKDGKQYESVLMVSIDQLL<br>DSMKEIGSNCLNNEFNFFKRHICDANKEGMFLFRAARKLRQFLKMNS<br>TGDFDLHLLKVSEGTTILLNCTGQVKGRKPAALGEAQPTKSLEENKSL<br>KEQKKLNDLCFLKRLLQEIKTCWNKILMGTKEH |
| SEQ ID NO: 40 | MSRLPVLLLLQLLVRPGLQAPMTQTTSLKTSWVNCSNMIDEIITHLKQ<br>PPLPLLDFNNLNGEDQDILMENNLRRPNLEAFNRAVKSLQNASAIESIL<br>KNLLPCLPLATAAPTRHPIHIKDGDWNEFRRKLTFYLKTLENAQAQQT<br>TLSLAIF |
| SEQ ID NO: 41 | MGLTSQLLPPLFFLLACAGNFVHGHKCDITLQEIIKTLNSLTEQKTLCT<br>ELTVTDIFAASKNTTEKETFCRAATVLRQFYSHHEKDTRCLGATAQQF<br>HRHKQLIRFLKRLDRNLWGLAGLNSCPVKEANQSTLENFLERLKTIM<br>REKYSKCSS |
| SEQ ID NO: 42 | MRMLLHLSLLALGAAYVYAIPTEIPTSALVKETLALLSTHRTLLIANET<br>LRIPVPVHKNHQLCTEEIFQGIGTLESQTVQGGTVERLFKNLSLIKKYI<br>DGQKKKCGEERRRVNQFLDYLQEFLGVMNTEWIIES |
| SEQ ID NO: 43 | MNSFSTSAFGPVAFSLGLLLVLPAAFPAPVPPGEDSKDVAAPHRQPLT<br>SSERIDKQIRYILDGISALRKETCNKSNMCESSKEALAENNLNLPKMA<br>EKDGCFQSGFNEETCLVKIITGLLEFEVYLEYLQNRFESSEEQARAVQ<br>MSTKVLIQFLQKKAKNLDAITTPDPTTNASLLTKLQAQNQWLQDMTT<br>HLILRSFKEFLQSSLRALRQM |
| SEQ ID NO: 44 | MVLTSALLLCSVAGQGCPTLAGILDINFLINKMQEDPASKCHCSANVT<br>SCLCLGIPSDNCTRPCFSERLSQMTNTTMQTRYPLIFSRVKKSVEVLKN<br>NKCPYFSCEQPCNQTTAGNALTFLKSLLEIFQKEKMRGMRGKI |
| SEQ ID NO: 45 | MHSSALLCCLVLLTGVRASPGQGTQSENSCTHFPGNLPNMLRDLRDA<br>FSRVKTFFQMKDQLDNLLLKESLLEDFKGYLGCQALSEMIQFYLEEV<br>MPQAENQDPDIKAHVNSLGENLKTLRLRLRRCHRFLPCENKSKAVEQ<br>VKNAFNKLQEKGIYKAMSEFDIFINYIEAYMTKIRN |
| SEQ ID NO: 46 | MALLLTTVIALTCLGGFASPGPVPPSTALRELIEELVNITQNQKAPLCN<br>GSMVWSINLTAGMYCAALESLINVSGCSAIEKTQRMLSGFCPHKVSA<br>GQFSSLHVRDTKIEVAQFVKDLLLHLKKLFREGQFNRNFESIIICRDRT |

TABLE 1-continued

Sequences of Immunological Fusion Partners

| SEQ ID NO | Sequence |
| --- | --- |
| SEQ ID NO: 47 | MDFQVQIFSFLLISASVIMSRANWVNVISDLKKIEDLIQSMHIDATLYT<br>ESDVHPSCKVTAMKCFLLELQVISLESGDASIHDTVENLIILANNSLSS<br>NGNVTESGCKECEELEEKNIKEFLQSFVHIVQMFINTS |
| SEQ ID NO: 49 | MIKLKFGVFFTVLLSSAYAHGTPQNITDLCAEYHNTQIYTLNDKIFSYT<br>ESLAGKREMAIITFKNGAIFQVEVPGSQHIDSQKKAIERMKDTLRIAYL<br>TEAKVEKLCVWNNKTPHAIAAISMAN |
| SEQ ID NO: 50 | MVKIIFVFFIFLSSFSYANDDKLYRADSRPPDEIKQSGGLMPRGQNEYF<br>DRGTQMNINLYDHARGTQTGFVRHDDGYVSTSISLRSAHLVGQTILS<br>GHSTYYTYVIATAPNMFVNDVLGAYSPHPDEQEVSALGGIPYSQIYG<br>WYRVHFGVLDEQLHRNRGYRDRYYSNLDIAPAADGYGLAGFPPEHR<br>AWREEPWIHHAPPGCGNAPRSSMSNTCDEKTQSLGVKFLDEYQSKV<br>KRQIFSGYQSDIDTHNRIKDEL |
| SEQ ID NO: 51 | MIKLKFGVFFTVLLSSAYAHGTPQNITDLCAEYHNTQIHTLNDKILSYT<br>ESLAGNREMAIITFKNGATFQVEVPGSQHIDSQKKAIERMKDTLRIAY<br>LTEAKVEKLCVWNNKTPHAIAAISMAN |
| SEQ ID NO: 52 | DPNAPKRPPSAFFLFCSE |
| SEQ ID NO: 53 | MCCTKSLLLAALMSVLLLHLCGESEAASNFDCCLGYTDRILHPKFIVG<br>FTRQLANEGCDINAIIFHTKKKLSVCANPKQTWVKYIVRLLSKKVKN<br>M |
| SEQ ID NO: 54 | MQVSTAALAVLLCTMALCNQFSASLAADTPTACCFSYTSRQIPQNFIA<br>DYFETSSQCSKPGVIFLTKRSRQVCADPSEEWVQKYVSDLELSA |
| SEQ ID NO: 55 | MWLQSLLLLGTVACSISAPARSPSPSTQPWEHVNAIQEARRLLNLSRD<br>TAAEMNETVEVISEMFDLQEPTCLQTRLELYKQGLRGSLTKLKGPLT<br>MMASHYKQHCPPTPETSCATQIITFESFKENLKDFLLVIPFDCWEPVQE |
| SEQ ID NO: 56 | MAGPATQSPMKLMALQLLLWHSALWTVQEATPLGPASSLPQSFLLK<br>CLEQVRKIQGDGAALQEKLCATYKLCHPEELVLLGHSLGIPWAPLSSC<br>PSQALQLAGCLSQLHSGLFLYQGLLQALEGISPELGPTLDTLQLDVAD<br>FATTIWQQMEELGMAPALQPTQGAMPAFASAFQRRAGGVLVASHLQ<br>SFLEVSYRVLRHLAQP |
| SEQ ID NO: 57 | QEINSSY |
| SEQ ID NO: 58 | SHPRLSA |
| SEQ ID NO: 59 | SMPNPMV |
| SEQ ID NO: 60 | GLQQVLL |
| SEQ ID NO: 61 | HELSVLL |
| SEQ ID NO: 62 | YAPQRLP |
| SEQ ID NO: 63 | TPRTLPT |
| SEQ ID NO: 64 | APVHSSI |
| SEQ ID NO: 65 | APPHALS |
| SEQ ID NO: 66 | TFSNRFI |
| SEQ ID NO: 67 | VVPTPPY |
| SEQ ID NO: 68 | ELAPDSP |
| SEQ ID NO: 69 | TPDCVTGKVEYTKYNDDDTFTVKVGDKELFTNRWNLQSLLLSAQITG<br>MTVTIKQNACHNGGGFSEVIFR |
| SEQ ID NO: 70 | MSRKLFASILIGALLGIGAPPSAHAGADDVVDSSKSFVMENFSSYHGT<br>KPGYVDSIQKGIQKPKSGTQGNYDDDWKGFYSTDNKYDAAGYSVDN<br>ENPLSGKAGGVVKVTYPGLTKVLALKVDNAETIKKELGLSLTEPLME<br>QVGTEEFIKRFGDGASRVVLSLPFAEGSSSVEYINNWEQAKALSVELEI<br>NFETRGKRGQDAMYEYMAQACAGNRVRRSVGSSLSCINLDWDVIRD<br>KTKTKIESLKEHGPIKNKMSESPNKTVSEEKAKQYLEEFHQTALEHPE<br>LSELKTVTGTNPVFAGANYAAWAVNVAQVIDSETADNLEKTTAALSI<br>LPGIGSVMGIADGAVHFINTEEIVAQSIALSSLMVAQAIPLVGELVDIGF<br>AAYNFVESIINLFQVVHNSYNRPAYSPGHKTQPFLHDGYAVSWNTVE<br>DSIIRTGFQGESGHDIKITAENTPLPIAGVLLPTIPGKLDVNKSKTHISVN |

TABLE 1-continued

Sequences of Immunological Fusion Partners

| SEQ ID NO | Sequence |
|---|---|
| | GRKIRMRCRAIDGDVTFCRPKSPVYVGNGVHANLHVAFHRSSSEKIH<br>SNEISSDSIGVLGYQKTVDHTKVNSKLSLFFEIKS |
| SEQ ID NO: 71 | NWVNVISDLKKIEDLIQSMHIDATLYTESDVHPSCKVTAMKCFLLELQ<br>VISLESGDASIHDTVENLIILANDSLSSNGNVTESGCKECEELEEKNIKE<br>FLQSFVHIVQMFINTS |
| SEQ ID NO: 72 | ITCPPPMSVEHADIWVKSYSLYSRERYICNSGFKRKAGTSSLTECVLN<br>KATNVAHWTTPSLKCIREPKSCDKTHTCPPCPAPELLGGPSVFLFPPKP<br>KDTLMISRTPEVTCVVVDVSHEDPEVKFNWYVDGVEVHNAKTKPRE<br>EQYNSTYRVVSVLTVLHQDWLNGKEYKCKVSNKALPAPIEKTISKAK<br>GQPREPQVYTLPPSRDELTKNQVSLTCLVKGFYPSDIAVEWESNGQPE<br>NNYKTTPPVLDSDGSFFLYSKLTVDKSRWQQGNVFSCSVMHEALHN<br>HYTQKSLSLSPGK |
| SEQ ID NO: 73 | GADDVVDSSKSFVMENFSSYHGTKPGYVDSIQKGIQKPKSGTQGNYD<br>DDWKEFYSTDNKYDAAGYSVDNENPLSGKAGGVVKVTYPGLTKVL<br>ALKVDNAETIKKELGLSLTEPLMEQVGTEEFIKRFGDGASRVVLSLPF<br>AEGSSSSVEYINNWEQAKALSVELEINFETRGKRGQDAMYEYMAQAC<br>AGNRVRRSVGSSLSCINLDWDVIRDKTKTKIESLKEHGPIKNKMSESP<br>NKTVSEEKAKQYLEEFHQTALEHPELSELKTVTGTNPVFAGANYAA<br>WAVNVAQVIDSETADNLEKTTAALSILPGIGSVMGIADGAVHHNTEEI<br>VAQSIALSSLMVAQAIPLVGELVDIGFAAYNFVESIINLFQVVHNSYNR<br>PAYSPGHKTQPFLHDGYAVSWNTVEDSIIRTGFQGESGHDIKITAENTP<br>LPIAGVLLPTIPGKLDVNKSKTHISVNGRKIRMRCRAIDGDVTFCRPKS<br>PVYVGNGVHANLHVAFHRSSSEKIHSNEISSDSIGVLGYQKTVDHTKV<br>NSKLSLFFEIKS |
| SEQ ID NO: 74 | MESHSRAGKSRKSAKFRSISRSLMLCNAKTSDDGSSPDEKYPDPFEISL<br>AQGKEGIFHSSVQLADTSEAGPSSVPDLALASEAAQLQAAGNDRGKT<br>CRRIFFMKESSTASSREKPGKLEAQSSNFLFPKACHQRARSNSTSVNPY<br>CTREIDFPMTKKSAAPTDRQPYSLCSNRKSLSQQLDCPAGKAAGTSRP<br>TRSLSTAQLVQPSGGLQASVISNIVLMKGQAKGLGFSIVGGKDSIYGPI<br>GIYVKTIFAGGAAAADGRLQEGDEILELNGESMAGLTHQDALQKFKQ<br>AKKGLLTLTVRTRLTAPPSLCSHLSPPLCRSLSSSTCITKDSSSFALESPS<br>APISTAKPNYRIMVEVSLQKEAGVGLGIGLCSVPYFQCISGIFVHTLSP<br>GSVAHLDGRLRCGDEIVEISDSPVHCLTLNEVYTILSRCDPGPVPIIVSR<br>HPDPQVSEQQLKEAVAQAVENTKFGKERHQWSLEGVKRLESSWHGR<br>PTLEKEREKNSAPPHRRAQKVMIRSSSDSSYMSGSPGGSPGSGSAEKP<br>SSDVDISTHSPSLPLAREPVVLSIASSRLPQESPPLPESRDSHPPLRLKKS<br>FEILVRKPMSSKPKPPPRKYFKSDSDPQKSLEERENSSCSSGHTPPTCG<br>QEARELLPLLLPQEDTAGRSPSASAGCPGPGIGPQTKSSTEGEPGWRR<br>ASPVTQTSPIKHPLLKRQARMDYSFDTTAEDPWVRISDCIKNLFSPIMS<br>ENHGIEMPLQPNASLNEEEGTQGHPDGTPPKLDTANGTPKVYKSADSS<br>TVKKGPPVAPKPAWFRQSLKGLRNRASDPRGLPDPALSTQPAPASRE<br>HLGSHIRASSSSSSIRQRISSFETFGSSQLPDKGAQRLSLQPSSGEAAKP<br>LGKHEEGRFSGLLRGRGAAPTLVPQQPEQVLSSGSPAASEARDPGVSES<br>PPPGRQPNQKTLPPGPDPLLRLLSTQAEESQGPVLKMPSQRARSFPLTR<br>SQSCETKLLDEKTSKLYSISSQVSSAVMKSLLCLPSSISCAQTPCIPKEG<br>ASPTSSSNEDSAANGSAETSALDTGFSLNLSELREYTEGLTEAKEDDD<br>GDHSSLQSGQSVISLLSSEELKKIEEVKVLDEATLKQLDGIHVTILHK<br>EEGAGLGFSLAGGADLENKVITVHRVFPNGLASQEGTIQKGNEVLSIN<br>GKSLKGTTHHDALAILRQAREPRQAVIVTRKLTPEAMPDLNSSTDSAA<br>SASAAASDVSVESTEATVCTVTLEKMSAGLGFSLEGGKGSLHGDKPLTI<br>NRIFKGAASEQSETVQPGDEILQLGGTAMQGLTRFEAWNIIKALPDGP<br>VTIVIRRKSLQSKETTAAGDS |
| SEQ ID NO: 75 | MTPGKTSLVSLLLLLSLEAIVKAGITIPRNPGCPNSEDKNFPRTVMVNL<br>NIHNRNTNTNPKRSSDYYNRSTSPWNLHRNEDPERYPSVIWEAKCRH<br>LGCINADGNVDYHMNSVPIQQEILVLRREPPHCPNSFRLEKILVSVGCT<br>CVTPIVHHVA |
| SEQ ID NO: 76 | RAVPGGSSPAWTQCQQLSQKLCTLAWSAHPLVGHMDLREEGDEETT<br>NDVPHIQCGDGCDPQGLRDNSQFCLQRIHQGLIFYEKLLGSDIFTGEPS<br>LLPDSPVGQLHASLLGLSQLLQPEGHHWETQQIPSLSPSQPWQRLLLR<br>FKILRSLQAFVAVAARVFAHGAATLSPIWELKKDVYVVELDWYPDAP<br>GEMVVLTCDTPEEDGITWTLDQSSEVLGSGKTLTIQVKEFGDAGQYT<br>CHKGGEVLSHSLLLLHKKEDGIWSTDILKDQKEPKNKTFLRCEAKNY<br>SGRFTCWWLTTISTDLTFSVKSSRGSSDPQGVTCGAATLSAERVRGDN<br>KEYEYSVECQEDSACPAAEESLPIEVMVDAVHKLKYENYTSSFFIRDII<br>KPDPPKNLQLKPLKNSRQVEVSWEYPDTWSTPHSYFSLTFCVQVQGK<br>SKREKKDRVFTDKTSATVKRKNASISVRAQDRYYSSSWSEWASVPC<br>S |
| SEQ ID NO: 77 | MCFPKVLSDDMKKLKARMVMLLPTSAQGLGAWVSACDTEDTVGHL<br>GPWRDKDPALWCQLCLSSQHQAIERFYDKMQNAESGRGQVMSSLAE |

TABLE 1-continued

Sequences of Immunological Fusion Partners

| SEQ ID NO | Sequence |
|---|---|
| | LEDDFKEGYLETVAAYYEEQHPELTPLLEKERDGLRCRGNRSPVPDV EDPATEEPGESFCDKVMRWFQAMLQRLQTWWHGVLAWVKEKVVA LVHAVQALWKQFQSFCCSLSELFMSSFQSYGAPRGDKEELTPQKCSE PQSSK |
| SEQ ID NO: 93 | GACTACGTTGGTGTAGAAAAATCCTGCCGCCCGGACCCTTAAGGC TGGGACAATTTCTGATAGCTACCCCGACACAGGAGGTTACGGGAT GAGCAATTCGCGCCGCCGCTCACTCAGGTGGTCATGTTGCTGAGC GTGCTGGCTGCCGTCGGGCTGGGCCTGGCCACGGCGCCGGCCCAG GCGGCCCCGCCGGCCTTGTCGCAGGACCGGTTCGCCGACTTCCCCG CGCTGCCCCTCGACCCGTCCGCGATGGTCGCCCAAGTGGGGCCAC AGGTGGTCAACATCAACACCAAACTGGGCTACAACAACGCCGTGG GCGCCGGGACCGGCATCGTCATCGATCCCAACGGTGTCGTGCTGA CCAACAACCACGTGATCGCGGGCGCCACCGACATCAATGCGTTCA GCGTCGGCTCCGGCCAAACCTACGGCGTCGATGTGGTCGGGTATG ACCGCACCCAGGATGTCGCGGTGCTGCAGCTGCGCGGTGCCGGTG GCCTGCCGTCGGCGGCGATCGGTGGCGGCGTCGCGGTTGGTGAGC CCGTCGTCGCGATGGGCAACAGCGGTGGGCAGGGCGGAACGCCCC GTGCGGTGCCTGGCAGGGTGGTCGCGCTCGGCCAAACCGTGCAGG CGTCGGATTCGCTGACCGGTGCCGAAGAGACATTGAACGGGTTGA TCCAGTTCGATGCCGCGATCCAGCCCGGTGATTCGGGCGGGCCCGT CGTCAACGGCCTAGGACAGGTGGTCGGTATGAACACGGCCGCGTC CGATAACTTCCAGCTGTCCCAGGGTGGGCAGGGATTCGCCATTCCG ATCGGGCAGGCGATGGCGATCGCGGGCCAGATCCGATCGGGTGGG GGGTCACCCACCGTTCATATCGGGCCTACCGCCTTCCTCGGCTTGG GTGTTGTCGACAACAACGGCAACGGCGCACGAGTCCAACGCGTGG TCGGGAGCGCTCCGGCGGCAAGTCTCGGCATCTCCACCGGCGACG TGATCACCGCGGTCGACGGCGCTCCGATCAACTCGGCCACCGCGA TGGCGGACGCGCTTAACGGGCATCATCCCGGTGACGTCATCTCGGT GACCTGGCAAACCAAGTCGGGCGGCACGCGTACAGGGAACGTGAC ATTGGCCGAGGGACCCCCGGCCTGATTTCGTCGCGGATACCACCC GCCGGCCGGCCAATTGGATTGGCGCCAGCCGTGATTGCCGCGTGA GCCCCCGAGTTCCGTCTCCCGTGCGCGTGGCATCGTGGAAGCAATG AACGAGGCAGAACACAGCGTCGAGCACCCTCCCGTGCAGGGCAGT CACGTCGAAGGCGGTGTGGTCGAGCATCCGGATGCCAAGGACTTC GGCAGCGCCGCCGCCCTGCCCGCCGATCCGACCTGGTTTAAGCAC GCCGTCTTCTACGAGGTGCTGGTCCGGGCGTTCTTCGACGCCAGCG CGGACGGTTCCGGCGATCTGCGTGGACTCATCGATCGCCTCGACTA CCTGCAGTGGCTTGGCATCGACTGCATCTGGTTGCCGCCGTTCTAC GACTCGCCGCTGCGCGACGGCGGTTACGACATTCGCGACTTCTACA AGGTGCTGCCCGAATTCGGCACCGTCGACGATTTCGTCGCCCTGGT CGACGCCGCTCACCGGCGAGGTATCCGCATCATCACCGACCTGGT GATGAATCACACCTCGGAGTCGCACCCCTGGTTTCAGGAGTCCCGC CGCGACCCAGACGGACCGTACGGTGACTATTACGTGTGGAGCGAC ACCAGCGAGCGCTACACCGACGCCCGGATCATCTTCGTCGACACC GAAGAGTCGAACTGGTCATTCGATCCTGTCCGCCGACAGTTCTACT GGCACCGATTCTT |
| SEQ ID NO: 94 | ACGGCCGCGTCCGATAACTTCCAGCTGTCCCAGGGTGGGCAGGGA TTCGCCATTCCGATCGGGCAGGCGATGGCGATCGCGGGCCAGATC CGATCGGGTGGGGGGTCACCCACCGTTCATATCGGGCCTACCGCCT TCCTCGGCTTGGGTGTTGTCGACAACAACGGCAACGGCGCACGAG TCCAACGCGTGGTCGGGAGCGCTCCGGCGGCAAGTCTCGGCATCT CCACCGGCGACGTGATCACCGCGGTCGACGGCGCTCCGATCAACT CGGCCACCGCGATGGCGGACGCGCTTAACGGGCATCATCCCGGTG ACGTCATCTCGGTGACCTGGCAAACCAAGTCGGGCGGCACGCGTA CAGGGAACGTGACATTGGCCGAGGGACCCCCGGCC |
| SEQ ID NO: 95 | CATATGCATCACCATCACCATCACACGGCCGCGTCCGATAACTTCC AGCTGTCCCAGGGTGGGCAGGGATTCGCCATTCCGATCGGGCAGG CGATGGCGATCGCGGGCCAGATCCGATCGGGTGGGGGGTCACCCA CCGTTCATATCGGGCCTACCGCCTTCCTCGGCTTGGGTGTTGTCGA CAACAACGGCAACGGCGCACGAGTCCAACGCGTGGTCGGGAGCGC TCCGGCGGCAAGTCTCGGCATCTCCACCGGCGACGTGATCACCGC GGTCGACGGCGCTCCGATCAACTCGGCCACCGCGATGGCGGACGC GCTTAACGGGCATCATCCCGGTGACGTCATCTCGGTGACCTGGCAA ACCAAGTCGGGCGGCACGCGTACAGGGAACGTGACATTGGCCGAG GGACCCCCGGCCGAATTCGACGACGACGACAAGGATCCACCTGAC CCGCATCAGCCGGACATGACGAAAGGCTATTGCCCGGGTGGCCGA TGGGGTTTTGGCGACTTGGCCGTGTGCGACGGCGAGAAGTACCCC GACGGCTCGTTTTGGCACCAGTGGATGCAAACGTGGTTTACCGGCC CACAGTTTTACTTCGATTGTGTCAGCGGCGGTGAGCCCCTCCCCGG CCCGCCGCCACCGGGTGGTTGCGGTGGGGCAATTCCGTCCGAGCA GCCCAACGCTCCCTGAGAATTC |

TABLE 1-continued

Sequences of Immunological Fusion Partners

| SEQ ID NO | Sequence |
|---|---|
| SEQ ID NO: 96 | CATATGCATCACCATCACCATCACACGGCCGCGTCCGATAACTTCC
AGCTGTCCCAGGGTGGGCAGGGATTCGCCATTCCGATCGGGCAGG
CGATGGCGATCGCGGGCCAGATCCGATCGGGTGGGGGGTCACCCA
CCGTTCATATCGGGCCTACCGCCTTCCTCGGCTTGGGTGTTGTCGA
CAACAACGGCAACGGCGCACGAGTCCAACGCGTGGTCGGGAGCGC
TCCGGCGGCAAGTCTCGGCATCTCCACCGGCGACGTGATCACCGC
GGTCGACGGCGCTCCGATCAACTCGGCCACCGCGATGGCGGACGC
GCTTAACGGGCATCATCCCGGTGACGTCATCTCGGTGACCTGGCAA
ACCAAGTCGGGCGGCACGCGTACAGGGAACGTGACATTGGCCGAG
GGACCCCCGGCCGAATTCCCGCTGGTGCCGCGCGGCAGCCCGATG
GGCTCCGACGTTCGGGACCTGAACGCACTGCTGCCGGCAGTTCCGT
CCCTGGGTGGTGGTGGTGGTTGCGCACTGCCGGTTAGCGGTGCAG
CACAGTGGGCTCCGGTTCTGGACTTCGCACCGCCGGGTGCATCCGC
ATACGGTTCCCTGGGTGGTCCGGCACCGCCGCCGGCACCGCCGCC
GCCGCCGCCGCCGCCGCACTCCTTCATCAAACAGGAACCGAG
CTGGGGTGGTGCAGAACCGCACGAAGAACAGTGCCTGAGCGCATT
CACCGTTCACTTCTCCGGCCAGTTCACTGGCACAGCCGGAGCCTGT
CGCTACGGGCCCTTCGGTCCTCCTCCGCCCAGCCAGGCGTCATCCG
GCCAGGCCAGGATGTTTCCTAACGCGCCCTACCTGCCCAGCTGCCT
CGAGAGCCAGCCCGCTATTCGCAATCAGGGTTACAGCACGGTCAC
CTTCGACGGGACGCCCAGCTACGGTCACACGCCCTCGCACCATGC
GGCGCAGTTCCCCAACCACTCATTCAAGCATGAGGATCCCATGGG
CCAGCAGGGCTCGCTGGGTGAGCAGCAGTACTCGGTGCCGCCCCC
GGTCTATGGCTGCCACACCCCCACCGACAGCTGCACCGGCAGCCA
GGCTTTGCTGCTGAGGACGCCCTACAGCAGTGACAATTTATACCAA
ATGACATCCCAGCTTGAATGCATGACCTGGAATCAGATGAACTTA
GGAGCCACCTTAAAGGGCCACAGCACAGGGTACGAGAGCGATAA
CCACACAACGCCCATCCTCTGCGGAGCCCAATACAGAATACACAC
GCACGGTGTCTTCAGAGGCATTCAGGATGTGCGACGTGTGCCTGG
AGTAGCCCCGACTCTTGTACGGTCGGCATCTGAGACCAGTGAGAA
ACGCCCCTTCATGTGTGCTTACTCAGGCTGCAATAAGAGATATTTT
AAGCTGTCCCACTTACAGATGCACAGCAGGAAGCACACTGGTGAG
AAACCATACCAGTGTGACTTCAAGGACTGTGAACGAAGGTTTTTTC
GTTCAGACCAGCTCAAAAGACACCAAAGGAGACATACAGGTGTGA
AACCATTCCAGTGTAAAACTTGTCAGCGAAAGTTCTCCCGGTCCGA
CCACCTGAAGACCCACACCAGGACTCATACAGGTGAAAAGCCCTT
CAGCTGTCGGTGGCCAAGTTGTCAGAAAAAGTTTGCCCGGTCAGA
TGAATTAGTCCGCCATCACAACATGCATCAGAGAAACATGACCAA
ACTCCAGCTGGCGCTTTGAGAATTC |
| SEQ ID NO: 97 | CATATGCATCACCATCACCATCACACGGCCGCGTCCGATAACTTCC
AGCTGTCCCAGGGTGGGCAGGGATTCGCCATTCCGATCGGGCAGG
CGATGGCGATCGCGGGCCAGATCCGATCGGGTGGGGGGTCACCCA
CCGTTCATATCGGGCCTACCGCCTTCCTCGGCTTGGGTGTTGTCGA
CAACAACGGCAACGGCGCACGAGTCCAACGCGTGGTCGGGAGCGC
TCCGGCGGCAAGTCTCGGCATCTCCACCGGCGACGTGATCACCGC
GGTCGACGGCGCTCCGATCAACTCGGCCACCGCGATGGCGGACGC
GCTTAACGGGCATCATCCCGGTGACGTCATCTCGGTGACCTGGCAA
ACCAAGTCGGGCGGCACGCGTACAGGGAACGTGACATTGGCCGAG
GGACCCCCGGCCGAATTCATCGAGGGAAGGGGCTCTGGCTGCCCC
TTATTGGAGAATGTGATTTCCAAGACAATCAATCCACAAGTGTCTA
AGACTGAATACAAAGAACTTCTTCAAGAGTTCATAGACGACAATG
CCACTACAAATGCCATAGATGAATTGAAGGAATGTTTTCTTAACCA
AACGGATGAAACTCTGAGCAATGTTGAGGTGTTTATGCAATTAAT
ATATGACAGCAGTCTTTGTGATTTATTTTAAGAATTC |
| SEQ ID NO: 98 | ATGCATCACCATCACCATCACACGGCCGCGTCCGATAACTTCCAGC
TGTCCCAGGGTGGGCAGGGATTCGCCATTCCGATCGGGCAGGCGA
TGGCGATCGCGGGCCAGATCCGATCGGGTGGGGGGTCACCCACCG
TTCATATCGGGCCTACCGCCTTCCTCGGCTTGGGTGTTGTCGACAA
CAACGGCAACGGCGCACGAGTCCAACGCGTGGTCGGGAGCGCTCC
GGCGGCAAGTCTCGGCATCTCCACCGGCGACGTGATCACCGCGGT
CGACGGCGCTCCGATCAACTCGGCCACCGCGATGGCGGACGCGCT
TAACGGGCATCATCCCGGTGACGTCATCTCGGTGACCTGGCAAAC
CAAGTCGGGCGGCACGCGTACAGGGAACGTGACATTGGCCGAGGG
ACCCCCGGCCGAATTCATGGTGGATTTCGGGGCGTTACCACCGGA
GATCAACTCCGCGAGGATGTACGCCGGCCCGGGTTCGGCCTCGCT
GGTGGCCGCGGCTCAGATGTGGGACAGCGTGGCGAGTGACCTGTT
TTCGGCCGCGTCGGCGTTTCAGTCGGTGGTCTGGGGTCTGACGGTG
GGGTCGTGGATAGGTTCGTCGGCGGGTCTGATGGTGGCGGCGGCC
TCGCCGTATGTGGCGTGGATGAGCGTCACCGCGGGGCAGGCCGAG
CTGACCGCCGCCCAGGTCCGGGTTGCTGCGGCGGCCTACGAGACG
GCGTATGGGCTGACGGTGCCCCCGCCGGTGATCGCCGAGAACCGT
GCTGAACTGATGATTCTGATAGCGACCAACCTCTTGGGGCAAAAC
ACCCCGGCGATCGCGGTCAACGAGGCCGAATACGGCGAGATGTGG |

TABLE 1-continued

| Sequences of Immunological Fusion Partners | |
|---|---|
| SEQ ID NO | Sequence |
| | GCCCAAGACGCCGCCGCGATGTTTGGCTACGCCGCGGCGACGGCG<br>ACGGCGACGGCGACGTTGCTGCCGTTCGAGGAGGCGCCGGAGATG<br>ACCAGCGCGGGTGGGCTCCTCGAGCAGGCCGCCGCGGTCGAGGAG<br>GCCTCCGACACCGCCGCGGCGAACCAGTTGATGAACAATGTGCCC<br>CAGGCGCTGCAACAGCTGGCCCAGCCCACGCAGGGCACCACGCCT<br>TCTTCCAAGCTGGGTGGCCTGTGGAAGACGGTCTCGCCGCATCGGT<br>CGCCGATCAGCAACATGGTGTCGATGGCCAACAACCACATGTCGA<br>TGACCAACTCGGGTGTGTCGATGACCAACACCTTGAGCTCGATGTT<br>GAAGGGCTTTGCTCCGGCGGCGGCCGCCCAGGCCGTGCAAACCGC<br>GGCGCAAAACGGGGTCCGGGCGATGAGCTCGCTGGGCAGCTCGCT<br>GGGTTCTTCGGGTCTGGGCGGTGGGGTGGCCGCCAACTTGGGTCG<br>GGCGGCCTCGGTCGGTTCGTTGTCGGTGCCGCAGGCCTGGGCCGC<br>GGCCAACCAGGCAGTCACCCCGGCGGCGCGGGCGCTGCCGCTGAC<br>CAGCCTGACCAGCGCCGCGGAAAGAGGGCCCGGGCAGATGCTGG<br>GCGGGCTGCCGGTGGGGCAGATGGGCGCCAGGGCCGGTGGTGGGC<br>TCAGTGGTGTGCTGCGTGTTCCGCCGCGACCCTATGTGATGCCGCA<br>TTCTCCGGCAGCCGGCGATATCGCCCCGCCGGCCTTGTCGCAGGAC<br>CGGTTCGCCGACTTCCCCGCGCTGCCCCTCGACCCGTCCGCGATGG<br>TCGCCCAAGTGGGGCCACAGGTGGTCAACATCAACACCAAACTGG<br>GCTACAACAACGCCGTGGGCGCCGGGACCGGCATCGTCATCGATC<br>CCAACGGTGTCGTGCTGACCAACAACCACGTGATCGCGGGCGCCA<br>CCGACATCAATGCGTTCAGCGTCGGCTCCGGCCAAACCTACGGCG<br>TCGATGTGGTCGGGTATGACCGCACCCAGGATGTCGCGGTGCTGC<br>AGCTGCGCGGTGCCGGTGGCCTGCCGTCGGCGGCGATCGGTGGCG<br>GCGTCGCGGTTGGTGAGCCCGTCGTCGCGATGGGCAACAGCGGTG<br>GGCAGGGCGGAACGCCCCGTGCGGTGCCTGGCAGGGTGGTCGCGC<br>TCGGCCAAACCGTGCAGGCGTCGGATTCGCTGACCGGTGCCGAAG<br>AGACATTGAACGGGTTGATCCAGTTCGATGCCGCGATCCAGCCCG<br>GTGATTCGGGCGGGCCCGTCGTCAACGGCCTAGGACAGGTGGTCG<br>GTATGAACACGGCCGCGTCCTAGG |
| SEQ ID NO: 107 | mcctkslllaalmsvlllhlcgeseasnfdcclgytdrilhpkfivgftrqlanegcdinaiifht<br>kkklsvcanpkqtwvkyivrllskkvknm |
| SEQ ID NO: 108 | ggGGTCAACGTTGAgggggg |
| SEQ ID NO: 109 | ggGGGACGA:TCGTCgggggg |
| SEQ ID NO: 110 | gggGACGAC:GTCGTGgggggg |
| SEQ ID NO: 111 | tccatgacgttcctgatgct |
| SEQ ID NO: 112 | tccatgacgttcctgacgtt |
| SEQ ID NO: 113 | tcgtcgttttgtcgttttgtcgtt |
| SEQ ID NO: 114 | tcg tcg ttg tcg ttt tgt cgt t |
| SEQ ID NO: 115 | tcg acg ttc gtc gtt cgt cgt tc |
| SEQ ID NO: 116 | tcg cga cgt tcg ccc gac gtt cgg ta |
| SEQ ID NO: 117 | tcgtcgttttcggcgc:gcgccg |
| SEQ ID NO: 118 | tcgtcgtcgttc:gaacgacgttgat |
| SEQ ID NO: 119 | tcg cga acg ttc gcc gcg ttc gaa cgc gg |

TABLE 2

| Tools to construct *Mycobacterium* sp.-Derived Ra12 Sequences | |
|---|---|
| SEQ ID NO | Sequence |
| SEQ ID NO: 99 | CAATTACATATGCATCACCATCACCATCACACGGCCGCGTCCGATA<br>ACTTC |
| SEQ ID NO: 100 | CTAATCGAATTCGGCCGGGGGTCCCTCGGCCAA |
| SEQ ID NO: 101 | CAATTAGAATTCGACGACGACGACAAGGATCCACCTGACCCGCAT<br>CAG |

TABLE 2-continued

| Tools to construct *Mycobacterium* sp.-Derived Ra12 Sequences | |
|---|---|
| SEQ ID NO | Sequence |
| SEQ ID NO: 102 | CAATTAGAATTCTCAGGGAGCGTTGGGCTGCTC |
| SEQ ID NO: 103 | GCGAAGCTTATGAAGTTGCTGATGGTCCTCATGC |
| SEQ ID NO: 104 | CGGCTCGAGTTAAAATAAATCACAAAGACTGCTGTC |
| SEQ ID NO: 105 | MHHHHHH |
| SEQ ID NO: 106 | DDDK |

In some embodiments, the nucleic acid sequences for the target antigen and the immunological fusion partner are not separated by any nucleic acids. In other embodiments, a nucleic acid sequence that encodes for a linker can be inserted between the nucleic acid sequence encoding for any target antigen described herein and the nucleic acid sequence encoding for any immunological fusion partner described herein. Thus, in certain embodiments, the protein produced following immunization with the viral vector containing a target antigen, a linker, and an immunological fusion partner can be a fusion protein comprising the target antigen of interest followed by the linker and ending with the immunological fusion partner, thus linking the target antigen to an immunological fusion partner that increases the immunogenicity of the target antigen of interest via a linker. In some embodiments, the sequence of linker nucleic acids can be from about 1 to about 150 nucleic acids long, from about 5 to about 100 nucleic acids along, or from about 10 to about 50 nucleic acids in length. In some embodiments, the nucleic acid sequences can encode one or more amino acid residues. In some embodiments, the amino acid sequence of the linker can be from about 1 to about 50, or about 5 to about 25 amino acid residues in length. In some embodiments, the sequence of the linker comprises less than 10 amino acids. In some embodiments, the linker can be a polyalanine linker, a polyglycine linker, or a linker with both alanines and glycines.

Nucleic acid sequences that encode for such linkers can be any one of SEQ ID NO: 78-SEQ ID NO: 92 and are summarized in TABLE 3.

TABLE 3

| Sequences of Linkers | |
|---|---|
| SEQ ID NO | Sequence |
| SEQ ID NO: 78 | MAVPMQLSCSR |
| SEQ ID NO: 79 | RSTG |
| SEQ ID NO: 80 | TR |
| SEQ ID NO: 81 | RSQ |
| SEQ ID NO: 82 | RSAGE |
| SEQ ID NO: 83 | RS |
| SEQ ID NO: 84 | GG |
| SEQ ID NO: 85 | GSGGSGGSG |
| SEQ ID NO: 86 | GGSGGSGGSGG |
| SEQ ID NO: 87 | GGSGGSGGSGGSGG |

TABLE 3-continued

| Sequences of Linkers | |
|---|---|
| SEQ ID NO | Sequence |
| SEQ ID NO: 88 | GGSGGSGGSGGSGGSGG |
| SEQ ID NO: 89 | GGSGGSGGSGGSGGSGGSGG |
| SEQ ID NO: 90 | GGSGGSGGSGGSGGSGGSGGSGG |
| SEQ ID NO: 91 | GGSGGSGGSGGSGGSG |
| SEQ ID NO: 92 | GSGGSGGSGGSGGSGG |

VI. Methods of Use

The adenovirus vectors can be used in a number of vaccine settings for generating an immune response against one or more alphavirus target antigens as described herein, especially chikungunya virus target antigens. The adenovirus vectors are of particular importance because of the finding that they can be used to generate immune responses in subjects who have preexisting immunity to adenovirus or adenovirus vectors and can be used in vaccination regimens that include multiple rounds of immunization using the adenovirus vectors, regimens not possible using previous generation adenovirus vectors.

Generally, generating an immune response can comprise an induction of a humoral response and/or a cell-mediated response. In certain embodiments, it is desirable to increase an immune response against a target antigen of interest. As such "generating an immune response" or "inducing an immune response" can comprise any statistically significant change, e.g., increase in the number of one or more immune cells (T cells, B cells, antigen-presenting cells, dendritic cells, neutrophils, and the like) or in the activity of one or more of these immune cells (CTL activity, HTL activity, cytokine secretion, change in profile of cytokine secretion, etc.).

The skilled artisan would readily appreciate that a number of methods for establishing whether an alteration in the immune response has taken place are available. A variety of methods for detecting alterations in an immune response (e.g., cell numbers, cytokine expression, cell activity) are known in the art and are useful in the context of the instant invention. Illustrative methods are described in Current Protocols in Immunology, Edited by: John E. Coligan, Ada M. Kruisbeek, David H. Margulies, Ethan M. Shevach, Warren Strober (2001 John Wiley & Sons, NY, NY) Ausubel et al. (2001 Current Protocols in Molecular Biology, Greene Publ. Assoc. Inc. & John Wiley & Sons, Inc., NY, NY); Sambrook et al. (1989 Molecular Cloning, Second Ed., Cold Spring Harbor Laboratory, Plainview, N.Y.); Maniatis et al. (1982 Molecular Cloning, Cold Spring Harbor Laboratory, Plainview, N.Y.) and elsewhere. Illustrative methods useful in this context can include intracellular cytokine staining (ICS), ELISpot, proliferation assays, cytotoxic T cell assays including chromium release or equivalent assays, and gene expression analysis using any number of polymerase chain reaction (PCR) or RT-PCR based assays.

In certain embodiments, generating an immune response comprises an increase in target antigen-specific CTL activity of about 1.5 to 20 or more fold, at least, about, or at most 1.5, 2, 3, 4, 5, 6, 7, 8, 9, 10, 11, 12, 13, 14, 15, 16, 17, 18, 19, or any range or number derived therefrom in a subject administered the adenovirus vectors as compared to a control. In another embodiment, generating an immune response comprises an increase in target-specific CTL activity of about 1.5 to 20, or more fold in a subject administered the adenovirus vectors as compared to a control. In a further embodiment, generating an immune response that comprises an increase in target antigen-specific cell mediated immunity activity as measured by ELISpot assays measuring cytokine secretion, such as interferon-gamma (IFN-γ), interleukin-2 (IL-2), tumor necrosis factor-alpha (TNF-α), granzyme, or other cytokines, of about 1.5 to 20, or more fold as compared to a control.

In a further embodiment, generating an immune response comprises an increase in target-specific antibody production of between 1.5 and 5 fold in a subject administered the adenovirus vectors as compared to an appropriate control. In another embodiment, generating an immune response comprises an increase in target-specific antibody production of about 1.5 to 20, or more fold in a subject administered the adenovirus vector as compared to a control.

Thus, certain aspects can provide methods for generating an immune response against an alphavirus target antigen of interest comprising administering to the subject an adenovirus vector comprising: a) a replication defective adenovirus vector, wherein the adenovirus vector has a deletion in the E2b region, and b) nucleic acids encoding the target antigen; and readministering the adenovirus vector at least once to the subject; thereby generating an immune response against the target antigen. Certain other aspects can provide methods for generating an immune response against alphavirus target antigens of interest comprising administering to the subject an adenovirus vector comprising: a) a replication defective adenovirus vector, wherein the adenovirus vector has a deletion in the E2b region, and b) nucleic acids encoding the target antigens; and readministering the adenovirus vector at least once to the subject; thereby generating an immune response against the target antigens. In certain embodiments, there can be provided methods wherein the vector administered is not a gutted vector.

In further embodiments, methods can be provided for generating an immune response against an alphavirus virus target antigen in a subject, wherein the subject has pre-existing immunity to Ad, by administering to the subject an adenovirus vector comprising: a) a replication defective adenovirus vector, wherein the adenovirus vector has a deletion in the E2b region, and b) nucleic acids encoding the target antigen; and re-administering the adenovirus vector at least once to the subject; thereby generating an immune response against the alphavirus virus target antigen. In still further embodiments, methods can be provided for generating an immune response against alphavirus virus target antigens in a subject, wherein the individual has pre-existing immunity to Ad, by administering to the subject an adenovirus vector comprising: a) a replication defective adenovirus vector, wherein the adenovirus vector has a deletion in the E2b region, and b) nucleic acids encoding the target antigens; and re-administering the adenovirus vector at least once to the subject; thereby generating an immune response against the alphavirus virus target antigens.

With regard to preexisting immunity to Ad, this can be determined using methods known in the art, such as antibody-based assays to test for the presence of Ad antibodies. Further, in certain embodiments, the methods can include first determining that an individual has preexisting immunity to Ad then administering the E2b deleted adenovirus vectors as described herein.

In certain aspects, there can be provided methods of generating an immune response against an alphavirus target antigen, such as those described elsewhere herein.

In particular aspects, there are provided methods of generating an immune response against an alphavirus, such as those described elsewhere herein.

VII. Pharmaceutical Compositions

As noted elsewhere herein, the adenovirus vector can comprise nucleic acid sequences that encode one or more target antigens of interest from any one or more of the infectious agents against which an immune response is to be generated. For example, a target antigen can include, but is not limited to, viral antigen protein, such as $E3_{ALPHA}$, $E2_{ALPHA}$, 6K, $E1_{ALPHA}$, nsP1, nsP2, nsP3, and nsP4.

For administration, the adenovirus vector stock can be combined with an appropriate buffer, physiologically acceptable carrier, excipient or the like. In certain embodiments, an appropriate number of adenovirus vector particles are administered in an appropriate buffer, such as, sterile PBS.

In certain circumstances it can be desirable to deliver the adenovirus vector composition disclosed herein parenterally, intravenously, intramuscularly, or even intraperitoneally. In certain embodiments, solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. In other embodiments, a E2b deleted adenovirus vector can be delivered in pill form, delivered by swallowing or by suppository.

Illustrative pharmaceutical forms suitable for injectable use include sterile aqueous solutions or dispersions and sterile powders for the extemporaneous preparation of sterile injectable solutions or dispersions (for example, see U.S. Pat. No. 5,466,468). The form can be sterile and can be fluid to the extent that easy syringability exists. It can be stable under the conditions of manufacture and storage and can be preserved against the contaminating action of microorganisms, such as bacteria, molds and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity can be maintained, for example, by the use of a coating, such as lecithin, by the maintenance of the required particle size in the case of dispersion and/or by the use of surfactants. The prevention of the action of microorganisms can be facilitated by various antibacterial and antifungal agents, for example, parabens, chlorobutanol, phenol, sorbic acid, thimerosal, and the like. In many cases, it can include isotonic agents, for example, sugars or sodium chloride. Prolonged absorption of the injectable compositions can be brought about by the use in the compositions of agents delaying absorption, for example, aluminum monostearate and gelatin.

In one embodiment, for parenteral administration in an aqueous solution, the solution should be suitably buffered if necessary and the liquid diluent first rendered isotonic with sufficient saline or glucose. These particular aqueous solutions can be especially suitable for intravenous, intramuscular, subcutaneous and intraperitoneal administration. In this connection, a sterile aqueous medium that can be employed will be known to those of skill in the art in light of the present disclosure. For example, one dosage can be dissolved in 1 ml of isotonic NaCl solution and either added to 1000 ml of hypodermoclysis fluid or injected at the proposed site of infusion, (see for example, "Remington's Pharmaceutical Sciences" $15^{th}$ Edition, pages 1035-1038 and 1570-1580). Some variation in dosage will necessarily occur depending on the condition of the subject being treated. Moreover, for human administration, preparations can need to meet sterility, pyrogenicity, and the general safety and purity standards as required by FDA Office of Biology standards.

The carriers can further comprise any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions. The phrase "pharmaceutically-acceptable" can refer to molecular entities and compositions that do not produce an allergic or similar untoward reaction when administered to a human.

Routes and frequency of administration of the therapeutic compositions described herein, as well as dosage, will vary from individual to individual, and from disease to disease, and can be readily established using standard techniques. In general, the pharmaceutical compositions and vaccines can be administered by injection (e.g., intracutaneous, intraperitoneal, intramuscular, intravenous or subcutaneous), intranasally (e.g., by aspiration), in pill form (e.g., swallowing, suppository for vaginal or rectal delivery). In certain embodiments, between 1 and 3 doses can be administered over a 6 week period and further booster vaccinations can be given periodically thereafter.

In various embodiments, the replication defective adenovirus is administered at a dose that suitable for effecting an immune response as described herein. In some embodiments, the replication defective adenovirus is administered at a dose from about $1\times10^8$ virus particles to about $5\times10^{13}$ virus particles per immunization. In some cases, the replication defective adenovirus is administered at a dose that is from about $1\times10^9$ to about $5\times10^{12}$ virus particles per immunization. In some embodiments, the replication defective adenovirus is administered at a dose from about $1\times10^8$ virus particles to about $5\times10^8$ virus particles per immunization. In some embodiments, the replication defective adenovirus is administered at a dose from about $5\times10^8$ virus particles to about $1\times10^9$ virus particles per immunization. In some embodiments, the replication defective adenovirus is administered at a dose from about $1\times10^9$ virus particles to about $5\times10^9$ virus particles per immunization. In some embodiments, the replication defective adenovirus is administered at a dose from about $5\times10^9$ virus particles to about $1\times10^{10}$ virus particles per immunization. In some embodiments, the replication defective adenovirus is administered at a dose from about $1\times10^{10}$ virus particles to about $5\times10^{10}$ virus particles per immunization. In some embodiments, the replication defective adenovirus is administered at a dose from about $5\times10^{10}$ virus particles to about $1\times10^{11}$ virus particles per immunization. In some embodiments, the replication defective adenovirus is administered at a dose from about $1\times10^{11}$ virus particles to about $5\times10^{11}$ virus particles per immunization. In some embodiments, the replication defective adenovirus is administered at a dose from about $5\times10^{11}$ virus particles to about $1\times10^{12}$ virus particles per immunization. In some embodiments, the replication defective adenovirus is administered at a dose from about $1\times10^{12}$ virus particles to about $5\times10^{12}$ virus particles per immunization. In some embodiments, the replication defective adenovirus is administered at a dose from about $5\times10^{12}$ virus particles to about $1\times10^{13}$ virus particles per immunization. In some embodiments, the replication defective adenovirus is administered at a dose from about $1\times10^{13}$ virus particles to about $5\times10^{13}$ virus particles per immunization. In some embodiments, the replication defective adenovirus is administered at a dose from about $1\times10^8$ virus particles to about $5\times10^{10}$ virus particles per immunization. In some embodiments, the replication defective adenovirus is administered at a dose from about $1\times10^{10}$ virus particles to about $5\times10^{12}$ virus particles per immunization. In some embodiments, the replication defective adenovirus is administered at a dose from about $1\times10^{11}$ virus particles to about $5\times10^{13}$ virus particles per immunization. In some embodiments, the replication defective adenovirus is administered at a dose from about $1\times10^8$ virus particles to about $1\times10^{10}$ virus particles per immunization. In some embodiments, the replication defective adenovirus is administered at a dose from about $1\times10^{10}$ virus particles to about $1\times10^{12}$ virus particles per immunization. In some embodiments, the replication defective adenovirus is administered at a dose from about $1\times10^{11}$ virus particles to about $5\times10^{13}$ virus particles per immunization. In some cases, the replication defective adenovirus is administered at a dose that is greater than or equal to $1\times10^9$, $2\times10^9$, $3\times10^9$, $4\times10^9$, $5\times10^9$, $6\times10^9$, $7\times10^9$, $8\times10$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles (VP) per immunization. In some cases, the replication defective adenovirus is administered at a dose that is less than or equal to $1\times10^9$, $2\times10^9$, $3\times10^9$, $4\times10^9$, $5\times10^9$, $6\times10^9$, $7\times10^9$, $8\times10^9$, $9\times10^9$, $1\times10^{10}$, $2\times10^{10}$, $3\times10^{10}$, $4\times10^{10}$, $5\times10^{10}$, $6\times10^{10}$, $7\times10^{10}$, $8\times10^{10}$, $9\times10^{10}$, $1\times10^{11}$, $2\times10^{11}$, $3\times10^{11}$, $4\times10^{11}$, $5\times10^{11}$, $6\times10^{11}$, $7\times10^{11}$, $8\times10^{11}$, $9\times10^{11}$, $1\times10^{12}$, $1.5\times10^{12}$, $2\times10^{12}$, $3\times10^{12}$, or more virus particles per immunization. In various embodiments, a desired dose described herein is administered in a suitable volume of formulation buffer, for example a volume of about 0.1-10 mL, 0.2-8 mL, 0.3-7 mL, 0.4-6 mL, 0.5-5 mL, 0.6-4 mL, 0.7-3 mL, 0.8-2 mL, 0.9-1.5 mL, 0.95-1.2 mL, or 1.0-1.1 mL. Those of skill in the art appreciate that the volume can fall within any range bounded by any of these values (e.g., about 0.5 mL to about 1.1 mL).

A suitable dose can be an amount of an adenovirus vector that, when administered as described above, is capable of promoting a target antigen immune response as described elsewhere herein. In certain embodiments, the immune response is at least 10-50% above the basal (i.e., untreated) level. Such response can be monitored by measuring the target antigen antibodies in a patient or by vaccine-dependent generation of cytolytic effector cells capable of killing alphavirus infected cells in vitro, or other methods known in the art for monitoring immune responses.

In general, an appropriate dosage regimen provides the adenovirus vectors in an amount sufficient to provide prophylactic benefit. Protective immune responses can generally be evaluated using standard proliferation, cytotoxicity or cytokine assays, which can be performed using samples obtained from a patient before and after immunization (vaccination).

While one advantage is the capability to administer multiple vaccinations with the same adenovirus vectors, particularly in individuals with preexisting immunity to Ad, the adenovirus vaccines can also be administered as part of a prime and boost regimen. A mixed modality priming and booster inoculation scheme can result in an enhanced immune response.

Thus, one aspect is a method of priming a subject with a plasmid vaccine, such as a plasmid vector comprising a target antigen of interest, by administering the plasmid vaccine at least one time, allowing a predetermined length of time to pass, and then boosting by administering the adenovirus vector. Multiple primings, e.g., 1-3, can be employed, although more can be used. The length of time between priming and boost can vary from about six months to a year, but other time frames can be used.

VIII. Kits

A composition, immunotherapy, or vaccine described herein can be supplied in the form of a kit. The kits of the present disclosure can further comprise instructions regarding the dosage and/or administration regimen information.

In some embodiments, a kit comprises a composition and method for providing a vaccine as described herein. In some embodiments kits can further comprise components useful in administering the kit components and instructions on how to prepare the components. In some embodiments, the kit can further comprise software for conducting monitoring of patients before and after vaccination with appropriate laboratory tests, or communicating results and patient data with medical staff.

The components of the kit can be in dry or liquid form. If they are in dry form, the kit can include a solution to solubilize the dried material. The kit can also include transfer factor in liquid or dry form. In some embodiments, if the transfer factor is in dry form, the kit includes a solution to solubilize the transfer factor. The kit can also include containers for mixing and preparing the components. The kit can also include instrument for assisting with the administration such as, for example, needles, tubing, applicator, inhalant, syringe, pipette, forceps, measured spoon, eye dropper, or any such medically approved delivery vehicle. The kits or drug delivery systems as described herein also can include a means for containing compositions of the present disclosure in close confinement for commercial sale and distribution.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety to the same extent as if each individual publication, patent, or patent application was specifically and individually indicated to be incorporated by reference.

Aspects of the embodiments can be modified, if necessary to employ concepts of the various patents, application and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

EXAMPLES

The following examples are included to further describe some aspects of the present disclosure, and should not be used to limit the scope of the present disclosure.

Example 1

Production of Single-targeted Ad5 [E1-, E2b-]-CHIKV Vaccine

This example illustrates the results of construction and expression of Ad5 [E1-, E2b-] vectors containing a CHIKV antigen.

Ad5 [E1-, E2b-]-CHIKV vaccine is an adenovirus serotype 5 (Ad5) vector that was modified by removal of E1, E2b, and E3 gene regions, and insertion of a CHIKV gene.

In this Example, the nucleic acid sequence encoding a CHIKV structural polyprotein (the amino acid sequence is set forth in SEQ ID NO: 2) including CHIKV structural proteins C, E3, E2, 6K, and E1 was cloned into an Ad5 [E1-, E2b-]-based platform to produce Ad5 [E1-, E2b-]-CHIKV$_{str}$ using a homologous recombination-based approach.

Figure 2:
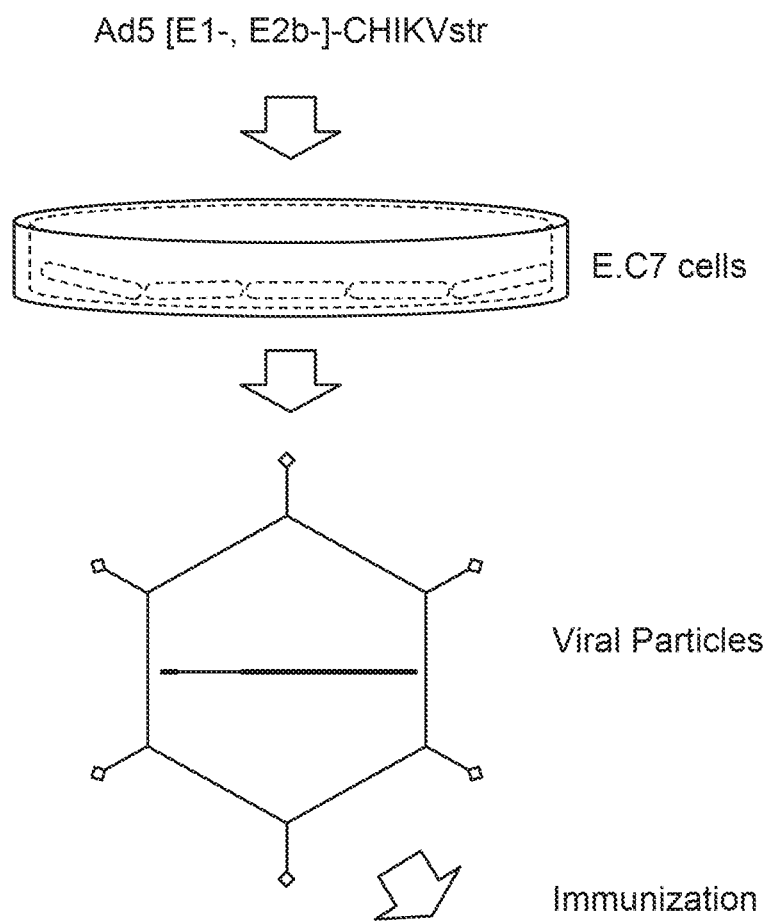
FIG. 2 exemplifies Ad5 [E1-, E2b-]-CHIKV$_{str}$ vaccine derived from nucleotide positions 7567 to 11313 of SEQ ID NO: 1 that has been generated.

Ad5 [E1-, E2b-]-CHIKV$_{str}$ was produced in E.C7 cells (FIG. 2). The replication-deficient virus was propagated in the E.C7 packaging cell line, purified by ultracentrifugation or ion exchange column purification, and 62ittered. Viral infectious titer was determined as plaque-forming units (PFUs) on an E.C7 cell monolayer. The VP concentration was determined by sodium dodecyl sulfate (SDS) disruption and spectrophotometry at 260 nm and 280 nm.

Figure 3:
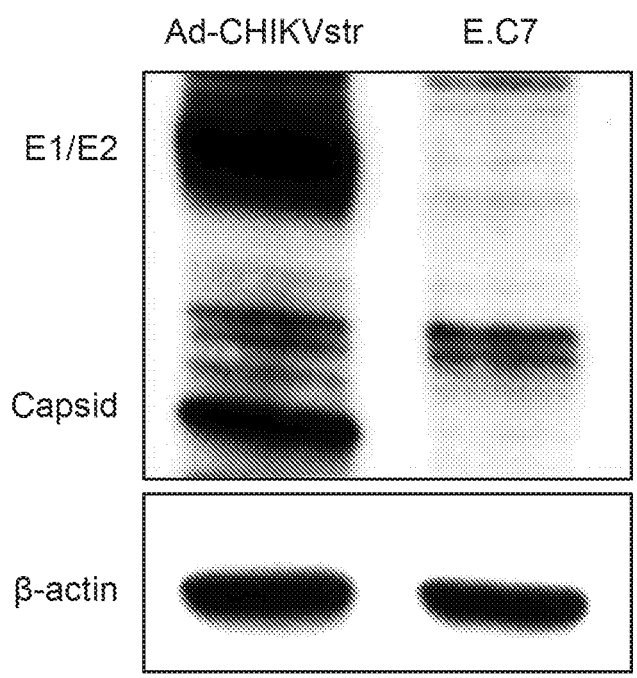
FIG. 3 exemplifies CHIKV structural protein expression in HEK 293 infected with Ad5 [E1-, E2b-]-CHIKV$_{str}$ vaccine, or mock infected. CHIKV protein expression was detected by western blot.

Infection of E.C7 cells with Ad5 [E1-, E2b-]-CHIKV$_{str}$ resulted in expression of CHIKV structural proteins. CHIKV structural protein expression was detectable by western blot with an anti-CHIKV antibody (FIG. 3).

Example 2

Multiple Injections of an Ad5 [E1-, E2b-]-CHIKV$_{str}$ Generated Protective Immunity Against CHIKV-Infection This example illustrates the results of injection of an Ad5 [E1-, E2b-]-CHIKV$_{str}$ for generating protective immunity against CHIKV infection.

Groups of ten (10) mice each were immunized two times subcutaneously at weekly intervals with a dose of $10^9$ VPs Ad5 [E1-, E2b-]-CHIKV$_{str}$. Control mice were injected with PBS. Mice were then challenged with a lethal dose of CHIKV by injection of the virus into the footpad. Control mice succumbed to infection within 7 days (FIG. 4A), lost weight (FIG. 4B), and demonstrated prolonged inflammation at the footpad (FIG. 4C). By contrast, vaccinated mice survived CHIKV infection (FIG. 4A), did not lose weight (FIG. 4B), and demonstrated rapid resolution of inflammation of the footpad (FIG. 4C).

Example 3

Production of a Multi-Targeted Ad5 [E1-, E2b-]-CHIKV Antigen Insert

This example illustrates construction of an Ad5 [E1-, E2b-] vector containing multiple CHIKV antigens.

Figure 5A:
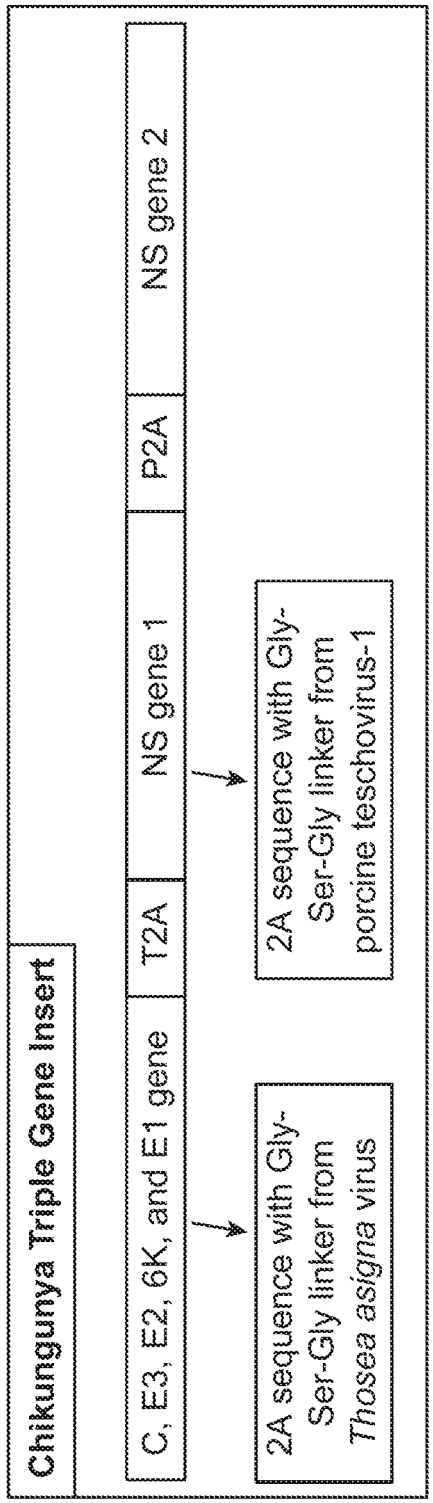
FIG. 5A illustrates a schematic representation of a multiple gene construct containing three Chikungunya genes (C, E3, E2, 6K, and E1 gene (nucleotides 767-11313 of SEQ ID NO: 1); NS gene 1; NS gene 2) to be used for insertion into Ad5 [E1-, E2b-].
Figure 5B:
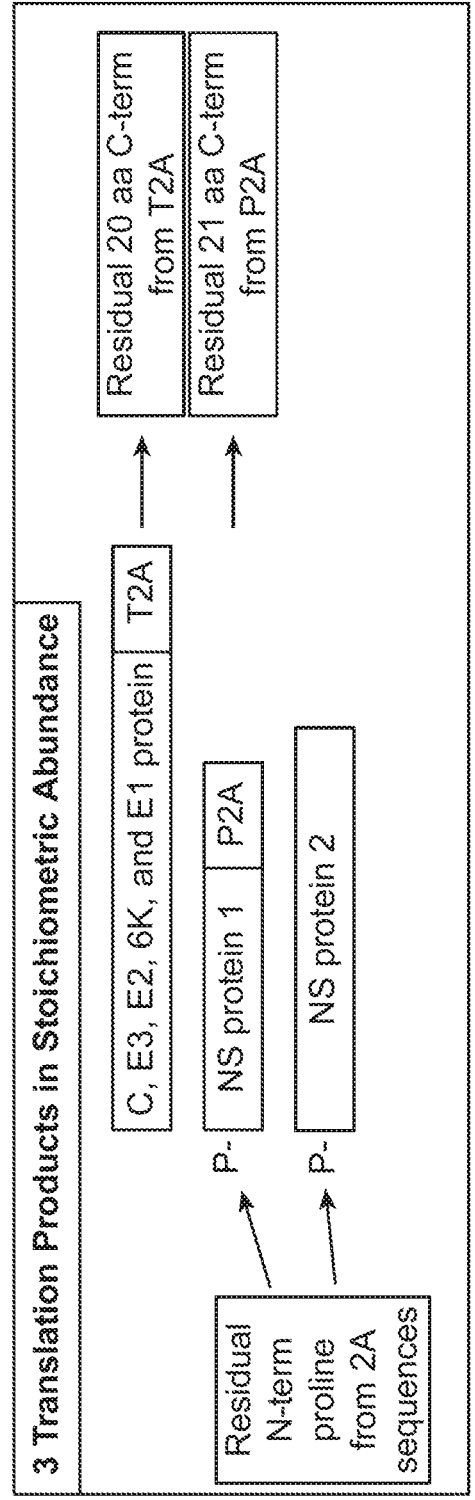
FIG. 5B illustrates the translation products of the gene construct in FIG. 5A and the stoichiometric abundance of each product.

To produce the Ad5 [E1-, E2b-] containing multiple CHIKV genes, three individual alphavirus antigen gene sequences ((1) C, E3, E2, 6K, and E1 gene ((nucleotides 7567-11313 of SEQ ID NO: 1); (2) NS gene 1; (3) NS gene 2) are separated by "self-cleaving" 2A peptide derived from *Porcine teschovirus*-1 and *Thosea asigna* virus respectively (FIG. 5A) (de Felipe P and Ryan M Traffic 2004 5(8), 616-26; Holst J et al. Nature Immunol. 2008 9:658-66; Kim J H et al. PloS One, 2011 6(4), e18556. Doi:10.1371/journal.pone.0018556). As the 2A peptides are translated on the ribosome, the peptide bond between the final two residues of the 2A peptide is never formed resulting in distinctly expressed proteins in one ribosomal pass (FIG. 5B). The use of two 2A peptide sequences separating the three genes are found in near stoichiometric expression of the three proteins (FIG. 5B).

Example 4

Production and Testing of a Single-Targeted Ad5 [E1-, E2b-]-ONNV Vaccine

This example illustrates the construction of Ad5 [E1-, E2b-] vectors containing an ONNV antigen, and testing for expression and protective immunity by multiple injections of the vectors.

Ad5 [E1-, E2b-]-ONNV$_{str}$ vaccine is an adenovirus serotype 5 (Ad5) vector that is modified by removal of E1, E2b, and E3 gene regions, and insertion of the nucleic acid sequence encoding an ONNV structural polyprotein (the amino acid sequence is set forth in SEQ ID NO: 5) using a homologous recombination-based approach.

Ad5 [E1-, E2b-]-ONNV$_{str}$ is produced in E.C7 cells. The replication-deficient virus is propagated in the E.C7 packaging cell line, purified by ultracentrifugation or ion exchange column purification, and is 63ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

ONNV structural proteins are expressed as a result of infection of E.C7 cells with Ad5 [E1-, E2b-]-ONNV$_{str}$. ONNV structural protein expression is detected by western blot with an anti-ONNV antibody.

Groups of ten (10) mice each are immunized two times subcutaneously at weekly intervals with a dose of $10^9$ VPs Ad5 [E1-, E2b-]-ONNV$_{str}$. Control mice are injected with PBS or $10^9$ VPs Ad5-null. Mice are then challenged with a lethal dose of ONNV by injection of the virus. The survival rate, immune response, and weight are compared between the mice injected with the vaccine and the control group.

Example 5

Production and Testing of a Single-Targeted Ad5 [E1-, E2b-]-MAYV Vaccine

This example illustrates the construction of Ad5 [E1-, E2b-] vectors containing an MAYV antigen and testing for expression and protective immunity by multiple injection of the vectors.

Ad5 [E1-, E2b-]-MAYV$_{str}$ vaccine is an adenovirus serotype 5 (Ad5) vector that is modified by removal of E1, E2b, and E3 gene regions, and insertion of the nucleic acid sequence encoding an MAYV structural polyprotein (the amino acid sequence is set forth in SEQ ID NO: 8) using a homologous recombination-based approach.

Ad5 [E1-, E2b-]-MAYV$_{str}$ is produced in E.C7 cells. The replication-deficient virus is propagated in the E.C7 packaging cell line, purified by ultracentrifugation or ion exchange column purification, and 64ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

MAYV structural proteins are expressed as a result of infection of E.C7 cells with Ad5 [E1-, E2b-]-MAYV$_{str}$. MAYV structural protein expression is detected by western blot with an anti-MAYV antibody.

Groups of ten (10) mice each are immunized two times subcutaneously at weekly intervals with a dose of $10^9$ VP Ad5 [E1-, E2b-]-MAYV$_{str}$. Control mice are injected with PBS or $10^9$ VPs Ad5-null. Mice are then challenged with a lethal dose of MAYV by injection of the virus. The survival rate, immune response, and weight are compared between the mice injected with the vaccine and the control group.

Example 6

Production and Testing of a Single-Targeted Ad5 [E1-, E2b-]-RRV Vaccine

This example illustrates the construction of Ad5 [E1-, E2b-] vectors containing a RRV antigen and testing for expression and protective immunity by multiple injection of the vectors.

Ad5 [E1-, E2b-]-RRV$_{str}$ vaccine is an adenovirus serotype 5 (Ad5) vector that is modified by removal of E1, E2b, and E3 gene regions, and insertion of the nucleic acid sequence encoding a RRV structural polyprotein (the amino acid sequence is set forth in SEQ ID NO: 11) using a homologous recombination-based approach.

Ad5 [E1-, E2b-]-RRV$_{str}$ is produced in E.C7 cells. The replication-deficient virus is propagated in the E.C7 packaging cell line, purified by ultracentrifugation or ion exchange column purification, and 65ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

RRV structural proteins are expressed as a result of infection of E.C7 cells with Ad5 [E1-, E2b-]-RRV$_{str}$. RRV structural protein expression is detected by western blot with an anti-RRV antibody.

Groups of ten (10) mice each are immunized two times subcutaneously at weekly intervals with a dose of $10^9$ VP Ad5 [E1-, E2b-]-RRV$_{str}$. Control mice are injected with PBS or $10^9$ VPs Ad5-null. Mice are then challenged with a lethal dose of RRV by injection of the virus. The survival rate, immune response, and weight are compared between the mice injected with the vaccine and the control group.

Example 7

Production and Testing of a Single-Targeted Ad5 [E1-, E2b-]-VEEV Vaccine

This example illustrates the construction of Ad5 [E1-, E2b-] vectors containing a VEEV antigen and testing for expression and protective immunity by multiple injection of the vectors.

Ad5 [E1-, E2b-]-VEEV$_{str}$ vaccine is an adenovirus serotype 5 (Ad5) vector that is modified by removal of E1, E2b, and E3 gene regions, and insertion of the nucleic acid sequence encoding a VEEV structural polyprotein (the amino acid sequence is set forth in SEQ ID NO: 14) using a homologous recombination-based approach.

Ad5 [E1-, E2b-]-VEEV$_{str}$ is produced in E.C7 cells. The replication-deficient virus is propagated in the E.C7 packaging cell line, purified by ultracentrifugation or ion exchange column purification, and 65ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

VEEV structural proteins are expressed as a result of infection of E.C7 cells with Ad5 [E1-, E2b-]-VEEV$_{str}$. VEEV structural protein expression is detected by western blot with an anti-VEEV antibody.

Groups of ten (10) mice each are immunized two times subcutaneously at weekly intervals with a dose of $10^9$ VP Ad5 [E1-, E2b-]-VEEV$_{str}$. Control mice are injected with PBS or $10^9$ VPs Ad5-null. Mice are then challenged with a lethal dose of VEEV by injection of the virus. The survival rate, immune response, and weight are compared between the mice injected with the vaccine and the control group.

Example 8

Production and Testing of a Single-Targeted Ad5 [E1-, E2b-]-EEEV Vaccine

This example illustrates the construction of Ad5 [E1-, E2b-] vectors containing an EEEV antigen and testing for expression and protective immunity by multiple injection of the vectors.

Ad5 [E1-, E2b-]-EEEV$_{str}$ vaccine is an adenovirus serotype 5 (Ad5) vector that is modified by removal of E1, E2b, and E3 gene regions, and insertion of the nucleic acid sequence encoding an EEEV structural polyprotein (the amino acid sequence is set forth in SEQ ID NO: 17) using a homologous recombination-based approach.

Ad5 [E1-, E2b-]-EEEV$_{str}$ is produced in E.C7 cells. The replication-deficient virus is propagated in the E.C7 packaging cell line, purified by ultracentrifugation or ion exchange column purification, and 66ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

EEEV structural proteins are expressed as a result of infection of E.C7 cells with Ad5 [E1-, E2b-]-EEEV$_{str}$. EEEV structural protein expression is detected by western blot with an anti-EEEV antibody.

Groups of ten (10) mice each are immunized two times subcutaneously at weekly intervals with a dose of $10^9$ VP Ad5 [E1-, E2b-]-EEEV$_{str}$. Control mice are injected with PBS or $10^9$ VPs Ad5-null. Mice are then challenged with a lethal dose of EEEV by injection of the virus. The survival rate, immune response, and weight are compared between the mice injected with the vaccine and the control group.

Example 9

Production and Testing of a Single-Targeted Ad5 [E1-, E2b-]-WEEV Vaccine

This example illustrates the construction of Ad5 [E1-, E2b-] vectors containing a WEEV antigen and testing for expression and protective immunity by multiple injection of the vectors.

Ad5 [E1-, E2b-]-WEEV$_{str}$ vaccine is an adenovirus serotype 5 (Ad5) vector that has been modified by removal of E1, E2b, and E3 gene regions, and insertion of the nucleic acid sequence encoding a WEEV structural polyprotein (the amino acid sequence is set forth in SEQ ID NO: 20) using a homologous recombination-based approach.

Ad5 [E1-, E2b-]-WEEV$_{str}$ is produced in E.C7 cells. The replication-deficient virus is propagated in the E.C7 packaging cell line, purified by ultracentrifugation or ion exchange column purification, and 66ittered. Viral infectious titer is determined as plaque-forming units (PFUs) on an E.C7 cell monolayer. The VP concentration is determined by sodium dodecyl sulfate (SDS) disruption and spectrophotometry at 260 nm and 280 nm.

WEEV structural proteins are expressed as a result of infection of E.C7 cells with Ad5 [E1-, E2b-]-WEEV$_{str}$. WEEV structural protein expression is detected by western blot with an anti-WEEV antibody.

Groups of ten (10) mice each are immunized two times subcutaneously at weekly intervals with a dose of $10^9$ VPs Ad5 [E1-, E2b-]-WEEV$_{str}$. Control mice are injected with PBS or $10^9$ VPs Ad5-null. Mice are then challenged with a lethal dose of WEEV by injection of the virus. The survival rate, immune response, and weight are compared between the mice injected with the vaccine and the control group.

Example 10

Pre-Clinical Studies of Ad5 [E1-, E2b-]-Chikungunya Vaccines in Mice

This example illustrates pre-clinical studies of Ad5 [E1-, E2b-]-Chikungunya vaccines in mice, including assessment of cell mediate immune (CMI) responses, cytolytic T lymphocyte (CTL) responses, intracellular cytokine expression, and antibody secretion. Pre-clinical studies included administration of Ad5 [E1-, E2b-]-Chikungunya vaccines, a comparison to controls, and an assessment of the immune responses in mice.

Pre-Clinical Assessment of Ad5 [E1-, E2b-]-Chikungunya Vaccines

CMI and CTL Responses.

Figure 6A:
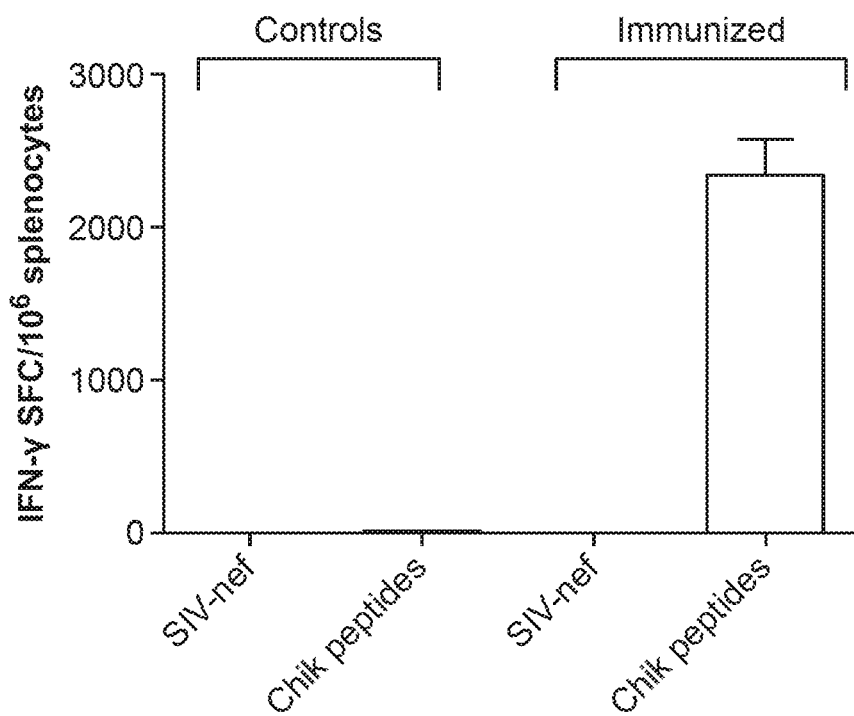
FIG. 6A illustrates CMI responses in Ad5 [E1-, E2b-]-CHIK immunized and control C57BL/6 mice as measured by IFN-γ secreting SFCs using an ELISpot assay.
Figure 6B:
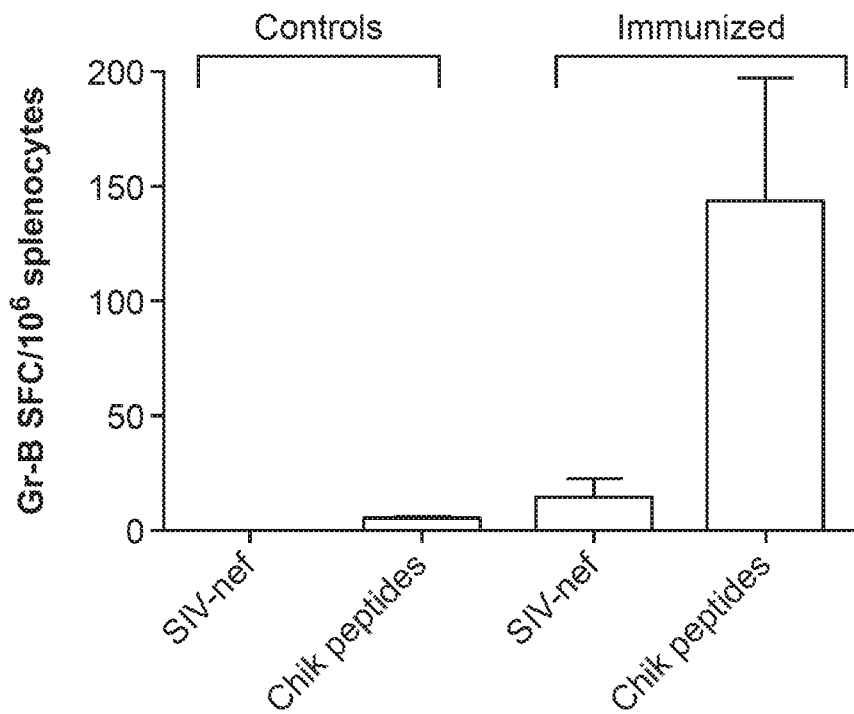
FIG. 6B illustrates CTL responses in Ad5 [E1-, E2b-]-CHIK immunized and control C57BL/6 mice as measured by Granzyme B (GR-B) secreting SFCs using an ELISpot assay.

CMI and CTL responses in mice were evaluated by an enzyme-linked immunospot (ELISPOT) assay. FIG. 6 illustrates CMI responses (IFN-γ) and CTL responses and Granzyme B responses in splenocytes from immunized or control mice using an ELISpot assay. C57BL/6 mice were immunized two times at two-week intervals with $1 \times 10^{10}$ VPs Ad5 [E1-, E2b-]-CHIK vaccine comprising SEQ ID NO: 1 or with $1 \times 10^9$ VPs Ad5 [E1-, E2b-]-null (empty vector controls). One week after the final immunization, splenocytes from individual mice were tested for induction of immune responses after exposure of cells to Chikungunya virus peptides. The data show the cumulative number of spot forming cells (SFCs) per $10^6$ splenocytes after exposure to three separate pools of Chikungunya virus peptides (peptide numbers for Chikungunya were large enough to merit division into three separate pools to use in assays—CHIKV peptide pool 1 comprised peptides 1-103, CHIKV peptide pool 2 comprising peptides 104-207, and peptide pool 3 comprising peptides 208-3 10). Additional splenocytes were separately exposed to an SIV-nef peptide pools as a negative control prior to assay measurements. FIG. 6A illustrates CMI responses in Ad5 [E1-, E2b-]-CHIK immunized and control C57BL/6 mice as measured by IFN-γ secreting SFCs using an ELISpot assay. Specificity of the response is evidenced by the lack of reactivity of splenocytes to the negative control SIV-nef peptide pool. A high number of IFN-γ secreting SFCs were induced in Ad5 [E1-, E2b-]-CHIK immunized mice as compared to control mice. FIG. 6B illustrates CTL responses in Ad5 [E1-, E2b-]-CHIK immunized and control C57BL/6 mice as measured by Granzyme B (Gr-B) secreting SFCs using an ELISpot assay. Specificity of the response is evidenced by the lack of reactivity of splenocytes to the negative control SIV-nef peptide pool. A high number of Granzyme B secreting SFCs were induced in Ad5 [E1-, E2b-]-CHIK immunized mice as compared to control mice.

Intracellular Cytokine Expression.

Figure 7A:
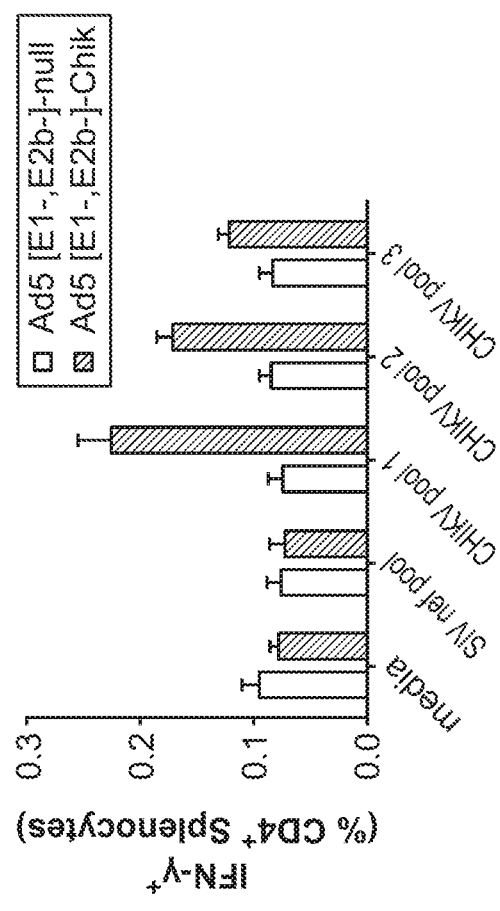
FIG. 7A illustrates lymphocyte activation as measured by flow cytometry analysis of intracellular expression of IFN-γ in CD8+ splenocytes after exposure of splenocytes from immunized mice and control mice to three separate pools of Chikungunya virus peptides and controls (media and SIV-nef peptide pools).
Figure 7B:
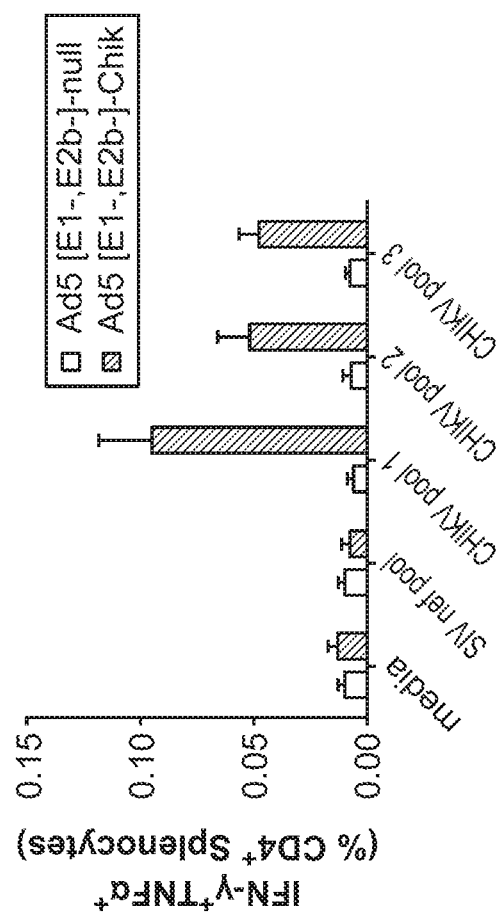
FIG. 7B illustrates lymphocyte activation as measured by flow cytometry analysis of intracellular expression of IFN-γ in CD4+ splenocytes after exposure of splenocytes from immunized mice and control mice to three separate pools of Chikungunya virus peptides and controls (media and SIV-nef peptide pools).
Figure 7C:
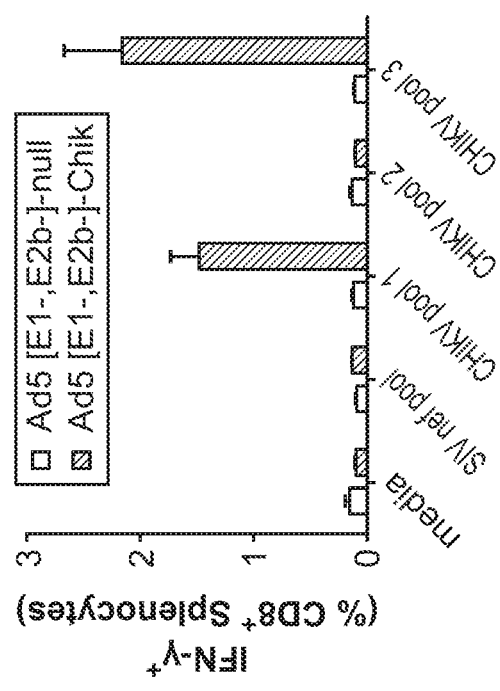
FIG. 7C illustrates lymphocyte activation as measured by flow cytometry analysis of intracellular expression of IFN-γ and TNF-α in CD8+ splenocytes after exposure of splenocytes from immunized mice and control mice to three separate pools of Chikungunya virus peptides and controls (media and SIV-nef peptide pools).
Figure 7D:
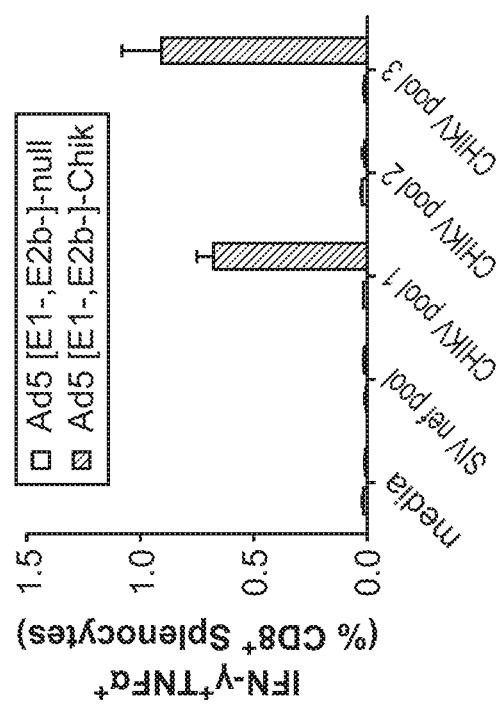
FIG. 7D illustrates lymphocyte activation as measured by flow cytometry analysis of intracellular expression of IFN-γ and TNF-α in CD4+ splenocytes after exposure of splenocytes from immunized mice and control mice to three separate pools of Chikungunya virus peptides and controls (media and SIV-nef peptide pools).

Flow cytometry analysis revealed the levels of lymphocyte activation as measured by evaluating intracellular cytokine expression. FIG. 7 illustrates lymphocyte activation in splenocytes from immunized or control C57BL/6 mice as measured by intracellular expression of IFN-γ or IFN-γ/TNF-α analyzed by flow cytometry. C57BL/6 mice were immunized two times at two-week intervals with $1\times10^{10}$ VPs Ad5 [E1-, E2b-]-CHIK vaccine comprising SEQ ID NO: 1 or with $1\times10^{10}$ VPs Ad5 [E1-, E2b-]-null (empty vector controls). One week after the final immunization, splenocytes from individual mice were exposed to three separate pools of Chikungunya virus peptides (peptide numbers for Chikungunya were large enough to merit division into three separate pools to use in assays—CHIKV peptide pool 1 comprised peptides 1-103, CHIKV peptide pool 2 comprising peptides 104-207, and peptide pool 3 comprising peptides 208-310) and analyzed by flow cytometry for induction of intracellular cytokine expression. FIG. 7A illustrates lymphocyte activation as measured by flow cytometry analysis of intracellular expression of IFN-γ in CD8+ splenocytes after exposure of splenocytes from immunized mice and control mice to three separate pools of Chikungunya virus peptides and controls (media and SIV-nef peptide pools). A higher percentage of CD8+ splenocytes from immunized mice expressed intracellular IFN-γ as compared to negative controls. FIG. 7B illustrates lymphocyte activation as measured by flow cytometry analysis of intracellular expression of IFN-γ in CD4+ splenocytes after exposure of splenocytes from immunized mice and control mice to three separate pools of Chikungunya virus peptides and controls (media and SIV-nef peptide pools). A higher percentage of CD4+ splenocytes from immunized mice expressed intracellular IFN-γ as compared to negative controls. FIG. 7C illustrates lymphocyte activation as measured by flow cytometry analysis of intracellular expression of IFN-γ and TNF-α in CD8+ splenocytes after exposure of splenocytes from immunized mice and control mice to three separate pools of Chikungunya virus peptides and controls (media and SIV-nef peptide pools). A higher percentage of CD8+ splenocytes from immunized mice expressed intracellular IFN-γ and TNF-α as compared to negative controls. FIG. 7D illustrates lymphocyte activation as measured by flow cytometry analysis of intracellular expression of IFN-γ and TNF-α in CD4+ splenocytes after exposure of splenocytes from immunized mice and control mice to three separate pools of Chikungunya virus peptides and controls (media and SIV-nef peptide pools). A higher percentage of CD4+ splenocytes from immunized mice expressed intracellular IFN-γ and TNF-α as compared to negative controls.

Antigen-Specific Antibody Production.

Figure 8:
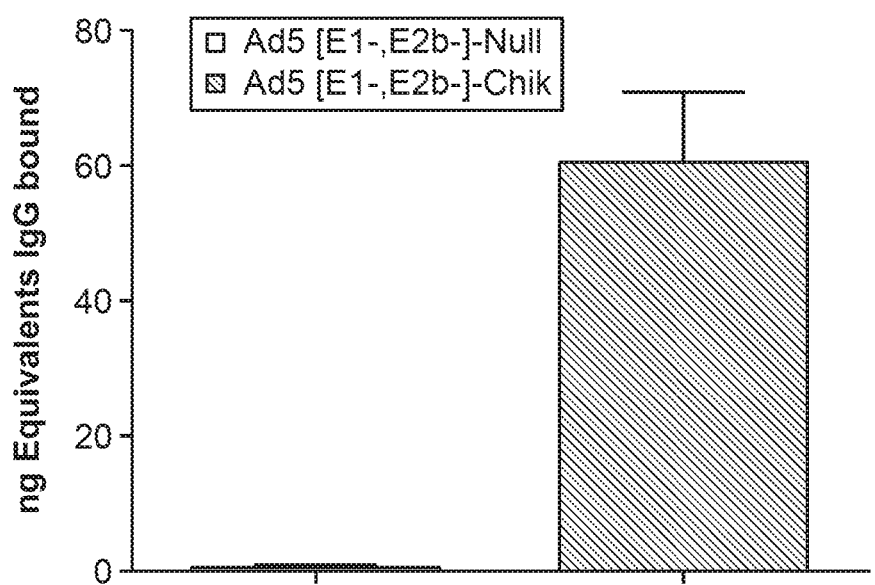
FIG. 8 illustrates anti-Chikungunya envelope protein-2 antibody responses in immunized mice as compared to control mice as measured by a quantitative enzyme-linked immunosorbent assay (ELISA). C57BL/6 mice were immunized two times at two-week intervals with $1\times10^{10}$ VPs Ad5 [E1-, E2b-]-CHIK vaccine comprising SEQ ID NO: 1 or with $1\times10^{10}$ VPs Ad5 [E1-, E2b-]-null (empty vector control). One week after the final immunization, sera from mice were evaluated for induction of antibody responses. Blood was collected by cheek pouch laceration under anesthesia.

Chikungunya-specific IgG antibodies were measured in the serum of immunized mice by an enzyme-linked immunosorbent assay (ELISA). FIG. 8 illustrates anti-Chikungunya envelope protein-2 antibody responses in immunized mice as compared to control mice as measured by a quantitative enzyme-linked immunosorbent assay (ELISA). C57BL/6 mice were immunized two times at two-week intervals with $1\times10^{10}$ VPs Ad5 [E1-, E2b-]-CHIK vaccine comprising SEQ ID NO: 1 or with $1\times10^{10}$ VPs Ad5 [E1-, E2b-]-null (empty vector controls). One week after the final immunization, sera from mice were evaluated for induction of antibody responses. Blood was collected by cheek pouch laceration under anesthesia. Anti-Chikungunya specific antibody responses were induced at higher levels in immunized mice as compared to control mice.

Example 11

Prevention of Chikungunya Infection with Ad5 [E1-, E2b-]-Chikungunya Vaccine

This example illustrates prevention of Chikungunya infection by prophylaxis with any Ad5 [E1-, E2b-]-Chikungunya vaccine of this disclosure including an Ad5 [E1-, E2b-] with any one of, or any combination of, Chikungunya antigens (e.g., SEQ ID NO: 1-SEQ ID NO: 3) inserted into the adenovirus vector. An Ad5 [E1-, E2b-]-Chikungunya vaccine is constructed as described in EXAMPLE 1 for a single-targeted Chikungunya vaccine or is constructed as described in EXAMPLE 3 for a multi-targeted Chikungunya vaccine. The Ad5 [E1-, E2b-]-Chikungunya vaccine is administered to a subject subcutaneously, intradermally, or intramuscularly, once or every two weeks for a total of two immunizations. Cellular and humoral immune responses against Chikungunya virus and protection against infection by Chikungunya virus is induced after immunization of a subject with the Ad5 [E1-, E2b-]-Chikungunya vaccine. In other words, immunity by prophylaxis with the Ad5 [E1-, E2b-]-Chikungunya vaccine is conferred to the subject. The subject is any animal including a human, a non-human primate, or any other non-human animal.

Example 12

Prevention of Chikungunya Infection with Ad5 [E1-, E2b-]-Chikungunya Vaccine and a Co-Stimulatory Molecule This example illustrates prevention of Chikungunya infection by prophylaxis with any Ad5 [E1-, E2b-]-Chikungunya vaccine of this disclosure including an Ad5 [E1-, E2b-] with any one of, or any combination of, Chikungunya antigens (e.g., SEQ ID NO: 1-SEQ ID NO: 3) inserted into the adenovirus vector in combination with any co-stimulatory molecule described herein. An Ad5 [E1-, E2b-]-Chikungunya vaccine is constructed as described in EXAMPLE 1 for a single-targeted Chikungunya vaccine or is constructed as described in EXAMPLE 3 for a multi-targeted Chikungunya vaccine. The Ad5 [E1-, E2b-]-Chikungunya vaccine is administered subcutaneously, intradermally, or intramuscularly to a subject once or every two weeks for a total of two immunizations. The Ad vaccine is co-administered with a co-stimulatory molecule, such as a toll-like receptor (TLR) agonist mixed with the vaccine formulation. Cellular and humoral immune responses against Chikungunya virus and protection against infection by Chikungunya virus is induced after immunization of a subject with the combination of Ad5 [E1-, E2b-]-Chikungunya vaccine and co-stimulatory molecule. In other words, immunity by prophylaxis with the Ad5 [E1-, E2b-]-Chikungunya vaccine and co-stimulatory molecule is conferred to the subject.

Example 13

Prevention of Chikungunya Infection with Ad5 [E1-, E2b-]-Chikungunya Vaccine and an Immunological Fusion Partner This example illustrates prevention of Chikungunya infection by prophylaxis with any Ad5 [E1-, E2b-]-CHIK vaccine of this disclosure including an Ad5 [E1-, E2b-] with any one of, or any combination of, Chikungunya antigens (e.g., SEQ ID NO: 1-SEQ ID NO: 3) inserted into the adenovirus vector as well as any immunological fusion partner described herein, also encoded by the adenovirus vector. An Ad5 [E1-, E2b-]-CHIK vaccine is constructed as described in EXAMPLE 1 for a single-targeted Chikungunya vaccine or is constructed as described in EXAMPLE 3 for a multi-targeted Chikungunya vaccine with the Ad vector additionally encoding for any immunological fusion partner disclosed herein. The Ad5 [E1-, E2b-]-Chikungunya vaccine is administered subcutaneously, intradermally, or intramuscularly to a subject, once or every two weeks for a total of two immunizations. Vaccines with immunological fusion partners are administered subcutaneously, intradermally, or intramuscularly. Cellular and humoral immune responses against Chikungunya virus and protection against infection by Chikungunya virus is induced after immunization of a subject with Ad5 [E1-, E2b-]-Chikungunya vaccine-immunological fusion partner and co-stimulatory molecule. In other words, immunity by prophylaxis with the Ad5 [E1-, E2b-]-Chikungunya vaccine-immunological fusion partner is conferred to the subject. The subject is any animal including a human, a non-human primate, or any other non-human animal.

Example 14

Prevention of O'Nyong Nyong Virus Infection with Ad5 [E1-, E2b-]-O'Nyong Nyong Virus (ONNV) Vaccine This example illustrates prevention of o'nyong-nyong virus (ONNV) infection by prophylaxis with any Ad5 [E1-, E2b-]-ONNV vaccine of this disclosure including an Ad5 [E1-, E2b-] with any one of, or any combination of, ONNV antigens (e.g., SEQ ID NO: 4-SEQ ID NO: 6) inserted into the adenovirus vector. An Ad5 [E1-, E2b-]-ONNV vaccine is constructed as adapted from EXAMPLE 1 or as described in EXAMPLE 4 for a single-targeted ONNV vaccine or is constructed as adapted from EXAMPLE 3 for a multi-targeted ONNV vaccine. The Ad5 [E1-, E2b-]-ONNV vaccine is administered to a subject subcutaneously, intradermally, or intramuscularly, once or every two weeks for a total of two immunizations. Cellular and humoral immune responses against ONNV virus and protection against infection by ONNV virus is induced after immunization of a subject with the Ad5 [E1-, E2b-]-ONNV vaccine. In other words, immunity by prophylaxis with the Ad5 [E1-, E2b-]-ONNV vaccine is conferred to the subject. The subject is any animal including a human, a non-human primate, or any other non-human animal.

Example 15

Prevention of Ross River Virus Infection with Ad5 [E1-, E2b-]-Ross River Virus (RRV) Vaccine This example illustrates prevention of Ross River virus (RRV) infection by prophylaxis with any Ad5 [E1-, E2b-]-RRV vaccine of this disclosure including an Ad5 [E1-, E2b-] with any one of, or any combination of, RRV antigens (e.g., SEQ ID NO: 10-SEQ ID NO: 12) inserted into the adenovirus vector. An Ad5 [E1-, E2b-]-RRV vaccine is constructed as adapted from EXAMPLE 1 or described in EXAMPLE 6 for a single-targeted RRV vaccine or is constructed as adapted from EXAMPLE 3 for a multi-targeted RRV vaccine. The Ad5 [E1-, E2b-]-RRV vaccine is administered to a subject subcutaneously, intradermally, or intramuscularly, once or every two weeks for a total of two immunizations. Cellular and humoral immune responses against RRV virus and protection against infection by RRV virus is induced after immunization of a subject with the Ad5 [E1-, E2b-]-RRV vaccine. In other words, immunity by prophylaxis with the Ad5 [E1-, E2b-]-RRV vaccine is conferred to the subject. The subject is any animal including a human, a non-human primate, or any other non-human animal.

Example 16

Prevention of Mayaro Fever Virus Infection with Ad5 [E1-, E2b-]-Mayaro Fever Virus (MAYV) Vaccine This example illustrates prevention of Marayo fever virus (MAYV) infection by prophylaxis with any Ad5 [E1-, E2b-]-MAYV vaccine of this disclosure including an Ad5 [E1-, E2b-] with any one of, or any combination of, MAYV antigens (e.g., SEQ ID NO: 7-SEQ ID NO: 9) inserted into the adenovirus vector. An Ad5 [E1-, E2b-]-MAYV vaccine is constructed as adapted from EXAMPLE 1 or described in EXAMPLE 5 for a single-targeted MAYV vaccine or is constructed as adapted from EXAMPLE 3 for a multi-targeted MAYV vaccine. The Ad5 [E1-, E2b-]-MAYV vaccine is administered to a subject subcutaneously, intradermally, or intramuscularly, once or every two weeks for a total of two immunizations. Cellular and humoral immune responses against MAYV virus and protection against infection by MAYV virus is induced after immunization of a subject with the Ad5 [E1-, E2b-]-MAYV vaccine. In other words, immunity by prophylaxis with the Ad5 [E1-, E2b-]-MAYV vaccine is conferred to the subject. The subject is any animal including a human, a non-human primate, or any other non-human animal.

Example 17

Prevention of Venezuelan Equine Encephalitis Virus Infection with Ad5 [E1-, E2b-]-Venezuelan Equine Encephalitis Virus (VEEV) Vaccine This example illustrates prevention of Venezuelan equine encephalitis virus (VEEV) infection by prophylaxis with any Ad5 [E1-, E2b-]-VEEV vaccine of this disclosure including an Ad5 [E1-, E2b-] with any one of, or any combination of, VEEV antigens (e.g., SEQ ID NO: 13-SEQ ID NO: 15) inserted into the adenovirus vector. An Ad5 [E1-, E2b-]-VEEV vaccine is constructed as adapted from EXAMPLE 1 or described in EXAMPLE 7 for a single-targeted VEEV vaccine or is constructed as adapted from EXAMPLE 3 for a multi-targeted VEEV vaccine. The Ad5 [E1-, E2b-]-VEEV vaccine is administered to a subject subcutaneously, intradermally, or intramuscularly, once or every two weeks for a total of two immunizations. Cellular and humoral immune responses against VEEV virus and protection against infection by VEEV virus is induced after immunization of a subject with the Ad5 [E1-, E2b-]-VEEV vaccine. In other words, immunity by prophylaxis with the Ad5 [E1-, E2b-]-VEEV vaccine is conferred to the subject. The subject is any animal including a human, a non-human primate, or any other non-human animal.

Example 18

Prevention of Western Equine Encephalomyelitis Virus Infection with Ad5 [E1-, E2b-]-Western Equine Encephalomyelitis Virus (WEEV) Vaccine This example illustrates prevention of Western equine encephalomyelitis virus (WEEV) infection by prophylaxis with any Ad5 [E1-, E2b-]-WEEV vaccine of this disclosure including an Ad5 [E1-, E2b-] with any one of, or any combination of, WEEV antigens (e.g., SEQ ID NO: 19-SEQ ID NO: 21) inserted into the adenovirus vector. An Ad5 [E1-, E2b-]-WEEV vaccine is constructed as adapted from EXAMPLE 1 or described in EXAMPLE 9 for a single-targeted WEEV vaccine or is constructed as adapted from EXAMPLE 3 for a multi-targeted WEEV vaccine. The Ad5 [E1-, E2b-]-WEEV vaccine is administered to a subject subcutaneously, intradermally, or intramuscularly, once or every two weeks for a total of two immunizations. Cellular and humoral immune responses against WEEV virus and protection against infection by WEEV virus is induced after immunization of a subject with the Ad5 [E1-, E2b-]-WEEV vaccine. In other words, immunity by prophylaxis with the Ad5 [E1-, E2b-]-WEEV vaccine is conferred to the subject. The subject is any animal including a human, a non-human primate, or any other non-human animal.

Example 19

Prevention of Eastern Equine Encephalitis Virus Infection with Ad5 [E1-, E2b-]-Eastern Equine Encephalitis Virus (EEEV) Vaccine This example illustrates prevention of Eastern equine encephalitis virus (EEEV) infection by prophylaxis with any Ad5 [E1-, E2b-]-EEEV vaccine of this disclosure including an Ad5 [E1-, E2b-] with any one of, or any combination of, EEEV antigens (e.g., SEQ ID NO: 16-SEQ ID NO: 18) inserted into the adenovirus vector. An Ad5 [E1-, E2b-]-EEEV vaccine is constructed as adapted from EXAMPLE 1 or described in EXAMPLE 8 for a single-targeted EEEV vaccine or is constructed as adapted from EXAMPLE 3 for a multi-targeted EEEV vaccine. The Ad5 [E1-, E2b-]-EEEV vaccine is administered to a subject subcutaneously, intradermally, or intramuscularly, once or every two weeks for a total of two immunizations. Cellular and humoral immune responses against EEEV virus and protection against infection by EEEV virus is induced after immunization of a subject with the Ad5 [E1-, E2b-]-EEEV vaccine. In other words, immunity by prophylaxis with the Ad5 [E1-, E2b-]-EEEV vaccine is conferred to the subject. The subject is any animal including a human, a non-human primate, or any other non-human animal.

Example 20

Prevention of Alphavirus Infections with Ad5 [E1-, E2b-]-Alphavirus Vaccine

This example illustrates prevention of alphavirus infections by prophylaxis with any Ad5 [E1-, E2b-]-alphavirus vaccine. The Ad5 [E1-, E2b-]-alphavirus vaccine is comprised of any of combination of: single-targeted or multi-targeted Ad5 [E1, E2b]-ONNV vector as described in EXAMPLE 15, single-targeted or multi-targeted Ad5 [E1, E2b]-CHIK vector as described in EXAMPLE 11, single-targeted or multi-targeted Ad5 [E1, E2b]-RRV vector as described in EXAMPLE 16, single-targeted or multi-targeted Ad5 [E1, E2b]-MAYV vector as described in EXAMPLE 17, single-targeted or multi-targeted Ad5 [E1, E2b]-VEEV vector as described in EXAMPLE 18, single-targeted or multi-targeted Ad5 [E1, E2b]-WEEV vector as described in EXAMPLE 19, an single-targeted or multi-targeted Ad5 [E1, E2b]-RRV vector as described in EXAMPLE 20. Alternatively, the Ad5 [E1-, E2b-]-alphavirus vaccine is comprised of an Ad5 [E1-, E2b-] with any combination of at least two antigens from different alphaviruses inserted into the adenovirus vector. For example, the at least two antigens is comprised of any combination of an ONNV antigen (e.g., any one of SEQ ID NO: 4-SEQ ID NO: 6), a CHIK antigen (e.g., any one of SEQ ID NO: 1-SEQ ID NO: 3), an EEEV antigen (e.g., any one of SEQ ID NO: 16-SEQ ID NO: 18), a WEEV antigen (e.g., any one of SEQ ID NO: 19-SEQ ID NO: 21), a VEEV antigen (e.g., any one of SEQ ID NO: 13-SEQ ID NO: 15), a MAYV antigen (e.g., any one of SEQ ID NO: 7-SEQ ID NO: 9), and/or a RRV antigen (e.g., any one of SEQ ID NO: 10-SEQ ID NO: 12). The Ad5 [E1-, E2b-]-alphavirus vaccine is administered to a subject subcutaneously, intradermally, or intramuscularly, once or every two weeks for a total of two immunizations. Cellular and humoral immune responses against alphaviruses and protection against infection by alphavirus is induced after immunization of a subject with the Ad5 [E1-, E2b-]-alphavirus vaccine. In other words, immunity by prophylaxis with the Ad5 [E1-, E2b-]-alphavirus vaccine is conferred to the subject. The subject is any animal including a human, a non-human primate, or any other non-human animal.

While preferred embodiments of the present invention have been shown and described herein, it will be apparent to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

SEQUENCES

| SEQ ID NO | Sequence |
| --- | --- |
| SEQ ID NO: 1 | ATGGCTGCGTGAGACACACGTAGCCTACCAGTTTCTTACTGCTCTAC<br>TCTGCAAAGCAAGAGATTAAGAACCCATCATGGATCCTGTGTACGT<br>GGACATAGACGCTGACAGCGCCTTTTTGAAGGCCCTGCAACGTGCG<br>TACCCCATGTTTGAGGTGGAACCTAGGCAGGTCACACCGAATGACC<br>ATGCTAATGCTAGAGCGTTCTCGCATCTAGCTATAAAACTAATAGA<br>GCAGGAAATTGATCCCGACTCAACCATCCTGGATATTGGTAGTGCG<br>CCAGCAAGGAGGATGATGTCGGACAGGAAGTACCACTGCGTTTGCC<br>CGATGCGCAGTGCAGAAGATCCCGAGAGACTCGCCAATTATGCGA<br>GAAAGCTAGCATCTGCCGCAGGAAAAGTCCTGGACAGAAACATCT<br>CTGGAAAGATCGGGGACTTACAAGCAGTAATGGCCGTGCCAGACA<br>CGGAGACGCCAACATTCTGCTTACACACAGATGTATCATGTAGACA<br>GAGAGCAGACGTCGCGATATACCAAGACGTCTATGCTGTACACGCA<br>CCCACGTCGCTATACCACCAGGCGATTAAAGGGGTCCGATTGGCGT<br>ACTGGGTAGGGTTTGACACAACCCCGTTCATGTACAATGCCATGGC<br>GGGTGCCTACCCCTCATACTCGACAAATTGGGCAGATGAGCAGGTA<br>CTGAAGGCTAAGAACATAGGATTATGTTCAACAGACCTGACGGAA<br>GGTAGACGAGGCAAATTGTCTATTATGAGAGGAAAAAAGCTAGAA<br>CCGTGCGACCGTGTGCTGTTCTCAGTAGGGTCAACGCTCTACCCGG<br>AAAGCCGTAAGCTACTTAAGAGCTGGCACCTACCATCGGTGTTCCA<br>TTTAAAGGGCAAGCTCAGCTTCACATGCCGCTGTGATACAGTGGTT<br>TCGTGCGAAGGCTACGTCGTTAAGAGAATAACGATGAGCCCAGGCC<br>TTTACGAAAAACCACAGGGTATGCGGTAACCCACCACGCAGACG<br>GATTCCTGATGTGCAAGACCACCGACACGGTTGACGGCGAAAGAGT<br>GTCATTCTCGGTGTGCACGTACGTGCCGGCGACCATTTGTGATCAA<br>ATGACCGGCATCCTTGCTACAGAAGTCACGCCGGAGGATGCACAGA<br>AGCTGTTGGTGGGGCTGAACCAGAGAATAGTGGTTAACGGCAGAA<br>CGCAACGGAATACGAACACCATGAAAAACTATATGATTCCCGTGGT<br>CGCCCAAGCCTTCAGTAAGTGGGCAAAGGAGTGCCGGAAAGACAT<br>GGAAGATGAAAAACTCCTGGGGGTCAGAGAAAGAACACTGACCTG<br>CTGCTGTCTATGGGCATTTAAGAAGCAGAAAACACACACGGTCTAC<br>AAGAGGCCTGATACCCAGTCAATTCAGAAGGTTCAGGCCGAGTTTG<br>ACAGCTTTGTGGTACCGAGCCTGTGGTCGTCCGGGTTGTCAATCCC<br>GTTGAGGACTAGAATCAAATGGTTGTTAAGCAAGGTGCCAAAAACC<br>GACCTGACCCCATACAGCGGGGACGCCCAAGAAGCCCGGGACGCA<br>GAAAAAGAAGCAGAGGAAGAACGAGAAGCAGAACTGACTCTTGAA<br>GCCCTACCACCCCTTCAGGCAGCACAGGAAGATGTTCAGGTCGAAA<br>TCGACGTGGAACAGCTTGAGGACAGAGCGGGTGCAGGAATAATAG<br>AGACTCCGAGAGGAGCTATCAAAGTTACTGCCCAACCAACAGACC<br>ACGTCGTGGGAGAGTACTTGGTTCTTTCCCCGCAGACCGTACTACG<br>TAGCCAAAAGCTTAGCCTGATTCACGCTTTGGCGGAGCAAGTGAAG<br>ACGTGCACGCACAGCGGACGAGCAGGGAGGTATGCGGTCGAAGCG<br>TACGACGGCAGAGTCCTAGTGCCCTCAGGCTACGCAATCTCGCCTG<br>AAGACTTCCAGAGCCTAAGCGAAAGCGCAACGATGGTGTACAACG<br>AAAGAGAGTTCGTAAACAGAAAGCTACACCATATTGCGATGCATG<br>GACCAGCCCTGAACACCGACGAAGAGTCGTATGAGCTGGTGAGGG<br>CAGAGAGGACAGAACACGAGTACGTCTACGACGTGGACCAGAGAA<br>GATGCTGTAAGAAGGAAGAAGCTGCAGGACTGGTACTGGTGGGCG<br>ACTTGACTAATCCGCCCTACCACGAATTCGCATATGAAGGGCTAAA<br>AATCCGCCCTGCCTGCCCATACAAAATTGCAGTCATAGGAGTCTTC<br>GGAGTACCAGGATCTGGCAAGTCAGCTATTATCAAGAACCTAGTTA<br>CCAGGCAAGACCTGGTGACTAGCGGAAAGAAAGAAAACTGCCAAG<br>AAATCACCACCGACGTGATGAGACAGAGAGGTCTAGAGATATCTG<br>CACGTACGGTTGACTCGCTGCTCTTGAATGGATGTAACAGACCAGT<br>CGACGTGTTGTACGTAGACGAGGCGTTTGCGTGCCACTCTGGAACG<br>TTACTTGCATTGATCGCCTTGGTGAGACCAAGACAGAAAGTTGTAC<br>TTTGTGGTGACCCGAAGCAGTGCGGCTTCTTCAATATGATGCAGAT<br>GAAAGTCAACTATAATCACAACATCTGCACCCAAGTGTACCACAAA<br>AGTATCTCCAGGCGGTGTACACTGCCTGTGACTGCCATTGTGTCATC<br>GTTGCATTACGAAGGCAAAATGCGCACTACAGGCTCAACAAAACCTGACCCTGGA<br>GCCGATTGTAGTGGACACTACAGGCTCAACAAAACCTGACCCTGGA<br>GATCTCGTGTTAACGTGCTTCAGAGGATGGGTTAAACAACTGCAAA<br>TTGACTATCGTGGACACGAGGTCATGACAGCAGCCGCATCCCAAGG<br>GTTAACCAGAAAAGGAGTTTACGCAGTTAGGCAAAAAGTTAACGA<br>AAACCCGCTTTATGCATCAACGTCAGAGCACGTCAACGTACTCCTA<br>ACGCGTACGGAAGGTAAACTGGTATGGAAGACACTCTCCGGTGACC<br>CGTGGATAAAGACGCTGCAGAACCCACCGAAAGGAAACTTCAAAG<br>CAACTATTAAGGAGTGGGAGGTGGAGCATGCATCAATAATGGCGG<br>GCATCTGCAGTCACCAAATGACCTTTGATACATTCCAAACAAAGC<br>CAACGTTTGTTGGGCTAAGAGTTTGGTCCCTATCCTCGAAACAGCG<br>GGGATAAAACTAAACGACAGGCAGTGGTCCCAGATAATTCAAGCC<br>TTCAAAGAAGACAAAGCATATTCACCCGAAGTAGCCCTGAATGAA<br>ATATGCACGCGCATGTATGGGGTGGATCTAGACAGCGGGCTATTTT<br>CTAAACCGTTGGTGTCTGTGTATTACGCGGATAACCACTGGGATAA<br>TAGGCCTGGAGGGAAGATGTTCGGATTCAACCCCGAGGCAGCATCC<br>ATTCTAGAAAGAAAGTATCCATTTACAAAAGGGAAGTGGAACATC<br>AACAAGCAGATCTGCGTGACTACCAGGAGGATAGAAGACTTCAAC<br>CCTACCACCAACATTATACCGGCCAACAGGAGACTACCACACTCAT |

| SEQ ID NO | Sequence |
|---|---|
| | TAGTGGCCGAACACCGCCCAGTAAAAGGGGAAAGAATGGAATGGC<br>TGGTTAACAAGATAAACGGCCACCACGTGCTCCTGGTCAGTGGCTG<br>TAGCCTTGCACTGCCTACTAAGAGAGTCACTTGGGTAGCGCCACTA<br>GGTGTCCGCGGAGCGGACTATACATACAACCTAGAGTTGGGTCTGC<br>CAGCAACGCTTGGTAGGTATGACCTAGTGGTCATAAACATCCACAC<br>ACCTTTTCGCATACACCATTATCAACAGTGCGTAGACCACGCAATG<br>AAACTGCAAATGCTCGGGGGTGACTCATTGAGACTGCTCAAACCGG<br>GTGGCTCTCTATTGATCAGAGCATATGGTTACGCAGATAGAACCAG<br>TGAACGAGTCATCTGCGTATTGGGACGCAAGTTTAGATCATCTAGA<br>GCGTTGAAACCACCATGTGTCACCAGCAACACTGAGATGTTTTTCT<br>ATTCAGCAACTTTGACAATGGCAGAAGGAATTTCACAACTCATGTC<br>ATGAACAATCAACTGAATGCAGCCTTTGTAGGACAGGCCACCCGAG<br>CAGGATGTGCACCGTCGTACCGGGTAAAACGCATGGATATCGCGAA<br>GAACGATGAAGAGTGCGTAGTCAACGCCGCCAACCCTCGCGGGTTA<br>CCAGGTGACGGTGTTTGCAAGGCAGTATACAAAAAATGGCCGGAG<br>TCCTTTAAGAACAGTGCAACACCAGTGGGAACCGCAAAAACAGTC<br>ATGTGCGGTACGTATCCAGTAATCCACGCCGTTGGACCAAACTTCT<br>CTAATTATTCGGAGTCTGAAGGGGACCGAGAATTGGCGGCTGCCTA<br>TCGAGAAGTCGCAAAGGAGGTAACTAGACTGGGAGTAAATAGTGT<br>AGCTATACCTCTCCTCTCCACAGGTGTATACTCAGGAGGGAAAGAC<br>AGGCTGACCCAGTCACTGAACCACCTCTTTACAGCCATGGACTCGA<br>CGGATGCAGACGTGGTCATCTACTGCCGCGACAAAGAATGGGAGA<br>AGAAAATATCTGAGGCCATACAGATGCGGACCCAAGTGGAGCTGC<br>TGGATGAGCACATCTCCATAGACTGCGATGTTGTTCGCGTGCACCC<br>TGACAGCAGCTTGGCAGGCAGAAAAGGATACAGCACCACGGAAGG<br>CGCACTGTACTCATATCTAGAAGGGACCCGTTTTCACCAAACGGCA<br>GTGGATATGGCAGAGATATATACTATGTGGCCAAAGCAAACAGAG<br>GCCAACGAGCAAGTTTGCCTATATGCCCTGGGGGAAAGTATTGAAT<br>CGATCAGGCAGAAATGCCCGGTGGATGATGCAGATGCATCATCTCC<br>CCCGAAAACTGTCCCGTGCCTCTGCCGTTACGCCATGACACCGAAA<br>CGCGTTACCCGACTTCGCATGAACCATGTCACAAGCATAATTGTGT<br>GTTCTTCGTTTCCCCTTCCAAAGTACAAAATAGAAGGAGTGCAAAA<br>AGTCAAATGCTCCAAGGTAATGCTATTTGACCACAACGTGCCATCG<br>CGCGTAAGTCCAAGGGAATACAGACCTTCCCAGGAGTCTGTACAGG<br>AAGCGAGTACGACCACGTCACTGACGCATAGCCAATTCGATCTAAG<br>CGTTGACGGCAAGATACTGCCCGTCCCGTCAGACCTGGATGCTGAC<br>GCCCCAGCCCTAGAACCAGCCCTTGACGACGGGCGATACACACGT<br>TGCCATCTGCAACCGGAAACCTTGCGGCCGTGTCTGACTGGGTAAT<br>GAGCACCGTACCTGTCGCGCCGCCCAGAAGAAGGCGAGGGAGAAA<br>CCTGACTGTGACATGCGACGAGAGAGAAGGGAATATAACACCCAT<br>GGCTAGCGTCCGATTCTTTAGGGCAGAGCTGTGTCCAGTCGTACAA<br>GAAACAGCGGAGACGCGTGACACAGCTATGTCTCTTCAGGCACCGC<br>CGAGTACCGCCACGGAACTGAGTCACCCGCCGATCTCCTTCGGTGC<br>ACCAAGCGAGACGTTCCCCATCACATTTGGGGACTTCAACGAAGGA<br>GAAATCGAAAGCTTGTCTTCTGAGCTACTAACTTTCGGAGACTTCCT<br>ACCCGGAGAAGTGGATGATTTGACAGATAGCGACTGGTCCACGTGC<br>TCAGACACGGACGACGAGTTACGACTAGACAGGGCAGGTGGGTAT<br>ATATTCTCGTCGGACACTGGTCCAGGTCATTTACAACAGAAGTCAG<br>TACGCCAGTCAGTGCTGCCGGTGAACACCCTGGAGGAAGTCCACGA<br>GGAGAAGTGTTACCCACCTAAGCTGGATGAAGCAAAGGAGCAACT<br>ACTACTTAAGAAACTCCAGGAGAGTGCATCCATGGCCAACAGAAG<br>CAGGTATCAGTCGCGCAAAGTAGAAAACATGAAAGCAACAATCAT<br>CCAGAGACTAAAGAGAGGCTGTAGATTATACTTAATGTCAGAGACC<br>CCAAAAGTCCCTACCTACCGGACCACATATCCGGCGCCTGTGTACT<br>CGCCTCCGATTAACGTCCGACTGTCCAACCCCGAGTCCGCAGTGGC<br>AGCATGCAATGAGTTCTTGGCTAGAAACTATCCAACTGTTTCATCAT<br>ACCAAATCACCGACGAGTATGATGCATATCTAGACATGGTGGACGG<br>GTCGGAGAGTTGTCTGGACCGAGCGACATTCAATCCGTCAAAACTT<br>AGGAGCTACCCAAAACAGCACGCTTACCACGCGCCCTCCATCAGAA<br>GCGCTGTACCGTCCCCATTCCAGAACACACTACAGAATGTACTGGC<br>AGCAGCCACGAAAAGAAACTGCAACGTCACACAGATGAGGGAATT<br>ACCCACTTTGGACTCAGCAGTATTCAACGTGGAGTGTTTCAAAAAA<br>TTCGCATGCAACCAAGAATACTGGGAAGAATTTGCTGCCAGCCCTA<br>TCAGGATAACAACTGAGAATTTAACAACCTATGTTACTAAACTAAA<br>GGGGCCAAAAGCAGCAGCGCTATTTGCAAAAACCCATAATCTGCTG<br>CCACTGCAGGAAGTGCCAATGGATAGGTTCACAGTAGACATGAAA<br>AGGGATGTGAAGGTGACTCCTGGTACAAAGCACACAGAGGAAAGA<br>CCTAAGGTACAGGTTATACAGGCGGCTGAACCCTTGGCAACAGCAT<br>ACCTATGTGGGATTCACAGAGAGCTGGTTAGGAGGCTGAACGCCGT<br>CCTCCTACCCAATGTACATACACTATTTGACATGTCTGCCGAGGATT<br>TCGATGCCATCATAGCCGCACACTTTAAGCCAGGAGACACTGTTTT<br>AGAAACGGACATAGCCTCCTTTGATAAGAGCCAAGATGATTCACTT<br>GCGCTTACTGCTTTAATGCTGTTAGAGGATTTAGGGGTGGATCACTC<br>CCTGTTGGACTTGATAGAGGCTGCTTTCGGAGAGATTTCCAGCTGTC<br>ATCTACCGACAGGTACGCGCTTCAAGTTCGGCGCCATGATGAAATC |

| SEQ ID NO | Sequence |
|---|---|
| | TGGTATGTTCCTAACTCTGTTCGTCAACACACTGCTAAATATCACCA<br>TCGCCAGCCGAGTGCTGGAAGATCGTCTGACAAAATCCGCGTGCGC<br>AGCCTTCATCGGCGACGACAACATAATACATGGAGTCGTCTCCGAT<br>GAATTGATGGCAGCCAGATGCGCCACTTGGATGAACATGGAAGTG<br>AAGATCATAGATGCAGTTGTATCCCAGAAAGCCCCTTACTTTTGTG<br>GAGGGTTTATACTGCACGATATCGTGACAGGAACAGCTTGCAGAGT<br>GGCAGACCCGCTAAAAAGGCTATTTAAACTGGGCAAACCGCTAGC<br>GGCAGGTGACGAACAAGATGAGGATAGAAGACGAGCGCTGGCTGA<br>CGAAGTGGTCAGATGGCAACGAACAGGGCTAATTGATGAGTTGGA<br>GAAAGCGGTATACTCTAGGTATGAAGTGCAGGGTATATCAGTTGTG<br>GTAATGTCCATGGCCACCTTTGCAAGCTCCAGATCCAACTTCGAGA<br>AGCTCAGAGGACCCGTCGTAACTTTGTACGGCGGTCCTAAATAGGT<br>ACGCACTACAGCTACCTATTTTGCAGAAGCCGACAGTAAGTACCTA<br>AACACTAATCAGCTACAATGGAGTTCATCCCAACCCAAACTTTTTA<br>CAACAGGAGGTACCAGCCTCGACCCTGGACTCCGCGCCCTACTATC<br>CAAGTCATCAGGCCCAGACCGCGCCCGCAGAGGCAAGCTGGGCAA<br>CTTGCCCAGCTGATCTCAGCAGTTAATAAACTGACAATGCGCGCGG<br>TACCCCAACAGAAGCCACGCAAGAATCGGAAGAATAAGAAGCAAA<br>AGCAAAAGCAGCAGGCGCCACAAAACAACACAAACCAAAAGAAG<br>CAGCCACCTAAAAAGAAACCAGCTCAAAAGAAAAAGAAGCCGGGC<br>CGCAGAGAGGATGTGCATGAAAATCGAAAATGACTGTATTTTCG<br>AAGTCAAGCACGAAGGTAAGGTAACAGGTTACGCGTGCTTGGTGG<br>GGGACAAAGTAATGAAACCAGCACACGTAAAGGGGACCATCGATA<br>ACGCGGACCTGGCCAAATTGGCCTTTAAGCGGTCATCTAAGTACGA<br>CCTTGAATGCGCGCAGATACCCGTGCACATGAAGTCCGACGCTTCG<br>AAGTTCACCCATGAGAAACCGGAGGGGTACTACAACTGGCACCAC<br>GGAGCAGTACAGTACTCAGGAGGCCGGTTCACCATCCCTACAGGTG<br>CGGGCAAACCAGGGGACAGCGGTAGACCGATCTTCGACAACAAGG<br>GACGCGTGGTGGCCATAGTCTTAGGAGGAGCTAATGAAGGAGCCC<br>GTACAGCCCTCTCAGTGGTGACCTGGAATAAAGACATTGTCACTAA<br>AATCACCCCTGAGGGAGCCGAAGAGTGGAGTCTTGCCATCCCAGTT<br>ATGTGCCTGTTGGCAAATACCACGTTCCCCTGCTCCCAGCCCCTTG<br>CATACCCTGCTGCTACGAAAAGGAACCGGAGGAAACCCTACGCAT<br>GCTTGAGGACAACGTCATGAGACCTGGGTACTATCAGCTGCTACAA<br>GCATCATTAACATGTTCTCCCCACCGCCAGCGACGCAGCACCAAGG<br>ACAACTTCAATGTCTATAAAGCCACAAGACCATACCTAGCTCACTG<br>TCCCGACTGTGGAGAAGGGCACTCGTGCCATAGTCCCGTAGCACTA<br>GAACGCATCAGAAATGAAGCGACAGACGGGACGCTGAAAATCCAG<br>GTCTCCTTGCAAATTGGAATAGGGACGGATGATAGCCATGATTGGA<br>CCAAGCTGCGTTACATGGACAATCACATACCAGCAGACGCAGGGA<br>GGGCCGGGCTATTTGTAAGAACATCAGCACCATGCACGATTACTGG<br>AACAATGGGACACTTCATCCTGGCCCGATGTCCGAAAGGAGAAACT<br>CTGACGGTGGGATTCACTGACAGTAGGAAGATTAGTCACTCATGTA<br>CGCACCCATTTCACCACGACCCTCCTGTGATAGGCCGGGAAAAATT<br>CCATTCCCGACCGCAGCACGGTAAAGAGCTACCTTGCAGCACGTAC<br>GTGCAGAGCAACGCCGCAACTGCCGAGGAGATAGAGGTACACATG<br>CCCCCAGACACCCCTGATCGCACATTGCTGTCACAACAGTCCGGCA<br>ACGTAAAGATCACAGTCAATAGTCAGACGGTGCGGTATAAGTGTAA<br>TTGCGGTGGCTCAAATGAAGGACTAATAACTACAGATAAAGTGATT<br>AATAACTGCAAGGTTGATCAATGTCATGCCGCGGTCACCAATCACA<br>AAAAGTGGCAGTATAACTCCCCTCTGGTCCCGCGTAACGCTGAACT<br>CGGGGACCGAAAAGGAAAAATTCACATCCCGTTTCCGCTGGCAAAT<br>GTAACATGCATGGTGCCTAAAGCAAGGAACCCCACCGTGACGTACG<br>GGAAAAACCAAGTCATCATGCTACTGTATCCTGACCACCCAACACT<br>CCTGTCCTACCGGAGTATGGGAGAAGAACCAAACTATCAAGAAGA<br>GTGGGTGACGCACAAGAAGGAGGTCGTGCTAACCGTGCCGACTGA<br>AGGGCTCGAGGTTACGTGGGGCAACAACGAGCCGTATAAGTATTG<br>GCCGCAGTTATCTGCAAACGGTACAGCCCACGGCCACCCGCATGAG<br>ATAATCTTGTACTATTATGAGCTGTACCCTACTATGACTGTAGTAGT<br>TGTGTCAGTGGCCTCGTTCATACTCCTGTCGATGGTGGGTATGGCAG<br>TGGGGATGTGCATGTGTGCACGACGCAGATGCATCACACCATACGA<br>ACTGACACCAGGAGCTACCGTCCCTTTCCTGCTTAGCCTAATATGCT<br>GCATCAGAACAGCTAAAGCGGCCACATACCAAGAGGCTGCGGTAT<br>ACCTGTGGAACGAGCAGCAACCTTTGTTTTGGCTACAAGCCCTTATT<br>CCGCTGGCAGCCCTGATTGTCCTATGCAACTGTCTGAGACTCTTACC<br>ATGCTGTTGTAAAACGTTGGCTTTTTTAGCCGTAATGAGCATCGGTG<br>CCCACACTGTGAGCGCGTACGAACACGTAACAGTGATCCCGAACAC<br>GGTGGGAGTACCGTATAAGACTCTAGTCAACAGACCGGGCTACAGC<br>CCCATGGTACTGGAGATGGAGCTACTGTCAGTCACTTTGGAGCCAA<br>CGCTATCGCTTGATTACATCACGTGCGAATACAAAACCGTCATCCC<br>GTCTCCGTACGTGAAATGCTGCGGTACAGCAGAGTGCAAGGACAA<br>AAACCTACCTGACTACAGCTGTAAGGTCTTCACCGGCGTCTACCCA<br>TTTATGTGGGCGGCGCCTACTGCTTCTGCGACGCTGAAAACACGC<br>AATTGAGCGAAGCACATGTGGAGAAGTCCGAATCATGCAAAACAG<br>AATTTGCATCAGCATACAGGGCTCATACCCGCATCCGCATCAGCTAA |

| SEQ ID NO | Sequence |
|---|---|
| | GCTCCGCGTCCTTTACCAAGGAAATAACATCACTGTAACTGCCTAT
GCAAACGGCGACCATGCCGTCACAGTTAAGGACGCCAAATTCATTG
TGGGGCCAATGTCTTCAGCCTGGACACCTTTTGACAACAAATCGT
GGTGTACAAAGGTGACGTTTACAACATGGACTACCCGCCCTTTGGC
GCAGGAAGACCAGGACAATTTGGCGATATCCAAAGTCGCACGCCT
GAGAGCAAAGACGTCTATGCTAACACACAACTGGTACTGCAGAGA
CCGGCTGCGGGTACGGTACACGTGCCATACTCTCAGGCACCATCTG
GCTTTAAGTATTGGTTAAAAGAACGAGGGGCGTCGCTACAGCACAC
AGCACCATTTGGCTGCCAAATAGCAACAAACCCGGTAAGAGCGAT
GAACTGCGCCGTAGGGAACATGCCCATCTCCATCGACATACCGGAT
GCGGCCTTCACTAGGGTCGTCGACGCGCCCTCTTTAACGGACATGT
CATGCGAGGTACCAGCCTGCACCCATTCCTCAGACTTTGGGGGCGT
CGCCATTATTAAATATGCAGTCAGCAAGAAAGGCAAGTGTGCGGTG
CATTCGATGACCAACGCCGTCACTATCCGGGAAGCTGAGATAGAAG
TTGAAGGGAATTCTCAGCTGCAAATCTCTTTCTCGACGGCCTTGGCC
AGCGCCGAATTCCGCGTACAAGTCTGTTCTACACAAGTACACTGTG
CAGCCGAGTGCCACCCTCCGAAGGACCACATAGTCAACTACCCGGC
GTCACATACCACCCTCGGGGTCCAGGACATTTCCGCTACGGCGATG
TCATGGGTGCAGAAGATCACGGGAGGTGTGGGACTGGTTGTCGCTG
TTGCAGCACTGATTCTAATCGTGGTGCTATGCGTGTCGTTCAGCAGG
CACTAACTTGACGACTAAGCATGAAGGTATATGTGTCCCCTAAGAG
ACACACCGTATATAGCTAATAATCTGTAGATCAAAGGGCTATATAA
CCCCTGAATAGTAACAAAATACAAAATCACTAAAAATTATAAAAA
AAAAAAAAAAAAACAGAAAATATATAAATAGGTATACGTGTCC
CCTAAGAGACACATTGTATGTAGGTGATAAGTATAGATCAAAGGGC
CGAACAACCCTGAATAGTAACAAAATATAAAAATTAATAAAAT
CATAAAATAGAAAAACCATAAACAGAAGTAGTTCAAAGGGCTATA
AAAACCCCTGAATAGTAACAAAACATAAAACTAATAAAAATCAAA
TGAATACCATAATTGGCAAACGGAAGAGATGTAGGTACTTAAGCTT
CCTAAAAGCAGCCGAACTCACTTTGAGATGTAGGCATAGCATACCG
AACTCTTCCACGATTCTCCGAACCCACAGGGACGTAGGAGATGTTA
TTTTGTTTTTAATATTTC |
| SEQ ID NO: 2 | MEFIPTQTFYNRRYQPRPWTPRPTIQVIRPRPRPQRQAGQLAQLISAVN
KLTMRAVPQQKPRKNRKNKKQKQKQQAPQNNTNQKKQPPKICKPAQ
KKKKKPGRRERMCMKIENDCIFEVKHEGKVTGYACLVGDKVMKPAHV
KGTIDNADLAKLAFKRSSKYDLECAQIPVIIMKSDASKFTHEKPEGYYN
WHHGAVQYSGGRFTIPTGAGKPGDSGRPIFDNKGRVVAIVLGGANEG
ARTALSVVTWNKDIVTKITPEGAEEWSLAIPVMCLLANTTFPCSQPPCI
PCCYEKEPEETLRMLEDNVMRPGYYQLLQASLTCSPHRQRRSTKDNF
NVYKATRPYLAHCPDCGEGHSCHSPVALERIRNEATDGTLKIQVSLQI
GIGTDDSHDWTKLRYMDNHIPADAGRAGLFVRTSAPCTITGTMGHFIL
ARCPKGETLTVGFTDSRKISHSCTHPFHHDPPVIGREKFHSRPQHGKEL
PCSTYVQSNAATAEEIEVHIMPPDTPDRTLLSQQSGNVKITVNSQTVRY
KCNCGGSNEGLITTDKVINNCKVDQCHAAVTNHKKWQYNSPLVPRN
AELGDRKGKIHIPFPLANVTCMVPKARNPTVTYGKNQVIMLLYPDHPT
LLSYRSMGEEPNYQEEWVTHKKEVVLTVPTEGLEVTWGNNEPYKYW
PQLSANGTAHGHPHEIILYYYELYPTMTVVVVSVASFILLSMVGMAVG
MCMCARRRCITPYELTPGATVPFLLSLICCIRTAKAATYQEAAVYLWN
EQQPLFWLQALIPLAALIVLCNCLRLLPCCCKTLAFLAVMSIGAHTVSA
YEHVTVIPNTVGVPYKTLVNRPGYSPMVLEMELLSVTLEPTLSLDYITC
EYKTVIPSPYVKCCGTAECKDKNLPDYSCKVFTGVYPFMWGGAYCFC
DAENTQLSEAHVEKSESCKTEFASAYRAHTASASAKLRVLYQGNNITV
TAYANGDHAVTVKDAKFIVGPMSSAWTPFDNKIVVYKGDVYNMDYP
PFGAGRPGQFGDIQSRTPESKDVYANTQLVLQRPAAGTVHVPYSQAPS
GFKYWLKERGASLQHTAPFGCQIATNPVRAMNCAVGNMPISIDIPDAA
FTRVVDAPSLTDMSCEVPACTHSSDFGGVAIIKYAVSICKGKCAVHSMT
NAVTIREAEIEVEGNSQLQISFSTALASAEFRVQVCSTQVHCAAECHIPP
KDHIVNYPASHTTLGVQDISATAMSWVQKITGGVGLVVAVAALILIVV
LCVSFSRH |
| SEQ ID NO: 3 | MDPVYVDIDADSAFLKALQRAYPMFEVEPRQVTPNDHANARAFSHLA
IKLIEQEIDPDSTILDIGSAPARRMMSDRKYHCVCPMRSAEDPERLANY
ARKLASAAGKVLDRNISGKIGDLQAVMAVPDTETPTFCLHTDVSCRQR
ADVAIYQDVYAVHAPTSLYHQAIKGVRLAYWVGFDTTPFMYNAMAG
AYPSYSTNWADEQVLKAKNIGLCSTDLTEGRRGKLSIMRGKKLEPCDR
VLFSVGSTLYPESRKLLKSWHLPSVFHLKGKLSFTCRCDTVVSCEGYV
VKRITMSPGLYGKTTGYAVTHHADGFLMCKTTDTVDGERVSFSVCTY
VPATICDQMTGILATEVTPEDAQKLLVGLNQRIVVNGRTQRNTNTMK
NYMIPVVAQAFSKWAKECRKDMEDEKLLGVRERTLTCCCLWAFKKQ
KTHTVYKRPDTQSIQKVQAEFDSFVVPSLWSSGLSIPLRTRIKWLLSKV
PKTDLTPYSGDAQEARDAEKEAEEEREAELTLEALPPLQAAQEDVQVE
IDVEQLEDRAGAGIIETPRGAIKVTAQPTDHVVGEYLVLSPQTVLRSQK
LSLIHALAEQVKTCTHSGRAGRYAVEAYDGRVLVPSGYAISPEDFQSL
SESESATMVYNEREFVNRKLHHIAMHGPALNIDEESYELVRAERTEHEY |

SEQUENCES

| SEQ ID NO | Sequence |
|---|---|
| | VYDVDQRRCCKKEEAAGLVLVGDLTNPPYHEFAYEGLKIRPACPYKIA<br>VIGVFGVPGSGKSAIIKNLVTRQDLVTSGKKENCQEITTDVMRQRGLEI<br>SARTVDSLLLNGCNRPVDVLYVDEAFACHSGTLLALIALVRPRQKVVL<br>CGDPKQCGFFNMMQMKVNYNHNICTQVYHKSISRRCTLPVTAIVSSL<br>HYEGKMRTTNEYNKPIVVDTTGSTKPDPGDLVLTCFRGWVKQLQIDY<br>RGHEVMTAAASQGLTRKGVYAVRQKVNENPLYASTSEHVNVLLTRT<br>EGKLVWKILSGDPWIKTLQNPPKGNFKATIKEWEVEHASIMAGICSHQ<br>MTFDTFQNKANVCWAKSLVPILETAGIKLNDRQWSQIIQAFKEDKAYS<br>PEVALNEICTRMYGVDLDSGLFSKPLVSVYYADNHWDNRPGGKMFGF<br>NPEAASILERKYPFTKGKWNINKQICVTTRRIEDFNPTTNIIPANRRLPH<br>SLVAEHRPVKGERMEWLVNKINGHHVLLVSGCSLALPTKRVTWVAPL<br>GVRGADYTYNLELGLPATLGRYDLVVINIHTPFRIHHYQQCVDHAMK<br>LQMLGGDSLRLLKPGGSLLIRAYGYADRTSERVICVLGRKFRSSRALK<br>PPCVTSNTEMFFLFSNFDNGRRNFTTHVMNNQLNAAFVGQATRAGCA<br>PSYRVKRMDIAKNDEECVVNAANPRGLPGDGVCKAVYKKWPESFKN<br>SATPVGTAKTVMCGTYPVIHAVGPNFSNYSESEGDRELAAAYREVAK<br>EVTRLGVNSVAIPLLSTGVYSGGKDRLTQSLNHLFTAMDSTDADVVIY<br>CRDKEWEKKISEAIQMRTQVELLDEHISIDCDVVRVHPDSSLAGRKGY<br>STTEGALYSYLEGTRFHQTAVDMAEIYTMWPKQTEANEQVCLYALGE<br>SIESIRQKCPVDDADASSPPKTVPCLCRYAMTPERVTRLRMNHVTSIIV<br>CSSFPLPKYKIEGVQKVKCSKVMLFDHNVPSRVSPREYRPSQESVQEA<br>STTTSLTHSQFDLSVDGKILPVPSDLDADAPALEPALDDGAIHTLPSAT<br>GNLAAVSDWVMSTVPVAPPRRRRGRNLTVTCDEREGNITPMASVRFF<br>RAELCPVVQETAETRDTAMSLQAPPSTATELSHPPISFGAPSETFPITFG<br>DFNEGEIESLSSELLTFGDFLPGEVDDLTDSDWSTCSDTDDELRLDRAG<br>GYIFSSDTGPGHLQQKSVRQSVLPVNTLEEVHEEKCYPPKLDEAKEQL<br>LLKKLQESASMNRSRYQSRKVENMKATIIQRLKRGCRLYLMSETPK<br>VPTYRTTYPAPVYSPPINVRLSNPESAVAACNEFLARNYPTVSSYQITD<br>EYDAYLDMVDGSESCLDRATFNPSKLRSYPKQHAYHAPSIRSAVPSPF<br>QNTLQNVLAAATKRNCNVTQMRELPTLDSAVFNVECFKKFACNQEY<br>WEEFAASPIRITTENLTTYVTKLKGPKAAALFAKTHNLLPLQEVPMDR<br>FTVDMKRDVKVTPGTKHTEERPKVQVIQAAEPLATAYLCGIHRELVRR<br>LNAVLLPNVHTLFDMSAEDFDAIIAAHFKPGDTVLETDIASFDKSQDDS<br>LALTALMLLEDLGVDHSLLDLIEAAFGEISSCHLPTGTRFKFGAMMKS<br>GMFLTLFVNTLLNITIASRVLEDRLTKSACAAFIGDDNIIHGVVSDELM<br>AARCATWMNMEVKIIDAVVSQKAPYFCGGFILHDIVTGTACRVADPL<br>KRLFKLGKPLAAGDEQDEDRRRALADEVVRWQRTGLIDELEKAVYSR<br>YEVQGISVVVMSMATFASSRSNFEKLRGPVVTLYGGPK |
| SEQ ID NO: 4 | ATGGCTGCGTGAGACACACGTAGCCTACCAGTTTCTTACTGCTCTAC<br>TCTGCTTAGCAAGAGACTTGAGAACCCATCATGGATCCCGTGTACG<br>TGGACATAGACGCCGACAGCGCCTTTTTAAAGGCCCTGCAGCGTGC<br>GTACCCCATGTTTGAGGTGGAACCAAGGCAGGTCACACCGAATGCA<br>CATGCCAATGCTAGAGCATTCTCGCATCTAGCTATAAAACTAATAG<br>AGCAGGAAATTGATCCCGACTCAACCATCCTGGACATAGGCAGCGC<br>GCCAGCAAGGAGGATGATGTCGGATAGGAAGTACCACTGCGTTTGC<br>CCTATGCGCAGCGCAGAAGACCCTGAGAGACTCGCCAACTACGCG<br>AGAAAACTAGCATCTGCCGCAGGAAAAGTCTTGGACAGAAACATC<br>TCCGAAAAATTGGAGATCTACAAGCAGTAATGGCTGTACCAGACG<br>CAGAAACGCCCACATTCTGCTTGCACACTGACGTCTCATGTAGACA<br>AAGGGCGGACGTCGCTATATACCAGGATGTCTACGCCGTGCATGCA<br>CCAACATCGCTGTACCACCAGGCGATTAAAGGAGTCCGTGTAGCAT<br>ACTGGATAGGGTTTGATACAACCCCGTTCATGTATAATGCCATGGC<br>AGGTGCATACCCCTCGTACTCGACAAACTGGGCAGATGAGCAGGTG<br>CTGAAGGCAAAGAACATAGGATTATGTTCAACAGACCTGACGGAA<br>GGTAGACGAGGTAAATTGTCTATCATGAGAGGAAAAAAGATGAAG<br>CCATGTGACCGCGTACTGTTCTCAGTCGGGTCAACGCTTTACCCGG<br>AGAGCCGTAAGCTTCTTAAGAGTTGGCACTTACCTTCAGTGTTCCAT<br>CTAAAAGGGAAGCTCAGCTTCACGTGCCGCTGTGATACAGTGGTTT<br>CGTGTGAAGGCTATGTCGTTAAGAGAATAACGATTAGCCCGGGCCT<br>CTACGGTAAAACCACAGGGTACGCAGTAACCCACCATGCAGACGG<br>ATTCCTAATGTGCAAAACAACCGATACGGTAGATGGCGAGAGAGT<br>GTCATTTTCGGTATGCACGTACGTACCCGCAACCATTTGTGATCAAA<br>TGACAGGTATTCTTGCCACGGAGGTTACACCGGAGGATGCACAGAA<br>GCTGCTGGTGGGACTGAACCAGAGGATAGTGGTCAATGGCAGAAC<br>GCAGAGGAACACGAACACAATGAAGAATTACTTGCTTCCTGTAGTT<br>GCCCAAGCCTTCAGTAAGTGGGCAAAGGAATGCCGGAAAGATATG<br>GAAGATGAAAAACTTTTGGGCATCAGAGAAGGACACTGACATGC<br>TGCTGCCTTTGGGCGTTCAAGAAGCAGAAGACACACGGTCTACA<br>AGAGGCCTGACACTCAGTCAATTCAGAAAGTCCCAGCCGAATTTGA<br>CAGCTTTGTGGTACCAAGTCTGTGGTCATCTGGACTGTCGATCCCGC<br>TACGGACCAGAATCAAGTGGCTGCTAAGCAAAGTGCCAAAGACTG<br>ATTTGATCCCTTACAGCGGTGACGCCAAAGAAGCCCGCGACGCTGA<br>AAAAGAAGCAGAAGAAGAACGAGAAGCGGAGCTAACTCGCGAGG<br>CACTACCACCACTACAGGCGGCACAGGACGACGTCCAGGTCGAAA |

SEQUENCES

| SEQ ID NO | Sequence |
|---|---|
| | TTGACGTGGAACAGCTCGAAGACAGAGCTGGGGCAGGAATAATTG<br>AAACTCCAAGAGGAGCTATCAAAGTCACTGCCCAACCAACAGACC<br>ACGTCGTGGGAGAGTACTTGGTACTTTCCCCGCAGACCGTGTTACG<br>AAGCCAGAAGCTCAGCCTGATCCACGCATTGGCGGAACAAGTGAA<br>GACATGCACACACAGCGGACGGGCAGGAAGGTACGCGGTCGAAGC<br>ATATGACGGCAGAATCCTTGTGCCCTCAGGCTATGCAATATCACCT<br>GAAGACTTCCAGAGCCTGAGCGAAAGTGCGACGATGGTGTACAAC<br>GAAAGGGAGTTCGTAAATAGGAAATTACACCATATCGCGTTGCACG<br>GACCAGCCCTGAACACTGACGAGGAGTCGTACGAGCTGGTAAGGG<br>CAGAAAGGACAGAGCATGAGTACGTCTATGATGTGGACCAAAGAA<br>GGTGCTGCAAGAAAGAGGAGGCAGCCGGGCTGGTACTGGTCGGCG<br>ACTTGACCAACCCGCCCTACCATGAGTTCGCATATGAAGGGCTGAG<br>AATCCGCCCCGCCTGCCCATACAAGACCGCAGTAATAGGGGTCTTT<br>GGAGTGCCAGGATCCGGCAAATCAGCAATCATTAAGAACCTAGTTA<br>CCAGGCAAGACCTAGTGACCAGTGGAAAGAAAGAAAACTGCCAAG<br>AAATCTCCACCGACGTGATGCGACAGAGGAACCTGGAGATATCTGC<br>ACGCACGGTCGACTCACTGCTCTTGAACGGATGCAATAGACCAGTC<br>GACGTGTTGTACGTCGACGAAGCTTTTGCGTGCCATTCTGGCACGCT<br>ACTTGCTCTGATAGCCTTGGTGAGACCGAGGCAGAAAGTCGTGCTA<br>TGCGGTGATCCGAAACAGTGCGGCTTCTTCAATATGATGCAGATGA<br>AAGTTAACTACAACCATAACATCTGCACCCAAGTGTACCATAAAAG<br>TATTTCCAGGCGGTGTACACTGCCTGTGACTGCCATTGTGTCCTCGT<br>TGCATTACGAAGGCAAAATGCGCACAACAAATGAGTACAACAAGC<br>CAATTGTAGTGGATACTACAGGCTCGACAAAACCCGACCCCGGAGA<br>CCTTGTGCTAACATGTTTCAGAGGGTGGGTTAAGCAACTGCAAATT<br>GACTATCGTGGACACGAGGTCATGACAGCAGCTGCATCTCAGGGGC<br>TAACCAGAAAAGGGGTCTATGCCGTCAGGCAAAAAGTTAATGAAA<br>ACCCCCTTTACGCATCAACATCAGAGCACGTGAACGTGCTACTGAC<br>GCGTACGGAAGGCAAACTAGTATGGAAGACACTTTCTGGAGACCC<br>ATGGATAAAGACACTGCAGAACCCGCCGAAAGGAAATTTTAAAGC<br>AACAATTAAGGAATGGGAAGTGGAACATGCTTCAATAATGGCGGG<br>TATCTGTAACCACCAAGTGACCTTTGACACGTTCCAGAATAAAGCC<br>AATGTCTGCTGGGCGAAGAGCTTAGTCCCCATCCTAGAAACAGCAG<br>GGATAAAATTAAACGACAGGCAGTGGTCCCAGATAATCCAGGCTTT<br>TAAAGAAGACAGAGCATACTCACCCGAGGTGGCCCTGAATGAGAT<br>ATGCACGCGCATGTACGGGGTAGACCTGGACAGCGGACTGTTCTCT<br>AAACCACTGGTGTCCGTGCATTATGCGGATAATCACTGGGACAACA<br>GGCCGGGAGGGAAGATGTTCGGATTCAACCCCGAAGCGGCGTCCA<br>TACTGGAGAGGAAATACCCGTTTACAAAAGGGAAGTGGAATACCA<br>ACAAGCAAATCTGTGTGACTACTAGGAGGATTGAAGATTTTAACCC<br>GAACACCAACATTATACCTGCCAACAGGAGATTACCGCATTCATTG<br>GTGGCCGAACATCGCCCGGTAAAAGGGGAGAGGATGGAATGGTTG<br>GTCAACAAATAAATGGCCACCATGTGCTCCTGGTCAGCGGCTACA<br>ACCTCGTTCTGCCCACTAAGAGAGTCACCTGGGTGGCGCCGCTGGG<br>CATTCGGGGAGCTGACTACACATACAACCTAGAGTTAGGCCTACCA<br>GCAACGCTCGGTAGATATGACCTAGTGATTATAAACATCCACACAC<br>CCTTTCGCATACATCATTACCAACAGTGCGTGGATCACGCAATGAA<br>GCTGCAGATGCTCGGAGGAGACTCCCTGAGACTGCTCAAGCCGGGT<br>GGTTCATTACTGATCAGGGCATACGGCTACGCAGACAGAACAAGCG<br>AACGAGTAGTCTGCGTATTGGGACGCAAGTTTCGATCATCCAGAGC<br>GTTGAAACCGCCGTGCGTCACTAGCAACACCGAGATGTTTTCTTGT<br>TCAGCAACTTTGATAACGGCAGAAGGAACTTTACGACGCACGTAAT<br>GAACAACCAGCTGAATGCTGCTTTTGTTGGTCAGGCCACCCGAGCA<br>GGGTGCGCACCGTCGTACCGGGTTAAACGCATGGACATCGCAAAG<br>AACGATGAAGAGTGTGTAGTCAACGCCGCCAACCCTCGTGGGCTAC<br>CAGGCGATGGCGTCTGTAAAGCAGTATACAAAAAATGGCCGGAGT<br>CCTTCAAGAACAGTGCAACACCAGTGGGAACCGCAAAGACAGTCA<br>TGTGCGGTACATACCCGGTAATCCATGCAGTAGGACCTAATTTCTC<br>AAATTACTCTGAGTCCGAAGGAGACCGGGAATTGGCAGCTGCTTAC<br>CGAGAAGTCGCTAAGGAGGTGACTAGACTAGGAGTAAACAGCGTA<br>GCTATACCGCTCCTTTCCACCGGTGTGTACTCTGGAGGGAAAGACA<br>GGCTGACTCAGTCACTAAACCACCTTTTTACAGCATTAGACTCAACT<br>GATGCAGATGTGGTTATCTACTGCCGCGACAAGGAGTGGGAGAAG<br>AAAATAGCTGAGGCCATACAAATGAGGACCCAAGTGGAATTACTA<br>GACGAACACATCTCTGTAGACTGCGATATCATCCGAGTGCACCCTG<br>ACAGCAGTTTGGCAGGTAGAAAAGGGTACAGCACTACAGAAGGTT<br>CACTGTACTCCTACTTGGAAGGGACACGGTTCCATCAGACGGCAGT<br>GGACATGGCAGAAGTATACACCATGTGGCCAAAGCAGACGGAGGC<br>TAATGAACAAGTTTGCTTGTACGCATTGGGGGAAAGTATAGAATCA<br>ATCAGGCAAAAGTGCCCAGTGGATGACGCAGATGCATCGTCGCCCC<br>CAAAAACCGTCCCGTGCCTCTGCCGTTATGCCATGACACCCGAACG<br>AGTCACCAGGCTTCGTATGAACCATGTCACAAGCATAATAGTATGC<br>TCATCATTCCCCCTTCCAAAGTATAAAATAGAAGGAGTGCAGAAAG<br>TCAAGTGTTCTAAAGTGATGCTGTTCGACCATAACGTGCCATCACG<br>CGTTAGTCCAAGGGAATATAAATCGCCTCAGGAGACCGCACAAGA |

SEQUENCES

| SEQ ID NO | Sequence |
|---|---|
| | AGTAAGTTCGACCACGTCACTGACGCACAGCCAATTCGACCTTAGC |
| | GTTGACGGTGAGGAACTGCCCGCTCCGTCTGACTTGGAAGCTGACG |
| | CTCCGATTCCGGAACCAACACCAGACGACAGAGCGGTACTTACTTT |
| | GCCTCCCACGATTGATAATTTTTCGGCTGTGTCAGACTGGGTAATGA |
| | ATACCGCGCCAGTCGCACCACCCAGAAGAAGACGTGGGAAAAACT |
| | TGAATGTCACCTGCGACGAGAGAGAAGGGAACGTACTTCCCATGGC |
| | TAGCGTTCGGTTCTTCAGAGCGGATCTGCACTCCATCGTACAGGAA |
| | ACGGCAGAGATACGCGATACGGCCGCGTCCCTCCAGGCGCCCCTGA |
| | GTGTCGCTACAGAACCGAATCAACTGCCGATCTCATTTGGAGCACC |
| | AAACGAGACTTTCCCCATAACGTTCGGGGATTTTGATGAAGGGGAG |
| | ATTGAAAGCTTGTCCTCTGAGTTACTGACCTTTGGGGACTTCTCGCC |
| | GGGCGAAGTGGATGACCTGACAGACAGCGACTGGTCCACGTGTTCA |
| | GACACGGACGACGAATTATGACTAGATAGGGCAGGTGGGTACATA |
| | TTCTCATCTGACACCGGCCCCGGCCACCTGCAACAGAGGTCTGTCC |
| | GTCAGACAGTACTGCCGGTAAATACCTTGGAGGAAGTTCAGGAGG |
| | AGAAATGTTACCCACCTAAGTTGGATGAAGTGAAAGAGCAGTTGTT |
| | ACTTAAGAAACTCCAGGAAAGTGCGTCCATGGCTAACAGAAGCAG |
| | GTACCAATCCCGCAAAGTAGAGAACATGAAAGCAACAATAGTCCA |
| | AAGGCTGAAGGGTGGTTGCAAACTTTATTTAATGTCGGAGACCCCG |
| | AAAGTTCCTACCTACCGAACTACATATCCGGCACCAGTGTACTCAC |
| | CCCCAATCAATATCCGACTGTCCAACCCCGAGTCTGCTGTGGCAGC |
| | GTGCAATGAGTTCCTAGCAAGGAACTATCCGACAGTTGCGTCGTAC |
| | CAAATCACCGATGAGTACGATGCATACCTAGACATGGTGGACGGGT |
| | CGGAAAGTTGCCTTGACCGGGCGACGTTCAACCCATCAAAGCTTAG |
| | AAGTTATCCAAAACAGCACTCCTACCATGCACCCACAATCAGAAGT |
| | GCCGTACCTTCCCCGTTCCAGAACACGCTGCAGAACGTACTGGCTG |
| | CTGCCACGAAAAGAAATTGCAACGTCACACAGATGAGAGAACTGC |
| | CTACTTTGGATTCAGCGGTATTTAATGTTGAGTGCTTTAAAAAATTT |
| | GCGTGCAATCAAGAATACTGGAAGGAATTTGCCGCCAGCCCTATTA |
| | GGATAACGACTGAGAACTTGACAACTTATGTCACAAAACTAAAAG |
| | GACCAAAAGCAGCAGCACTGTTTGCCAAGACACATAACCTGCTACC |
| | ACTGCAGGAGGTGCCGATGGACAGGTTTACTGTAGACATGAAAAG |
| | GGACGTGAAGGTGACTCCGGGGACGAAGCACACTGAGGAAAGACC |
| | TAAAGTGCAGGTCATACAGGCAGCCGAACCTTTGGCAACAGCATAT |
| | CTGTGTGGGATCCACAGAGAGTTGGTCAGAAGGCTGAATGCAGTCC |
| | TTCTACCTAATGTACACACGCTGTTTGACATGTCTGCCGAGGACTTT |
| | GACGCCATTATTGCCGCGCACTTCAAGCCGGGGGACGCCGTATTGG |
| | AAACCGATATAGCCTCCTTTGACAAGAGCCAAGACGACTCATTGGC |
| | GCTCACTGCTCTAATGTTGCTAGAGGATTTGGGGGTGGATCATCCC |
| | CTGTTGGACTTGATAGAGGCTGCCTTCGGGGAGATCTCCAGCTGCC |
| | ACCTACCGACGGGCACCCGTTTTAAGTTCGGCGCCATGATGAAGTC |
| | TGGTATGTTCCTAACCCTGTTCGTCAACACACTGCTAAACATCACCA |
| | TAGCCAGCCGAGTGCTGGAGGACCGCTTGACAAGGTCTGCGTGCGC |
| | GGCCTTCATCGGCGACGACAATATAATACATGGGGTTGTCTCTGAC |
| | GAACTGATGGCAGCAAGGTGTGCTACATGGATGAACATGGAAGTG |
| | AAGATCATAGATGCGGTCGTGTCTCAGAAAGCCCCGTACTTCTGCG |
| | GAGGGTTTATACTGTATGACACAGTAGCAGGCACGGCCTGCAGAGT |
| | GGCAGACCCGCTAAAGCGGCTGTTCAAGCTGGGCAAACCGCTGGC |
| | AGCGGGAGATGAACAAGACGACGACAGAAGACGTGCACTGGCTGA |
| | CGAAGTGGTTAGATGGCAACGAACAGGACTAACTGATGAGCTAGA |
| | AAAAGCGGTACACTCCAGGTATGAAGTGCAGGGCATATCTGTCGTG |
| | GTAATGTCTATGGCCACCTTTGCAAGCTCTAGATCTAACTTTGAGAA |
| | GCTCAGAGGACCCGTCGTAACCCTGTACGGTGGTCCTAAATAGGTA |
| | CGCACTACAGCTACCTATTTCGTCAGAAACCAATCGCAGCTACTTG |
| | CATACCTACCAGCTACAATGGAGTTCATCCGACGCAAACTTTCTA |
| | TAACAGAAGGTACCAACCCCGACCCTGGGCCCCACGCCCTACAATT |
| | CAAGTAATTAGACCTAGACCACGTCCACAGAGGCAGGCTGGGCAA |
| | CTCGCCCAGCTGATCTCCGCAGTCAACAAATTGACCATGCGCGCGG |
| | TACCTCAACAGAAGCCTCGCAGAAATCGGAAAAACAAGAAGCAAA |
| | GGCAGAAGAAGCAGGCGCCGCAAAACGACCCAAAGCAAAGAAG |
| | CAACCACCACAAAAGAAGCCGGCTCAAAAGAAGAAAACCAGGC |
| | CGTAGGGAGAGAATGTGCATGAAAATTGAAATGATTGCATCTTCG |
| | AAGTCAAGCATGAAGGCAAAGTGATGGGCTACGCATGCCTGGTGG |
| | GGGATAAAGTAATGAAACCAGCACATGTGAAGGGAACTATCGACA |
| | ATGCCGATCTGGCTAAACTGGCCTTTAAGCGGTCGTCTAAATACGA |
| | TCTTGAATGTGCACAGATACCGGTGCACATGAAGTCTGATGCCTCG |
| | AAGTTTACCCACGAGAAACCCGAGGGGTACTATAACTGGCATCACG |
| | GAGCAGTGCAGTATTCAGGAGGCCGGTTCACTATCCCGACGGGTGC |
| | AGGCAAGCCGGGAGACAGCGGCAGACCGATCTTCGACAACAAAGG |
| | ACGGGTGGTGGCCATCGTCCTAGGAGGGGCAACGAAGGTGCCCG |
| | CACGGCCCCTCTCCGTGGTGACGTGGAACAAAGACATCGTCACAAAA |
| | ATTACCCCTGAGGGAGCCGAAGAGTGGAGCCTCGCCCTCCCGGTCT |
| | TGTGCCTGTTGGCAAACACTACATTCCCCTGCTCTCAGCCGCCTTGC |
| | ACACCCTGCTGCTACGAAAAGGAACCGGAAAGCACCTTGCGCATGC |
| | TTGAGGACAACGTGATGAGACCCGGATACTACCAGCTACTAAAAGC |

| SEQ ID NO | Sequence |
|---|---|
| | ATCGCTGACTTGCTCTCCCCACCGCCAAAGACGCAGTACTAAGGAC
AATTTTAATGTCTATAAAGCCACAAGACCATATCTAGCTCATTGTCC
TGACTGCGGAGAAGGGCATTCGTGCCACAGCCCTATCGCATTGGAG
CGCATCAGAAATGAAGCAACGGACGGAACGCTGAAAATCCAGGTC
TCTTTGCAGATCGGGATAAAGACAGATGACAGCCACGATTGGACCA
AGCTGCGCTATATGGATAGCCATACGCCAGCGGACGCGGAGCGAG
CCGGATTGCTTGTAAGGACTTCAGCACCGTGCACGATCACCGGGAC
CATGGGACACTTTATTCTCGCCCGATGCCCGAAAGGAGAGACGCTG
ACAGTGGGATTTACGGACAGCAGAAAGATCAGCCACACATGCACA
CACCCGTTCCATCATGAACCACCTGTGATAGGTAGGGAGAGGTTCC
ACTCTCGACCACAACATGGTAAAGAGTTACCTTGCAGCACGTACGT
GCAGAGCACCGCTGCCACTGCTGAGGAGATAGAGGTGCATATGCCC
CCAGATACTCCTGACCGCACGCTGATGACGCAGCAGTCTGGCAACG
TGAAGATCACAGTTAATGGGCAGACGGTGCGGTACAAGTGCAACT
GCGGTGGCTCAAACGAGGGACTGACAACCACAGACAAAGTGATCA
ATAACTGCAAATTGATCAGTGCCATGCTGCAGTCACTAATCACAA
GAATTGGCAATACAACTCCCCTTTAGTCCCGCGCAACGCTGAACTC
GGGGACCGTAAAGGAAAGATCCACATCCCATTCCCATTGGCAACG
TGACTTGCAGAGTGCCAAAAGCAAGAAACCCTACAGTAACTTACGG
AAAAAACCAAGTCACCATGCTGCTGTATCCTGACCATCCGACACTC
TTGTCTTACCGTAACATGGGACAGGAACCAAATTACCACGAGGAGT
GGGTGACACACAAGAAGGAGGTTACCTTGACCGTGCCTACTGAGG
GTCTGGAGGTCACTTGGGGCAACAACGAACCATACAAGTACTGGCC
GCAGATGTCTACGAACGGTACTGCTCATGGTCACCCACATGAGATA
ATCTTGTACTATTATGAGCTGTACCCCACTATGACTGTAGTCATTGT
GTCGGTGGCCTCGTTCGTGCTTCTGTCGATGGTGGGCACAGCAGTG
GGAATGTGTGTGTGCGCACGGCGCAGATGCATTACACCATATGAAT
TAACACCAGGAGCCACTGTTCCCTTCCTGCTCAGCCTGCTATGCTGC
GTCAGAACGACCAAGGCGGCCACATATTACGAGGCTGCGGCATATC
TATGGAACGAACAGCAGCCCCTGTTCTGGTTGCAGGCTCTTATCCC
GCTGGCCGCCTTGATCGTCCTGTGCAACTGTCTGAAACTCTTGCCAT
GCTGCTGTAAGACCCTGGCTTTTTTAGCCGTAATGAGCATCGGTGCC
CACACTGTGAGCGCGTACGAACACGTAACAGTGATCCCGAACACG
GTGGGAGTACCGTATAAGACTCTTGTCAACAGACCGGGTTACAGCC
CCATGGTGTTGGAGATGGAGCTACAATCAGTCACCTTGGAACCAAC
ACTGTCACTTGACTACATCACGTGCGAGTACAAAACTGTCATCCCC
TCCCCGTACGTGAAGTGCTGTGGTACAGCAGAGTGCAAGGACAAG
AGCCTACCAGACTACAGCTGCAAGGTCTTTACTGGAGTCTACCCAT
TTATGTGGGGCGGCGCCTACTGCTTTTGCGACGCCGAAAATACGCA
ATTGAGCGAGGCACATGTAGAGAAATCTGAATCTTGCAAAACAGA
GTTTGCATCGGCCTACAGAGCCCACACCGCATCGGCGTCGGCGAAG
CTCCGCGTCCTTTACCAAGGAAACAACATTACCGTAGCTGCCTACG
CTAACGGTGACCATGCCGTCACAGTAAAGGACGCCAAGTTTGTCGT
GGGCCCAATGTCCTCCGCCTGGACACCTTTTGACAACAAAATCGTG
GTGTACAAAGGCGACGTCTACAACATGGACTACCCACCTTTTGGCG
CAGGAAGACCAGGACAATTTGGTGACATTCAAAGTCGTACACCGG
AAAGTAAAGACGTTTATGCCAACACTCAGTTGGTACTACAGAGGCC
AGCAGCAGGCACGGTACATGTACCATACTCTCAGGCACCATCTGGC
TTCAAGTATTGGCTGAAGGAACGAGGAGCATCGCTACAGCACACG
GCACCGTTCGGTTGCCAGATTGCGACAAACCCGGTAAGAGCTGTAA
ATTGCGCTGTGGGGAACATACCAATTTCCATCGACATACCGGATGC
GGCCTTTACTAGGGTTGTCGATGCACCCTCTGTAACGGACATGTCAT
GCGAAGTACCAGCCTGCACTCACTCCTCCGACTTTGGGGGCGTCGC
CATCATCAAATACACAGCTAGCAAGAAAGGTAAATGTGCAGTACAT
TCGATGACCAACGCCGTTACCATTCGAGAAGCCGACGTAGAAGTAG
AGGGGAACTCCCAGCTGCAAATATCCTTCTCAACAGCCCTGGCAAG
CGCCGAGTTTCGCGTGCAAGTGTGCTCCACACAAGTACACTGCGCA
GCCGCATGCCACCCTCCAAAGGACCACATAGTCAATTACCCAGCAT
CACACACCACCCTTGGGGTCCAGGATATATCCACAACGGCAATGTC
TTGGGTGCAGAAGATTACGGGAGGAGTAGGATTAATTGTTGCTGTT
GCTGCCTTAATTTTAATTGTGGTGCTATGCGTGTCGTTTAGCAGGCA
CTAAACCGATGATAAGGCACGAAATAACTAAATAGCAAAAGTAGA
AAGTACATAACCAGGTATATGTGCCCCTTAAGAGGCACAATATATA
TAGCTAAGCACTATTAGATCAAAGGGCTATACAACCCTGAATAGT
AACAAAACACAAAAACCAATAAAAATCATAAAAAGAAAAATCTCA
TAAACAGGTATAAGTGTCCCCTAAGAGACACATTGTATGTAGGTAG
TAAGTATAGATCAAAGGGCTATATTAACCCCTGAATAGTAACAAAA
CACAAAAACAATAAAAACTACAAAATAGAAAATCTATAAACAAAA
GTAGTTCAAAGGGCTACAAAACCCCTGAATAGTAACAAAACATAA
AATGTAATAAAAATTAAGTGTGTACCCAAAAGAGGTACAGTAAGA
ATCAGTGAATATCACAATTGGCAACGAGAAGAGACGTAGGTATTTA
AGCTTCCTAAAAGCAGCCGAACTCACTTTGAGACGTAGGCATAGCA
TACCGAACTCTTCCACTATTCTCCGAACCCACAGGGACGTAGGAGA
TGTTATTTTGTTTTTAATATTTC |

| SEQ ID NO | Sequence |
|---|---|
| SEQ ID NO: 5 | MEFIPTQTFYNRRYQPRPWAPRPTIQVIRPRPRPQRQAGQLAQLISAVN
KLTMRAVPQQKPRRNRKNKKQRQKKQAPQNDPKQKKQPPQKKPAQ
KKKKPGRRERMCMKIENDCIFEVKHEGKVMGYACLVGDKVMKPAHV
KGTIDNADLAKLAFKRSSKYDLECAQIPVHMKSDASKFTHEKPEGYYN
WHHGAVQYSGGRFTIPTGAGKPGDSGRPIFDNKGRVVAIVLGGANEG
ARTALSVVTWNKDIVTKITPEGAEEWSLALPVLCLLANTTFPCSQPPCT
PCCYEKEPESTLRMLEDNVMRPGYYQLLKASLTCSPHRQRRSTKDNF
NVYKATRPYLAHCPDCGEGHSCHSPIALERIRNEATDGTLKIQVSLQIGI
KTDDSHDWTKLRYMDSHTPADAERAGLLVRTSAPCTITGTMGHFILA
RCPKGETLTVGFTDSRKISHTCTHPFHHEPPVIGRERFHSRPQHGKELPC
STYVQSTAATAEEIEVIEVIPPDTPDRTLMTQQSGNVKITVNGQTVRYKC
NCGGSNEGLTTTDKVINNCKIDQCHAAVTNHKNWQYNSPLVPRNAEL
GDRKGKIHIPFPLANVTCRVPKARNPTVTYGKNQVTMLLYPDHPTLLS
YRNMGQEPNYHEEWVTHKKEVTLTVPTEGLEVTWGNNEPYKYWPQ
MSTNGTAHGHPHEIILYYYELYPTMTVVIVSVASFVLLSMVGTAVGMC
VCARRRCITPYELTPGATVPFLLSLLCCVRTTKAATYYEAAAYLWNEQ
QPLFWLQALIPLAALIVLCNCLKLLPCCCKTLAFLAVMSIGAHTVSAYE
HVTVIPNTVGVPYKTLVNRPGYSPMVLEMELQSVTLEPTLSLDYITCEY
KTVIPSPYVKCCGTAECKDKSLPDYSCKVFTGVYPFMWGGAYCFCDA
ENTQLSEAHVEKSESCKTEFASAYRAHTASASAKLRVLYQGNNITVAA
YANGDHAVTVKDAKFVVGPMSSAWTPFDNKIVVYKGDVYNMDYPPF
GAGRPGQFGDIQSRTPESKDVYANTQLVLQRPAAGTVHVPYSQAPSGF
KYWLKERGASLQHTAPFGCQIATNPVRAVNCAVGNIPISIDIPDAAFTR
VVDAPSVTDMSCEVPACTHSSDFGGVAIIKYTASKKGKCAVHSMTNA
VTIREADVEVEGNSQLQISFSTALASAEFRVQVCSTQVHCAAACHPPK
DHIVNYPASHTTLGVQDISTTAMSWVQKITGGVGLIVAVAALILIVVLC
VSFSRH |
| SEQ ID NO: 6 | MDPVYVDIDADSAFLKALQRAYPMFEVEPRQVTPNDHANARAFSHLA
IKLIEQEIDPDSTILDIGSAPARRMMSDRKYHCVCPMRSAEDPERLANY
ARKLASAAGKVLDRNISEKIGDLQAVMAVPDAETPTFCLHTDVSCRQR
ADVAIYQDVYAVHAPTSLYHQAIKGVRVAYWIGFDTTPFMYNAMAG
AYPSYSTNWADEQVLKAKNIGLCSTDLTEGRRGKLSIMRGKKMKPCD
RVLFSVGSTLYPESRKLLKSWHLPSVFHLKGKLSFTCRCDTVVSCEGY
VVKRITISPGLYGKTTGYAVTHHADGFLMCKTTDTVDGERVSFSVCTY
VPATICDQMTGILATEVTPEDAQKLLVGLNQRIVVNGRTQRNTNTMK
NYLLPVVAQAFSKWAKECRKDMEDEKLLGIRERTLTCCCLWAFKKQ
KTHTVYKRPDTQSIQKVPAEFDSFVVPSLWSSGLSIPLRTRIKWLLSKV
PKTDLIPYSGDAKEARDAEKEAEEEREAELTREALPPLQAAQDDVQVE
IDVEQLEDRAGAGIIETPRGAIKVTAQPTDHVVGEYLVLSPQTVLRSQK
LSLIHALAEQVKTCTHSGRAGRYAVEAYDGRILVPSGYAISPEDFQSLS
ESATMVYNEREFVNRKLHHIALHGPALNTDEESYELVRAERTEHEYV
YDVDQRRCCKKEEAAGLVLVGDLTNPPYHEFAYEGLRIRPACPYKTA
VIGVFGVPGSGKSAIIKNLVTRQDLVTSGKKENCQEISTDVMRQRNLEI
SARTVDSLLLNGCNRPVDVLYVDEAFACHSGTLLALIALVRPRQKVVL
CGDPKQCGFFNMMQMKVNYNHNICTQVYHKSISRRCTLPVTAIVSSL
HYEGKMRTTNEYNKPIVVDTTGSTKPDPGDLVLTCFRGWVKQLQIDY
RGHEVMTAAASQGLTRKGVYAVRQKVNENPLYASTSEHVNVLLTRT
EGKLVWKTLSGDPWIKTLQNPPKGNFKATIKEWEVEHASIMAGICNH
QVTFDTFQNKANVCWAKSLVPILETAGIKLNDRQWSQIIQAFKEDRAY
SPEVALNEICTRMYGVDLDSGLFSKPLVSVHYADNHWDNRPGGKMFG
FNPEAASILERKYPFTKGKWNINKQICVTTRRIEDFNPNTNIIPANRRLP
HSLVAEHRPVKGERMEWLVNKINGHHVLLVSGYNLVLPTKRVTWVA
PLGIRGADYTYNLELGLPATLGRYDLVIINIHTPFRIHHYQQCVDHAMK
LQMLGGDSLRLLKPGGSLLIRAYGYADRTSERVVCVLGRKFRSSRALK
PPCVTSNTEMFFLFSNFDNGRRNFTTHVMNNQLNAAFVGQATRAGCA
PSYRVKRMDIAKNDEECVVNAANPRGLPGDGVCKAVYKKWPESFKN
SATPVGTAKTVMCGTYPVIHAVGPNFSNYSESEGDRELAAAYREVAK
EVTRLGVNSVAIPLLSTGVYSGGKDRLTQSLNHLFTALDSTDADVVIY
CRDKEWEKKIAEAIQMRTQVELLDEHISVDCDIIRVHPDSSLAGRKGYS
TTEGSLYSYLEGTRFHQTAVDMAEVYTMWPKQTEANEQVCLYALGE
SIESIRQKCPVDDADASSPPKTVPCLCRYAMTPERVTRLRMNHVTSIIV
CSSFPLPKYKIEGVQKVKCSKVMLFDHNVPSRVSPREYKSPQETAQEV
SSTTSLTHSQFDLSVDGEELPAPSDLEADAPIPEPTPDDRAVLTLPPTID
NFSAVSDWVMNTAPVAPPRRRRGKNLNVTCDEREGNVLPMASVRFF
RADLHSIVQETAEIRDTAASLQAPLSVATEPNQLPISFGAPNETFPITFGD
FDEGEIESLSSELLTFGDFSPGEVDDLTDSWSTCSDTDDELLDRAGGY
IFSSDTGPGHLQQRSVRQTVLPVNTLEEVQEEKCYPPKLDEVKEQLLLK
KLQESASMANRSRYQSRKVENMKATIVQRLKGGCKLYLMSETPKVPT
YRTTYPAPVYSPPINIRLSNPESAVAACNEFLARNYPTVASYQITDEYD
AYLDMVDGSESCLDRATFNPSKLRSYPKQHSYHAPTIRSAVPSPFQNT
LQNVLAAATKRCNVTQMRELPTLDSAVFNVECFKKFACNQEYWKE
FAASPIRITTENLTTYVTKLKGPKAAALFAKTHNLLPLQEVPMDRFTVD
MKRDVKVTPGTKHTEERPKVQVIQAAEPLATAYLCGIHRELVRRLNA
VLLPNVHTLFDMSAEDFDAIIAAHFKPGDAVLETDIASFDKSQDDSLAL |

| SEQ ID NO | Sequence |
|---|---|
| | TALMLLEDLGVDHPLLDLIEAAFGEISSCHLPTGTRFKFGAMMKSGMF<br>LTLFVNTLLNITIASRVLEDRLTRSACAAFIGDDNIIHGVVSDELMAARC<br>ATWMNMEVKIIDAVVSQKAPYFCGGFILYDTVAGTACRVADPLKRLF<br>KLGKPLAAGDEQDDDRRRALADEVVRWQRTGLTDELEKAVHSRYEV<br>QGISVVVMSMATFASSRSNFEKLRGPVVTLYGGPK |
| SEQ ID NO: 7 | ATGGCGGGCAAGTGACACTTGTTCCGCCGGACGTCTCTAAGCTCTT<br>CCTCTGCATTGCAAGAGTTTACCACTCAGTATGTCGAAAGTCTTTGT<br>AGATATCGAGGCCGAGAGCCCGTTTTTAAAATCACTACAGAGAGCG<br>TTTCCAGCATTTGAAGTGGAAGCACAGCAGGTTACACCAAATGACC<br>ATGCTAACGCCAGAGCATTCTCGCATCTGGCTACTAAATTGATAGA<br>GCAAGAGACCGAAAAAGACACACTCATCCTGGATATCGGCAGTGC<br>GCCTGCCAGGAGAATGATGTCTGAGCACACGTACCATTGTGTGTGCA<br>CCAATGCGCAGCGCTGAGGACCCAGAGCGTCTGCTGTATTATGCCA<br>GGAAGTTAGCCAAGGCATCAGGTGAAGTCGTTGACAGAAATATTGC<br>AGCGAAGATAGACGACCTGCAGTCAGTGATGGCGACCCCGGACAA<br>TGAGTCACGGACATTTTGCCTTCACACAGATCAGACATGCAGGACT<br>CCAGCTGAGGTGGCAGTCTATCAGGATGTCTATGCAGTTCACGCAC<br>CGACTTCTTTGTACTTCCAGGCAATGAAAGGAGTACGCACAGCGTA<br>CTGGATTGGGTTCGACACTACCCCATTCATGTTCGATACAATGGCC<br>GGGGCTTATCCAACATATGCAACCAACTGGGCCGACGAACAGGTGT<br>TGAAAGCCAGGAACATAGGACTGTGCTCCGCGGCACTGACTGAGG<br>GACACCTTGGCAAGCTATCAATAATGAGGAAGAAGAGAATGAAAC<br>CGAGTGACCAGATAATGTTCTCGGTAGGTTCCACATTGTATACGGA<br>AAGCCGACGTCTGCTAAAGAGTTGGCATCTGCCGTCAGTGTTTCAT<br>CTGAAAGGACGACAATCATATACGTGCCGGTGCGATACAATAGTGT<br>CATGTGAGGGCTACGTTGTTAAGAAGATAACGATGAGCCCAGGGGT<br>ATTCGGAAAAACGTCAGGGTACGCCGTCACACATCACGCAGAAGG<br>ATTTCTGGTATGTAAAACCACTGACACTATCGCAGGAGAACGAGTT<br>TCGTTCCCCGTTTGCACGTATGTGCCGTCGACGATCTGTGACCAAAT<br>GACAGGCATTCTGGCGACTGAGGTCACGCCCGAGGATGCGCAAAA<br>ATTGCTTGTCGGATTAAACCAGAGGATCGTCGTGAATGGGAGGACC<br>CAGAGAAACACTAATACAATGAAGAACTACCTGCTCCCAGTGGTGT<br>CACAAGCATTTAGTAAGTGGGCGAAAGAGTATCGGCTTGACCAAG<br>ACGATGAGAAAAACATGGGTATGCGCGAACGCACCCTGACTTGCTG<br>CTGCCTGTGGGCCTTTAAGACCCATAAGAATCACACCATGTATAAG<br>AAGCCAGACACACAGACGATCGTCAGTGTCCCGTCGGAGTTCAACT<br>CCTTCGTGATCCCTAGCCTGTGGTCAGCGGGGTTGTCGATCGGAATT<br>AGACACAGGATCAGGCTTCTTTTGCAGTCAAGACGTGCCGAGCCGC<br>TCGTTCCATTTATGGATGCTAGTGAAGCCAGAGCAGCAGAGAAGGA<br>GGCTGCAGAAGCTAAGGAGGCAGAAGAGACACTGGCAGCCCTACC<br>ACCTCTGATCCCGACCGCTCCGCTGCTCGATGACATCCCTGAAGTTG<br>ATGTAGAGGAGCTGGAGTTTCGAGCAGGAGCCGGTGTTGTCGAAAC<br>GCCTCGGAACGCCCTCAAAGTTACACCACAAGACAGAGACACTATG<br>GTAGGTAGCTATCTCGTTCTGTCTCCCCAGACAGTCCTGAAAAGTGT<br>TAAACTGCAGGTACTGCACTCCTTGGCAGAGCAAGTAAGAATCATT<br>ACCCACAAAGGCCGTGCAGGGCGCTACCAAGTGGATGCCTATGAC<br>GGCCGTGTTTTAATCCCGACAGGCGCGGCTATCCCGGTACCCGATT<br>TCCAGGCTCTAAGTGAGAGTGCGACTATGGTGTACAACGAACGTGA<br>GTTTATCAATCGCAAATTGTACCACATAGCCGTACATGGGGCAGCC<br>CTGAACACCGATGAGGAGGGTTACGAGAAAGTGCGGGCCGAAAGG<br>ACAGATGCCGAGTACGTTTTTGACGTGGATCGCAAACAGTGCGTTA<br>AGAGGGAGGATGCCGAGGGTCTCGTGATGATCGGAGACCTGGTCA<br>ACCCACCATTCCACGAATTTGCGTATGAAGGACTGAAACGAAGACC<br>AGCGGCTCCATACAAAACAACTGTAGTCGGAGTCTTCGGCGTGCCT<br>GGATCTGGAAAATCGGGTATAATCAAAAGCCTGGTCACACGTGCGG<br>ACTTGGTCACCAGTGGAAAGAGAGAGAACTGTCAGGAGATCATGC<br>ACGACGTCAAGAGATACAGAGACCTGGACATCACTGCAAAAACGG<br>TGGATTCCGTACTGTTGAATGCGTTAAGCAGACTGTCGACGTCTT<br>GTACGTCGATGAGGCTTTCGCTTGCCATGCAGGGACATTGCTAGCG<br>CTTATCGCCACGGTGCGACCACGTAAGAAGGTTGTGCTTTGCGGCG<br>ACCCGAAACAGTGCGGTTTCTTCAACTTGATGCAACTACAGGTTAA<br>CTTTAACCACAACATCTGCACCGAGGTACACCATAAGAGCATTTCC<br>AGAAGATGCACGCTACCAGTCACCGCCATTGTCTCAACACTACACT<br>ATGAGGGCAAAATGCGCACCACTAACCCATACAATAAACCCGTTGT<br>CATTGACACCACAGGCCAGACTAAACCAAACCGCGAGGACATTGT<br>GTTAACATGTTTCCGCGGTTGGGTTAAGCAGCTGCAACTTGACTATC<br>GTGGACACGAAGTCATGACAGCCGCTGCATCCCAGGGGTTGACCCG<br>AAAGGGCGTGTACGCCGTCCGAATGAAGGTCAACGAAAACCCACT<br>GTACGCACAATCATCGGAGCATGTTAATGTTCTACTGACACGCACA<br>GAGGGCAGACTAGTGTGAAGACACTGTCAGGAGATCCCTGGATC<br>AAAACTTTGAGCAACATCCCAAAAGGGAATTTCACAGCAACTTTGG<br>AAGATTGGCAACAAGAGCACGACGCCATTATGAGGGCAATAACAC<br>AAGAAGCAGCCCCTTTGGACGTGTTCCAAAATAAGGCTAAGGTGTG<br>TTGGGCCAAGTGCTTGGTACCCGTTTTGGAAACCGCGGGGATCAAG |

| SEQ ID NO | Sequence |
|---|---|
| | TTGTCAGCCGCCGATTGGAGCTCAATCATTTTGGCTTTCAAAGAAG |
| | ACAGAGCTTATTCACCAGAGGTTGCACTGAATGAGATTTGCACTAA |
| | AATCTACGGGGCGGATTTGGACAGCGGCCTGTTTTCGGCTCCACGC |
| | GTGTCGCTACACTATACTACAAATCATTGGGATAACTCGCCTGGAG |
| | GAAGGATGTACGGGTTTTCCGTCGAGGCCGCCAACCGCCTAGAACA |
| | ACGGCACCCGTTCTACAGGGGACGGTGGGCTTCTGGGCAGGTGTTG |
| | GTCGCAGAACGAAGAACTCAGCCGATTGACATCACTTGCAACCTAA |
| | TCCCCTTCAACCGGAGACTCCCACACGCGCTGGTCACGGAATATCA |
| | TCCAGTTAAGGGAGAAAGAGTGGAGTGGCTTGTGAATAAGATCCC |
| | AGGCTATCACTTGCTACTGGTTAGCGAGTATAACCTCATACTGCCTA |
| | GAAGGAAGGTAACGTGGATTGCCCCGCCGACTGTGACAGGAGCCG |
| | ATTTAACCCACGACTTGGATTTAGGACTACCGCCTAATGCTGGCAG |
| | GTATGACCTAGTCTTCGTCAACATGCATACACCGTATAGGCTCCATC |
| | ACTACCAACAATGCGTCGATCACGCCATGAAATTACAGATGCTGGG |
| | CGGCGACGCACTCTACCTGTTGAAACCCGGGGGAAGCCTCCTTTTG |
| | AGAGCCTACGGTTATGCCGATAGAACGAGCGAGGCTGTGGTGACG |
| | GCTCTCGCTCGTCGGTTCTCGTCCTTCAGAGCGGTCAGACCTCCATG |
| | TGTGACTAGTAACACCGAGGTGTTCTTACTGTTCACGAACTTTGACA |
| | ACGGTAGAAGAACAGTAACCCTGCATCCTACAAATGGTAAATTATC |
| | ATCAATTTATGCAGGTACAGTGCTGCAGGCGGCCGGCTGCGCTCCC |
| | GCTTATACTGTCAAAAGGGCAGACATCGCGACCGCCATTGAGGATG |
| | CGGTGGTCAATGCAGCTAACCACCGTGACAAGTGGGCGACGGAG |
| | TCTGCAGGGCAGTAGCACGGAAATGGCCTCAAGCCTTCCGCAACGC |
| | AGCGACACCTGTCGGAACCGCAAAAACCGTCAAGTGCGACGAGAC |
| | TTACATCATCCACGCGGTGGGTCCAAATTTTAACAATACATCTGAG |
| | GCTGAAGGGGATCGTGACTTGGCGGCGGCATACAGGGCCGTAGCA |
| | GCGGAGATTAACCGACTGTCTATAAGTAGTGTGGCGATTCCACTGC |
| | TTTCCACAGGTATATTCAGTGCAGGAAAAGATAGAGTGCATCAGTC |
| | GCTTTCGCACCTTCTAGCGGCAATGGACACCACTGAAGCACGGGTT |
| | ACTATCTACTGCCGCGATAAAACGTGGGACAAAAGATCAAAACA |
| | GTTCTGCAGAATCGCTGCGCCACTGAACTGGTGTCTGATGTGCTAC |
| | AGCTTGAAGTCAATTTGACCAGAGTCCATCCGGACAGCAGCCTGGT |
| | GGGACGTCCAGGGTATAGCACCACTGATGGGACCTTATATTCCTAT |
| | ATGGAAGGTACTAAGTTCCACCAAGCGGCTCTTGACATGGCTGAGA |
| | TCACGACCTTGTGGCCGAGAGTTCAGGATGCAAATGAACACATCTG |
| | CATGTATGCACTGGGCGAGACGATGGACAACATCCGCTCTAGATGC |
| | CCAGTTGAGGATAGTGACTCATCGACTCCACCGAAGACAGTCCCAT |
| | GTCTCTGTCGGTACGCTATGACACCAGAGAGAGTCACAAGACTACG |
| | AATGCATCACACAAAAGATTTTGTGGTCTGCTCGTCTTTCCAGCTAC |
| | CGAAGTACCGCATAGCTGGTGTGCAGCGAGTAAAGTGCGAAAAAG |
| | TGATGCTTTTTGATGCAACTCCACCGGCCTCTGTTAGTCCTGTGCAA |
| | TACCTGACGAGTCACAGTGAAACTACTGTAAGCTTGAGCTCGTTCT |
| | CAATTACATCTGACAGCAGCTCCCTAAGCACCTTCCCGGATCTGGA |
| | GTCACTAGAAGAACTGGGCAATGATCCACAGTCCATGCGGATGGAC |
| | GAGTCTGACAACCGGCAACCCATATCAACGGTAGAACCGGTTGTTC |
| | GACCCGTACCACCTCCGCGTCCTAAACGTGCCAGGCGACTAGCGGC |
| | TGCACGTATGCAGGTCCAGGCGGAAGTGCACCACCCACCCGTCGTC |
| | CAAAGGACGAAACCGGTCCCAGCACCGCGCACCAGTTTGCGTCCCG |
| | TCCCCGCGCCCAGAAGGTGTATGCCAAGACCAGCAGTAGAGCTGCC |
| | CTGGCCGCAGGAGGCCGTCGACATAGAGTTCGGGGCGCCGACCGA |
| | AGAGGAGAGTGAAATCACATTCGGAGACTTTTCTGCTTCGGAGTGG |
| | GAGACCATCAGCAACTCATCCTGACTAGGCCGAGCGGGGGCTTATA |
| | TCTTCTCATCAGACGTCGGTCCAGGGCATCTGCAACAGAAATCAGT |
| | GAGACAGCACGATCTAGAGGTGCCGATTATGGATCGCGTAGTCGAG |
| | GAGAAAGTCTACCCGCCGAAACTAGATGAGGCAAAAGAGAAACAG |
| | CTGCTCCTAAAACTGCAGATGCATGCCACAGACGCCAACCGGAGCC |
| | GGTACCAATCAAGGAAAGTTGAGAACATAAAAGCAACGATCATTG |
| | ACCGGCTGAAACAAGGCAGCGCATCCTACATCTCGGCTGAGGCCAA |
| | TAAAGCAATCACATACCATGTCAAATATGCTAAGCCTCGGTACTCT |
| | GTGCCGGTGATGCAAAGACTTAGCAGTGCAACCACCGCAGTTGCCG |
| | CTTGCAATGAATTCCTGGCCCGGAACTACCCTACAGTGGCGTCATA |
| | TCAGATCACCGATGAGTACGACGCTTATTTAGATATGGTGGACGGG |
| | TCAGAAAGCTGCCTAGACAGAGCAAACTTCTGCCCGGCGAAGTTGC |
| | GCTGCTATCCAAAACACCATGCATACCATGTACCCCAGATTAGAAG |
| | TGCTGTTCCTTCGCCATTCCAAAACACGTTGCAGAATGTATTAGCGG |
| | CCGCCACTAAGCGTAATTGCAACGTCACCCAGATGCGTGAACTACC |
| | AACCCTGGATTCAGCCGTGTACAACGTGGAATGTTTCCGCAAGTAC |
| | GCCTGTAACAACGAATATTGGGAAGAGTTTGCTGCTAAACCTATCA |
| | GAATTACAACAGAGAATTTGACCACTTATGTGACCAAATTAAAAGG |
| | TGGAAAGGCAGCCGCCCTGTTTGCAAAGACGCATAACTTAGTTCCA |
| | CTGCAGGAGGTTCCAATGGATAGATTCGTCATGGACATGAAGCGCG |
| | ATGTGAAGGTTACACCAGGGACGAAGCACACAGAGGAACGACCAA |
| | AGGTCCAAGTGATTCAAGCTGCCGAGCCTCTGGCTACCGCCTACCT |
| | GTGTGGAATTCACAGAGAACTGGTTCGCCGGCTCAATGCTGTGTTG |
| | CTACCTAACATCCATACCCTGTTTGACATGTCTGCTGAAGATTTTGA |

SEQUENCES

| SEQ ID NO | Sequence |
|---|---|
| | TGCCATCATATCAGAGCACTTCAAGCCAGGGGACCATGTCTTGGAA |
| | ACGGACATCGCTTCTTTTGACAAAAGCCAGGACGATTCACTGGCAC |
| | TAACGGGGCTAATGATACTGGAAGACTTGGGCGTCGATAACCAGTT |
| | ATTGGATCTTATCGAGGCTGCATTTGGTCAGATTACCAGCTGCCACC |
| | TGCCTACAGGGACTAGGTTTAAATTTGGGGCTATGATGAAGTCAGG |
| | CATGTTTCTTACATTGTTCATTAACACCGTTTTGAACATTACCATTG |
| | CCAGTAGAGTGCTGGAAGCCAGATTAACTAACTCAGCCTGTGCCGC |
| | ATTTATCGGCGACGACAACGTGGTTCACGGAGTCGTCTCCGATAAA |
| | CTGATGGCAGATAGATGTGCCACTTGGGTTAACATGGAGGTTAAAA |
| | TAATAGATGCAGTCATGTGTGCAAAGCCACCGTATTTCTGTGGAGG |
| | CTTTTTGGTCTATGATCATGTCACAAGGACGTCATGTCGAATAGCG |
| | GATCCATTAAAAAGGTTATTCAAATTGGGCAAACCCCTGCCGGCAG |
| | ACGACTGCCAAGATGAAGACCGCCGTAGGGCATTGCACGACGAGG |
| | TTAAAAAATGGTTTAGATCAGGCTTGGGTTCGGAGATTGAGGTCGC |
| | CCTCGCCACCAGATACGAGGTGGAAGGGGGTCACAACCTACTGCTG |
| | GCTATGTCCACCTTTGCACACAGCATGAAGAATTTTTCTGCATTGAG |
| | GGGACCCGTCATACACTTGTACGGCGGTCCTAAATAGGTGCTCTAC |
| | ACGACACCTATACCACCATGGATTTCCTACCAACACAAGTGTTTTAT |
| | GGCAGGCGATGGAGACCACGAATGCCGCCACGCCCTTGGAGGCCA |
| | CGCCCACCTACAATTCAAAGACCAGATCAACAGGCCCGACAAATG |
| | CAGCAGCTGATTGCTGCGGTCAGTACGCTTGCCCTTAGGCAAAACG |
| | CTGCTGCCCCTCAGCGTGGAAGAAAGAAGCAACCACGTAGAAAGA |
| | AACCAAAACCACAACCCGAGAAACCTAAGAAGCAAGAGCAGAAAC |
| | CGAAGCAAAAGAAGACCCCTAAGAAGAAGCCCGGGAGAAGGGAG |
| | CGCATGTGCATGAAGATTGAGCACGATTGCATCTTTGAGGTCAAGC |
| | ACGAAGGAAAGGTCACAGGCTATGCTTGCCTTGTCGGTGACAAGT |
| | AATGAAGCCGGCACACGTCCCTGGAGTGATAGACAACATCGATCTC |
| | GCACGTCTATCGTATAAGAAATCTAGTAAGTATGACCTGGAATGTG |
| | CACAGATACCGGTGGCTATGAAGTCAGATGCATCGAAATACACCCA |
| | TGAAAAACCCGAAGGTCACTATAACTGGCACTATGGGCCGTCCAG |
| | TACACAGGAGGCAGATTCACGGTGCCCACAGGAGTGGGTAAGCCT |
| | GGCGACAGCGGCCGGCCCATCTTTGATAACAAGGGCCGCGTTGTCG |
| | CAATAGTGCTAGGAGGAGCTAATGAAGGTGCCAGAACCGCGCTCTC |
| | TGTCGTGACGTGGAATAAAGACATGGTCACCAAGATCACACCGGA |
| | GGGCACAGAGGAGTGGGCAGCTCCGACAGTGACAGCTATGTGCCTT |
| | CTGGCGAATGTATCCTTCCCATGTTTCCAACCGAGCTGCTCTCCATG |
| | CTGTTATGAAAAGGGGCCTGAGCCGACGCTGAGAATGCTGGAAGA |
| | GAACGTAAACTCAGAGGGATACTATGAATTGTTGCATGCTGCCGTG |
| | TACTGCAAAAACAGCTCGAGGTCGAAGAGGAGCACTGCAAATCAC |
| | TTTAACGCATACAAATTGACTCGTCCATACGTAGCCTACTGTGCAG |
| | ACTGTGGCATGGGCCATTCTTGCCACAGTCCCGCCATGATTGAAAA |
| | TGTGCAGGCGGATGCTACAGATGGCACGTTAAAGATTCAATTCGCT |
| | TCTCAAATTGGCCTAACGAAAGCGGACACGCATGATCATACAAAGA |
| | TTAGATATGCAGAAGGGCATGATATAGCGGAGGCTGCCAGGTCAA |
| | CTCTTAAGGTCCATAGCAGCAGTGAGTGCGCGGTGACAGGAACGAT |
| | GGGACACTTTATCTTGGCCAAATGTCCACCAGGCGAAGTCATTAGT |
| | GTCTCATTTGTTGATTCAAAAAATGAACAGCGGACCTGTCGGATAG |
| | CCTACCACCATGAACAGAGGCTAATAGGGCGTGAAAGATTCACGGT |
| | ACGACCACATCATGGGATTGAGCTACCCTGCACCCACTTACCAGCTA |
| | ACGACCGCCGAAACCTCTGAAGAGATAGACATGCACATGCCGCCG |
| | GACATTCCGGACAGAACTATCCTTTCCCAGCAATCAGGAAATGTCA |
| | AGATAACGGTCAACGGGCGGACCGTCAAGTATAGCTGCTCATGTGG |
| | TTCTAAACCATCAGGCACAACAACTACAGACAAGACTATCAATAGC |
| | TGCACCGTTGACAAATGCCAGGCATATGTCACGAGCCATACGAAAT |
| | GGCAATTTAATTCACCTTTCGTTCCGCGCGCGGAGCAAGCGGAGCG |
| | TAAGGGCAAGGTGCACATTCCCTTTCCACTTATCAACACCACCTGC |
| | CGAGTACCATTGGCTCCCGAAGCCCTAGTCAGGAGCGGTAAACGAG |
| | AAGCTACGCTCTCACTGCACCCGATACATCCCACATTGCTAAGTTA |
| | CAGAACACTGGGACGCGAGCCAGTTTTTGATGAACAGTGGATCACC |
| | ACCCAGACGGAGGTAACAATCCCAGTACCAGTGGAGGGAGTGGAG |
| | TATCGGTGGGCAACCACAAACCACAACGCTTGTGGTCACAGCTAA |
| | CAACTGATGGCAGAGCACATGGCTGGCCCCATGAAATTATCGAGTA |
| | CTACTACGGGCTGCATCCTACGACAACCATTGTCGTGGTGGTTGCT |
| | GTCTCAGTAGTGGTGCTCTTGTCAGTTGCTGCATCTGTTTATATGTG |
| | TGTAGTGGCACGCAACAAGTGCCTGACACCATATGCACTCACCCCG |
| | GGGGCCGTTGTCCCTGTTACTATCGGGGTATTATGCTGTGCACCGA |
| | AAGCGCACGCAGCTAGCTTTGCTGAAGGCATGGCCTACCTGTGGGA |
| | TAATAACCAGTCAATGTTCTGGATGGAGTTGACTGGACCTTTGGCT |
| | CTTCTTATCCTGACTACATGTTGCGCCCGATCACTACTTTCCTGCTG |
| | CAAGGGATCTTTTTTAGTCGCAGTGAGCGTCGGGAGTGCCGTTGCC |
| | AGTGCTTACGAGCACACGGCAGTCATTCCAAATCAAGTGGGATTCC |
| | CGTATAAGGCTCATGTTGCACGTGAAGGATACAGCCCGCTGACACT |
| | GCAGATGCAGGTGGTTGAAACCAGTCTAGAGCCAACGCTCAACCTG |
| | GAGTATATCACTTGCGACTACAAAACAAAGGTTCCATCCCCGTACG |
| | TAAAGTGCTGTGGCACAGCTGAATGCCGCACGCAGGACAAGCCCG |

| SEQ ID NO | Sequence |
|---|---|
| | AATACAAGTGTGCGGTGTTCACGGGCGTGTACCCTTTTATGTGGGG<br>AGGTGCATACTGTTTTTGTGACTCGGAAAACACACAGATGAGTGAG<br>GCCTACGTGGAGCGCGCTGACGTGTGCAAACACGACTACGCAGCCG<br>CCTACCGCGCCCACACTGCTTCCCTCAGAGCCAAAATCAAGGTAAC<br>ATATGGCACCGTAAATCAGACTGTCGAGGCGTATGTGAACGGTGAC<br>CATGCCGTAACGATTGCCGGGACGAAGTTTATCTTTGGTCCGGTGT<br>CAACGGCCTGGACACCGTTCGATACTAAATCGTGGTCTATAAAGG<br>GGAGGTATACAACCAGGACTTTCCCCCTTATGGTGCCGGGCAGCCT<br>GGAAGATTCGGAGACATCCAGAGTAGGACGTTGGACAGTAAGGAC<br>CTATATGCAAACACGGGCCTTAAGCTGGCAAGACCAGCAGCCGGC<br>AACATCCACGTCCCCTATACCCAGACACCATCTGGTTTTAAAACAT<br>GGCAAAAAGACAGGGACTCACCGTTAAACGCTAAGGCACCCTTTG<br>GATGCACAATCCAGACAAATCCGGTCAGAGCGATGAATTGCGCTGT<br>CGGCAACATACCCGTTTCGATGGATATCGCCGACAGCGCATTCACT<br>AGACTGACTGATGCGCCTATAATATCAGAGCTGCTGTGCACTGTAT<br>CTACATGCACGCATTCTTCAGACTTCGGTGGAGTCGCTGTACTTTCT<br>TACAAGGTGGAAAAAGCAGGCAGGTGCGACGTCCATTCGCACTCG<br>AATGTCGCGGTACTCCAGGAAGTTTCCATCGAGGCAGAAGGTCGAT<br>CAGTGATCCACTTTTCGACCGCATCAGCCGCCCCTTCCTTCATAGTA<br>TCCGTCTGCAGCTCGCGTGCCACGTGCACAGCTAAATGTGAACCAC<br>CGAAAGACCATGTGGTCACTTACCCGGCAAATCACAACGGGATAAC<br>TTTGCCGGACTTATCCAGCACTGCAATGACTTGGGCGCAACATCTT<br>GCCGGTGGAGTCGGGCTATTGATAGCACTGGCAGTGCTAATTCTAG<br>TAATAGTTACTTGCATAACTTTGAGAAGGTGAATCATAAGTACCAT<br>GTATAATGCGGGCTGGCATATATGTAACCATTATTATATATTTTAAC<br>CATATTAACATTCGAATATCAAATTAGGTGCCGTGCATGATGCGGA<br>CCGATTTATTATTCACATATGTAACCTTTATCATATTACATCATATA<br>TTCAATTTTAAAATTTCTATACGCGTCTCTAATGGCGCATATAATAA<br>CCACCTACAATTTTCTTCATTTTCTTTATTTGTGCCACTATAGGGCAC<br>TTACTAACCATAGAAGTAATTCATTTTGTTTTTAATATTTC |
| SEQ ID NO: 8 | MDFLPTQVFYGRRWRPMPPRPWRPRPPTIQRPDQQARQMQQLIAAV<br>STLALRQNAAAPQRGRKKQPRRKKPKPQPEKPKKQEQKPKQKKTPKK<br>KPGRRERMCMKIEHDCIFEVKHEGKVTGYACLVGDKVMKPAHVPGVI<br>DNIDLARLSYKKSSKYDLECAQIPVAMKSDASKYTHEKPEGHYNWHY<br>GAVQYTGGRFTVPTGVGKPGDSGRPIFDNKGRVVAIVLGGANEGART<br>ALSVVTWNKDMVTKITPEGTEEWAAPTVTAMCLLANVSFPCFQPSCSP<br>CCYEKGPEPTLRMLEENVNSEGYYELLHAAVYCKNSSRSKRSTANHF<br>NAYKLTRPYVAYCADCGMGHSCHSPAMIENVQADATDGTLKIQFASQ<br>IGLTKADTHDHTKIRYAEGHDIAEAARSTLKVHSSSECAVTGTMGHFIL<br>AKCPPGEVISVSFVDSKNEQRTCRIAYHHEQRLIGRERFTVRPHHGIELP<br>CTTYQLTTAETSEEIDMHNIPPDIPDRTILSQQSGNVKITVNGRTVKYSC<br>SCGSKPSGTTITDKTINSCTVDKCQAYVTSHTKWQFNSPFVPRAEQAE<br>RKGKVHIPFPLINTTCRVPLAPEALVRSGKREATLSLHPIHPTLLSYRTL<br>GREPVFDEQWITTQTEVTIPVPVEGVEYRWGNHKPQRLWSQLTTDGR<br>AHGWPHEIIEYYYGLHPTTTIVVVVAVSVVVLLSVAASVYMCVVARN<br>KCLTPYALTPGAVVPVTIGVLCCAPKAHAASFAEGMAYLWDNNQSMF<br>WMELTGPLALLILTTCCARSLLSCCKGSFLVAVSVGSAVASAYEHTAV<br>IPNQVGFPYKAHVAREGYSPLTLQMQVVETSLEPTLNLEYITCDYKTK<br>VPSPYVKCCGTAECRTQDKPEYKCAVFTGVYPFMWGGAYCFCDSENT<br>QMSEAYVERADVCKHDYAAAYRAHTASLRAKIKVTYGTVNQTVEAY<br>VNGDHAVTIAGTKFIFGPVSTAWTPFDTKIVVYKGEVYNQDFPPYGAG<br>QPGRFGDIQSRTLDSKDLYANTGLKLARPAAGNIHVPYTQTPSGFKTW<br>QKDRDSPLNAKAPFGCTIQTNPVRAMNCAVGNIPVSMDIADSAFTRLT<br>DAPIISELLCTVSTCTHSSDFGGVAVLSYKVEKAGRCDVHSHSNVAVL<br>QEVSIEAEGRSVIRESTASAAPSFIVSVCSSRATCTAKCEPPKDHVVTYP<br>ANHNGITLPDLSSTAMTWAQHLAGGVGLLIALAVLILVIVTCITLRR |
| SEQ ID NO: 9 | MSKVFVDIEAESPPFLKSLQRAFPAFEVEAQQVTPNDHANARAFSHLAT<br>KLIEQETEICDTLILDIGSAPARRIVIMSEHTYHCVCPMRSAEDPERLLYY<br>ARKLAKASGEVVDRNIAAKIDDLQSVMATPDNESRTFCLHTDQTCRTP<br>AEVAVYQDVYAVHAPTSLYFQAMKGVRTAYWIGFDTTPFMFDTMAG<br>AYPTYATNWADEQVLKARNIGLCSAALTEGHLGKLSIMRKKRMKPSD<br>QIMDFSVGSTLYTESRRLLKSWHLPSVPHLKGRQSYTCRCDTIVSCEGY<br>VVKKITMSPGVFGKTSGYAVTHHAEGFLVCKTTDTIAGERVSFPVCTY<br>VPSTICDQMTGILATEVTPEDAQKLIVGLNQRIVVNGRTQRNTNTMKN<br>YLLPVVSQAFSKWAKEYRLDQDDEKNMGMRERTLTCCCLWAFKTHK<br>NHTMYKKPDTQTIVSVPSEFNSFVIPSLWSAGLSIGIRHRIRLLLQSRRA<br>EPLVPFMDASEARAAEKEAAEAKEAEETLAALPPLIPTAPLLDDIPEVD<br>VEELEFRAGAGVVETPRNALKVTPQDRDTMVGSYLVLSPQTVLKSVK<br>LQVVLHSLAEQVRIITHKGRAGRYQVDAYDGRVLIPTGAAIPVPDFQALS<br>ESATMVYNEREFINRKLYHIAVHGAALNTDEEGYEKVRAERTDAEYV<br>FDVDRKQCVKREDAEGLVMIGDLVNPPFHEFAYEGLKRRPAAPYKTT<br>VVGVFGVPGSGKSGIIKSLVTRADLVTSGKRENCQEIMHDVKRYRDLD<br>ITAKTVDSVLLNGVKQTVDVLYVDEAFACHAGTLLALIATVRPRKKV |

| SEQ ID NO | Sequence |
|---|---|
| | VLCGDPKQCGFFNLMQLQVNFNHNICTEVHHKSISRRCTLPVTAIVSTL<br>HYEGKMRTTNPYNKPVVIDTTGQTKPNREDIVLTCFRGWVKQLQLDY<br>RGHEVMTAAASQGLTRKGVYAVRMKVNENPLYAQSSEHVNVLLTRT<br>EGRLVWKTLSGDPWIKTLSNIPKGNFTATLEDWQQEHDAIMRAITQEA<br>APLDVFQNICAKVCWAKCLVPVLETAGIKLSAADWSSIILAFKEDRAYS<br>PEVALNEICTKIYGADLDSGLFSAPRVSLHYTTNHWDNSPGGRMYGFS<br>VEAANRLEQRHPFYRGRWASGQVLVAERRTQPIDITCNLIPFNRRLPH<br>ALVTEYHPVKGERVEWLVNKIPGYHLLLVSEYNLILPRRKVTWIAPPT<br>VTGADLTHDLDLGLPPNAGRYDLVFVNMHTPYRLHHYQQCVDHAMK<br>LQMLGGDALYLLKPGGSLLLRAYGYADRTSEAVVTALARRFSSFRAV<br>RPPCVTSNTEVFLLFTNFDNGRRTVTLHPTNGKLSSIYAGTVLQAAGC<br>APAYTVKRADIATAIEDAVVNAANHRGQVGDGVCRAVARKWPQAFR<br>NAATPVGTAKTVKCDETYIIHAVGPNFNNTSEAEGDRDLAAAYRAVA<br>AEINRLSISSVAIPLLSTGIFSAGKDRVHQSLSHLLAAMDTTEARVTIYC<br>RDKTWEQKIKTVLQNRCATELVSDVLQLEVNLTRVHPDSSLVGRPGY<br>STTDGTLYSYMEGTKFHQAALDMAEITTLWPRVQDANEHICMYALGE<br>TMDNIRSRCPVEDSDSSTPPKTVPCLCRYAMTPERVTRLRMHHTKDFV<br>VCSSFQLPKYRIAGVQRVKCEKVMLFDATPPASVSPVQYLTSHSETTV<br>SLSSFSITSDSSSLSTFPDLESLEELGNDPQSMRMDESDNRQPISTVEPVV<br>RPVPPPRPKRARRLAAARMQVQAEVHHPPVVQRTKPVPAPRTSLRPVP<br>APRRCMPRPAVELPWPQEAVDIEFGAPTEEESEITFGDFSASEWETISNS<br>SLGRAGAYIFSSDVGPGHLQQKSVRQHDLEVPIMDRVVEEKVYPPKLD<br>EAKEKQLLLKLQMHATDANRSRYQSRKVENIKATHDRLKQGSASYIS<br>AEANKAITYHVKYAKPRYSVPVMQRLSSATTAVAACNEFLARNYPTV<br>ASYQITDEYDAYLDMVDGSESCLDRANFCPAKLRCYPKHHAYHVPQI<br>RSAVPSPFQNTLQNVLAAATKRNCNVTQMRELPTLDSAVYNVECFRK<br>YACNNEYWEEFAAKPIRITTENLTTYVTKLKGGKAAALFAKTHNLVPL<br>QEVPMDRFVMDMKRDVKVTPGTKHTEERPKVQVIQAAEPLATAYLC<br>GIHRELVRRLNAVLLPNIHTLFDMSAEDFDAIISEHFKPGDHVLETDIAS<br>FDKSQDDSLALTGLMILEDLGVDNQLLDLIEAAFGQITSCHLPTGTRFK<br>FGAMMKSGMFLTLFINTVLNITIASRVLEARLTNSACAAFIGDDNVVH<br>GVVSDKLMADRCATWVNMEVKIIDAVMCAKPPYFCGGFLVYDHVTR<br>TSCRIADPLKRLFKLGKPLPADDCQDEDRRRALHDEVKKWFRSGLGSE<br>IEVALATRYEVEGGHNLLLAMSTFAHSMKNFSALRGPVIHLYGGPK |
| SEQ ID NO: 10 | TGGCGGACGTGTGACATCACCGTTCGCCTTTCTTGGATCCCTTGTTA<br>CTCCACGTAGTGAGAGATAAACAACCCAGAATGAAGGTCACTGTA<br>GATGTTGAGGCTGATAGCCCATTTTTGAAGGCCCTTCAGAAAGCAT<br>TCCCGGCTTTTGAGGTTGAATCACAGCAGGTCACACCCAATGACCA<br>TGCTAATGCCAGAGCTTTTTCGCATCTGGCCACAAAGTTAATTGAA<br>CAAGAGGTTCCAACCAACATCACCATCCTGGATGTGGGCAGCGCGC<br>CCGCAAGGAGGTTGATGTCTGATCACAGCTACCACTGCATTTGTCC<br>CATGAAGAGTGCGGAAGACCCAGAGAGATTAGCGAACTATGCCCG<br>GAAACTGGCAAAAGCAGCAGGGGAAGTGCTAGACAAAAATGTGTC<br>CGGTAAGATCACGGACCTGCAGGACGTCATGGCAACCCCCGATCTG<br>GAATCTCCAACGTTCTGTCTCCACACCGACGAGACGTGTCGCACTA<br>GAGCTGAAGTAGCTGTGTACCAGGACGTGTACGCGGTGCACGCACC<br>GACCTCGCTTTATCATCAAGCGATGAAAGGGGTCAGGACAGTATAC<br>TGGATAGGATTTGACACCACCCCATTCATGTTCGAGGTTTTGGCTGG<br>CGCATACCCAACGTATTCCACGAATTGGGCGGACGAGCAGGTCCTG<br>CAGGCACGTAACATCGGCCTATGTGCGACCAGTCTCAGCGAAGGAC<br>ATCGAGGAAAACTCTCTATTATGAGGAAGAAACGCCTAAGGCCAA<br>GCGACAGGGTCATGTTCTCGGTTGGGTCAACGCTATATATAGAAAG<br>TAGACGCCTTCTTAAGAGTTGGCATCTTCCCTCCGTGTTCCACCTGA<br>AAGGCAAGAATAGCTTTACTTGCAGGTGCGACACAATAGTTTCATG<br>CGAGGGCTACGTTGTTAAAAAGATCACAATGAGCCCAGGGACGTA<br>CGGGAAGACGGTCGGATACGCCGTTACGCATCATGCAGAAGGTTTC<br>CTAATGTGCAAGGTGACGGACACTGTGCGCGGGGAGAGAGTATCA<br>TTCCCGGTATGCACTTATGTGCCTGCAACCATTTGCGATCAGATGAC<br>AGGAATCCTGGCTACCGACGTCACACCCGAAGATGCGCAGAAACTC<br>CTGGTGGGGTTGAACCAACGTATAGTTGTGAACGGCAGAACCCAAA<br>GAAATACCAACACAATGAAAAACTACCTATTGCCGGTAGTGGCCCA<br>AGCTTTCAGCAAGTGGGCACGAGAAGCAAAAGCAGACATGGAGGA<br>TGAGAAACCTCTGGGAACCAGAGAAAGAACCCTGACGTGCTGTTGC<br>CTGTGGGCATTCAAGAGCCACAAGACACACACCATGTACAAAAGG<br>CCGGATACCCAAACTATAGTCAAGGTGCCATCTACTTTTGACTCGTT<br>TGTGATTCCAAGCCTGTGGTCATCCAGCCTATCCATAGGCCTACGG<br>CAAAGAATAAAACTGCTATTAGGCCCAAAACTCTCGCGGGACCTCC<br>CGTACTCTGGAGACCGAAACGAAGCGCGAGAAGCAGAGAAGGAAG<br>CCGAAGAGACCAAGGAAGCAGAATTGACACGGGAAGCACTGCCAC<br>CATTGGTGGGAAGCAACTGCGCTGATGACGTCGATCGGGTAGATGT<br>GGAAGAGCTGACGTACCGCGCCGGAGCAGGGGTAGTGGAGACACC<br>CAGGAATGCGCTCAGAGTGACACCACAAGAGCGCGATCAGCTGAT<br>CGGCGCGTACCTGATCTTGTCTCCGCAAGCAGTACTGAAGAGTGAA<br>AAACTCACACCGATACATCCACTGGCTGAGCAAGTGACAATCATGA |

SEQUENCES

| SEQ ID NO | Sequence |
|---|---|
| | CGCACTCTGGAAGATCTGGCAGATACCCGGTTGACCGCTACGACGG<br>ACGGGTGTTGGTCCCGACGGGCGCAGCGATCCCCGTCAGCGAATTT<br>CAAGCACTCAGTGAGAGTGCTACTATGGTCTACAACGAACGTGAGT<br>TCATCAATCGCAAGTTGCACCATATAGCACTCTACGGCCCCGCCCT<br>AAACACTGAGGAGGAGAACTACGAAAAAGTAAGGGCAGAGAGAG<br>CCGAAGCTGAATACGTGTTTGACGTTGACAAGAGGATGTGCGTGAA<br>GAGAGAAGAAGCATCAGGCCTTGTACTGGTTGGTGACTTAATCAAC<br>CCACCCTTCCATGAGTTCGCGTATGAAGGACTGAAGATACGGCCCG<br>CAACGCCTTTCCAAACCACGGTCATTGGCGTCTTCGGGGTACCTGG<br>TTCGGGCAAGTCAGCCATAATCAAGAGTGTGGTGACTACGAGGGAC<br>CTGGTCGCCAGTGGGAAGAAGGAGAACTGCCAGGAGATAGTTAAT<br>GATGTCAAAAAGCAGAGAGGACTGGATGTAACAGCCAGGACTGTT<br>GACTCTATCCTGTTGAACGGGTGCAGAAGAGGAGTAGAGAACCTAT<br>ACGTGGACGAAGCATTTGCCTGTCATTCAGGTACACTGTTGGCTCTT<br>ATTGCCATGGTGAAACCAACTGGCAAGGTGATCCTATGCGGAGACC<br>CAAAACAGTGTGGATTTTTTAACCTGATGCAACTGAAGGTGAACTT<br>CAACCACGATATCTGCACACAAGTGCTCCACAAAAGCATATCCAGA<br>AGATGCACCCTCCCGATCACGGCTATCGTCTCGACCCTACACTATC<br>AGGGTAAGATGAGAACCACGAACTTATGTAGTGCACCCATCCAGAT<br>AGACACAACAGGTACCACTAAACCAGCCAAAGGAGACATCGTGTT<br>AACATGCTTCCGCGGTTGGGTAAAGCAACTGCAGATAGACTACCGT<br>GGACACGAAGTCATGACAGCAGCTGCATCACAAGGACTGACTAGA<br>AAAGGGGTATACGCCGTTAGGCAGAAAGTGAATGAAAACCCGCTT<br>TATGCCCCTTCATCAGAACATGTCAACGTATTGCTGACTAGAACTG<br>AAAACCGGCTGGTGTGGAAAACACTGTCGGGAGACCCGTGGATAA<br>AGGTGTTAACCAATATCCCCAAGGGCGATTTCAGCGCTACGTTGGA<br>GGAGTGGCAAGAGGAGCATGACAACATCATGAACGCCCTTCGCGA<br>GAGGTCGACAGCAGTAGACCCGTTCCAGAACAAAGCCAAAGTCTG<br>CTGGGCAAAGTGCCTCGTGCAGGTCCTAGAAACGGCTGGGATACGC<br>ATGACGGCAGAGGAGTGGGATACAGTGTTGGCTTTCCGCGAAGAC<br>AGGGCGTACTCACCCGAAGTGGCTCTGAACGAGATCTGTACCAAGT<br>ATTACGGCGTTGACTTAGACAGCGGATTGTTCTCCGCCCAATCGGT<br>CTCATTGTACTATGAAAACAACCACTGGGACAATAGACCGGGCGGC<br>CGGATGTATGGATTCAACCGCGAAGTCGCCCGTAAGTTTGAGCAAC<br>GCTACCCATTCCTGAGAGGCAAGATGGACTCGGGGCTACAAGTTAA<br>TGTTCCAGAGAGAAAAGTACAGCCATTCAATGCGGAATGTAATATA<br>TTACCATCAAACAGGCGACTTCCGCACGCCCTCGTCACCAGCTACC<br>AGCAGTGCCAGGGCGAGAGGGTAGAATGGCTTTTGAAGAAGCTTC<br>CCGGATACCATTTATTGCTGGTAAGCGAGTACAATCTGGCGCTGCC<br>CCATAAAAGAGTCTTTTGGATTGCACCACCCCATGTGTCTGGTGCA<br>GATCGTATTTATGATCTTGACCTAGGATTACCCCTGAATGCAGGCC<br>GTTACGACTTGGTATTTGTGAACATACACACTGAGTACAGGACGCA<br>CCACTACCAACAGTGCGTCGACCACTCTATGAAGTTACAGATGTTG<br>GGCGGTGACTCCTTACATCTATTGAAACCAGGCGGCTCACTGCTTA<br>TCCGTGCTTACGGGTACGCCGACAGAGTCAGCGAAATGGTGGTCAC<br>TGCATTAGCTAGGAAGITTTCCGCCTTCAGAGTCTTGAGACCAGCA<br>TGTGTAACAAGTAACACTGAAGTCTTTCTGTTGTTCACCAATTTTGA<br>TAACGGCAGAAGGGCTGTGACTCTTCACCAGGCCAATCAGAGGCTC<br>AGCTCCATGTTTGCATGCAACGGGCTACACACAGCCGGATGCGCAC<br>CCTCATACCGTGTGCGTAGGACCGACATTTCCGGGCACGCTGAAGA<br>GGCGGTTGTTAATGCCGCCAACGCGAAGGGCACAGTCGGCGATGG<br>GGTTTGCAGAGCGGTGGCGAGAAAATGGCCAGACTCCTTCAAAGGT<br>GCCGCGACTCCCGTGGGTACGGCTAAGTTGGTACAGGCCAACGGTA<br>TGAATGTCATCCACGCGGTAGGCCCGAATTTCTCCACGGTGACCGA<br>GGCAGAGGGCGACAGAGAGTTGGCCGCCGCATACCGTGCCGTGGC<br>GGGTATTATCAATGCTAGTAACATTAAGAGTGTAGCCATCCCTCTG<br>TTGTCGACGGGAGTGTTCTCCGGAGGTAAAGATAGAGTCATGCAGT<br>CACTAAATCACCTGTTTACCGCAATGGACACCACGGACGCTGACGT<br>AGTCATCTATTGCCGCGACAAAGCCTGGGAGAAGAAAATCCAGGA<br>GGCTATCGATCGCCGCACCGCCGTGGAATTGGTATCTGAAGACATC<br>TCACTCGAGTCTGACTTGATACGGGTACACCCAGATAGTTGCTTGG<br>TAGGCAGAAAAGGTTACAGCATAACAGATGGGAAGCTGCATTCAT<br>ACCTGGAAGGTACCCGCTTTCATCAGACTGCGGTGGACATGGCTGA<br>GATATCTACCTTGTGGCCGAAACTTCAGGACGCAAACGAACAAATA<br>TGCTTGTATGCATTGGGTGAGAGTATGGACAGCATCAGAACGAAAT<br>GCCCTGTTGAGGACGCCGATTCGTCCACGCCTCCGAAAACAGTTCC<br>GTGTCTGTGTAGGTACGCTATGACTGCTGAGAGTGGCAAGACTT<br>CGGATGAACAACACTAAGGCCATAATTGTGTGCTCCTCCTTCCCTTT<br>ACCGAAGTACAGGATTGAAGGCGTCAGAAGGTCAAGTGCGACCG<br>AGTGCTGATTTTTGACCAGACGGTGCCATCTCTGGTTAGTCCAAGG<br>AAGTACATACCAGCCGCCGCCTCTACGCACGCAGATACCGTGAGCT<br>TGGATTCTACAGTATCCACAGGATCCGCGTGGTCATTCCCATCTGA<br>GGCCACGTATGAGACCATGGAAGTAGTAGCAGAGGTGCACCACTC<br>GGAACCACCAGTCCCGCCACCGCGCAGGCGTCGTGCGCAGGTGAC<br>GATGCACCACCAGGAGCTGTTGGAAGTCTCTGACATGCACACCCCG |

| SEQ ID NO | Sequence |
|---|---|
| | ATTGCGGCAAGGGTCGAGATCCCCGTGTACGATACCGCTGTTGTAG |
| | TGGAGAGAGTGGCAATTCCTTGCACAAGCGAGTATGCAAAACCCAT |
| | ACCAGCACCACGGGCAGCAAGGGTCGTACCCGTGCCGGCACCACG |
| | CATTCAGCGAGCGTCGACGTACAGAGTCTCTCCTACACCCACGCCT |
| | CGCGTTCTGAGAGCCTCGGTATGCAGTGTGACCACTAGCGCTGGGG |
| | TAGAGTTCCCTTGGGCGCCTGAAGATCTGGAGGTACTCACCGAGCC |
| | TGTGCACTGCAAAATGCGCGAGCCGGTTGAGTTACCGTGGGAGCCT |
| | GAGGACGTTGATATCCAGTTCGGAGATTTTGAAACATCCGACAAAA |
| | TCCAATTCGGCGATATTGATTTTGACCAATTCTGACTAGGCAGAGC |
| | GGGGGCGTACATCTTCTCGTCTGATACCGGACCAGGGCACTTACAA |
| | CAGAAGTCAGTACGGCAACACGCACTACCGTGCGAAATGCTATACG |
| | TCCACGAGGAAGAACGGACGTACCCCCCCGCACTGGATGAGGCCA |
| | GGGAGAAACTGCTGCAGGCAAAAATGCAGATGGCCACCTACGGAAG |
| | CAAACAAGAGCAGGTACCAATCAAGGAAGGTTGAAAACATGAAGG |
| | CAGTGATCATAGATAGGCTGAAGGATGGAGCAAGAACCTACCTGA |
| | CAGAACAGTCAGAGAAGATTCCAACCTATGTTAGTAAGTACCCGCG |
| | GCCAGTTTACTCGCCGTCGGTAGAGGATAGCTTGCAGAATCCCGAG |
| | GTCGCTGTGGCGGCCTGCAATGCTTTCCTGGAAGCCAATTACCCGA |
| | CAGTGGCTAGTTACCAGATCACGGACGAGTATGATGCCTACTTGGA |
| | TATGGTTGATGGGTCAGAGAGTTGTTTAGACCGGGCAACCTTCTGC |
| | CCGGCAAAATTACGCTGCTACCCAAAGCATCATGCTTACCACCAAC |
| | CGCAGGTTAGGAGCGCGGTCCCATCACCATTTCAAAACACCCTGCA |
| | GAATGTGCTAGCAGCAGCCACGAAGAGAAACTGCAATGTTACACA |
| | GATGAGAGAGCTACCCACTCTAGACTCAGCCGTGCTTAACGTGGAA |
| | TGCTTCAAAAAATTCGCATGCAACGGAGAATACTGGCAGGAATTCA |
| | AAGACAACCCAATAAGAATAACTACAGAGAACATAACAACTTATG |
| | TTACTAGGCTTAAGGGCCCTAAAGCAGCGGCGCTGTTTGCAAAGAC |
| | TCACAATCTAGTCCCGCTGCAGGAGGTGCCCATGGACCGGTTTGTG |
| | GTAGATATGAAGAGAGACGTGAAAGTTACCCCTGGCACCAAACAT |
| | ACCGAGGAACGCCCAAAGGTGCAAGTCATCCAGGCCGCCGAACCT |
| | TTAGCTACAGCTTATTTATGTGGCATTCACAGGGAGTTAGTCCGCCG |
| | CCTGAAGGCCGTCCTGGCCCCGAACATACATCATTGTTCGATATG |
| | TCGGCAGAAGATTTTGATGCCATCATAGCTGCACATTTCCAACCAG |
| | GCGACGCAGTTTTGGAAACGGACATAGCCTCCTTTGACAAGAGCCA |
| | AGATGACTCTCTGGCGTTGACGGCACTGATGCTGTTGGAAGACCTC |
| | GGGGTTGACCAAGAACTACTAGACTTGATAGAGGCAGCGTTCGGG |
| | GAAATTACCAGCGTCCACCTGCCAACAGGTACGCGGTTCAAGTTTG |
| | GCGCCATGATGAAGTCCGGAATGTTCCTGACACTGTTTGTAAATAC |
| | CCTGTTAAACATTGTCATAGCATGCCGTGTACTGCGTGAGAAGCTG |
| | ACAAACTCCGTCTGCGCCGCGTTTATCGGGGATGACAACATAGTGC |
| | ACGGGGTAAGATCCGACCCGTTGATGGCTGAAAGGTGCGCCAGCTG |
| | GGTTAATATGGAGGTAAAGATAATTGACGCTACCATGTGCGAGAAA |
| | CCACCATATTTCTGCGGCGGGTTTATATTGTATGACAAAGTCACCG |
| | GATCGGCGTGCCGAGTGGCCGACCCTCTGAAAAGGTTATTTAAACT |
| | AGGTAAACCTTTACCCGCCGGAGACACCCAAGATGAAGATCGTAG |
| | GCGTGCATTGAAGGATGAGACGGATAGGTGGGCACGAGTAGGGCT |
| | GAAGTCTGAACTGGAAATAGCACTAAGTTCTCGGTATGAGGTGAAC |
| | GGGACCGGCAACATAGTGCGAGCAATGGCCACACTGGCCAAGAGC |
| | CTGAAGAATTTTAAAAAGCTGCGTGGACCCATCGTACACCTCTACG |
| | GCGGTCCTAAATAGATGCAGAGACACACCTTCATCTAATACAGCTC |
| | ACAACAGTAAACATGAATTACATACCAACCCAGACTTTTTACGGAC |
| | GCCGTTGGCGGCCTCGCCCGGCGTTCCGTCCATGGCAGGTGCCGAT |
| | GCAGCCGACACCTACTATGGTTACACCCATGCTGCAAGCACCAGAC |
| | CTACAGGCCCAACAGATGCAACAACTGATCAGCGCTGTCTCTGCAT |
| | TAACCACCAAACAGAATGTAAAAGCACCAAAAGGGCAACGGAAGA |
| | AGAAACAGCAGAAACCAAAGGAAAAGAAGGAAAACCAGAAGAAA |
| | AAGCCGACGCAAAAGAAGAAGCAGCAGCAGAAACCAAAACCACA |
| | GGCTAAGAAGAAGAAACCAGGGAGAAGAGAAAGAATGTGCATGA |
| | AGATCGAGAATGACTGCATATTCGAGGTCAAACTGGATGGCAAGGT |
| | TACCGGTTATGCGTGCCTAGTCGGAGACAAGGTCATGAAGCCGGCT |
| | CACGTTAAAGGCACAATTGATAACCCAGACCTTGCGAAGCTGACTT |
| | ACAAGAAATCCAGTAAGTATGACCTCGAATGCGCCCAGATACCAGT |
| | GCACATGAAGTCCGACGCCTCCAAGTACACACATGAAAAACCCGA |
| | AGGTCATTACAATTGGCACCATGGAGCAGTGCAGTACAGCGGAGG |
| | AAGGTTTACCATCCCCACAGGCGCCGGCAAACCGGGAGATAGCGG |
| | TAGGCCTATTTTTGACAACAAAGGGCGAGTAGTGGCCATCGTGTTA |
| | GGCGGGGCCAACGAAGGTGCTCGCACTGCGCTGTCTGTGGTGACGT |
| | GGACAAAAGACATGGTCACTCGGGTAACGCCAGAAGGAACTGAAG |
| | AGTGGTCTGCCGCGCTGATGATGTGTATCCTTGCCAACACCTCTTTC |
| | CCCTGCTCATCACCTCCCTGCTACCCCTGCTGCTACGAAAAACAGC |
| | CAGAACAGACACTGCGGATGCTGGAAGACAATGTGAATAGACCAG |
| | GGTACTATGAGCTACTGGAAGCGTCCATGACATGCAGAAACAGATC |
| | ACGCCACCGCCGTAGTGTAACAGAGCACTTCAATGTGTATAAGGCT |
| | ACTAGACCGTACTTAGCGTATTGCGCTGACTGTGGGACGGGTACT |
| | TCTGCTATAGCCCAGTTGCTATCGAGAAGATCCGAGATGAGGCGTC |

| SEQ ID NO | Sequence |
|---|---|
| | TGACGGCATGCTCAAGATCCAAGTCTCCGCCCAAATAGGTCTGGAC<br>AAGGCAGGTACCCACGCCCACACGAAGATCCGATATATGGCTGGTC<br>ATGATGTTCAGGAATCTAAGAGAGATTCCTTGAGGGTGTACACGTC<br>CGCAGCGTGCTCTATACATGGGACGATGGGACACTTCATCGTCGCA<br>CATTGTCCGCCAGGCGACTACCTCAAGGTTTCGTTCGAGGACGCAG<br>AYTCACACGTGAAGGCATGTAAGGTCCAATACAAGCACGACCCATT<br>GCCGGTGGGTAGAGAGAAGTTCGTGGTTAGACCCCACTTTGGCGTA<br>GAGCTGCCATGCACCTCATACCAGCTGACAACAGCTCCCACCGACG<br>AGGAGATCGACATGCACACACCGCCAGATATACCGGATCGACCCT<br>GCTATCACAGACGGCGGGCAACGTCAAAATAACAGCAGGCGGCAG<br>GACTATCAGGTACAATTGTACCTGTGGCCGTGACAACGTAGGCACT<br>ACCAGTACTGACAAGACCATCAACACATGCAAGATTGACCAATGCC<br>ATGCTGCCGTTACCAGCCATGACAAATGGCAATTTACCTCTCCATTT<br>GTTCCCAGGGCTGATCAGACAGCTAGGAGGGGCAAAGTGCATGTTC<br>CATTCCCTTTGACTAACGTCACCTGCCGAGTGCCGTTGGCTCGAGCG<br>CCGGATGTCACCTATGGTAAGAAGGAGGTGACCCTGAGATTACACC<br>CAGATCATCCGACGCTCTTCTCCTATAGGAGTTTAGGAGCCGAACC<br>GCACCCGTACGAGGAGTGGGTTGACAAGTTCTCTGAGCGCATCATC<br>CCAGTGACGGAAGAAGGGATTGAGTACCAGTGGGGCAACAACCCG<br>CCGGTCCGCCTATGGGCGCAACTGACGACCGAGGGCAAACCCCAT<br>GGCTGGCCACATGAAATCATTCAGTACTATTATGGACTATACCCCG<br>CCGCCACCATTGCCGCAGTATCGGGGCGAGTCTGATGGCCCTCCT<br>AACTCTAGCGGCCACATGCTGCATGCTGGCCACCGCGAGGAGAAA<br>GTGCCTAACACCATACGCCTTGACGCCAGGAGCGGTGGTACCGTTG<br>ACACTGGGGCTGCTTTGCTGCGCACCGAGGGCGAACGCAGCATCAT<br>TCGCTGAGACTATGGCATATCTGTGGGACGAGAACAAAACCCTCTT<br>TTGGATGGAATTCGCGGCCCCAGCCGCAGCGCTTGCTTTGCTGGCA<br>TGCTGTATCAAAAGCCTGATCTGCTGTTGTAAGCCATTTTCTTTTTT<br>AGTGTTACTGAGCCTGGGAGCCTCCGCAAAAGCTTACGAGCACACA<br>GCCACAATTCCGAATGTGGTGGGGTTCCCGTATAAGGCTCACATTG<br>AAAGGAATGGCTTCTCGCCCATGACTCTGCAGCTTGAAGTGGTGGA<br>GACAAGCTTGGAACCCACACTTAACCTGGAGTACATTACCTGCGAA<br>TACAAGACGGTGGTCCCTTCGCCATTCATCAAATGTTGCGGAACAT<br>CAGAATGCTCATCCAAGGAGCAGCCAGACTACCAATGCAAGGTGT<br>ACACGGGTGTATACCCATTCATGTGGGGTGGAGCCTACTGTTTCTG<br>CGACTCCGAGAACACGCAGCTCAGCGAGGCCTATGTCGACAGGTCA<br>GACGTTTGCAAACATGATCACGCATCGGCCTACAAGGCACACACGG<br>CCTCTCTAAAAGCAACAATCAGGATCAGTTATGGCACCATCAACCA<br>GACCACCGAGGCCTTCGTTAATGGTGAACACGCGGTCAACGTGGGC<br>GGAAGCAAGTTCATCTTTGGACCGATCTCAACAGCTTGGTCACCGT<br>TCGACAATAAAATTGTCGTGTATAAAGATGATGTCTACAACCAGGA<br>CTTCCCACCCTACGGATCAGGCCAGCCGGGTAGATTCGGAGACATT<br>CAGAGCAGGACAGTGGAGAGCAAAGACTTGTATGCCAACACGCC<br>CTAAAACTCTCAAGACCATCACCCGGGGTTGTGCATGTGCCATACA<br>CGCAGACACCATCCGGATTTAAATATTGGCTGAAGGAGAAAGGATC<br>TTCATTGAATACAAAGGCCCCTTTTGGCTGCAAGATAAAGACCAAT<br>CCAGTCAGAGCCATGGATTGTGCAGTTGGCAGTATACCTGTGTCGA<br>TGGACATACCTGACAGTGCATTCACACGAGTGGTAGATGCCCCGGC<br>TGTAACAGACCTGAGCTGCCAGGTAGTGGTCTGTACACACTCCTCC<br>GATTTCGGAGGAGTTGCCACATTGTCTTACAAAACGGACAAACCCG<br>GCAAGTGCGCTGTCCACTCACATTCCAACGTCGCAACGTTGCAAGA<br>GGCGACGGTGGATGTCAAGGAGGATGGCAAGGTCACAGTGCACTT<br>TTCCACGGCGTCCGCCTCCCCGGCCTTCAAAGTGTCCGTCTGTGACG<br>CAAAAACAACGTGCACGGCGGCGTGCGAGCCTCCAAAAGACCACA<br>TCGTCCCTTATGGGCGAGCCATAACAACCAGGTCTTTCCGGACAT<br>GTCAGGAACTGCGATGACGTGGGTGCAGAGGCTGGCCAGTGGGTT<br>AGGTGGGCTGGCTCTCATCGCGGTGGTTGTGCTGGTCTTGGTAACCT<br>GCATAACAATGCGTCGGTAAGCTTTAGTTCAAAGGGCCATATAAAC<br>CCCTGAATAGTAACAAAATATAAAAATTACAAAATATGTAGTTCAA<br>AGGGCTATACTACCCCTGATTAGTAACAAAATAGAAAACCACAAA<br>ATATGTAGTTAAGTATTATAAGATGTGTAGTTCAAAGGGCTATATC<br>ACCCCTGATTAGTAACAAAATATAAAAACAAAAATATGTAGTTAAG<br>TACTAACCAACAAGTAGACAAATAGATGCTAACCATATATATAACC<br>AGCTATAGTATACTATATTTAGCTAAGCAGTTGCAGTAGTAAGAAT<br>GTAGTTCAAAGGGCTATACAACCCCTGAATAGTAACAAAATACAAA<br>AATACTAATAAAAATTTAAAAATCACTAGAAATCCAATCATTAAAT<br>TATTAATTGGCTAGCCGAACTCTAAGGAGATGTAGGCGTCCGAACT<br>CTGCGGAGATGTAGGACTAAATTCTGCCGAACCCCATAACACCGGG<br>GACGTAGGCGTCTAATTTGTTTTTTAATATTTTACAAAAAAAAAAA<br>AAAAAAAAAAAAAAAAAA |
| SEQ ID NO: 11 | MNYIPTQTFYGRRWRPRPAFRPWQVPMQPTPTMVTPMLQAPDLQAQ<br>QMQQLISAVSALTTKQNVKAPKGQRKKKQQKPKEKKENQKKKPTQK<br>KKQQQKPKPQAKKKKPGRRERMCMKIENDCIFEVKLDGKVTGYACL<br>VGDKVMKPAHVKGTIDNPDLAKLTYKKSSKYDLECAQIPVHMKSDAS |

| SEQ ID NO | Sequence |
|---|---|
| | KYTHEKPEGHYNWHHGAVQYSGGRFTIPTGAGKPGDSGRPIFDNKGR
VVAIVLGGANEGARTALSVVTWTKDMVTRVTPEGTEEWSAALMMCI
LANTSFPCSSPPCYPCCYEKQPEQTLRMLEDNVNRPGYYELLEASMTC
RNRSRHRRSVTEHFNVYKATRPYLAYCADCGDGYFCYSPVAIEKIRDE
ASDGMLKIQVSAQIGLDKAGTHAHTKIRYMAGHDVQESKRDSLRVYT
SAACSIHGTMGHFIVAHCPPGDYLKVSFEDADSHVKACKVQYKHDPL
PVGREKFVVRPHFGVELPCTSYQLTTAPTDEEIDMHTPPDIPDRTLLSQ
TAGNVKITAGGRTIRYNCTCGRDNVGTTSTDKTINTCKIDQCHAAVTS
HDKWQFTSPFVPRADQTARRGKVHVPFPLTNVTCRVPLARAPDVTYG
KKEVTLRLHPDHPTLFSYRSLGAEPHPYEEWVDKFSERIIPVTEEGIEYQ
WGNNPPVRLWAQLTTEGKPHGWPHEIIQYYYGLYPAATIAAVSGASL
MALLTLAATCCMLATARRKCLTPYALTPGAVVPLTLGLLCCAPRANA
ASFAETMAYLWDENKTLFWMEFAAPAAALALLACCIKSLICCCKPFSF
LVLLSLGASAKAYEHTATIPNVVGFPYKAHIERNGFSPMTLQLEVVETS
LEPTLNLEYITCEYKTVVPSPFIKCCGTSECSSKEQPDYQCKVYTGVYP
FMWGGAYCFCDSENTQLSEAYVDRSDVCKHDHASAYKAHTASLKAT
IRISYGTINQTTEAFVNGEHAVNVGGSKFIFGPISTAWSPFDNKIVVYKD
DVYNQDFPPYGSGQPGRFGDIQSRTVESKDLYANTALKLSRPSPGVVH
VPYTQTPSGFKYWLKEKGSSLNTKAPFGCKIKTNPVRAMDCAVGSIPV
SMDIPDSAFTRVVDAPAVTDLSCQVVVCTHSSDFGGVATLSYKTDKPG
KCAVHSHSNVATLQEATVDVKEDGKVTVHFSTASASPAFKVSVCDAK
TTCTAACEPPKDHIVPYGASHNNQVFPDMSGTAMTWVQRLASGLGGL
ALIAVVVLVLVTCITMRR |
| SEQ ID NO: 12 | MKVTVDVEADSPFLKALQKAFPAFEVESQQVTPNDHANARAFSHLAT
KLIEQEVPTNITILDVGSAPARRLMSDHSYHCICPMKSAEDPERLANYA
RKLAKAAGEVLDKNVSGKITDLQDVMATPDLESPTFCLHTDETCRTR
AEVAVYQDVYAVHAPTSLYHQAMKGVRTVYWIGFDTTPFMFEVLAG
AYPTYSTNWADEQVLQARNIGLCATSLSEGHRGKLSIMRKKRLRPSDR
VMFSVGSTLYIESRRLLKSWHLPSVFHLKGKNSFTCRCDTIVSCEGYV
VKKITMSPGTYGKTVGYAVTHHAEGFLMCKVTDTVRGERVSFPVCTY
VPATICDQMTGILATDVTPEDAQKLLVGLNQRIVVNGRTQRNTNTMK
NYLLPVVAQAFSKWAREAKADMEDEKPLGTRERTLTCCCLWAFKSH
KTHTMYKRPDTQTIVKVPSTFDSFVIPSLWSSSLSIGLRQRIKLLLGPKL
SRDLPYSGDRNEAREAEKEAEETKEAELTREALPPLVGSNCADDVDRV
DVEELTYRAGAGVVETPRNALRVTPQERDQLIGAYLILSPQAVLKSEK
LTPIHPLAEQVTIMTHSGRSGRYPVDRYDGRVLVPTGAAIPVSEFQALS
ESATMVYNEREFINRKLEHIALYGPALNTEEENYEKVRAERAEAEYVF
DVDKRMCVKREEASGLVLVGDLINPPFHEFAYEGLKIRPATPFQTTVIG
VFGVPGSGKSAIIKSVVTTRDLVASGKKENCQEIVNDVKKQRGLDVTA
RTVDSILLNGCRRGVENLYVDEAFACHSGTLLALIAMVKPTGKVILCG
DPKQCGFFNLMLQKVNFNHDICTQVLHKSISRRCTLPITAIVSTLHYQG
KMRTTNLCSAPIQIDTTGTTKPAKGDIVLTCFRGWVKQLQIDYRGHEV
MTAAASQGLTRKGVYAVRQKVNENPLYAPSSEHVNVLLTRTENRLV
WKTLSGDPWIKVLTNIPKGDFSATLEEWQEEHDNIMNALRERSTAVDP
FQNKAKVCWAKCLVQVLETAGIRMTAEEWDTVLAFREDRAYSPEVA
LNEICTKYYGVDLDSGLFSAQSVSLYYENNHWDNRPGGRMYGFNREV
ARKFEQRYPFLRGKMDSGLQVNVPERKVQPFNAECNILPSNRRLPHAL
VTSYQQCQGERVEWLLKKLPGYHLLLVSEYNLALPHKRVFWIAPPHV
SGADRIYDLDLGLPLNAGRYDLVFVNIHTEYRTHHYQQCVDHSMKLQ
MLGGDSLHLLKPGGSLLIRAYGYADRVSEMVVTALARKFSAFRVLRP
ACVTSNTEVFLLFTNFDNGRRAVTLHQANQRLSSMFACNGLHTAGCA
PSYRVRRTDISGHAEEAVVNAANAKGTVGDGVCRAVARKWPDSFKG
AATPVGTAKLVQANGMNVIHAVGPNFSTVTEAEGDRELAAAYRAVA
GIINASNIKSVAIPLLSTGVFSGGKDRVMQSLNHLFTAMDTTADVVIY
CRDKAWEKKIQEAIDRRTAVELVSEDISLESDLIRVHPDSCLVGRKGYS
ITDGKLIISYLEGTRFHQTAVDMAEISTLWPKLQDANEQICLYALGESM
DSIRTKCPVEDADSSTPPKTVPCLCRYAMTAERVARLRMNNTKAIIVC
SSFPLPKYRIEGVQKVKCDRVLIFDQTVPSLVSPRKYIPAAASTHADTV
SLDSTVSTGSAWSFPSEATYETMEVVAEVHHSEPPVPPPRRRRAQVTM
HHQELLEVSDMHTPIAARVEIPVYDTAVVVERVAIPCTSEYAKPIPAPR
AARVVPVPAPRIQRASTYRVSPTPTPRVLRASVCSVTTSAGVEFPWAPE
DLEVLTEPVHCKMREPVELPWEPEDVDIQFGDFETSDKIQFGDIDFDQF
LGRAGAYIFSSDTGPGHLQQKSVRQHALPCEMLYVHEEERTYPPALDE
AREKLLQAKMQMAPTEANKSRYQSRKVENMKAVIIDRLKDGARTYL
TEQSEKIPTYVSKYPRPVYSPSVEDSLQNPEVAVAACNAFLEANYPTV
ASYQITDEYDAYLDMVDGSESCLDRATFCPAKLRCYPKHHAYHQPQV
RSAVPSPFQNTLQNVLAAATKRNCNVTQMRELPTLDSAVLNVECFKK
FACNGEYWQEFICDNPIRITTENITTYVTRLKGPKAAALFAKTHNLVPL
QEVPMDRFVVDMKRDVKVTPGTKHTEERPKVQVIQAAEPLATAYLCG
IHRELVRRLKAVLAPNIHTLFDMSAEDFDAIIAAHFQPGDAVLETDIASF
DKSQDDSLALTALMLLEDLGVDQELLDLIEAAFGEITSVHLPTGTRFKF
GAMMKSGMFLTLFVNTLLNIVIACRVLREKLTNSVCAAFIGDDNIVHG |

| SEQ ID NO | Sequence |
|---|---|
| | VRSDPLMAERCASWVNMEVKIIDATMCEKPPYFCGGFILYDKVTGSA
CRVADPLKRLFKLGKPLPAGDTQDEDRRRALKDETDRWARVGLKSEL
EIALSSRYEVNGIGNIVRAMATLAKSLKNFKKLRGPIVHLYGGPK |
| SEQ ID NO: 13 | ATGGGCGGCGCATGAGAGAAGCCCACACCAATTACCTACCCAAAA
ATGGAGAGAGTTCACGTTGACATCGAGGAAGACAGCCCATTCCTCA
GAGCTTTGCAACGGAGCTTCCCGCAGTTTGAGGTAGAAGCCAAGCA
GGTCACTGATAATGACCATGCTAATGCCAGAGCGTTTTCGCATCTG
GCTTCAAAATTGATCGAAACGGAGGTGGACCCATCCGACACGATCC
TTGACATTGGAAGTGCGCCCGCCCGCAGAATGTATTCTAAGCATAA
GTATCATTGCATCTGTCCGATGAGATGCGCGGAAGATCCGGACAGA
TTGTACAAGTATGCAACTAAGCTGAAGAAAAATTGCAAGGAAATA
ACTGACAAGGAATTGGACAAGAAAATGAAGGAGCTCGCCGCCGTC
ATGAGCGACCCTGACCTGGAAACTGAGACTATGTGCCTCCACGACG
ATGAGTCGTGTCGCTACGAAGGGCAAGTCGCTGTTTACCAGGATGT
ATACGCAGTTGACGGACCGACAAGTCTCTATCACCAAGCCAACAAG
GGAGTTAGAGTCGCCTATTGGATAGGCTTTGACACCACCCCTTTTAT
GTTTAAGAACTTGGCTGGAGCATATCCATCATACTCTACTAACTGG
GCCGACGAAACCGTGTTAACGGCTCGTAATATAGGCCTATGCAGCT
CCGACGTTATGGAGCGGTCACGCAGAGGAATGTCCATTCTTAGGAA
GAAGTATTTGAAACCATCCAATAATGTCTTATTCTCTGTTGGCTCGA
CCATCTACCACGAGAAGAGGGACTTACTGAGGAGCTGGCACCTGCC
GTCTGTATTTCACTTACGTGGCAAGCAAAATTACACATGTCGGTGT
GAGACTATAGTTAGTTGCGACGGGTACGTCGTTAAAAGAATAGCTA
TCAGTCCAGGCCTGTATGGGAAGCCTTCAGGCTATGCTGCTACGAT
GCACCGCGAGGGATTCTTGTGCTGCAAAGTGACAGACACATTGAAC
GGGGAGAGGGTCTCTTTTCCCGTGTGCACGTATGTGCCAGCTACAT
TGTGTGACCAAATGACTGGCATACTGGCAACAGATGTCAGTCGGA
CGACGCGCAAAAACTGCTGGTTGGGCTCAACCAGCGCATAGTCGTC
AACGGTCGCACCCAAAGAAATACCAATACCATGAAGAATTATCTTT
TGCCCGTAGTGGCCCAGGCATTTGCTAGGTGGGCAAAGGAATATAA
GGAAGATCAAGAAGATGAGAGGCCACTAGGACTACGAGATAGACA
GTTAGTCATGGGGTGCTGCTGGGCTTTTAGAAGGCATAAGATAACA
TCTATTTATAAGCGCCCAGATACCCAAACCATCATCAAAGTGAACA
GCGATTTCCACTCATTCGTGCTGCCCAGGATAGGCAGTAACACATT
GGAGATCGGGCTGAGAACAAGAATCAGGAAAATGCTAGAAGAGCA
CAAGGAGCCGTCACCTCTCATTACTGCCGAGGACATACAAGAAGCT
AAGTGCGCAGCCGATGAGGCTAAGGAGGTGCGTGAAGCCGAGGAG
TTGCGCGCCGCACTACCACCTTTGGCAGCTGATGTTGAGGAGCCCA
CTCTGGAAGCCGATGTTGACTTGATGTTACAAGAGGCTGGGGCCGG
CTCAGTGGAGACACCTCGTGGCTTGATAAAGGTTACCAGCTATGCC
GGCGAGGACAAGATCGGCTCTTACGCAGTGCTTTCTCCGCAGGCTG
TACTTAAGAGTGAGAAACTATCTTGCATTCACCCTCTCGCTGAACA
AGTCATAGTGATAACACACTCTGGCCGAAAAGGGCGTTACGCCGTG
GAACCCTACCATGGAAAAGTAGTGGTGCCAGAGGGACATGCAATA
CCCGTCCAGGACTTTCAAGCTCTGAGTGAAAGTGCTACCATTGTGT
ACAACGAACGAGAGTTCGTAAACAGGTATCTGCACCATATTGCCAC
ACATGGAGGAGCGCTGAACACAGATGAAGAATATTACAAAACTGT
CAAGCCCAGCGAGCACGATGGCGAATACCTGTATGACATCGACAG
GAAACAGTGCGTCAAGAAAGAACTAGTCACTGGGCTAGGGCTTAC
AGGCGAGCTGGTGGACCCTCCCTTCCATGAATTCGCCTACGAGAGT
CTGAGAACACGACCGGCCGCTCCTTACCAAGTACCAACCATAGGGG
TGTATGGCGTGCCGGGATCAGGCAAGTCTGGCATCATCAAAGCGC
AGTCACCAAAAAAGATCTGGTGGTGAGCGCCAAGAAAGAAAACTG
CGCAGAAATAATAAGGGACGTCAAGAAAATGAGAGGGCTGGACGT
CAATGCCAGAACTGTGGACTCAGTGCTCTTGAATGGATGCAAACAC
CCCGTAGAGACCCTGTATATTGACGAAGCTTTTGCTTGTCATGCAG
GCACTCTCAGAGCGCTCATAGCCATCATAAGACCTAAAAAGGCAGT
GCTCTGCGGGGATCCAAAACAGTGCGGCTTTTTCAATATGATGTGT
CTGAAAGTGCATTTTAACCACGAGATTTGCACGCAGGTCTTCCACA
AAAGCATCTCTCGTCGTTGCACTAAATCTGTGACTTCGGTCGTCTCA
ACCTTGTTTTACGACAAAAGAATGAGAACGACGAACCCGAAAGAG
ACTAAGATTGAGATTGACACTACTGGCAGTACCAAACCAAAGCAG
GACGATCTCATTCTCACTTGTTTTAGAGGGTGGGTGAAGCAGTTGC
AAATAGATTACAAAGGCAACGAGATAATGACGGCAGCTGCCTCTC
AAGGGCTGACCCGTAAAGGCGTGTATGCCGTTCGGTACAAGGTGAA
TGAAAACCCCTGTACGCACCCACCTCAGAACACGTGAACGTCCTA
CTGACCCGCACGGAGGACCGTATCGTGTGGAAAACACTAGCCGGC
GATCCATGGATAAAAACACTGACGGCCAAGTATCCTGGGAATTTCA
CTGCCACGATAGAGGAATGGCAAGCAGAGCATGATGCCATCATGA
GGCACATCTTGGAGAGACCGGACCCTACCGATGTTTTCCAAAATAA
GGCGAACGTGTGTTGGGCCAAGGCTTTGGTGCCGGTACTGAAGACT
GCAGGCATAGACATGACCACTGAACAATGGAACACTGTGGATTATT
TCGAAACGGACAAAGCTCACTCAGCAGAGATAGTGTTGAACCAACT
ATGCGTGAGGTTCTTTGGACTCGACCTGGACTCCGGTCTATTTTCTG |

| SEQ ID NO | Sequence |
|---|---|
| | CACCCACTGTTCCGCTGTCCATTAGGAATAATCACTGGGATAATTCC<br>CCGTCGCCTAACATGTACGGGCTGAATAAAGAAGTGGTCCGTCAGC<br>TCTCCCGCCGGTACCCACAACTGCCTCGAGCAGTTGCCACTGGAAG<br>AGTCTATGACATGAACACTGGTACACTGCGCAATTATGATCCGCGC<br>ATAAATCTAGTACCTGTGAACAGAAGACTGCCTCATGCTTTAGTCC<br>TCCACCATAATGAACACCCGCAGAGTGATTTTTCTTCATTCGTCAGC<br>AAACTGAAGGGCAGAACTGTCTTGGTGGTCGGGGAGAAGTTGTCCG<br>TCCCAGGCAAAACGGTTGATTGGTTGTCAGACAAGCCTGAGGCTAC<br>CTTCAGAGCTCGGCTGGATTTAGGTATCCCAGGTGACGTGCCCAAA<br>TACGACATTATATTTATTAACGTGAGGACTCCATATAAATACCATC<br>ATTATCAGCAGTGTGAAGACCACGCCATTAAGCTTAGTATGTTGAC<br>CAAGAAAGCTTGTCTGCATCTGAATCCCGGCGGAACCTGCGTCAGC<br>ATAGGTTATGGTTACGCTGACAGGGCCAGCGAAAGCATCATTGGTG<br>CTATAGCGCGGCAGTTCAAGTTCTCCCGGGTATGCAAACCTAAATC<br>CTCACTTGAAGAGACAGAAGTTCTGTTTGTATTCATTGGGTACGATC<br>GCAAGGCCCGTACGCATAATCCTTACAAGCTTTCATCTACCTTGACC<br>AACATCTATACAGGTTCCAGACTCCACGAAGCCGGATGCGCACCCT<br>CATATCATGTGGTGCGAGGGGATATTGCCATGGCCACCGAAGGAGT<br>GATCATAAATGCCGCTAACAGCAAAGGACAACCTGGCGGAGGGGT<br>GTGCGGAGCGCTGTATAAGAAATTCCCGGAAAGCTTCGATTTACAG<br>CCAATCGAAGTGGGAAAAGCGCGACTGGTCAAAGGTGCAGCTAAA<br>CACATCATTCATGCCGTAGGGCCCAACTTCAACAAAGTTTCGGAAG<br>TTGAAGGTGACAAACAGTTGGCAGAGGCTTATGAGTCCATCGCTAA<br>AATTGTCAACGATAACAATTACAAGTCAGTAGCGATTCCACTGTTG<br>TCTACCGGCATCTTTTCTGGTAACAAAGATCGACTAACCCAATCATT<br>GAACCATTTGCTGACAGCTTTAGACACCACTGATGCAGATGTAGCC<br>ATATACTGCAGGGACAAGAAATGGGAAATGACTCTCAAGGAAGCA<br>GTGGCTAGGAGAGAAGCAGTGGAGGAGATATGCATATCCGACGAC<br>TCTTCGGTGACAGAACCGGATGCAGAGCTGGTGAGGGTACATCCGA<br>AGAGTTCTTTGGCTGGCAGGAAGGGCTACAGCACAAGTGATGGCA<br>AGACTTTCTCATATTTGGAAGGGACTAAATTCCACCAGGCGGCCAA<br>GGATATAGCAGAAATTAATGCCATGTGGCCTGTTGCAACGGAGGCC<br>AATGAGCAAGTATGCATGTATATCCTCGGTGAAAGCATGAGCAGCA<br>TTAGGTCAAAATGCCCCGTCGAAGAATCGGAAGCCTCCACACCACC<br>TAGCACGCTGCCTTGCTTGTGCATCCATGCTATGACTCCAGAAAGA<br>GTACAACGCCTAAAAGCCTCGCGTCCAGAACAAATTACTGTGTGCT<br>CATCCTTTCCATTGCCGAAGTATAGAATCACTGGTGTGCAGAAGAT<br>CCAGTGCTCCCAGCCTATACTGTTCTCACCGAAGGTGCCTGCGTAC<br>ATTCATCCACGGAAGTACCTCGTGGAAACACCACCGGTGGAAGAG<br>ATTCCGGAGCTGCCGGCGGAGAACCAATCCACAGAGGGGACATCT<br>GAACAACCAGCACCAAACGTGGATGCAACCAGGACTAGAACGCCT<br>GAACCGATCATCATTGAAGAGGAAGAAGAGGATAGTATAAGTTTG<br>CTGTCAGACGGCCCGACCCACCAGGTGCTGCAAGTCGAGGCAGAC<br>ATCCACGGGCCGCCTTCTGTATCCAGCTCATCCTGGTCCATTCCTCA<br>CGCATCCGACTTTGATGTGGACAGTTTATCCATCCTTGCCCTGGAGG<br>GAGCTAGCGTGACTAGCGAGGCAGCGTCAGCCGAGACTAACTCAT<br>ACTTCGCAAGGAGCATGGAGTTTCTGGCGCGACCGGTGCCTGCGCC<br>TCGAACAGTATTCAGGAACCCTCCACATCCCGCTCCACGCACAAGA<br>ACACCGTCACTTGCACCCAGCAGGGCCAGCTCGAGAACTAGCCTGG<br>TTTTCCACCCCGCCAGGCGTGAATAGGGTGATTACTAGAGAGGAGCT<br>CGAGGCGCTTACCCCGTCCCGCGCTCCTAGCAGGTCGGCCTCAAGA<br>ACTAGTCTGGTCTCTAACCCGCCAGGCGTAAATAGGGTGATTACAA<br>GAGAGGAGTTTGAGGCGTTCGTGGCACAACAACAATGACGGTTTGA<br>CGCGGGTGCATACATCTTTTCCTCCGATACCGGTCAAGGGCATTTAC<br>AACAAAAATCAGTAAGGCAAACGGTGCTATCCGAAGTGGTTTTGGA<br>GAGGACCGAATTGGAGATTTCGTATGCCCCGCGCCTCGACCAAGAA<br>AAAGAAGAACTACTACGCAAGAAATTACAGCTGAATCCCACACCT<br>GCTAACAGAAGCAGATACCAGTCCAGAAGGGTGGAGAACATGAAA<br>GCCATAACAGCTAGACGTATTCTGCAAGGCCTAGGACATTATTTGA<br>AGGCAGAAGGAAAAGTGGAGTGCTATCGAACCCTGCATCCTGTTCC<br>TTTGTATTCATCTAGTGTGAATCGTGCTTTTTCAAGCCCCAAGGTCG<br>CAGTGGAAGCCTGCAATGCCATGCTGAAAGAAAACTTTCCGACTGT<br>AGCTTCTTACTGTATAATTCCAGAGTACGATGCCTATCGGACATGG<br>TTGACGGCGCTTCTTGTTGCTTAGACACTGCCAGTTTTTGCCCTGCG<br>AAGCTGCGCAGTTTTCCAAAGAAACACTCTTACTTGGAACCCACAA<br>TACGGTCGGCAGTGCCATCGGCGATTCAGAACACGCTCCAGAATGT<br>CCTGGCAGCTGCCACAAAAAGAAATTGCAACGTCACGCAAATGAG<br>AGAATTGCCCGTATTGGACTCGGCTGCCTTTAATGTGGAATGCTTCA<br>AGAAATATGCGTGCAATAATGAATATTGGGAAACGTTTAAAGAAA<br>ACCCCATCAGGCTTACTGAAGAAAATGTGGTAAATTACATTACTAA<br>ATTAAAAGGACCAAAAGCTGCTGCTCTTTTTGCGAAGACACATAAT<br>TTAAATATGTTACAGGACATACCAATGGACAGGTTTGTAATGGACT<br>TAAAGAGGGACGTGAAAGTGACTCCAGGAACAAAACATACTGAAG<br>AACGACCCAAGGTACAGGTGATCCAGGCCGCCGATCCGCTAGCGA<br>CAGCGTATCTGTGCGGAATCCACCGGGAGTTGGTTAGGAGATTAAA |

| SEQ ID NO | Sequence |
|---|---|
| | TGCTGTCCTGCTTCCGAACATCCATACACTGTTTGACATGTCGGCTG<br>AAGACTTTGACGCTATTATTGCCGAGCATTTCCAGCCTGGGGACTG<br>TGTTCTGGAAACTGACATTGCGTCGTTTGATAAAAGTGAGGACGAC<br>GCCATGGCTCTGACCGCGTTGATGATTCTGGAAGATCTAGGAGTGG<br>ACGCAGAGCTGTTGACGCTGATTGAGGCGGCTTTCGGCGAAATATC<br>ATCAATACATTTGCCCACCAAAACTAAATTTAAATTCGGAGCCATG<br>ATGAAATCCGGAATGTTCCTCACACTGTTTGTGAACACAGTCATTA<br>ACATCGTAATCGCAAGCAGAGTGTTAAGAGAGCGGCTAACCGGAT<br>CACCATGTGCAGCATTCATTGGAGATGACAATATCGTGAAAGGAGT<br>CAAATCTGACAAATTAATGGCAGACAGGTGCGCCACTTGGTTGAAC<br>ATGGAAGTCAAGATCATAGACGCCGTGGTGGGCGAGAAAGCGCCC<br>TATTTCTGTGGAGGGTTTATTTTGTGTGACTCCGTGACCGGCACAGC<br>GTGCCGTGTGGCAGACCCCCTAAAAAGGCTGTTTAAGCTTGGCAAA<br>CCTCTGGCAGCAGACGATGAACATGACGATGACAGGAGAAGGGCA<br>TTATACGAAGAGTCAACACGCTGGAATCGAGTGGGAATTCTTCCAG<br>AGCTGTGTAAGGCAGTAGAATCAAGGTATGAAACCGTAGGAACTTC<br>CATCATAGTTATGGCCATGACTACTCTAGCTAGCAGTGTTAAGTCGT<br>TCAGCTACCTGAGAGGGCCCCTATAACTCTCTACGGCTAACCTGA<br>ATGGACTACGACATAGTCTAGTCCGCCAAGATGTTCCCGTTCCAAC<br>CAATGTATCCGATGCAGCCAATGCCCTATCGTAACCCGTTCGCGGC<br>CCCGCGCAGGCCCTGGTTCCCCAGAACCGATCCTTTTCTGGCGATG<br>CAGGTGCAGGAATTAACCCGCTCGATGGCTAACCTGACGTTCAAGC<br>AACGCCGGGATGCGCCACCTGAAGGGCCACCCGCTAAGAAACCGA<br>AGCGGGAGGCCCCGCAAAACAAAAAGGGGGAGGCCAAGGGAAG<br>AAGAAGAAGAATCAGGGGAAGAAGAAGGCTAAGACGGGGCCACC<br>TAATCCGAAGGCACAGAGTGGAAACAAGAAGAAGACCAACAAGAA<br>ACCAGGCAAGAGACAGCGCATGGTCATGAAATTGGAATCTGACAA<br>GACATTCCCAATTATGCTGGAAGGGAAGATTAACGGCTACGCTTGC<br>GTGGTCGGAGGGAAGTTATTCAGGCCGATGCACGTGGAAGGCAAG<br>ATCGACAATGACGTTCTGGCCGCACTTAAGACGAAGAAAGCATCCA<br>AATATGATCTTGAGTATGCAGATGTGCCACAGAACATGCGGGCCGA<br>TACATTCAAGTACACCCACGAGAAGCCCCAAGGCTATTATAGCTGG<br>CATCATGGAGCAGTCCAATATGAAAATGGGCGTTTCACGGTGCCAA<br>AAGGAGTTGGGGCCAAGGGAGACAGCGGACGACCCATTCTGGACA<br>ATCAGGGACGGGTGGTCGCTATTGTGCTGGGAGGTGTGAATGAAGG<br>ATCTAGGACAGCCCTTTCAGTCGTCATGTGGAACGAGAAGGGAGTA<br>ACTGTGAAGTATACTCCGGAGAACTGCGAGCAATGGTCACTAGTGA<br>CCACCCTGTGTCTGCTCGCCAATGTGACGTTCCCATGTGCCCAACCA<br>CCAATTTGCTACGACAGAAAACCAGCAGAGACCTTGGCCATGCTCA<br>GCGTTAACGTTGACAACCCGGGCTACGATGAGCTGCTGGAAGCAGC<br>TGTTAGGTGCCCCGGAAGAAAAAGGAGATCTACCGAGGAGCTGTTT<br>AAGGAGTATAAGCTAACGCGCCCTTACATGGCCAGATGCATCAGAT<br>GTGCCGTTGGGAGCTGCCATAGTCCAATAGCAATTGAGGCAGTGAA<br>GAGCGACGGGCACGACGGCTATGTTAGACTTCAGACTTCCTCGCAG<br>TACGGCCTGGATTCCTCTGGCAACTTAAAGGGAAGGACCATGCGGT<br>ATGACATGCACGGAACCATTGAAGAGATACCGCTACATCAAGTGTC<br>ACTCCACACATCTCGCCCGTGTCACATTGTGGATGGGCATGGTTATT<br>TTCTGCTTGCTAGGTGCCCGGCAGGGGACTCCATCACTATGGAATTT<br>AAGAAAGATTCAGTCACACACTCCTGCTCAGTGCCGTATGAAGTGA<br>AATTTAATCCTGTAGGCAGAGAACTCTACACTCATCCCCCAGAACA<br>CGGAGCAGAGCAAGCGTGCCAAGTCTACGCGCATGATGCACAGAA<br>CAGAGGAGCTTATGTCGAGATGCACCTCCCGGGCTCAGAAGTGGAC<br>AGCAGTTTGGTTTCCTTGAGCGGCAGTTCAGTCACCGTGACACCTCC<br>TGCTGGGACTAGCGCCCTGGTGGAATGCGAGTGCGGCGGCACAAA<br>GATCTCCGAGACCATCAACACGGCAAAACAGTTCAGCCAGTGCACA<br>AAGAAGGAGCAATGCAGAGCATATCGACTGCAGAATGACAAATGG<br>GTGTATAATTCTGACAAACTGCCCAAAGCAGCGGGAGCCACCCTAA<br>AAGGAAAACTACACGTCCCATTTTTGCTGGCAGACGGCAAATGCAC<br>CGTGCCTCTAGCACCGGAACCTATGATAACCTTCGGTTTCCGATCA<br>GTGTCACTGAAACTGCACCCTAAGAATCCCACATATCTGACCACTC<br>GCCAACTTGCTGATGAGCCTCATTACACGCACGAGCTCATATCTGA<br>ACCAGCTGTTAGGAATTTTACCGTCACTGAAAAGGGGTGGGAGTTT<br>GTATGGGGAAACCACCCGCCGAAAAGGTTTTGGGCACAGGAAACA<br>GCACCCGGAAATCCACATGGGCTGCCACACGAGGTGATAACTCATT<br>ATTACCACAGATACCCTATGTCCACCATCCTGGGTTTATCAATTTGC<br>GCCGCCATTGTAACCGTTTCCGTTGCAGCGTCTACCTGGCTGTTCTG<br>CAAATCCAGAGTTTCGTGCCTAACTCCTTACCGGCTAACACCTAAC<br>GCCAGGATGCCGCTTTGCCTGGCTGTGCTTTGCTGCGCTCGCACTGC<br>CCGGGCCGAGACCACCTGGGAGTCCTTGGATCACCTATGGAACAAT<br>AACCAGCAGATGTTCTGGATTCAATTGCTGATCCCCCTGGCCGCCTT<br>GATTGTAGTGACTCGCCTGCTCAAGTGCGTGTGCTGTGTAGTGCCTT<br>TTTTAGTCGTGGCCGGCGCCGCAGGCGCCGGCGCCTACGAGCACGC<br>GACCACGATGCCGAGCCAAGTGGGAATCTCGTATAACACCATAGTC<br>AACAGAGCAGGCTACGCGCCACTCCCTATCAGCATAACACCAACA<br>AAGATCAAGCTGATACCTACAGTGAACTTGGAGTACATCACCTGCC |

| SEQ ID NO | Sequence |
|---|---|
| | ACTACAAAACAGGAATGGATTCACCAGCCATTAAGTGCTGCGGATC<br>TCAGGAATGTACTCCAACTTACAGGCCTGATGAACAGTGCAAAGTC<br>TTCACTGGGGTTTACCCGTTCATGTGGGGAGGCGCATATTGCTTTTG<br>CGACACTGAGAACACCCAAGTCAGCAAGGCCTACGTAATGAAATCT<br>GACGACTGCCTTGCTGATCACGCTGAAGCATACAAAGCGCACACAG<br>CCTCAGTGCAGGCGTTCCTCAACATCACAGTGGGAGAACACTCTAT<br>TGTGACCACCGTGTATGTGAATGGAGAAACTCCTGTGAACTTCAAT<br>GGGGTCAAATTAACTGCAGGTCCACTTTCCACAGCTTGGACACCCT<br>TTGACCGCAAAATCGTGCAGTATGCCGGGGAGATCTATAATTACGA<br>TTTTCCTGAGTACGGGGCAGGACAACCAGGAGCATTTGGAGACATA<br>CAATCCAGAACAGTCTCGAGCTCAGATCTGTATGCCAATACCAACC<br>TAGTGCTGCAGAGACCCAAAGCAGGAGCGATCCATGTGCCATACAC<br>TCAGGCACCATCGGGTTTTGAGCAATGGAAGAAAGATAAAGCTCCG<br>TCATTGAAATTCACCGCCCCTTTCGGATGCGAAATATATACAAACC<br>CCATTCGCGCCGAAAATTGTGCCGTAGGGTCAATTCCATTAGCCTTT<br>GACATCCCCGACGCCTTGTTCACCAGGGTGTCAGACACACCGACAC<br>TTTCAGCGGCCGAATGCACTCTTAACGAGTGCGTGTATTCATCCGA<br>CTTTGGCGGGATCGCCACGGTCAAGTATTCGGCCAGCAAGTCAGGC<br>AAGTGCGCAGTCCATGTGCCATCAGGGACTGCTACCCTAAAAGAAG<br>CAGCAGTCGAGTTAACCGAGCAAGGGTCGGTGACCATTCATTTCTC<br>GACCGCAAATATCCACCCGGAGTTCAGGCTCCAAATATGCACATCA<br>TATGTCATGTGCAAAGGTGATTGTCACCCCCCGAAAGACCACATTG<br>TGACACACCCACAGTATCACGCCCAAACATTTACAGCCGCGGTGTC<br>AAAAACCGCGTGGACGTGGTTAACATCCCTGCTGGGAGGATCGGCC<br>GTAATTATTATAATTGGCTTAGTGCTGGCTACTATTGTGGCCATGTA<br>CGTGCTGACCAACCAGAAACATAATTGAACATAGCAGCAATTGGCA<br>AGCTGCTTATATAGAACTCGCGGCGATTGGCATGCCGCTTTAAAAT<br>TTTATTTTATTTTCTTTTCTTTTC |
| SEQ ID NO: 14 | MFPFQPMYPMQPMPYRNPFAAPRRPWFPRTDPFLAMQVQELTRSMAN<br>LTFKQRRDAPPEGPPAKKPKREAPQKQKGGGQGKKKKNQGKKKAKT<br>GPPNPKAQSGNKKKTNKKPGKRQRMVMKLESDKTFPIMLEGKINGYA<br>CVVGGKLFRPMHVEGKIDNDVLAALKTKKASKYDLEYADVPQNMRA<br>DTFKYTHEKPQGYYSWHHGAVQYENGRFTVPKGVGAKGDSGRPILD<br>NQGRVVAIVLGGVNEGSRTALSVVMWNEKGVTVKYTPENCEQWSLV<br>TTLCLLANVTFPCAQPPICYDRKPAETLAMLSVNVDNPGYDELLEAAV<br>RCPGRKRRSTEELFKEYKLTRPYMARCIRCAVGSCHSPIAIEAVKSDGH<br>DGYVRLQTSSQYGLDSSGNLKGRTMRYDMHGTIEEIPLHQVSLHTSRP<br>CHIVDGHGYFLLARCPAGDSITMEFKKDSVTHSCSVPYEVKFNPVGE<br>LYTHPPEHGAEQACQVYAHDAQNRGAYVEMHLPGSEVDSSLVSLSGS<br>SVTVTPPAGTSALVECECGGTKISETINTAKQFSQCTKKEQCRAYRLQN<br>DKWVYNSDKLPKAAGATLKGKLHVPFLLADGKCTVPLAPEPMITFGF<br>RSVSLKLHPKNPTYLTTRQLADEPHYTHELISEPAVRNFTVTEKGWEF<br>VWGNHPPKRFWAQETAPGNPHGLPHEVITHYYHRYPMSTILGLSICAA<br>IVTVSVAASTWLFCKSRVSCLTPYRLTPNARMPLCLAVLCCARTARAE<br>TTWESLDHLWNNNQQMFWIQLLIPLAALIVVTRLLKCVCCVVPFLVV<br>AGAAGAGAYEHATTMPSQVGISYNTIVNRAGYAPLPISITPTKIKLIPTV<br>NLEYITCHYKTGMDSPAIKCCGSQECTPTYRPDEQCKVFTGVYPFMW<br>GGAYCFCDTENTQVSKAYVMKSDDCLADHAEAYKAHTASVQAFLNI<br>TVGEHSIVTTVYVNGETPVNFNGVKLTAGPLSTAWTPFDRKIVQYAGE<br>IYNYDFPEYGAGQPGAFGDIQSRTVSSSDLYANTNLVLQRPKAGAIHV<br>PYTQAPSGFEQWKKDKAPSLKFTAPFGCEIYTNPIRAENCAVGSIPLAF<br>DIPDALFTRVSDTPTLSAAECTLNECVYSSDFGGIATVKYSASKSGKCA<br>VHVPSGTATLKEAAVELTEQGSVTIHYSTANIHPEFRLQICTSYVMCKG<br>DCHPPKDHIVTHPQYHAQTFTAAVSKTAWTWLTSLLGGSAVIIIGLVL<br>ATIVAMYVLTNQKHN |
| SEQ ID NO: 15 | MERVHVDIEEDSPFLRALQRSFPQFEVEAKQVTDNDHANARAFSHLAS<br>KLIETEVDPSDTILDIGSAPARRMYSKHKYHCICPMRCAEDPDRLYKYA<br>TKLKKNCKEITDKELDKKMKELAAVMSDPDLETETMCLHDDESCRYE<br>GQVAVYQDVYAVDGPTSLYHQANKGVRVAYWIGFDTTPPMFKNLAG<br>AYPSYSTNWADETVLTARNIGLCSSDVMERSRRGMSILRKKYLKPSNN<br>VLFSVGSTIYHEKRDLLRSWHLPSVFHLRGKQNYTCRCETIVSCDGYV<br>VKRIAISPGLYGKPSGYAATMHREGFLCCKVTDTLNGERVSFPVCTYV<br>PATLCDQMTGILATDVSADDAQKLLVGLNQRIVVNGRTQRNTNTMKN<br>YLLPVVAQAFARWAKEYKEDQEDERPLGLRDRQLVMGCCWAFRRHK<br>ITSIYKRPDTQTIIKVNSDFHSFVLPRIGSNTLEIGLRTRIRKMLEEHKEPS<br>PLITAEDIQEAKCAADEAKEVREAEELRAALPPLAADVEEPTLEADVD<br>LMLQEAGAGSVETPRGLIKVTSYAGEDKIGSYAVLSPQAVLKSEKLSCI<br>HPLAEQVIVITHSGRKGRYAVEPYHGKVVVPEGHAIPVQDFQALSESA<br>TIVYNEREFVNRYLHHIATHGGALNTDEEYYKTVKPSEHDGEYLYDID<br>RKQCVKKELVTGLGLTGELVDPPPHEFAYESLRTRPAAPYQVPTIGVY<br>GVPGSGKSGIIKSAVTKKDLVVSAKKENCAEIIRDVKKMRGLDVNART<br>VDSVLLNGCKHPVETLYIDEAFACHAGTLRALIAIIRPKKAVLCGDPKQ<br>CGFFNMMCLKVHFNHEICTQVFHKSISRRCTKSVTSVVSTLFYDKRMR |

| SEQ ID NO | Sequence |
|---|---|
| | TTNPKETKIEIDTTGSTKPKQDDLILTCFRGWVKQLQIDYKGNEIMTAA<br>ASQGLTRKGVYAVRYKVNENPLYAPTSEHVNVLLTRTEDRIVWKTLA<br>GDPWIKTLTAKYPGNFTATIEEWQAEHDAIMRHILERPDPTDVFQNKA<br>NVCWAKALVPVLKTAGIDMTTEQWNTVDYFETDKAHSAEIVLNQLC<br>VRFFGLDLDSGLFSAPTVPLSIRNNHWDNSPSPNMYGLNKEVVRQLSR<br>RYPQLPRAVATGRVYDMNTGTLRNYDPRINLVPVNRRLPHALVLHHN<br>EHPQSDFSSFVSKLKGRTVLVVGEKLSVPGKTVDWLSDKPEATFRARL<br>DLGIPGDVPKYDIIFINVRTPYKYHHYQQCEDHAIKLSMLTKKACLHLN<br>PGGTCVSIGYGYADRASESIIGAIARQFKFSRVCKPKSSLEETEVLFVFI<br>GYDRKARTHNPYKLSSTLTNIYTGSRLHEAGCAPSYHVVRGDIAMATE<br>GVIINAANSKGQPGGGVCGALYKKFPESFDLQPIEVGKARLVKGAAKH<br>IIHAVGPNFNKVSEVEGDKQLAEAYESIAKIVNDNNYKSVAIPLLSTGIF<br>SGNKDRLTQSLNHLLTALDTTDADVAIYCRDKKWEMTLKEAVARRE<br>AVEEICISDDSSVTEPDAELVRVHPKSSLAGRKGYSTSDGKTFSYLEGT<br>KFHQAAKDIAEINAMWPVATEANEQVCMYILGESMSSIRSKCPVEESE<br>ASTPPSTLPCLCIHAMTPERVQRLKASRPEQITVCSSFPLPKYRITGVQKI<br>QCSQPILFSPKVPAYIHPRKYLVETPPVEEIPELPAENQSTEGTSEQPAPN<br>VDATRTRTPEPIIIEEEEEDSISLLSDGPTHQVLQVEADIHGPPSVSSSSW<br>SIPHASDFDVDSLSILALEGASVTSEAASAETNSYFARSMEFLARPVPAP<br>RTVFRNPPHPAPRTRIPSLAPSRASSRTSLVSTPPGVNRVITREELEALT<br>PSRAPSRSASRTSLVSNPPGVNRVITREEFEAFVAQQQRRFDAGAYIFSS<br>DTGQGHLQQKSVRQTVLSEVVLERTELEISYAPRLDQEKEELLRKKLQ<br>LNPTPANRSRYQSRRVENMKAITARRILQGLGHYLKAEGKVECYRTLH<br>PVPLYSSSVNRAFSSPKVAVEACNAMLKENFPTVASYCIIPEYDAYLD<br>MVDGASCCLDTASFCPAKLRSFPKKHSYLEPTIRSAVPSAIQNTLQNVL<br>AAATKRNCNVTQMRELPVLDSAAFNVECFKKYACNNEYWETFKENPI<br>RLTEENVVNYITKLKGPKAAALFAKTHNLNMLQDIPMDRFVMDLKRD<br>VKVTPGTKHTEERPKVQVIQAADPLATAYLCGIHRELVRRLNAVLLPN<br>IHTLFDMSAEDFDAIIAEHFQPGDCVLETDIASFDKSEDDAMALTALMI<br>LEDLGVDAELLTLIEAAFGEISSIHLPTKTKFKFGAMMKSGMFLTLFVN<br>TVINIVIASRVLRERLTGSPCAAFIGDDNIVKGVKSDKLMADRCATWL<br>NMEVKIIDAVVGEKAPYFCGGFILCDSVTGTACRVADPLKRLFKLGKP<br>LAADDEHDDDRRRALYEESTRWNRVGILPELCKAVESRYETVGTSIIV<br>MAMTTLASSVKFSYLRGAPITLYG |
| SEQ ID NO: 16 | TAGAGGCAACCACCCTATTTCCACCTATCCAAAATGGAGAAAGTTC<br>ATGTTGACTTAGACGCAGACAGCCCATTCGTCAAGTCACTGCAAAG<br>ATGCTTTCCACATTTTGAGATAGAAGCAACGCAGGTCACTGACAAT<br>GACCATGCTAATGCTAGGGCGTTTTCGCACCTAGCTACTAAGCTCA<br>TTGAGGGAGAAGTGGATACAGACCAGGTGATCCTGGATATTGGGA<br>GCGCGCCTGTAAGGCACACGCATTCCAAACATAAGTACCACTGTAT<br>TTGCCCAATGAAGAGCGCAGAAGACCCTGACAGACTCTACCGCTAC<br>GCAGACAAGCTTAGAAAGAGTGATGTCACTGACAAATGTATTGCCT<br>CTAAGGCCGCGGACCTGCTAACAGTAATGTCGACGCCTGACGCTGA<br>GACACCCTCGTTATGCATGCACACTGACTCAACTTGCAGGTACCAC<br>GGCTCCGTGGCCGTATATCAGGATGTATATGCAGTGCATGCACCGA<br>CTTCCATTTACTACCAGGCGCTGAAAGGTGTACGAACTATCTATTG<br>GATCGGGTTCGATACTACACCGTTCATGTATAAGAACATGGCAGGC<br>GCCTACCCTACATACAACACTAATTGGGCCGATGAAAGTGTGTTGG<br>AAGCCAGAAATATAGGGCTGGGTAGTTCAGACTTGCACGAAAAGA<br>GTTTCGGAAAAGTATCCATTATGAGGAAGAAGAAATTACAACCCAC<br>CAATAAAGTAATATTTTCTGTGGGGTCAACTATTTATACTGAAGAG<br>AGAATACTGTTACGCAGTTGGCATCTACCTAATGTTTTTCATCTAAA<br>AGGTAAAACTAGCTTTACAGGCAGATGTAATACTATCGTCAGCTGC<br>GAAGGTTACGTTGTCAAGAAGATTACGCTCAGTCCTGGGATTTACG<br>GGAAAGTGGATAATCTTGCTTCGACCATGCACCGAGAGGGATTCTT<br>AAGTTGCAAGGTTACAGATACGTTAAGAGGGGAGAGGGTCTCTTTT<br>CCCGTGTGTACGTACGTGCCAGCGACACTGTGCGACCAGATGACCG<br>GGATACTGGCGACTGACGTCAGTGTCGATGACGCCCAGAAGCTGCT<br>GGTTGGGCTCAACCAGCGAATTGTCGTCAATGGCAGAACACAACGT<br>AACACAAATACCATGCAGAATTATCTATTACCAGTGGTCGCCCAGG<br>CGTTCTCGCGGTGGGCGCGGGAACACCGCGCAGACCTGGAGGACG<br>AAAAAGGGCTAGGGGTACGGGAACGTTCCCTAGTCATGGGCTGCTG<br>CTGGGCTTTCAAAACTCACAAGATCACATCCATTTACAAGAGACCT<br>GGGACTCAAACTATCAAGAAGGTGCCCGCCGTATTCAATTCCTTTG<br>TCATCCCACAACCAACCAGCTATGGGCTTGATATAGGGTTGCGTCG<br>CCGCATTAAGATGCTATTCGACGCAAAGAAGGCACCCGCTCCAATT<br>ATTACTGAGGCCGACGTTGCACACCTTAAAGGCCTGCAGGATGAAG<br>CTGAAGCCGTGGCAGAGGCTGAAGCCGTACGTGCAGCACTACCACC<br>ACTTCTGCCGGAGGTCGACAAGGAGACCGTAGAGGCTGACATCGA<br>CCTGATCATGCAGGAGGCAGGAGCAGGTAGCGTGGAGACACCTAG<br>ACGACACATCAAGGTCACGACGTACCCAGGAGAAGAAATGATCGG<br>CTCGTACGCAGTGCTTTCACCACAAGCGGTCCTTAACAGCGAGAAG<br>CTCGCTTGTATTCACCCGTTAGCTGAGCAAGTGCTCGTGATGACTCA<br>CAAGGGGCGCGCAGGACGATACAAGGTAGAGCCATACCACGGTAG |

| SEQUENCES | |
|---|---|
| SEQ ID NO | Sequence |
| | AGTTATCGTCCCTAGTGGTACAGCTATACCAATCCCCGATTTCCAGG<br>CTCTGAGTGAAAGTGCAACCATAGTATTTAACGAACGGGAGTTCGT<br>TAACCGTTACTTACACCACATTGCCGTTAACGGAGGGGCACTGAAT<br>ACAGATGAAGAGTACTACAAGGTTGTGAAAAGCACTGAGACAGAC<br>TCTGAGTACGTATTTGACATCGACGCAAAGAAGTGCGTGAAGAAG<br>GGGATGCCGGACCAATGTGCCTGGTCGGCGAATTAGTAGACCCGCC<br>ATTCCACGAATTCGCGTACGAGAGTTTAAAAACACGTCCTGCTGCA<br>CCACACAAAGTGCCTACCATCGGAGTTTATGGAGTCCCAGGTTCCG<br>GAAAGTCTGGTATAATCAAAAGCGCTGTTACCAAACGTGATCTGGT<br>GGTCAGTGCAAAGAAAGAAAATTGCATGGAAATCATTAAAGACGT<br>CAAACGTATGCGCGGCATGGACATCGCCGCCCGCACAGTGGATTCG<br>GTGCTGCTAAATGGGGTAAAACACTCCGTCGACACACTGTACATAG<br>ACGAGGCATTCGCTTGCCATGCAGGGACCCTGCTAGCACTTATTGC<br>CATCGTCAAGCCAAAGAAAGTTGTATTGTGTGGAGATCCGAAACAA<br>TGCGGCTTCTTTAACATGATGTGTCTAAAAGTGCATTTTAACCACGA<br>GATATGCACAGAAGTGTATCACAAGAGTATTTCTCGGCGATGCACT<br>AAGACAGTGACATCCATCGTTTCCACCCTGTTCTATGATAAACGCA<br>TGAGAACTGTCAACCCATGCAATGATAAGATCATAATAGATACCAC<br>CAGTACTACCAAACCTTTAAAGGATGACATAATATTAACCTGCTTT<br>AGAGGGTGGGTTAAACAACTGCAGATTGACTACAAGAACCACGAG<br>ATCATGACTGCAGCGGCCTCACAGGGGCTTACTAGAAAAGGGGTAT<br>ACGCAGTGCGCTACAAGGTCAATGAGAACCCACTATACGCACAGA<br>CATCTGAGCATGTGAATGTATTACTTACACGCACTGAAAAACGTAT<br>AGTATGGAAGACTTTGGCCGGTGACCCTTGGATCAAGACGTTGACA<br>GCATCGTATCCGGGTAATTTCACCGCCACACTGGAAGAATGGCAAG<br>CTGAGCATGACGCTATCATGGCGAAAATACTTGAGCACCAGCTAG<br>CAGCGACGTTTTCCAAAATAAAGTGAACGTCTGCTGGGCCAAAGCG<br>CTAGAACCTGTGTTGGCCACCGCCAATATTACGCTGACCCGCTCGC<br>AGTGGGAGACCATTCCAGCGTTCAAGGATGACAAAGCGTATTCGCC<br>TGAGATGGCCTTAAACTTTTTCTGCACCAGATTCTTTGGCGTCGACA<br>TCGACAGCGGGTTGTTCTCCGCGCCAACTGTTCCGCTGACTTACACC<br>AATGAACACTGGGATAATAGCCCAGGTCCAAACATGTATGGTTTGT<br>GCATGCGCACTGCTAAAGAACTTGCACGTCGGTATCCTTGTATTCTG<br>AAAGCCGTGGATACAGGTAGAGTGGCTGACGTTCGCACAGACACT<br>ATCAAAGACTATAACCCGCTAATAAATGTGGTACCCTTGAATAGAA<br>GACTCCCACACTCATTGGTTGTCACACATAGATACACTGGGAACGG<br>TGATTACTCCCAGCTAGTGACCAAGATGACCGGAAAGACCGTACTA<br>GTAGTGGGTACACCTATGAACATACCAGGAAAGAGAGTCGAGACA<br>CTAGGCCCAAGCCCACAATGTACATATAAAGCGGAACTGGACCTGG<br>GCATTCCTGCCGCTTTAGGCAAATATGACATCATTTTTATTAACGTG<br>AGGACTCCCTACCGACACCACCATTACCAACAGTGCGAGGACCATG<br>CGATCCACCACAGCATGCTTACCAGAAAAGCAGTGGACCATTTGAA<br>CAAAGGCGGTACGTGCATCGCATTGGGCTATGGGACTGCGGACAG<br>AGCCACCGAGAACATTATCTCTGCAGTCGCCCGCTCATTCAGGTTCT<br>CACGTGTGTGCCAGCCGAAGTGTGCCTGGGAAAACACTGAGGTCGC<br>GTTCGTGTTTTTCGGCAAGGACAACGGCAACCATCTCCAAGATCAA<br>GATAGGCTGAGTGTTGTGCTAAACAACATATACCAAGGGTCAACTC<br>AACATGAAGCTGGCAGAGCACCTGCGTACAGAGTGGTGCGCGGCG<br>ACATAACAAAGAGCAATGATGAGGTTATTGTTAACGCGGCGAACA<br>ACAAAGGGCAACCCGGTGGCGGTGTGTGGCGCCCTTTACAGGAA<br>GTGGCCTGGAGCTTTTGATAAGCAGCCGGTAGCAACTGGTAAAGCG<br>CACCTCGTCAAGCATTCTCCGAACGTCATCCATGCTGTTGGTCCTAA<br>TTTCTCTCGGCTATCAGAAAACGAAGGAGACCAGAAATTGTCTGAA<br>GTGTACATGGACATTGCCAGAATTATCAACAACGAGAGGTTTACTA<br>AAGTCTCCATTCCGTTGTTATCTACCGGCATCTACGCAGGTGGTAAG<br>GACAGGGTTATGCAATCGCTGAACCATTTATTTACAGCCATGGATA<br>CTACCGACGCAGACATTACTATTTACTGTCTAGATAAGCAATGGGA<br>GTCAAGAATAAAGGAAGCTATCACTCGGAAGGAAAGCGTTGAAGA<br>GCTTACTGAGGATGACAGACCAGTTGACATTGAACTGGTACGGGTG<br>CACCCGTTGAGCAGCTTGGCAGGTAGACCTGGTTATTCAACCACCG<br>AGGGCAAGGTGTATTCGTATCTAGAGGGGACTAGGTTTCATCAAAC<br>TGCCAAAGACATAGCTGAAATTTACGCTATGTGGCCTAACAAGCAA<br>GAAGCAAACGAGCAGATTTGCTTATACGTGTTGGGAGAGAGTATGA<br>ACAGCATCCGCTCTAAGTGTCCAGTTGAAGAGTCGGAGGCCTCTTC<br>CCCCCCTCACACCATCCCGTGTCTGTGCAACTATGCAATGACTGCA<br>GAGCGAGTTTACAGATTACGTATGGCAAAGAATGAACAATTCGCAG<br>TTTGTTCGTCCTTTCAGTTACCGAAATACAGGATTACAGGGGTTCAG<br>AAAATTCAATGCAGTAAACCTGTGATATTCTCTGGCACTGTACCCC<br>CGGCCATACATCCAAGAAAATTCGCATCCGTGACAGTGGAAGCAC<br>TCCGATGGTCCAACCTGAAAGGTTGGTGCCTAGGCGACCTGCACCG<br>CCTGTGCCCGTACCTGCAAGAATCCCCAGCCCTCCATGTACATCGA<br>CCAATGGATCGACGACCAGTATACAATCACTGGGGAGGATCAAA<br>GCGCATCTGCTTCTAGCGGAGCTGAAATCTCTGTAGACACCAGGTTTC<br>GCTATGGAGCATACCCAGCGCTACCGGGTTCGATGTGCGTACCTCC<br>TCATCGTTGAGCCTAGAGCAGCCTACCTTTCCGACAATGGTTGTCG |

| SEQ ID NO | Sequence |
|---|---|
| | AAGCAGAGATTCACGCCAGTCAAGGATCACTGTGGAGCATACCCA |
| | GTATCACCGGATCTGAAACCCGTGCTCCGTCACCTCCAAGTCAGGA |
| | TAGTAGACCTTCCACCCCATCTGCAAGTGGTTCACACACGTCCGTG |
| | GACTTAATCACGTTTGACAGCGTTGCAGAGATTTTGGAGGATTTCA |
| | GTCGTTCGCCGTTTCAATTTTTGTCTGAAATCAAACCTATTCCTGCA |
| | CCTCGTACCCGAGTTACTAACATGAGCCGCAGCGCAGACACGATCA |
| | AACCAATTCCAAAGCCGCGTAAATGCCAGGTGAAGTACACGCAGC |
| | CACCTGGCGTCGCCAGGGCCATATCGGCAGCGGAATTTGACGAGTT |
| | TGTGCGGAGGCACTCGAATTGACGGTACGAAGCGGGTGCGTACATT |
| | TTCTCATCCGAGACGGGACAAGGGCACCTGCAACAAAAATCTACGC |
| | GGCAATGCAAACTCCAGTATCCAATCCTGGAGCGTTCCGTCCATGA |
| | GAAATTTTACGCCCCGCGCCTCGATCTCGAGCGTGAGAAGCTGTTG |
| | CAGAAGAAACTACAATTGTGTGCTTCTGAAGGTAATCGGAGCAGGT |
| | ATCAGTCTCGTAAAGTAGAGAACATGAAGGCAATCACCGTTGAGCG |
| | TCTACTGCAGGGGATAGGCTCATACCTCTCTGCAGAACCGCAACCA |
| | GTTGAATGCTACAAAGTCACCTATCCTGCTCCCATGTATTCAAGTAC |
| | TGCAAGCAACAGCTITTCATCAGCAGAAGTGGCCGTCAAAGTCTGC |
| | AACCTAGTACTGCAAGAGAATTTTCCCACCGTAGCCAGCTATAACA |
| | TAACGGATGAGTATGATGCCTATCTTGATATGGTGGACGGAGCATC |
| | CTGCTGTTTAGATACTGCCACCTTTTGCCCAGCCAAATTAAGGAGCT |
| | TTCCAAAGAAGCACAGTTATTTGCGGCCTGAGATACGGTCAGCAGT |
| | GCCATCACCGATTCAAAACACGCTCCAGAATGTACTAGCAGCAGCC |
| | ACGAAACGGAATTGCAATGTCACTCAAATGAGGGAACTTCCAGTGT |
| | TGGATTCAGCTGCCTTCAACGTGGAGTGTTTCAAAAAGTACGCCTG |
| | TAACGATGAGTACTGGGACTTCTACAAGACAAACCCGATAAGACTC |
| | ACCGCAGAAAATGTTACTCAGTATGTTACTAAGTTAAAGGGACCCA |
| | AAGCAGCTGCCCTTTTTGCGAAAACGCATAACTTACAGCCATTGCA |
| | TGAGATACCAATGGATAGATTCGTGATGGACCTTAAACGGGATGTT |
| | AAGGTTACACCCGGGACAAAACATACTGAAGAAAGACCAAAAGTT |
| | CAGGTGATACAGGCAGCTGATCCACTTGCAACCGCCTACCTATGTG |
| | GTATACATCGAGAGCTTGTGCGCAGGTTGAACGCAGTGCTGCTACC |
| | GAACATCCACACTTTGTTTGACATGTCTGCAGAAGATTTTGATGCTA |
| | TCATTGCCGAACACTTTCAATTCGGCGACTCGGTGTTAGAGACAGA |
| | CATAGCTTCTTTTGATAAAAGCGAGGACGATGCTATCGCCATGTCT |
| | GCTCTAATGATTCTTGAAGACCTAGGAGTTGATCAGGCACTGTTAA |
| | ACCTAATTGAAGCAGCCTTTGGGAACATAACATCTGTGCACTTACC |
| | AACAGGCACCCGATTTAAGTTCGGGGCAATGATGAAATCCGGGATG |
| | TTTTTGACACTCTTTATTAATACTGTTGTCAATATCATGATCGCTAG |
| | CCGCGTGCTCCGCGAGCGGTTGACCACTTCCCCCTGCGCAGCATTT |
| | ATCGGCGACGACAACATCGTGAAAGGGGTTACATCTGACGAGCTG |
| | ATGGCAGAGCGGTGCGCCACGTGGTTGAACATGGAAGTGAAGATC |
| | ATCGATGCAGTAGTCGGAGTAAAGGCACCGTACTTTTGCGGAGGGT |
| | TCATCGTAGTCGATCAGATCACAGGAACTGCGTGCAGAGTCGCCGA |
| | CCCCCTGAAGAGACTGTTTAAGCTAGGTAAGCCGCTTCCATTGGAC |
| | GATGACCAAGACGTCGACAGGCGCAGAGCTCTGCATGATGAAGCG |
| | GCACGTTGGAACAGAATTGGCATCACTGAAGAGCTGGTGAAAGCA |
| | GTTGAATCACGCTACGAGGTGAACTACGTGTCACTAATCATTACAG |
| | CGTTGACTACATTAGCATCTACAGTTAGCAACTTTAAACACATAAG |
| | AGGTCACCCCATAACCCTCTACGGCTGACCTAAATAGGTTGTGCAT |
| | TAGTACCTAACCTATTTATATTATATTGCTATCTAAATATCAGAGAT |
| | GTTCCCATACCCTACACTTAACTACCCGCCTATGGCGCCGATTAACC |
| | CGATGGCCTACCGGGATCCTAATCCGCCTAGGCGCAGGTGGCGGCC |
| | CTTTAGGCCACCACTTGCAGCTCAAATTGAGGACCTGAGACGTTCC |
| | ATTGCTAACCTGACTTTGAAACAACGAGCACCTAACCCTCCAGCAG |
| | GACCGCCCGCCAAACGCAAGAAGCCTGCGCCCAAGCCTAAGCCTG |
| | CGCAGGCGAAAAAGAAGCGACCACCACCACCTGCCAAGAAACAAA |
| | AACGTAAACCTAAACCAGGCAAACGACAGCGAATGTGTATGAAGC |
| | TAGAGTCAGATAAAACGTTTCCGATCATGTTGAACGGACAGGTGAA |
| | TGGTTACGCGTGCGTCGTGGGTGGACGAGTGTTTAAACCGCTGCAC |
| | GTAGAAGGCAGAATAGACAATGAGCAACTGGCCGCTATCAAGCTG |
| | AAGAAGGCCAGCATATATGACCTTGAGTACGGTGATGTGCCACAAT |
| | GCATGAAATCAGATACCCTCCAGTACACCAGTGACAAGCCTCCTGG |
| | CTTTTTATAACTGGCATCATGGAGCTGTGCAGTATGAGAACAACAGG |
| | TTCACCGTACCACGAGGGGTAGGTGGAAAGGGCGACAGCGGGAGA |
| | CCTATTCTTGACAACAAAGGTAGAGTCGTCGCAATTGTCCTGGGTG |
| | GAGTCAACGAAGGATCCAGGACGGCTCTATCAGTGGTGACATGGA |
| | ACCAAAAGGGGGTTACAGTCAAAGATACACCAGAGGGGTCAGAGC |
| | CATGGTCGCTCGCCACTGTCATGTGCGTCCTGGCCAATATCACGTTT |
| | CCATGTGATCAACCACCCTGCATGCCATGTCTGTTATGAAAAGAATC |
| | CACACGAAACACTCACCATGCTGGAACAGAATTACGACAGCCGAG |
| | CCTATGATCAGCTGCTCGATGCCGCTGTGAAATGTAATGCTAGGAG |
| | AACCAGGAGAGATTTGGACACTCATTTCACCCAGTATAAGTTGGCA |
| | CGCCCGTATATTGCTGATTGCCCTAACTGTGGGCATAGTCGGTGCG |
| | ACAGCCCTATAGCTATAGAAGAAGTCAGAGGGGATGCGCATGCAG |
| | GAGTCATCCGCATCCAGACATCAGCTATGTTTGGTCTGAAGACGGA |

| SEQ ID NO | Sequence |
|---|---|
| | TGGAGTCGATTTGGCCTACATGAGTTTCATGAACGGCAAAACGCAG<br>AAATCAATAAAGATCGACAACCTGCATGTGCGCACCTCAGCCCCTT<br>GTTCCCTCGTGTCGCACCACGGCTATTACATCTTGGCTCAATGCCCA<br>CCAGGGGACACGGTTACAGTTGGGTTTCACGACGGGCCTAACCGCC<br>ATACGTGCACAGTTGCCCATAAGGTAGAATTCAGGCCAGTGGGTAG<br>AGAGAAATACCGTCACCCACCTGAACATGGAGTTGAATTACCGTGT<br>AACCGTTACACTCACAAGCGTGCAGACCAAGGACACTATGTTGAGA<br>TGCATCAACCAGGGCTAGTTGCCGACCACTCTCTCCTTAGCATCCAC<br>AGTGCCAAGGTGAAAATTACGGTACCGAGCGGCGCCCAAGTGAAA<br>TACTACTGCAAGTGTCCAGATGTACGAGAGGGAATTACCAGCAGCG<br>ACCATACAACCACCTGCACGGATGTCAAACAATGCAGGGCTTACCT<br>GATTGACAACAAGAAATGGGTGTACAACTCTGGAAGACTGCCTCGA<br>GGAGAGGGCGACACTTTTAAAGGAAAACTTCATGTGCCCTTTGTGC<br>CTGTTAAGGCCAAGTGCATCGCCACGCTGGCACCGGAGCCTCTAGT<br>TGAGCACAAACACCGCACCCTGATTTTACACCTGCACCCGGACCAC<br>CCGACCTTGCTGACGACCAGGTCACTTGGAAGTGATGCAAATCCAA<br>CTCGACAATGGATTGAGCGACCAACAACTGTCAATTTCACAGTCAC<br>CGGAGAAGGGTTGGAGTATACCTGGGGAAACCATCCACCAAAAAG<br>AGTATGGGCTCAAGAGTCAGGAGAAGGGAACCCACATGGATGGCC<br>GCACGAAGTGGTAGTCTATTACTACAACAGATACCCGCTAACCACA<br>ATTATCGGGTTATGCACCTGTGTGGCTATCATCATGGTCTCTTGTGT<br>CACATCCGTGTGGCTCCTTTGCAGGACTCGCAATCTTTGCATAACCC<br>CGTATAAACTAGCCCCGAACGCTCAAGTCCCAATACTCCTGGCGTT<br>ACTTTGCTGCATTAAGCCGACGAGGGCAGACGACACCTTGCAAGTG<br>CTGAATTATCTGTGGAACAACAATCAAAACTTTTTCTGGATGCAGA<br>CGCTTATCCCACTTGCAGCGCTTATCGTATGCATGCGCATGCTGCGT<br>TGCTTATTTTGCTGTGGGCCGGCTTTTTTACTTGTCTGCGGCGCCTTG<br>GGCGCCGCAGCGTACGAACACACAGCAGTGATGCCGAACAAGGTG<br>GGGATCCCGTATAAAGCTTTAGTCGAACGCCCAGGGTATGCACCCG<br>TTCACCTACAGATACAGCTGGTTAATACCAGGATAATTCCATCAAC<br>TAACCTGGAGTACATCACCTGCAAGTACAAGACAAAAGTGCCGTCT<br>CCAGTAGTGAAATGCTGCGGTGCCACTCAATGTACCTCTAAACCCC<br>ATCCTGACTATCAGTGTCAGGTGTTTACAGGTGTTTACCCATTCATG<br>TGGGGAGGAGCCTACTGCTTCTGCGACACCGAAAACACCCAGATGA<br>GCGAGGCGTATGTAGAGCGCTCGGAAGAGTGCTCTATCGACCACGC<br>AAAAGCTTATAAAGTACACACAGGCACTGTTCAGGCAATGGTGAAC<br>ATAACTTATGGGAGCGTCAGCTGGAGATCTGCAGATGTCTACGTCA<br>ATGGTGAAACTCCCGCGAAAATAGGAGATGCCAAACTCATCATAG<br>GTCCACTGTCATCTGCGTGGTCCCCATTCGATAACAAGGTGGTGGTT<br>TATGGGCATGAAGTGTATAATTACGACTTTCCTGAGTACAGCACCG<br>GCAAAGCAGGCTCTTTCGGAGACCTGCAATCACGCACATCAACCAG<br>CAACGATCTGTACGCAAATACCAACTTGAAGCTACAACGACCCCAG<br>GCTGGTATCGTGCACACACCTTTCACCCAGGCGCCCTCTGGCTTCGA<br>ACGATGGAAAAGGGACAAAGGGGCACCGTTGAACGACGTAGCCCC<br>GTTTGGCTGTTCAATTGCCCTGGAGCCGCTCCGTGCAGAAATTGT<br>GCAGTGGGAAGCATCCCTATATCTATAGATATACCCGATGCGGCTT<br>TCACCAGAATATCTGAAACACCGACAGTCTCAGACCTGGAATGCAA<br>AATTACGGAGTGTACTTATGCCTCCGATTTCGGTGGTATAGCCACC<br>GTTGCCTACAAATCCAGTAAAGCAGGAAACTGTCCAATTCATTCTC<br>CATCGGGTGTTGCAGTTATTAAAGAGAATGACGTCACCCTTGCTGA<br>GAGCGGATCATTTACATTCCACTTCTCCACTGCAAACATCCATCCTG<br>CTTTTAAGCTGCAGGTCTGCACCAGTGCAGTTACCTGCAAAGGAGA<br>TTGCAAGCCACCGAAAGATCATATCGTCGATTATCCAGCACAACAT<br>ACCGAATCCTTTACGTCGGCGATATCCGCCACCGCGTGGTCGTGGC<br>TAAAAGTGCTGGTAGGAGGAACATCAGCATTTATTGTTCTGGGGCT<br>TATTGCTACAGCAGTGGTTGCCCTAGTTCTGTTCTTCCATAGACATT<br>AACATCTTGTCAACCACATAACACTACAGGCAGTGTATAAGGCTGT<br>CTTACTAAACACTAAAATCACCCTAGTTCGATGTACTTCCGAGCTAT<br>GGTGACGGTGGTGCATAATGCCGCCGATGCAGTGCATAAGGCTGCT<br>ATATTACCAAATTATAACACTAAGGGCAGTGCATAATGCTGCTCCT<br>AAGTAATTTTATACACACTTTATAATCAGGCATAATTGCCGTATATA<br>CAATTACACTACAGGTAATATACCGCCTCTTATAAACACTACAGGC<br>AGCGCATAATGCTGTCTTTTATATCAATTTACAAAATCATAT |
| SEQ ID NO: 17 | MFPYPTLNYPPMAPINPMAYRDPNPPRRRWRPFRPPLAAQIEDLRRSIA<br>NLTLKQRAPNPPAGPPAKRKKPAPKPKPAQAKKKRPPPPAKKQKRKP<br>KPGKRQRMCMKLESDKTFPIMLNGQVNGYACVVGGRVFKPLHVEGRI<br>DNEQLAAIKLKKASIYDLEYGDVPQCMKSDTLQYTSDKPPGFYNWHH<br>GAVQYENNRFTVPRGVGGKGDSGRPILDNKGRVVAIVLGGVNEGSRT<br>ALSVVTWNQKGVTVKDTPEGSEPWSLATVMCVLANITFPCDQPPCMP<br>CCYEKNPHETLTMLEQNYDSRAYDQLLDAAVKCNARRTRRDLDTHFT<br>QYKLARPYIADCPNCGHSRCDSPIAIEEVRGDAHAGVIRIQTSAMFGLK<br>TDGVDLAYMSFMNGKTQKSIKIDNLHVRTSAPCSLVSHHGYYILAQCP<br>PGDTVTVGFHDGPNRHTCTVAHKVEFRPVGREKYRHIPPEHGVELPCN<br>RYTHKRADQGHYVEMHQPGLVADHSLLSIHSAKVKITVPSGAQVKYY |

| SEQ ID NO | Sequence |
|---|---|
| | CKCPDVREGITSSDHTTTCTDVKQCRAYLIDNKKWVYNSGRLPRGEG<br>DTFKGKLHVPFVPVKAKCIATLAPEPLVEHKHRTLILHLHPDHPTLLTT<br>RSLGSDANPTRQWIERPTTVNFTVTGEGLEYTWGNHPPKRVWAQESG<br>EGNPHGWPHEVVVYYNRYPLTTIIGLCTCVAIIMVSCVTSVWLLCRT<br>RNLCITPYKLAPNAQVPILLALLCCIKPTRADDTLQVLNYLWNNNQPF<br>FWMQTLIPLAALIVCMRMLRCLFCCGPAFLLVCGALGAAAYEHTAVM<br>PNKVGIPYKALVERPGYAPVHLQIQLVNTRIIPSTNLEYITCKYKTKVPS<br>PVVKCCGATQCTSKPHPDYQCQVFTGVYPFMWGGAYCFCDTENTQM<br>SEAYVERSEECSIDHAKAYKVHTGTVQAMVNITYGSVSWRSADVYVN<br>GETPAICIGDAKLIIGPLSSAWSPFDNKVVVYGHEVYNYDFPEYSTGKA<br>GSFGDLQSRTSTSNDLYANTNLKLQRPQAGIVHTPFTQAPSGFERWKR<br>DKGAPLNDVAPFGCSIALEPLRAENCAVGSIPISIDIPDAAFTRISETPTV<br>SDLECKITECTYASDFGGIATVAYKSSKAGNCPIHSPSGVAVIKENDVT<br>LAESGSFTFHFSTANIHPAFKLQVCTSAVTCKGDCKPPKDHIVDYPAQH<br>TESFTSAISATAWSWLKVLVGGTSAFIVLGLIATAVVALVLFFHRH |
| SEQ ID NO: 18 | MEKVHVDLDADSPPFVKSLQRCFPHFEIEATQVTDNDHANARAFSHLA<br>TKLIEGEVDTDQVILDIGSAPVRHTHSKHKYHCICPMKSAEDPDRLYRY<br>ADKLRKSDVTDKCIASKAADLLTVMSTPDAETPSLCMHTDSTCRYHG<br>SVAVYQDVYAVHAPTSIYYQALKGVRTIYWIGFDTTPFMYKNMAGAY<br>PTYNTNWADESVLEARNIGLSSDLHEKSFGKVSIMRKKKLQPTNKVI<br>FSVGSTIYTEERILLRSWHLPNVFHLKGKTSFTGRCNTIVSCEGYVVKKI<br>TLSPGIYGKVDNLASTMHREGFLSCKVTDTLRGERVSFPVCTYVPATL<br>CDQMTGILATDVSVDDAQKLLVGLNQRIVVNGRTQRNTNTMQNYLLP<br>VVAQAFSRWAREHRADLEDEKGLGVRERSLVMGCCWAFKTHKITSIY<br>KRPGTGTQTIKKVPAVFNSFVIPQPTSYGLDIGLRRRIKMLFDAKKAPAPII<br>TEADVAHLKGLQDEAEAVAEAEAVRAALPPLLPEVDKETVEADIDLIM<br>QEAGAGSVETPRRHIKVTTYPGEEMIGSYAVLSPQAVLNSEKLACIHPL<br>AEQVLVMTHKGRAGRYKVEPYHGRVIVPSGTAIPIPDFQALSESATIVF<br>NEREFVNRYLHHIAVNGGALNTDEEYYKVVKSTETDSEYVFDIDAKK<br>CVKKGDAGPMCLVGELVDPPFHEFAYESLKTRPAAPHKVPTIGVYGV<br>PGSGKSGIIKSAVTKRDLVVSAKKENCMEIIKDVKRMRGMDIAARTVD<br>SVLLNGVKHSVDTLYIDEAFACHAGTLLALIAIVKPKKVVLCGDPKQC<br>GFFNMMCLKVHFNHEICTEVYHKSISRRCTKTVTSIVSTLFYDKRMRT<br>VNPCNDKIIIDTTSTTKPLKDDIILTCFRGWVKQLQIDYKNHEIMTAAAS<br>QGLTRKGVYAVRYKVNENPLYAQTSEHVNVLLTRTEKRIVWKTLAG<br>DPWIKTLTASYPGNFTATLEEWQAEHDAIMAKILETPASSDVFQNKVN<br>VCWAKALEPVLATANITLTRSQWETIPAFKDDKAYSPEMALNFFCTRF<br>FGVDIDSGLFSAPTVPLTYTNEHWDNSPGPNMYGLCMRTAKELARRY<br>PCILKAVDTGRVADVRTDTIKDYNPLINVVPLNRRLPHSLVVTHRYTG<br>NGDYSQLVTKMTGKTVLVVGTPMNIPGKRVETLGPSPQCTYKAELDL<br>GIPAALGKYDIIFINVRTPYRHHHYQQCEDHAIHHSMLTRKAVDHLNK<br>GGTCIALGYGTADRATENIISAVARSFRFSRVCQPKCAWENTEVAFVFF<br>GKDNGNHLQDQDRLSVVLNNIYQGSTQHEAGRAPAYRVVRGDITKSN<br>DEVIVNAANNKGQPGGGVCGALYRKWPGAFDKQPVATGKAHLVKHS<br>PNVIHAVGPNFSRLSENEGDQKLSEVYMDIARIINNERFTKVSIPLLSTGI<br>YAGGKDRVMQSLNHLFTAMDTTDADITIYCLDKQWESRIKEAITRKES<br>VEELTEDDRPVDIELVRVHPLSSLAGRPGYSTTEGKVYSYLEGTRFHQT<br>AKDIAEIYAMWPNKQEANEQICLYVLGESMNSIRSKCPVEESEASSPPH<br>TIPCLCNYAMTAERVYRLRMAKNEQFAVCSSFQLPKYRITGVQKIQCS<br>KPVIFSGTVPPAIHPRKFASVTVEDTPMVQPERLVPRRPAPPVPVPARIP<br>SPPCTSTNGSTTSIQSLGEDQSASASSGAEISVDQVSLWSIPSATGFDVR<br>TSSSLSLEQPTFPTMVVEAEIHASQGSLWSIPSITGSETRAPSPPSQDSRP<br>STPSASGSHTSVDLITFDSVAEILEDFSRSPFQFLSEIKPIPAPRTRVTNMS<br>RSADTIKPIPKPRKCQVKYTQPPGVARAISAAEFDEFVRRHSNRRYEAG<br>AYIFSSETGQGHLQQKSTRQCKLQYPILERSVHEKFYAPRLDLEREKLL<br>QKKLQLCASEGNRSRYQSRKVENMKAITVERLLQGIGSYLSAEPQPVE<br>CYKVTYPAPMYSSTASNSFSSAEVAVKVCNLVLQENFPTVASYNITDE<br>YDAYLDMVDGASCCLDTATFCPAKLRSFPKKHSYLRPEIRSAVPSPIQN<br>TLQNVLAAATKRNCNVTQMRELPVLDSAAFNVECFKKYACNDEYWD<br>FYKTNPIRLTAENVTQYVTKLKGPKAAALFAKTHNLQPLHEIPMDRFV<br>MDLKRDVKVTPGTKHTEERPKVQVIQAADPLATAYLCGIHRELVRRL<br>NAVLLPNIHTLFDMSAEDFDAIIAEHFQFGDSVLETDIASFDKSEDDAIA<br>MSALMILEDLGVDQALLNLIEAAFGNITSVHLPTGTRFKFGAMMKSG<br>MFLTLFINTVVNIMIASRVLRERLTTSPCAAFIGDDNIVKGVTSDELMA<br>ERCATWLNMEVKIIDAVVGVKAPYFCGGFIVVDQITGTACRVADPLKR<br>LFKLGKPLPLDDDQDVDRRRALHDEAARWNRIGITEELVKAVESRYE<br>VNYVSLIITALTTLASTVSNFKHIRGHPITLYG |
| SEQ ID NO: 19 | AACTAATCGATCCAATATGAAAGAATTCACGTTGACTTAGATGCT<br>GACAGCCCGTATGTCAAGTCGTTACAGCGGAGCTTTCCACAATTTG<br>AGATCGAAGCAAGGCAGGTCACTGACAATGACCATGCCAATGCCA<br>GAGCGTTTTCGCATGTGGCAACAAAGCTCATTGAGAGCGAAGTCGA<br>CCGGGACCAAGTTATCTTGGACATTGGAAGTGCGCCCGTCAGACAT<br>GCACATTCCAATCACCGCTATCATTGTATCTGCCCTATGATAAGCGC |

| SEQ ID NO | Sequence |
|---|---|
| | TGAAGACCCGGACAGACTACAACGGTATGCAGAAAGACTTAAGAA<br>AAGTGACATTACCGACAAGAACATAGCCTCTAAGGCGGCAGACCT<br>GCTGGAAGTCATGTCAACACCAGACGCAGAGACTCCATCTCTGTGT<br>ATGCACACAGACGCCACGTGTAGGTACTTTGGAAGTGTAGCAGTAT<br>ACCAAGATGTGTACGCAGTCCATGCACCGACATCAATCTACCACCA<br>GGCGCTTAAAGGAGTTAGGACAATTTACTGGATAGGCTTTGACACG<br>ACCCCTTTTATGTACAAAAACATGGCAGGTTCTTACCCTACTTACAA<br>CACGAACTGGGCTGACGAGAGAGTATTGGAAGCACGTAACATTGG<br>CCTCGGTAACTCAGATCTTCAGGAGAGCAGGCTTGGAAACCTCTCA<br>ATCCTTAGGAAGAAGAGGCTCCAACCTACTAATAAGATCATATTCT<br>CGGTTGGTTCAACAATCTACACAGAAGATAGATCACTGTTACGTAG<br>CTGGCATCTTCCAAACGTGTTCCACTTGAAAGGAAAGTCTAACTTC<br>ACAGGTAGATGTGGGACCATTGTCAGCTGTGAAGGGTACGTCATAA<br>AAAAAATTACAATCAGCCCAGGACTATACGGTAAAGTTGAGAACTT<br>GGCGTCCACAATGCATCGCGAGGGTTTCTTGAGTTGCAAAGTCACA<br>GATACGTTGCGCGGCGAGAGGGTTTCTTTTGCTGTGTGTACGTATGT<br>ACCAGCCACACTTTGCGATCAGATGACAGGGATTCTGGCAACTGAC<br>GTTAGTGTGGATGACGCACAAAAACTATTGGTTGGGCTCAACCAAA<br>GGATTGTCGTCAATGGTAGGACGCAAAGAAATACTAACACAATGC<br>AGAACTATCTATTACCAGTGGTCGCCCAGGCGTTTTCCAGGTGGGC<br>GCGTGAACATCGTGCCGACTTGGACGACGAGAAAGAACTAGGGGT<br>GCGGGAGCGCACTCTTACTATGGGCTGCTGCTGGGCTTTCAAGACC<br>CAGAAAATCACATCCATCTACAAGAAGCCTGGTACGCAAACAATTA<br>AGAAAGTACCTGCCGTCTTTGACTCATTTGTGTTTCCACGCCTTACC<br>AGCCACGGGCTCGATATGGGCTTCCGCCGTAGGCTCAAGCTGCTGC<br>TTGAACCAACTGTCAAACCCGCACCGGCTATTACAATGGCCGATGT<br>GGAGCATCTGCGTGGCTTACAGCAAGAAGCTGAAGAAGTGGCTGC<br>AGCGGAAGAGATCAGAGAAGCCCTGCCGCCCTTGCTCCCTGAAATA<br>GAAAAAGAGACCGTAGAGGCAGAAGTAGACCTCATTATGCAAGAG<br>GCAGGAGCAGGTAGCGTGGAGACACCACGAGGACACATCAGGGTG<br>ACAAGTTACCCAGGCGAAGAGAAGATTGGGTCTTACGCTGTACTTT<br>CACCCCAGGCGGTATTGAATAGTGAAAAACTGGCGTGTATCCACCC<br>ATTGGCGGAACAAGTACTGGTAATGACTCACAAAGGTAGGGCTGG<br>GAGATACAAGGTCGAGCCATACCACGGTAAGGTCATTGTACCAGA<br>AGGGACGGCGGTCCCTGTTCAGGACTTCCAGGCATTGAGTGAGAGC<br>GCTACGATCGTTTTCAACGAGAGGGAGTTCGTAAACAGATACCTGC<br>ATCACATCGCAATCAACGGAGGAGCGCTAAACACTGACGAAGAGT<br>ACTATAAGACTGTAAAGACTCAGGACACAGACTCAGAATACGTCTT<br>CGACGTTGACGCACGAAAGTGTGTTAAGCGAGAAGACGCAGGTCC<br>GTTGTGCCTAACCGGTGATCTGGTAGATCCGCCATTTCACGAGTTTG<br>CGTACGAGAGTCTTAGGACGCGACCAGCAGCACCTCACAAAGTCCC<br>AACCATTGGAGTCTATGGAGTGCCAGGTTCGGGTAAATCTGGAATC<br>ATCAAAAGCGCTGTGACCAAGAAAGATCTGGTTGTGAGTGCGAAA<br>AAGGAAAACTGCGCAGAAATCATCAGGGATGTAAGGAGGATGAGA<br>TGTATGGATGTTGCTGCTAGGACTGTAGATTCTGTGCTGCTGAATGG<br>GGTTAAGCACCCCGTTAACACTCTGTACATTGATGAGGCATTTGCCT<br>GCCATGCAGGGACGCTGCTGGCACTGATTGCCATCGTCAAACCTAA<br>GAAAGTGGTATTGTGCGGGGACCCAAAACAATGCGGCTTCTTTAAC<br>ATGATGTGCCTGAAAGTACATTTTAACCATGACATATGCACTGAAG<br>TGTACCATAAAAGCATCTCTAGGAGGTGCACACAGACTGTAACCGC<br>TATCGTCTCCACGCTCTTTTACGACAAGCGAATGAAGACGGTTAAC<br>CCATGTGCTGACAAAATCATCATAGATACCACAGGGACCACAAAGC<br>CGCACAAAGATGATCTGATTCTAACCTGTTTCAGAGGATGGGTGAA<br>ACAGCTACAGATTGACTATAAAAATCATGAAATCATGACTGCGGCT<br>GCATCGCAAGGACTTACGCGGAAAGCGTTTATGCTGTCAGGTACA<br>AAGTCAACGAGAATCCACTCTACTCGCAGACTTCTGAGCACGTGAA<br>CGTGTTACTTACACGCACAGAAAAACGCATTGTCTGGAAGACGCTA<br>GCTGGTGATCCCTGGATAAAGATACTTACAGCTAAATATTCCGGGG<br>ATTTCACGGCTTCATTGGACGACTGGCAGCGAGAACATGATGCCAT<br>TATGGCACGCGTTCTTGATAAGCCGCAGACAGCTGATGTGTTCCAG<br>AATAAGGTGAACGTCTGCTGGGCGAAGGCTCTAGAGCCAGTCTTGG<br>CCACGGCCAACATTGTGCTGACGAGACAGCAGTGGGAGACGTTGC<br>ACCCATTCAAGCATGACAGAGCGTACTCACCTGAAATGGCACTGAA<br>CTTCTTTTGCACCAGGTTCTTTGGAGTAGACCTGGACAGTGGGTTGT<br>TTTCCGCTCCTACCGTCGCACTTACTTATAGGGATCAGCACTGGGAT<br>AACTCGCCAGGGAAGAACATGTATGGGCTTAATAGAGAGGTAGCA<br>AAGGAGTTGTCACGGCGATATCCGTGCATCACAAAAGCGGTTGACA<br>CAGGCAGGGTAGCTGATATAAGGAATAATACCATCAAGGACTACTC<br>TCCAACAATTAATGTGGTTCCATTAAATCGTCGGTTACCCCACTCGT<br>TGATCGTTGACCACAAAGGACAGGGTACAACTGATCACAGCGGATT<br>CCTATCTAAGATGAAGGGCAAATCTGTGTTGGTGATCGGCGATCCT<br>ATCAGCATTCCAGGGAAGAAAGTAGAGTCCATGGGTCCATTGCCCA<br>CTAATACCATCAGGTGTGATCTAGATTTGGGAATACCTAGCCATGT<br>CGGTAAATATGACATTATATTTGTCAATGTTAGGACCCCGTATAAG<br>AACCATCACTACCAACAGTGCGAGGATCACGCTATCCACCACAGCA |

| SEQ ID NO | Sequence |
|---|---|
| | TGTTAACGTGTAAGGCTGTCCACCACCTGAACACTGGCGGAACATG<br>TGTGGCTATAGGGTATGGGCTTGCTGATCGCGCAACCGAGAATATC<br>ATCACTGCGGTAGCGCGCTCATTTAGGTTTACCCGTGTCTGTCAGCC<br>TAAGAACACTGCCGAAAATACTGAGGTTCTCTTCGTGTTCTTCGGC<br>AAGGACAACGGCAACCACACACATGACCAGGACAGACTCGCTGTA<br>GTGCTTGACAACATCTACCAAGGGTCAACCAGGTACGAGGCAGGG<br>AGAGCTCCAGCGTACAGAGTGATCAGAGGTGACATTAGCAAGAGC<br>GCTGACCAAGCTATCGTTAATGCTGCTAATAGCAAAGGTCAACCAG<br>GTTCCGGAGTGTGCGGTGCACTGTACCGAAAATGGCCGGCTGCTTT<br>TGATAGACAGCCAATAGCTGTCGGGACGGCTAGACTTGTGAAGCAC<br>GAACCGCTCATCATACATGCTGTAGGACCCAATTTTTCTAAGATGC<br>CGGAACCGGAGGGCGACCTTAAGCTCGCAGCTGCCTACATGAGCAT<br>AGCGTCAATCGTCAACGCTGAACGGATTACTAAAATATCAGTACCG<br>CTACTGTCAACCGGCATCTATTCTGGTGGCAAAGATCGAGTGATGC<br>AATCATTGCATCACCTGTTCACTGCTTTCGACACTACGGATGCCGAT<br>GTCACCATATATTGCTTGGATAAACAATGGGAGACCAGGATAATCG<br>AGGCCATTCACCGCAAAGAAAGCGTCGAAATACTGGATGATGACA<br>AGCCAGTAGACATTGACTTGGTTAGGGTCCATCCAAACAGCGCTTT<br>GGCAGGCAGACCTGGTTACTCCGTCAATGAGGGCAAGCTGTATTCA<br>TACCTGGAAGGTACACGATTCCATCAGACCGCCAAGGACATTGCCG<br>AAATCCATGCAATGTGGCCCAACAAATCTGAGGCTAATGAGCAGAT<br>TTGCTTGTACATCCTGGGTGAGAGTATGTCCAGCATCCGCTCCAAAT<br>GCCCAGTAGAGGAGTCAGAGGCGTCTGCTCCACCTCACACACTGCC<br>GTGCCTGTGTAATTACGCTATGACGGCTGAGCGCGTATACAGGTTG<br>CGCTCTGCGAAGAAAGAACAGTTCGCCGTATGCTCATCATTCCTGT<br>TGCCGAAGTACAGGATCACAGGCGTGCAGAAGCTACAATGCAGCA<br>AACCAGTCCTGTTTTCAGGCGTCGTACCGCCGGCTGTACACCCCAG<br>GAAGTACGCGGAAATAATTCTAGAAACGCCACCACCGCCAGTAAC<br>GACAACCGTAATATGTGAACCCACTGTGCCAGAACGTATACCCAGT<br>CCGGCGATTTCTAGAGCACCAAGTGCGGAATCACTGCTATCTTTTA<br>GCGGCGTCTCGTTCTCTAGCTCTGCCACACGCTCGTCAACCGCCTGG<br>AGCGACTATGACAGGCGGTTTGTGGTTACAGCTGACGTGCATCAAG<br>CGAACATATCTACGTGGAGCATCCCTAGTGCTCCTGGCTTGGACGT<br>CCAAATACCTTCTGACGTCAGTGATTCCCACTGGAGTGTTCCGAGT<br>GCATCAGGCTTCGAAGTGAGAACACCATCTGTACAGGACCTAACTG<br>CGGAGTGTGCAAAGCCTCGTGGGCTGGCCGAAATAATGCAAGACTT<br>CAATACTGCCCCTTTCCAGTTTCTTTCGGACCACAGACCAGTACCGG<br>CACCACGGAGACGCCCCATCCCATCACCTAGATCGACGGTTTCCGC<br>ACCTCCAGTTCCAAAGCCACGCAGGACTAAGTACCAACAACCACCA<br>GGAGTCGCTAGAGCGATCTCAGAAGCGGAGCTGGACGAGTACATC<br>CGTCAACACTCCAATTGACGGTATGAAGCGGGAGCGTATATTTTCT<br>CATCGGAAACAGGCCAAGGTCACCTTCAACAGAAATCAGTACGTCA<br>ATGTAAACTACAAGAACCTATATTGGACCGGGCCGTCCATGAGAAG<br>TATTACGCCCCGCGCCTCGATCTCGAAAGAGAGAAAATGTTACAGA<br>AGAAATTGCAATTATGTGCCTCTGAAGGAAATAGAAGCAGGTATCA<br>ATCACGAAAAGTAGAAAATATGAAAGCAATTACAGCGGAGCGACT<br>CATTTCTGGATTGGGCACATACCTATCATCAGAAGTGAATCCTGTC<br>GAGTGTTACAGAGTCAACTATCCTGTACCAATCTACTCGTCAACGG<br>TAATTAACAGGTTTACATCTGCAGAGGTCGCGGTTAAAACGTGCAA<br>CTTAGTTATCCAAGAGAATTACCCTACAGTAGCCAGTTATTGTATA<br>ACAGATGAATACGATGCGTATCTTGACATGGTGGACGGCGCATCGT<br>GCTGTCTAGATACAGCCACTTTTTGTCCGGCTAAACTGAGAAGCTA<br>CCCAAAGAAGCATAGCTATTTGCAGCCAGAGATAAGATCAGCCGTC<br>CCATCGCCTATACAGAATACATTACAAAATGTATTGGCTGCAGCTA<br>CTAAAAGGAATTGCAACGTTACCCAAATGCGAGAATTACCTGTCTT<br>AGATTCGGCGGCATTTAACGTTGATTGTTTCAAGAAATACGCATGC<br>AATGATGAGTACTGGGATACCTTTCGCGATAACCCTATTCGGCTAA<br>CTACAGAGAACGTTACGCAATATGTGACAAAGCTGAAAGGCCGA<br>AAGCAGCAGCATTGTTTGCGAAAACTCACAATCTAAAACCGTTGCA<br>GGAGATACCAATGGATCAATTCGTCATGGATCTAAAAAGAGATGTC<br>AAAGTTACTCCCGGCACGAAACATACAGAGGAGCGGCCTAAGGTG<br>CAGGTTATTCAGGCTGCAGACCCCCTTGCTACCGCTTACCTTTGCGG<br>GATCCACCGGGAATTAGTCCGTAGACTGAACGCTGTGCTTCTGCCG<br>AATATCCATACTCTCTTCGACATGTCAGCGGAAGATTTTGATGCGAT<br>TATTGCTGGACATTTCCACCACGGCGACCCAGTATTGGAAACGGAC<br>ATCGCGTCGTTTGATAAAAGCGAAGACGACGCTATCGCCATTTCGG<br>CGATGATGATCCTTGAGGACTTAGGCGTCGACCAACCGCTCTTAGA<br>TTTGATAGAGGCGGCGTTCGGCAATATCACATCTGTGCACCTACCT<br>ACAGGAACGAGGTTTAAATTTGGTGCCATGATGAAATCCGGCATGT<br>TCTTAACGCTGTTTGTCAACACACTAGTCAATATCATGATTGCTAGC<br>AGAGTACTACGTGAACGGTTAACCACGTCAGCGTGCGCGGCCTTTA<br>TCGGCGACGATAACATAGTGCATGGTGTCGTCTCCGACACCTTGAT<br>GGCGGAGAGATGCGCCACTTGGCTGAACATGGAAGTAAAAATTATT<br>GATGCAGTCATTGGTATCAAAGCACCCTACTTCTGCGGGGGATTTA<br>TCCTGGTGGACCAGATAACAGGCACAGCCTGCAGGGTCGCAGACCC |

-continued

| SEQUENCES | |
|---|---|
| SEQ ID NO | Sequence |
| | TCTAAAAAGGCTTTTTAAGCTTGGAAAACCGTTGTCAGTTGAAGAC<br>ACCCAAGACTGCGACCGCCGCCGGGCACTGCATGATGAAGCAATG<br>CGATGGAACAGAATCGGAATTACGGACGAGTTGGTGAAGGCCGTA<br>GAATCCAGATACGAGATCATACTGGCAGGCCTGATCATCACGTCTC<br>TGTCCACGTTAGCCGAAAGCGTTAAGAACTTCAAGAGCATAAGAGG<br>GAGCCCAATCACCCTCTACGGCTGACCTAAATAGGTGACGTAGTAG<br>ACACGCACCTACCCATCGCCATAATGTTTCCATACCCTCAGCTGAA<br>CTTTCCACCAGTTTACCCTACAAATCCGATGGCTTACCGAGATCCAA<br>ACCCTCCTAGGCGCCGCTGGAGGCCGTTCCGGCCCCCGCTGGCTGC<br>TCAAATCGAAGATCTTAGGAGGTCGATAGCTAACTTGACTTTCAAA<br>CAACGATCACCTAATCCGCCGCCAGGTCCACCGCCAAAGAAGAAG<br>AAGAGTGCTCCTAAGCCAAAACCTACTCAGCCTAAAAAGAAGAAG<br>CAGCAAGCCAAGAGGACGAAACGTAAGCCTAAACCAGGGAAACGA<br>CAGCGTATGTGTATGAAGTTGGAGTCGGACAAGACATTTCCGATCA<br>TGCTGAACGGCCAAGTGAATGGATACGCTTGCGTTGTCGGAGGAAG<br>GCTGATGAAACCACTCCACGTTGAAGGAAAAATTGATAATGAGCA<br>ATTAGCGGCCGTGAAATTGAAGAAGGCTAGCAAGTACGACTTAGA<br>GTATGGCGACGTTCCCCAGAATATGAAATCAGACACGCTGCAGTAC<br>ACCAGTGACAAACCACCGGGCTTCTACAACTGGCACCATGGCGCAG<br>TCCAGTATGAGAATGGGAGATTCACCGTACCGAGAGGAGTGGGCG<br>GGAAAGGCGACAGCGGAAGACCGATCCTGGACAACAGAGGCAGAG<br>TTGTGGCTATTGTTCTAGGAGGTGCAAATGAGGGCACGCGTACGGC<br>GCTTTCAGTGGTCACTTGGAACCAGAAAGGGGTGACCGTTTGGGAT<br>CCCCCCGAAGGTTCTGAACCGTGGTCACTAGTTACAGCGCTGTGCG<br>TGCTTTCGAATGTCACTTTCCCATGTGACAAACCACCCGTGTGCTAT<br>TCACTGGCGCCAGAACGAACACTCGACGTGCTCGAAGAGAACGTC<br>GACAATCCAAATTACGACACGCTGCTGGAGAACGTCTTGAAATGTC<br>CATCACACCGGCCCAAACGAAGCATTACCGATGACTTCACACTGAC<br>CAGTCCCTACTTGGGGTTCTGCCCGTATTGCAGACACTCAACGCCGT<br>GTTTCAGCCCAATAAAAATTGAGAACGTGTGGGACGAATCTGATGA<br>TGGATCGATTAGAATCCAGGTCTCGGCACAATTCGGTTACAATCAG<br>GCAGGCACTGCAGATGTCACTAAATTCCGTTACATGTCTTTCGACC<br>ACGACCATGACATCAAGGAAGACAGTATGGAGAAAATAGCCATCA<br>GCACATCCGGACCCTGCCGTCGTCTTGGCCACAAAGGGTATTTCCT<br>GTTAGCTCAATGTCCTCCAGGTGACAGTGTAACCGTCAGTATCACG<br>AGCGGAACTGCTGAGAACTCATGCACCGTGGAGAGAAAGATCAGG<br>AGGAAGTTTGTCGGTAGAGAGGAGTACTTGCTCCCACCCATCCATG<br>GAAAGCAGGTAAAGTGCCACGTTTACGATCACTTGAAAGAGACGTC<br>TGCCGGGTATATAACCATGCACAGGCCAGGCCCACACGCGTATAAG<br>TCCTATCTGGAGGAAGCGTCAGGCGAAGTGTATATTAAACCACCTT<br>CTGGCAAGAACGTCACCTACGAATGTAAGTGTGGCGACTACAGCAC<br>AGGTATCGTGAGCACGCGAACGAAGATAAACGGCTGCACTAAAGC<br>AAAACAGTGCATTGCCTACAAGAGCGACCAAACGAAATGGGTCTTC<br>AACTCGCCGGATCTTATTAGGCACACAGACCACTCAGTGCAAGGTA<br>AACTGCATATTCCATTCCGCTTGACACCGACAGTCTGCCCGGTTCCG<br>TTAGCTCACACGCCTACAGTCATGAAGTGGTTCAAAGGCATCACCC<br>TCCACCTGACTGCAACGCGACCAACATTGCTGACAACGAGAAAATT<br>GGGGCTGCGAGCAGACGCAACAGCAGAATGGATTACAGGGACTAC<br>ATCCAGGAATTTTTCTGTGGGGCGAGAAGGGCTGGAGTACGTATGG<br>GGCAACCATGAACCGGTCAGAGTCTGGGCCCAGGAGTCGGCACCA<br>GGCGACCCACATGGATGGCCGCATGAGATTATCATTCACTATTATC<br>ATCGGCATCCAGTCTACACCGTCATTGTGCTGTGTGGTGTCGCTCTT<br>GCTATCCTGGTAGGCACTGCATCGTCAGCAGCTTGTATCTCCAAAG<br>CAAGAAGAGACTGCCTGACGCCATACGCGCTTGCACCGAACGCGA<br>CGGTACCCACAGCATTAGTGGTTTTGTGCTGCATTCGGCCAACCAA<br>CGCTGAAACACTTGGAGAAACTTTGAACCATCTGTGGTTTAACAAC<br>CAACCGTTTCTCTGGGCACAGTTGTGCATTCCTCTGGCGGTCTTAT<br>TATTCTGTTCCGCTGCTTTTCATGCTGCATGCCTTTTTTATTGGTTGC<br>AGGCGTCTGCCTGGGGAAGGTAGACGCCTTCGAACATGCGACCACT<br>GTGCCAAATGTTCCGGGGATCCCGTATAAGGCGTTGGTCGAACGTG<br>CAGGTTACGCGCCACTTAACCTGGAGATCACTGTTGTCTCATCGGA<br>ATTAACACCCTCAACTAATAAGGAGTACGTGACCTGCAAATTCCAC<br>ACAGTCATTCCTTCACCACAAGTTAAATGCTGCGGGTCCCTCGAGT<br>GTAAGGCATCCTCAAGGGCGGATTACACATGCCGCGTTTTTGGCCG<br>TGTGTACCCTTTCATGTGGGGAGGCGCACAATGCTTCTGTGACAGT<br>GAGAACACACAACTGAGTGAGGCATACGTCGAGTTCGCTCCGGACT<br>GCACTATAGATCACGCAGTCGCACTAAAAGTTCATACAGCTGCTCT<br>GAAAGTCGGCCTGCGTATAGTGTACGGTAATACCACCGCGCACCTG<br>GATACGTTCGTCAACGGCGTCACACCAGGTTCCTCACGGGACCTGA<br>AGGTCATAGCAGGGCCGATATCAGCCGCTTTTTCACCCTTTGACCAT<br>AAGGTCGTCATCAGAAAGGGGTTTGTTTACAACTACGACTTCCCTG<br>AGTATGGTGCTATGAAACCAGGAGCGTTCGGCGATATTCAAGCATC<br>CTCTCTTGATGCTACAGACATAGTAGCCCGCACTGACATACGGCTG<br>CTGAAGCCTTCTGTCAAGAACATCCACGTCCCCTACACCCAAGCAG<br>TATCAGGGTATGAAATGTGGAAGAACAACTCAGGACGACCCCTGC |

| SEQ ID NO | Sequence |
|---|---|
| | AAGAAACAGCACCATTTGGATGTAAAATTGAAGTGGAGCCTCTGCG<br>AGCGTCTAACTGTGCTTACGGGCACATTCCTATCTCGATTGACATCC<br>CTGATGCAGCTTTCGTGAGATCATCAGAATCACCAACAATTTTAGA<br>AGTTAGCTGCACAGTAGCAGACTGCATTTATTCTGCAGACTTTGGT<br>GGTTCTCTAACATTACAGTACAAAGCTGATAGGGAGGGACATTGTC<br>CAGTTCACTCCCACTCCACGACAGCTGTTTTGAAGGAAGCGACCAC<br>ACATGTGACTGCCGTAGGCAGCATAACACTACATTTTAGCACATCG<br>AGCCCACAAGCAAATTTTATAGTTTCGCTATGCGGCAAGAAGTCCA<br>CCTGCAATGCTGAATGTAAACCACCGGCCGACCACATAATTGGAGA<br>ACCGCATAAAGTCGACCAAGAATTCCAAGCGGCAGTTTCCACAACA<br>TCTTGGAACTGGCTGCTTGCACTGTTTGGGGGAGCATCATCCCTCAT<br>TGTTGTAGGACTTATAGTGTTGGTCTGCAGCTCTATGCTTATAAACA<br>CACGTAGATGACTGAGCGCGGACACTGACATAGCGGTAAAAACTC<br>GATGTACTTCCGAGGAAGCGTGGTGCATAATGCCACGCGCCGCTTG<br>ACACTAAAACTCGATGTATTTCCGAGGAAGCACAGTGCATAATGCT<br>GTGCAGTGTCACATTAATCGCATATCACACTATATATTAACAACAC<br>TATATCACTTTTATAAGACTCACTATGGGTCTCTAATATACACTACA<br>CATATTTTACTTAAAAACACTATACACACTTTATAAGTTCTTTTATA<br>ATTTTTCTTTTGTTTTTATTTTGTTTTTAAAATTT |
| SEQ ID NO: 20 | MFPYPQLNFPPVYPTNPMAYRDPNPPRRRWRPFRPPLAAQIEDLRRSIA<br>NLTFKQRSPNPPPGPPPKKKKSAPKPKPTQPKKKKQQAKRTKRKPKPG<br>KRQRMCMKLESDKTFPIMLNGQVNGYACVVGGRLMKPLHVEGKIDN<br>EQLAAVKLKKASKYDLEYGDVPQNMKSDTLQYTSDKPPGFYNWHHG<br>AVQYENGRFTVPRGVGGKGDSGRPILDNRGRVVAIVLGGANEGTRTA<br>LSVVTWNQKGVTVWDPPEGSEPWSLVTALCVLSNVTFPCDKPPVCYS<br>LAPERTLDVLEENVDNPNYDTLLENVLKCPSHRPKRSITDDFTLTSPYL<br>GFCPYCRHSTPCFSPIKIENVWDESDDGSTRIQVSAQFGYNQAGTADVT<br>KFRYMSFDHDHDIKEDSMEKIAISTSGPCRRLGHKGYFLLAQCPPGDS<br>VTVSITSGTAENSCTVERKIRRKFVGREEYLLPPIHGKQVKCHVVDHLK<br>ETSAGYITMHRPGPHAYKSYLEEASGEVYTKPPSGKNVTYECKCGDYS<br>TGIVSTRTKINGCTKAKQCIAYKSDQTKWVFNSPDLIRHTDHSVQGKL<br>HIPFRLTPTVCPVPLAHTPTVMKWFKGITLHLTATRPTLLTTRKLGLRA<br>DATAEWITGTTSRNFSVGREGLEYVWGNHEPVRVWAQESAPGDPHG<br>WPHEIIIHYYHRHPVYTVIVLCGVALAILVGTASSAACISKARRDCLTP<br>YALAPAPNATVPTALVVLCCIRPTNAETLGETLNHLWFNNQPFLWAQLCI<br>PLAALIILFRCFSCCMPFLLVAGVCLGKVDAFEHATTVPNVPGIPYKAL<br>VERAGYAPLNLEITVVSSELTPSTNKEYVTCKFHTVIPSPQVKCCGSLE<br>CKASSRADYTCRVFGGVYPFMWGGAQCFCDSENTQLSEAYVEFAPDC<br>TIDHAVALKVHTAALKVGLRIVYGNTTAHLDTFVNGVTPGSSRDLKVI<br>AGPISAAFSPFDHKVVIRKGFVYNYDFPEYGAM1CPGAFGDIQASSLDA<br>TDIVARTDIRLLKPSVKNIHVPYTQAVSGYEMWKNNSGRPLQETAPFG<br>CKIEVEPLRASNCAYGHIPISIDIPDAAFVRSSESPTILEVSCTVADCIYSA<br>DFGGSTITQYKADREGHCPVHSHSTTAVLKEATTHVTAVGSITLHTST<br>SSPQANFIVSLCGKKSTCNAECKPPADHIIGEPHKVDQEFQAAVSTTSW<br>NWLLALFGGASSLIVVGLIVLVCSSMLINTRR |
| SEQ ID NO: 21 | MERIHVDLDADSPYVKSLQRSFPQFETEARQVIDNDHANARAFSHVAT<br>KLIESEVDRDQVILDIGSAPVRHAHSNHRYHCICPMISAEDPDRLQRYA<br>ERLKKSDITDKNIASKAADLLEVMSTPDAETPSLCMHTDATCRYFGSV<br>AVYQDVYAVHAPTSIYHQALKGVRTIYWIGFDTTPFMYKNMAGSYPT<br>YNTNWADERVLEARNIGLGNSDLQESRLGNLSILRKKRLQPTNKTIFSV<br>GSTIYTEDRSLLRSWHLPNVFHLKGKSNFTGRCGTIVSCEGYVIKKITIS<br>PGLYGKVENLASTMHREGFLSCKVTDTLRGERVSFAVCTYVPATLCD<br>QMIGILATDVSVDDAQKLLVGLNQRIVVNGRTQRNTNTMQNYLLPV<br>VAQAFSRWAREHRADLDDEKELGVRERTLTMGCCWAFKTQKITSTYK<br>KPGTQTIKKVPAVFDSFVPPRLTSHGLDMGFRRRLKLLLEPTVKPAPAI<br>TMADVEHLRGLQQEAEEVAAAEEIREALPPLLPEIEKETVEAEVDLIMQ<br>EAGAGSVETPRGHIRVTSYPGEEKIGSYAVLSPQAVLNSEKLACIHPLA<br>EQVLVMTHKGRAGRYKVEPYHGKVIVPEGTAVPVQDFQALSESATIV<br>FNEREFVNRYLHHIAINGGALNTDEEYYKTVKTQDTDSEYVFDVDAR<br>KCVKREDAGPLCLTGDLVDPPFHEFAYESLRTRPAAPHKVPTIGVYGV<br>PGSGKSGIIKSAVTKKDLVVSAKKENCAEIIRDVRRMCMDVAARTVD<br>SVLLNGVICHPVNTLYIDEAFACHAGTLLALIAIVKPKKVVLCGDPKQC<br>GFFNMMCLKVHFNHDICTEVYHKSISRRCTQTVTAIVSTLFYDKRMKT<br>VNPCADKIIIDTTGTTKPHKDDLILTCFRGWVKQLQIDYKNHEIMTAAA<br>SQGLTRKGVYAVRYKVNENPLYSQTSEHVNVLLTRTEKRIVWKTLAG<br>DPWIKILTAKYSGDFTASLDDWQREHDAIMARVLDKPQTADVFQNKV<br>NVCWAKALEPVLATANIVLTRQQWETLHPFKHDRAYSPEMALNFFCT<br>RFFGVDLDSGLFSAPTVALTYRDQHWDNSPGKNMYGLNREVAKELSR<br>RYPCITKAVDTGRVADIRNNTIKDYSPTINVVPLNRRLPHSLIVDHKGQ<br>GTTDHSGFLSKMKGKSVLVIGDPISIPGKKVESMGPLPTNTIRCDLDLGI<br>PSHVGKYDIIFVNVRTPYKNHHYQQCEDHAIHHSMLTCKAVHHLNTG<br>GTCVAIGYGLADRATENIITAVARSFRFTRVCQPKNTAENTEVLFVFFG<br>KDNGNHTHDQDRLAVVLDNIYQGSTRYEAGRAPAYRVIRGDISKSAD |

| SEQUENCES | |
|---|---|
| SEQ ID NO | Sequence |
| | QAIVNAANSKGQPGSGVCGALYRKWPAAFDRQPIAVGTARLVKHEPL<br>IIHAVGPNFSKMPEPEGDLKLAAAYMSIASIVNAERITKISVPLLSTGIYS<br>GGKDRVMQSLHHLFTAFDTTDADVTIYCLDKQWETRIIEAIHRKESVEI<br>LDDDKPVDIDLVRVHPNSALAGRPGYSVNEGKLYSYLEGTRFHQTAK<br>DIAEIHAMWPNKSEANEQICLYILGESMSSIRSKCPVEESEASAPPHTLP<br>CLCNYAMTAERVYRLRSAKKEQFAVCSSFLLPKYRITGVQKLQCSKPV<br>LFSGVVPPAVHPRKYAEIILETPPPPVTTTVICEPTVPERIPSPAISRAPSA<br>ESLLSFSGVSFSSSATRSSTAWSDYDRRFVVTADVHQANISTWSIPSAP<br>GLDVQIPSDVSDSHWSVPSASGFEVRTPSVQDLTAECAKPRGLAEIMQ<br>DFNTAPFQFLSDHRPVPAPRRRPIPSPRSTVSAPPVPKPRRTKYQQPPGV<br>ARAISEAELDEYIRQHSNRYEAGAYIFSSETGQGHLQQKSVRQCKLQEP<br>ILDRAVHEKYYAPRLDLEREKMLQKKLQLCASEGNRSRYQSRKVENM<br>KAITAERLISGLGTYLSSEVNPVECYRVNYPVPIYSSTVINRFTSAEVAV<br>KTCNLVIQENYPTVASYCITDEYDAYLDMVDGASCCLDTATFCPAKLR<br>SYPKKHSYLQPEIRSAVPSPIQNTLQVNVLAAATKRNCNVTQMRELPVL<br>DSAAFNVDCFKKYACNDEYWDTFRDNPIRLTTENVTQYVTKLKGPKA<br>AALFAKTHNLKPLQEIPMDQFVMDLKRDVKVTPGTKHTEERPKVQVI<br>QAADPLATAYLCGIHRELVRRLNAVLLPNIHTLFDMSAEDFDAIIAGHF<br>HHGDPVLETDIASPDKSEDDAIAISAMMILEDLGVDQPLLDLIEAAFGNI<br>TSVHLPTGTRFKFGAMMKSGMFLTLFVNTLVNIMIASRVLRERLTTSA<br>CAAFIGDDNIVHGVVSDTLMAERCATWLNMEVKIIDAVIGIKAPYFCG<br>GFILVDQITGTACRVADPLKRLFKLGKPLSVEDTQDCDRRRALHDEAM<br>RWNRIGITDELVKAVESRYEIILAGLIITSLSTLAESVKNFKSIRGSPITLY<br>G |
| SEQ ID NO: 48 | MEGDGSDPEPPDAGEDSKSENGENAPIYCICRKPDINCFMIGCDNCNE<br>WFHGDCIRITEKMAKAIREWYCRECREKDPKLEIRYRHKKSRERDGNE<br>RDSSEPRDEGGGRKRPVPDPNLQRRAGSGTGVGAMLARGSASPHKSS<br>PQPLVATPSQHHQQQQQIKRSARMCGECEACRRTEDCGHCDFCRDM<br>KKFGGPNKIRQKCRLRQCQLRARESYKYFPSSLSPVTPSESLPRPRRPLP<br>TQQQPQPSQKLGRIREDEGAVASSTVKEPPEATATPEPLSDEDLPLDPD<br>LYQDFCAGAFDDNGLPWMSDTEESPFLDPALRKRAVKVKHVKRREK<br>KSEKKKEERYKRHRQKQHKDKWKHPERADAKDPASLPQCLGPGCV<br>RPAQPSSKYCSDDCGMKLAANRIYEILPQRIQQWQQSPCIAEEHGKKL<br>LERIRREQQSARTRLQEMERRFHELEAHLRAKQQAVREDEESNEGDSD<br>DTDLQIFCVSCGHPINPRVALRHMERCYAKYESQTSFGSMYPTRIEGAT<br>RLFCDVYNPQSKTYCKRLQVLCPEHSRDPKVPADEVCGCPLVRDVFEL<br>TGDPFCRLPKRQCNRHYCWEKLRRAEVDLERVRVWYKLDELFEQERN<br>VRTAMTNRAGLLALMLHQTIQHDPLTTDLRSSADR |

What is claimed is:

1. A composition comprising a replication defective adenovirus 5 (Ad5) vector wherein the Ad5 vector comprises an E1 gene region deletion and E2b gene region deletion, and wherein the Ad5 vector further comprises a sequence encoding an antigen, wherein the antigen has at least 85% sequence identity to SEQ ID NO:2 or SEQ ID NO:5.

2. The composition of claim 1, wherein the antigen is SEQ ID NO:2.

3. The composition of claim 1, wherein the sequence encoding the antigen comprises a plurality of gene inserts each corresponding to a target antigen, wherein each gene insert is separated by a nucleic acid sequence encoding a self-cleaving 2A peptide.

4. The composition of claim 3, wherein the self-cleaving 2A peptide is a *Porcine teschovirus*-1 2A peptide or a *Thosea asigna* virus 2A peptide.

5. The composition of claim 1, wherein the replication defective Ad5 vector further comprises a deletion in an E3 gene region, E4 gene region, or any combination thereof.

6. The composition of claim 1, wherein the replication defective Ad5 vector further comprises an element to increase an expression of the alphavirus target antigen, wherein the element comprises an internal ribosome binding site, a constitutive promoter, and inducible promoter, a transcription enhancer or combinations thereof.

7. The composition of claim 1, wherein the replication defective Ad5 vector further comprises a nucleic acid sequence encoding a protein that increases alphavirus target antigen immunogenicity wherein the sequence is SEQ ID NO: 71.

8. The composition of claim 1, wherein the composition or the replication defective Ad5 vector further comprises a sequence encoding a costimulatory molecule or an immunological fusion partner.

9. A pharmaceutical composition comprising the composition of claim 1 and a pharmaceutically acceptable carrier.

10. An isolated cell comprising the composition according to the pharmaceutical composition of claim 9.

11. The cell of claim 10, wherein the cell is a dendritic cell (DC).

12. A method of generating an immune response against an alphavirus target antigen in a subject, comprising: administering to the subject a composition according to claim 1.

13. A method of preventing a Chikungunya virus infection in a subject, the method comprising administering to the subject a composition comprising the composition of claim 1.

14. The method of claim 13, wherein the subject has preexisting immunity to an adenovirus or an adenovirus vector.

15. The method of claim 13, wherein the administering to the subject comprises $1\times10^9$ to $5\times10^{12}$ virus particles per dose.

16. The composition of claim 6, wherein the transcription enhancer is a Rous sarcoma virus (RSV) enhancer.

17. The composition of claim 6, wherein the element does not contain a palindromic sequence.

* * * * *

SEQUENCE LISTING

<160> NUMBER OF SEQ ID NOS: 119

<210> SEQ ID NO 1
<211> LENGTH: 11826
<212> TYPE: DNA
<213> ORGANISM: Chikungunya virus

<400> SEQUENCE: 1

```
atggctgcgt gagacacacg tagcctacca gtttcttact gctctactct gcaaagcaag      60
agattaagaa cccatcatgg atcctgtgta cgtggacata gacgctgaca gcgcctttt     120
gaaggccctg caacgtgcgt accccatgtt tgaggtggaa cctaggcagg tcacaccgaa    180
tgaccatgct aatgctagag cgttctcgca tctagctata aaactaatag agcaggaaat    240
tgatcccgac tcaaccatcc tggatattgg tagtgcgcca gcaaggagga tgatgtcgga    300
caggaagtac cactgcgttt gcccgatgcg cagtgcagaa gatcccgaga gactcgccaa    360
ttatgcgaga aagctagcat ctgccgcagg aaaagtcctg gacagaaaca tctctggaaa    420
gatcgggga ttacaagcag taatggccgt gccagacacg agacgccaa cattctgctt    480
acacacagat gtatcatgta cagagagagc agacgtcgcg ataaccaag acgtctatgc    540
tgtacacgca cccacgtcgc tataccacca ggcgattaaa ggggtccgat ggcgtactg    600
```

```
ggtagggttt gacacaaccc cgttcatgta caatgccatg gcgggtgcct acccctcata    660
ctcgacaaat tgggcagatg agcaggtact gaaggctaag aacataggat tatgttcaac    720
agacctgacg gaaggtagac gaggcaaatt gtctattatg agaggaaaaa agctagaacc    780
gtgcgaccgt gtgctgttct cagtagggtc aacgctctac ccggaaagcc gtaagctact    840
taagagctgg cacctaccat cggtgttcca tttaaagggc aagctcagct tcacatgccg    900
ctgtgataca gtggtttcgt gcgaaggcta cgtcgttaag agaataacga tgagcccagg    960
cctttacgga aaaccacagg gtatgcggt aacccaccac gcagacggat tcctgatgtg    1020
caagaccacc gacacggttg acggcgaaag agtgtcattc tcggtgtgca cgtacgtgcc    1080
ggcgaccatt tgtgatcaaa tgaccggcat ccttgctaca gaagtcacgc cggaggatgc    1140
acagaagctg ttggtggggc tgaaccagag aatagtggtt aacggcagaa cgcaacggaa    1200
tacgaacacc atgaaaaact atatgattcc cgtggtcgcc caagccttca gtaagtgggc    1260
aaaggagtgc cggaaagaca tggaagatga aaaactcctg ggggtcagag aaagaacact    1320
gacctgctgc tgtctatggg catttaagaa gcagaaaaca cacacggtct acaagaggcc    1380
tgatacccag tcaattcaga aggttcaggc cgagtttgac agctttgtgg taccgagcct    1440
gtggtcgtcc gggttgtcaa tcccgttgag gactagaatc aaatggttgt taagcaaggt    1500
gccaaaaacc gacctgaccc catacagcgg ggacgcccaa gaagcccggg acgcagaaaa    1560
agaagcagag gaagaacgag aagcagaact gactcttgaa gccctaccac cccttcaggc    1620
agcacaggaa gatgttcagg tcgaaatcga cgtggaacag cttgaggaca gagcgggtgc    1680
aggaataata gagactccga gaggagctat caaagttact gcccaaccaa cagaccacgt    1740
cgtgggagag tacttggttc ttttccccgca gaccgtacta cgtagccaaa agcttagcct    1800
gattcacgct ttggcggagc aagtgaagac gtgcacgcac agcggacgag cagggaggta    1860
tgcggtcgaa gcgtacgacg gcagagtcct agtgccctca ggctacgcaa tctcgcctga    1920
agacttccag agcctaagcg aaagcgcaac gatggtgtac aacgaaagag agttcgtaaa    1980
cagaaagcta caccatattg cgatgcatgg accagccctg aacaccgacg aagagtcgta    2040
tgagctggtg agggcagaga ggacagaaca cgagtacgtc tacgacgtgg accagagaag    2100
atgctgtaag aaggaagaag ctgcaggact ggtactggtg ggcgacttga ctaatccgcc    2160
ctaccacgaa ttcgcatatg aagggctaaa aatccgccct gcctgcccat acaaaattgc    2220
agtcatagga gtcttcggag taccaggatc tggcaagtca gctattatca agaacctagt    2280
taccaggcaa gacctggtga ctagcggaaa gaaagaaaac tgccaagaaa tcaccaccga    2340
cgtgatgaga cagagaggtc tagagatatc tgcacgtacg gttgactcgc tgctcttgaa    2400
tggatgtaac agaccagtcg acgtgttgta cgtagacgag gcgtttgcgt gccactctgg    2460
aacgttactt gcattgatcg ccttggtgag accaagacag aaagttgtac tttgtggtga    2520
cccgaagcag tgcggcttct tcaatatgat gcagatgaaa gtcaactata atcacaacat    2580
ctgcacccaa gtgtaccaca aaagtatctc caggcggtgt acactgcctg tgactgccat    2640
tgtgtcatcg ttgcattacg aaggcaaaat gcgcactacg aatgagtaca acaagccgat    2700
tgtagtggac actacaggct caacaaaacc tgaccctgga gatctcgtgt taacgtgctt    2760
cagaggatgg gttaaacaac tgcaaattga ctatcgtgga cacgaggtca tgacagcagc    2820
cgcatcccaa gggttaacca gaaaggagt ttacgcagtt aggcaaaaag ttaacgaaaa    2880 cccgcttat gcatcaacgt cagagcacgt caacgtactc ctaacgcgta cggaaggtaa    2940
actggtatgg aagacactct ccggtgaccc gtggataaag acgctgcaga acccaccgaa    3000
```

```
aggaaacttc aaagcaacta ttaaggagtg ggaggtggag catgcatcaa taatggcggg   3060
catctgcagt caccaaatga cctttgatac attccaaaac aaagccaacg tttgttgggc   3120
taagagtttg gtccctatcc tcgaaacagc ggggataaaa ctaaacgaca ggcagtggtc   3180
ccagataatt caagccttca aagaagacaa agcatattca cccgaagtag ccctgaatga   3240
aatatgcacg cgcatgtatg gggtggatct agacagcggg ctattttcta aaccgttggt   3300
gtctgtgtat tacgcggata accactggga taataggcct ggagggaaga tgttcggatt   3360
caaccccgag gcagcatcca ttctagaaag aaagtatcca tttacaaaag ggaagtggaa   3420
catcaacaag cagatctgcg tgactaccag gaggatagaa gacttcaacc ctaccaccaa   3480
cattataccg gccaacagga gactaccaca ctcattagtg gccgaacacc gcccagtaaa   3540
aggggaaaga atggaatggc tggttaacaa gataaacggc caccacgtgc tcctggtcag   3600
tggctgtagc cttgcactgc ctactaagag agtcacttgg gtagcgccac taggtgtccg   3660
cggagcggac tatacataca acctagagtt gggtctgcca gcaacgcttg gtaggtatga   3720
cctagtggtc ataaacatcc acacaccttt tcgcatacac cattatcaac agtgcgtaga   3780
ccacgcaatg aaaactgcaa atgctcgggg tgactcattg agactgctca aaccgggtgg   3840
ctctctattg atcagagcat atggttacgc agatagaacc agtgaacgag tcatctgcgt   3900
attgggacgc aagtttagat catctagagc gttgaaacca ccatgtgtca ccagcaacac   3960
tgagatgttt tttctattca gcaactttga caatggcaga aggaatttca caactcatgt   4020
catgaacaat caactgaatg cagcctttgt aggacaggcc acccgagcag gatgtgcacc   4080
gtcgtaccgg gtaaaacgca tggatatcgc gaagaacgat gaagagtgcg tagtcaacgc   4140
cgccaaccct cgcgggttac caggtgacgg tgtttgcaag gcagtataca aaaatggcc   4200 ggagtccttt aagaacagtg caacaccagt gggaaccgca aaaacagtca tgtgcggtac   4260
gtatccagta atccacgccg ttggaccaaa cttctctaat tattcggagt ctgaagggga   4320
ccgagaattg gcggctgcct atcgagaagt cgcaaaggag gtaactagac tgggagtaaa   4380
tagtgtagct atacctctcc tctccacagg tgtatactca ggagggaaag acaggctgac   4440
ccagtcactg aaccacctct ttacagccat ggactcgacg gatgcagacg tggtcatcta   4500
ctgccgcgac aaagaatggg agaagaaaat atctgaggcc atacagatgc ggacccaagt   4560
ggagctgctg gatgagcaca tctccataga ctgcgatgtt gttcgcgtgc accctgacag   4620
cagcttggca ggcagaaaag gatacagcac cacggaaggc gcactgtact catatctaga   4680
agggacccgt tttcaccaaa cggcagtgga tatggcagag atatatacta tgtggccaaa   4740
gcaaacagag gccaacgagc aagtttgcct atatgccctg ggggaaagta ttgaatcgat   4800
caggcagaaa tgcccggtgg atgatgcaga tgcatcatct cccccgaaaa ctgtcccgtg   4860
cctctgccgt tacgccatga caccagaacg cgttacccga cttcgcatga accatgtcac   4920
aagcataatt gtgtgttctt cgtttccact tccaaagtac aaaatagaag gagtgcaaaa   4980
agtcaaatgc tccaaggtaa tgctatttga ccacaacgtg ccatcgcgcg taagtccaag   5040
ggaatacaga ccttcccagg agtctgtaca ggaagcgagt acgaccacgt cactgacgca   5100
tagccaattc gatctaagcg ttgacggcaa gatactgccc gtcccgtcag acctggatgc   5160
tgacgcccca gccctagaac cagcccttga cgacggggcg atacacacgt tgccatctgc   5220
aaccggaaac cttgcggccg tgtctgactg ggtaatgagc accgtacctg tcgcgccgcc   5280
cagaagaagg cgagggagaa acctgactgt gacatgcgac gagagagaag ggaatataac   5340
```

```
acccatggct agcgtccgat tctttagggc agagctgtgt ccagtcgtac aagaaacagc      5400
ggagacgcgt gacacagcta tgtctcttca ggcaccgccg agtaccgcca cggaactgag      5460
tcacccgccg atctccttcg gtgcaccaag cgagacgttc cccatcacat ttggggactt      5520
caacgaagga gaaatcgaaa gcttgtcttc tgagctacta actttcggag acttcctacc      5580
cggagaagtg gatgatttga cagatagcga ctggtccacg tgctcagaca cggacgacga      5640
gttacgacta gacagggcag gtgggtatat attctcgtcg acactggtc caggtcattt       5700 acaacagaag tcagtacgcc agtcagtgct gccggtgaac accctggagg aagtccacga      5760
ggagaagtgt tacccaccta agctggatga agcaaaggag caactactac ttaagaaact      5820
ccaggagagt gcatccatgg ccaacagaag caggtatcag tcgcgcaaag tagaaaacat      5880
gaaagcaaca atcatccaga gactaaagag aggctgtaga ttatacttaa tgtcagagac      5940
cccaaaagtc cctacctacc ggaccacata tccggcgcct gtgtactcgc ctccgattaa      6000
cgtccgactg tccaacccg agtccgcagt ggcagcatgc aatgagttct tggctagaaa       6060
ctatccaact gtttcatcat accaaatcac cgacgagtat gatgcatatc tagacatggt      6120
ggacgggtcg gagagttgtc tggaccgagc gacattcaat ccgtcaaaac ttaggagcta      6180
cccaaaacag cacgcttacc acgcgccctc catcagaagc gctgtaccgt ccccattcca      6240
gaacacacta cagaatgtac tggcagcagc cacgaaaaga aactgcaacg tcacacagat      6300
gagggaatta cccactttgg actcagcagt attcaacgtg gagtgtttca aaaaattcgc      6360
atgcaaccaa gaatactggg aagaatttgc tgccagccct atcaggataa caactgagaa      6420
tttaacaacc tatgttacta aactaaaggg gccaaaagca gcagcgctat ttgcaaaaac      6480
ccataatctg ctgccactgc aggaagtgcc aatggatagg ttcacagtag acatgaaaag      6540
ggatgtgaag gtgactcctg gtacaaagca cacagaggaa agacctaagg tacaggttat      6600
acaggcggct gaaccttgg caacagcata cctatgtggg attcacagag agctggttag       6660 gagggctgaac gccgtcctcc tacccaatgt acatacacta tttgacatgt ctgccgagga     6720
tttcgatgcc atcatagccg cacactttaa gccaggagac actgttttag aaacggacat      6780
agcctccttt gataagagcc aagatgattc acttgcgctt actgctttaa tgctgttaga      6840
ggattagggg gtggatcact ccctgttgga cttgatagag gctgctttcg gagagatttc      6900
cagctgtcat ctaccgacag gtacgcgctt caagttcggc gccatgatga aatctggtat      6960
gttcctaact ctgttcgtca acacactgct aaatatcacc atcgccagcc gagtgctgga      7020
agatcgtctg acaaaatccg cgtgcgcagc cttcatcggc gacgacaaca atacatgg       7080 agtcgtctcc gatgaattga tggcagccag atgcgccact tggatgaaca tggaagtgaa      7140
gatcatagat gcagttgtat cccagaaagc ccctacttt tgtggagggt ttatactgca       7200
cgatatcgtg acaggaacag cttgcagagt ggcagacccg ctaaaaaggc tatttaaact      7260
gggcaaaccg ctagcggcag gtgacgaaca agatgaggat agaagacgag cgctggctga     7320
cgaagtggtc agatggcaac gaacagggct aattgatgag ttggagaaag cggtatactc      7380
taggtatgaa gtgcagggta tatcagttgt ggtaatgtcc atggccacct ttgcaagctc      7440
cagatccaac ttcgagaagc tcagaggacc cgtcgtaact ttgtacgcg gtcctaaata       7500 ggtacgcact acagctacct attttgcaga agccgacagt aagtacctaa acactaatca      7560
gctacaatgg agttcatccc aacccaaaact ttttacaaca ggaggtacca gcctcgaccc     7620
tggactccgc gccctactat ccaagtcatc aggcccagac cgcgcccgca gaggcaagct      7680
gggcaacttg cccagctgat ctcagcagtt aataaactga caatgcgcgc ggtaccccaa      7740
```

```
cagaagccac gcaagaatcg gaagaataag aagcaaaagc aaaagcagca ggcgccacaa   7800
aacaacacaa accaaaagaa gcagccacct aaaaagaaac cagctcaaaa gaaaagaag    7860 ccgggccgca gagagaggat gtgcatgaaa atcgaaaatg actgtatttt cgaagtcaag   7920
cacgaaggta aggtaacagg ttacgcgtgc ttggtggggg acaaagtaat gaaaccagca   7980
cacgtaaagg ggaccatcga taacgcggac ctggccaaat tggcctttaa gcggtcatct   8040
aagtacgacc ttgaatgcgc gcagataccc gtgcacatga agtccgacgc ttcgaagttc   8100
acccatgaga aaccggaggg gtactacaac tggcaccacg gagcagtaca gtactcagga   8160
ggccggttca ccatccctac aggtgcgggc aaaccagggg acagcggtag accgatcttc   8220
gacaacaagg gacgcgtggt ggccatagtc ttaggaggag ctaatgaagg agcccgtaca   8280
gccctctcag tggtgacctg gaataaagac attgtcacta aaatcacccc tgagggagcc   8340
gaagagtgga gtcttgccat cccagttatg tgcctgttgg caaataccac gttcccctgc   8400
tcccagcccc cttgcatacc ctgctgctac gaaaaggaac cggaggaaac cctacgcatg   8460
cttgaggaca acgtcatgag acctgggtac tatcagctgc tacaagcatc attaacatgt   8520
tctccccacc gccagcgacg cagcaccaag gacaacttca atgtctataa agccacaaga   8580
ccatacctag ctcactgtcc cgactgtgga gaagggcact cgtgccatag tcccgtagca   8640
ctagaacgca tcagaaatga agcgacagac gggacgctga aaatccaggt ctccttgcaa   8700
attggaatag ggacggatga tagccatgat tggaccaagc tgcgttacat ggacaatcac   8760
ataccagcag acgcagggag ggccgggcta tttgtaagaa catcagcacc atgcacgatt   8820
actggaacaa tgggacactt catcctggcc cgatgtccga aaggagaaac tctgacggtg   8880
ggattcactg acagtaggaa gattagtcac tcatgtacgc acccatttca ccacgaccct   8940
cctgtgatag gccgggaaaa attccattcc cgaccgcagc acggtaaaga gctaccttgc   9000
agcacgtacg tgcagagcaa cgccgcaact gccgaggaga tagaggtaca catgcccca    9060 gacacccctg atcgcacatt gctgtcacaa cagtccggca acgtaaagat cacagtcaat   9120
agtcagacgg tgcggtataa gtgtaattgc ggtggctcaa atgaaggact aataactaca   9180
gataaagtga ttaataactg caaggttgat caatgtcatg ccgcggtcac caatcacaaa   9240
aagtggcagt ataactcccc tctggtcccg cgtaacgctg aactcgggga ccgaaaagga   9300
aaaattcaca tcccgtttcc gctggcaaat gtaacatgca tggtgcctaa agcaaggaac   9360
cccaccgtga cgtacgggaa aaaccaagtc atcatgctac tgtatcctga ccacccaaca   9420
ctcctgtcct accggagtat gggagaagaa ccaaactatc aagaagagtg ggtgacgcac   9480
aagaaggagg tcgtgctaac cgtgccgact gaagggctcg aggttacgtg gggcaacaac   9540
gagccgtata agtattggcc gcagttatct gcaaacggta cagcccacgg ccacccgcat   9600
gagataatct tgtactatta tgagctgtac cctactatga ctgtagtagt tgtgtcagtg   9660
gcctcgttca tactcctgtc gatggtgggt atggcagtgg ggatgtgcat gtgtgcacga   9720
cgcagatgca tcacaccata cgaactgaca ccaggagcta ccgtcccttt cctgcttagc   9780
ctaatatgct gcatcagaac agctaaagcg gccacatacc aagaggctgc ggtatacctg   9840
tggaacgagc agcaaccttt gttttggcta caagccctta ttccgctggc agccctgatt   9900
gtcctatgca actgtctgag actcttacca tgctgttgta aaacgttggc tttttagcc    9960 gtaatgagca tcggtgccca cactgtgagc gcgtacgaac acgtaacagt gatcccgaac  10020
acggtgggag taccgtataa gactctagtc aacagaccgg gctacagccc catggtactg  10080
```

-continued

```
gagatggagc tactgtcagt cactttggag ccaacgctat cgcttgatta catcacgtgc    10140
gaatacaaaa ccgtcatccc gtctccgtac gtgaaatgct gcggtacagc agagtgcaag    10200
gacaaaaacc tacctgacta cagctgtaag gtcttcaccg gcgtctaccc atttatgtgg    10260
ggcggcgcct actgcttctg cgacgctgaa aacacgcaat tgagcgaagc acatgtggag    10320
aagtccgaat catgcaaaac agaatttgca tcagcataca gggctcatac cgcatccgca    10380
tcagctaagc tccgcgtcct ttaccaagga ataacatca ctgtaactgc ctatgcaaac     10440
ggcgaccatg ccgtcacagt taaggacgcc aaattcattg tggggccaat gtcttcagcc    10500
tggacacctt ttgacaacaa atcgtggtg tacaaaggtg acgtttacaa catggactac     10560 ccgcccttg gcgcaggaag accaggacaa tttggcgata tccaaagtcg cacgcctgag     10620
agcaaagacg tctatgctaa cacacaactg gtactgcaga gaccggctgc gggtacggta    10680
cacgtgccat actctcaggc accatctggc tttaagtatt ggttaaaaga acgaggggcg    10740
tcgctacagc acacagcacc atttggctgc caaatagcaa caaacccggt aagagcgatg    10800
aactgcgccg tagggaacat gcccatctcc atcgacatac cggatgcggc cttcactagg    10860
gtcgtcgacg cgccctcttt aacggacatg tcatgcgagg taccagcctg cacccattcc    10920
tcagactttg ggggcgtcgc cattattaaa tatgcagtca gcaagaaagg caagtgtgcg    10980
gtgcattcga tgaccaacgc cgtcactatc cgggaagctg agatagaagt tgaagggaat    11040
tctcagctgc aaatctcttt ctcgacggcc ttggccagcg ccgaattccg cgtacaagtc    11100
tgttctacac aagtacactg tgcagccgag tgccacccct cgaaggacca catagtcaac    11160
tacccggcgt cacataccac cctcgggggtc caggacattt ccgctacggc gatgtcatgg    11220
gtgcagaaga tcacgggagg tgtgggactg gttgtcgctg ttgcagcact gattctaatc    11280
gtggtgctat gcgtgtcgtt cagcaggcac taacttgacg actaagcatg aaggtatatg    11340 tgtccctaa gagacacacc gtatatagct aataatctgt agatcaaagg ctatataac     11400 ccctgaatag taacaaaata caaaatcact aaaaattata aaaaaaaaa aaaaaaaca     11460 gaaaaatata taaataggta tacgtgtccc ctaagagaca cattgtatgt aggtgataag    11520
tatagatcaa agggccgaac aaccccctgaa tagtaacaaa atataaaaat taataaaaat    11580
cataaaatag aaaaaccata aacagaagta gttcaaaggg ctataaaaac ccctgaatag    11640
taacaaaaca taaaactaat aaaaatcaaa tgaataccat aattggcaaa cggaagagat    11700
gtaggtactt aagcttccta aaagcagccg aactcacttt gagatgtagg catagcatac    11760
cgaactcttc cacgattctc cgaacccaca gggacgtagg agatgttatt ttgttttaa     11820 tatttc                                                              11826
```

<210> SEQ ID NO 2
<211> LENGTH: 1248
<212> TYPE: PRT
<213> ORGANISM: Chikungunya virus

<400> SEQUENCE: 2

```
Met Glu Phe Ile Pro Thr Gln Thr Phe Tyr Asn Arg Arg Tyr Gln Pro
1               5                   10                  15

Arg Pro Trp Thr Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Lys Asn
    50                  55                  60
```

```
Arg Lys Asn Lys Lys Gln Lys Gln Lys Gln Gln Ala Pro Gln Asn Asn
65                  70                  75                  80

Thr Asn Gln Lys Lys Gln Pro Pro Lys Lys Pro Ala Gln Lys Lys
            85                  90                  95

Lys Lys Pro Gly Arg Arg Glu Arg Met Cys Met Lys Ile Glu Asn Asp
                100                 105                 110

Cys Ile Phe Glu Val Lys His Glu Gly Lys Val Thr Gly Tyr Ala Cys
            115                 120                 125

Leu Val Gly Asp Lys Val Met Lys Pro Ala His Val Lys Gly Thr Ile
130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
            195                 200                 205

Lys Pro Gly Asp Ser Gly Arg Pro Ile Phe Asp Asn Lys Gly Arg Val
210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Ile Pro Val Met Cys Leu Leu Ala
            260                 265                 270

Asn Thr Thr Phe Pro Cys Ser Gln Pro Pro Cys Ile Pro Cys Cys Tyr
            275                 280                 285

Glu Lys Glu Pro Glu Glu Thr Leu Arg Met Leu Glu Asp Asn Val Met
290                 295                 300

Arg Pro Gly Tyr Tyr Gln Leu Leu Gln Ala Ser Leu Thr Cys Ser Pro
305                 310                 315                 320

His Arg Gln Arg Arg Ser Thr Lys Asp Asn Phe Asn Val Tyr Lys Ala
                325                 330                 335

Thr Arg Pro Tyr Leu Ala His Cys Pro Asp Cys Gly Glu Gly His Ser
            340                 345                 350

Cys His Ser Pro Val Ala Leu Glu Arg Ile Arg Asn Glu Ala Thr Asp
            355                 360                 365

Gly Thr Leu Lys Ile Gln Val Ser Leu Gln Ile Gly Ile Gly Thr Asp
            370                 375                 380

Asp Ser His Asp Trp Thr Lys Leu Arg Tyr Met Asp Asn His Ile Pro
385                 390                 395                 400

Ala Asp Ala Gly Arg Ala Gly Leu Phe Val Arg Thr Ser Ala Pro Cys
                405                 410                 415

Thr Ile Thr Gly Thr Met Gly His Phe Ile Leu Ala Arg Cys Pro Lys
            420                 425                 430

Gly Glu Thr Leu Thr Val Gly Phe Thr Asp Ser Arg Lys Ile Ser His
            435                 440                 445

Ser Cys Thr His Pro Phe His His Asp Pro Pro Val Ile Gly Arg Glu
450                 455                 460

Lys Phe His Ser Arg Pro Gln His Gly Lys Glu Leu Pro Cys Ser Thr
465                 470                 475                 480
```

Tyr Val Gln Ser Asn Ala Ala Thr Ala Glu Glu Ile Glu Val His Met
              485                 490                 495

Pro Pro Asp Thr Pro Asp Arg Thr Leu Leu Ser Gln Gln Ser Gly Asn
            500                 505                 510

Val Lys Ile Thr Val Asn Ser Gln Thr Val Arg Tyr Lys Cys Asn Cys
            515                 520                 525

Gly Gly Ser Asn Glu Gly Leu Ile Thr Thr Asp Lys Val Ile Asn Asn
            530                 535                 540

Cys Lys Val Asp Gln Cys His Ala Ala Val Thr Asn His Lys Lys Trp
545                 550                 555                 560

Gln Tyr Asn Ser Pro Leu Val Pro Arg Asn Ala Glu Leu Gly Asp Arg
                565                 570                 575

Lys Gly Lys Ile His Ile Pro Phe Pro Leu Ala Asn Val Thr Cys Met
            580                 585                 590

Val Pro Lys Ala Arg Asn Pro Thr Val Thr Tyr Gly Lys Asn Gln Val
        595                 600                 605

Ile Met Leu Leu Tyr Pro Asp His Pro Thr Leu Leu Ser Tyr Arg Ser
    610                 615                 620

Met Gly Glu Glu Pro Asn Tyr Gln Glu Glu Trp Val Thr His Lys Lys
625                 630                 635                 640

Glu Val Val Leu Thr Val Pro Thr Glu Gly Leu Glu Val Thr Trp Gly
                645                 650                 655

Asn Asn Glu Pro Tyr Lys Tyr Trp Pro Gln Leu Ser Ala Asn Gly Thr
            660                 665                 670

Ala His Gly His Pro His Glu Ile Ile Leu Tyr Tyr Tyr Glu Leu Tyr
            675                 680                 685

Pro Thr Met Thr Val Val Val Ser Val Ala Ser Phe Ile Leu Leu
    690                 695                 700

Ser Met Val Gly Met Ala Val Gly Met Cys Met Cys Ala Arg Arg Arg
705                 710                 715                 720

Cys Ile Thr Pro Tyr Glu Leu Thr Pro Gly Ala Thr Val Pro Phe Leu
                725                 730                 735

Leu Ser Leu Ile Cys Cys Ile Arg Thr Ala Lys Ala Ala Thr Tyr Gln
            740                 745                 750

Glu Ala Ala Val Tyr Leu Trp Asn Glu Gln Gln Pro Leu Phe Trp Leu
            755                 760                 765

Gln Ala Leu Ile Pro Leu Ala Ala Leu Ile Val Leu Cys Asn Cys Leu
    770                 775                 780

Arg Leu Leu Pro Cys Cys Cys Lys Thr Leu Ala Phe Leu Ala Val Met
785                 790                 795                 800

Ser Ile Gly Ala His Thr Val Ser Ala Tyr Glu His Val Thr Val Ile
                805                 810                 815

Pro Asn Thr Val Gly Val Pro Tyr Lys Thr Leu Val Asn Arg Pro Gly
            820                 825                 830

Tyr Ser Pro Met Val Leu Glu Met Glu Leu Leu Ser Val Thr Leu Glu
            835                 840                 845

Pro Thr Leu Ser Leu Asp Tyr Ile Thr Cys Glu Tyr Lys Thr Val Ile
    850                 855                 860

Pro Ser Pro Tyr Val Lys Cys Cys Gly Thr Ala Glu Cys Lys Asp Lys
865                 870                 875                 880

Asn Leu Pro Asp Tyr Ser Cys Lys Val Phe Thr Gly Val Tyr Pro Phe
                885                 890                 895

Met Trp Gly Gly Ala Tyr Cys Phe Cys Asp Ala Glu Asn Thr Gln Leu

```
            900                 905                 910
Ser Glu Ala His Val Glu Lys Ser Glu Ser Cys Lys Thr Glu Phe Ala
            915                 920                 925

Ser Ala Tyr Arg Ala His Thr Ala Ser Ala Ser Ala Lys Leu Arg Val
            930                 935                 940

Leu Tyr Gln Gly Asn Asn Ile Thr Val Thr Ala Tyr Ala Asn Gly Asp
945                 950                 955                 960

His Ala Val Thr Val Lys Asp Ala Lys Phe Ile Val Gly Pro Met Ser
                965                 970                 975

Ser Ala Trp Thr Pro Phe Asp Asn Lys Ile Val Val Tyr Lys Gly Asp
            980                 985                 990

Val Tyr Asn Met Asp Tyr Pro Pro Phe Gly Ala Gly Arg Pro Gly Gln
            995                 1000                1005

Phe Gly Asp Ile Gln Ser Arg Thr Pro Glu Ser Lys Asp Val Tyr
    1010                1015                1020

Ala Asn Thr Gln Leu Val Leu Gln Arg Pro Ala Ala Gly Thr Val
    1025                1030                1035

His Val Pro Tyr Ser Gln Ala Pro Ser Gly Phe Lys Tyr Trp Leu
    1040                1045                1050

Lys Glu Arg Gly Ala Ser Leu Gln His Thr Ala Pro Phe Gly Cys
    1055                1060                1065

Gln Ile Ala Thr Asn Pro Val Arg Ala Met Asn Cys Ala Val Gly
    1070                1075                1080

Asn Met Pro Ile Ser Ile Asp Ile Pro Asp Ala Ala Phe Thr Arg
    1085                1090                1095

Val Val Asp Ala Pro Ser Leu Thr Asp Met Ser Cys Glu Val Pro
    1100                1105                1110

Ala Cys Thr His Ser Ser Asp Phe Gly Gly Val Ala Ile Ile Lys
    1115                1120                1125

Tyr Ala Val Ser Lys Lys Gly Lys Cys Ala Val His Ser Met Thr
    1130                1135                1140

Asn Ala Val Thr Ile Arg Glu Ala Glu Ile Glu Val Glu Gly Asn
    1145                1150                1155

Ser Gln Leu Gln Ile Ser Phe Ser Thr Ala Leu Ala Ser Ala Glu
    1160                1165                1170

Phe Arg Val Gln Val Cys Ser Thr Gln Val His Cys Ala Ala Glu
    1175                1180                1185

Cys His Pro Pro Lys Asp His Ile Val Asn Tyr Pro Ala Ser His
    1190                1195                1200

Thr Thr Leu Gly Val Gln Asp Ile Ser Ala Thr Ala Met Ser Trp
    1205                1210                1215

Val Gln Lys Ile Thr Gly Gly Val Gly Leu Val Val Ala Val Ala
    1220                1225                1230

Ala Leu Ile Leu Ile Val Val Leu Cys Val Ser Phe Ser Arg His
    1235                1240                1245

<210> SEQ ID NO 3
<211> LENGTH: 2474
<212> TYPE: PRT
<213> ORGANISM: Chikungunya virus

<400> SEQUENCE: 3

Met Asp Pro Val Tyr Val Asp Ile Asp Ala Asp Ser Ala Phe Leu Lys
1               5                   10                  15
```

-continued

```
Ala Leu Gln Arg Ala Tyr Pro Met Phe Glu Val Glu Pro Arg Gln Val
            20                  25                  30
Thr Pro Asn Asp His Ala Asn Ala Arg Ala Phe Ser His Leu Ala Ile
        35                  40                  45
Lys Leu Ile Glu Gln Glu Ile Asp Pro Asp Ser Thr Ile Leu Asp Ile
    50                  55                  60
Gly Ser Ala Pro Ala Arg Arg Met Met Ser Asp Arg Lys Tyr His Cys
65                  70                  75                  80
Val Cys Pro Met Arg Ser Ala Glu Asp Pro Glu Arg Leu Ala Asn Tyr
                85                  90                  95
Ala Arg Lys Leu Ala Ser Ala Ala Gly Lys Val Leu Asp Arg Asn Ile
            100                 105                 110
Ser Gly Lys Ile Gly Asp Leu Gln Ala Val Met Ala Val Pro Asp Thr
        115                 120                 125
Glu Thr Pro Thr Phe Cys Leu His Thr Asp Val Ser Cys Arg Gln Arg
    130                 135                 140
Ala Asp Val Ala Ile Tyr Gln Asp Val Tyr Ala Val His Ala Pro Thr
145                 150                 155                 160
Ser Leu Tyr His Gln Ala Ile Lys Gly Val Arg Leu Ala Tyr Trp Val
                165                 170                 175
Gly Phe Asp Thr Thr Pro Phe Met Tyr Asn Ala Met Ala Gly Ala Tyr
            180                 185                 190
Pro Ser Tyr Ser Thr Asn Trp Ala Asp Glu Gln Val Leu Lys Ala Lys
        195                 200                 205
Asn Ile Gly Leu Cys Ser Thr Asp Leu Thr Glu Gly Arg Arg Gly Lys
    210                 215                 220
Leu Ser Ile Met Arg Gly Lys Lys Leu Glu Pro Cys Asp Arg Val Leu
225                 230                 235                 240
Phe Ser Val Gly Ser Thr Leu Tyr Pro Glu Ser Arg Lys Leu Leu Lys
                245                 250                 255
Ser Trp His Leu Pro Ser Val Phe His Leu Lys Gly Lys Leu Ser Phe
            260                 265                 270
Thr Cys Arg Cys Asp Thr Val Val Ser Cys Glu Gly Tyr Val Val Lys
        275                 280                 285
Arg Ile Thr Met Ser Pro Gly Leu Tyr Gly Lys Thr Thr Gly Tyr Ala
    290                 295                 300
Val Thr His His Ala Asp Gly Phe Leu Met Cys Lys Thr Thr Asp Thr
305                 310                 315                 320
Val Asp Gly Glu Arg Val Ser Phe Ser Val Cys Thr Tyr Val Pro Ala
                325                 330                 335
Thr Ile Cys Asp Gln Met Thr Gly Ile Leu Ala Thr Glu Val Thr Pro
            340                 345                 350
Glu Asp Ala Gln Lys Leu Leu Val Gly Leu Asn Gln Arg Ile Val Val
        355                 360                 365
Asn Gly Arg Thr Gln Arg Asn Thr Asn Thr Met Lys Asn Tyr Met Ile
    370                 375                 380
Pro Val Val Ala Gln Ala Phe Ser Lys Trp Ala Lys Glu Cys Arg Lys
385                 390                 395                 400
Asp Met Glu Asp Glu Lys Leu Leu Gly Val Arg Glu Arg Thr Leu Thr
                405                 410                 415
Cys Cys Cys Leu Trp Ala Phe Lys Lys Gln Lys Thr His Thr Val Tyr
            420                 425                 430
Lys Arg Pro Asp Thr Gln Ser Ile Gln Lys Val Gln Ala Glu Phe Asp
```

```
                435                 440                 445
Ser Phe Val Pro Ser Leu Trp Ser Gly Leu Ser Ile Pro Leu
450                 455                 460

Arg Thr Arg Ile Lys Trp Leu Leu Ser Lys Val Pro Lys Thr Asp Leu
465                 470                 475                 480

Thr Pro Tyr Ser Gly Asp Ala Gln Glu Ala Arg Asp Ala Glu Lys Glu
                485                 490                 495

Ala Glu Glu Arg Glu Ala Glu Leu Thr Leu Glu Ala Leu Pro Pro
            500                 505                 510

Leu Gln Ala Ala Gln Glu Asp Val Gln Val Glu Ile Asp Val Glu Gln
            515                 520                 525

Leu Glu Asp Arg Ala Gly Ala Gly Ile Ile Glu Thr Pro Arg Gly Ala
530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Ser Gly Arg Ala
            580                 585                 590

Gly Arg Tyr Ala Val Glu Ala Tyr Asp Gly Arg Val Leu Val Pro Ser
            595                 600                 605

Gly Tyr Ala Ile Ser Pro Glu Asp Phe Gln Ser Leu Ser Glu Ser Ala
610                 615                 620

Thr Met Val Tyr Asn Glu Arg Glu Phe Val Asn Arg Lys Leu His His
625                 630                 635                 640

Ile Ala Met His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670

Gln Arg Arg Cys Cys Lys Lys Glu Ala Ala Gly Leu Val Leu Val
            675                 680                 685

Gly Asp Leu Thr Asn Pro Pro Tyr His Glu Phe Ala Tyr Glu Gly Leu
690                 695                 700

Lys Ile Arg Pro Ala Cys Pro Tyr Lys Ile Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
            740                 745                 750

Thr Thr Asp Val Met Arg Gln Arg Gly Leu Glu Ile Ser Ala Arg Thr
            755                 760                 765

Val Asp Ser Leu Leu Leu Asn Gly Cys Asn Arg Pro Val Asp Val Leu
770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
            820                 825                 830

His Asn Ile Cys Thr Gln Val Tyr His Lys Ser Ile Ser Arg Arg Cys
            835                 840                 845

Thr Leu Pro Val Thr Ala Ile Val Ser Ser Leu His Tyr Glu Gly Lys
850                 855                 860
```

```
Met Arg Thr Thr Asn Glu Tyr Asn Lys Pro Ile Val Asp Thr Thr
865                 870                 875                 880

Gly Ser Thr Lys Pro Asp Pro Gly Asp Leu Val Leu Thr Cys Phe Arg
            885                 890                 895

Gly Trp Val Lys Gln Leu Gln Ile Asp Tyr Arg Gly His Glu Val Met
                900                 905                 910

Thr Ala Ala Ala Ser Gln Gly Leu Thr Arg Lys Gly Val Tyr Ala Val
            915                 920                 925

Arg Gln Lys Val Asn Glu Asn Pro Leu Tyr Ala Ser Thr Ser Glu His
            930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
            980                 985                 990

Met Ala Gly Ile Cys Ser His Gln Met Thr Phe Asp Thr Phe Gln Asn
            995                 1000                1005

Lys Ala Asn Val Cys Trp Ala Lys Ser Leu Val Pro Ile Leu Glu
1010                1015                1020

Thr Ala Gly Ile Lys Leu Asn Asp Arg Gln Trp Ser Gln Ile Ile
1025                1030                1035

Gln Ala Phe Lys Glu Asp Lys Ala Tyr Ser Pro Glu Val Ala Leu
1040                1045                1050

Asn Glu Ile Cys Thr Arg Met Tyr Gly Val Asp Leu Asp Ser Gly
1055                1060                1065

Leu Phe Ser Lys Pro Leu Val Ser Val Tyr Tyr Ala Asp Asn His
1070                1075                1080

Trp Asp Asn Arg Pro Gly Gly Lys Met Phe Gly Phe Asn Pro Glu
1085                1090                1095

Ala Ala Ser Ile Leu Glu Arg Lys Tyr Pro Phe Thr Lys Gly Lys
1100                1105                1110

Trp Asn Ile Asn Lys Gln Ile Cys Val Thr Thr Arg Arg Ile Glu
1115                1120                1125

Asp Phe Asn Pro Thr Thr Asn Ile Ile Pro Ala Asn Arg Arg Leu
1130                1135                1140

Pro His Ser Leu Val Ala Glu His Arg Pro Val Lys Gly Glu Arg
1145                1150                1155

Met Glu Trp Leu Val Asn Lys Ile Asn Gly His His Val Leu Leu
1160                1165                1170

Val Ser Gly Cys Ser Leu Ala Leu Pro Thr Lys Arg Val Thr Trp
1175                1180                1185

Val Ala Pro Leu Gly Val Arg Gly Ala Asp Tyr Thr Tyr Asn Leu
1190                1195                1200

Glu Leu Gly Leu Pro Ala Thr Leu Gly Arg Tyr Asp Leu Val Val
1205                1210                1215

Ile Asn Ile His Thr Pro Phe Arg Ile His His Tyr Gln Gln Cys
1220                1225                1230

Val Asp His Ala Met Lys Leu Gln Met Leu Gly Gly Asp Ser Leu
1235                1240                1245

Arg Leu Leu Lys Pro Gly Gly Ser Leu Leu Ile Arg Ala Tyr Gly
1250                1255                1260
```

```
Tyr Ala Asp Arg Thr Ser Glu Arg Val Ile Cys Val Leu Gly Arg
    1265            1270            1275

Lys Phe Arg Ser Ser Arg Ala Leu Lys Pro Pro Cys Val Thr Ser
    1280            1285            1290

Asn Thr Glu Met Phe Phe Leu Phe Ser Asn Phe Asp Asn Gly Arg
    1295            1300            1305

Arg Asn Phe Thr Thr His Val Met Asn Asn Gln Leu Asn Ala Ala
    1310            1315            1320

Phe Val Gly Gln Ala Thr Arg Ala Gly Cys Ala Pro Ser Tyr Arg
    1325            1330            1335

Val Lys Arg Met Asp Ile Ala Lys Asn Asp Glu Glu Cys Val Val
    1340            1345            1350

Asn Ala Ala Asn Pro Arg Gly Leu Pro Gly Asp Gly Val Cys Lys
    1355            1360            1365

Ala Val Tyr Lys Lys Trp Pro Glu Ser Phe Lys Asn Ser Ala Thr
    1370            1375            1380

Pro Val Gly Thr Ala Lys Thr Val Met Cys Gly Thr Tyr Pro Val
    1385            1390            1395

Ile His Ala Val Gly Pro Asn Phe Ser Asn Tyr Ser Glu Ser Glu
    1400            1405            1410

Gly Asp Arg Glu Leu Ala Ala Ala Tyr Arg Glu Val Ala Lys Glu
    1415            1420            1425

Val Thr Arg Leu Gly Val Asn Ser Val Ala Ile Pro Leu Leu Ser
    1430            1435            1440

Thr Gly Val Tyr Ser Gly Gly Lys Asp Arg Leu Thr Gln Ser Leu
    1445            1450            1455

Asn His Leu Phe Thr Ala Met Asp Ser Thr Asp Ala Asp Val Val
    1460            1465            1470

Ile Tyr Cys Arg Asp Lys Glu Trp Glu Lys Lys Ile Ser Glu Ala
    1475            1480            1485

Ile Gln Met Arg Thr Gln Val Glu Leu Leu Asp Glu His Ile Ser
    1490            1495            1500

Ile Asp Cys Asp Val Val Arg Val His Pro Asp Ser Ser Leu Ala
    1505            1510            1515

Gly Arg Lys Gly Tyr Ser Thr Thr Glu Gly Ala Leu Tyr Ser Tyr
    1520            1525            1530

Leu Glu Gly Thr Arg Phe His Gln Thr Ala Val Asp Met Ala Glu
    1535            1540            1545

Ile Tyr Thr Met Trp Pro Lys Gln Thr Glu Ala Asn Glu Gln Val
    1550            1555            1560

Cys Leu Tyr Ala Leu Gly Glu Ser Ile Glu Ser Ile Arg Gln Lys
    1565            1570            1575

Cys Pro Val Asp Asp Ala Asp Ala Ser Ser Pro Lys Thr Val
    1580            1585            1590

Pro Cys Leu Cys Arg Tyr Ala Met Thr Pro Glu Arg Val Thr Arg
    1595            1600            1605

Leu Arg Met Asn His Val Thr Ser Ile Ile Val Cys Ser Ser Phe
    1610            1615            1620

Pro Leu Pro Lys Tyr Lys Ile Glu Gly Val Gln Lys Val Lys Cys
    1625            1630            1635

Ser Lys Val Met Leu Phe Asp His Asn Val Pro Ser Arg Val Ser
    1640            1645            1650

Pro Arg Glu Tyr Arg Pro Ser Gln Glu Ser Val Gln Glu Ala Ser
```

```
              1655                1660                1665

Thr Thr Thr Ser Leu Thr His Ser Gln Phe Asp Leu Ser Val Asp
        1670            1675            1680

Gly Lys Ile Leu Pro Val Pro Ser Asp Leu Asp Ala Asp Ala Pro
        1685            1690            1695

Ala Leu Glu Pro Ala Leu Asp Asp Gly Ala Ile His Thr Leu Pro
        1700            1705            1710

Ser Ala Thr Gly Asn Leu Ala Ala Val Ser Asp Trp Val Met Ser
        1715            1720            1725

Thr Val Pro Val Ala Pro Pro Arg Arg Arg Gly Arg Asn Leu
        1730            1735            1740

Thr Val Thr Cys Asp Glu Arg Glu Gly Asn Ile Thr Pro Met Ala
        1745            1750            1755

Ser Val Arg Phe Phe Arg Ala Glu Leu Cys Pro Val Val Gln Glu
        1760            1765            1770

Thr Ala Glu Thr Arg Asp Thr Ala Met Ser Leu Gln Ala Pro Pro
        1775            1780            1785

Ser Thr Ala Thr Glu Leu Ser His Pro Pro Ile Ser Phe Gly Ala
        1790            1795            1800

Pro Ser Glu Thr Phe Pro Ile Thr Phe Gly Asp Phe Asn Glu Gly
        1805            1810            1815

Glu Ile Glu Ser Leu Ser Ser Glu Leu Leu Thr Phe Gly Asp Phe
        1820            1825            1830

Leu Pro Gly Glu Val Asp Asp Leu Thr Asp Ser Asp Trp Ser Thr
        1835            1840            1845

Cys Ser Asp Thr Asp Asp Glu Leu Arg Leu Asp Arg Ala Gly Gly
        1850            1855            1860

Tyr Ile Phe Ser Ser Asp Thr Gly Pro Gly His Leu Gln Gln Lys
        1865            1870            1875

Ser Val Arg Gln Ser Val Leu Pro Val Asn Thr Leu Glu Glu Val
        1880            1885            1890

His Glu Glu Lys Cys Tyr Pro Pro Lys Leu Asp Glu Ala Lys Glu
        1895            1900            1905

Gln Leu Leu Leu Lys Lys Leu Gln Glu Ser Ala Ser Met Ala Asn
        1910            1915            1920

Arg Ser Arg Tyr Gln Ser Arg Lys Val Glu Asn Met Lys Ala Thr
        1925            1930            1935

Ile Ile Gln Arg Leu Lys Arg Gly Cys Arg Leu Tyr Leu Met Ser
        1940            1945            1950

Glu Thr Pro Lys Val Pro Thr Tyr Arg Thr Thr Tyr Pro Ala Pro
        1955            1960            1965

Val Tyr Ser Pro Pro Ile Asn Val Arg Leu Ser Asn Pro Glu Ser
        1970            1975            1980

Ala Val Ala Ala Cys Asn Glu Phe Leu Ala Arg Asn Tyr Pro Thr
        1985            1990            1995

Val Ser Ser Tyr Gln Ile Thr Asp Glu Tyr Asp Ala Tyr Leu Asp
        2000            2005            2010

Met Val Asp Gly Ser Glu Ser Cys Leu Asp Arg Ala Thr Phe Asn
        2015            2020            2025

Pro Ser Lys Leu Arg Ser Tyr Pro Lys Gln His Ala Tyr His Ala
        2030            2035            2040

Pro Ser Ile Arg Ser Ala Val Pro Ser Pro Phe Gln Asn Thr Leu
        2045            2050            2055
```

```
Gln Asn Val Leu Ala Ala Ala Thr Lys Arg Asn Cys Asn Val Thr
    2060                2065                2070

Gln Met Arg Glu Leu Pro Thr Leu Asp Ser Ala Val Phe Asn Val
    2075                2080                2085

Glu Cys Phe Lys Lys Phe Ala Cys Asn Gln Glu Tyr Trp Glu Glu
    2090                2095                2100

Phe Ala Ala Ser Pro Ile Arg Ile Thr Thr Glu Asn Leu Thr Thr
    2105                2110                2115

Tyr Val Thr Lys Leu Lys Gly Pro Lys Ala Ala Ala Leu Phe Ala
    2120                2125                2130

Lys Thr His Asn Leu Leu Pro Leu Gln Glu Val Pro Met Asp Arg
    2135                2140                2145

Phe Thr Val Asp Met Lys Arg Asp Val Lys Val Thr Pro Gly Thr
    2150                2155                2160

Lys His Thr Glu Glu Arg Pro Lys Val Gln Val Ile Gln Ala Ala
    2165                2170                2175

Glu Pro Leu Ala Thr Ala Tyr Leu Cys Gly Ile His Arg Glu Leu
    2180                2185                2190

Val Arg Arg Leu Asn Ala Val Leu Leu Pro Asn Val His Thr Leu
    2195                2200                2205

Phe Asp Met Ser Ala Glu Asp Phe Asp Ala Ile Ile Ala Ala His
    2210                2215                2220

Phe Lys Pro Gly Asp Thr Val Leu Glu Thr Asp Ile Ala Ser Phe
    2225                2230                2235

Asp Lys Ser Gln Asp Asp Ser Leu Ala Leu Thr Ala Leu Met Leu
    2240                2245                2250

Leu Glu Asp Leu Gly Val Asp His Ser Leu Leu Asp Leu Ile Glu
    2255                2260                2265

Ala Ala Phe Gly Glu Ile Ser Ser Cys His Leu Pro Thr Gly Thr
    2270                2275                2280

Arg Phe Lys Phe Gly Ala Met Met Lys Ser Gly Met Phe Leu Thr
    2285                2290                2295

Leu Phe Val Asn Thr Leu Leu Asn Ile Thr Ile Ala Ser Arg Val
    2300                2305                2310

Leu Glu Asp Arg Leu Thr Lys Ser Ala Cys Ala Ala Phe Ile Gly
    2315                2320                2325

Asp Asp Asn Ile Ile His Gly Val Val Ser Asp Glu Leu Met Ala
    2330                2335                2340

Ala Arg Cys Ala Thr Trp Met Asn Met Glu Val Lys Ile Ile Asp
    2345                2350                2355

Ala Val Val Ser Gln Lys Ala Pro Tyr Phe Cys Gly Gly Phe Ile
    2360                2365                2370

Leu His Asp Ile Val Thr Gly Thr Ala Cys Arg Val Ala Asp Pro
    2375                2380                2385

Leu Lys Arg Leu Phe Lys Leu Gly Lys Pro Leu Ala Ala Gly Asp
    2390                2395                2400

Glu Gln Asp Glu Asp Arg Arg Arg Ala Leu Ala Asp Glu Val Val
    2405                2410                2415

Arg Trp Gln Arg Thr Gly Leu Ile Asp Glu Leu Glu Lys Ala Val
    2420                2425                2430

Tyr Ser Arg Tyr Glu Val Gln Gly Ile Ser Val Val Val Met Ser
    2435                2440                2445
```

```
Met Ala Thr Phe Ala Ser Ser Arg Ser Asn Phe Glu Lys Leu Arg
    2450                2455                2460

Gly Pro Val Val Thr Leu Tyr Gly Gly Pro Lys
    2465                2470
```

<210> SEQ ID NO 4
<211> LENGTH: 11881
<212> TYPE: DNA
<213> ORGANISM: O'nyong nyong virus

<400> SEQUENCE: 4

| | | | | | |
|---|---|---|---|---|---|
| atggctgcgt | gagacacacg | tagcctacca | gtttcttact | gctctactct | gcttagcaag | 60 |
| agacttgaga | acccatcatg | gatcccgtgt | acgtggacat | agacgccgac | agcgcctttt | 120 |
| taaaggccct | gcagcgtgcg | tacccccatgt | ttgaggtgga | accaaggcag | gtcacaccga | 180 |
| atgaccatgc | caatgctaga | gcattctcgc | atctagctat | aaaactaata | gagcaggaaa | 240 |
| ttgatcccga | ctcaaccatc | ctggacatag | gcagcgcgcc | agcaaggagg | atgatgtcgg | 300 |
| ataggaagta | ccactgcgtt | tgccctatgc | gcagcgcaga | gaccctgag | agactcgcca | 360 |
| actacgcgag | aaaactagca | tctgccgcag | gaaaagtctt | ggacagaaac | atctccgaaa | 420 |
| aaattggaga | tctacaagca | gtaatggctg | taccagacgc | agaaacgccc | acattctgct | 480 |
| tgcacactga | cgtctcatgt | agacaaaggg | cggacgtcgc | tatataccag | gatgtctacg | 540 |
| ccgtgcatgc | accaacatcg | ctgtaccacc | aggcgattaa | aggagtccgt | gtagcatact | 600 |
| ggatagggtt | tgatacaacc | ccgttcatgt | ataatgccat | ggcaggtgca | tacccctcgt | 660 |
| actcgacaaa | ctgggcagat | gagcaggtgc | tgaaggcaaa | gaacatagga | ttatgttcaa | 720 |
| cagacctgac | ggaaggtaga | cgaggtaaat | tgtctatcat | gagaggaaaa | aagatgaagc | 780 |
| catgtgaccg | cgtactgttc | tcagtcgggt | caacgcttta | cccggagagc | cgtaagcttc | 840 |
| ttaagagttg | gcacttacct | tcagtgttcc | atctaaaagg | gaagctcagc | ttcacgtgcc | 900 |
| gctgtgatac | agtggtttcg | tgtgaaggct | atgtcgttaa | gagaataacg | attagcccgg | 960 |
| gcctctacgg | taaaaccaca | gggtacgcag | taacccacca | tgcagacgga | ttcctaatgt | 1020 |
| gcaaaacaac | cgatacggta | gatggcgaga | gagtgtcatt | tcggtatgc | acgtacgtac | 1080 |
| ccgcaaccat | ttgtgatcaa | atgacaggta | ttcttgccac | ggaggttaca | ccggaggatg | 1140 |
| cacagaagct | gctggtggga | ctgaaccaga | ggatagtggt | caatggcaga | acgcagagga | 1200 |
| acacgaacac | aatgaagaat | tacttgcttc | ctgtagttgc | ccaagccttc | agtaagtggg | 1260 |
| caaaggaatg | ccggaaagat | atggaagatg | aaaaactttt | gggcatcaga | gaaaggacac | 1320 |
| tgacatgctg | ctgcctttgg | gcgttcaaga | agcagaagac | acacacggtc | tacaagaggc | 1380 |
| ctgacactca | gtcaattcag | aaagtcccag | ccgaatttga | cagctttgtg | gtaccaagtc | 1440 |
| tgtggtcatc | tggactgtcg | atcccgctac | ggaccagaat | caagtggctg | ctaagcaaag | 1500 |
| tgccaaagac | tgatttgatc | ccttacagcg | gtgacgccaa | agaagcccgc | gacgctgaaa | 1560 |
| aagaagcaga | agaagaacga | gaagcggagc | taactcgcga | ggcactacca | ccactacagg | 1620 |
| cggcacagga | cgacgtccag | gtcgaaattg | acgtggaaca | gctcgaagac | agagctgggg | 1680 |
| caggaataat | tgaaactcca | agaggagcta | tcaaagtcac | tgcccaacca | acagaccacg | 1740 |
| tcgtgggaga | gtacttggta | ctttcccgc | agaccgtgtt | acgaagccag | aagctcagcc | 1800 |
| tgatccacgc | attggcggaa | caagtgaaga | catgcacaca | cagcggacgg | caggaaggt | 1860 |
| acgcggtcga | agcatatgac | ggcagaatcc | ttgtgccctc | aggctatgca | atatcacctg | 1920 |
| aagacttcca | gagcctgagc | gaaagtgcga | cgatggtgta | caacgaaagg | gagttcgtaa | 1980 |

-continued

```
ataggaaatt acaccatatc gcgttgcacg gaccagccct gaacactgac gaggagtcgt    2040
acgagctggt aagggcagaa aggacagagc atgagtacgt ctatgatgtg gaccaaagaa    2100
ggtgctgcaa gaaagaggag gcagccgggc tggtactggt cggcgacttg accaacccgc    2160
cctaccatga gttcgcatat gaagggctga gaatccgccc cgcctgccca tacaagaccg    2220
cagtaatagg ggtctttgga gtgccaggat ccggcaaatc agcaatcatt aagaacctag    2280
ttaccaggca agacctagtg accagtggaa agaaagaaaa ctgccaagaa atctccaccg    2340
acgtgatgcg acagaggaac ctggagatat ctgcacgcac ggtcgactca ctgctcttga    2400
acggatgcaa tagaccagtc gacgtgttgt acgtcgacga agcttttgcg tgccattctg    2460
gcacgctact tgctctgata gccttggtga gaccgaggca gaaagtcgtg ctatgcggtg    2520
atccgaaaca gtgcggcttc ttcaatatga tgcagatgaa agttaactac aaccataaca    2580
tctgcaccca agtgtaccat aaaagtattt ccaggcggtg tacactgcct gtgactgcca    2640
ttgtgtcctc gttgcattac gaaggcaaaa tgcgcacaac aaatgagtac aacaagccaa    2700
ttgtagtgga tactacaggc tcgacaaaac ccgaccccgg agaccttgtg ctaacatgtt    2760
tcagagggtg ggttaagcaa ctgcaaattg actatcgtgg acacgaggtc atgacagcag    2820
ctgcatctca ggggctaacc agaaaagggg tctatgccgt caggcaaaaa gttaatgaaa    2880 accccttta cgcatcaaca tcagagcacg tgaacgtgct actgacgcgt acggaaggca    2940
aactagtatg gaagacactt tctggagacc catggataaa gacactgcag aacccgccga    3000
aaggaaattt taaagcaaca attaaggaat gggaagtgga acatgcttca ataatggcgg    3060
gtatctgtaa ccaccaagtg acctttgaca cgttccagaa taaagccaat gtctgctggg    3120
cgaagagctt agtccccatc ctagaaacag cagggataaa attaaacgac aggcagtggt    3180
cccagataat ccaggctttt aaagaagaca gagcatactc acccgaggtg gccctgaatg    3240
agatatgcac gcgcatgtac ggggtagacc tggacagcgg actgttctct aaaccactgg    3300
tgtccgtgca ttatgcggat aatcactggg acaacaggcc gggagggaag atgttcggat    3360
tcaaccccga agcggcgtcc atactggaga ggaaataccc gtttacaaaa gggaagtgga    3420
ataccaacaa gcaaatctgt gtgactacta ggaggattga agattttaac ccgaacacca    3480
acattatacc tgccaacagg agattaccgc attcattggt ggccgaacat cgcccggtaa    3540
aaggggagag gatggaatgg ttggtcaaca aaataaatgg ccaccatgtg ctcctggtca    3600
gcggctacaa cctcgttctg cccactaaga gagtcacctg ggtggcgccg ctgggcattc    3660
ggggagctga ctacacatac aacctagagt taggcctacc agcaacgctc ggtagatatg    3720
acctagtgat tataaacatc cacacaccct ttcgcataca tcattaccaa cagtgcgtgg    3780
atcacgcaat gaagctgcag atgctcggag gagactccct gagactgctc aagccgggtg    3840
gttcattact gatcagggca tacggctacg cagacagaac aagcgaacga gtagtctgcg    3900
tattgggacg caagtttcga tcatccagag cgttgaaacc gccgtgcgtc actagcaaca    3960
ccgagatgtt tttcttgttc agcaactttg ataacggcag aaggaacttt acgacgcacg    4020
taatgaacaa ccagctgaat gctgcttttg ttggtcaggc cacccgagca gggtgcgcac    4080
cgtcgtaccg ggttaaacgc atggacatcg caaagaacga tgaagagtgt gtagtcaacg    4140
ccgccaaccc tcgtgggcta ccaggcgatg gcgtctgtaa agcagtatac aaaaaatggc    4200
cggagtcctt caagaacagt gcaacaccag tgggaaccgc aaagacagtc atgtgcggta    4260 cataccggt aatccatgca gtaggaccta atttctcaaa ttactctgag tccgaaggag    4320
```

```
accgggaatt ggcagctgct taccgagaag tcgctaagga ggtgactaga ctaggagtaa    4380
acagcgtagc tataccgctc ctttccaccg gtgtgtactc tggagggaaa gacaggctga    4440
ctcagtcact aaaccacctt tttacagcat tagactcaac tgatgcagat gtggttatct    4500
actgccgcga caaggagtgg gagaagaaaa tagctgaggc catacaaatg aggacccaag    4560
tggaattact agacgaacac atctctgtag actgcgatat catccgagtg caccctgaca    4620
gcagtttggc aggtagaaaa gggtacagca ctacagaagg ttcactgtac tcctacttgg    4680
aagggacacg gttccatcag acggcagtgg acatggcaga agtatacacc atgtggccaa    4740
agcagacgga ggctaatgaa caagtttgct tgtacgcatt gggggaaagt atagaatcaa    4800
tcaggcaaaa gtgcccagtg gatgacgcag atgcatcgtc gcccccaaaa accgtcccgt    4860
gcctctgccg ttatgccatg acacccgaac gagtcaccag gcttcgtatg aaccatgtca    4920
caagcataat agtatgctca tcattccccc ttccaaagta taaaatagaa ggagtgcaga    4980
aagtcaagtg ttctaaagtg atgctgttcg accataacgt gccatcacgc gttagtccaa    5040
gggaatataa atcgcctcag gagaccgcac aagaagtaag ttcgaccacg tcactgacgc    5100
acagccaatt cgaccttagc gttgacggtg aggaactgcc cgctccgtct gacttggaag    5160
ctgacgctcc gattccggaa ccaacaccag acgacagagc ggtacttact ttgcctccca    5220
cgattgataa ttttccggct gtgtcagact gggtaatgaa taccgcgcca gtcgcaccac    5280
ccagaagaag acgtgggaaa aacttgaatg tcacctgcga cgagagagaa gggaacgtac    5340
ttcccatggc tagcgttcgg ttcttcagag cggatctgca ctccatcgta caggaaacgg    5400
cagagatacg cgatacggcc gcgtccctcc aggcgcccct gagtgtcgct acagaaccga    5460
atcaactgcc gatctcattt ggagcaccaa acgagacttt ccccataacg ttcgggatt    5520 ttgatgaagg ggagattgaa agcttgtcct ctgagttact gaccttgggg gacttctcgc    5580
cgggcgaagt ggatgacctg acagacagcg actggtccac gtgttcagac acggacgacg    5640
aattatgact agataggca ggtgggtaca tattctcatc tgacaccggc cccggccacc    5700
tgcaacagag gtctgtccgt cagacagtac tgccggtaaa taccttggag gaagttcagg    5760
aggagaaatg ttacccacct aagttggatg aagtgaaaga gcagttgtta cttaagaaac    5820
tccaggaaag tgcgtccatg gctaacagaa gcaggtacca atcccgcaaa gtagagaaca    5880
tgaaagcaac aatagtccaa aggctgaagg gtggttgcaa actttattta atgtcggaga    5940
ccccgaaagt tcctacctac cgaactacat atccggcacc agtgtactca cccccaatca    6000
atatccgact gtccaacccc gagtctgctg tggcagcgtg caatgagttc tagcaagga    6060 actatccgac agttgcgtcg taccaaatca ccgatgagta cgatgcatac ctagacatgg    6120
tggacgggtc ggaaagttgc cttgaccggg cgacgttcaa cccatcaaag cttagaagtt    6180
atccaaaaca gcactcctac catgcaccca caatcagaag tgccgtacct tccccgttcc    6240
agaacacgct gcagaacgta ctggctgctg ccacgaaaag aaattgcaac gtcacacaga    6300
tgagagaact gcctactttg gattcagcgg tatttaatgt tgagtgcttt aaaaaatttg    6360
cgtgcaatca agaatactgg aaggaatttg ccgccagccc tattaggata acgactgaga    6420
acttgacaac ttatgtcaca aaactaaaag gaccaaaagc agcagcactg tttgccaaga    6480
cacataacct gctaccactg caggaggtgc cgatggacag gtttactgta gacatgaaaa    6540
gggacgtgaa ggtgactccg gggacgaagc acactgagga aagacctaaa gtgcaggtca    6600
tacaggcagc cgaacctttg gcaacagcat atctgtgtgg gatccacaga gagttggtca    6660
gaaggctgaa tgcagtcctt ctacctaatg tacacacgct gtttgacatg tctgccgagg    6720
```

```
actttgacgc cattattgcc gcgcacttca agccggggga cgccgtattg gaaaccgata   6780
tagcctcctt tgacaagagc caagacgact cattggcgct cactgctcta atgttgctag   6840
aggatttggg ggtggatcat cccctgttgg acttgataga ggctgccttc ggggagatct   6900
ccagctgcca cctaccgacg ggcacccgtt ttaagttcgg cgccatgatg aagtctggta   6960
tgttcctaac cctgttcgtc aacacactgc taaacatcac catagccagc cgagtgctgg   7020
aggaccgctt gacaaggtct gcgtgcgcgg ccttcatcgg cgacgacaat ataatacatg   7080
gggttgtctc tgacgaactg atggcagcaa ggtgtgctac atggatgaac atggaagtga   7140
agatcataga tgcggtcgtg tctcagaaag ccccgtactt ctgcggaggg tttatactgt   7200
atgacacagt agcaggcacg gcctgcagag tggcagaccc gctaaagcgg ctgttcaagc   7260
tgggcaaacc gctggcagcg ggagatgaac aagacgacga cagaagacgt gcactggctg   7320
acgaagtggt tagatggcaa cgaacaggac taactgatga gctagaaaaa gcggtacact   7380
ccaggtatga agtgcagggc atatctgtcg tggtaatgtc tatggccacc tttgcaagct   7440
ctagatctaa ctttgagaag ctcagaggac ccgtcgtaac cctgtacggt ggtcctaaat   7500
aggtacgcac tacagctacc tatttcgtca gaaaccaatc gcagctactt gcatacctac   7560
cagctacaat ggagttcatc ccgacgcaaa ctttctataa cagaaggtac caaccccgac   7620
cctgggcccc acgccctaca attcaagtaa ttagacctag accacgtcca cagaggcagg   7680
ctgggcaact cgcccagctg atctccgcag tcaacaaatt gaccatgcgc gcggtacctc   7740
aacagaagcc tcgcagaaat cggaaaaaca agaagcaaag gcagaagaag caggcgccgc   7800
aaaacgaccc aaagcaaaag aagcaaccac cacaaaagaa gccggctcaa aagaagaaga   7860
aaccaggccg tagggagaga atgtgcatga aaattgaaaa tgattgcatc ttcgaagtca   7920
agcatgaagg caaagtgatg ggctacgcat gcctggtggg ggataaagta atgaaaccag   7980
cacatgtgaa gggaactatc gacaatgccg atctggctaa actggccttt aagcggtcgt   8040
ctaaatacga tcttgaatgt gcacagatac cggtgcacat gaagtctgat gcctcgaagt   8100
ttacccacga gaaacccgag gggtactata actggcatca cggagcagtg cagtattcag   8160
gaggccggtt cactatcccg acgggtgcag gcaagccggg agacagcggc agaccgatct   8220
tcgacaacaa aggacgggtg gtggccatcg tcctaggagg ggccaacgaa ggtgcccgca   8280
cggccctctc cgtggtgacg tggaacaaag acatcgtcac aaaaattacc cctgagggag   8340
ccgaagagtg gagcctcgcc ctcccggtct tgtgcctgtt ggcaaacact acattcccct   8400
gctctcagcc gccttgcaca ccctgctgct acgaaaagga accggaaagc accttgcgca   8460
tgcttgagga caacgtgatg agacccggat actaccagct actaaaagca tcgctgactt   8520
gctctcccca ccgccaaaga cgcagtacta aggacaattt taatgtctat aaagccacaa   8580
gaccatatct agctcattgt cctgactgcg gagaagggca ttcgtgccac agccctatcg   8640
cattggagcg catcagaaat gaagcaacgg acggaacgct gaaaatccag gtctctttgc   8700
agatcgggat aaagacagat gacagccacg attggaccaa gctgcgctat atggatagcc   8760
atacgccagc ggacgcggag cgagccggat tgcttgtaag gacttcagca ccgtgcacga   8820
tcaccgggac catgggacac tttattctcg cccgatgccc gaaaggagag acgctgacag   8880
tgggatttac ggacagcaga aagatcagcc acacatgcac acacccgttc catcatgaac   8940
cacctgtgat aggtagggag aggttccact ctcgaccaca acatggtaaa gagttacctt   9000
gcagcacgta cgtgcagagc accgctgcca ctgctgagga gatagaggtg catatgcccc   9060
```

```
cagatactcc tgaccgcacg ctgatgacgc agcagtctgg caacgtgaag atcacagtta    9120
atgggcagac ggtgcggtac aagtgcaact gcggtggctc aaacgaggga ctgacaacca    9180
cagacaaagt gatcaataac tgcaaaattg atcagtgcca tgctgcagtc actaatcaca    9240
agaattggca atacaactcc cctttagtcc cgcgcaacgc tgaactcggg gaccgtaaag    9300
gaaagatcca catcccattc ccattggcaa acgtgacttg cagagtgcca aaagcaagaa    9360
accctacagt aacttacgga aaaaaccaag tcaccatgct gctgtatcct gaccatccga    9420
cactcttgtc ttaccgtaac atgggacagg aaccaaatta ccacgaggag tgggtgacac    9480
acaagaagga ggttaccttg accgtgccta ctgagggtct ggaggtcact tggggcaaca    9540
acgaaccata caagtactgg ccgcagatgt ctacgaacgg tactgctcat ggtcacccac    9600
atgagataat cttgtactat tatgagctgt accccactat gactgtagtc attgtgtcgg    9660
tggcctcgtt cgtgcttctg tcgatggtgg gcacagcagt gggaatgtgt gtgtgcgcac    9720
ggcgcagatg cattacacca tatgaattaa caccaggagc cactgttccc ttcctgctca    9780
gcctgctatg ctgcgtcaga acgaccaagg cggcccacata ttacgaggct gcggcatatc    9840
tatgaaacga acagcagccc ctgttctggt tgcaggctct tatcccgctg gccgccttga    9900
tcgtcctgtg caactgtctg aaactcttgc catgctgctg taagaccctg gctttttag    9960
ccgtaatgag catcggtgcc cacactgtga gcgcgtacga acacgtaaca gtgatcccga   10020
acacggtggg agtaccgtat aagactcttg tcaacgacc gggttacagc ccatggtgt    10080
tggagatgga gctacaatca gtcaccttgg aaccaacact gtcacttgac tacatcacgt   10140
gcgagtacaa aactgtcatc ccctcccgt acgtgaagtg ctgtggtaca gcagagtgca   10200
aggacaagag cctaccagac tacagctgca aggtcttac tggagtctac ccatttatgt   10260
ggggcggcgc ctactgcttt tgcgacgccg aaaatacgca attgagcgag gcacatgtag   10320
agaaatctga atcttgcaaa acagagtttg catcggccta cagagcccac accgcatcgg   10380
cgtcggcgaa gctccgcgtc ctttaccaag gaaacaacat taccgtagct gcctacgcta   10440
acggtgacca tgccgtcaca gtaaaggacg ccaagtttgt cgtgggccca atgtcctccg   10500
cctggacacc ttttgacaac aaaatcgtgg tgtacaaagg cgacgtctac aacatggact   10560
acccacctt tggcgcagga agaccaggac aatttggtga cattcaaagt cgtacaccgg   10620
aaagtaaaga cgtttatgcc aacactcagt tggtactaca gaggccagca gcaggcacgg   10680
tacatgtacc atactctcag gcaccatctg gcttcaagta ttggctgaag gaacgaggag   10740
catcgctaca gcacacggca ccgttcggtt gccagattgc gacaaacccg gtaagagctg   10800
taaattgcgc tgtggggaac ataccaattt ccatcgacat accggatgcg gcctttacta   10860
gggttgtcga tgcacccctct gtaacggaca tgtcatgcga agtaccagcc tgcactcact   10920
cctccgactt tggggggcgtc gccatcatca aatacacagc tagcaagaaa ggtaaatgtg   10980
cagtacattc gatgaccaac gccgttacca ttcgagaagc cgacgtagaa gtagagggga   11040
actcccagct gcaaatatcc ttctcaacag ccctggcaag cgccgagttt cgcgtgcaag   11100
tgtgctccac acaagtacac tgcgcagccg catgccaccc tccaaaggac cacatagtca   11160
attacccagc atcacacacc acccttgggg tccaggatat atccacaacg gcaatgtctt   11220
gggtgcagaa gattacggga ggagtaggat taattgttgc tgttgctgcc ttaattttaa   11280
ttgtggtgct atgcgtgtcg tttagcaggc actaaaccga tgataaggca cgaaataact   11340
aaatagcaaa agtagaaagt acataaccag gtatatgtgc cccttaagag gcacaatata   11400
tatagctaag cactattaga tcaaagggct atacaacccc tgaatagtaa caaaacacaa   11460
```

-continued

```
aaaccaataa aaatcataaa aagaaaaatc tcataaacag gtataagtgt cccctaagag    11520
acacattgta tgtaggtagt aagtatagat caaagggcta tattaacccc tgaatagtaa    11580
caaaacacaa aaacaataaa aactacaaaa tagaaaatct ataaacaaaa gtagttcaaa    11640
gggctacaaa acccctgaat agtaacaaaa cataaaatgt aataaaaatt aagtgtgtac    11700
ccaaaagagg tacagtaaga atcagtgaat atcacaattg gcaacgagaa gagacgtagg    11760
tatttaagct tcctaaaagc agccgaactc actttgagac gtaggcatag cataccgaac    11820
tcttccacta ttctccgaac ccacagggac gtaggagatg ttattttgtt tttaatattt    11880
c                                                                    11881
```

<210> SEQ ID NO 5
<211> LENGTH: 1248
<212> TYPE: PRT
<213> ORGANISM: O'nyong nyong virus

<400> SEQUENCE: 5

```
Met Glu Phe Ile Pro Thr Gln Thr Phe Tyr Asn Arg Arg Tyr Gln Pro
1               5                   10                  15

Arg Pro Trp Ala Pro Arg Pro Thr Ile Gln Val Ile Arg Pro Arg Pro
            20                  25                  30

Arg Pro Gln Arg Gln Ala Gly Gln Leu Ala Gln Leu Ile Ser Ala Val
        35                  40                  45

Asn Lys Leu Thr Met Arg Ala Val Pro Gln Gln Lys Pro Arg Arg Asn
    50                  55                  60

Arg Lys Asn Lys Lys Gln Arg Gln Lys Lys Ala Pro Gln Asn Asp
65                  70                  75                  80

Pro Lys Gln Lys Lys Gln Pro Pro Gln Lys Lys Pro Ala Gln Lys Lys
                85                  90                  95

Lys Lys Pro Gly Arg Arg Glu Arg Met Cys Met Lys Ile Glu Asn Asp
            100                 105                 110

Cys Ile Phe Glu Val Lys His Glu Gly Lys Val Met Gly Tyr Ala Cys
        115                 120                 125

Leu Val Gly Asp Lys Val Met Lys Pro Ala His Val Lys Gly Thr Ile
    130                 135                 140

Asp Asn Ala Asp Leu Ala Lys Leu Ala Phe Lys Arg Ser Ser Lys Tyr
145                 150                 155                 160

Asp Leu Glu Cys Ala Gln Ile Pro Val His Met Lys Ser Asp Ala Ser
                165                 170                 175

Lys Phe Thr His Glu Lys Pro Glu Gly Tyr Tyr Asn Trp His His Gly
            180                 185                 190

Ala Val Gln Tyr Ser Gly Gly Arg Phe Thr Ile Pro Thr Gly Ala Gly
        195                 200                 205

Lys Pro Gly Asp Ser Gly Arg Pro Ile Phe Asp Asn Lys Gly Arg Val
    210                 215                 220

Val Ala Ile Val Leu Gly Gly Ala Asn Glu Gly Ala Arg Thr Ala Leu
225                 230                 235                 240

Ser Val Val Thr Trp Asn Lys Asp Ile Val Thr Lys Ile Thr Pro Glu
                245                 250                 255

Gly Ala Glu Glu Trp Ser Leu Ala Leu Pro Val Leu Cys Leu Leu Ala
            260                 265                 270

Asn Thr Thr Phe Pro Cys Ser Gln Pro Pro Cys Thr Pro Cys Cys Tyr
        275                 280                 285
```

```
Glu Lys Glu Pro Glu Ser Thr Leu Arg Met Leu Glu Asp Asn Val Met
    290                 295                 300
Arg Pro Gly Tyr Tyr Gln Leu Leu Lys Ala Ser Leu Thr Cys Ser Pro
305                 310                 315                 320
His Arg Gln Arg Arg Ser Thr Lys Asp Asn Phe Asn Val Tyr Lys Ala
                325                 330                 335
Thr Arg Pro Tyr Leu Ala His Cys Pro Asp Cys Gly Glu Gly His Ser
            340                 345                 350
Cys His Ser Pro Ile Ala Leu Glu Arg Ile Arg Asn Glu Ala Thr Asp
        355                 360                 365
Gly Thr Leu Lys Ile Gln Val Ser Leu Gln Ile Gly Ile Lys Thr Asp
    370                 375                 380
Asp Ser His Asp Trp Thr Lys Leu Arg Tyr Met Asp Ser His Thr Pro
385                 390                 395                 400
Ala Asp Ala Glu Arg Ala Gly Leu Leu Val Arg Thr Ser Ala Pro Cys
                405                 410                 415
Thr Ile Thr Gly Thr Met Gly His Phe Ile Leu Ala Arg Cys Pro Lys
            420                 425                 430
Gly Glu Thr Leu Thr Val Gly Phe Thr Asp Ser Arg Lys Ile Ser His
        435                 440                 445
Thr Cys Thr His Pro Phe His His Glu Pro Pro Val Ile Gly Arg Glu
    450                 455                 460
Arg Phe His Ser Arg Pro Gln His Gly Lys Glu Leu Pro Cys Ser Thr
465                 470                 475                 480
Tyr Val Gln Ser Thr Ala Ala Thr Ala Glu Glu Ile Glu Val His Met
                485                 490                 495
Pro Pro Asp Thr Pro Asp Arg Thr Leu Met Thr Gln Gln Ser Gly Asn
            500                 505                 510
Val Lys Ile Thr Val Asn Gly Gln Thr Val Arg Tyr Lys Cys Asn Cys
        515                 520                 525
Gly Gly Ser Asn Glu Gly Leu Thr Thr Thr Asp Lys Val Ile Asn Asn
    530                 535                 540
Cys Lys Ile Asp Gln Cys His Ala Ala Val Thr Asn His Lys Asn Trp
545                 550                 555                 560
Gln Tyr Asn Ser Pro Leu Val Pro Arg Asn Ala Glu Leu Gly Asp Arg
                565                 570                 575
Lys Gly Lys Ile His Ile Pro Phe Pro Leu Ala Asn Val Thr Cys Arg
            580                 585                 590
Val Pro Lys Ala Arg Asn Pro Thr Val Thr Tyr Gly Lys Asn Gln Val
        595                 600                 605
Thr Met Leu Leu Tyr Pro Asp His Pro Thr Leu Leu Ser Tyr Arg Asn
    610                 615                 620
Met Gly Gln Glu Pro Asn Tyr His Glu Glu Trp Val Thr His Lys Lys
625                 630                 635                 640
Glu Val Thr Leu Thr Val Pro Thr Glu Gly Leu Glu Val Thr Trp Gly
                645                 650                 655
Asn Asn Glu Pro Tyr Lys Tyr Trp Pro Gln Met Ser Thr Asn Gly Thr
            660                 665                 670
Ala His Gly His Pro His Glu Ile Ile Leu Tyr Tyr Glu Leu Tyr
        675                 680                 685
Pro Thr Met Thr Val Val Ile Val Ser Val Ala Ser Phe Val Leu Leu
    690                 695                 700
Ser Met Val Gly Thr Ala Val Gly Met Cys Val Cys Ala Arg Arg Arg
```

-continued

```
        705                 710                 715                 720
Cys Ile Thr Pro Tyr Glu Leu Thr Pro Gly Ala Thr Pro Phe Leu
                725                 730                 735
Leu Ser Leu Leu Cys Cys Val Arg Thr Thr Lys Ala Ala Thr Tyr Tyr
                740                 745                 750
Glu Ala Ala Ala Tyr Leu Trp Asn Glu Gln Gln Pro Leu Phe Trp Leu
                755                 760                 765
Gln Ala Leu Ile Pro Leu Ala Ala Leu Ile Val Leu Cys Asn Cys Leu
    770                 775                 780
Lys Leu Leu Pro Cys Cys Cys Lys Thr Leu Ala Phe Leu Ala Val Met
785                 790                 795                 800
Ser Ile Gly Ala His Thr Val Ser Ala Tyr Glu His Val Thr Val Ile
                    805                 810                 815
Pro Asn Thr Val Gly Val Pro Tyr Lys Thr Leu Val Asn Arg Pro Gly
                820                 825                 830
Tyr Ser Pro Met Val Leu Glu Met Glu Leu Gln Ser Val Thr Leu Glu
                835                 840                 845
Pro Thr Leu Ser Leu Asp Tyr Ile Thr Cys Glu Tyr Lys Thr Val Ile
    850                 855                 860
Pro Ser Pro Tyr Val Lys Cys Cys Gly Thr Ala Glu Cys Lys Asp Lys
865                 870                 875                 880
Ser Leu Pro Asp Tyr Ser Cys Lys Val Phe Thr Gly Val Tyr Pro Phe
                    885                 890                 895
Met Trp Gly Gly Ala Tyr Cys Phe Cys Asp Ala Glu Asn Thr Gln Leu
                900                 905                 910
Ser Glu Ala His Val Glu Lys Ser Glu Ser Cys Lys Thr Glu Phe Ala
                915                 920                 925
Ser Ala Tyr Arg Ala His Thr Ala Ser Ala Ser Ala Lys Leu Arg Val
                930                 935                 940
Leu Tyr Gln Gly Asn Asn Ile Thr Val Ala Ala Tyr Ala Asn Gly Asp
945                 950                 955                 960
His Ala Val Thr Val Lys Asp Ala Lys Phe Val Val Gly Pro Met Ser
                965                 970                 975
Ser Ala Trp Thr Pro Phe Asp Asn Lys Ile Val Val Tyr Lys Gly Asp
                980                 985                 990
Val Tyr Asn Met Asp Tyr Pro Pro  Phe Gly Ala Gly Arg  Pro Gly Gln
                995                 1000                1005
Phe Gly  Asp Ile Gln Ser Arg  Thr Pro Glu Ser Lys  Asp Val Tyr
        1010                1015                1020
Ala Asn  Thr Gln Leu Val Leu  Gln Arg Pro Ala Ala  Gly Thr Val
        1025                1030                1035
His Val  Pro Tyr Ser Gln Ala  Pro Ser Gly Phe Lys  Tyr Trp Leu
        1040                1045                1050
Lys Glu  Arg Gly Ala Ser Leu  Gln His Thr Ala Pro  Phe Gly Cys
        1055                1060                1065
Gln Ile  Ala Thr Asn Pro Val  Arg Ala Val Asn Cys  Ala Val Gly
        1070                1075                1080
Asn Ile  Pro Ile Ser Ile Asp  Ile Pro Asp Ala Ala  Phe Thr Arg
        1085                1090                1095
Val Val  Asp Ala Pro Ser Val  Thr Asp Met Ser Cys  Glu Val Pro
        1100                1105                1110
Ala Cys  Thr His Ser Ser Asp  Phe Gly Gly Val Ala  Ile Ile Lys
        1115                1120                1125
```

```
Tyr Thr Ala Ser Lys Lys Gly Lys Cys Ala Val His Ser Met Thr
        1130                1135                1140

Asn Ala Val Thr Ile Arg Glu Ala Asp Val Glu Val Glu Gly Asn
        1145                1150                1155

Ser Gln Leu Gln Ile Ser Phe Ser Thr Ala Leu Ala Ser Ala Glu
        1160                1165                1170

Phe Arg Val Gln Val Cys Ser Thr Gln Val His Cys Ala Ala Ala
        1175                1180                1185

Cys His Pro Pro Lys Asp His Ile Val Asn Tyr Pro Ala Ser His
        1190                1195                1200

Thr Thr Leu Gly Val Gln Asp Ile Ser Thr Thr Ala Met Ser Trp
        1205                1210                1215

Val Gln Lys Ile Thr Gly Gly Val Gly Leu Ile Val Ala Val Ala
        1220                1225                1230

Ala Leu Ile Leu Ile Val Val Leu Cys Val Ser Phe Ser Arg His
        1235                1240                1245

<210> SEQ ID NO 6
<211> LENGTH: 2473
<212> TYPE: PRT
<213> ORGANISM: O'nyong nyong virus

<400> SEQUENCE: 6

Met Asp Pro Val Tyr Val Asp Ile Asp Ala Asp Ser Ala Phe Leu Lys
1               5                   10                  15

Ala Leu Gln Arg Ala Tyr Pro Met Phe Glu Val Glu Pro Arg Gln Val
            20                  25                  30

Thr Pro Asn Asp His Ala Asn Ala Arg Ala Phe Ser His Leu Ala Ile
        35                  40                  45

Lys Leu Ile Glu Gln Glu Ile Asp Pro Asp Ser Thr Ile Leu Asp Ile
    50                  55                  60

Gly Ser Ala Pro Ala Arg Arg Met Met Ser Asp Arg Lys Tyr His Cys
65                  70                  75                  80

Val Cys Pro Met Arg Ser Ala Glu Asp Pro Glu Arg Leu Ala Asn Tyr
                85                  90                  95

Ala Arg Lys Leu Ala Ser Ala Ala Gly Lys Val Leu Asp Arg Asn Ile
            100                 105                 110

Ser Glu Lys Ile Gly Asp Leu Gln Ala Val Met Ala Val Pro Asp Ala
        115                 120                 125

Glu Thr Pro Thr Phe Cys Leu His Thr Asp Val Ser Cys Arg Gln Arg
    130                 135                 140

Ala Asp Val Ala Ile Tyr Gln Asp Val Tyr Ala Val His Ala Pro Thr
145                 150                 155                 160

Ser Leu Tyr His Gln Ala Ile Lys Gly Val Arg Val Ala Tyr Trp Ile
                165                 170                 175

Gly Phe Asp Thr Thr Pro Phe Met Tyr Asn Ala Met Ala Gly Ala Tyr
            180                 185                 190

Pro Ser Tyr Ser Thr Asn Trp Ala Asp Glu Gln Val Leu Lys Ala Lys
        195                 200                 205

Asn Ile Gly Leu Cys Ser Thr Asp Leu Thr Glu Gly Arg Arg Gly Lys
    210                 215                 220

Leu Ser Ile Met Arg Gly Lys Lys Met Lys Pro Cys Asp Arg Val Leu
225                 230                 235                 240

Phe Ser Val Gly Ser Thr Leu Tyr Pro Glu Ser Arg Lys Leu Leu Lys
```

```
                245                 250                 255
Ser Trp His Leu Pro Ser Val Phe His Leu Lys Gly Lys Leu Ser Phe
                260                 265                 270

Thr Cys Arg Cys Asp Thr Val Ser Cys Glu Gly Tyr Val Val Lys
            275                 280             285

Arg Ile Thr Ile Ser Pro Gly Leu Tyr Gly Lys Thr Thr Gly Tyr Ala
            290                 295                 300

Val Thr His His Ala Asp Gly Phe Leu Met Cys Lys Thr Thr Asp Thr
305                 310                 315                 320

Val Asp Gly Glu Arg Val Ser Phe Ser Val Cys Thr Tyr Val Pro Ala
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
                355                 360                 365

Asn Gly Arg Thr Gln Arg Asn Thr Asn Thr Met Lys Asn Tyr Leu Leu
            370                 375                 380

Pro Val Val Ala Gln Ala Phe Ser Lys Trp Ala Lys Glu Cys Arg Lys
385                 390                 395                 400

Asp Met Glu Asp Glu Lys Leu Leu Gly Ile Arg Glu Arg Thr Leu Thr
                405                 410                 415

Cys Cys Cys Leu Trp Ala Phe Lys Lys Gln Lys Thr His Thr Val Tyr
            420                 425                 430

Lys Arg Pro Asp Thr Gln Ser Ile Gln Lys Val Pro Ala Glu Phe Asp
            435                 440                 445

Ser Phe Val Val Pro Ser Leu Trp Ser Gly Leu Ser Ile Pro Leu
            450                 455                 460

Arg Thr Arg Ile Lys Trp Leu Leu Ser Lys Val Pro Lys Thr Asp Leu
465                 470                 475                 480

Ile Pro Tyr Ser Gly Asp Ala Lys Glu Ala Arg Asp Ala Glu Lys Glu
                485                 490                 495

Ala Glu Glu Glu Arg Glu Ala Glu Leu Thr Arg Glu Ala Leu Pro Pro
                500                 505                 510

Leu Gln Ala Ala Gln Asp Asp Val Gln Val Glu Ile Asp Val Glu Gln
            515                 520                 525

Leu Glu Asp Arg Ala Gly Ala Gly Ile Ile Glu Thr Pro Arg Gly Ala
            530                 535                 540

Ile Lys Val Thr Ala Gln Pro Thr Asp His Val Val Gly Glu Tyr Leu
545                 550                 555                 560

Val Leu Ser Pro Gln Thr Val Leu Arg Ser Gln Lys Leu Ser Leu Ile
                565                 570                 575

His Ala Leu Ala Glu Gln Val Lys Thr Cys Thr His Ser Gly Arg Ala
            580                 585                 590

Gly Arg Tyr Ala Val Glu Ala Tyr Asp Gly Arg Ile Leu Val Pro Ser
            595                 600                 605

Gly Tyr Ala Ile Ser Pro Glu Asp Phe Gln Ser Leu Ser Glu Ser Ala
            610                 615                 620

Thr Met Val Tyr Asn Glu Arg Glu Phe Val Asn Arg Lys Leu His His
625                 630                 635                 640

Ile Ala Leu His Gly Pro Ala Leu Asn Thr Asp Glu Glu Ser Tyr Glu
                645                 650                 655

Leu Val Arg Ala Glu Arg Thr Glu His Glu Tyr Val Tyr Asp Val Asp
            660                 665                 670
```

```
Gln Arg Arg Cys Cys Lys Lys Glu Glu Ala Ala Gly Leu Val Leu Val
            675                 680                 685

Gly Asp Leu Thr Asn Pro Pro Tyr His Glu Phe Ala Tyr Glu Gly Leu
    690                 695                 700

Arg Ile Arg Pro Ala Cys Pro Tyr Lys Thr Ala Val Ile Gly Val Phe
705                 710                 715                 720

Gly Val Pro Gly Ser Gly Lys Ser Ala Ile Ile Lys Asn Leu Val Thr
                725                 730                 735

Arg Gln Asp Leu Val Thr Ser Gly Lys Lys Glu Asn Cys Gln Glu Ile
                740                 745                 750

Ser Thr Asp Val Met Arg Gln Arg Asn Leu Glu Ile Ser Ala Arg Thr
                755                 760                 765

Val Asp Ser Leu Leu Leu Asn Gly Cys Asn Arg Pro Val Asp Val Leu
770                 775                 780

Tyr Val Asp Glu Ala Phe Ala Cys His Ser Gly Thr Leu Leu Ala Leu
785                 790                 795                 800

Ile Ala Leu Val Arg Pro Arg Gln Lys Val Val Leu Cys Gly Asp Pro
                805                 810                 815

Lys Gln Cys Gly Phe Phe Asn Met Met Gln Met Lys Val Asn Tyr Asn
                820                 825                 830

His Asn Ile Cys Thr Gln Val Tyr His Lys Ser Ile Ser Arg Arg Cys
                835                 840                 845

Thr Leu Pro Val Thr Ala Ile Val Ser Ser Leu His Tyr Glu Gly Lys
850                 855                 860

Met Arg Thr Thr Asn Glu Tyr Asn Lys Pro Ile Val Val Asp Thr Thr
865                 870                 875                 880

Gly Ser Thr Lys Pro Asp Pro Gly Asp Leu Val Leu Thr Cys Phe Arg
                885                 890                 895

Gly Trp Val Lys Gln Leu Gln Ile Asp Tyr Arg Gly His Glu Val Met
                900                 905                 910

Thr Ala Ala Ala Ser Gln Gly Leu Thr Arg Lys Gly Val Tyr Ala Val
                915                 920                 925

Arg Gln Lys Val Asn Glu Asn Pro Leu Tyr Ala Ser Thr Ser Glu His
                930                 935                 940

Val Asn Val Leu Leu Thr Arg Thr Glu Gly Lys Leu Val Trp Lys Thr
945                 950                 955                 960

Leu Ser Gly Asp Pro Trp Ile Lys Thr Leu Gln Asn Pro Pro Lys Gly
                965                 970                 975

Asn Phe Lys Ala Thr Ile Lys Glu Trp Glu Val Glu His Ala Ser Ile
                980                 985                 990

Met Ala Gly Ile Cys Asn His Gln Val Thr Phe Asp Thr Phe Gln Asn
                995                 1000                1005

Lys Ala Asn Val Cys Trp Ala Lys Ser Leu Val Pro Ile Leu Glu
                1010                1015                1020

Thr Ala Gly Ile Lys Leu Asn Asp Arg Gln Trp Ser Gln Ile Ile
                1025                1030                1035

Gln Ala Phe Lys Glu Asp Arg Ala Tyr Ser Pro Glu Val Ala Leu
                1040                1045                1050

Asn Glu Ile Cys Thr Arg Met Tyr Gly Val Asp Leu Asp Ser Gly
                1055                1060                1065

Leu Phe Ser Lys Pro Leu Val Ser Val Tyr Ala Asp Asn His
                1070                1075                1080
```

```
Trp Asp Asn Arg Pro Gly Gly Lys Met Phe Gly Phe Asn Pro Glu
1085                1090                1095

Ala Ala Ser Ile Leu Glu Arg Lys Tyr Pro Phe Thr Lys Gly Lys
1100                1105                1110

Trp Asn Thr Asn Lys Gln Ile Cys Val Thr Thr Arg Arg Ile Glu
1115                1120                1125

Asp Phe Asn Pro Asn Thr Asn Ile Ile Pro Ala Asn Arg Arg Leu
1130                1135                1140

Pro His Ser Leu Val Ala Glu His Arg Pro Val Lys Gly Glu Arg
1145                1150                1155

Met Glu Trp Leu Val Asn Lys Ile Asn Gly His His Val Leu Leu
1160                1165                1170

Val Ser Gly Tyr Asn Leu Val Leu Pro Thr Lys Arg Val Thr Trp
1175                1180                1185

Val Ala Pro Leu Gly Ile Arg Gly Ala Asp Tyr Thr Tyr Asn Leu
1190                1195                1200

Glu Leu Gly Leu Pro Ala Thr Leu Gly Arg Tyr Asp Leu Val Ile
1205                1210                1215

Ile Asn Ile His Thr Pro Phe Arg Ile His His Tyr Gln Gln Cys
1220                1225                1230

Val Asp His Ala Met Lys Leu Gln Met Leu Gly Gly Asp Ser Leu
1235                1240                1245

Arg Leu Leu Lys Pro Gly Gly Ser Leu Leu Ile Arg Ala Tyr Gly
1250                1255                1260

Tyr Ala Asp Arg Thr Ser Glu Arg Val Val Cys Val Leu Gly Arg
1265                1270                1275

Lys Phe Arg Ser Ser Arg Ala Leu Lys Pro Pro Cys Val Thr Ser
1280                1285                1290

Asn Thr Glu Met Phe Phe Leu Phe Ser Asn Phe Asp Asn Gly Arg
1295                1300                1305

Arg Asn Phe Thr Thr His Val Met Asn Asn Gln Leu Asn Ala Ala
1310                1315                1320

Phe Val Gly Gln Ala Thr Arg Ala Gly Cys Ala Pro Ser Tyr Arg
1325                1330                1335

Val Lys Arg Met Asp Ile Ala Lys Asn Asp Glu Glu Cys Val Val
1340                1345                1350

Asn Ala Ala Asn Pro Arg Gly Leu Pro Gly Asp Gly Val Cys Lys
1355                1360                1365

Ala Val Tyr Lys Lys Trp Pro Glu Ser Phe Lys Asn Ser Ala Thr
1370                1375                1380

Pro Val Gly Thr Ala Lys Thr Val Met Cys Gly Thr Tyr Pro Val
1385                1390                1395

Ile His Ala Val Gly Pro Asn Phe Ser Asn Tyr Ser Glu Ser Glu
1400                1405                1410

Gly Asp Arg Glu Leu Ala Ala Ala Tyr Arg Glu Val Ala Lys Glu
1415                1420                1425

Val Thr Arg Leu Gly Val Asn Ser Val Ala Ile Pro Leu Leu Ser
1430                1435                1440

Thr Gly Val Tyr Ser Gly Gly Lys Asp Arg Leu Thr Gln Ser Leu
1445                1450                1455

Asn His Leu Phe Thr Ala Leu Asp Ser Thr Asp Ala Asp Val Val
1460                1465                1470

Ile Tyr Cys Arg Asp Lys Glu Trp Glu Lys Lys Ile Ala Glu Ala
```

-continued

```
            1475                1480                1485
Ile Gln Met Arg Thr Gln Val Glu Leu Leu Asp Glu His Ile Ser
        1490                1495                1500
Val Asp Cys Asp Ile Ile Arg Val His Pro Asp Ser Ser Leu Ala
        1505                1510                1515
Gly Arg Lys Gly Tyr Ser Thr Thr Glu Gly Ser Leu Tyr Ser Tyr
        1520                1525                1530
Leu Glu Gly Thr Arg Phe His Gln Thr Ala Val Asp Met Ala Glu
        1535                1540                1545
Val Tyr Thr Met Trp Pro Lys Gln Thr Glu Ala Asn Glu Gln Val
        1550                1555                1560
Cys Leu Tyr Ala Leu Gly Glu Ser Ile Glu Ser Ile Arg Gln Lys
        1565                1570                1575
Cys Pro Val Asp Asp Ala Asp Ala Ser Ser Pro Pro Lys Thr Val
        1580                1585                1590
Pro Cys Leu Cys Arg Tyr Ala Met Thr Pro Glu Arg Val Thr Arg
        1595                1600                1605
Leu Arg Met Asn His Val Thr Ser Ile Ile Val Cys Ser Ser Phe
        1610                1615                1620
Pro Leu Pro Lys Tyr Lys Ile Glu Gly Val Gln Lys Val Lys Cys
        1625                1630                1635
Ser Lys Val Met Leu Phe Asp His Asn Val Pro Ser Arg Val Ser
        1640                1645                1650
Pro Arg Glu Tyr Lys Ser Pro Gln Glu Thr Ala Gln Glu Val Ser
        1655                1660                1665
Ser Thr Thr Ser Leu Thr His Ser Gln Phe Asp Leu Ser Val Asp
        1670                1675                1680
Gly Glu Glu Leu Pro Ala Pro Ser Asp Leu Glu Ala Asp Ala Pro
        1685                1690                1695
Ile Pro Glu Pro Thr Pro Asp Arg Ala Val Leu Thr Leu Pro
        1700                1705                1710
Pro Thr Ile Asp Asn Phe Ser Ala Val Ser Asp Trp Val Met Asn
        1715                1720                1725
Thr Ala Pro Val Ala Pro Pro Arg Arg Arg Arg Gly Lys Asn Leu
        1730                1735                1740
Asn Val Thr Cys Asp Glu Arg Glu Gly Asn Val Leu Pro Met Ala
        1745                1750                1755
Ser Val Arg Phe Phe Arg Ala Asp Leu His Ser Ile Val Gln Glu
        1760                1765                1770
Thr Ala Glu Ile Arg Asp Thr Ala Ala Ser Leu Gln Ala Pro Leu
        1775                1780                1785
Ser Val Ala Thr Glu Pro Asn Gln Leu Pro Ile Ser Phe Gly Ala
        1790                1795                1800
Pro Asn Glu Thr Phe Pro Ile Thr Phe Gly Asp Phe Asp Glu Gly
        1805                1810                1815
Glu Ile Glu Ser Leu Ser Ser Glu Leu Leu Thr Phe Gly Asp Phe
        1820                1825                1830
Ser Pro Gly Glu Val Asp Asp Leu Thr Asp Ser Asp Trp Ser Thr
        1835                1840                1845
Cys Ser Asp Thr Asp Asp Glu Leu Leu Asp Arg Ala Gly Gly Tyr
        1850                1855                1860
Ile Phe Ser Ser Asp Thr Gly Pro Gly His Leu Gln Gln Arg Ser
        1865                1870                1875
```

```
Val Arg Gln Thr Val Leu Pro Val Asn Thr Leu Glu Glu Val Gln
1880               1885               1890

Glu Glu Lys Cys Tyr Pro Pro Lys Leu Asp Glu Val Lys Glu Gln
1895               1900               1905

Leu Leu Leu Lys Lys Leu Gln Glu Ser Ala Ser Met Ala Asn Arg
1910               1915               1920

Ser Arg Tyr Gln Ser Arg Lys Val Glu Asn Met Lys Ala Thr Ile
1925               1930               1935

Val Gln Arg Leu Lys Gly Gly Cys Lys Leu Tyr Leu Met Ser Glu
1940               1945               1950

Thr Pro Lys Val Pro Thr Tyr Arg Thr Thr Tyr Pro Ala Pro Val
1955               1960               1965

Tyr Ser Pro Pro Ile Asn Ile Arg Leu Ser Asn Pro Glu Ser Ala
1970               1975               1980

Val Ala Ala Cys Asn Glu Phe Leu Ala Arg Asn Tyr Pro Thr Val
1985               1990               1995

Ala Ser Tyr Gln Ile Thr Asp Glu Tyr Asp Ala Tyr Leu Asp Met
2000               2005               2010

Val Asp Gly Ser Glu Ser Cys Leu Asp Arg Ala Thr Phe Asn Pro
2015               2020               2025

Ser Lys Leu Arg Ser Tyr Pro Lys Gln His Ser Tyr His Ala Pro
2030               2035               2040

Thr Ile Arg Ser Ala Val Pro Ser Pro Phe Gln Asn Thr Leu Gln
2045               2050               2055

Asn Val Leu Ala Ala Thr Lys Arg Asn Cys Asn Val Thr Gln
2060               2065               2070

Met Arg Glu Leu Pro Thr Leu Asp Ser Ala Val Phe Asn Val Glu
2075               2080               2085

Cys Phe Lys Lys Phe Ala Cys Asn Gln Glu Tyr Trp Lys Glu Phe
2090               2095               2100

Ala Ala Ser Pro Ile Arg Ile Thr Thr Glu Asn Leu Thr Thr Tyr
2105               2110               2115

Val Thr Lys Leu Lys Gly Pro Lys Ala Ala Ala Leu Phe Ala Lys
2120               2125               2130

Thr His Asn Leu Leu Pro Leu Gln Glu Val Pro Met Asp Arg Phe
2135               2140               2145

Thr Val Asp Met Lys Arg Asp Val Lys Val Thr Pro Gly Thr Lys
2150               2155               2160

His Thr Glu Glu Arg Pro Lys Val Gln Val Ile Gln Ala Ala Glu
2165               2170               2175

Pro Leu Ala Thr Ala Tyr Leu Cys Gly Ile His Arg Glu Leu Val
2180               2185               2190

Arg Arg Leu Asn Ala Val Leu Leu Pro Asn Val His Thr Leu Phe
2195               2200               2205

Asp Met Ser Ala Glu Asp Phe Asp Ala Ile Ile Ala Ala His Phe
2210               2215               2220

Lys Pro Gly Asp Ala Val Leu Glu Thr Asp Ile Ala Ser Phe Asp
2225               2230               2235

Lys Ser Gln Asp Asp Ser Leu Ala Leu Thr Ala Leu Met Leu Leu
2240               2245               2250

Glu Asp Leu Gly Val Asp His Pro Leu Leu Asp Leu Ile Glu Ala
2255               2260               2265
```

| | | | | | | | | | | | |
|---|---|---|---|---|---|---|---|---|---|---|---|
|Ala|Phe|Gly|Glu|Ile|Ser|Ser|Cys|His|Leu|Pro|Thr|Gly|Thr|Arg|
|2270| | | | |2275| | | | |2280| | | | |

Ala Phe Gly Glu Ile Ser Ser Cys His Leu Pro Thr Gly Thr Arg
    2270                2275                2280

Phe Lys Phe Gly Ala Met Met Lys Ser Gly Met Phe Leu Thr Leu
    2285                2290                2295

Phe Val Asn Thr Leu Leu Asn Ile Thr Ile Ala Ser Arg Val Leu
    2300                2305                2310

Glu Asp Arg Leu Thr Arg Ser Ala Cys Ala Ala Phe Ile Gly Asp
    2315                2320                2325

Asp Asn Ile Ile His Gly Val Val Ser Asp Glu Leu Met Ala Ala
    2330                2335                2340

Arg Cys Ala Thr Trp Met Asn Met Glu Val Lys Ile Ile Asp Ala
    2345                2350                2355

Val Val Ser Gln Lys Ala Pro Tyr Phe Cys Gly Gly Phe Ile Leu
    2360                2365                2370

Tyr Asp Thr Val Ala Gly Thr Ala Cys Arg Val Ala Asp Pro Leu
    2375                2380                2385

Lys Arg Leu Phe Lys Leu Gly Lys Pro Leu Ala Ala Gly Asp Glu
    2390                2395                2400

Gln Asp Asp Asp Arg Arg Arg Ala Leu Ala Asp Glu Val Val Arg
    2405                2410                2415

Trp Gln Arg Thr Gly Leu Thr Asp Glu Leu Glu Lys Ala Val His
    2420                2425                2430

Ser Arg Tyr Glu Val Gln Gly Ile Ser Val Val Val Met Ser Met
    2435                2440                2445

Ala Thr Phe Ala Ser Ser Arg Ser Asn Phe Glu Lys Leu Arg Gly
    2450                2455                2460

Pro Val Val Thr Leu Tyr Gly Gly Pro Lys
    2465                2470

<210> SEQ ID NO 7
<211> LENGTH: 11429
<212> TYPE: DNA
<213> ORGANISM: Mayaro virus

<400> SEQUENCE: 7

```
atggcgggca agtgacactt gttccgccgg acgtctctaa gctcttcctc tgcattgcaa    60
gagtttacca ctcagtatgt cgaaagtctt tgtagatatc gaggccgaga gcccgttttt   120
aaaatcacta cagagagcgt tccagcattt tgaagtggaa gcacagcagg ttacaccaaa   180
tgaccatgct aacgccagag cattctcgca tctggctact aaattgatag agcaagagac   240
cgaaaaagac acactcatcc tggatatcgg cagtgcgcct gccaggagaa tgatgtctga   300
gcacacgtac cattgtgtgt gcccaatgcg cagcgctgag gacccagagc gtctgctgta   360
ttatgccagg aagttagcca aggcatcagg tgaagtcgtt gacagaaata ttgcagcgaa   420
gatagacgac ctgcagtcag tgatggcgac cccggacaat gagtcacgga cattttgcct   480
tcacacagat cagacatgca ggactccagc tgaggtggca gtctatcagg atgtctatgc   540
agttcacgca ccgacttctt tgtacttcca ggcaatgaaa ggagtacgca cagcgtactg   600
gattgggttc gacactaccc cattcatgtt cgatacaatg gccggggctt atccaacata   660
tgcaaccaac tgggccgacg aacaggtgtt gaaagccagg aacataggac tgtgctccgc   720
ggcactgact gagggacacc ttggcaagct atcaataatg aggaagaaga gaatgaaacc   780
gagtgaccag ataatgttct cggtaggttc cacattgtat acggaaagcc gacgtctgct   840
aaagagttgg catctgccgt cagtgtttca tctgaaagga cgacaatcat atacgtgccg   900
```

```
gtgcgataca atagtgtcat gtgagggcta cgttgttaag aagataacga tgagcccagg     960
ggtattcgga aaaacgtcag ggtacgccgt cacacatcac gcagaaggat ttctggtatg    1020
taaaaccact gacactatcg caggagaacg agtttcgttc cccgtttgca cgtatgtgcc    1080
gtcgacgatc tgtgaccaaa tgacaggcat tctggcgact gaggtcacgc ccgaggatgc    1140
gcaaaaattg cttgtcggat taaaccagag gatcgtcgtg aatgggagga cccagagaaa    1200
cactaataca atgaagaact acctgctccc agtggtgtca caagcattta gtaagtgggc    1260
gaaagagtat cggcttgacc aagacgatga gaaaaacatg ggtatgcgcg aacgcaccct    1320
gacttgctgc tgcctgtggg cctttaagac ccataagaat cacaccatgt ataagaagcc    1380
agacacacag acgatcgtca gtgtcccgtc ggagttcaac tccttcgtga tccctagcct    1440
gtggtcagcg gggttgtcga tcggaattag acacaggatc aggcttcttt tgcagtcaag    1500
acgtgccgag ccgctcgttc catttatgga tgctagtgaa gccagagcag cagagaagga    1560
ggctgcagaa gctaaggagg cagaagagac actggcagcc ctaccacctc tgatcccgac    1620
cgctccgctg ctcgatgaca tccctgaagt tgatgtagag gagctggagt ttcgagcagg    1680
agccggtgtt gtcgaaacgc ctcggaacgc cctcaaagtt acaccacaag acagagacac    1740
tatggtaggt agctatctcg ttctgtctcc ccagacagtc ctgaaaagtg ttaaactgca    1800
ggtactgcac tccttggcag agcaagtaag aatcattacc cacaaaggcc gtgcagggcg    1860
ctaccaagtg gatgcctatg acggccgtgt tttaatcccg acaggcgcgg ctatcccggt    1920
acccgatttc caggctctaa gtgagagtgc gactatggtg tacaacgaac gtgagtttat    1980
caatcgcaaa ttgtaccaca tagccgtaca tggggcagcc ctgaacaccg atgaggaggg    2040
ttacgagaaa gtgcgggccg aaaggacaga tgccgagtac gttttttgacg tggatcgcaa    2100 acagtgcgtt aagagggagg atgccgaggg tctcgtgatg atcggagacc tggtcaaccc    2160
accattccac gaatttgcgt atgaaggact gaaacgaaga ccagcggctc catacaaaac    2220
aactgtagtc ggagtcttcg gcgtgcctgg atctggaaaa tcgggtataa tcaaaagcct    2280
ggtcacacgt gcggacttgg tcaccagtgg aaagagagag aactgtcagg agatcatgca    2340
cgacgtcaag agatacagag acctggacat cactgcaaaa acggtggatt ccgtactgtt    2400
gaatggcgtt aagcagactg tcgacgtctt gtacgtcgat gaggctttcg cttgccatgc    2460
agggacattg ctagcgctta tcgccacggt gcgaccacgt aagaaggttg tgcttttgcgg    2520 cgacccgaaa cagtgcggtt tcttcaactt gatgcaacta caggttaact ttaaccacaa    2580
catctgcacc gaggtacacc ataagagcat ttcagaagat gcacgctac cagtcaccgc    2640 cattgtctca acactacact atgagggcaa aatgcgcacc actaacccat acaataaacc    2700
cgttgtcatt gacaccacag gccagactaa accaaaccgc gaggacattg tgttaacatg    2760
tttccgcggt tgggttaagc agctgcaact tgactatcgt ggacacgaag tcatgacagc    2820
cgctgcatcc cagggggttga cccgaaaggg cgtgtacgcc gtccgaatga aggtcaacga    2880
aaacccactg tacgcacaat catcggagca tgttaatgtt ctactgacac gcacagaggg    2940
cagactagtg tggaagacac tgtcaggaga tccctggatc aaaactttga gcaacatccc    3000
aaaagggaat tcacagcaa ctttggaaga ttggcaacaa gagcacgacg ccattatgag    3060
ggcaataaca caagaagcag ccccttttgga cgtgttccaa aataaggcta aggtgtgttg    3120
ggccaagtgc ttggtacccg ttttggaaac cgcggggat aagttgtcag ccgccgattg    3180
gagctcaatc attttggctt tcaaagaaga cagagcttat tcaccagagg ttgcactgaa    3240
```

```
tgagatttgc actaaaatct acggggcgga tttggacagc ggcctgtttt cggctccacg    3300
cgtgtcgcta cactatacta caaatcattg ggataactcg cctggaggaa ggatgtacgg    3360
gttttccgtc gaggccgcca accgcctaga acaacggcac ccgttctaca ggggacggtg    3420
ggcttctggg caggtgttgg tcgcagaacg aagaactcag ccgattgaca tcacttgcaa    3480
cctaatcccc ttcaaccgga gactcccaca cgcgctggtc acggaatatc atccagttaa    3540
gggagaaaga gtggagtggc ttgtgaataa gatcccaggc tatcacttgc tactggttag    3600
cgagtataac ctcatactgc ctagaaggaa ggtaacgtgg attgccccgc cgactgtgac    3660
aggagccgat ttaacccacg acttggattt aggactaccg cctaatgctg gcaggtatga    3720
cctagtcttc gtcaacatgc atacaccgta taggctccat cactaccaac aatgcgtcga    3780
tcacgccatg aaattacaga tgctgggcgg cgacgcactc tacctgttga aacccggggg    3840
aagcctcctt ttgagagcct acggttatgc cgatagaacg agcgaggctg tggtgacggc    3900
tctcgctcgt cggttctcgt ccttcagagc ggtcagacct ccatgtgtga ctagtaacac    3960
cgaggtgttc ttactgttca cgaactttga caacggtaga agaacagtaa ccctgcatcc    4020
tacaaatggt aaattatcat caatttatgc aggtacagtg ctgcaggcgg ccggctgcgc    4080
tcccgcttat actgtcaaaa gggcagacat cgcgaccgcc attgaggatg cggtggtcaa    4140
tgcagctaac caccgtggac aagtgggcga cggagtctgc agggcagtag cacggaaatg    4200
gcctcaagcc ttccgcaacg cagcgacacc tgtcggaacc gcaaaaaccg tcaagtgcga    4260
cgagacttac atcatccacg cggtgggtcc aaattttaac aatacatctg aggctgaagg    4320
ggatcgtgac ttggcggcgg catacagggc cgtagcagcg gagattaacc gactgtctat    4380
aagtagtgtg gcgattccac tgctttccac aggtatattc agtgcaggaa aagatagagt    4440
gcatcagtcg ctttcgcacc ttctagcggc aatggacacc actgaagcac gggttactat    4500
ctactgccgc gataaaacgt gggagcaaaa gatcaaaaca gttctgcaga atcgctgcgc    4560
cactgaactg gtgtctgatg tgctacagct tgaagtcaat ttgaccagag tccatccgga    4620
cagcagcctg gtgggacgtc cagggtatag caccactgat gggaccttat attcctatat    4680
ggaaggtact aagttccacc aagcggctct tgacatggct gagatcacga ccttgtggcc    4740
gagagttcag gatgcaaatg aacacatctg catgtatgca ctgggcgaga cgatggacaa    4800
catccgctct agatgcccag ttgaggatag tgactcatcg actccaccga agacagtccc    4860
atgtctctgt cggtacgcta tgacaccaga gagagtcaca agactacgaa tgcatcacac    4920
aaaagatttt gtggtctgct cgtctttcca gctaccgaag taccgcatag ctggtgtgca    4980
gcgagtaaag tgcgaaaaag tgatgctttt tgatgcaact ccaccggcct ctgttagtcc    5040
tgtgcaatac ctgacgagtc acagtgaaac tactgtaagc ttgagctcgt tctcaattac    5100
atctgacagc agctccctaa gcaccttccc ggatctggag tcactagaag aactgggcaa    5160
tgatccacag tccatgcgga tggacgagtc tgacaaccgg caacccatat caacggtaga    5220
accggttgtt cgacccgtac cacctccgcg tcctaaacgt gccaggcgac tagcggctgc    5280
acgtatgcag gtccaggcgg aagtgcacca cccacccgtc gtccaaagga cgaaaccggt    5340
cccagcaccg cgcaccagtt tgcgtcccgt cccgcgcccc agaaggtgta tgccaagacc    5400
agcagtagag ctgccctggc cgcaggaggc cgtcgacata gagttcgggg cgccgaccga    5460
agaggagagt gaaatcacat tcggagactt ttctgcttcg gagtgggaga ccatcagcaa    5520
ctcatcctga ctaggccgag cggggcctta tatcttctca tcagacgtcg gtccaggca    5580
tctgcaacag aaatcagtga gacagcacga tctagaggtg ccgattatgg atcgcgtagt    5640
```

```
cgaggagaaa gtctacccgc cgaaactaga tgaggcaaaa gagaaacagc tgctcctaaa    5700
actgcagatg catgccacag acgccaaccg gagccggtac caatcaagga aagttgagaa    5760
cataaaagca acgatcattg accggctgaa acaaggcagc gcatcctaca tctcggctga    5820
ggccaataaa gcaatcacat accatgtcaa atatgctaag cctcggtact ctgtgccggt    5880
gatgcaaaga cttagcagtg caaccaccgc agttgccgct tgcaatgaat tcctggcccg    5940
gaactaccct acagtggcgt catatcagat caccgatgag tacgacgctt atttagatat    6000
ggtggacggg tcagaaagct gcctagacag agcaaacttc tgcccggcga agttgcgctg    6060
ctatccaaaa caccatgcat accatgtacc ccagattaga agtgctgttc cttcgccatt    6120
ccaaaacacg ttgcagaatg tattagcggc cgccactaag cgtaattgca acgtcaccca    6180
gatgcgtgaa ctaccaaccc tggattcagc cgtgtacaac gtggaatgtt ccgcaagta    6240 cgcctgtaac aacgaatatt gggaagagtt tgctgctaaa cctatcagaa ttacaacaga    6300
gaatttgacc acttatgtga ccaaattaaa aggtggaaag gcagccgccc tgtttgcaaa    6360
gacgcataac ttagttccac tgcaggaggt tccaatggat agattcgtca tggacatgaa    6420
gcgcgatgtg aaggttacac cagggacgaa gcacacagag aacgaccaa aggtccaagt    6480 gattcaagct gccgagcctc tggctaccgc ctacctgtgt ggaattcaca gagaactggt    6540
tcgccggctc aatgctgtgt tgctacctaa catccatacc ctgtttgaca tgtctgctga    6600
agattttgat gccatcatat cagagcactt caagccaggg gaccatgtct ggaaacgga    6660 catcgcttct tttgacaaaa gccaggacga ttcactggca ctaacggggc taatgatact    6720
ggaagacttg ggcgtcgata accagttatt ggatcttatc gaggctgcat ttggtcagat    6780
taccagctgc caccgtgccta cagggactag gttttaaattt ggggctatga tgaagtcagg    6840 catgttctt acattgttca ttaacaccgt tttgaacatt accattgcca gtagagtgct    6900
ggaagccaga ttaactaact cagcctgtgc cgcatttatc ggcgacgaca acgtggttca    6960
cggagtcgtc tccgataaac tgatggcaga tagatgtgcc acttgggtta acatggaggt    7020
taaaataata gatgcagtca tgtgtgcaaa gccaccgtat ttctgtggag gcttttttggt    7080 ctatgatcat gtcacaagga cgtcatgtcg aatagcggat ccattaaaaa ggttattcaa    7140
attgggcaaa cccctgccgg cagacgactg ccaagatgaa gaccgccgta gggcattgca    7200
cgacgaggtt aaaaaatggt ttagatcagg cttgggttcg gagattgagg tcgccctcgc    7260
caccagatac gaggtggaag ggggtcacaa cctactgctg gctatgtcca cctttgcaca    7320
cagcatgaag aattttttctg cattgagggg acccgtcata cacttgtacg gcggtcctaa    7380
ataggtgctc tacacgacac ctataccacc atggatttcc taccaacaca agtgttttat    7440
ggcaggcgat ggagaccacg aatgccgcca cgcccttgga ggccacgccc acctacaatt    7500
caaagaccag atcaacaggc ccgacaaatg cagcagctga ttgctgcggt cagtacgctt    7560
gcccttaggc aaaacgctgc tgcccctcag cgtggaagaa agaagcaacc acgtagaaag    7620
aaaccaaaac cacaacccga gaaacctaag aagcaagagc agaaaccgaa gcaaaagaag    7680
acccctaaga agaagcccgg gagaagggag cgcatgtgca tgaagattga gcacgattgc    7740
atctttgagg tcaagcacga aggaaaggtc acaggctatg cttgccttgt cggtgacaaa    7800
gtaatgaagc cggcacacgt ccctggagtg atagacaaca tcgatctcgc acgtctatcg    7860
tataagaaat ctagtaagta tgacctggaa tgtgcacaga taccggtggc tatgaagtca    7920
gatgcatcga aatacaccca tgaaaaaccc gaaggtcact ataactggca ctatgggcc    7980
```

| | |
|---|---|
| gtccagtaca caggaggcag attcacggtg cccacaggag tgggtaagcc tggcgacagc | 8040 |
| ggccggccca tctttgataa caagggccgc gttgtcgcaa tagtgctagg aggagctaat | 8100 |
| gaaggtgcca gaaccgcgct ctctgtcgtg acgtggaata aagacatggt caccaagatc | 8160 |
| acaccggagg gcacagagga gtgggcagct ccgacagtga cagctatgtg ccttctggcg | 8220 |
| aatgtatcct tcccatgttt ccaaccgagc tgctctccat gctgttatga aaagggcct | 8280 |
| gagccgacgc tgagaatgct ggaagagaac gtaaactcag agggatacta tgaattgttg | 8340 |
| catgctgccg tgtactgcaa aaacagctcg aggtcgaaga ggagcactgc aaatcacttt | 8400 |
| aacgcataca aattgactcg tccatacgta gcctactgtg cagactgtgg catgggccat | 8460 |
| tcttgccaca gtcccgccat gattgaaaat gtgcaggcgg atgctacaga tggcacgtta | 8520 |
| aagattcaat tcgcttctca aattggccta acgaaagcgg acacgcatga tcatacaaag | 8580 |
| attagatatg cagaagggca tgatatagcg gaggctgcca ggtcaactct taaggtccat | 8640 |
| agcagcagtg agtgcgcggt gacaggaacg atgggacact ttatcttggc caaatgtcca | 8700 |
| ccaggcgaag tcattagtgt ctcatttgtt gattcaaaaa atgaacagcg acctgtcgg | 8760 |
| atagcctacc accatgaaca gaggctaata gggcgtgaaa gattcacggt acgaccacat | 8820 |
| catgggattg agctaccctg caccacttac cagctaacga ccgccgaaac ctctgaagag | 8880 |
| atagacatgc acatgccgcc ggacattccg gacagaacta tcctttccca gcaatcagga | 8940 |
| aatgtcaaga taacggtcaa cgggcggacc gtcaagtata gctgctcatg tggttctaaa | 9000 |
| ccatcaggca aacaactac agacaagact atcaatagct gcaccgttga caaatgccag | 9060 |
| gcatatgtca cgagccatac gaaatggcaa tttaattcac ctttcgttcc gcgcgcggag | 9120 |
| caagcggagc gtaagggcaa ggtgcacatt ccctttccac ttatcaacac cacctgccga | 9180 |
| gtaccattgg ctcccgaagc cctagtcagg agcggtaaac gagaagctac gctctcactg | 9240 |
| cacccgatac atcccacatt gctaagttac agaacactgg gacgcgagcc agttttgat | 9300 |
| gaacagtgga tcaccaccca gacggaggta acaatcccag taccagtgga gggagtggag | 9360 |
| tatcggtggg gcaaccacaa accacaacgc ttgtggtcac agctaacaac tgatggcaga | 9420 |
| gcacatggct ggcccatga aattatcgag tactactacg gctgcatcc tacgacaacc | 9480 |
| attgtcgtgg tggttgctgt ctcagtagtg gtgctcttgt cagttgctgc atctgtttat | 9540 |
| atgtgtgtag tggcacgcaa caagtgcctg acaccatatg cactcacccc ggggccgtt | 9600 |
| gtccctgtta ctatcggggt attatgctgt gcaccgaaag cgcacgcagc tagctttgct | 9660 |
| gaaggcatgg cctacctgtg ggataataac cagtcaatgt tctggatgga gttgactgga | 9720 |
| cctttggctc ttcttatcct gactacatgt gtgcgcccgat cactactttc ctgctgcaag | 9780 |
| ggatctttt tagtcgcagt gagcgtcggg agtgccgttg ccagtgctta cgagcacacg | 9840 |
| gcagtcattc caaatcaagt gggattcccg tataaggctc atgttgcacg tgaaggatac | 9900 |
| agcccgctga cactgcagat gcaggtggtt gaaaccagtc tagagccaac gctcaacctg | 9960 |
| gagtatatca cttgcgacta caaaacaaag gttccatccc cgtacgtaaa gtgctgtggc | 10020 |
| acagctgaat gccgcacgca ggacaagccc gaatacaagt gtgcggtgtt cacgggcgtg | 10080 |
| tacccttta tgtggggagg tgcatactgt ttttgtgact cggaaaacac acagatgagt | 10140 |
| gaggcctacg tggagcgcgc tgacgtgtgc aaacacgact acgcagccgc ctaccgcgcc | 10200 |
| cacactgctt ccctcagagc caaaatcaag gtaacatatg gcaccgtaaa tcagactgtc | 10260 |
| gaggcgtatg tgaacggtga ccatgccgta acgattgccg ggacgaagtt tatctttggt | 10320 |
| ccggtgtcaa cggcctggac accgttcgat actaaaatcg tggtctataa agggaggta | 10380 |

-continued

```
tacaaccagg actttccccc ttatggtgcc gggcagcctg gaagattcgg agacatccag    10440
agtaggacgt tggacagtaa ggacctatat gcaaacacgg gccttaagct ggcaagacca    10500
gcagccggca acatccacgt cccctatacc cagacaccat ctggttttaa aacatggcaa    10560
aaagacaggg actcaccgtt aaacgctaag cacccttg  gatgcacaat ccagacaaat    10620
ccggtcagag cgatgaattg cgctgtcggc aacatacccg tttcgatgga tatcgccgac    10680
agcgcattca ctagactgac tgatgcgcct ataatatcag agctgctgtg cactgtatct    10740
acatgcacgc attcttcaga cttcggtgga gtcgctgtac tttcttacaa ggtggaaaaa    10800
gcaggcaggt gcgacgtcca ttcgcactcg aatgtcgcgg tactccagga agtttccatc    10860
gaggcagaag gtcgatcagt gatccacttt tcgaccgcat cagccgcccc ttccttcata    10920
gtatccgtct gcagctcgcg tgccacgtgc acagctaaat gtgaaccacc gaaagaccat    10980
gtggtcactt acccggcaaa tcacaacggg ataactttgc cggacttatc cagcactgca    11040
atgacttggg cgcaacatct tgccggtgga gtcgggctat tgatagcact ggcagtgcta    11100
attctagtaa tagttacttg cataactttg agaaggtgaa tcataagtac catgtataat    11160
gcgggctggc atatatgtaa ccattattat atatttaac  catattaaca ttcgaatatc    11220
aaattaggtg ccgtgcatga tgcggaccga tttattattc acatatgtaa cctttatcat    11280
attacatcat atattcaatt ttaaaatttc tatacgcgtc tctaatggcg catataataa    11340
ccacctacaa ttttcttcat tttctttatt tgtgccacta tagggcactt actaaccata    11400
gaagtaattc attttgtttt taatatttc                                      11429
```

<210> SEQ ID NO 8
<211> LENGTH: 1242
<212> TYPE: PRT
<213> ORGANISM: Mayaro virus

<400> SEQUENCE: 8

```
Met Asp Phe Leu Pro Thr Gln Val Phe Tyr Gly Arg Arg Trp Arg Pro
1               5                   10                  15

Arg Met Pro Pro Arg Pro Trp Arg Pro Arg Pro Pro Thr Ile Gln Arg
            20                  25                  30

Pro Asp Gln Gln Ala Arg Gln Met Gln Gln Leu Ile Ala Ala Val Ser
        35                  40                  45

Thr Leu Ala Leu Arg Gln Asn Ala Ala Ala Pro Gln Arg Gly Arg Lys
    50                  55                  60

Lys Gln Pro Arg Arg Lys Lys Pro Lys Pro Gln Pro Glu Lys Pro Lys
65                  70                  75                  80

Lys Gln Glu Gln Lys Pro Lys Gln Lys Lys Thr Pro Lys Lys Lys Pro
                85                  90                  95

Gly Arg Arg Glu Arg Met Cys Met Lys Ile Glu His Asp Cys Ile Phe
            100                 105                 110

Glu Val Lys His Glu Gly Lys Val Thr Gly Tyr Ala Cys Leu Val Gly
        115                 120                 125

Asp Lys Val Met Lys Pro Ala His Val Pro Gly Val Ile Asp Asn Ile
    130                 135                 140

Asp Leu Ala Arg Leu Ser Tyr Lys Lys Ser Ser Lys Tyr Asp Leu Glu
145                 150                 155                 160

Cys Ala Gln Ile Pro Val Ala Met Lys Ser Asp Ala Ser Lys Tyr Thr
                165                 170                 175

His Glu Lys Pro Glu Gly His Tyr Asn Trp His Tyr Gly Ala Val Gln
```

```
            180                 185                 190
Tyr Thr Gly Gly Arg Phe Thr Val Pro Thr Gly Val Gly Lys Pro Gly
            195                 200                 205

Asp Ser Gly Arg Pro Ile Phe Asp Asn Lys Gly Arg Val Val Ala Ile
210                 215                 220

Val Leu Gly Gly Ala Asn Glu Gly Ala Arg Thr Ala Leu Ser Val Val
225                 230                 235                 240

Thr Trp Asn Lys Asp Met Val Thr Lys Ile Thr Pro Glu Gly Thr Glu
                245                 250                 255

Glu Trp Ala Ala Pro Thr Val Thr Ala Met Cys Leu Leu Ala Asn Val
                260                 265                 270

Ser Phe Pro Cys Phe Gln Pro Ser Cys Ser Pro Cys Cys Tyr Glu Lys
            275                 280                 285

Gly Pro Glu Pro Thr Leu Arg Met Leu Glu Glu Asn Val Asn Ser Glu
            290                 295                 300

Gly Tyr Tyr Glu Leu Leu His Ala Ala Val Tyr Cys Lys Asn Ser Ser
305                 310                 315                 320

Arg Ser Lys Arg Ser Thr Ala Asn His Phe Asn Ala Tyr Lys Leu Thr
                325                 330                 335

Arg Pro Tyr Val Ala Tyr Cys Ala Asp Cys Gly Met Gly His Ser Cys
                340                 345                 350

His Ser Pro Ala Met Ile Glu Asn Val Gln Ala Asp Ala Thr Asp Gly
            355                 360                 365

Thr Leu Lys Ile Gln Phe Ala Ser Gln Ile Gly Leu Thr Lys Ala Asp
            370                 375                 380

Thr His Asp His Thr Lys Ile Arg Tyr Ala Glu Gly His Asp Ile Ala
385                 390                 395                 400

Glu Ala Ala Arg Ser Thr Leu Lys Val His Ser Ser Glu Cys Ala
                405                 410                 415

Val Thr Gly Thr Met Gly His Phe Ile Leu Ala Lys Cys Pro Pro Gly
            420                 425                 430

Glu Val Ile Ser Val Ser Phe Val Asp Ser Lys Asn Glu Gln Arg Thr
            435                 440                 445

Cys Arg Ile Ala Tyr His His Glu Gln Arg Leu Ile Gly Arg Glu Arg
            450                 455                 460

Phe Thr Val Arg Pro His His Gly Ile Glu Leu Pro Cys Thr Thr Tyr
465                 470                 475                 480

Gln Leu Thr Thr Ala Glu Thr Ser Glu Glu Ile Asp Met His Met Pro
                485                 490                 495

Pro Asp Ile Pro Asp Arg Thr Ile Leu Ser Gln Gln Ser Gly Asn Val
            500                 505                 510

Lys Ile Thr Val Asn Gly Arg Thr Val Lys Tyr Ser Cys Ser Cys Gly
            515                 520                 525

Ser Lys Pro Ser Gly Thr Thr Thr Thr Asp Lys Thr Ile Asn Ser Cys
530                 535                 540

Thr Val Asp Lys Cys Gln Ala Tyr Val Thr Ser His Thr Lys Trp Gln
545                 550                 555                 560

Phe Asn Ser Pro Phe Val Pro Arg Ala Glu Gln Ala Glu Arg Lys Gly
                565                 570                 575

Lys Val His Ile Pro Phe Pro Leu Ile Asn Thr Thr Cys Arg Val Pro
            580                 585                 590

Leu Ala Pro Glu Ala Leu Val Arg Ser Gly Lys Arg Glu Ala Thr Leu
            595                 600                 605
```

-continued

```
Ser Leu His Pro Ile His Pro Thr Leu Leu Ser Tyr Arg Thr Leu Gly
    610             615                 620

Arg Glu Pro Val Phe Asp Glu Gln Trp Ile Thr Thr Gln Thr Glu Val
625                 630                 635                 640

Thr Ile Pro Val Pro Val Glu Gly Val Glu Tyr Arg Trp Gly Asn His
                645                 650                 655

Lys Pro Gln Arg Leu Trp Ser Gln Leu Thr Thr Asp Gly Arg Ala His
                660                 665                 670

Gly Trp Pro His Glu Ile Ile Glu Tyr Tyr Gly Leu His Pro Thr
                675                 680                 685

Thr Thr Ile Val Val Val Ala Val Ser Val Val Leu Leu Ser
    690                 695                 700

Val Ala Ala Ser Val Tyr Met Cys Val Ala Arg Asn Lys Cys Leu
705                 710                 715                 720

Thr Pro Tyr Ala Leu Thr Pro Gly Ala Val Pro Val Thr Ile Gly
                725                 730                 735

Val Leu Cys Cys Ala Pro Lys Ala His Ala Ala Ser Phe Ala Glu Gly
                740                 745                 750

Met Ala Tyr Leu Trp Asp Asn Asn Gln Ser Met Phe Trp Met Glu Leu
                755                 760                 765

Thr Gly Pro Leu Ala Leu Leu Ile Leu Thr Thr Cys Cys Ala Arg Ser
770                 775                 780

Leu Leu Ser Cys Cys Lys Gly Ser Phe Leu Val Ala Val Ser Val Gly
785                 790                 795                 800

Ser Ala Val Ala Ser Ala Tyr Glu His Thr Ala Val Ile Pro Asn Gln
                805                 810                 815

Val Gly Phe Pro Tyr Lys Ala His Val Ala Arg Glu Gly Tyr Ser Pro
                820                 825                 830

Leu Thr Leu Gln Met Gln Val Val Glu Thr Ser Leu Glu Pro Thr Leu
                835                 840                 845

Asn Leu Glu Tyr Ile Thr Cys Asp Tyr Lys Thr Lys Val Pro Ser Pro
850                 855                 860

Tyr Val Lys Cys Cys Gly Thr Ala Glu Cys Arg Thr Gln Asp Lys Pro
865                 870                 875                 880

Glu Tyr Lys Cys Ala Val Phe Thr Gly Val Tyr Pro Phe Met Trp Gly
                885                 890                 895

Gly Ala Tyr Cys Phe Cys Asp Ser Glu Asn Thr Gln Met Ser Glu Ala
                900                 905                 910

Tyr Val Glu Arg Ala Asp Val Cys Lys His Asp Tyr Ala Ala Ala Tyr
                915                 920                 925

Arg Ala His Thr Ala Ser Leu Arg Ala Lys Ile Lys Val Thr Tyr Gly
    930                 935                 940

Thr Val Asn Gln Thr Val Glu Ala Tyr Val Asn Gly Asp His Ala Val
945                 950                 955                 960

Thr Ile Ala Gly Thr Lys Phe Ile Phe Gly Pro Val Ser Thr Ala Trp
                965                 970                 975

Thr Pro Phe Asp Thr Lys Ile Val Val Tyr Lys Gly Glu Val Tyr Asn
                980                 985                 990

Gln Asp Phe Pro Pro Tyr Gly Ala Gly Gln Pro Gly Arg Phe Gly Asp
                995                 1000                1005

Ile Gln Ser Arg Thr Leu Asp Ser Lys Asp Leu Tyr Ala Asn Thr
    1010                1015                1020
```

Gly Leu Lys Leu Ala Arg Pro Ala Ala Gly Asn Ile His Val Pro
1025                1030                1035

Tyr Thr Gln Thr Pro Ser Gly Phe Lys Thr Trp Gln Lys Asp Arg
1040                1045                1050

Asp Ser Pro Leu Asn Ala Lys Ala Pro Phe Gly Cys Thr Ile Gln
1055                1060                1065

Thr Asn Pro Val Arg Ala Met Asn Cys Ala Val Gly Asn Ile Pro
1070                1075                1080

Val Ser Met Asp Ile Ala Asp Ser Ala Phe Thr Arg Leu Thr Asp
1085                1090                1095

Ala Pro Ile Ile Ser Glu Leu Leu Cys Thr Val Ser Thr Cys Thr
1100                1105                1110

His Ser Ser Asp Phe Gly Gly Val Ala Val Leu Ser Tyr Lys Val
1115                1120                1125

Glu Lys Ala Gly Arg Cys Asp Val His Ser His Ser Asn Val Ala
1130                1135                1140

Val Leu Gln Glu Val Ser Ile Glu Ala Glu Gly Arg Ser Val Ile
1145                1150                1155

His Phe Ser Thr Ala Ser Ala Ala Pro Ser Phe Ile Val Ser Val
1160                1165                1170

Cys Ser Ser Arg Ala Thr Cys Thr Ala Lys Cys Glu Pro Pro Lys
1175                1180                1185

Asp His Val Val Thr Tyr Pro Ala Asn His Asn Gly Ile Thr Leu
1190                1195                1200

Pro Asp Leu Ser Ser Thr Ala Met Thr Trp Ala Gln His Leu Ala
1205                1210                1215

Gly Gly Val Gly Leu Leu Ile Ala Leu Ala Val Leu Ile Leu Val
1220                1225                1230

Ile Val Thr Cys Ile Thr Leu Arg Arg
1235                1240

<210> SEQ ID NO 9
<211> LENGTH: 2434
<212> TYPE: PRT
<213> ORGANISM: Mayaro virus

<400> SEQUENCE: 9

Met Ser Lys Val Phe Val Asp Ile Glu Ala Glu Ser Pro Phe Leu Lys
1               5                   10                  15

Ser Leu Gln Arg Ala Phe Pro Ala Phe Glu Val Glu Ala Gln Gln Val
                20                  25                  30

Thr Pro Asn Asp His Ala Asn Ala Arg Ala Phe Ser His Leu Ala Thr
            35                  40                  45

Lys Leu Ile Glu Gln Glu Thr Glu Lys Asp Thr Leu Ile Leu Asp Ile
        50                  55                  60

Gly Ser Ala Pro Ala Arg Arg Met Met Ser Glu His Thr Tyr His Cys
65                  70                  75                  80

Val Cys Pro Met Arg Ser Ala Glu Asp Pro Glu Arg Leu Leu Tyr Tyr
                85                  90                  95

Ala Arg Lys Leu Ala Lys Ala Ser Gly Glu Val Val Asp Arg Asn Ile
            100                 105                 110

Ala Ala Lys Ile Asp Asp Leu Gln Ser Val Met Ala Thr Pro Asp Asn
        115                 120                 125

Glu Ser Arg Thr Phe Cys Leu His Thr Asp Gln Thr Cys Arg Thr Pro
    130                 135                 140

```
Ala Glu Val Ala Val Tyr Gln Asp Val Tyr Ala Val His Ala Pro Thr
145                 150                 155                 160

Ser Leu Tyr Phe Gln Ala Met Lys Gly Val Arg Thr Ala Tyr Trp Ile
            165                 170                 175

Gly Phe Asp Thr Thr Pro Phe Met Phe Asp Thr Met Ala Gly Ala Tyr
            180                 185                 190

Pro Thr Tyr Ala Thr Asn Trp Ala Asp Glu Gln Val Leu Lys Ala Arg
            195                 200                 205

Asn Ile Gly Leu Cys Ser Ala Ala Leu Thr Glu Gly His Leu Gly Lys
            210                 215                 220

Leu Ser Ile Met Arg Lys Arg Met Lys Pro Ser Asp Gln Ile Met
225                 230                 235                 240

Phe Ser Val Gly Ser Thr Leu Tyr Thr Glu Ser Arg Arg Leu Leu Lys
                245                 250                 255

Ser Trp His Leu Pro Ser Val Phe His Leu Lys Gly Arg Gln Ser Tyr
            260                 265                 270

Thr Cys Arg Cys Asp Thr Ile Val Ser Cys Glu Gly Tyr Val Val Lys
        275                 280                 285

Lys Ile Thr Met Ser Pro Gly Val Phe Gly Lys Thr Ser Gly Tyr Ala
290                 295                 300

Val Thr His His Ala Glu Gly Phe Leu Val Cys Lys Thr Thr Asp Thr
305                 310                 315                 320

Ile Ala Gly Glu Arg Val Ser Phe Pro Val Cys Thr Tyr Val Pro Ser
                325                 330                 335

Thr Ile Cys Asp Gln Met Thr Gly Ile Leu Ala Thr Glu Val Thr Pro
            340                 345                 350

Glu Asp Ala Gln Lys Leu Leu Val Gly Leu Asn Gln Arg Ile Val Val
            355                 360                 365

Asn Gly Arg Thr Gln Arg Asn Thr Asn Thr Met Lys Asn Tyr Leu Leu
370                 375                 380

Pro Val Val Ser Gln Ala Phe Ser Lys Trp Ala Lys Glu Tyr Arg Leu
385                 390                 395                 400

Asp Gln Asp Asp Glu Lys Asn Met Gly Met Arg Glu Arg Thr Leu Thr
                405                 410                 415

Cys Cys Cys Leu Trp Ala Phe Lys Thr His Lys Asn His Thr Met Tyr
            420                 425                 430

Lys Lys Pro Asp Thr Gln Thr Ile Val Ser Val Pro Ser Glu Phe Asn
            435                 440                 445

Ser Phe Val Ile Pro Ser Leu Trp Ser Ala Gly Leu Ser Ile Gly Ile
            450                 455                 460

Arg His Arg Ile Arg Leu Leu Leu Gln Ser Arg Arg Ala Glu Pro Leu
465                 470                 475                 480

Val Pro Phe Met Asp Ala Ser Glu Ala Arg Ala Ala Lys Glu Ala
                485                 490                 495

Ala Glu Ala Lys Glu Ala Glu Glu Thr Leu Ala Ala Leu Pro Pro Leu
            500                 505                 510

Ile Pro Thr Ala Pro Leu Leu Asp Asp Ile Pro Glu Val Asp Val Glu
            515                 520                 525

Glu Leu Glu Phe Arg Ala Gly Ala Gly Val Val Glu Thr Pro Arg Asn
            530                 535                 540

Ala Leu Lys Val Thr Pro Gln Asp Arg Asp Thr Met Val Gly Ser Tyr
545                 550                 555                 560
```

-continued

Leu Val Leu Ser Pro Gln Thr Val Leu Lys Ser Val Lys Leu Gln Val
            565                 570                 575

Leu His Ser Leu Ala Glu Gln Val Arg Ile Ile Thr His Lys Gly Arg
            580                 585                 590

Ala Gly Arg Tyr Gln Val Asp Ala Tyr Asp Gly Arg Val Leu Ile Pro
            595                 600                 605

Thr Gly Ala Ala Ile Pro Val Pro Asp Phe Gln Ala Leu Ser Glu Ser
            610                 615                 620

Ala Thr Met Val Tyr Asn Glu Arg Glu Phe Ile Asn Arg Lys Leu Tyr
625                 630                 635                 640

His Ile Ala Val His Gly Ala Ala Leu Asn Thr Asp Glu Glu Gly Tyr
                645                 650                 655

Glu Lys Val Arg Ala Glu Arg Thr Asp Ala Glu Tyr Val Phe Asp Val
            660                 665                 670

Asp Arg Lys Gln Cys Val Lys Arg Glu Asp Ala Glu Gly Leu Val Met
            675                 680                 685

Ile Gly Asp Leu Val Asn Pro Pro Phe His Glu Phe Ala Tyr Glu Gly
            690                 695                 700

Leu Lys Arg Arg Pro Ala Ala Pro Tyr Lys Thr Thr Val Val Gly Val
705                 710                 715                 720

Phe Gly Val Pro Gly Ser Gly Lys Ser Gly Ile Ile Lys Ser Leu Val
                725                 730                 735

Thr Arg Ala Asp Leu Val Thr Ser Gly Lys Arg Glu Asn Cys Gln Glu
            740                 745                 750

Ile Met His Asp Val Lys Arg Tyr Arg Asp Leu Asp Ile Thr Ala Lys
            755                 760                 765

Thr Val Asp Ser Val Leu Leu Asn Gly Val Lys Gln Thr Val Asp Val
770                 775                 780

Leu Tyr Val Asp Glu Ala Phe Ala Cys His Ala Gly Thr Leu Leu Ala
785                 790                 795                 800

Leu Ile Ala Thr Val Arg Pro Arg Lys Lys Val Val Leu Cys Gly Asp
                805                 810                 815

Pro Lys Gln Cys Gly Phe Phe Asn Leu Met Gln Leu Gln Val Asn Phe
            820                 825                 830

Asn His Asn Ile Cys Thr Glu Val His His Lys Ser Ile Ser Arg Arg
            835                 840                 845

Cys Thr Leu Pro Val Thr Ala Ile Val Ser Thr Leu His Tyr Glu Gly
850                 855                 860

Lys Met Arg Thr Thr Asn Pro Tyr Asn Lys Pro Val Val Ile Asp Thr
865                 870                 875                 880

Thr Gly Gln Thr Lys Pro Asn Arg Glu Asp Ile Val Leu Thr Cys Phe
                885                 890                 895

Arg Gly Trp Val Lys Gln Leu Gln Leu Asp Tyr Arg Gly His Glu Val
            900                 905                 910

Met Thr Ala Ala Ala Ser Gln Gly Leu Thr Arg Lys Gly Val Tyr Ala
            915                 920                 925

Val Arg Met Lys Val Asn Glu Asn Pro Leu Tyr Ala Gln Ser Ser Glu
930                 935                 940

His Val Asn Val Leu Leu Thr Arg Thr Glu Gly Arg Leu Val Trp Lys
945                 950                 955                 960

Thr Leu Ser Gly Asp Pro Trp Ile Lys Thr Leu Ser Asn Ile Pro Lys
                965                 970                 975

Gly Asn Phe Thr Ala Thr Leu Glu Asp Trp Gln Gln Glu His Asp Ala

```
                980             985              990
Ile Met Arg Ala Ile Thr Gln Glu  Ala Ala Pro Leu Asp  Val Phe Gln
               995             1000             1005

Asn Lys  Ala Lys Val Cys Trp  Ala Lys Cys Leu Val  Pro Val Leu
         1010            1015             1020

Glu Thr  Ala Gly Ile Lys Leu  Ser Ala Ala Asp Trp  Ser Ser Ile
         1025            1030             1035

Ile Leu  Ala Phe Lys Glu Asp  Arg Ala Tyr Ser Pro  Glu Val Ala
         1040            1045             1050

Leu Asn  Glu Ile Cys Thr Lys  Ile Tyr Gly Ala Asp  Leu Asp Ser
         1055            1060             1065

Gly Leu  Phe Ser Ala Pro Arg  Val Ser Leu His Tyr  Thr Thr Asn
         1070            1075             1080

His Trp  Asp Asn Ser Pro Gly  Gly Arg Met Tyr Gly  Phe Ser Val
         1085            1090             1095

Glu Ala  Ala Asn Arg Leu Glu  Gln Arg His Pro Phe  Tyr Arg Gly
         1100            1105             1110

Arg Trp  Ala Ser Gly Gln Val  Leu Val Ala Glu Arg  Arg Thr Gln
         1115            1120             1125

Pro Ile  Asp Ile Thr Cys Asn  Leu Ile Pro Phe Asn  Arg Arg Leu
         1130            1135             1140

Pro His  Ala Leu Val Thr Glu  Tyr His Pro Val Lys  Gly Glu Arg
         1145            1150             1155

Val Glu  Trp Leu Val Asn Lys  Ile Pro Gly Tyr His  Leu Leu Leu
         1160            1165             1170

Val Ser  Glu Tyr Asn Leu Ile  Leu Pro Arg Arg Lys  Val Thr Trp
         1175            1180             1185

Ile Ala  Pro Pro Thr Val Thr  Gly Ala Asp Leu Thr  His Asp Leu
         1190            1195             1200

Asp Leu  Gly Leu Pro Pro Asn  Ala Gly Arg Tyr Asp  Leu Val Phe
         1205            1210             1215

Val Asn  Met His Thr Pro Tyr  Arg Leu His His Tyr  Gln Gln Cys
         1220            1225             1230

Val Asp  His Ala Met Lys Leu  Gln Met Leu Gly Gly  Asp Ala Leu
         1235            1240             1245

Tyr Leu  Leu Lys Pro Gly Gly  Ser Leu Leu Leu Arg  Ala Tyr Gly
         1250            1255             1260

Tyr Ala  Asp Arg Thr Ser Glu  Ala Val Val Thr Ala  Leu Ala Arg
         1265            1270             1275

Arg Phe  Ser Ser Phe Arg Ala  Val Arg Pro Pro Cys  Val Thr Ser
         1280            1285             1290

Asn Thr  Glu Val Phe Leu Leu  Phe Thr Asn Phe Asp  Asn Gly Arg
         1295            1300             1305

Arg Thr  Val Thr Leu His Pro  Thr Asn Gly Lys Leu  Ser Ser Ile
         1310            1315             1320

Tyr Ala  Gly Thr Val Leu Gln  Ala Ala Gly Cys Ala  Pro Ala Tyr
         1325            1330             1335

Thr Val  Lys Arg Ala Asp Ile  Ala Thr Ala Ile Glu  Asp Ala Val
         1340            1345             1350

Val Asn  Ala Ala Asn His Arg  Gly Gln Val Gly Asp  Gly Val Cys
         1355            1360             1365

Arg Ala  Val Ala Arg Lys Trp  Pro Gln Ala Phe Arg  Asn Ala Ala
         1370            1375             1380
```

```
Thr Pro Val Gly Thr Ala Lys Thr Val Lys Cys Asp Glu Thr Tyr
    1385                1390                1395

Ile Ile His Ala Val Gly Pro Asn Phe Asn Asn Thr Ser Glu Ala
    1400                1405                1410

Glu Gly Asp Arg Asp Leu Ala Ala Ala Tyr Arg Ala Val Ala Ala
    1415                1420                1425

Glu Ile Asn Arg Leu Ser Ile Ser Ser Val Ala Ile Pro Leu Leu
    1430                1435                1440

Ser Thr Gly Ile Phe Ser Ala Gly Lys Asp Arg Val His Gln Ser
    1445                1450                1455

Leu Ser His Leu Leu Ala Ala Met Asp Thr Thr Glu Ala Arg Val
    1460                1465                1470

Thr Ile Tyr Cys Arg Asp Lys Thr Trp Glu Gln Lys Ile Lys Thr
    1475                1480                1485

Val Leu Gln Asn Arg Cys Ala Thr Glu Leu Val Ser Asp Val Leu
    1490                1495                1500

Gln Leu Glu Val Asn Leu Thr Arg Val His Pro Asp Ser Ser Leu
    1505                1510                1515

Val Gly Arg Pro Gly Tyr Ser Thr Thr Asp Gly Thr Leu Tyr Ser
    1520                1525                1530

Tyr Met Glu Gly Thr Lys Phe His Gln Ala Ala Leu Asp Met Ala
    1535                1540                1545

Glu Ile Thr Thr Leu Trp Pro Arg Val Gln Asp Ala Asn Glu His
    1550                1555                1560

Ile Cys Met Tyr Ala Leu Gly Glu Thr Met Asp Asn Ile Arg Ser
    1565                1570                1575

Arg Cys Pro Val Glu Asp Ser Asp Ser Ser Thr Pro Pro Lys Thr
    1580                1585                1590

Val Pro Cys Leu Cys Arg Tyr Ala Met Thr Pro Glu Arg Val Thr
    1595                1600                1605

Arg Leu Arg Met His His Thr Lys Asp Phe Val Val Cys Ser Ser
    1610                1615                1620

Phe Gln Leu Pro Lys Tyr Arg Ile Ala Gly Val Gln Arg Val Lys
    1625                1630                1635

Cys Glu Lys Val Met Leu Phe Asp Ala Thr Pro Ala Ser Val
    1640                1645                1650

Ser Pro Val Gln Tyr Leu Thr Ser His Ser Glu Thr Thr Val Ser
    1655                1660                1665

Leu Ser Ser Phe Ser Ile Thr Ser Asp Ser Ser Leu Ser Thr
    1670                1675                1680

Phe Pro Asp Leu Glu Ser Leu Glu Glu Leu Gly Asn Asp Pro Gln
    1685                1690                1695

Ser Met Arg Met Asp Glu Ser Asp Asn Arg Gln Pro Ile Ser Thr
    1700                1705                1710

Val Glu Pro Val Val Arg Pro Val Pro Pro Arg Pro Lys Arg
    1715                1720                1725

Ala Arg Arg Leu Ala Ala Ala Arg Met Gln Val Gln Ala Glu Val
    1730                1735                1740

His His Pro Pro Val Val Gln Arg Thr Lys Pro Val Pro Ala Pro
    1745                1750                1755

Arg Thr Ser Leu Arg Pro Val Pro Ala Pro Arg Arg Cys Met Pro
    1760                1765                1770
```

-continued

Arg Pro Ala Val Glu Leu Pro Trp Pro Gln Glu Ala Val Asp Ile
1775                1780                1785

Glu Phe Gly Ala Pro Thr Glu Glu Ser Glu Ile Thr Phe Gly
1790                1795                1800

Asp Phe Ser Ala Ser Glu Trp Glu Thr Ile Ser Asn Ser Ser Leu
1805                1810                1815

Gly Arg Ala Gly Ala Tyr Ile Phe Ser Ser Asp Val Gly Pro Gly
1820                1825                1830

His Leu Gln Gln Lys Ser Val Arg Gln His Asp Leu Glu Val Pro
1835                1840                1845

Ile Met Asp Arg Val Val Glu Glu Lys Val Tyr Pro Pro Lys Leu
1850                1855                1860

Asp Glu Ala Lys Glu Lys Gln Leu Leu Leu Lys Leu Gln Met His
1865                1870                1875

Ala Thr Asp Ala Asn Arg Ser Arg Tyr Gln Ser Arg Lys Val Glu
1880                1885                1890

Asn Ile Lys Ala Thr Ile Ile Asp Arg Leu Lys Gln Gly Ser Ala
1895                1900                1905

Ser Tyr Ile Ser Ala Glu Ala Asn Lys Ala Ile Thr Tyr His Val
1910                1915                1920

Lys Tyr Ala Lys Pro Arg Tyr Ser Val Pro Val Met Gln Arg Leu
1925                1930                1935

Ser Ser Ala Thr Thr Ala Val Ala Ala Cys Asn Glu Phe Leu Ala
1940                1945                1950

Arg Asn Tyr Pro Thr Val Ala Ser Tyr Gln Ile Thr Asp Glu Tyr
1955                1960                1965

Asp Ala Tyr Leu Asp Met Val Asp Gly Ser Glu Ser Cys Leu Asp
1970                1975                1980

Arg Ala Asn Phe Cys Pro Ala Lys Leu Arg Cys Tyr Pro Lys His
1985                1990                1995

His Ala Tyr His Val Pro Gln Ile Arg Ser Ala Val Pro Ser Pro
2000                2005                2010

Phe Gln Asn Thr Leu Gln Asn Val Leu Ala Ala Thr Lys Arg
2015                2020                2025

Asn Cys Asn Val Thr Gln Met Arg Glu Leu Pro Thr Leu Asp Ser
2030                2035                2040

Ala Val Tyr Asn Val Glu Cys Phe Arg Lys Tyr Ala Cys Asn Asn
2045                2050                2055

Glu Tyr Trp Glu Glu Phe Ala Ala Lys Pro Ile Arg Ile Thr Thr
2060                2065                2070

Glu Asn Leu Thr Thr Tyr Val Thr Lys Leu Lys Gly Gly Lys Ala
2075                2080                2085

Ala Ala Leu Phe Ala Lys Thr His Asn Leu Val Pro Leu Gln Glu
2090                2095                2100

Val Pro Met Asp Arg Phe Val Met Asp Met Lys Arg Asp Val Lys
2105                2110                2115

Val Thr Pro Gly Thr Lys His Thr Glu Glu Arg Pro Lys Val Gln
2120                2125                2130

Val Ile Gln Ala Ala Glu Pro Leu Ala Thr Ala Tyr Leu Cys Gly
2135                2140                2145

Ile His Arg Glu Leu Val Arg Arg Leu Asn Ala Val Leu Leu Pro
2150                2155                2160

Asn Ile His Thr Leu Phe Asp Met Ser Ala Glu Asp Phe Asp Ala

```
    2165                2170                2175

Ile Ile  Ser Glu His Phe Lys  Pro Gly Asp His Val  Leu Glu Thr
    2180                2185                2190

Asp Ile  Ala Ser Phe Asp Lys  Ser Gln Asp Asp Ser  Leu Ala Leu
    2195                2200                2205

Thr Gly  Leu Met Ile Leu Glu  Asp Leu Gly Val Asp  Asn Gln Leu
    2210                2215                2220

Leu Asp  Leu Ile Glu Ala Ala  Phe Gly Gln Ile Thr  Ser Cys His
    2225                2230                2235

Leu Pro  Thr Gly Thr Arg Phe  Lys Phe Gly Ala Met  Met Lys Ser
    2240                2245                2250

Gly Met  Phe Leu Thr Leu Phe  Ile Asn Thr Val Leu  Asn Ile Thr
    2255                2260                2265

Ile Ala  Ser Arg Val Leu Glu  Ala Arg Leu Thr Asn  Ser Ala Cys
    2270                2275                2280

Ala Ala  Phe Ile Gly Asp Asp  Asn Val Val His Gly  Val Val Ser
    2285                2290                2295

Asp Lys  Leu Met Ala Asp Arg  Cys Ala Thr Trp Val  Asn Met Glu
    2300                2305                2310

Val Lys  Ile Ile Asp Ala Val  Met Cys Ala Lys Pro  Pro Tyr Phe
    2315                2320                2325

Cys Gly  Gly Phe Leu Val Tyr  Asp His Val Thr Arg  Thr Ser Cys
    2330                2335                2340

Arg Ile  Ala Asp Pro Leu Lys  Arg Leu Phe Lys Leu  Gly Lys Pro
    2345                2350                2355

Leu Pro  Ala Asp Asp Cys Gln  Asp Glu Asp Arg Arg  Arg Ala Leu
    2360                2365                2370

His Asp  Glu Val Lys Lys Trp  Phe Arg Ser Gly Leu  Gly Ser Glu
    2375                2380                2385

Ile Glu  Val Ala Leu Ala Thr  Arg Tyr Glu Val Glu  Gly Gly His
    2390                2395                2400

Asn Leu  Leu Leu Ala Met Ser  Thr Phe Ala His Ser  Met Lys Asn
    2405                2410                2415

Phe Ser  Ala Leu Arg Gly Pro  Val Ile His Leu Tyr  Gly Gly Pro
    2420                2425                2430
Lys

<210> SEQ ID NO 10
<211> LENGTH: 11883
<212> TYPE: DNA
<213> ORGANISM: Ross river virus

<400> SEQUENCE: 10
tggcggacgt gtgacatcac cgttcgcctt tcttggatcc cttgttactc cacgtagtga      60
gagataaaca acccagaatg aaggtcactg tagatgttga ggctgatagc ccatttttga     120
aggcccttca gaaagcattc ccggcttttg aggttgaatc acagcaggtc acacccaatg     180
accatgctaa tgccagagct tttcgcatcc tggccacaaa gttaattgaa caagaggttc     240
caaccaacat caccatcctg gatgtgggca gcgcgcccgc aaggaggttg atgtctgatc     300
acagctacca ctgcatttgt cccatgaaga gtgcggaaga cccagagaga ttagcgaact     360
atgcccggaa actggcaaaa gcagcagggg aagtgctaga caaaaatgtg tccggtaaga     420
tcacggacct gcaggacgtc atggcaaccc ccgatctgga atctccaacg ttctgtctcc     480
```

```
acaccgacga gacgtgtcgc actagagctg aagtagctgt gtaccaggac gtgtacgcgg    540
tgcacgcacc gacctcgctt tatcatcaag cgatgaaagg ggtcaggaca gtatactgga    600
taggatttga caccaccca ttcatgttcg aggttttggc tggcgcatac ccaacgtatt    660
ccacgaattg ggcggacgag caggtcctgc aggcacgtaa catcggccta tgtgcgacca    720
gtctcagcga aggacatcga ggaaaactct ctattatgag gaagaaacgc ctaaggccaa    780
gcgacagggt catgttctcg gttgggtcaa cgctatatat agaaagtaga cgccttctta    840
agagttggca tcttccctcc gtgttccacc tgaaaggcaa gaatagcttt acttgcaggt    900
gcgacacaat agtttcatgc gagggctacg ttgttaaaaa gatcacaatg agcccaggga    960
cgtacgggaa gacggtcgga tacgccgtta cgcatcatgc agaaggtttc ctaatgtgca   1020
aggtgacgga cactgtgcgc ggggagagag tatcattccc ggtatgcact tatgtgcctg   1080
caaccatttg cgatcagatg acaggaatcc tggctaccga cgtcacaccc gaagatgcgc   1140
agaaactcct ggtggggttg aaccaacgta tagttgtgaa cggcagaacc caagaaaata   1200
ccaacacaat gaaaaactac ctattgccgg tagtggccca agctttcagc aagtgggcac   1260
gagaagcaaa agcagacatg gaggatgaga aacctctggg aaccagagaa agaaccctga   1320
cgtgctgttg cctgtgggca ttcaagagcc acaagacaca caccatgtac aaaaggccgg   1380
atacccaaac tatagtcaag gtgccatcta cttttgactc gtttgtgatt ccaagcctgt   1440
ggtcatccag cctatccata ggcctacggc aaagaataaa actgctatta ggcccaaaac   1500
tctcgcggga cctcccgtac tctggagacc gaaacgaagc gcgagaagca gagaaggaag   1560
ccgaagagac caaggaagca gaattgacac gggaagcact gccaccattg gtgggaagca   1620
actgcgctga tgacgtcgat cgggtagatg tggaagagct gacgtaccgc gccggagcag   1680
gggtagtgga gacacccagg aatgcgctca gagtgacacc acaagagcgc gatcagctga   1740
tcggcgcgta cctgatcttg tctccgcaag cagtactgaa gagtgaaaaa ctcacaccga   1800
tacatccact ggctgagcaa gtgacaatca tgacgcactc tggaagatct ggcagatacc   1860
cggttgaccg ctacgacgga cgggtgttgg tcccgacggg cgcagcgatc cccgtcagcg   1920
aatttcaagc actcagtgag agtgctacta tggtctacaa cgaacgtgag ttcatcaatc   1980
gcaagttgca ccatatagca ctctacggcc ccgccctaaa cactgaggag gagaactacg   2040
aaaaagtaag ggcagagaga gccgaagctg aatacgtgtt tgacgttgac aagaggatgt   2100
gcgtgaagag agaagaagca tcaggccttg tactggttgg tgacttaatc aacccaccct   2160
tccatgagtt cgcgtatgaa ggactgaaga tacggcccgc aacgcctttc caaaccacgg   2220
tcattggcgt cttcggggta cctggttcgg gcaagtcagc cataatcaag agtgtggtga   2280
ctacgagga cctggtcgcc agtgggaaga aggagaactg ccaggagata gttaatgatg   2340
tcaaaagca gagaggactg gatgtaacag ccaggactgt tgactctatc ctgttgaacg   2400
ggtgcagaag aggagtagag aacctatacg tggacgaagc atttgcctgt cattcaggta   2460
cactgttggc tcttattgcc atggtgaaac caactggcaa ggtgatccta tgcggagacc   2520
caaaacagtg tggattttt aacctgatgc aactgaaggt gaacttcaac cacgatatct   2580
gcacacaagt gctccacaaa agcatatcca aagatgcac cctcccgatc acggctatcg   2640
tctcgaccct acactatcag ggtaagatga aaccacgaa cttatgtagt gcacccatcc   2700
agatagacac aacaggtacc actaaaccag ccaaaggaga catcgtgtta acatgcttcc   2760
gcggttgggt aaagcaactg cagatagact accgtggaca cgaagtcatg acagcagctg   2820
catcacaagg actgactaga aaagggggtat acgccgttag gcagaaagtg aatgaaaacc   2880
```

```
cgctttatgc cccttcatca gaacatgtca acgtattgct gactagaact gaaaaccggc   2940
tggtgtggaa aacactgtcg ggagacccgt ggataaaggt gttaaccaat atccccaagg   3000
gcgatttcag cgctacgttg gaggagtggc aagaggagca tgacaacatc atgaacgccc   3060
ttcgcgagag gtcgacagca gtagacccgt tccagaacaa agccaaagtc tgctgggcaa   3120
agtgcctcgt gcaggtccta gaaacggctg ggatacgcat gacggcagag gagtgggata   3180
cagtgttggc tttccgcgaa gacagggcgt actcacccga agtggctctg aacgagatct   3240
gtaccaagta ttacggcgtt gacttagaca gcggattgtt ctccgcccaa tcggtctcat   3300
tgtactatga aaacaaccac tgggacaata gaccgggcgg ccggatgtat ggattcaacc   3360
gcgaagtcgc ccgtaagttt gagcaacgct acccattcct gagaggcaag atggactcgg   3420
ggctacaagt taatgttcca gagagaaaag tacagccatt caatgcggaa tgtaatatat   3480
taccatcaaa caggcgactt ccgcacgccc tcgtcaccag ctaccagcag tgccagggcg   3540
agagggtaga atggcttttg aagaagcttc ccggatacca tttattgctg gtaagcgagt   3600
acaatctggc gctgccccat aaaagagtct tttggattgc accaccccat gtgtctggtg   3660
cagatcgtat ttatgatctt gacctaggat taccccctgaa tgcaggccgt tacgacttgg   3720
tatttgtgaa catacacact gagtacagga cgcaccacta ccaacagtgc gtcgaccact   3780
ctatgaagtt acagatgttg ggcggtgact ccttacatct attgaaacca ggcggctcac   3840
tgcttatccg tgcttacggg tacgccgaca gagtcagcga atggtggtc actgcattag   3900
ctaggaagtt ttccgccttc agagtcttga gaccagcatg tgtaacaagt aacactgaag   3960
tctttctgtt gttcaccaat tttgataacg gcagaagggc tgtgactctt caccaggcca   4020
atcagaggct cagctccatg tttgcatgca acgggctaca cacagccgga tgcgcaccct   4080
cataccgtgt gcgtaggacc gacatttccg ggcacgctga agaggcggtt gttaatgccg   4140
ccaacgcgaa gggcacagtc ggcgatgggg tttgcagagc ggtggcgaga aaatggccag   4200
actccttcaa aggtgccgcg actcccgtgg gtacggctaa gttggtacag gccaacggta   4260
tgaatgtcat ccacgcggta ggcccgaatt tctccacggt gaccgaggca gagggcgaca   4320
gagagttggc cgccgcatac cgtgccgtgg cgggtattat caatgctagt aacattaaga   4380
gtgtagccat ccctctgttg tcgacgggag tgttctccgg aggtaaagat agagtcatgc   4440
agtcactaaa tcacctgttt accgcaatgg acaccacgga cgctgacgta gtcatctatt   4500
gccgcgacaa agcctgggag aagaaaatcc aggaggctat cgatcgccgc accgccgtgg   4560
aattggtatc tgaagacatc tcactcgagt ctgacttgat acgggtacac ccagatagtt   4620
gcttggtagg cagaaaaggt tacagcataa cagatgggaa gctgcattca tacctggaag   4680
gtacccgctt tcatcagact gcggtggaca tggctgagat atctaccttg tggccgaaac   4740
ttcaggacgc aaacgaacaa atatgcttgt atgcattggg tgagagtatg gacagcatca   4800
gaacgaaatg ccctgttgag gacgccgatt cgtccacgcc tccgaaaaca gttccgtgtc   4860
tgtgtaggta cgctatgact gctgagagag tggcaagact tcggatgaac aacactaagg   4920
ccataattgt gtgctcctcc ttccctttac cgaagtacag gattgaaggc gtccagaagg   4980
tcaagtgcga ccgagtgctg atttttgacc agacggtgcc atctctggtt agtccaagga   5040
agtacatacc agccgccgcc tctacgcacg cagataccgt gagcttggat tctacagtat   5100
ccacaggatc cgcgtggtca ttcccatctg aggccacgta tgagaccatg gaagtagtag   5160
cagaggtgca ccactcggaa ccaccagtcc cgccaccgcg caggcgtcgt gcgcaggtga   5220
```

```
cgatgcacca ccaggagctg ttggaagtct ctgacatgca caccccgatt gcggcaaggg    5280
tcgagatccc cgtgtacgat accgctgttg tagtggagag agtggcaatt ccttgcacaa    5340
gcgagtatgc aaaacccata ccagcaccac gggcagcaag ggtcgtaccc gtgccggcac    5400
cacgcattca gcgagcgtcg acgtacagag tctctcctac acccacgcct cgcgttctga    5460
gagcctcggt atgcagtgtg accactagcg ctggggtaga gttcccttgg gcgcctgaag    5520
atctggaggt actcaccgag cctgtgcact gcaaaatgcg cgagccggtt gagttaccgt    5580
gggagcctga ggacgttgat atccagttcg agattttga aacatccgac aaaatccaat    5640
tcggcgatat tgattttgac caattctgac taggcagagc gggggcgtac atcttctcgt    5700
ctgataccgg accagggcac ttacaacaga agtcagtacg gcaacacgca ctaccgtgcg    5760
aaatgctata cgtccacgag gaagaacgga cgtaccccc cgcactggat gaggccaggg    5820
agaaactgct gcaggcaaaa atgcagatgg cacctacgga agcaaacaag agcaggtacc    5880
aatcaaggaa ggttgaaaac atgaaggcag tgatcataga taggctgaag gatggagcaa    5940
gaacctacct gacagaacag tcagagaaga ttccaaccta tgttagtaag tacccgcggc    6000
cagtttactc gccgtcggta gaggatagct tgcagaatcc cgaggtcgct gtggcggcct    6060
gcaatgcttt cctggaagcc aattacccga cagtggctag ttaccagatc acggacgagt    6120
atgatgccta cttggatatg gttgatgggt cagagagttg tttagaccgg gcaaccttct    6180
gcccggcaaa attacgctgc tacccaaagc atcatgctta ccaccaaccg caggttagga    6240
gcgcggtccc atcaccattt caaaacaccc tgcagaatgt gctagcagca gccacgaaga    6300
gaaactgcaa tgttacacag atgagagagc tacccactct agactcagcc gtgcttaacg    6360
tggaatgctt caaaaaattc gcatgcaacg gagaatactg gcaggaattc aaagacaacc    6420
caataagaat aactacagag aacataacaa cttatgttac taggcttaag ggccctaaag    6480
cagcggcgct gtttgcaaag actcacaatc tagtcccgct gcaggaggtg cccatggacc    6540
ggtttgtggt agatatgaag agagacgtga aagttacccc tggcaccaaa cataccgagg    6600
aacgcccaaa ggtgcaagtc atccaggccg ccgaaccttt agctacagct tatttatgtg    6660
gcattcacag ggagttagtc cgccgcctga aggccgtcct ggccccgaac atacatacat    6720
tgttcgatat gtcggcagaa gattttgatg ccatcatagc tgcacatttc caaccaggcg    6780
acgcagtttt ggaaacggac atagcctcct ttgacaagag ccaagatgac tctctgcgt    6840 tgacggcact gatgctgttg gaagacctcg ggttgacca agaactacta gacttgatag    6900
aggcagcgtt cggggaaatt accagcgtcc acctgccaac aggtacgcgg ttcaagtttg    6960
gcgccatgat gaagtccgga atgttcctga cactgtttgt aaatacctg ttaaacattg    7020 tcatagcatg ccgtgtactg cgtgagaagc tgacaaactc cgtctgcgcc gcgtttatcg    7080
gggatgacaa catagtgcac ggggtaagat ccgacccgtt gatggctgaa aggtgcgcca    7140
gctgggttaa tatggaggta aagataattg acgctaccat gtgcgagaaa ccaccatatt    7200
tctgcggcgg gtttatattg tatgacaaag tcaccggatc ggcgtgccga gtggccgacc    7260
ctctgaaaag gttatttaaa ctaggtaaac ctttacccgc cggagacacc caagatgaag    7320
atcgtaggcg tgcattgaag gatgagacga taggtgggc acgagtaggg ctgaagtctg    7380
aactggaaat agcactaagt tctcggtatg aggtgaacgg gaccggcaac atagtgcgag    7440
caatggccac actggccaag agcctgaaga atttttaaaaa gctgcgtgga cccatcgtac    7500
acctctacgg cggtcctaaa tagatgcaga gacacacctt catctaatac agctcacaac    7560
agtaaacatg aattacatac caacccagac ttttacgga cgccgttggc ggcctcgccc    7620
```

```
ggcgttccgt ccatggcagg tgccgatgca gccgacacct actatggtta cacccatgct   7680
gcaagcacca gacctacagg cccaacagat gcaacaactg atcagcgctg tctctgcatt   7740
aaccaccaaa cagaatgtaa aagcaccaaa agggcaacgg aagaagaaac agcagaaacc   7800
aaaggaaaag aaggaaaacc agaagaaaaa gccgacgcaa aagaagaagc agcagcagaa   7860
accaaaacca caggctaaga agaagaaacc agggagaaga gaaagaatgt gcatgaagat   7920
cgagaatgac tgcatattcg aggtcaaact ggatggcaag gttaccggtt atgcgtgcct   7980
agtcggagac aaggtcatga agccggctca cgttaaaggc acaattgata acccagacct   8040
tgcgaagctg acttacaaga aatccagtaa gtatgacctc gaatgcgccc agataccagt   8100
gcacatgaag tccgacgcct ccaagtacac acatgaaaaa cccgaaggtc attacaattg   8160
gcaccatgga gcagtgcagt acagcggagg aaggtttacc atccccacag cgccggcaa    8220 accgggagat agcggtaggc ctattttga caacaaaggg cgagtagtgg ccatcgtgtt    8280
aggcggggcc aacgaaggtg ctcgcactgc gctgtctgtg gtgacgtgga caaaagacat   8340
ggtcactcgg gtaacgccag aaggaactga agagtggtct gccgcgctga tgatgtgtat   8400
ccttgccaac acctctttcc cctgctcatc acctccctgc tacccctgct gctacgaaaa   8460
acagccagaa cagacactgc ggatgctgga agacaatgtg aatagaccag ggtactatga   8520
gctactggaa gcgtccatga catgcagaaa cagatcacgc caccgccgta gtgtaacaga   8580
gcacttcaat gtgtataagg ctactagacc gtacttagcg tattgcgctg actgtgggga   8640
cgggtacttc tgctatagcc cagttgctat cgagaagatc cgagatgagg cgtctgacgg   8700
catgctcaag atccaagtct ccgcccaaat aggtctggac aaggcaggta cccacgccca   8760
cacgaagatc cgatatatgg ctggtcatga tgttcaggaa tctaagagag attccttgag   8820
ggtgtacacg tccgcagcgt gctctataca tgggacgatg ggacacttca tcgtcgcaca   8880
ttgtccgcca ggcgactacc tcaaggtttc gttcgaggac gcagaytcac acgtgaaggc   8940
atgtaaggtc caatacaagc acgacccatt gccggtgggt agagagaagt tcgtggttag   9000
accccacttt ggcgtagagc tgccatgcac ctcataccag ctgacaacag ctccccaccga  9060 cgaggagatc gacatgcaca caccgccaga tataccggat cgcaccctgc tatcacagac   9120
ggcgggcaac gtcaaaataa cagcaggcgg caggactatc aggtacaatt gtacctgtgg   9180
ccgtgacaac gtaggcacta ccagtactga caagaccatc aacacatgca agattgacca   9240
atgccatgct gccgttacca gccatgacaa atggcaattt acctctccat tgttcccag    9300 ggctgatcag acagctagga ggggcaaagt gcatgttcca ttcccttga ctaacgtcac    9360 ctgccgagtg ccgttggctc gagcgccgga tgtcacctat ggtaagaagg aggtgaccct   9420
gagattacac ccagatcatc cgacgctctt ctcctatagg agtttaggag ccgaaccgca   9480
cccgtacgag gagtgggttg acaagttctc tgagcgcatc atcccagtga cggaagaagg   9540
gattgagtac cagtggggca caacccgcc ggtccgccta tgggcgcaac tgacgaccga    9600
gggcaaaccc catggctggc cacatgaaat cattcagtac tattatggac tataccccgc   9660
cgccaccatt gccgcagtat ccggggcgag tctgatggcc ctcctaactc tagcggccac   9720
atgctgcatg ctggccaccg cgaggagaaa gtgcctaaca ccatacgcct tgacgccagg   9780
agcggtggta ccgttgacac tggggctgct ttgctgcgca ccgagggcga acgcagcatc   9840
attcgctgag actatggcat atctgtggga cgagaacaaa accctctttt ggatggaatt   9900 cgcggccccca gccgcagcgc ttgctttgct ggcatgctgt atcaaaagcc tgatctgctg   9960
```

```
ttgtaagcca ttttcttttt tagtgttact gagcctggga gcctccgcaa aagcttacga  10020
gcacacagcc acaattccga atgtggtggg gttcccgtat aaggctcaca ttgaaaggaa  10080
tggcttctcg cccatgactc tgcagcttga agtggtggag acaagcttgg aacccacact  10140
taacctggag tacattacct gcgaatacaa gacggtggtc ccttcgccat tcatcaaatg  10200
ttgcggaaca tcagaatgct catccaagga gcagccagac taccaatgca aggtgtacac  10260
gggtgtatac ccattcatgt ggggtggagc ctactgtttc tgcgactccg agaacacgca  10320
gctcagcgag gcctatgtcg acaggtcaga cgtttgcaaa catgatcacg catcggccta  10380
caaggcacac acggcctctc taaaagcaac aatcaggatc agttatggca ccatcaacca  10440
gaccaccgag gccttcgtta atggtgaaca cgcggtcaac gtgggcggaa gcaagttcat  10500
ctttggaccg atctcaacag cttggtcacc gttcgacaat aaaattgtcg tgtataaaga  10560
tgatgtctac aaccaggact tcccacccta cggatcaggc cagccgggta gattcggaga  10620
cattcagagc aggacagtgg agagcaaaga cttgtatgcc aacacggccc taaaactctc  10680
aagaccatca cccggggttg tgcatgtgcc atacacgcag acaccatccg gatttaaata  10740
ttggctgaag gagaaaggat cttcattgaa tacaaaggcc ccttttggct gcaagataaa  10800
gaccaatcca gtcagagcca tggattgtgc agttggcagt atacctgtgt cgatggacat  10860
acctgacagt gcattcacac gagtggtaga tgccccggct gtaacagacc tgagctgcca  10920
ggtagtggtc tgtacacact cctccgattt cggaggagtt gccacattgt cttacaaaac  10980
ggacaaaccc ggcaagtgcg ctgtccactc acattccaac gtcgcaacgt tgcaagaggc  11040
gacggtggat gtcaaggagg atggcaaggt cacagtgcac ttttccacgg cgtccgcctc  11100
cccggccttc aaagtgtccg tctgtgacgc aaaaacaacg tgcacggcgg cgtgcgagcc  11160
tccaaaagac cacatcgtcc cttatggggc gagccataac aaccaggtct ttccggacat  11220
gtcaggaact gcgatgacgt gggtgcagag gctggccagt gggttaggtg ggctggctct  11280
catcgcggtg gttgtgctgg tcttggtaac ctgcataaca atgcgtcggt aagctttagt  11340
tcaaagggcc atataaaccc ctgaatagta acaaaatata aaaattacaa aatatgtagt  11400
tcaaagggct atactacccc tgattagtaa caaaatagaa aaccacaaaa tatgtagtta  11460
agtattataa gatgtgtagt tcaaagggct atatcacccc tgattagtaa caaaatataa  11520
aaacaaaaat atgtagttaa gtactaacca acaagtagac aaatagatgc taaccatata  11580
tataaccagc tatagtatac tatatttagc taagcagttg cagtagtaag aatgtagttc  11640
aaagggctat acaacccctg aatagtaaca aaatacaaaa atactaataa aaatttaaaa  11700
atcactagaa atccaatcat taaattatta attggctagc cgaactctaa ggagatgtag  11760
gcgtccgaac tctgcggaga tgtaggacta aattctgccg aaccccataa caccggggac  11820
gtaggcgtct aatttgtttt ttaatatttt acaaaaaaaa aaaaaaaaaa aaaaaaaaaa  11880
aaa                                                                11883
```

<210> SEQ ID NO 11
<211> LENGTH: 1254
<212> TYPE: PRT
<213> ORGANISM: Ross river virus

<400> SEQUENCE: 11

```
Met Asn Tyr Ile Pro Thr Gln Thr Phe Tyr Gly Arg Arg Trp Arg Pro
1               5                   10                  15

Arg Pro Ala Phe Arg Pro Trp Gln Val Pro Met Gln Pro Thr Pro Thr
            20                  25                  30
```

-continued

```
Met Val Thr Pro Met Leu Gln Ala Pro Asp Leu Gln Ala Gln Gln Met
             35                  40                  45

Gln Gln Leu Ile Ser Ala Val Ser Ala Leu Thr Thr Lys Gln Asn Val
 50                  55                  60

Lys Ala Pro Lys Gly Gln Arg Lys Lys Gln Gln Lys Pro Lys Glu
 65                  70                  75                  80

Lys Lys Glu Asn Gln Lys Lys Pro Thr Gln Lys Lys Gln Gln
                 85                  90                  95

Gln Lys Pro Lys Pro Gln Ala Lys Lys Lys Pro Gly Arg Arg Glu
                100                 105                 110

Arg Met Cys Met Lys Ile Glu Asn Asp Cys Ile Phe Glu Val Lys Leu
                115                 120                 125

Asp Gly Lys Val Thr Gly Tyr Ala Cys Leu Val Gly Asp Lys Val Met
    130                 135                 140

Lys Pro Ala His Val Lys Gly Thr Ile Asp Asn Pro Asp Leu Ala Lys
145                 150                 155                 160

Leu Thr Tyr Lys Lys Ser Ser Lys Tyr Asp Leu Glu Cys Ala Gln Ile
                165                 170                 175

Pro Val His Met Lys Ser Asp Ala Ser Lys Tyr Thr His Glu Lys Pro
                180                 185                 190

Glu Gly His Tyr Asn Trp His His Gly Ala Val Gln Tyr Ser Gly Gly
            195                 200                 205

Arg Phe Thr Ile Pro Thr Gly Ala Gly Lys Pro Gly Asp Ser Gly Arg
    210                 215                 220

Pro Ile Phe Asp Asn Lys Gly Arg Val Val Ala Ile Val Leu Gly Gly
225                 230                 235                 240

Ala Asn Glu Gly Ala Arg Thr Ala Leu Ser Val Val Thr Trp Thr Lys
                245                 250                 255

Asp Met Val Thr Arg Val Thr Pro Glu Gly Thr Glu Glu Trp Ser Ala
            260                 265                 270

Ala Leu Met Met Cys Ile Leu Ala Asn Thr Ser Phe Pro Cys Ser Ser
    275                 280                 285

Pro Pro Cys Tyr Pro Cys Cys Tyr Glu Lys Gln Pro Glu Gln Thr Leu
290                 295                 300

Arg Met Leu Glu Asp Asn Val Asn Arg Pro Gly Tyr Tyr Glu Leu Leu
305                 310                 315                 320

Glu Ala Ser Met Thr Cys Arg Asn Arg Ser Arg His Arg Arg Ser Val
                325                 330                 335

Thr Glu His Phe Asn Val Tyr Lys Ala Thr Arg Pro Tyr Leu Ala Tyr
            340                 345                 350

Cys Ala Asp Cys Gly Asp Gly Tyr Phe Cys Tyr Ser Pro Val Ala Ile
    355                 360                 365

Glu Lys Ile Arg Asp Glu Ala Ser Asp Gly Met Leu Lys Ile Gln Val
370                 375                 380

Ser Ala Gln Ile Gly Leu Asp Lys Ala Gly Thr His Ala His Thr Lys
385                 390                 395                 400

Ile Arg Tyr Met Ala Gly His Asp Val Gln Glu Ser Lys Arg Asp Ser
                405                 410                 415

Leu Arg Val Tyr Thr Ser Ala Ala Cys Ser Ile His Gly Thr Met Gly
            420                 425                 430

His Phe Ile Val Ala His Cys Pro Pro Gly Asp Tyr Leu Lys Val Ser
    435                 440                 445
```

```
Phe Glu Asp Ala Asp Ser His Val Lys Ala Cys Lys Val Gln Tyr Lys
    450                 455                 460
His Asp Pro Leu Pro Val Gly Arg Glu Lys Phe Val Arg Pro His
465                 470                 475                 480
Phe Gly Val Glu Leu Pro Cys Thr Ser Tyr Gln Leu Thr Thr Ala Pro
                485                 490                 495
Thr Asp Glu Glu Ile Asp Met His Thr Pro Asp Ile Pro Asp Arg
        500                 505                 510
Thr Leu Leu Ser Gln Thr Ala Gly Asn Val Lys Ile Thr Ala Gly Gly
        515                 520                 525
Arg Thr Ile Arg Tyr Asn Cys Thr Cys Gly Arg Asp Asn Val Gly Thr
530                 535                 540
Thr Ser Thr Asp Lys Thr Ile Asn Thr Cys Lys Ile Asp Gln Cys His
545                 550                 555                 560
Ala Ala Val Thr Ser His Asp Lys Trp Gln Phe Thr Ser Pro Phe Val
                565                 570                 575
Pro Arg Ala Asp Gln Thr Ala Arg Arg Gly Lys Val His Val Pro Phe
                580                 585                 590
Pro Leu Thr Asn Val Thr Cys Arg Val Pro Leu Ala Arg Ala Pro Asp
                595                 600                 605
Val Thr Tyr Gly Lys Lys Glu Val Thr Leu Arg Leu His Pro Asp His
        610                 615                 620
Pro Thr Leu Phe Ser Tyr Arg Ser Leu Gly Ala Glu Pro His Pro Tyr
625                 630                 635                 640
Glu Glu Trp Val Asp Lys Phe Ser Glu Arg Ile Ile Pro Val Thr Glu
                645                 650                 655
Glu Gly Ile Glu Tyr Gln Trp Gly Asn Asn Pro Pro Val Arg Leu Trp
                660                 665                 670
Ala Gln Leu Thr Thr Glu Gly Lys Pro His Gly Trp Pro His Glu Ile
        675                 680                 685
Ile Gln Tyr Tyr Tyr Gly Leu Tyr Pro Ala Ala Thr Ile Ala Ala Val
        690                 695                 700
Ser Gly Ala Ser Leu Met Ala Leu Leu Thr Leu Ala Ala Thr Cys Cys
705                 710                 715                 720
Met Leu Ala Thr Ala Arg Arg Lys Cys Leu Thr Pro Tyr Ala Leu Thr
                725                 730                 735
Pro Gly Ala Val Val Pro Leu Thr Leu Gly Leu Leu Cys Cys Ala Pro
                740                 745                 750
Arg Ala Asn Ala Ala Ser Phe Ala Glu Thr Met Ala Tyr Leu Trp Asp
                755                 760                 765
Glu Asn Lys Thr Leu Phe Trp Met Glu Phe Ala Ala Pro Ala Ala Ala
        770                 775                 780
Leu Ala Leu Leu Ala Cys Cys Ile Lys Ser Leu Ile Cys Cys Cys Lys
785                 790                 795                 800
Pro Phe Ser Phe Leu Val Leu Leu Ser Leu Gly Ala Ser Ala Lys Ala
                805                 810                 815
Tyr Glu His Thr Ala Thr Ile Pro Asn Val Val Gly Phe Pro Tyr Lys
                820                 825                 830
Ala His Ile Glu Arg Asn Gly Phe Ser Pro Met Thr Leu Gln Leu Glu
        835                 840                 845
Val Val Glu Thr Ser Leu Glu Pro Thr Leu Asn Leu Glu Tyr Ile Thr
850                 855                 860
Cys Glu Tyr Lys Thr Val Val Pro Ser Pro Phe Ile Lys Cys Cys Gly
```

```
865                 870                 875                 880
Thr Ser Glu Cys Ser Ser Lys Glu Gln Pro Asp Tyr Gln Cys Lys Val
                885                 890                 895
Tyr Thr Gly Val Tyr Pro Phe Met Trp Gly Gly Ala Tyr Cys Phe Cys
                900                 905                 910
Asp Ser Glu Asn Thr Gln Leu Ser Glu Ala Tyr Val Asp Arg Ser Asp
                915                 920                 925
Val Cys Lys His Asp His Ala Ser Ala Tyr Lys Ala His Thr Ala Ser
                930                 935                 940
Leu Lys Ala Thr Ile Arg Ile Ser Tyr Gly Thr Ile Asn Gln Thr Thr
945                 950                 955                 960
Glu Ala Phe Val Asn Gly Glu His Ala Val Asn Val Gly Gly Ser Lys
                965                 970                 975
Phe Ile Phe Gly Pro Ile Ser Thr Ala Trp Ser Pro Phe Asp Asn Lys
                980                 985                 990
Ile Val Val Tyr Lys Asp Asp Val Tyr Asn Gln Asp Phe Pro Pro Tyr
                995                 1000                1005
Gly Ser Gly Gln Pro Gly Arg Phe Gly Asp Ile Gln Ser Arg Thr
            1010                1015            1020
Val Glu Ser Lys Asp Leu Tyr Ala Asn Thr Ala Leu Lys Leu Ser
        1025            1030            1035
Arg Pro Ser Pro Gly Val Val His Val Pro Tyr Thr Gln Thr Pro
        1040            1045            1050
Ser Gly Phe Lys Tyr Trp Leu Lys Glu Lys Gly Ser Ser Leu Asn
        1055            1060            1065
Thr Lys Ala Pro Phe Gly Cys Lys Ile Lys Thr Asn Pro Val Arg
        1070            1075            1080
Ala Met Asp Cys Ala Val Gly Ser Ile Pro Val Ser Met Asp Ile
        1085            1090            1095
Pro Asp Ser Ala Phe Thr Arg Val Val Asp Ala Pro Ala Val Thr
        1100            1105            1110
Asp Leu Ser Cys Gln Val Val Val Cys Thr His Ser Ser Asp Phe
        1115            1120            1125
Gly Gly Val Ala Thr Leu Ser Tyr Lys Thr Asp Lys Pro Gly Lys
        1130            1135            1140
Cys Ala Val His Ser His Ser Asn Val Ala Thr Leu Gln Glu Ala
        1145            1150            1155
Thr Val Asp Val Lys Glu Asp Gly Lys Val Thr Val His Phe Ser
        1160            1165            1170
Thr Ala Ser Ala Ser Pro Ala Phe Lys Val Ser Val Cys Asp Ala
        1175            1180            1185
Lys Thr Thr Cys Thr Ala Ala Cys Glu Pro Pro Lys Asp His Ile
        1190            1195            1200
Val Pro Tyr Gly Ala Ser His Asn Asn Gln Val Phe Pro Asp Met
        1205            1210            1215
Ser Gly Thr Ala Met Thr Trp Val Gln Arg Leu Ala Ser Gly Leu
        1220            1225            1230
Gly Gly Leu Ala Leu Ile Ala Val Val Val Leu Val Leu Val Thr
        1235            1240            1245
Cys Ile Thr Met Arg Arg
        1250

<210> SEQ ID NO 12
```

```
<211> LENGTH: 2480
<212> TYPE: PRT
<213> ORGANISM: Ross river virus

<400> SEQUENCE: 12
```

| | | | | | | | | | | | | | | | |
|---|---|---|---|---|---|---|---|---|---|---|---|---|---|---|---|
| Met | Lys | Val | Thr | Val | Asp | Val | Glu | Ala | Asp | Ser | Pro | Phe | Leu | Lys | Ala |
| 1 | | | | 5 | | | | | 10 | | | | | 15 | |
| Leu | Gln | Lys | Ala | Phe | Pro | Ala | Phe | Glu | Val | Glu | Ser | Gln | Gln | Val | Thr |
| | | | 20 | | | | | 25 | | | | | 30 | | |
| Pro | Asn | Asp | His | Ala | Asn | Ala | Arg | Ala | Phe | Ser | His | Leu | Ala | Thr | Lys |
| | | 35 | | | | | 40 | | | | | 45 | | | |
| Leu | Ile | Glu | Gln | Glu | Val | Pro | Thr | Asn | Ile | Thr | Ile | Leu | Asp | Val | Gly |
| 50 | | | | | 55 | | | | | 60 | | | | | |
| Ser | Ala | Pro | Ala | Arg | Arg | Leu | Met | Ser | Asp | His | Ser | Tyr | His | Cys | Ile |
| 65 | | | | 70 | | | | | 75 | | | | | 80 | |
| Cys | Pro | Met | Lys | Ser | Ala | Glu | Asp | Pro | Glu | Arg | Leu | Ala | Asn | Tyr | Ala |
| | | | 85 | | | | | 90 | | | | | 95 | | |
| Arg | Lys | Leu | Ala | Lys | Ala | Ala | Gly | Glu | Val | Leu | Asp | Lys | Asn | Val | Ser |
| | | | 100 | | | | | 105 | | | | | 110 | | |
| Gly | Lys | Ile | Thr | Asp | Leu | Gln | Asp | Val | Met | Ala | Thr | Pro | Asp | Leu | Glu |
| | | | 115 | | | | | 120 | | | | | 125 | | |
| Ser | Pro | Thr | Phe | Cys | Leu | His | Thr | Asp | Glu | Thr | Cys | Arg | Thr | Arg | Ala |
| | | 130 | | | | | 135 | | | | | 140 | | | |
| Glu | Val | Ala | Val | Tyr | Gln | Asp | Val | Tyr | Ala | Val | His | Ala | Pro | Thr | Ser |
| 145 | | | | | 150 | | | | | 155 | | | | | 160 |
| Leu | Tyr | His | Gln | Ala | Met | Lys | Gly | Val | Arg | Thr | Val | Tyr | Trp | Ile | Gly |
| | | | | 165 | | | | | 170 | | | | | 175 | |
| Phe | Asp | Thr | Thr | Pro | Phe | Met | Phe | Glu | Val | Leu | Ala | Gly | Ala | Tyr | Pro |
| | | | | 180 | | | | | 185 | | | | | 190 | |
| Thr | Tyr | Ser | Thr | Asn | Trp | Ala | Asp | Glu | Gln | Val | Leu | Gln | Ala | Arg | Asn |
| | | | 195 | | | | | 200 | | | | | 205 | | |
| Ile | Gly | Leu | Cys | Ala | Thr | Ser | Leu | Ser | Glu | Gly | His | Arg | Gly | Lys | Leu |
| | | | 210 | | | | | 215 | | | | | 220 | | |
| Ser | Ile | Met | Arg | Lys | Lys | Arg | Leu | Arg | Pro | Ser | Asp | Arg | Val | Met | Phe |
| 225 | | | | | 230 | | | | | 235 | | | | | 240 |
| Ser | Val | Gly | Ser | Thr | Leu | Tyr | Ile | Glu | Ser | Arg | Arg | Leu | Leu | Lys | Ser |
| | | | | 245 | | | | | 250 | | | | | 255 | |
| Trp | His | Leu | Pro | Ser | Val | Phe | His | Leu | Lys | Gly | Lys | Asn | Ser | Phe | Thr |
| | | | 260 | | | | | 265 | | | | | 270 | | |
| Cys | Arg | Cys | Asp | Thr | Ile | Val | Ser | Cys | Glu | Gly | Tyr | Val | Val | Lys | Lys |
| | | 275 | | | | | 280 | | | | | 285 | | | |
| Ile | Thr | Met | Ser | Pro | Gly | Thr | Tyr | Gly | Lys | Thr | Val | Gly | Tyr | Ala | Val |
| | 290 | | | | | 295 | | | | | 300 | | | | |
| Thr | His | His | Ala | Glu | Gly | Phe | Leu | Met | Cys | Lys | Val | Thr | Asp | Thr | Val |
| 305 | | | | | 310 | | | | | 315 | | | | | 320 |
| Arg | Gly | Glu | Arg | Val | Ser | Phe | Pro | Val | Cys | Thr | Tyr | Val | Pro | Ala | Thr |
| | | | | 325 | | | | | 330 | | | | | 335 | |
| Ile | Cys | Asp | Gln | Met | Thr | Gly | Ile | Leu | Ala | Thr | Asp | Val | Thr | Pro | Glu |
| | | | 340 | | | | | 345 | | | | | 350 | | |
| Asp | Ala | Gln | Lys | Leu | Leu | Val | Gly | Leu | Asn | Gln | Arg | Ile | Val | Val | Asn |
| | | | 355 | | | | | 360 | | | | | 365 | | |
| Gly | Arg | Thr | Gln | Arg | Asn | Thr | Asn | Thr | Met | Lys | Asn | Tyr | Leu | Leu | Pro |
| | 370 | | | | | 375 | | | | | 380 | | | | |
| Val | Val | Ala | Gln | Ala | Phe | Ser | Lys | Trp | Ala | Arg | Glu | Ala | Lys | Ala | Asp |

```
385                 390                 395                 400
Met Glu Asp Glu Lys Pro Leu Gly Thr Arg Glu Arg Thr Leu Thr Cys
                405                 410                 415

Cys Cys Leu Trp Ala Phe Lys Ser His Lys Thr His Thr Met Tyr Lys
                420                 425                 430

Arg Pro Asp Thr Gln Thr Ile Val Lys Val Pro Ser Thr Phe Asp Ser
                435                 440                 445

Phe Val Ile Pro Ser Leu Trp Ser Ser Ser Leu Ser Ile Gly Leu Arg
        450                 455                 460

Gln Arg Ile Lys Leu Leu Leu Gly Pro Lys Leu Ser Arg Asp Leu Pro
465                 470                 475                 480

Tyr Ser Gly Asp Arg Asn Glu Ala Arg Glu Ala Lys Glu Ala Glu
                    485                 490                 495

Glu Thr Lys Glu Ala Glu Leu Thr Arg Glu Ala Leu Pro Pro Leu Val
                500                 505                 510

Gly Ser Asn Cys Ala Asp Asp Val Asp Arg Val Asp Val Glu Glu Leu
            515                 520                 525

Thr Tyr Arg Ala Gly Ala Val Val Glu Thr Pro Arg Asn Ala Leu
    530                 535                 540

Arg Val Thr Pro Gln Glu Arg Asp Gln Leu Ile Gly Ala Tyr Leu Ile
545                 550                 555                 560

Leu Ser Pro Gln Ala Val Leu Lys Ser Glu Lys Leu Thr Pro Ile His
                565                 570                 575

Pro Leu Ala Glu Gln Val Thr Ile Met Thr His Ser Gly Arg Ser Gly
                580                 585                 590

Arg Tyr Pro Val Asp Arg Tyr Asp Gly Arg Val Leu Val Pro Thr Gly
            595                 600                 605

Ala Ala Ile Pro Val Ser Glu Phe Gln Ala Leu Ser Glu Ser Ala Thr
        610                 615                 620

Met Val Tyr Asn Glu Arg Glu Phe Ile Asn Arg Lys Leu His His Ile
625                 630                 635                 640

Ala Leu Tyr Gly Pro Ala Leu Asn Thr Glu Glu Asn Tyr Glu Lys
                645                 650                 655

Val Arg Ala Glu Arg Ala Glu Ala Glu Tyr Val Phe Asp Val Asp Lys
                660                 665                 670

Arg Met Cys Val Lys Arg Glu Glu Ala Ser Gly Leu Val Leu Val Gly
            675                 680                 685

Asp Leu Ile Asn Pro Pro Phe His Glu Phe Ala Tyr Glu Gly Leu Lys
    690                 695                 700

Ile Arg Pro Ala Thr Pro Phe Gln Thr Thr Val Ile Gly Val Phe Gly
705                 710                 715                 720

Val Pro Gly Ser Gly Lys Ser Ala Ile Ile Lys Ser Val Val Thr Thr
                725                 730                 735

Arg Asp Leu Val Ala Ser Gly Lys Lys Glu Asn Cys Gln Glu Ile Val
            740                 745                 750

Asn Asp Val Lys Lys Gln Arg Gly Leu Asp Val Thr Ala Arg Thr Val
        755                 760                 765

Asp Ser Ile Leu Leu Asn Gly Cys Arg Arg Gly Val Glu Asn Leu Tyr
    770                 775                 780

Val Asp Glu Ala Phe Ala Cys His Ser Gly Thr Leu Leu Ala Leu Ile
785                 790                 795                 800

Ala Met Val Lys Pro Thr Gly Lys Val Ile Leu Cys Gly Asp Pro Lys
                805                 810                 815
```

```
Gln Cys Gly Phe Phe Asn Leu Met Gln Leu Lys Val Asn Phe Asn His
                820                 825                 830

Asp Ile Cys Thr Gln Val Leu His Lys Ser Ile Ser Arg Arg Cys Thr
                835                 840                 845

Leu Pro Ile Thr Ala Ile Val Ser Thr Leu His Tyr Gln Gly Lys Met
                850                 855                 860

Arg Thr Thr Asn Leu Cys Ser Ala Pro Ile Gln Ile Asp Thr Thr Gly
865                 870                 875                 880

Thr Thr Lys Pro Ala Lys Gly Asp Ile Val Leu Thr Cys Phe Arg Gly
                885                 890                 895

Trp Val Lys Gln Leu Gln Ile Asp Tyr Arg Gly His Glu Val Met Thr
                900                 905                 910

Ala Ala Ala Ser Gln Gly Leu Thr Arg Lys Gly Val Tyr Ala Val Arg
                915                 920                 925

Gln Lys Val Asn Glu Asn Pro Leu Tyr Ala Pro Ser Ser Glu His Val
                930                 935                 940

Asn Val Leu Leu Thr Arg Thr Glu Asn Arg Leu Val Trp Lys Thr Leu
945                 950                 955                 960

Ser Gly Asp Pro Trp Ile Lys Val Leu Thr Asn Ile Pro Lys Gly Asp
                965                 970                 975

Phe Ser Ala Thr Leu Glu Glu Trp Gln Glu Glu His Asp Asn Ile Met
                980                 985                 990

Asn Ala Leu Arg Glu Arg Ser Thr Ala Val Asp Pro Phe Gln Asn Lys
            995                 1000                1005

Ala Lys Val Cys Trp Ala Lys Cys Leu Val Gln Val Leu Glu Thr
        1010                1015                1020

Ala Gly Ile Arg Met Thr Ala Glu Glu Trp Asp Thr Val Leu Ala
        1025                1030                1035

Phe Arg Glu Asp Arg Ala Tyr Ser Pro Glu Val Ala Leu Asn Glu
        1040                1045                1050

Ile Cys Thr Lys Tyr Tyr Gly Val Asp Leu Asp Ser Gly Leu Phe
        1055                1060                1065

Ser Ala Gln Ser Val Ser Leu Tyr Tyr Glu Asn Asn His Trp Asp
        1070                1075                1080

Asn Arg Pro Gly Gly Arg Met Tyr Gly Phe Asn Arg Glu Val Ala
        1085                1090                1095

Arg Lys Phe Glu Gln Arg Tyr Pro Phe Leu Arg Gly Lys Met Asp
        1100                1105                1110

Ser Gly Leu Gln Val Asn Val Pro Glu Arg Lys Val Gln Pro Phe
        1115                1120                1125

Asn Ala Glu Cys Asn Ile Leu Pro Ser Asn Arg Arg Leu Pro His
        1130                1135                1140

Ala Leu Val Thr Ser Tyr Gln Gln Cys Gln Gly Glu Arg Val Glu
        1145                1150                1155

Trp Leu Leu Lys Lys Leu Pro Gly Tyr His Leu Leu Leu Val Ser
        1160                1165                1170

Glu Tyr Asn Leu Ala Leu Pro His Lys Arg Val Phe Trp Ile Ala
        1175                1180                1185

Pro Pro His Val Ser Gly Ala Asp Arg Ile Tyr Asp Leu Asp Leu
        1190                1195                1200

Gly Leu Pro Leu Asn Ala Gly Arg Tyr Asp Leu Val Phe Val Asn
        1205                1210                1215
```

-continued

| | | | | | | | | | | | |
|---|---|---|---|---|---|---|---|---|---|---|---|
| Ile | His | Thr | Glu | Tyr | Arg | Thr | His | His | Tyr | Gln | Gln | Cys | Val | Asp |
| | 1220 | | | | | 1225 | | | | 1230 | | | | |

| His | Ser | Met | Lys | Leu | Gln | Met | Leu | Gly | Gly | Asp | Ser | Leu | His | Leu |
| | 1235 | | | | | 1240 | | | | 1245 | | | | |

| Leu | Lys | Pro | Gly | Gly | Ser | Leu | Leu | Ile | Arg | Ala | Tyr | Gly | Tyr | Ala |
| | 1250 | | | | | 1255 | | | | 1260 | | | | |

| Asp | Arg | Val | Ser | Glu | Met | Val | Val | Thr | Ala | Leu | Ala | Arg | Lys | Phe |
| | 1265 | | | | | 1270 | | | | 1275 | | | | |

| Ser | Ala | Phe | Arg | Val | Leu | Arg | Pro | Ala | Cys | Val | Thr | Ser | Asn | Thr |
| | 1280 | | | | | 1285 | | | | 1290 | | | | |

| Glu | Val | Phe | Leu | Leu | Phe | Thr | Asn | Phe | Asp | Asn | Gly | Arg | Arg | Ala |
| | 1295 | | | | | 1300 | | | | 1305 | | | | |

| Val | Thr | Leu | His | Gln | Ala | Asn | Gln | Arg | Leu | Ser | Ser | Met | Phe | Ala |
| | 1310 | | | | | 1315 | | | | 1320 | | | | |

| Cys | Asn | Gly | Leu | His | Thr | Ala | Gly | Cys | Ala | Pro | Ser | Tyr | Arg | Val |
| | 1325 | | | | | 1330 | | | | 1335 | | | | |

| Arg | Arg | Thr | Asp | Ile | Ser | Gly | His | Ala | Glu | Glu | Ala | Val | Val | Asn |
| | 1340 | | | | | 1345 | | | | 1350 | | | | |

| Ala | Ala | Asn | Ala | Lys | Gly | Thr | Val | Gly | Asp | Gly | Val | Cys | Arg | Ala |
| | 1355 | | | | | 1360 | | | | 1365 | | | | |

| Val | Ala | Arg | Lys | Trp | Pro | Asp | Ser | Phe | Lys | Gly | Ala | Ala | Thr | Pro |
| | 1370 | | | | | 1375 | | | | 1380 | | | | |

| Val | Gly | Thr | Ala | Lys | Leu | Val | Gln | Ala | Asn | Gly | Met | Asn | Val | Ile |
| | 1385 | | | | | 1390 | | | | 1395 | | | | |

| His | Ala | Val | Gly | Pro | Asn | Phe | Ser | Thr | Val | Thr | Glu | Ala | Glu | Gly |
| | 1400 | | | | | 1405 | | | | 1410 | | | | |

| Asp | Arg | Glu | Leu | Ala | Ala | Ala | Tyr | Arg | Ala | Val | Ala | Gly | Ile | Ile |
| | 1415 | | | | | 1420 | | | | 1425 | | | | |

| Asn | Ala | Ser | Asn | Ile | Lys | Ser | Val | Ala | Ile | Pro | Leu | Leu | Ser | Thr |
| | 1430 | | | | | 1435 | | | | 1440 | | | | |

| Gly | Val | Phe | Ser | Gly | Gly | Lys | Asp | Arg | Val | Met | Gln | Ser | Leu | Asn |
| | 1445 | | | | | 1450 | | | | 1455 | | | | |

| His | Leu | Phe | Thr | Ala | Met | Asp | Thr | Thr | Asp | Ala | Asp | Val | Val | Ile |
| | 1460 | | | | | 1465 | | | | 1470 | | | | |

| Tyr | Cys | Arg | Asp | Lys | Ala | Trp | Glu | Lys | Lys | Ile | Gln | Glu | Ala | Ile |
| | 1475 | | | | | 1480 | | | | 1485 | | | | |

| Asp | Arg | Arg | Thr | Ala | Val | Glu | Leu | Val | Ser | Glu | Asp | Ile | Ser | Leu |
| | 1490 | | | | | 1495 | | | | 1500 | | | | |

| Glu | Ser | Asp | Leu | Ile | Arg | Val | His | Pro | Asp | Ser | Cys | Leu | Val | Gly |
| | 1505 | | | | | 1510 | | | | 1515 | | | | |

| Arg | Lys | Gly | Tyr | Ser | Ile | Thr | Asp | Gly | Lys | Leu | His | Ser | Tyr | Leu |
| | 1520 | | | | | 1525 | | | | 1530 | | | | |

| Glu | Gly | Thr | Arg | Phe | His | Gln | Thr | Ala | Val | Asp | Met | Ala | Glu | Ile |
| | 1535 | | | | | 1540 | | | | 1545 | | | | |

| Ser | Thr | Leu | Trp | Pro | Lys | Leu | Gln | Asp | Ala | Asn | Glu | Gln | Ile | Cys |
| | 1550 | | | | | 1555 | | | | 1560 | | | | |

| Leu | Tyr | Ala | Leu | Gly | Glu | Ser | Met | Asp | Ser | Ile | Arg | Thr | Lys | Cys |
| | 1565 | | | | | 1570 | | | | 1575 | | | | |

| Pro | Val | Glu | Asp | Ala | Asp | Ser | Ser | Thr | Pro | Pro | Lys | Thr | Val | Pro |
| | 1580 | | | | | 1585 | | | | 1590 | | | | |

| Cys | Leu | Cys | Arg | Tyr | Ala | Met | Thr | Ala | Glu | Arg | Val | Ala | Arg | Leu |
| | 1595 | | | | | 1600 | | | | 1605 | | | | |

| Arg | Met | Asn | Asn | Thr | Lys | Ala | Ile | Ile | Val | Cys | Ser | Ser | Phe | Pro |

```
              1610                1615               1620
Leu Pro Lys Tyr Arg Ile Glu Gly Val Gln Lys Val Lys Cys Asp
         1625                1630               1635

Arg Val Leu Ile Phe Asp Gln Thr Val Pro Ser Leu Val Ser Pro
         1640                1645               1650

Arg Lys Tyr Ile Pro Ala Ala Ser Thr His Ala Asp Thr Val
         1655                1660               1665

Ser Leu Asp Ser Thr Val Ser Thr Gly Ser Ala Trp Ser Phe Pro
         1670                1675               1680

Ser Glu Ala Thr Tyr Glu Thr Met Glu Val Val Ala Glu Val His
         1685                1690               1695

His Ser Glu Pro Pro Val Pro Pro Arg Arg Arg Ala Gln
         1700                1705               1710

Val Thr Met His His Gln Leu Leu Glu Val Ser Asp Met His
         1715                1720               1725

Thr Pro Ile Ala Ala Arg Val Glu Ile Pro Val Tyr Asp Thr Ala
         1730                1735               1740

Val Val Val Glu Arg Val Ala Ile Pro Cys Thr Ser Glu Tyr Ala
         1745                1750               1755

Lys Pro Ile Pro Ala Pro Arg Ala Ala Arg Val Val Pro Val Pro
         1760                1765               1770

Ala Pro Arg Ile Gln Arg Ala Ser Thr Tyr Arg Val Ser Pro Thr
         1775                1780               1785

Pro Thr Pro Arg Val Leu Arg Ala Ser Val Cys Ser Val Thr Thr
         1790                1795               1800

Ser Ala Gly Val Glu Phe Pro Trp Ala Pro Glu Asp Leu Glu Val
         1805                1810               1815

Leu Thr Glu Pro Val His Cys Lys Met Arg Glu Pro Val Glu Leu
         1820                1825               1830

Pro Trp Glu Pro Glu Asp Val Asp Ile Gln Phe Gly Asp Phe Glu
         1835                1840               1845

Thr Ser Asp Lys Ile Gln Phe Gly Asp Ile Asp Phe Asp Gln Phe
         1850                1855               1860

Leu Gly Arg Ala Gly Ala Tyr Ile Phe Ser Ser Asp Thr Gly Pro
         1865                1870               1875

Gly His Leu Gln Gln Lys Ser Val Arg Gln His Ala Leu Pro Cys
         1880                1885               1890

Glu Met Leu Tyr Val His Glu Glu Arg Thr Tyr Pro Pro Ala
         1895                1900               1905

Leu Asp Glu Ala Arg Glu Lys Leu Leu Gln Ala Lys Met Gln Met
         1910                1915               1920

Ala Pro Thr Glu Ala Asn Lys Ser Arg Tyr Gln Ser Arg Lys Val
         1925                1930               1935

Glu Asn Met Lys Ala Val Ile Ile Asp Arg Leu Lys Asp Gly Ala
         1940                1945               1950

Arg Thr Tyr Leu Thr Glu Gln Ser Glu Lys Ile Pro Thr Tyr Val
         1955                1960               1965

Ser Lys Tyr Pro Arg Pro Val Tyr Ser Pro Ser Val Glu Asp Ser
         1970                1975               1980

Leu Gln Asn Pro Glu Val Ala Val Ala Ala Cys Asn Ala Phe Leu
         1985                1990               1995

Glu Ala Asn Tyr Pro Thr Val Ala Ser Tyr Gln Ile Thr Asp Glu
         2000                2005               2010
```

-continued

```
Tyr Asp Ala Tyr Leu Asp Met Val Asp Gly Ser Glu Ser Cys Leu
    2015                2020                2025

Asp Arg Ala Thr Phe Cys Pro Ala Lys Leu Arg Cys Tyr Pro Lys
    2030                2035                2040

His His Ala Tyr His Gln Pro Gln Val Arg Ser Ala Val Pro Ser
    2045                2050                2055

Pro Phe Gln Asn Thr Leu Gln Asn Val Leu Ala Ala Ala Thr Lys
    2060                2065                2070

Arg Asn Cys Asn Val Thr Gln Met Arg Glu Leu Pro Thr Leu Asp
    2075                2080                2085

Ser Ala Val Leu Asn Val Glu Cys Phe Lys Lys Phe Ala Cys Asn
    2090                2095                2100

Gly Glu Tyr Trp Gln Glu Phe Lys Asp Asn Pro Ile Arg Ile Thr
    2105                2110                2115

Thr Glu Asn Ile Thr Thr Tyr Val Thr Arg Leu Lys Gly Pro Lys
    2120                2125                2130

Ala Ala Ala Leu Phe Ala Lys Thr His Asn Leu Val Pro Leu Gln
    2135                2140                2145

Glu Val Pro Met Asp Arg Phe Val Val Asp Met Lys Arg Asp Val
    2150                2155                2160

Lys Val Thr Pro Gly Thr Lys His Thr Glu Glu Arg Pro Lys Val
    2165                2170                2175

Gln Val Ile Gln Ala Ala Glu Pro Leu Ala Thr Ala Tyr Leu Cys
    2180                2185                2190

Gly Ile His Arg Glu Leu Val Arg Arg Leu Lys Ala Val Leu Ala
    2195                2200                2205

Pro Asn Ile His Thr Leu Phe Asp Met Ser Ala Glu Asp Phe Asp
    2210                2215                2220

Ala Ile Ile Ala Ala His Phe Gln Pro Gly Asp Ala Val Leu Glu
    2225                2230                2235

Thr Asp Ile Ala Ser Phe Asp Lys Ser Gln Asp Asp Ser Leu Ala
    2240                2245                2250

Leu Thr Ala Leu Met Leu Leu Glu Asp Leu Gly Val Asp Gln Glu
    2255                2260                2265

Leu Leu Asp Leu Ile Glu Ala Ala Phe Gly Glu Ile Thr Ser Val
    2270                2275                2280

His Leu Pro Thr Gly Thr Arg Phe Lys Phe Gly Ala Met Met Lys
    2285                2290                2295

Ser Gly Met Phe Leu Thr Leu Phe Val Asn Thr Leu Leu Asn Ile
    2300                2305                2310

Val Ile Ala Cys Arg Val Leu Arg Glu Lys Leu Thr Asn Ser Val
    2315                2320                2325

Cys Ala Ala Phe Ile Gly Asp Asp Asn Ile Val His Gly Val Arg
    2330                2335                2340

Ser Asp Pro Leu Met Ala Glu Arg Cys Ala Ser Trp Val Asn Met
    2345                2350                2355

Glu Val Lys Ile Ile Asp Ala Thr Met Cys Glu Lys Pro Pro Tyr
    2360                2365                2370

Phe Cys Gly Gly Phe Ile Leu Tyr Asp Lys Val Thr Gly Ser Ala
    2375                2380                2385

Cys Arg Val Ala Asp Pro Leu Lys Arg Leu Phe Lys Leu Gly Lys
    2390                2395                2400
```

```
Pro Leu Pro Ala Gly Asp Thr Gln Asp Glu Asp Arg Arg Ala
    2405              2410                2415

Leu Lys Asp Glu Thr Asp Arg Trp Ala Arg Val Gly Leu Lys Ser
2420              2425                2430

Glu Leu Glu Ile Ala Leu Ser Ser Arg Tyr Glu Val Asn Gly Thr
    2435              2440                2445

Gly Asn Ile Val Arg Ala Met Ala Thr Leu Ala Lys Ser Leu Lys
    2450              2455                2460

Asn Phe Lys Lys Leu Arg Gly Pro Ile Val His Leu Tyr Gly Gly
    2465              2470                2475

Pro Lys
    2480

<210> SEQ ID NO 13
<211> LENGTH: 11412
<212> TYPE: DNA
<213> ORGANISM: Venezualan equine encephalitis virus

<400> SEQUENCE: 13
atgggcggcg catgagagaa gcccacacca attacctacc caaaaatgga gagagttcac      60
gttgacatcg aggaagacag cccattcctc agagctttgc aacggagctt cccgcagttt     120
gaggtagaag ccaagcaggt cactgataat gaccatgcta atgccagagc gttttcgcat     180
ctggcttcaa aattgatcga aacggaggtg acccatccg acacgatcct tgacattgga     240
agtgcgcccg cccgcagaat gtattctaag cataagtatc attgcatctg tccgatgaga     300
tgcgcggaag atccggacag attgtacaag tatgcaacta agctgaagaa aaattgcaag     360
gaaataactg acaaggaatt ggacaagaaa atgaaggagc tcgccgccgt catgagcgac     420
cctgacctgg aaactgagac tatgtgcctc acgacgatg agtcgtgtcg ctacgaaggg     480
caagtcgctg tttaccagga tgtatacgca gttgacggac cgacaagtct ctatcaccaa     540
gccaacaagg gagttagagt cgcctattgg ataggctttg acaccacccc ttttatgttt     600
aagaacttgg ctggagcata tccatcatac tctactaact gggccgacga aaccgtgtta     660
acggctcgta atataggcct atgcagctcc gacgttatgg agcggtcacg cagaggaatg     720
tccattctta ggaagaagta tttgaaacca tccaataatg tcttattctc tgttggctcg     780
accatctacc acgagaagag ggacttactg aggagctggc acctgccgtc tgtatttcac     840
ttacgtggca agcaaaatta cacatgtcgg tgtgagacta gttagttg cgacgggtac     900 gtcgttaaaa gaatagctat cagtccaggc ctgtatggga gccttcagg ctatgctgct     960 acgatgcacc gcgagggatt cttgtgctgc aaagtgacag acacattgaa cggggagagg    1020
gtctcttttc ccgtgtgcac gtatgtgcca gctacattgt gtgaccaaat gactggcata    1080
ctggcaacag atgtcagtgc ggacgacgcg caaaaactgc tggttgggct caaccagcgc    1140
atagtcgtca acggtcgcac ccaaagaaat accaatacca tgaagaatta tcttttgccc    1200
gtagtggccc aggcatttgc taggtgggca aggaatata aggaagatca agaagatgag    1260
aggccactag gactacgaga tagacagtta gtcatggggt gctgctgggc ttttagaagg    1320
cataagataa catctatttta taagcgccca gatacccaaa ccatcatcaa agtgaacagc    1380
gatttccact cattcgtgct gcccaggata ggcagtaaca cattggagat cgggctgaga    1440
acaagaatca ggaaaatgct agaagagcac aaggagccgt cacctctcat tactgccgag    1500
gacatacaag aagctaagtg cgcagccgat gaggctaagg aggtgcgtga agccgaggag    1560
ttgcgcgccg cactaccacc tttggcagct gatgttgagg agcccactct ggaagccgat    1620
```

```
gttgacttga tgttacaaga ggctggggcc ggctcagtgg agacacctcg tggcttgata    1680
aaggttacca gctatgccgg cgaggacaag atcggctctt acgcagtgct ttctccgcag    1740
gctgtactta agagtgagaa actatcttgc attcaccctc tcgctgaaca agtcatagtg    1800
ataacacact ctggccgaaa agggcgttac gccgtggaac cctaccatgg aaaagtagtg    1860
gtgccagagg gacatgcaat acccgtccag gactttcaag ctctgagtga agtgctacc     1920 attgtgtaca cgaacgaga gttcgtaaac aggtatctgc accatattgc cacacatgga    1980
ggagcgctga acacagatga agaatattac aaaactgtca agcccagcga gcacgatggc    2040
gaatacctgt atgacatcga caggaaacag tgcgtcaaga aagaactagt cactgggcta    2100
gggcttacag gcgagctggt ggaccctccc ttccatgaat tcgcctacga gagtctgaga    2160
acacgaccgg ccgctcctta ccaagtacca accataggg tgtatggcgt gccgggatca    2220
ggcaagtctg gcatcatcaa aagcgcagtc accaaaaaag atctggtggt gagcgccaag    2280
aaagaaaact gcgcagaaat aataagggac gtcaagaaaa tgagagggct ggacgtcaat    2340
gccagaactg tggactcagt gctcttgaat ggatgcaaac accccgtaga gaccctgtat    2400
attgacgaag cttttgcttg tcatgcaggc actctcagag cgctcatagc catcataaga    2460
cctaaaaagg cagtgctctg cggggatcca aaacagtgcg gcttttcaa tatgatgtgt    2520 ctgaaagtgc attttaacca cgagatttgc acgcaggtct tccacaaaag catctctcgt    2580
cgttgcacta aatctgtgac ttcggtcgtc tcaaccttgt tttacgacaa aagaatgaga    2640
acgacgaacc cgaaagagac taagattgag attgacacta ctggcagtac caaaccaaag    2700
caggacgatc tcattctcac ttgttttaga gggtgggtga agcagttgca aatagattac    2760
aaaggcaacg agataatgac ggcagctgcc tctcaagggc tgacccgtaa aggcgtgtat    2820
gccgttcggt acaaggtgaa tgaaaacccc ctgtacgcac ccacctcaga acacgtgaac    2880
gtcctactga cccgcacgga ggaccgtatc gtgtggaaaa cactagccgg cgatccatgg    2940
ataaaaacac tgacggccaa gtatcctggg aatttcactg ccacgataga ggaatggcaa    3000
gcagagcatg atgccatcat gaggcacatc ttggagagac cggaccctac cgatgttttc    3060
caaaataagg cgaacgtgtg ttgggccaag gctttggtgc cggtactgaa gactgcaggc    3120
atagacatga ccactgaaca atggaacact gtggattatt cgaaacggaa caaagctcac    3180
tcagcagaga tagtgttgaa ccaactatgc gtgaggttct ttggactcga cctggactcc    3240
ggtctatttt ctgcacccac tgttccgctg tccattagga taatcactg ggataattcc    3300 ccgtcgccta acatgtacgg gctgaataaa gaagtggtcc gtcagctctc ccgccggtac    3360
ccacaactgc ctcgagcagt tgccactgga agagtctatg acatgaacac tggtacactg    3420
cgcaattatg atccgcgcat aaatctagta cctgtgaaca agagactgcc tcatgcttta    3480
gtcctccacc ataatgaaca cccgcagagt gattttctt cattcgtcag caaactgaag    3540
ggcagaactg tcttggtggt cggggagaag ttgtccgtcc caggcaaaac ggttgattgg    3600
ttgtcagaca agcctgaggc taccttcaga gctcggctgg atttaggtat cccaggtgac    3660
gtgcccaaat acgacattat atttattaac gtgaggactc catataaata ccatcattat    3720
cagcagtgtg aagaccacgc cattaagctt agtatgttga ccaagaaagc ttgtctgcat    3780
ctgaatcccg gcggaacctg cgtcagcata ggttatggtt acgctgacag ggccagcgaa    3840
agcatcattg gtgctatagc gcggcagttc aagttctccc gggtatgcaa acctaaatcc    3900
tcacttgaag agacagaagt tctgtttgta ttcattgggt acgatcgcaa ggcccgtacg    3960
```

-continued

```
cataatcctt acaagctttc atctaccttg accaacatct atacaggttc cagactccac    4020
gaagccggat gcgcaccctc atatcatgtg gtgcgagggg atattgccat ggccaccgaa    4080
ggagtgatca taaatgccgc taacagcaaa ggacaacctg gcggaggggt gtgcggagcg    4140
ctgtataaga aattcccgga aagcttcgat ttacagccaa tcgaagtggg aaaagcgcga    4200
ctggtcaaag gtgcagctaa acacatcatt catgccgtag gcccaacttc aacaaagtt     4260
tcggaagttg aaggtgacaa acagttggca gaggcttatg agtccatcgc taaaattgtc    4320
aacgataaca attacaagtc agtagcgatt ccactgttgt ctaccggcat ctttctggt     4380
aacaaagatc gactaaccca atcattgaac catttgctga cagctttaga caccactgat    4440
gcagatgtag ccatatactg cagggacaag aaatgggaaa tgactctcaa ggaagcagtg    4500
gctaggagag aagcagtgga ggagatatgc atatccgacg actcttcggt gacagaaccg    4560
gatgcagagc tggtgagggt acatccgaag agttctttgg ctggcaggaa gggctacagc    4620
acaagtgatg gcaagacttt ctcatatttg aagggacta aattccacca ggcggccaag    4680
gatatagcag aaattaatgc catgtggcct gttgcaacgg aggccaatga gcaagtatgc    4740
atgtatatcc tcggtgaaag catgagcagc attaggtcaa aatgccccgt cgaagaatcg    4800
gaagcctcca caccacctag cacgctgcct tgcttgtgca tccatgctat gactccagaa    4860
agagtacaac gcctaaaagc ctcgcgtcca gaacaaatta ctgtgtgctc atcctttcca    4920
ttgccgaagt atagaatcac tggtgtgcag aagatccagt gctcccagcc tatactgttc    4980
tcaccgaagg tgcctgcgta cattcatcca cggaagtacc tcgtggaaac accaccggtg    5040
gaagagattc cggagctgcc ggcggagaac caatccacag aggggacatc tgaacaacca    5100
gcaccaaacg tggatgcaac caggactaga acgcctgaac cgatcatcat tgaagaggaa    5160
gaagaggata gtataagttt gctgtcagac ggcccgaccc accaggtgct gcaagtcgag    5220
gcagacatcc acgggccgcc ttctgtatcc agctcatcct ggtccattcc tcacgcatcc    5280
gactttgatg tggacagttt atccatcctt gccctggagg gagctagcgt gactagcgag    5340
gcagcgtcag ccgagactaa ctcatacttc gcaaggagca tggagttcct ggcgcgaccg    5400
gtgcctgcgc ctcgaacagt attcaggaac cctccacatc ccgctccacg cacaagaaca    5460
ccgtcacttg cacccagcag ggccagctcg agaactagcc tggtttccac cccgccaggc    5520
gtgaataggg tgattactag agaggagctc gaggcgctta ccccgtcccg cgctcctagc    5580
aggtcggcct caagaactag tctggtctct aacccgccag gcgtaaatag ggtgattaca    5640
agagaggagt ttgaggcgtt cgtggcacaa caacaatgac ggtttgacgc gggtgcatac    5700
atcttttcct ccgataccgg tcaagggcat ttacaacaaa aatcagtaag gcaaacggtg    5760
ctatccgaag tggttttgga gaggaccgaa ttggagattt cgtatgcccc gcgcctcgac    5820
caagaaaaag aagaactact acgcaagaaa ttacagctga tcccacacc  tgctaacaga    5880
agcagatacc agtccagaag ggtggagaac atgaaagcca taacagctag acgtattctg    5940
caaggcctag gacattattt gaaggcagaa ggaaaagtgg agtgctatcg aaccctgcat    6000
cctgttcctt tgtattcatc tagtgtgaat cgtgcttttt caagccccaa ggtcgcagtg    6060
gaagcctgca atgccatgct gaaagaaaac tttccgactg tagcttctta ctgtataatt    6120
ccagagtacg atgcctatct ggacatggtt gacggcgctt cttgttgctt agacactgcc    6180
agttttgcc ctgcgaagct gcgcagtttt ccaaagaaac actcttactt ggaacccaca    6240
atacggtcgg cagtgccatc ggcgattcag aacacgctcc agaatgtcct ggcagctgcc    6300
acaaaaagaa attgcaacgt cacgcaaatg agagaattgc ccgtattgga ctcggctgcc    6360
```

```
tttaatgtgg aatgcttcaa gaaatatgcg tgcaataatg aatattggga aacgtttaaa    6420
gaaaacccca tcaggcttac tgaagaaaat gtggtaaatt acattactaa attaaaagga    6480
ccaaaagctg ctgctctttt tgcgaagaca cataatttaa atatgttaca ggacatacca    6540
atggacaggt ttgtaatgga cttaaagagg acgtgaaag tgactccagg aacaaaacat    6600
actgaagaac gacccaaggt acaggtgatc caggccgccg atccgctagc gacagcgtat    6660
ctgtgcggaa tccaccggga gttggttagg agattaaatg ctgtcctgct tccgaacatc    6720
catacactgt ttgacatgtc ggctgaagac tttgacgcta ttattgccga gcatttccag    6780
cctggggact gtgttctgga aactgacatt gcgtcgtttg ataaaagtga ggacgacgcc    6840
atggctctga ccgcgttgat gattctggaa gatctaggag tggacgcaga gctgttgacg    6900
ctgattgagg cggctttcgg cgaaatatca tcaatacatt tgcccaccaa aactaaattt    6960
aaattcggag ccatgatgaa atccggaatg ttcctcacac tgtttgtgaa cacagtcatt    7020
aacatcgtaa tcgcaagcag agtgttaaga gagcggctaa ccggatcacc atgtgcagca    7080
ttcattggag atgacaatat cgtgaaagga gtcaaatctg acaaattaat ggcagacagg    7140
tgcgccactt ggttgaacat ggaagtcaag atcatgacg ccgtggtggg cgagaaagcg    7200
ccctatttct gtggagggtt tattttgtgt gactccgtga ccggcacagc gtgccgtgtg    7260
gcagaccccc taaaaggct gtttaagctt ggcaaacctc tggcagcaga cgatgaacat    7320
gacgatgaca ggagaagggc attatacgaa gagtcaacac gctggaatcg agtgggaatt    7380
cttccagagc tgtgtaaggc agtagaatca aggtatgaaa ccgtaggaac ttccatcata    7440
gttatggcca tgactactct agctagcagt gttaagtcgt tcagctacct gagaggggcc    7500
cctataactc tctacggcta acctgaatgg actacgacat agtctagtcc gccaagatgt    7560
tcccgttcca accaatgtat ccgatgcagc caatgcccta tcgtaacccg ttcgcggccc    7620
cgcgcaggcc ctggttcccc agaaccgatc cttttctggc gatgcaggtg caggaattaa    7680
cccgctcgat ggctaacctg acgttcaagc aacgccggga tgcgccacct gaagggccac    7740
ccgctaagaa accgaagcgg gaggccccgc aaaaacaaaa aggggaggc caagggaaga    7800 agaagaagaa tcagggaag aagaaggcta agacggggcc acctaatccg aaggcacaga    7860
gtggaaacaa gaagaagacc aacaagaaac caggcaagag acagcgcatg gtcatgaaat    7920
tggaatctga caagacattc ccaattatgc tggaaggaa gattaacggc tacgcttgcg    7980
tggtcggagg gaagttattc aggccgatgc acgtggaagg caagatcgac aatgacgttc    8040
tggccgcact taagacgaag aaagcatcca aatatgatct tgagtatgca gatgtgccac    8100
agaacatgcg ggccgataca ttcaagtaca cccacgagaa gccccaaggc tattatagct    8160
ggcatcatgg agcagtccaa tatgaaaatg gcgtttcac ggtgccaaaa ggagttgggg    8220
ccaagggaga cagcggacga cccattctgg acaatcaggg acgggtggtc gctattgtgc    8280
tgggaggtgt gaatgaagga tctaggacag cccctttcagt cgtcatgtgg aacgagaagg    8340
gagtaactgt gaagtatact ccggagaact gcgagcaatg gtcactagtg accaccctgt    8400
gtctgctcgc caatgtgacg ttcccatgtg cccaaccacc aatttgctac gacagaaaac    8460
cagcagagac cttggccatg ctcagcgtta acgttgacaa cccgggctac gatgagctgc    8520
tggaagcagc tgttaggtgc cccgaagaa aaggagatc taccgaggag ctgtttaagg    8580
agtataagct aacgcgccct tacatggcca gatgcatcag atgtgccgtt gggagctgcc    8640
atagtccaat agcaattgag gcagtgaaga gcgacgggca cgacggctat gttagacttc    8700
```

-continued

```
agacttcctc gcagtacggc ctggattcct ctggcaactt aaagggaagg accatgcggt    8760
atgacatgca cggaaccatt gaagagatac cgctacatca agtgtcactc cacacatctc    8820
gcccgtgtca cattgtggat gggcatggtt attttctgct tgctaggtgc ccggcagggg    8880
actccatcac tatggaattt aagaaagatt cagtcacaca ctcctgctca gtgccgtatg    8940
aagtgaaatt taatcctgta ggcagagaac tctacactca tcccccagaa cacggagcag    9000
agcaagcgtg ccaagtctac gcgcatgatg cacagaacag aggagcttat gtcgagatgc    9060
acctcccggg ctcagaagtg gacagcagtt tggtttcctt gagcggcagt tcagtcaccg    9120
tgacacctcc tgctgggact agcgccctgg tggaatgcga gtgcggcggc acaaagatct    9180
ccgagaccat caacacggca aaacagttca gccagtgcac aaagaaggag caatgcagag    9240
catatcgact gcagaatgac aaatgggtgt ataattctga caaactgccc aaagcagcgg    9300
gagccaccct aaaaggaaaa ctacacgtcc cattttttgct ggcagacggc aaatgcaccg    9360
tgcctctagc accggaacct atgataacct tcggtttccg atcagtgtca ctgaaactgc    9420
accctaagaa tcccacatat ctgaccactc gccaacttgc tgatgagcct cattacacgc    9480
acgagctcat atctgaacca gctgttagga attttaccgt cactgaaaag gggtgggagt    9540
ttgtatgggg aaaccacccg ccgaaaaggt tttgggcaca ggaaacagca cccggaaatc    9600
cacatgggct gccacacgag gtgataactc attattacca cagataccct atgtccacca    9660
tcctgggttt atcaatttgc gccgccattg taaccgtttc cgttcagcg tctacctggc    9720
tgttctgcaa atccagagtt tcgtgcctaa ctccttaccg gctaacacct aacgccagga    9780
tgccgctttg cctggctgtg ctttgctgcg ctcgcactgc ccgggccgag accacctggg    9840
agtccttgga tcacctatgg aacaataacc agcagatgtt ctggattcaa ttgctgatcc    9900
ccctggccgc cttgattgta gtgactcgcc tgctcaagtg cgtgtgctgt gtagtgcctt    9960
ttttagtcgt ggccggcgcc gcaggcgccg gcgcctacga gcacgcgacc acgatgccga   10020
gccaagtggg aatctcgtat aacaccatag tcaacagagc aggctacgcg ccactcccta   10080
tcagcataac accaacaaag atcaagctga tacctacagt gaacttggag tacatcacct   10140
gccactacaa aacaggaatg gattcaccag ccattaagtg ctgcggatct caggaatgta   10200
ctccaactta caggcctgat gaacagtgca aagtcttcac tggggtttac ccgttcatgt   10260
ggggaggcgc atattgcttt tgcgacactg agaacaccca agtcagcaag gcctacgtaa   10320
tgaaatctga cgactgcctt gctgatcacg ctgaagcata caaagcgcac acagcctcag   10380
tgcaggcgtt cctcaacatc acagtgggag aacactctat tgtgaccacc gtgtatgtga   10440
atggagaaac tcctgtgaac ttcaatgggg tcaaattaac tgcaggtcca ctttccacag   10500
cttggacacc ctttgaccgc aaaatcgtgc agtatgccgg ggagatctat aattacgatt   10560
ttcctgagta cggggcagga caaccaggag catttggaga catacaatcc agaacagtct   10620
cgagctcaga tctgtatgcc aataccaacc tagtgctgca gagacccaaa gcaggagcga   10680
tccatgtgcc atacactcag gcaccatcgg gttttgagca atggaagaaa gataaagctc   10740
cgtcattgaa attcaccgcc ctttcggat gcgaaatata caaaccccc attcgcgccg   10800
aaaattgtgc cgtagggtca attccattag cctttgacat ccccgacgcc ttgttcacca   10860
gggtgtcaga cacaccgaca ctttcagcgg ccgaatgcac tcttaacgag tgcgtgtatt   10920
catccgactt tggcgggatc gccacggtca gtattcggc cagcaagtca ggcaagtgcg   10980
cagtccatgt gccatcaggg actgctaccc taaaagaagc agcagtcgag ttaaccgagc   11040
aagggtcggt gaccattcat ttctcgaccg caaatatcca cccggagttc aggctccaaa   11100
```

-continued

```
tatgcacatc atatgtcatg tgcaaaggtg attgtcaccc cccgaaagac cacattgtga    11160
cacacccaca gtatcacgcc caaacattta cagccgcggt gtcaaaaacc gcgtggacgt    11220
ggttaacatc cctgctggga ggatcggccg taattattat aattggctta gtgctggcta    11280
ctattgtggc catgtacgtg ctgaccaacc agaaacataa ttgaacatag cagcaattgg    11340
caagctgctt atatagaact cgcggcgatt ggcatgccgc tttaaaattt tattttattt    11400
tcttttcttt tc                                                        11412
```

<210> SEQ ID NO 14
<211> LENGTH: 1255
<212> TYPE: PRT
<213> ORGANISM: Venezualan equine encephalitis virus

<400> SEQUENCE: 14

```
Met Phe Pro Phe Gln Pro Met Tyr Pro Met Gln Met Pro Tyr Arg
1               5                   10                  15

Asn Pro Phe Ala Ala Pro Arg Arg Pro Trp Phe Pro Arg Thr Asp Pro
            20                  25                  30

Phe Leu Ala Met Gln Val Gln Glu Leu Thr Arg Ser Met Ala Asn Leu
        35                  40                  45

Thr Phe Lys Gln Arg Arg Asp Ala Pro Pro Glu Gly Pro Pro Ala Lys
    50                  55                  60

Lys Pro Lys Arg Glu Ala Pro Gln Lys Gln Lys Gly Gly Gly Gln Gly
65                  70                  75                  80

Lys Lys Lys Lys Asn Gln Gly Lys Lys Ala Lys Thr Gly Pro Pro
                85                  90                  95

Asn Pro Lys Ala Gln Ser Gly Asn Lys Lys Thr Asn Lys Lys Pro
            100                 105                 110

Gly Lys Arg Gln Arg Met Val Met Lys Leu Glu Ser Asp Lys Thr Phe
        115                 120                 125

Pro Ile Met Leu Glu Gly Lys Ile Asn Gly Tyr Ala Cys Val Val Gly
    130                 135                 140

Gly Lys Leu Phe Arg Pro Met His Val Glu Gly Lys Ile Asp Asn Asp
145                 150                 155                 160

Val Leu Ala Ala Leu Lys Thr Lys Lys Ala Ser Lys Tyr Asp Leu Glu
                165                 170                 175

Tyr Ala Asp Val Pro Gln Asn Met Arg Ala Asp Thr Phe Lys Tyr Thr
            180                 185                 190

His Glu Lys Pro Gln Gly Tyr Tyr Ser Trp His His Gly Ala Val Gln
        195                 200                 205

Tyr Glu Asn Gly Arg Phe Thr Val Pro Lys Gly Val Gly Ala Lys Gly
    210                 215                 220

Asp Ser Gly Arg Pro Ile Leu Asp Asn Gln Gly Arg Val Val Ala Ile
225                 230                 235                 240

Val Leu Gly Gly Val Asn Glu Gly Ser Arg Thr Ala Leu Ser Val Val
                245                 250                 255

Met Trp Asn Glu Lys Gly Val Thr Val Lys Tyr Thr Pro Glu Asn Cys
            260                 265                 270

Glu Gln Trp Ser Leu Val Thr Thr Leu Cys Leu Leu Ala Asn Val Thr
        275                 280                 285

Phe Pro Cys Ala Gln Pro Pro Ile Cys Tyr Asp Arg Lys Pro Ala Glu
    290                 295                 300

Thr Leu Ala Met Leu Ser Val Asn Val Asp Asn Pro Gly Tyr Asp Glu
```

-continued

```
                305                 310                 315                 320
Leu Leu Glu Ala Ala Val Arg Cys Pro Gly Arg Lys Arg Arg Ser Thr
                325                 330                 335
Glu Glu Leu Phe Lys Glu Tyr Lys Leu Thr Arg Pro Tyr Met Ala Arg
                340                 345                 350
Cys Ile Arg Cys Ala Val Gly Ser Cys His Ser Pro Ile Ala Ile Glu
                355                 360                 365
Ala Val Lys Ser Asp Gly His Asp Gly Tyr Val Arg Leu Gln Thr Ser
    370                 375                 380
Ser Gln Tyr Gly Leu Asp Ser Ser Gly Asn Leu Lys Gly Arg Thr Met
385                 390                 395                 400
Arg Tyr Asp Met His Gly Thr Ile Glu Glu Ile Pro Leu His Gln Val
                405                 410                 415
Ser Leu His Thr Ser Arg Pro Cys His Ile Val Asp Gly His Gly Tyr
                420                 425                 430
Phe Leu Leu Ala Arg Cys Pro Ala Gly Asp Ser Ile Thr Met Glu Phe
                435                 440                 445
Lys Lys Asp Ser Val Thr His Ser Cys Ser Val Pro Tyr Glu Val Lys
    450                 455                 460
Phe Asn Pro Val Gly Arg Glu Leu Tyr Thr His Pro Pro Glu His Gly
465                 470                 475                 480
Ala Glu Gln Ala Cys Gln Val Tyr Ala His Asp Ala Gln Asn Arg Gly
                485                 490                 495
Ala Tyr Val Glu Met His Leu Pro Gly Ser Glu Val Asp Ser Ser Leu
                500                 505                 510
Val Ser Leu Ser Gly Ser Ser Val Thr Val Thr Pro Pro Ala Gly Thr
                515                 520                 525
Ser Ala Leu Val Glu Cys Glu Cys Gly Gly Thr Lys Ile Ser Glu Thr
    530                 535                 540
Ile Asn Thr Ala Lys Gln Phe Ser Gln Cys Thr Lys Lys Glu Gln Cys
545                 550                 555                 560
Arg Ala Tyr Arg Leu Gln Asn Asp Lys Trp Val Tyr Asn Ser Asp Lys
                565                 570                 575
Leu Pro Lys Ala Ala Gly Ala Thr Leu Lys Gly Lys Leu His Val Pro
                580                 585                 590
Phe Leu Leu Ala Asp Gly Lys Cys Thr Val Pro Leu Ala Pro Glu Pro
                595                 600                 605
Met Ile Thr Phe Gly Phe Arg Ser Val Ser Leu Lys Leu His Pro Lys
    610                 615                 620
Asn Pro Thr Tyr Leu Thr Thr Arg Gln Leu Ala Asp Glu Pro His Tyr
625                 630                 635                 640
Thr His Glu Leu Ile Ser Glu Pro Ala Val Arg Asn Phe Thr Val Thr
                645                 650                 655
Glu Lys Gly Trp Glu Phe Val Trp Gly Asn His Pro Pro Lys Arg Phe
                660                 665                 670
Trp Ala Gln Glu Thr Ala Pro Gly Asn Pro His Gly Leu Pro His Glu
                675                 680                 685
Val Ile Thr His Tyr Tyr His Arg Tyr Pro Met Ser Thr Ile Leu Gly
                690                 695                 700
Leu Ser Ile Cys Ala Ala Ile Val Thr Val Ser Val Ala Ala Ser Thr
705                 710                 715                 720
Trp Leu Phe Cys Lys Ser Arg Val Ser Cys Leu Thr Pro Tyr Arg Leu
                725                 730                 735
```

```
Thr Pro Asn Ala Arg Met Pro Leu Cys Leu Ala Val Leu Cys Cys Ala
            740                 745                 750

Arg Thr Ala Arg Ala Glu Thr Thr Trp Glu Ser Leu Asp His Leu Trp
            755                 760                 765

Asn Asn Asn Gln Gln Met Phe Trp Ile Gln Leu Leu Ile Pro Leu Ala
            770                 775                 780

Ala Leu Ile Val Val Thr Arg Leu Leu Lys Cys Val Cys Cys Val Val
785                 790                 795                 800

Pro Phe Leu Val Val Ala Gly Ala Ala Gly Ala Gly Ala Tyr Glu His
                805                 810                 815

Ala Thr Thr Met Pro Ser Gln Val Gly Ile Ser Tyr Asn Thr Ile Val
            820                 825                 830

Asn Arg Ala Gly Tyr Ala Pro Leu Pro Ile Ser Ile Thr Pro Thr Lys
            835                 840                 845

Ile Lys Leu Ile Pro Thr Val Asn Leu Glu Tyr Ile Thr Cys His Tyr
850                 855                 860

Lys Thr Gly Met Asp Ser Pro Ala Ile Lys Cys Cys Gly Ser Gln Glu
865                 870                 875                 880

Cys Thr Pro Thr Tyr Arg Pro Asp Glu Gln Cys Lys Val Phe Thr Gly
            885                 890                 895

Val Tyr Pro Phe Met Trp Gly Gly Ala Tyr Cys Phe Cys Asp Thr Glu
            900                 905                 910

Asn Thr Gln Val Ser Lys Ala Tyr Val Met Lys Ser Asp Asp Cys Leu
            915                 920                 925

Ala Asp His Ala Glu Ala Tyr Lys Ala His Thr Ala Ser Val Gln Ala
            930                 935                 940

Phe Leu Asn Ile Thr Val Gly Glu His Ser Ile Val Thr Thr Val Tyr
945                 950                 955                 960

Val Asn Gly Glu Thr Pro Val Asn Phe Asn Gly Val Lys Leu Thr Ala
            965                 970                 975

Gly Pro Leu Ser Thr Ala Trp Thr Pro Phe Asp Arg Lys Ile Val Gln
            980                 985                 990

Tyr Ala Gly Glu Ile Tyr Asn Tyr Asp Phe Pro Glu Tyr Gly Ala Gly
            995                 1000                1005

Gln Pro Gly Ala Phe Gly Asp Ile Gln Ser Arg Thr Val Ser Ser
    1010                1015                1020

Ser Asp Leu Tyr Ala Asn Thr Asn Leu Val Leu Gln Arg Pro Lys
    1025                1030                1035

Ala Gly Ala Ile His Val Pro Tyr Thr Gln Ala Pro Ser Gly Phe
    1040                1045                1050

Glu Gln Trp Lys Lys Asp Lys Ala Pro Ser Leu Lys Phe Thr Ala
    1055                1060                1065

Pro Phe Gly Cys Glu Ile Tyr Thr Asn Pro Ile Arg Ala Glu Asn
    1070                1075                1080

Cys Ala Val Gly Ser Ile Pro Leu Ala Phe Asp Ile Pro Asp Ala
    1085                1090                1095

Leu Phe Thr Arg Val Ser Asp Thr Pro Thr Leu Ser Ala Ala Glu
    1100                1105                1110

Cys Thr Leu Asn Glu Cys Val Tyr Ser Ser Asp Phe Gly Gly Ile
    1115                1120                1125

Ala Thr Val Lys Tyr Ser Ala Ser Lys Ser Gly Lys Cys Ala Val
    1130                1135                1140
```

His Val Pro Ser Gly Thr Ala Thr Leu Lys Glu Ala Ala Val Glu
    1145                1150                1155

Leu Thr Glu Gln Gly Ser Val Thr Ile His Phe Ser Thr Ala Asn
    1160                1165                1170

Ile His Pro Glu Phe Arg Leu Gln Ile Cys Thr Ser Tyr Val Met
    1175                1180                1185

Cys Lys Gly Asp Cys His Pro Pro Lys Asp His Ile Val Thr His
    1190                1195                1200

Pro Gln Tyr His Ala Gln Thr Phe Thr Ala Ala Val Ser Lys Thr
    1205                1210                1215

Ala Trp Thr Trp Leu Thr Ser Leu Leu Gly Gly Ser Ala Val Ile
    1220                1225                1230

Ile Ile Ile Gly Leu Val Leu Ala Thr Ile Val Ala Met Tyr Val
    1235                1240                1245

Leu Thr Asn Gln Lys His Asn
    1250                1255

<210> SEQ ID NO 15
<211> LENGTH: 2491
<212> TYPE: PRT
<213> ORGANISM: Venezualan equine encephalitis virus

<400> SEQUENCE: 15

Met Glu Arg Val His Val Asp Ile Glu Glu Asp Ser Pro Phe Leu Arg
1               5                   10                  15

Ala Leu Gln Arg Ser Phe Pro Gln Phe Glu Val Glu Ala Lys Gln Val
                20                  25                  30

Thr Asp Asn Asp His Ala Asn Ala Arg Ala Phe Ser His Leu Ala Ser
            35                  40                  45

Lys Leu Ile Glu Thr Glu Val Asp Pro Ser Asp Thr Ile Leu Asp Ile
        50                  55                  60

Gly Ser Ala Pro Ala Arg Arg Met Tyr Ser Lys His Lys Tyr His Cys
65                  70                  75                  80

Ile Cys Pro Met Arg Cys Ala Glu Asp Pro Asp Arg Leu Tyr Lys Tyr
                85                  90                  95

Ala Thr Lys Leu Lys Lys Asn Cys Lys Glu Ile Thr Asp Lys Glu Leu
                100                 105                 110

Asp Lys Lys Met Lys Glu Leu Ala Ala Val Met Ser Asp Pro Asp Leu
            115                 120                 125

Glu Thr Glu Thr Met Cys Leu His Asp Asp Glu Ser Cys Arg Tyr Glu
        130                 135                 140

Gly Gln Val Ala Val Tyr Gln Asp Val Tyr Ala Val Asp Gly Pro Thr
145                 150                 155                 160

Ser Leu Tyr His Gln Ala Asn Lys Gly Val Arg Val Ala Tyr Trp Ile
                165                 170                 175

Gly Phe Asp Thr Thr Pro Phe Met Phe Lys Asn Leu Ala Gly Ala Tyr
                180                 185                 190

Pro Ser Tyr Ser Thr Asn Trp Ala Asp Glu Thr Val Leu Thr Ala Arg
            195                 200                 205

Asn Ile Gly Leu Cys Ser Ser Asp Val Met Glu Arg Ser Arg Arg Gly
        210                 215                 220

Met Ser Ile Leu Arg Lys Lys Tyr Leu Lys Pro Ser Asn Asn Val Leu
225                 230                 235                 240

Phe Ser Val Gly Ser Thr Ile Tyr His Glu Lys Arg Asp Leu Leu Arg
                245                 250                 255

```
Ser Trp His Leu Pro Ser Val Phe His Leu Arg Gly Lys Gln Asn Tyr
            260                 265                 270

Thr Cys Arg Cys Glu Thr Ile Val Ser Cys Asp Gly Tyr Val Val Lys
            275                 280                 285

Arg Ile Ala Ile Ser Pro Gly Leu Tyr Gly Lys Pro Ser Gly Tyr Ala
            290                 295                 300

Ala Thr Met His Arg Glu Gly Phe Leu Cys Cys Lys Val Thr Asp Thr
305                 310                 315                 320

Leu Asn Gly Glu Arg Val Ser Phe Pro Val Cys Thr Tyr Val Pro Ala
                325                 330                 335

Thr Leu Cys Asp Gln Met Thr Gly Ile Leu Ala Thr Val Ser Ala
            340                 345                 350

Asp Asp Ala Gln Lys Leu Leu Val Gly Leu Asn Gln Arg Ile Val Val
            355                 360                 365

Asn Gly Arg Thr Gln Arg Asn Thr Asn Thr Met Lys Asn Tyr Leu Leu
    370                 375                 380

Pro Val Val Ala Gln Ala Phe Ala Arg Trp Ala Lys Glu Tyr Lys Glu
385                 390                 395                 400

Asp Gln Glu Asp Glu Arg Pro Leu Gly Leu Arg Asp Arg Gln Leu Val
                405                 410                 415

Met Gly Cys Cys Trp Ala Phe Arg Arg His Lys Ile Thr Ser Ile Tyr
            420                 425                 430

Lys Arg Pro Asp Thr Gln Thr Ile Ile Lys Val Asn Ser Asp Phe His
            435                 440                 445

Ser Phe Val Leu Pro Arg Ile Gly Ser Asn Thr Leu Glu Ile Gly Leu
    450                 455                 460

Arg Thr Arg Ile Arg Lys Met Leu Glu Glu His Lys Glu Pro Ser Pro
465                 470                 475                 480

Leu Ile Thr Ala Glu Asp Ile Gln Glu Ala Lys Cys Ala Ala Asp Glu
                485                 490                 495

Ala Lys Glu Val Arg Glu Ala Glu Glu Leu Arg Ala Ala Leu Pro Pro
            500                 505                 510

Leu Ala Ala Asp Val Glu Pro Thr Leu Glu Ala Asp Val Asp Leu
            515                 520                 525

Met Leu Gln Glu Ala Gly Ala Gly Ser Val Glu Thr Pro Arg Gly Leu
530                 535                 540

Ile Lys Val Thr Ser Tyr Ala Gly Glu Asp Lys Ile Gly Ser Tyr Ala
545                 550                 555                 560

Val Leu Ser Pro Gln Ala Val Leu Lys Ser Glu Lys Leu Ser Cys Ile
            565                 570                 575

His Pro Leu Ala Glu Gln Val Ile Val Thr His Ser Gly Arg Lys
            580                 585                 590

Gly Arg Tyr Ala Val Glu Pro Tyr His Gly Lys Val Val Pro Glu
    595                 600                 605

Gly His Ala Ile Pro Val Gln Asp Phe Gln Ala Leu Ser Glu Ser Ala
    610                 615                 620

Thr Ile Val Tyr Asn Glu Arg Glu Phe Val Asn Arg Tyr Leu His His
625                 630                 635                 640

Ile Ala Thr His Gly Gly Ala Leu Asn Thr Asp Glu Glu Tyr Tyr Lys
            645                 650                 655

Thr Val Lys Pro Ser Glu His Asp Gly Glu Tyr Leu Tyr Asp Ile Asp
            660                 665                 670
```

```
Arg Lys Gln Cys Val Lys Lys Glu Leu Val Thr Gly Leu Gly Leu Thr
            675                 680                 685

Gly Glu Leu Val Asp Pro Pro Phe His Glu Phe Ala Tyr Glu Ser Leu
690                 695                 700

Arg Thr Arg Pro Ala Ala Pro Tyr Gln Val Pro Thr Ile Gly Val Tyr
705                 710                 715                 720

Gly Val Pro Gly Ser Gly Lys Ser Gly Ile Ile Lys Ser Ala Val Thr
            725                 730                 735

Lys Lys Asp Leu Val Val Ser Ala Lys Glu Asn Cys Ala Glu Ile
            740                 745                 750

Ile Arg Asp Val Lys Lys Met Arg Gly Leu Asp Val Asn Ala Arg Thr
            755                 760                 765

Val Asp Ser Val Leu Leu Asn Gly Cys Lys His Pro Val Glu Thr Leu
770                 775                 780

Tyr Ile Asp Glu Ala Phe Ala Cys His Ala Gly Thr Leu Arg Ala Leu
785                 790                 795                 800

Ile Ala Ile Ile Arg Pro Lys Lys Ala Val Leu Cys Gly Asp Pro Lys
            805                 810                 815

Gln Cys Gly Phe Phe Asn Met Met Cys Leu Lys Val His Phe Asn His
            820                 825                 830

Glu Ile Cys Thr Gln Val Phe His Lys Ser Ile Ser Arg Arg Cys Thr
            835                 840                 845

Lys Ser Val Thr Ser Val Val Ser Thr Leu Phe Tyr Asp Lys Arg Met
850                 855                 860

Arg Thr Thr Asn Pro Lys Glu Thr Lys Ile Glu Ile Asp Thr Thr Gly
865                 870                 875                 880

Ser Thr Lys Pro Lys Gln Asp Asp Leu Ile Leu Thr Cys Phe Arg Gly
            885                 890                 895

Trp Val Lys Gln Leu Gln Ile Asp Tyr Lys Gly Asn Glu Ile Met Thr
            900                 905                 910

Ala Ala Ala Ser Gln Gly Leu Thr Arg Lys Gly Val Tyr Ala Val Arg
            915                 920                 925

Tyr Lys Val Asn Glu Asn Pro Leu Tyr Ala Pro Thr Ser Glu His Val
930                 935                 940

Asn Val Leu Leu Thr Arg Thr Glu Asp Arg Ile Val Trp Lys Thr Leu
945                 950                 955                 960

Ala Gly Asp Pro Trp Ile Lys Thr Leu Thr Ala Lys Tyr Pro Gly Asn
            965                 970                 975

Phe Thr Ala Thr Ile Glu Glu Trp Gln Ala Glu His Asp Ala Ile Met
            980                 985                 990

Arg His Ile Leu Glu Arg Pro Asp Pro Thr Asp Val Phe Gln Asn Lys
            995                 1000                1005

Ala Asn Val Cys Trp Ala Lys Ala Leu Val Pro Val Leu Lys Thr
1010                1015                1020

Ala Gly Ile Asp Met Thr Thr Glu Gln Trp Asn Thr Val Asp Tyr
1025                1030                1035

Phe Glu Thr Asp Lys Ala His Ser Ala Glu Ile Val Leu Asn Gln
1040                1045                1050

Leu Cys Val Arg Phe Phe Gly Leu Asp Leu Asp Ser Gly Leu Phe
1055                1060                1065

Ser Ala Pro Thr Val Pro Leu Ser Ile Arg Asn Asn His Trp Asp
1070                1075                1080

Asn Ser Pro Ser Pro Asn Met Tyr Gly Leu Asn Lys Glu Val Val
```

```
             1085                1090                1095
Arg Gln Leu Ser Arg Arg Tyr Pro Gln Leu Pro Arg Ala Val Ala
        1100                1105                1110
Thr Gly Arg Val Tyr Asp Met Asn Thr Gly Thr Leu Arg Asn Tyr
        1115                1120                1125
Asp Pro Arg Ile Asn Leu Val Pro Val Asn Arg Arg Leu Pro His
        1130                1135                1140
Ala Leu Val Leu His His Asn Glu His Pro Gln Ser Asp Phe Ser
        1145                1150                1155
Ser Phe Val Ser Lys Leu Lys Gly Arg Thr Val Leu Val Val Gly
        1160                1165                1170
Glu Lys Leu Ser Val Pro Gly Lys Thr Val Asp Trp Leu Ser Asp
        1175                1180                1185
Lys Pro Glu Ala Thr Phe Arg Ala Arg Leu Asp Leu Gly Ile Pro
        1190                1195                1200
Gly Asp Val Pro Lys Tyr Asp Ile Ile Phe Ile Asn Val Arg Thr
        1205                1210                1215
Pro Tyr Lys Tyr His His Tyr Gln Gln Cys Glu Asp His Ala Ile
        1220                1225                1230
Lys Leu Ser Met Leu Thr Lys Lys Ala Cys Leu His Leu Asn Pro
        1235                1240                1245
Gly Gly Thr Cys Val Ser Ile Gly Tyr Gly Tyr Ala Asp Arg Ala
        1250                1255                1260
Ser Glu Ser Ile Ile Gly Ala Ile Ala Arg Gln Phe Lys Phe Ser
        1265                1270                1275
Arg Val Cys Lys Pro Lys Ser Ser Leu Glu Glu Thr Glu Val Leu
        1280                1285                1290
Phe Val Phe Ile Gly Tyr Asp Arg Lys Ala Arg Thr His Asn Pro
        1295                1300                1305
Tyr Lys Leu Ser Ser Thr Leu Thr Asn Ile Tyr Thr Gly Ser Arg
        1310                1315                1320
Leu His Glu Ala Gly Cys Ala Pro Ser Tyr His Val Val Arg Gly
        1325                1330                1335
Asp Ile Ala Met Ala Thr Glu Gly Val Ile Ile Asn Ala Ala Asn
        1340                1345                1350
Ser Lys Gly Gln Pro Gly Gly Val Cys Gly Ala Leu Tyr Lys
        1355                1360                1365
Lys Phe Pro Glu Ser Phe Asp Leu Gln Pro Ile Glu Val Gly Lys
        1370                1375                1380
Ala Arg Leu Val Lys Gly Ala Ala Lys His Ile Ile His Ala Val
        1385                1390                1395
Gly Pro Asn Phe Asn Lys Val Ser Glu Val Glu Gly Asp Lys Gln
        1400                1405                1410
Leu Ala Glu Ala Tyr Glu Ser Ile Ala Lys Ile Val Asn Asp Asn
        1415                1420                1425
Asn Tyr Lys Ser Val Ala Ile Pro Leu Leu Ser Thr Gly Ile Phe
        1430                1435                1440
Ser Gly Asn Lys Asp Arg Leu Thr Gln Ser Leu Asn His Leu Leu
        1445                1450                1455
Thr Ala Leu Asp Thr Thr Asp Ala Asp Val Ala Ile Tyr Cys Arg
        1460                1465                1470
Asp Lys Lys Trp Glu Met Thr Leu Lys Glu Ala Val Ala Arg Arg
        1475                1480                1485
```

```
Glu Ala Val Glu Glu Ile Cys Ile Ser Asp Asp Ser Ser Val Thr
    1490            1495                1500
Glu Pro Asp Ala Glu Leu Val Arg Val His Pro Lys Ser Ser Leu
    1505            1510                1515
Ala Gly Arg Lys Gly Tyr Ser Thr Ser Asp Gly Lys Thr Phe Ser
    1520            1525                1530
Tyr Leu Glu Gly Thr Lys Phe His Gln Ala Ala Lys Asp Ile Ala
    1535            1540                1545
Glu Ile Asn Ala Met Trp Pro Val Ala Thr Glu Ala Asn Glu Gln
    1550            1555                1560
Val Cys Met Tyr Ile Leu Gly Glu Ser Met Ser Ser Ile Arg Ser
    1565            1570                1575
Lys Cys Pro Val Glu Glu Ser Glu Ala Ser Thr Pro Pro Ser Thr
    1580            1585                1590
Leu Pro Cys Leu Cys Ile His Ala Met Thr Pro Glu Arg Val Gln
    1595            1600                1605
Arg Leu Lys Ala Ser Arg Pro Glu Gln Ile Thr Val Cys Ser Ser
    1610            1615                1620
Phe Pro Leu Pro Lys Tyr Arg Ile Thr Gly Val Gln Lys Ile Gln
    1625            1630                1635
Cys Ser Gln Pro Ile Leu Phe Ser Pro Lys Val Pro Ala Tyr Ile
    1640            1645                1650
His Pro Arg Lys Tyr Leu Val Glu Thr Pro Pro Val Glu Glu Ile
    1655            1660                1665
Pro Glu Leu Pro Ala Glu Asn Gln Ser Thr Glu Gly Thr Ser Glu
    1670            1675                1680
Gln Pro Ala Pro Asn Val Asp Ala Thr Arg Thr Arg Thr Pro Glu
    1685            1690                1695
Pro Ile Ile Ile Glu Glu Glu Glu Asp Ser Ile Ser Leu Leu
    1700            1705                1710
Ser Asp Gly Pro Thr His Gln Val Leu Gln Val Glu Ala Asp Ile
    1715            1720                1725
His Gly Pro Pro Ser Val Ser Ser Ser Ser Trp Ser Ile Pro His
    1730            1735                1740
Ala Ser Asp Phe Asp Val Asp Ser Leu Ser Ile Leu Ala Leu Glu
    1745            1750                1755
Gly Ala Ser Val Thr Ser Glu Ala Ala Ser Ala Glu Thr Asn Ser
    1760            1765                1770
Tyr Phe Ala Arg Ser Met Glu Phe Leu Ala Arg Pro Val Pro Ala
    1775            1780                1785
Pro Arg Thr Val Phe Arg Asn Pro Pro His Pro Ala Pro Arg Thr
    1790            1795                1800
Arg Thr Pro Ser Leu Ala Pro Ser Arg Ala Ser Ser Arg Thr Ser
    1805            1810                1815
Leu Val Ser Thr Pro Pro Gly Val Asn Arg Val Ile Thr Arg Glu
    1820            1825                1830
Glu Leu Glu Ala Leu Thr Pro Ser Arg Ala Pro Ser Arg Ser Ala
    1835            1840                1845
Ser Arg Thr Ser Leu Val Ser Asn Pro Pro Gly Val Asn Arg Val
    1850            1855                1860
Ile Thr Arg Glu Glu Phe Glu Ala Phe Val Ala Gln Gln Gln Arg
    1865            1870                1875
```

-continued

Arg Phe Asp Ala Gly Ala Tyr Ile Phe Ser Ser Asp Thr Gly Gln
1880                1885                1890

Gly His Leu Gln Gln Lys Ser Val Arg Gln Thr Val Leu Ser Glu
1895                1900                1905

Val Val Leu Glu Arg Thr Glu Leu Glu Ile Ser Tyr Ala Pro Arg
1910                1915                1920

Leu Asp Gln Glu Lys Glu Glu Leu Leu Arg Lys Lys Leu Gln Leu
1925                1930                1935

Asn Pro Thr Pro Ala Asn Arg Ser Arg Tyr Gln Ser Arg Arg Val
1940                1945                1950

Glu Asn Met Lys Ala Ile Thr Ala Arg Arg Ile Leu Gln Gly Leu
1955                1960                1965

Gly His Tyr Leu Lys Ala Glu Gly Lys Val Glu Cys Tyr Arg Thr
1970                1975                1980

Leu His Pro Val Pro Leu Tyr Ser Ser Ser Val Asn Arg Ala Phe
1985                1990                1995

Ser Ser Pro Lys Val Ala Val Glu Ala Cys Asn Ala Met Leu Lys
2000                2005                2010

Glu Asn Phe Pro Thr Val Ala Ser Tyr Cys Ile Ile Pro Glu Tyr
2015                2020                2025

Asp Ala Tyr Leu Asp Met Val Asp Gly Ala Ser Cys Cys Leu Asp
2030                2035                2040

Thr Ala Ser Phe Cys Pro Ala Lys Leu Arg Ser Phe Pro Lys Lys
2045                2050                2055

His Ser Tyr Leu Glu Pro Thr Ile Arg Ser Ala Val Pro Ser Ala
2060                2065                2070

Ile Gln Asn Thr Leu Gln Asn Val Leu Ala Ala Ala Thr Lys Arg
2075                2080                2085

Asn Cys Asn Val Thr Gln Met Arg Glu Leu Pro Val Leu Asp Ser
2090                2095                2100

Ala Ala Phe Asn Val Glu Cys Phe Lys Lys Tyr Ala Cys Asn Asn
2105                2110                2115

Glu Tyr Trp Glu Thr Phe Lys Glu Asn Pro Ile Arg Leu Thr Glu
2120                2125                2130

Glu Asn Val Val Asn Tyr Ile Thr Lys Leu Lys Gly Pro Lys Ala
2135                2140                2145

Ala Ala Leu Phe Ala Lys Thr His Asn Leu Asn Met Leu Gln Asp
2150                2155                2160

Ile Pro Met Asp Arg Phe Val Met Asp Leu Lys Arg Asp Val Lys
2165                2170                2175

Val Thr Pro Gly Thr Lys His Thr Glu Glu Arg Pro Lys Val Gln
2180                2185                2190

Val Ile Gln Ala Ala Asp Pro Leu Ala Thr Ala Tyr Leu Cys Gly
2195                2200                2205

Ile His Arg Glu Leu Val Arg Arg Leu Asn Ala Val Leu Leu Pro
2210                2215                2220

Asn Ile His Thr Leu Phe Asp Met Ser Ala Glu Asp Phe Asp Ala
2225                2230                2235

Ile Ile Ala Glu His Phe Gln Pro Gly Asp Cys Val Leu Glu Thr
2240                2245                2250

Asp Ile Ala Ser Phe Asp Lys Ser Glu Asp Asp Ala Met Ala Leu
2255                2260                2265

Thr Ala Leu Met Ile Leu Glu Asp Leu Gly Val Asp Ala Glu Leu

```
                    2270            2275            2280
Leu Thr  Leu Ile Glu Ala Ala  Phe Gly Glu Ile Ser  Ser Ile His
         2285             2290             2295

Leu Pro  Thr Lys Thr Lys Phe  Lys Phe Gly Ala Met  Met Lys Ser
         2300             2305             2310

Gly Met  Phe Leu Thr Leu Phe  Val Asn Thr Val Ile  Asn Ile Val
         2315             2320             2325

Ile Ala  Ser Arg Val Leu Arg  Glu Arg Leu Thr Gly  Ser Pro Cys
         2330             2335             2340

Ala Ala  Phe Ile Gly Asp Asp  Asn Ile Val Lys Gly  Val Lys Ser
         2345             2350             2355

Asp Lys  Leu Met Ala Asp Arg  Cys Ala Thr Trp Leu  Asn Met Glu
         2360             2365             2370

Val Lys  Ile Ile Asp Ala Val  Val Gly Glu Lys Ala  Pro Tyr Phe
         2375             2380             2385

Cys Gly  Gly Phe Ile Leu Cys  Asp Ser Val Thr Gly  Thr Ala Cys
         2390             2395             2400

Arg Val  Ala Asp Pro Leu Lys  Arg Leu Phe Lys Leu  Gly Lys Pro
         2405             2410             2415

Leu Ala  Ala Asp Asp Glu His  Asp Asp Asp Arg Arg  Arg Ala Leu
         2420             2425             2430

Tyr Glu  Glu Ser Thr Arg Trp  Asn Arg Val Gly Ile  Leu Pro Glu
         2435             2440             2445

Leu Cys  Lys Ala Val Glu Ser  Arg Tyr Glu Thr Val  Gly Thr Ser
         2450             2455             2460

Ile Ile  Val Met Ala Met Thr  Thr Leu Ala Ser Ser  Val Lys Ser
         2465             2470             2475

Phe Ser  Tyr Leu Arg Gly Ala  Pro Ile Thr Leu Tyr  Gly
         2480             2485             2490

<210> SEQ ID NO 16
<211> LENGTH: 11628
<212> TYPE: DNA
<213> ORGANISM: Eastern equine encephalitis virus

<400> SEQUENCE: 16
tagaggcaac cacctatttt ccacctatcc aaaatggaga aagttcatgt tgacttagac    60
gcagacagcc cattcgtcaa gtcactgcaa agatgctttc cacattttga gatagaagca   120
acgcaggtca ctgacaatga ccatgctaat gctagggcgt tttcgcacct agctactaag   180
ctcattgagg gagaagtgga tacagaccag gtgatcctgg atattgggag cgcgcctgta   240
aggcacacgc attccaaaca taagtaccac tgtatttgcc caatgaagag cgcagaagac   300
cctgacagac tctaccgcta cgcagacaag cttagaaaga gtgatgtcac tgacaaatgt   360
attgcctcta aggccgcgga cctgctaaca gtaatgtcga cgcctgacgc tgagacaccc   420
tcgttatgca tgcacactga ctcaacttgc aggtaccacg gctccgtggc cgtatatcag   480
gatgtatatg cagtgcatgc accgacttcc atttactacc aggcgctgaa aggtgtacga   540
actatctatt ggatcgggtt cgatactaca ccgttcatgt ataagaacat ggcaggcgcc   600
taccctacat acaacactaa ttgggccgat gaaagtgtgt tggaagccag aaatataggg   660
ctgggtagtt cagacttgca cgaaaagagt ttcggaaaag tatccattat gaggaagaag   720
aaattacaac ccaccaataa agtaatattt tctgtgggggt caactattta tactgaagag   780
agaatactgt tacgcagttg gcatctacct aatgttttc atctaaaagg taaaactagc   840
```

```
tttacaggca gatgtaatac tatcgtcagc tgcgaaggtt acgttgtcaa gaagattacg      900
ctcagtcctg ggatttacgg gaaagtggat aatcttgctt cgaccatgca ccgagaggga      960
ttcttaagtt gcaaggttac agatacgtta agaggggaga gggtctcttt tcccgtgtgt     1020
acgtacgtgc cagcgacact gtgcgaccag atgaccggga tactggcgac tgacgtcagt     1080
gtcgatgacg cccagaagct gctggttggg ctcaaccagc gaattgtcgt caatggcaga     1140
acacaacgta acacaaatac catgcagaat tatctattac cagtggtcgc ccaggcgttc     1200
tcgcggtggg cgcgggaaca ccgcgcagac ctggaggacg aaaaagggct aggggtacgg     1260
gaacgttccc tagtcatggg ctgctgctgg gctttcaaaa ctcacaagat cacatccatt     1320
tacaagagac ctgggactca aactatcaag aaggtgcccg ccgtattcaa ttcctttgtc     1380
atcccacaac caaccagcta tgggcttgat atagggttgc gtcgccgcat taagatgcta     1440
ttcgacgcaa agaaggcacc cgctccaatt attactgagg ccgacgttgc acaccttaaa     1500
ggcctgcagg atgaagctga agccgtggca gaggctgaag ccgtacgtgc agcactacca     1560
ccacttctgc cggaggtcga caaggagacc gtagaggctg acatcgacct gatcatgcag     1620
gaggcaggag caggtagcgt ggagacacct agacgacaca tcaaggtcac gacgtaccca     1680
ggagaagaaa tgatcggctc gtacgcagtg ctttcaccac aagcggtcct taacagcgag     1740
aagctcgctt gtattcaccc gttagctgag caagtgctcg tgatgactca caaggggcgc     1800
gcaggacgat acaaggtaga gccataccac ggtagagtta tcgtccctag tggtacagct     1860
ataccaatcc ccgatttcca ggctctgagt gaaagtgcaa ccatagtatt taacgaacgg     1920
gagttcgtta accgttactt acaccacatt gccgttaacg gagggggcact gaatacagat     1980
gaagagtact acaaggttgt gaaaagcact gagacagact ctgagtacgt atttgacatc     2040
gacgcaaaga agtgcgtgaa gaaggggggat gccggaccaa tgtgcctggt cggcgaatta     2100
gtagacccgc cattccacga attcgcgtac gagagtttaa aaacacgtcc tgctgcacca     2160
cacaaagtgc ctaccatcgg agtttatgga gtcccaggtt ccggaaagtc tggtataatc     2220
aaaagcgctg ttaccaaacg tgatctggtg gtcagtgcaa agaaagaaaa ttgcatggaa     2280
atcattaaag acgtcaaacg tatgcgcggc atggacatcg ccgcccgcac agtggattcg     2340
gtgctgctaa atgggggtaaa acactccgtc gacacactgt acatagacga ggcattcgct     2400
tgccatgcag ggaccctgct agcacttatt gccatcgtca agccaaagaa agttgtattg     2460
tgtggagatc cgaaacaatg cggcttcttt aacatgatgt gtctaaaagt gcattttaac     2520
cacgagatat gcacagaagt gtatcacaag agtatttctc ggcgatgcac taagacagtg     2580
acatccatcg tttccaccct gttctatgat aaacgcatga aactgtcaa cccatgcaat     2640
gataagatca taatagatac caccagtact accaaacctt taaggatga cataatatta     2700
acctgcttta gagggtgggt taaacaactg cagattgact acaagaacca cgagatcatg     2760
actgcagcgg cctcacaggg gcttactaga aaaggggtat acgcagtgcg ctacaaggtc     2820
aatgagaacc cactatacgc acagacatct gagcatgtga atgtattact tacacgcact     2880
gaaaaacgta tagtatggaa gactttggcc ggtgaccctt ggatcaagac gttgacagca     2940
tcgtatccgg gtaatttcac cgccacactg gaagaatggc aagctgagca tgacgctatc     3000
atggcgaaaa tacttgagac accagctagc agcgacgttt tccaaaataa agtgaacgtc     3060
tgctgggcca aagcgctaga acctgtgttg gccaccgcca atattacgct gacccgctcg     3120
cagtgggaga ccattccagc gttcaaggat gacaaagcgt attcgcctga gatggcctta     3180
```

```
aactttttct gcaccagatt ctttggcgtc gacatcgaca gcgggttgtt ctccgcgcca    3240
actgttccgc tgacttacac caatgaacac tgggataata gcccaggtcc aaacatgtat    3300
ggtttgtgca tgcgcactgc taaagaactt gcacgtcggt atccttgtat tctgaaagcc    3360
gtggatacag gtagagtggc tgacgttcgc acagacacta tcaaagacta acccgcta     3420 ataaatgtgg taccc ttgaa tagaagactc ccacactcat tggttgtcac acatagatac    3480
actgggaacg gtgattactc ccagctagtg accaagatga ccggaaagac cgtactagta    3540
gtgggtacac ctatgaacat accaggaaag agagtcgaga cactaggccc aagcccacaa    3600
tgtacatata aagcggaact ggacctgggc attcctgccg ctttaggcaa atatgacatc    3660 attttatta acgtgaggac tccctaccga caccaccatt accaacagtg cgaggaccat      3720
gcgatccacc acagcatgct taccagaaaa gcagtggacc atttgaacaa aggcggtacg    3780
tgcatcgcat tgggctatgg gactgcggac agagccaccg agaacattat tctctgcagtc    3840 gcccgctcat tcaggttctc acgtgtgtgc cagccgaagt gtgcctggga aaacactgag    3900
gtcgcgttcg tgttttcgg caaggacaac ggcaaccatc tccaagatca agataggctg      3960
agtgttgtgc taaacaacat ataccaaggg tcaactcaac atgaagctgg cagagcacct    4020
gcgtacagag tggtgcgcgg cgacataaca aagagcaatg atgaggttat tgttaacgcg    4080
gcgaacaaca aagggcaacc cggtggcggt gtgtgtggcg ccctttacag gaagtggcct    4140
ggagcttttg ataagcagcc ggtagcaact ggtaaagcgc acctcgtcaa gcattctccg    4200
aacgtcatcc atgctgttgg tcctaatttc tctcggctat cagaaaacga aggagaccag    4260
aaattgtctg aagtgtacat ggacattgcc agaattatca caacgagag gtttactaaa     4320 gtctccattc cgttgttatc taccggcatc tacgcaggtg gtaaggacag ggttatgcaa    4380
tcgctgaacc atttatttac agccatggat actaccgacg cagacattac tatttactgt    4440
ctagataagc aatgggagtc aagaataaag gaagctatca ctcggaagga aagcgttgaa    4500
gagcttactg aggatgacag accagttgac attgaactgg tacgggtgca cccgttgagc    4560
agcttggcag gtagacctgg ttattcaacc accgagggca aggtgtattc gtatctagag    4620
gggactaggt ttcatcaaac tgccaaagac atagctgaaa tttacgctat gtggcctaac    4680
aagcaagaag caaacgagca gatttgctta tacgtgttgg gagagagtat gaacagcatc    4740
cgctctaagt gtccagttga agagtcggag gcctcttccc cccctcacac catcccgtgt    4800
ctgtgcaact atgcaatgac tgcagagcga gtttacagat tacgtatggc aaagaatgaa    4860
caattcgcag tttgttcgtc ctttcagtta ccgaaataca ggattacagg ggttcagaaa    4920
attcaatgca gtaaacctgt gatattctct ggcactgtac ccccggccat acatccaaga    4980
aaattcgcat ccgtgacagt ggaagacact ccgatggtcc aacctgaaag gttggtgcct    5040
aggcgacctg caccgcctgt gcccgtacct gcaagaatcc ccagccctcc atgtacatcg    5100
accaatggat cgacgaccag tatacaatca ctgggggagg atcaaagcgc atctgcttct    5160
agcggagctg aaatctctgt agaccaggtt tcgctatgga gcatacccag cgctaccggg    5220
ttcgatgtgc gtacctcctc atcgttgagc ctagagcagc ctaccttcc gacaatggtt      5280 gtcgaagcag agattcacgc cagtcaagga tcactgtgga gcatacccag tatcaccgga    5340
tctgaaaccc gtgctccgtc acctccaagt caggatagta gaccttccac cccatctgca    5400
agtggttcac acacgtccgt ggacttaatc acgtttgaca gcgttgcaga gattttggag    5460
gatttcagtc gttcgccgtt tcaattttg tctgaaatca aacctattcc tgcacctcgt      5520
acccgagtta ctaacatgag ccgcagcgca gacacgatca aaccaattcc aaagccgcgt    5580
```

```
aaatgccagg tgaagtacac gcagccacct ggcgtcgcca gggccatatc ggcagcggaa    5640
tttgacgagt ttgtgcggag gcactcgaat tgacggtacg aagcgggtgc gtacattttc    5700
tcatccgaga cgggacaagg gcacctgcaa caaaaatcta cgcggcaatg caaactccag    5760
tatccaatcc tggagcgttc cgtccatgag aaattttacg ccccgcgcct cgatctcgag    5820
cgtgagaagc tgttgcagaa gaaactacaa ttgtgtgctt ctgaaggtaa tcggagcagg    5880
tatcagtctc gtaaagtaga gaacatgaag gcaatcaccg ttgagcgtct actgcagggg    5940
ataggctcat acctctctgc agaaccgcaa ccagttgaat gctacaaagt cacctatcct    6000
gctcccatgt attcaagtac tgcaagcaac agcttttcat cagcagaagt ggccgtcaaa    6060
gtctgcaacc tagtactgca agagaatttt cccaccgtag ccagctataa cataacggat    6120
gagtatgatg cctatcttga tatggtggac ggagcatcct gctgtttaga tactgccacc    6180
ttttgcccag ccaaattaag gagctttcca agaagcaca gttatttgcg gcctgagata    6240
cggtcagcag tgccatcacc gattcaaaac acgctccaga atgtactagc agcagccacg    6300
aaacggaatt gcaatgtcac tcaaatgagg gaacttccag tgttggattc agctgccttc    6360
aacgtggagt gtttcaaaaa gtacgcctgt aacgatgagt actgggactt ctacaagaca    6420
aacccgataa gactcaccgc agaaaatgtt actcagtatg ttactaagtt aaagggaccc    6480
aaagcagctg cccttttttgc gaaaacgcat aacttacagc cattgcatga gataccaatg    6540
gatagattcg tgatggacct taaacgggat gttaaggtta cacccgggac aaaacatact    6600
gaagaaagac caaaagttca ggtgatacag gcagctgatc cacttgcaac cgcctaccta    6660
tgtggtatac atcgagagct tgtgcgcagg ttgaacgcag tgctgctacc gaacatccac    6720
actttgtttg acatgtctgc agaagatttt gatgctatca ttgccgaaca ctttcaattc    6780
ggcgactcgg tgttagagac agacatagct tcttttgata aaagcgagga cgatgctatc    6840
gccatgtctg ctctaatgat tcttgaagac ctaggagttg atcaggcact gttaaaccta    6900
attgaagcag ccttttgggaa cataacatct gtgcacttac caacaggcac ccgatttaag    6960 ttcgggcaa tgatgaaatc cgggatgttt ttgacactct ttattaatac tgttgtcaat    7020
atcatgatcg ctagccgcgt gctccgcgag cggttgacca cttcccctg cgcagcattt    7080 atcggcgacg acaacatcgt gaaagggggtt acatctgacg agctgatggc agagcggtgc    7140
gccacgtggt tgaacatgga agtgaagatc atcgatgcag tagtcggagt aaaggcaccg    7200
tacttttgcg gagggttcat cgtagtcgat cagatcacag gaactgcgtg cagagtcgcc    7260
gaccccctga agagactgtt taagctaggt aagccgcttc cattggacga tgaccaagac    7320
gtcgacaggc gcagagctct gcatgatgaa gcggcacgtt ggaacagaat tggcatcact    7380
gaagagctgg tgaaagcagt tgaatcacgc tacgaggtga actacgtgtc actaatcatt    7440
acagcgttga ctacattagc atctacagtt agcaacttta aacacataag aggtcacccc    7500
ataaccctct acgctgacc taaataggtt gtgcattagt acctaaccta tttatattat    7560
attgctatct aaatatcaga gatgttccca taccctacac ttaactaccc gcctatggcg    7620
ccgattaacc cgatggccta ccgggatcct aatccgccta ggcgcaggtg gcggcccttt    7680
aggccaccac ttgcagctca aattgaggac ctgagacgtt ccattgctaa cctgactttg    7740
aaacaacgag cacctaaccc tccagcagga ccgcccgcca aacgcaagaa gcctgcgccc    7800
aagcctaagc ctgcgcaggc gaaaagaag cgaccaccac cacctgccaa gaaacaaaaa    7860
cgtaaaccta aaccaggcaa acgacagcga atgtgtatga agctagagtc agataaaacg    7920
```

```
tttccgatca tgttgaacgg acaggtgaat ggttacgcgt gcgtcgtggg tggacgagtg   7980
tttaaaccgc tgcacgtaga aggcagaata acaatgagc aactggccgc tatcaagctg    8040
aagaaggcca gcatatatga ccttgagtac ggtgatgtgc acaatgcat gaaatcagat    8100
accctccagt acaccagtga caagcctcct ggcttttata actggcatca tggagctgtg   8160
cagtatgaga acaacaggtt caccgtacca cgaggggtag gtggaaaggg cgacagcggg   8220
agacctattc ttgacaacaa aggtagagtc gtcgcaattg tcctgggtgg agtcaacgaa   8280
ggatccagga cggctctatc agtggtgaca tggaaccaaa aggggttac agtcaaagat    8340
acaccagagg ggtcagagcc atggtcgctc gccactgtca tgtgcgtcct ggccaatatc   8400
acgtttccat gtgatcaacc accctgcatg ccatgctgtt atgaaaagaa tccacacgaa   8460
acactcacca tgctggaaca gaattacgac agccgagcct atgatcagct gctcgatgcc   8520
gctgtgaaat gtaatgctag gagaaccagg agagatttgg acactcattt cacccagtat   8580
aagttggcac gcccgtatat tgctgattgc cctaactgtg gcatagtcg gtgcgacagc    8640
cctatagcta tagaagaagt cagaggggat gcgcatgcag gagtcatccg catccagaca   8700
tcagctatgt ttggtctgaa gacggatgga gtcgatttgg cctacatgag tttcatgaac   8760
ggcaaaacgc agaaatcaat aaagatcgac aacctgcatg tgcgcacctc agccccttgt   8820
tccctcgtgt cgcaccacgg ctattacatc ttggctcaat gcccaccagg ggacacggtt   8880
acagttgggt tcacgacgg gcctaaccgc catacgtgca cagttgccca taaggtagaa   8940
ttcaggccag tgggtagaga gaaataccgt cacccacctg aacatggagt tgaattaccg   9000
tgtaaccgtt acactcacaa gcgtgcagac caaggacact atgttgagat gcatcaacca   9060
gggctagttg ccgaccactc tctccttagc atccacagtg ccaaggtgaa aattacggta   9120
ccgagcggcg cccaagtgaa atactactgc aagtgtccag atgtacgaga gggaattacc   9180
agcagcgacc atacaaccac ctgcacggat gtcaaacaat gcagggctta cctgattgac   9240
aacaagaaat gggtgtacaa ctctggaaga ctgcctcgag gagagggcga cacttttaaa   9300
ggaaaacttc atgtgcccct tgtgcctgtt aaggccaagt gcatcgccac gctggcaccg   9360
gagcctctag ttgagcacaa acaccgcacc ctgattttac acctgcaccc ggaccacccg   9420
accttgctga cgaccaggtc acttggaagt gatgcaaatc caactcgaca atggattgag   9480
cgaccaacaa ctgtcaattt cacagtcacc ggagaagggt tggagtatac ctggggaaac   9540
catccaccaa aaagagtatg ggctcaagag tcaggagaag ggaacccaca tggatggccg   9600
cacgaagtgg tagtctatta ctacaacaga tacccgctaa ccacaattat cgggttatgc   9660
acctgtgtgg ctatcatcat ggtctcttgt gtcacatccg tgtggctcct ttgcaggact   9720
cgcaatcttt gcataacccc gtataaacta gccccgaacg ctcaagtccc aatactcctg   9780
gcgttacttt gctgcattaa ccgacgagg gcagacgaca ccttgcaagt gctgaattat   9840
ctgtggaaca caatcaaaa cttttttctgg atgcagacgc ttatcccact gcagcgctt    9900
atcgtatgca tgcgcatgct gcgttgctta ttttgctgtg ggccggcttt tttacttgtc   9960
tgcggcgcct tgggcgccgc agcgtacgaa cacacagcag tgatgccgaa caaggtgggg   10020
atcccgtata aagctttagt cgaacgccca gggtatgcac ccgttcacct acagatacag   10080
ctggttaata ccaggataat tccatcaact aacctggagt acatcacctg caagtacaag   10140
acaaaagtgc cgtctccagt agtgaaatgc tgcggtgcca ctcaatgtac ctctaaaccc   10200
catcctgact atcagtgtca ggtgtttaca ggtgtttacc cattcatgtg gggaggagcc   10260
tactgcttct gcgacaccga aaacacccag atgagcgagg cgtatgtaga gcgctcggaa   10320
```

-continued

```
gagtgctcta tcgaccacgc aaaagcttat aaagtacaca caggcactgt tcaggcaatg    10380
gtgaacataa cttatgggag cgtcagctgg agatctgcag atgtctacgt caatggtgaa    10440
actcccgcga aaataggaga tgccaaactc atcataggtc cactgtcatc tgcgtggtcc    10500
ccattcgata caaggtggt ggtttatggg catgaagtgt ataattacga ctttcctgag    10560
tacagcaccg gcaaagcagg ctctttcgga gacctgcaat cacgcacatc aaccagcaac    10620
gatctgtacg caaataccaa cttgaagcta caacgacccc aggctggtat cgtgcacaca    10680
cctttcaccc aggcgccctc tggcttcgaa cgatggaaaa gggacaaagg ggcaccgttg    10740
aacgacgtag ccccgtttgg ctgttcaatt gccctggagc cgctccgtgc agaaaattgt    10800
gcagtgggaa gcatccctat atctatagat atacccgatg cggctttcac cagaatatct    10860
gaaacaccga cagtctcaga cctggaatgc aaaattacgg agtgtactta tgcctccgat    10920
ttcggtggta tagccaccgt tgcctacaaa tccagtaaag caggaaactg tccaattcat    10980
tctccatcgg gtgttgcagt tattaaagag aatgacgtca cccttgctga gagcggatca    11040
tttacattcc acttctccac tgcaaacatc catcctgctt ttaagctgca ggtctgcacc    11100
agtgcagtta cctgcaaagg agattgcaag ccaccgaaag atcatatcgt cgattatcca    11160
gcacaacata ccgaatcctt tacgtcggcg atatccgcca ccgcgtggtc gtggctaaaa    11220
gtgctggtag gaggaacatc agcatttatt gttctggggc ttattgctac agcagtggtt    11280
gccctagttc tgttcttcca tagacattaa catcttgtca accacataac actacaggca    11340
gtgtataagg ctgtcttact aaacactaaa atcaccctag ttcgatgtac ttccgagcta    11400
tggtgacggt ggtgcataat gccgccgatg cagtgcataa ggctgctata ttaccaaatt    11460
ataacactaa gggcagtgca taatgctgct cctaagtaat tttatacaca ctttataatc    11520
aggcataatt gccgtatata caattacact acaggtaata taccgcctct tataaacact    11580
acaggcagcg cataatgctg tcttttatat caatttacaa aatcatat              11628
```

<210> SEQ ID NO 17
<211> LENGTH: 1242
<212> TYPE: PRT
<213> ORGANISM: Eastern equine encephalitis virus

<400> SEQUENCE: 17

```
Met Phe Pro Tyr Pro Thr Leu Asn Tyr Pro Met Ala Pro Ile Asn
1               5                   10                  15

Pro Met Ala Tyr Arg Asp Pro Asn Pro Pro Arg Arg Trp Arg Pro
                20                  25                  30

Phe Arg Pro Pro Leu Ala Ala Gln Ile Glu Asp Leu Arg Arg Ser Ile
        35                  40                  45

Ala Asn Leu Thr Leu Lys Gln Arg Ala Pro Asn Pro Pro Ala Gly Pro
    50                  55                  60

Pro Ala Lys Arg Lys Lys Pro Ala Pro Lys Pro Lys Pro Ala Gln Ala
65                  70                  75                  80

Lys Lys Lys Arg Pro Pro Pro Ala Lys Lys Gln Lys Arg Lys Pro
                85                  90                  95

Lys Pro Gly Lys Arg Gln Arg Met Cys Met Lys Leu Glu Ser Asp Lys
            100                 105                 110

Thr Phe Pro Ile Met Leu Asn Gly Gln Val Asn Gly Tyr Ala Cys Val
        115                 120                 125

Val Gly Gly Arg Val Phe Lys Pro Leu His Val Glu Gly Arg Ile Asp
    130                 135                 140
```

```
Asn Glu Gln Leu Ala Ala Ile Lys Leu Lys Lys Ala Ser Ile Tyr Asp
145                 150                 155                 160

Leu Glu Tyr Gly Asp Val Pro Gln Cys Met Lys Ser Asp Thr Leu Gln
            165                 170                 175

Tyr Thr Ser Asp Lys Pro Pro Gly Phe Tyr Asn Trp His His Gly Ala
        180                 185                 190

Val Gln Tyr Glu Asn Asn Arg Phe Thr Val Pro Arg Gly Val Gly Gly
    195                 200                 205

Lys Gly Asp Ser Gly Arg Pro Ile Leu Asp Asn Lys Gly Arg Val Val
210                 215                 220

Ala Ile Val Leu Gly Gly Val Asn Glu Gly Ser Arg Thr Ala Leu Ser
225                 230                 235                 240

Val Val Thr Trp Asn Gln Lys Gly Val Thr Val Lys Asp Thr Pro Glu
            245                 250                 255

Gly Ser Glu Pro Trp Ser Leu Ala Thr Val Met Cys Val Leu Ala Asn
            260                 265                 270

Ile Thr Phe Pro Cys Asp Gln Pro Cys Met Pro Cys Cys Tyr Glu
        275                 280                 285

Lys Asn Pro His Glu Thr Leu Thr Met Leu Glu Gln Asn Tyr Asp Ser
290                 295                 300

Arg Ala Tyr Asp Gln Leu Leu Asp Ala Ala Val Lys Cys Asn Ala Arg
305                 310                 315                 320

Arg Thr Arg Arg Asp Leu Asp Thr His Phe Thr Gln Tyr Lys Leu Ala
            325                 330                 335

Arg Pro Tyr Ile Ala Asp Cys Pro Asn Cys Gly His Ser Arg Cys Asp
            340                 345                 350

Ser Pro Ile Ala Ile Glu Glu Val Arg Gly Asp Ala His Ala Gly Val
            355                 360                 365

Ile Arg Ile Gln Thr Ser Ala Met Phe Gly Leu Lys Thr Asp Gly Val
370                 375                 380

Asp Leu Ala Tyr Met Ser Phe Met Asn Gly Lys Thr Gln Lys Ser Ile
385                 390                 395                 400

Lys Ile Asp Asn Leu His Val Arg Thr Ser Ala Pro Cys Ser Leu Val
            405                 410                 415

Ser His His Gly Tyr Tyr Ile Leu Ala Gln Cys Pro Pro Gly Asp Thr
            420                 425                 430

Val Thr Val Gly Phe His Asp Gly Pro Asn Arg His Thr Cys Thr Val
            435                 440                 445

Ala His Lys Val Glu Phe Arg Pro Val Gly Arg Glu Lys Tyr Arg His
450                 455                 460

Pro Pro Glu His Gly Val Glu Leu Pro Cys Asn Arg Tyr Thr His Lys
465                 470                 475                 480

Arg Ala Asp Gln Gly His Tyr Val Glu Met His Gln Pro Gly Leu Val
            485                 490                 495

Ala Asp His Ser Leu Leu Ser Ile His Ser Ala Lys Val Lys Ile Thr
            500                 505                 510

Val Pro Ser Gly Ala Gln Val Lys Tyr Tyr Cys Lys Cys Pro Asp Val
            515                 520                 525

Arg Glu Gly Ile Thr Ser Ser Asp His Thr Thr Thr Cys Thr Asp Val
530                 535                 540

Lys Gln Cys Arg Ala Tyr Leu Ile Asp Asn Lys Lys Trp Val Tyr Asn
545                 550                 555                 560
```

```
Ser Gly Arg Leu Pro Arg Gly Glu Gly Asp Thr Phe Lys Gly Lys Leu
                565                 570                 575

His Val Pro Phe Val Pro Val Lys Ala Lys Cys Ile Ala Thr Leu Ala
            580                 585                 590

Pro Glu Pro Leu Val Glu His Lys His Arg Thr Leu Ile Leu His Leu
        595                 600                 605

His Pro Asp His Pro Thr Leu Leu Thr Thr Arg Ser Leu Gly Ser Asp
610                 615                 620

Ala Asn Pro Thr Arg Gln Trp Ile Glu Arg Thr Thr Val Asn Phe
625                 630                 635                 640

Thr Val Thr Gly Glu Gly Leu Glu Tyr Thr Trp Gly Asn His Pro Pro
                645                 650                 655

Lys Arg Val Trp Ala Gln Glu Ser Gly Glu Gly Asn Pro His Gly Trp
            660                 665                 670

Pro His Glu Val Val Val Tyr Tyr Asn Arg Tyr Pro Leu Thr Thr
        675                 680                 685

Ile Ile Gly Leu Cys Thr Cys Val Ala Ile Met Val Ser Cys Val
    690                 695                 700

Thr Ser Val Trp Leu Leu Cys Arg Thr Arg Asn Leu Cys Ile Thr Pro
705                 710                 715                 720

Tyr Lys Leu Ala Pro Asn Ala Gln Val Pro Ile Leu Ala Leu Leu
                725                 730                 735

Cys Cys Ile Lys Pro Thr Arg Ala Asp Asp Thr Leu Gln Val Leu Asn
            740                 745                 750

Tyr Leu Trp Asn Asn Asn Gln Asn Phe Phe Trp Met Gln Thr Leu Ile
        755                 760                 765

Pro Leu Ala Ala Leu Ile Val Cys Met Arg Met Leu Arg Cys Leu Phe
    770                 775                 780

Cys Cys Gly Pro Ala Phe Leu Leu Val Cys Gly Ala Leu Gly Ala Ala
785                 790                 795                 800

Ala Tyr Glu His Thr Ala Val Met Pro Asn Lys Val Gly Ile Pro Tyr
                805                 810                 815

Lys Ala Leu Val Glu Arg Pro Gly Tyr Ala Pro Val His Leu Gln Ile
            820                 825                 830

Gln Leu Val Asn Thr Arg Ile Ile Pro Ser Thr Asn Leu Glu Tyr Ile
        835                 840                 845

Thr Cys Lys Tyr Lys Thr Lys Val Pro Ser Pro Val Val Lys Cys Cys
    850                 855                 860

Gly Ala Thr Gln Cys Thr Ser Lys Pro His Pro Asp Tyr Gln Cys Gln
865                 870                 875                 880

Val Phe Thr Gly Val Tyr Pro Phe Met Trp Gly Gly Ala Tyr Cys Phe
                885                 890                 895

Cys Asp Thr Glu Asn Thr Gln Met Ser Glu Ala Tyr Val Glu Arg Ser
            900                 905                 910

Glu Glu Cys Ser Ile Asp His Ala Lys Ala Tyr Lys Val His Thr Gly
        915                 920                 925

Thr Val Gln Ala Met Val Asn Ile Thr Tyr Gly Ser Val Ser Trp Arg
    930                 935                 940

Ser Ala Asp Val Tyr Val Asn Gly Glu Thr Pro Ala Lys Ile Gly Asp
945                 950                 955                 960

Ala Lys Leu Ile Ile Gly Pro Leu Ser Ser Ala Trp Ser Pro Phe Asp
                965                 970                 975

Asn Lys Val Val Val Tyr Gly His Glu Val Tyr Asn Tyr Asp Phe Pro
```

| | | | | | | | | | | | | | |
|---|---|---|---|---|---|---|---|---|---|---|---|---|---|
| | | 980 | | | | 985 | | | | 990 | | | |
| Glu | Tyr | Ser | Thr | Gly | Lys | Ala | Gly | Ser | Phe | Gly | Asp | Leu | Gln Ser Arg |
| | | | | 995 | | | | | 1000 | | | | 1005 |
| Thr | Ser | Thr | Ser | Asn | Asp | Leu | Tyr | Ala | Asn | Thr | Asn | Leu | Lys Leu |
| | 1010 | | | | 1015 | | | | 1020 | | | | |
| Gln | Arg | Pro | Gln | Ala | Gly | Ile | Val | His | Thr | Pro | Phe | Thr | Gln Ala |
| | 1025 | | | | 1030 | | | | 1035 | | | | |
| Pro | Ser | Gly | Phe | Glu | Arg | Trp | Lys | Arg | Asp | Lys | Gly | Ala | Pro Leu |
| | 1040 | | | | 1045 | | | | 1050 | | | | |
| Asn | Asp | Val | Ala | Pro | Phe | Gly | Cys | Ser | Ile | Ala | Leu | Glu | Pro Leu |
| | 1055 | | | | 1060 | | | | 1065 | | | | |
| Arg | Ala | Glu | Asn | Cys | Ala | Val | Gly | Ser | Ile | Pro | Ile | Ser | Ile Asp |
| | 1070 | | | | 1075 | | | | 1080 | | | | |
| Ile | Pro | Asp | Ala | Ala | Phe | Thr | Arg | Ile | Ser | Glu | Thr | Pro | Thr Val |
| | 1085 | | | | 1090 | | | | 1095 | | | | |
| Ser | Asp | Leu | Glu | Cys | Lys | Ile | Thr | Glu | Cys | Thr | Tyr | Ala | Ser Asp |
| | 1100 | | | | 1105 | | | | 1110 | | | | |
| Phe | Gly | Gly | Ile | Ala | Thr | Val | Ala | Tyr | Lys | Ser | Ser | Lys | Ala Gly |
| | 1115 | | | | 1120 | | | | 1125 | | | | |
| Asn | Cys | Pro | Ile | His | Ser | Pro | Ser | Gly | Val | Ala | Val | Ile | Lys Glu |
| | 1130 | | | | 1135 | | | | 1140 | | | | |
| Asn | Asp | Val | Thr | Leu | Ala | Glu | Ser | Gly | Ser | Phe | Thr | Phe | His Phe |
| | 1145 | | | | 1150 | | | | 1155 | | | | |
| Ser | Thr | Ala | Asn | Ile | His | Pro | Ala | Phe | Lys | Leu | Gln | Val | Cys Thr |
| | 1160 | | | | 1165 | | | | 1170 | | | | |
| Ser | Ala | Val | Thr | Cys | Lys | Gly | Asp | Cys | Lys | Pro | Pro | Lys | Asp His |
| | 1175 | | | | 1180 | | | | 1185 | | | | |
| Ile | Val | Asp | Tyr | Pro | Ala | Gln | His | Thr | Glu | Ser | Phe | Thr | Ser Ala |
| | 1190 | | | | 1195 | | | | 1200 | | | | |
| Ile | Ser | Ala | Thr | Ala | Trp | Ser | Trp | Leu | Lys | Val | Leu | Val | Gly Gly |
| | 1205 | | | | 1210 | | | | 1215 | | | | |
| Thr | Ser | Ala | Phe | Ile | Val | Leu | Gly | Leu | Ile | Ala | Thr | Ala | Val Val |
| | 1220 | | | | 1225 | | | | 1230 | | | | |
| Ala | Leu | Val | Leu | Phe | Phe | His | Arg | His | | | | | |
| | 1235 | | | | 1240 | | | | | | | | |

<210> SEQ ID NO 18
<211> LENGTH: 2494
<212> TYPE: PRT
<213> ORGANISM: Eastern equine encephalitis virus

<400> SEQUENCE: 18

| | | | | | | | | | | | | | | |
|---|---|---|---|---|---|---|---|---|---|---|---|---|---|---|
| Met | Glu | Lys | Val | His | Val | Asp | Leu | Asp | Ala | Asp | Ser | Pro | Phe | Val Lys |
| 1 | | | | 5 | | | | | 10 | | | | | 15 |
| Ser | Leu | Gln | Arg | Cys | Phe | Pro | His | Phe | Glu | Ile | Glu | Ala | Thr | Gln Val |
| | | | 20 | | | | | 25 | | | | | 30 | |
| Thr | Asp | Asn | Asp | His | Ala | Asn | Ala | Arg | Ala | Phe | Ser | His | Leu | Ala Thr |
| | | 35 | | | | | 40 | | | | | 45 | | |
| Lys | Leu | Ile | Glu | Gly | Glu | Val | Asp | Thr | Asp | Gln | Val | Ile | Leu | Asp Ile |
| | 50 | | | | | 55 | | | | | 60 | | | |
| Gly | Ser | Ala | Pro | Val | Arg | His | Thr | His | Ser | Lys | His | Lys | Tyr | His Cys |
| 65 | | | | | 70 | | | | | 75 | | | | | 80 |
| Ile | Cys | Pro | Met | Lys | Ser | Ala | Glu | Asp | Pro | Asp | Arg | Leu | Tyr | Arg Tyr |
| | | | | 85 | | | | | 90 | | | | | 95 |

-continued

```
Ala Asp Lys Leu Arg Lys Ser Asp Val Thr Asp Lys Cys Ile Ala Ser
                100                 105                 110
Lys Ala Ala Asp Leu Leu Thr Val Met Ser Thr Pro Asp Ala Glu Thr
            115                 120                 125
Pro Ser Leu Cys Met His Thr Asp Ser Thr Cys Arg Tyr His Gly Ser
        130                 135                 140
Val Ala Val Tyr Gln Asp Val Tyr Ala Val His Ala Pro Thr Ser Ile
145                 150                 155                 160
Tyr Tyr Gln Ala Leu Lys Gly Val Arg Thr Ile Tyr Trp Ile Gly Phe
                165                 170                 175
Asp Thr Thr Pro Phe Met Tyr Lys Asn Met Ala Gly Ala Tyr Pro Thr
            180                 185                 190
Tyr Asn Thr Asn Trp Ala Asp Glu Ser Val Leu Glu Ala Arg Asn Ile
        195                 200                 205
Gly Leu Gly Ser Ser Asp Leu His Glu Lys Ser Phe Gly Lys Val Ser
        210                 215                 220
Ile Met Arg Lys Lys Leu Gln Pro Thr Asn Lys Val Ile Phe Ser
225                 230                 235                 240
Val Gly Ser Thr Ile Tyr Thr Glu Glu Arg Ile Leu Leu Arg Ser Trp
                245                 250                 255
His Leu Pro Asn Val Phe His Leu Lys Gly Lys Thr Ser Phe Thr Gly
            260                 265                 270
Arg Cys Asn Thr Ile Val Ser Cys Glu Gly Tyr Val Val Lys Lys Ile
        275                 280                 285
Thr Leu Ser Pro Gly Ile Tyr Gly Lys Val Asp Asn Leu Ala Ser Thr
        290                 295                 300
Met His Arg Glu Gly Phe Leu Ser Cys Lys Val Thr Asp Thr Leu Arg
305                 310                 315                 320
Gly Glu Arg Val Ser Phe Pro Val Cys Thr Tyr Val Pro Ala Thr Leu
                325                 330                 335
Cys Asp Gln Met Thr Gly Ile Leu Ala Thr Asp Val Ser Val Asp Asp
            340                 345                 350
Ala Gln Lys Leu Leu Val Gly Leu Asn Gln Arg Ile Val Val Asn Gly
        355                 360                 365
Arg Thr Gln Arg Asn Thr Asn Thr Met Gln Asn Tyr Leu Leu Pro Val
        370                 375                 380
Val Ala Gln Ala Phe Ser Arg Trp Ala Arg Glu His Arg Ala Asp Leu
385                 390                 395                 400
Glu Asp Glu Lys Gly Leu Gly Val Arg Glu Arg Ser Leu Val Met Gly
                405                 410                 415
Cys Cys Trp Ala Phe Lys Thr His Lys Ile Thr Ser Ile Tyr Lys Arg
            420                 425                 430
Pro Gly Thr Gln Thr Ile Lys Lys Val Pro Ala Val Phe Asn Ser Phe
        435                 440                 445
Val Ile Pro Gln Pro Thr Ser Tyr Gly Leu Asp Ile Gly Leu Arg Arg
        450                 455                 460
Arg Ile Lys Met Leu Phe Asp Ala Lys Ala Pro Ala Pro Ile Ile
465                 470                 475                 480
Thr Glu Ala Asp Val Ala His Leu Lys Gly Leu Gln Asp Glu Ala Glu
                485                 490                 495
Ala Val Ala Glu Ala Glu Ala Val Arg Ala Ala Leu Pro Pro Leu Leu
            500                 505                 510
Pro Glu Val Asp Lys Glu Thr Val Glu Ala Asp Ile Asp Leu Ile Met
```

```
              515                 520                 525
Gln Glu Ala Gly Ala Gly Ser Val Glu Thr Pro Arg Arg His Ile Lys
    530                 535                 540

Val Thr Thr Tyr Pro Gly Glu Glu Met Ile Gly Ser Tyr Ala Val Leu
545                 550                 555                 560

Ser Pro Gln Ala Val Leu Asn Ser Glu Lys Leu Ala Cys Ile His Pro
                565                 570                 575

Leu Ala Glu Gln Val Leu Val Met Thr His Lys Gly Arg Ala Gly Arg
                580                 585                 590

Tyr Lys Val Glu Pro Tyr His Gly Arg Val Ile Val Pro Ser Gly Thr
            595                 600                 605

Ala Ile Pro Ile Pro Asp Phe Gln Ala Leu Ser Glu Ser Ala Thr Ile
        610                 615                 620

Val Phe Asn Glu Arg Glu Phe Val Asn Arg Tyr Leu His His Ile Ala
625                 630                 635                 640

Val Asn Gly Gly Ala Leu Asn Thr Asp Glu Glu Tyr Tyr Lys Val Val
                645                 650                 655

Lys Ser Thr Glu Thr Asp Ser Glu Tyr Val Phe Asp Ile Asp Ala Lys
                660                 665                 670

Lys Cys Val Lys Lys Gly Asp Ala Gly Pro Met Cys Leu Val Gly Glu
            675                 680                 685

Leu Val Asp Pro Pro Phe His Glu Phe Ala Tyr Glu Ser Leu Lys Thr
        690                 695                 700

Arg Pro Ala Ala Pro His Lys Val Pro Thr Ile Gly Val Tyr Gly Val
705                 710                 715                 720

Pro Gly Ser Gly Lys Ser Gly Ile Ile Lys Ser Ala Val Thr Lys Arg
                725                 730                 735

Asp Leu Val Val Ser Ala Lys Lys Glu Asn Cys Met Glu Ile Ile Lys
                740                 745                 750

Asp Val Lys Arg Met Arg Gly Met Asp Ile Ala Ala Arg Thr Val Asp
            755                 760                 765

Ser Val Leu Leu Asn Gly Val Lys His Ser Val Asp Thr Leu Tyr Ile
        770                 775                 780

Asp Glu Ala Phe Ala Cys His Ala Gly Thr Leu Leu Ala Leu Ile Ala
785                 790                 795                 800

Ile Val Lys Pro Lys Lys Val Val Leu Cys Gly Asp Pro Lys Gln Cys
                805                 810                 815

Gly Phe Phe Asn Met Met Cys Leu Lys Val His Phe Asn His Glu Ile
                820                 825                 830

Cys Thr Glu Val Tyr His Lys Ser Ile Ser Arg Arg Cys Thr Lys Thr
            835                 840                 845

Val Thr Ser Ile Val Ser Thr Leu Phe Tyr Asp Lys Arg Met Arg Thr
        850                 855                 860

Val Asn Pro Cys Asn Asp Lys Ile Ile Asp Thr Thr Ser Thr Thr
865                 870                 875                 880

Lys Pro Leu Lys Asp Asp Ile Ile Leu Thr Cys Phe Arg Gly Trp Val
                885                 890                 895

Lys Gln Leu Gln Ile Asp Tyr Lys Asn His Glu Ile Met Thr Ala Ala
                900                 905                 910

Ala Ser Gln Gly Leu Thr Arg Lys Gly Val Tyr Ala Val Arg Tyr Lys
            915                 920                 925

Val Asn Glu Asn Pro Leu Tyr Ala Gln Thr Ser Glu His Val Asn Val
        930                 935                 940
```

-continued

```
Leu Leu Thr Arg Thr Glu Lys Arg Ile Val Trp Lys Thr Leu Ala Gly
945                 950                 955                 960

Asp Pro Trp Ile Lys Thr Leu Thr Ala Ser Tyr Pro Gly Asn Phe Thr
                965                 970                 975

Ala Thr Leu Glu Glu Trp Gln Ala Glu His Asp Ala Ile Met Ala Lys
                980                 985                 990

Ile Leu Glu Thr Pro Ala Ser Ser Asp Val Phe Gln Asn Lys Val Asn
                995                1000                1005

Val Cys Trp Ala Lys Ala Leu Glu Pro Val Leu Ala Thr Ala Asn
    1010                1015                1020

Ile Thr Leu Thr Arg Ser Gln Trp Glu Thr Ile Pro Ala Phe Lys
    1025                1030                1035

Asp Asp Lys Ala Tyr Ser Pro Glu Met Ala Leu Asn Phe Phe Cys
    1040                1045                1050

Thr Arg Phe Phe Gly Val Asp Ile Asp Ser Gly Leu Phe Ser Ala
    1055                1060                1065

Pro Thr Val Pro Leu Thr Tyr Thr Asn Glu His Trp Asp Asn Ser
    1070                1075                1080

Pro Gly Pro Asn Met Tyr Gly Leu Cys Met Arg Thr Ala Lys Glu
    1085                1090                1095

Leu Ala Arg Arg Tyr Pro Cys Ile Leu Lys Ala Val Asp Thr Gly
    1100                1105                1110

Arg Val Ala Asp Val Arg Thr Asp Thr Ile Lys Asp Tyr Asn Pro
    1115                1120                1125

Leu Ile Asn Val Val Pro Leu Asn Arg Arg Leu Pro His Ser Leu
    1130                1135                1140

Val Val Thr His Arg Tyr Thr Gly Asn Gly Asp Tyr Ser Gln Leu
    1145                1150                1155

Val Thr Lys Met Thr Gly Lys Thr Val Leu Val Val Gly Thr Pro
    1160                1165                1170

Met Asn Ile Pro Gly Lys Arg Val Glu Thr Leu Gly Pro Ser Pro
    1175                1180                1185

Gln Cys Thr Tyr Lys Ala Glu Leu Asp Leu Gly Ile Pro Ala Ala
    1190                1195                1200

Leu Gly Lys Tyr Asp Ile Ile Phe Ile Asn Val Arg Thr Pro Tyr
    1205                1210                1215

Arg His His His Tyr Gln Gln Cys Glu Asp His Ala Ile His His
    1220                1225                1230

Ser Met Leu Thr Arg Lys Ala Val Asp His Leu Asn Lys Gly Gly
    1235                1240                1245

Thr Cys Ile Ala Leu Gly Tyr Gly Thr Ala Asp Arg Ala Thr Glu
    1250                1255                1260

Asn Ile Ile Ser Ala Val Ala Arg Ser Phe Arg Phe Ser Arg Val
    1265                1270                1275

Cys Gln Pro Lys Cys Ala Trp Glu Asn Thr Glu Val Ala Phe Val
    1280                1285                1290

Phe Phe Gly Lys Asp Asn Gly Asn His Leu Gln Asp Gln Asp Arg
    1295                1300                1305

Leu Ser Val Val Leu Asn Asn Ile Tyr Gln Gly Ser Thr Gln His
    1310                1315                1320

Glu Ala Gly Arg Ala Pro Ala Tyr Arg Val Val Arg Gly Asp Ile
    1325                1330                1335
```

```
Thr Lys Ser Asn Asp Glu Val Ile Val Asn Ala Ala Asn Asn Lys
    1340            1345                1350
Gly Gln Pro Gly Gly Val Cys Gly Ala Leu Tyr Arg Lys Trp
1355            1360                1365
Pro Gly Ala Phe Asp Lys Gln Pro Val Ala Thr Gly Lys Ala His
1370            1375                1380
Leu Val Lys His Ser Pro Asn Val Ile His Ala Val Gly Pro Asn
1385            1390                1395
Phe Ser Arg Leu Ser Glu Asn Glu Gly Asp Gln Lys Leu Ser Glu
1400            1405                1410
Val Tyr Met Asp Ile Ala Arg Ile Ile Asn Asn Glu Arg Phe Thr
1415            1420                1425
Lys Val Ser Ile Pro Leu Leu Ser Thr Gly Ile Tyr Ala Gly Gly
1430            1435                1440
Lys Asp Arg Val Met Gln Ser Leu Asn His Leu Phe Thr Ala Met
1445            1450                1455
Asp Thr Thr Asp Ala Asp Ile Thr Ile Tyr Cys Leu Asp Lys Gln
1460            1465                1470
Trp Glu Ser Arg Ile Lys Glu Ala Ile Thr Arg Lys Glu Ser Val
1475            1480                1485
Glu Glu Leu Thr Glu Asp Arg Pro Val Asp Ile Glu Leu Val
1490            1495                1500
Arg Val His Pro Leu Ser Ser Leu Ala Gly Arg Pro Gly Tyr Ser
1505            1510                1515
Thr Thr Glu Gly Lys Val Tyr Ser Tyr Leu Glu Gly Thr Arg Phe
1520            1525                1530
His Gln Thr Ala Lys Asp Ile Ala Glu Ile Tyr Ala Met Trp Pro
1535            1540                1545
Asn Lys Gln Glu Ala Asn Glu Gln Ile Cys Leu Tyr Val Leu Gly
1550            1555                1560
Glu Ser Met Asn Ser Ile Arg Ser Lys Cys Pro Val Glu Glu Ser
1565            1570                1575
Glu Ala Ser Ser Pro Pro His Thr Ile Pro Cys Leu Cys Asn Tyr
1580            1585                1590
Ala Met Thr Ala Glu Arg Val Tyr Arg Leu Arg Met Ala Lys Asn
1595            1600                1605
Glu Gln Phe Ala Val Cys Ser Ser Phe Gln Leu Pro Lys Tyr Arg
1610            1615                1620
Ile Thr Gly Val Gln Lys Ile Gln Cys Ser Lys Pro Val Ile Phe
1625            1630                1635
Ser Gly Thr Val Pro Pro Ala Ile His Pro Arg Lys Phe Ala Ser
1640            1645                1650
Val Thr Val Glu Asp Thr Pro Met Val Gln Pro Glu Arg Leu Val
1655            1660                1665
Pro Arg Arg Pro Ala Pro Pro Val Pro Val Pro Ala Arg Ile Pro
1670            1675                1680
Ser Pro Pro Cys Thr Ser Thr Asn Gly Ser Thr Thr Ser Ile Gln
1685            1690                1695
Ser Leu Gly Glu Asp Gln Ser Ala Ser Ala Ser Ser Gly Ala Glu
1700            1705                1710
Ile Ser Val Asp Gln Val Ser Leu Trp Ser Ile Pro Ser Ala Thr
1715            1720                1725
Gly Phe Asp Val Arg Thr Ser Ser Ser Leu Ser Leu Glu Gln Pro
```

-continued

```
                  1730                1735                1740
Thr Phe Pro Thr Met Val Val Glu Ala Glu Ile His Ala Ser Gln
        1745                1750                1755

Gly Ser Leu Trp Ser Ile Pro Ser Ile Thr Gly Ser Glu Thr Arg
        1760                1765                1770

Ala Pro Ser Pro Pro Ser Gln Asp Ser Arg Pro Ser Thr Pro Ser
        1775                1780                1785

Ala Ser Gly Ser His Thr Ser Val Asp Leu Ile Thr Phe Asp Ser
        1790                1795                1800

Val Ala Glu Ile Leu Glu Asp Phe Ser Arg Ser Pro Phe Gln Phe
        1805                1810                1815

Leu Ser Glu Ile Lys Pro Ile Pro Ala Pro Arg Thr Arg Val Thr
        1820                1825                1830

Asn Met Ser Arg Ser Ala Asp Thr Ile Lys Pro Ile Pro Lys Pro
        1835                1840                1845

Arg Lys Cys Gln Val Lys Tyr Thr Gln Pro Pro Gly Val Ala Arg
        1850                1855                1860

Ala Ile Ser Ala Ala Glu Phe Asp Glu Phe Val Arg Arg His Ser
        1865                1870                1875

Asn Arg Arg Tyr Glu Ala Gly Ala Tyr Ile Phe Ser Ser Glu Thr
        1880                1885                1890

Gly Gln Gly His Leu Gln Gln Lys Ser Thr Arg Gln Cys Lys Leu
        1895                1900                1905

Gln Tyr Pro Ile Leu Glu Arg Ser Val His Glu Lys Phe Tyr Ala
        1910                1915                1920

Pro Arg Leu Asp Leu Glu Arg Glu Lys Leu Leu Gln Lys Lys Leu
        1925                1930                1935

Gln Leu Cys Ala Ser Glu Gly Asn Arg Ser Arg Tyr Gln Ser Arg
        1940                1945                1950

Lys Val Glu Asn Met Lys Ala Ile Thr Val Glu Arg Leu Leu Gln
        1955                1960                1965

Gly Ile Gly Ser Tyr Leu Ser Ala Glu Pro Gln Pro Val Glu Cys
        1970                1975                1980

Tyr Lys Val Thr Tyr Pro Ala Pro Met Tyr Ser Ser Thr Ala Ser
        1985                1990                1995

Asn Ser Phe Ser Ser Ala Glu Val Ala Val Lys Val Cys Asn Leu
        2000                2005                2010

Val Leu Gln Glu Asn Phe Pro Thr Val Ala Ser Tyr Asn Ile Thr
        2015                2020                2025

Asp Glu Tyr Asp Ala Tyr Leu Asp Met Val Asp Gly Ala Ser Cys
        2030                2035                2040

Cys Leu Asp Thr Ala Thr Phe Cys Pro Ala Lys Leu Arg Ser Phe
        2045                2050                2055

Pro Lys Lys His Ser Tyr Leu Arg Pro Glu Ile Arg Ser Ala Val
        2060                2065                2070

Pro Ser Pro Ile Gln Asn Thr Leu Gln Asn Val Leu Ala Ala Ala
        2075                2080                2085

Thr Lys Arg Asn Cys Asn Val Thr Gln Met Arg Glu Leu Pro Val
        2090                2095                2100

Leu Asp Ser Ala Ala Phe Asn Val Glu Cys Phe Lys Lys Tyr Ala
        2105                2110                2115

Cys Asn Asp Glu Tyr Trp Asp Phe Tyr Lys Thr Asn Pro Ile Arg
        2120                2125                2130
```

Leu Thr Ala Glu Asn Val Thr Gln Tyr Val Thr Lys Leu Lys Gly
2135                2140                2145

Pro Lys Ala Ala Ala Leu Phe Ala Lys Thr His Asn Leu Gln Pro
2150                2155                2160

Leu His Glu Ile Pro Met Asp Arg Phe Val Met Asp Leu Lys Arg
2165                2170                2175

Asp Val Lys Val Thr Pro Gly Thr Lys His Thr Glu Glu Arg Pro
2180                2185                2190

Lys Val Gln Val Ile Gln Ala Ala Asp Pro Leu Ala Thr Ala Tyr
2195                2200                2205

Leu Cys Gly Ile His Arg Glu Leu Val Arg Arg Leu Asn Ala Val
2210                2215                2220

Leu Leu Pro Asn Ile His Thr Leu Phe Asp Met Ser Ala Glu Asp
2225                2230                2235

Phe Asp Ala Ile Ile Ala Glu His Phe Gln Phe Gly Asp Ser Val
2240                2245                2250

Leu Glu Thr Asp Ile Ala Ser Phe Asp Lys Ser Glu Asp Asp Ala
2255                2260                2265

Ile Ala Met Ser Ala Leu Met Ile Leu Glu Asp Leu Gly Val Asp
2270                2275                2280

Gln Ala Leu Leu Asn Leu Ile Glu Ala Ala Phe Gly Asn Ile Thr
2285                2290                2295

Ser Val His Leu Pro Thr Gly Thr Arg Phe Lys Phe Gly Ala Met
2300                2305                2310

Met Lys Ser Gly Met Phe Leu Thr Leu Phe Ile Asn Thr Val Val
2315                2320                2325

Asn Ile Met Ile Ala Ser Arg Val Leu Arg Glu Arg Leu Thr Thr
2330                2335                2340

Ser Pro Cys Ala Ala Phe Ile Gly Asp Asp Asn Ile Val Lys Gly
2345                2350                2355

Val Thr Ser Asp Glu Leu Met Ala Glu Arg Cys Ala Thr Trp Leu
2360                2365                2370

Asn Met Glu Val Lys Ile Ile Asp Ala Val Val Gly Val Lys Ala
2375                2380                2385

Pro Tyr Phe Cys Gly Gly Phe Ile Val Val Asp Gln Ile Thr Gly
2390                2395                2400

Thr Ala Cys Arg Val Ala Asp Pro Leu Lys Arg Leu Phe Lys Leu
2405                2410                2415

Gly Lys Pro Leu Pro Leu Asp Asp Asp Gln Asp Val Asp Arg Arg
2420                2425                2430

Arg Ala Leu His Asp Glu Ala Ala Arg Trp Asn Arg Ile Gly Ile
2435                2440                2445

Thr Glu Glu Leu Val Lys Ala Val Glu Ser Arg Tyr Glu Val Asn
2450                2455                2460

Tyr Val Ser Leu Ile Ile Thr Ala Leu Thr Thr Leu Ala Ser Thr
2465                2470                2475

Val Ser Asn Phe Lys His Ile Arg Gly His Pro Ile Thr Leu Tyr
2480                2485                2490

Gly

<210> SEQ ID NO 19
<211> LENGTH: 11476
<212> TYPE: DNA

<213> ORGANISM: Western equine encephalitis virus

<400> SEQUENCE: 19

```
aactaatcga tccaatatgg aaagaattca cgttgactta gatgctgaca gcccgtatgt      60
caagtcgtta cagcggagct ttccacaatt tgagatcgaa gcaaggcagg tcactgacaa     120
tgaccatgcc aatgccagag cgttttcgca tgtggcaaca aagctcattg agagcgaagt     180
cgaccgggac caagttatct tggacattgg aagtgcgccc gtcagacatg cacattccaa     240
tcaccgctat cattgtatct gccctatgat aagcgctgaa gacccggaca gactacaacg     300
gtatgcagaa agacttaaga aaagtgacat taccgacaag aacatagcct ctaaggcggc     360
agacctgctg gaagtcatgt caacaccaga cgcagagact ccatctctgt gtatgcacac     420
agacgccacg tgtaggtact ttggaagtgt agcagtatac caagatgtgt acgcagtcca     480
tgcaccgaca tcaatctacc accaggcgct taaaggagtt aggacaattt actggatagg     540
ctttgacacg accccttta tgtacaaaaa catggcaggt tcttacccta cttacaacac     600
gaactgggct gacgagagag tattggaagc acgtaacatt ggcctcggta actcagatct     660
tcaggagagc aggcttggaa acctctcaat ccttaggaag aagaggctcc aacctactaa     720
taagatcata ttctcggttg gttcaacaat ctacacagaa gatagatcac tgttacgtag     780
ctggcatctt ccaaacgtgt tccacttgaa aggaaagtct aacttcacag gtagatgtgg     840
gaccattgtc agctgtgaag ggtacgtcat aaaaaaaatt acaatcagcc caggactata     900
cggtaaagtt gagaacttgg cgtccacaat gcatcgcgag ggtttcttga gttgcaaagt     960
cacagatacg ttgcgcggcg agagggtttc ttttgctgtg tgtacgtatg taccagccac    1020
actttgcgat cagatgacag ggattctggc aactgacgtt agtgtggatg acgcacaaaa    1080
actattggtt gggctcaacc aaaggattgt cgtcaatggt aggacgcaaa gaaatactaa    1140
cacaatgcag aactatctat taccagtggt cgcccaggcg ttttccaggt gggcgcgtga    1200
acatcgtgcc gacttggacg acgagaaaga actaggggtg cggagcgca ctcttactat     1260
gggctgctgc tgggctttca agacccagaa aatcacatcc atctacaaga agcctggtac    1320
gcaaacaatt aagaaagtac ctgccgtctt tgactcattt gtgtttccac gccttaccag    1380
ccacgggctc gatatgggct tccgccgtag gctcaagctg ctgcttgaac caactgtcaa    1440
acccgcaccg gctattacaa tggccgatgt ggagcatctg cgtggcttac agcaagaagc    1500
tgaagaagtg gctgcagcgg aagagatcag agaagccctg ccgcccttgc tccctgaaat    1560
agaaaaagag accgtagagg cagaagtaga cctcattatg caagaggcag gagcaggtag    1620
cgtggagaca ccacgaggac acatcagggt gacaagttac ccaggcgaag agaagattgg    1680
gtcttacgct gtactttcac cccaggcggt attgaatagt gaaaaactgg cgtgtatcca    1740
cccattggcg gaacaagtac tggtaatgac tcacaaaggt agggctggga gatacaaggt    1800
cgagccatac cacggtaagg tcattgtacc agaagggacg gcggtccctg ttcaggactt    1860
ccaggcattg agtgagagcg ctacgatcgt ttttaacgag agggagttcg taaacagata    1920
cctgcatcac atcgcaatca acggaggagc gctaaacact gacgaagagt actataagac    1980
tgtaaagact caggacacag actcagaata cgtcttcgac gttgacgcac gaaagtgtgt    2040
taagcgagaa gacgcaggtc cgttgtgcct aaccggtgat ctggtagatc cgccatttca    2100
cgagtttgcg tacagagtc ttaggacgcg accagcagca cctcacaaag tcccaaccat    2160
tggagtctat ggagtccag gttcgggtaa atctggaatc atcaaaagcg ctgtgaccaa    2220
gaaagatctg gttgtgagtg cgaagaagga aaactgcgca gaaatcatca gggatgtaag    2280
```

```
gaggatgaga tgtatggatg ttgctgctag gactgtagat tctgtgctgc tgaatggggt    2340
taagcacccc gttaacactc tgtacattga tgaggcattt gcctgccatg cagggacgct    2400
gctggcactg attgccatcg tcaaacctaa gaaagtggta ttgtgcgggg acccaaaaca    2460
atgcggcttc tttaacatga tgtgcctgaa agtacatttt aaccatgaca tatgcactga    2520
agtgtaccat aaaagcatct ctaggaggtg cacacagact gtaaccgcta tcgtctccac    2580
gctcttttac gacaagcgaa tgaagacggt taacccatgt gctgacaaaa tcatcataga    2640
taccacaggg accacaaagc cgcacaaaga tgatctgatt ctaacctgtt tcagaggatg    2700
ggtgaaacag ctacagattg actataaaaa tcatgaaatc atgactgcgg ctgcatcgca    2760
aggacttacg cggaaaggcg tttatgctgt caggtacaaa gtcaacgaga atccactcta    2820
ctcgcagact tctgagcacg tgaacgtgtt acttacacgc acagaaaaac gcattgtctg    2880
gaagacgcta gctggtgatc cctggataaa gatacttaca gctaaatatt ccggggattt    2940
cacggcttca ttggacgact ggcagcgaga acatgatgcc attatggcac gcgttcttga    3000
taagccgcag acagctgatg tgttccagaa taaggtgaac gtctgctggg cgaaggctct    3060
agagccagtc ttggccacgg ccaacattgt gctgacgaga cagcagtggg agacgttgca    3120
cccattcaag catgacagag cgtactcacc tgaaatggca ctgaacttct tttgcaccag    3180
gttctttgga gtagacctgg acagtgggtt gttttccgct cctaccgtcg cacttactta    3240
tagggatcag cactgggata ctcgccagg gaagaacatg tatgggctta atagagaggt    3300
agcaaaggag ttgtcacggc gatatccgtg catcacaaaa gcggttgaca caggcagggt    3360
agctgatata aggaataata ccatcaagga ctactctcca acaattaatg tggttccatt    3420
aaatcgtcgg ttaccccact cgttgatcgt tgaccacaaa ggacaggta caactgatca    3480 cagcggattc ctatctaaga tgaagggcaa atctgtgttg gtgatcggcg atcctatcag    3540
cattccaggg aagaaagtag agtccatggg tccattgccc actaatacca tcaggtgtga    3600
tctagatttg ggaataccta gccatgtcgg taaatatgac attatatttg tcaatgttag    3660
gaccccgtat aagaaccatc actaccaaca gtgcgaggat cacgctatcc accacagcat    3720
gttaacgtgt aaggctgtcc accacctgaa cactggcgga acatgtgtgg ctataggta    3780 tgggcttgct gatcgcgcaa ccgagaatat catcactgcg gtagcgcgct catttaggtt    3840
tacccgtgtc tgtcagccta agaacactgc cgaaaatact gaggttctct tcgtgttctt    3900
cggcaaggac aacggcaacc acacacatga ccaggacaga ctcgctgtag tgcttgacaa    3960
catctaccaa gggtcaacca ggtacgaggc agggagagct ccagcgtaca gagtgatcag    4020
aggtgacatt agcaagagcg ctgaccaagc tatcgttaat gctgctaata gcaaaggtca    4080
accaggttcc ggagtgtgcg gtgcactgta ccgaaaatgg ccggctgctt ttgatagaca    4140
gccaatagct gtcgggacgg ctagacttgt gaagcacgaa ccgctcatca tacatgctgt    4200
aggacccaat ttttctaaga tgccggaacc ggagggcgac cttaagctcg cagctgccta    4260
catgagcata gcgtcaatcg tcaacgctga acggattact aaaatatcag taccgctact    4320
gtcaaccggc atctattctg gtggcaaaga tcgagtgatg caatcattgc atccctgtt    4380 cactgctttc gacactacgg atgccgatgt caccatatat gcttggata aacaatggga    4440 gaccaggata atcgaggcca ttcaccgcaa agaaagcgtc gaaatactgg atgatgacaa    4500
gccagtagac attgacttgg ttagggtcca tccaaacagc gctttggcag gcagacctgg    4560
ttactccgtc aatgagggca agctgtattc atacctggaa ggtacacgat tccatcagac    4620
```

```
cgccaaggac attgccgaaa tccatgcaat gtggcccaac aaatctgagg ctaatgagca    4680
gatttgcttg tacatcctgg gtgagagtat gtccagcatc cgctccaaat gcccagtaga    4740
ggagtcagag gcgtctgctc cacctcacac actgccgtgc ctgtgtaatt acgctatgac    4800
ggctgagcgc gtatacaggt tgcgctctgc gaagaaagaa cagttcgccg tatgctcatc    4860
attcctgttg ccgaagtaca ggatcacagg cgtgcagaag ctacaatgca gcaaaccagt    4920
cctgttttca ggcgtcgtac cgccggctgt acaccccagg aagtacgcgg aaataattct    4980
agaaacgcca ccaccgccag taacgacaac cgtaatatgt gaacccactg tgccagaacg    5040
tatacccagt ccggcgattt ctagagcacc aagtgcggaa tcactgctat cttttagcgg    5100
cgtctcgttc tctagctctg ccacacgctc gtcaaccgcc tggagcgact atgacaggcg    5160
gtttgtggtt acagctgacg tgcatcaagc gaacatatct acgtggagca tccctagtgc    5220
tcctggcttg gacgtccaaa taccttctga cgtcagtgat tcccactgga gtgttccgag    5280
tgcatcaggc ttcgaagtga gaacaccatc tgtacaggac ctaactgcgg agtgtgcaaa    5340
gcctcgtggg ctggccgaaa taatgcaaga cttcaatact gcccctttcc agtttctttc    5400
ggaccacaga ccagtaccgg caccacggag acgccccatc ccatcaccta gatcgacggt    5460
ttccgcacct ccagttccaa agccacgcag gactaagtac caacaaccac caggagtcgc    5520
tagagcgatc tcagaagcgg agctggacga gtacatccgt caacactcca attgacggta    5580
tgaagcggga gcgtatattt tctcatcgga acaggccaa ggtcaccttc aacagaaatc    5640
agtacgtcaa tgtaaactac aagaacctat attggaccgg gccgtccatg agaagtatta    5700
cgccccgcgc ctcgatctcg aaagagagaa aatgttacag aagaaattgc aattatgtgc    5760
ctctgaagga aatagaagca ggtatcaatc acgaaaagta gaaatatga aagcaattac    5820 agcggagcga ctcatttctg gattgggcac ataccctatca tcagaagtga atcctgtcga    5880
gtgttacaga gtcaactatc ctgtaccaat ctactcgtca acggtaatta acaggtttac    5940
atctgcagag gtcgcggtta aaacgtgcaa cttagttatc caagagaatt ccctacagt    6000 agccagttat tgtataacag atgaatacga tgcgtatctt gacatggtgg acggcgcatc    6060
gtgctgtcta gatacagcca ctttttgtcc ggctaaactg agaagctacc caaagaagca    6120
tagctatttg cagccagaga taagatcagc cgtcccatcg cctatacaga atacattaca    6180
aaatgtattg gctgcagcta ctaaaaggaa ttgcaacgtt acccaaatgc gagaattacc    6240
tgtcttagat tcggcggcat ttaacgttga ttgtttcaag aaatacgcat gcaatgatga    6300
gtactgggat acctttcgcg ataaccctat tcggctaact acagagaacg ttacgcaata    6360
tgtgacaaag ctgaaagggc cgaaagcagc agcattgttt gcgaaaactc acaatctaaa    6420
accgttgcag gagataccaa tggatcaatt cgtcatggat ctaaaaagag atgtcaaagt    6480
tactcccggc acgaaacata cagaggagcg gcctaaggtg caggttattc aggctgcaga    6540 ccccccttgct accgcttacc tttgcgggat ccaccgggaa ttagtccgta gactgaacgc    6600
tgtgcttctg ccgaatatcc atactctctt cgacatgtca gcggaagatt ttgatgcgat    6660
tattgctgga catttccacc acggcgaccc agtattggaa acggacatcg cgtcgtttga    6720
taaaagcgaa gacgacgcta tcgccatttc ggcgatgatg atccttgagg acttaggcgt    6780
cgaccaaccg ctcttagatt tgatagaggc ggcgttcggc aatatcacat ctgtgcacct    6840
acctacagga acgaggttta aatttggtgc catgatgaaa tccggcatgt tcttaacgct    6900
gtttgtcaac acactagtca atatcatgat tgctagcaga gtactacgtg aacggttaac    6960
cacgtcagcg tgcgcggcct ttatcggcga cgataacata gtgcatggtg tcgtctccga    7020
```

```
caccttgatg gcggagagat gcgccacttg gctgaacatg gaagtaaaaa ttattgatgc      7080
agtcattggt atcaaagcac cctacttctg cggggatttt atcctggtgg accagataac      7140
aggcacagcc tgcagggtcg cagaccctct aaaaaggctt tttaagcttg gaaaaccgtt      7200
gtcagttgaa gacacccaag actgcgaccg ccgccgggca ctgcatgatg aagcaatgcg      7260
atggaacaga atcggaatta cggacgagtt ggtgaaggcc gtagaatcca gatacgagat      7320
catactggca ggcctgatca tcacgtctct gtccacgtta gccgaaagcg ttaagaactt      7380
caagagcata agagggagcc caatcaccct ctacggctga cctaaatagg tgacgtagta      7440
gacacgcacc tacccatcgc cataatgttt ccatacccte agctgaactt tccaccagtt      7500
taccctacaa atccgatggc ttaccgagat ccaaaccctc ctaggcgccg ctggaggccg      7560
ttccggcccc cgctggctgc tcaaatcgaa gatcttagga ggtcgatagc taacttgact      7620
ttcaaacaac gatcacctaa tccgccgcca ggtccaccgc caaagaagaa gaagagtgct      7680
cctaagccaa aacctactca gcctaaaaag aagaagcagc aagccaagag gacgaaacgt      7740
aagcctaaac cagggaaacg acagcgtatg tgtatgaagt tggagtcgga caagacattt      7800
ccgatcatgc tgaacggcca agtgaatgga tacgcttgcg ttgtcggagg aaggctgatg      7860
aaaccactcc acgttgaagg aaaaattgat aatgagcaat tagcggccgt gaaattgaag      7920
aaggctagca agtacgactt agagtatggc gacgttcccc agaatatgaa atcagacacg      7980
ctgcagtaca ccagtgacaa accaccgggc ttctacaact ggcaccatgg cgcagtccag      8040
tatgagaatg ggagattcac cgtaccgaga ggagtgggcg ggaaaggcga cagcggaaga      8100
ccgatcctgg acaacagagg cagagttgtg gctattgttc taggaggtgc aaatgagggc      8160
acgcgtacgg cgcttttcag tggtcacttgg aaccagaaag gggtgaccgt ttgggatccc      8220
cccgaaggtt ctgaaccgtg gtcactagtt acagcgctgt gcgtgctttc gaatgtcact      8280
ttcccatgtg acaaaccacc cgtgtgctat tcactggcgc cagaacgaac actcgacgtg      8340
ctcgaagaga acgtcgacaa tccaaattac gacacgctgc tggagaacgt cttgaaatgt      8400
ccatcacacc ggcccaaacg aagcattacc gatgacttca cactgaccag tccctacttg      8460
gggttctgcc cgtattgcag acactcaacg ccgtgtttca gcccaataaa aattgagaac      8520
gtgtgggacg aatctgatga tggatcgatt agaatccagg tctcggcaca attcggttac      8580
aatcaggcag gcactgcaga tgtcactaaa ttccgttaca tgtctttcga ccacgaccat      8640
gacatcaagg aagacagtat ggagaaaata gccatcagca catccggacc ctgccgtcgt      8700
cttggccaca aagggtattt cctgttagct caatgtcctc caggtgacag tgtaaccgtc      8760
agtatcacga gcggaactgc tgagaactca tgcaccgtgg agagaaagat caggaggaag      8820
tttgtcggta gagaggagta cttgctccca cccatccatg gaaagcaggt aaagtgccac      8880
gtttacgatc acttgaaaga gacgtctgcc gggtatataa ccatgcacag gccaggccca      8940
cacgcgtata agtcctatct ggaggaagcg tcaggcgaag tgtatattaa accaccttct      9000
ggcaagaacg tcacctacga atgtaagtgt ggcgactaca cgcacaggta tcgtgagcacg      9060 cgaacgaaga taaacggctg cactaaagca aaacagtgca ttgcctacaa gagcgaccaa      9120
acgaaatggg tcttcaactc gccggatctt attaggcaca cagaccactc agtgcaaggt      9180
aaactgcata ttccattccg cttgacaccg acagtctgcc cggttccgtt agctcacacg      9240
cctacagtca tgaagtggtt caaaggcatc accctccacc tgactgcaac gcgaccaaca      9300
ttgctgacaa cgagaaaatt ggggctgcga gcagacgcaa cagcagaatg gattacaggg      9360
```

| | | | | | |
|---|---|---|---|---|---|
| actacatcca | ggaatttttc | tgtggggcga | aagggctgg | agtacgtatg | gggcaaccat | 9420 |
| gaaccggtca | gagtctgggc | ccaggagtcg | gcaccaggcg | acccacatgg | atggccgcat | 9480 |
| gagattatca | ttcactatta | tcatcggcat | ccagtctaca | ccgtcattgt | gctgtgtggt | 9540 |
| gtcgctcttg | ctatcctggt | aggcactgca | tcgtcagcag | cttgtatctc | caaagcaaga | 9600 |
| agagactgcc | tgacgccata | cgcgcttgca | ccgaacgcga | cggtacccac | agcattagtg | 9660 |
| gttttgtgct | gcattcggcc | aaccaacgct | gaaacacttg | agaaactttt | gaaccatctg | 9720 |
| tggtttaaca | accaaccgtt | tctctgggca | cagttgtgca | ttcctctggc | ggctcttatt | 9780 |
| attctgttcc | gctgcttttc | atgctgcatg | ccttttttat | tggttgcagg | cgtctgcctg | 9840 |
| gggaaggtag | acgccttcga | acatgcgacc | actgtgccaa | atgttccggg | gatcccgtat | 9900 |
| aaggcgttgg | tcgaacgtgc | aggttacgcg | ccacttaacc | tggagatcac | tgttgtctca | 9960 |
| tcggaattaa | caccctcaac | taataaggag | tacgtgacct | gcaaattcca | cacagtcatt | 10020 |
| ccttcaccac | aagttaaatg | ctgcgggtcc | ctcgagtgta | aggcatcctc | aagggcggat | 10080 |
| tacacatgcc | gcgttttttgg | cggtgtgtac | cctttcatgt | ggggaggcgc | acaatgcttc | 10140 |
| tgtgacagtg | agaacacaca | actgagtgag | gcatacgtcg | agttcgctcc | ggactgcact | 10200 |
| atagatcacg | cagtcgcact | aaaagttcat | acagctgctc | tgaaagtcgg | cctgcgtata | 10260 |
| gtgtacggta | ataccaccgc | gcacctggat | acgttcgtca | acggcgtcac | accaggttcc | 10320 |
| tcacgggacc | tgaaggtcat | agcagggccg | atatcagccg | cttttcacc | ctttgaccat | 10380 |
| aaggtcgtca | tcagaaaggg | gtttgtttac | aactacgact | tccctgagta | tggtgctatg | 10440 |
| aaaccaggag | cgttcggcga | tattcaagca | tcctctcttg | atgctacaga | catagtagcc | 10500 |
| cgcactgaca | tacggctgct | gaagccttct | gtcaagaaca | tccacgtccc | ctacacccaa | 10560 |
| gcagtatcag | ggtatgaaat | gtggaagaac | aactcaggac | gaccccctgca | agaaacagca | 10620 |
| ccatttggat | gtaaaattga | agtggagcct | ctgcgagcgt | ctaactgtgc | ttacgggcac | 10680 |
| attcctatct | cgattgacat | ccctgatgca | gctttcgtga | gatcatcaga | atcaccaaca | 10740 |
| attttagaag | ttagctgcac | agtagcagac | tgcatttatt | ctgcagactt | tggtggttct | 10800 |
| ctaacattac | agtacaaagc | tgatagggag | ggacattgtc | cagttcactc | ccactccacg | 10860 |
| acagctgttt | tgaaggaagc | gaccacacat | gtgactgccg | taggcagcat | aacactacat | 10920 |
| tttagcacat | cgagcccaca | agcaaatttt | atagtttcgc | tatgcggcaa | gaagtccacc | 10980 |
| tgcaatgctg | aatgtaaacc | accggccgac | cacataattg | gagaaccgca | taaagtcgac | 11040 |
| caagaattcc | aagcggcagt | ttccacaaca | tcttggaact | ggctgcttgc | actgtttggg | 11100 |
| ggagcatcat | ccctcattgt | tgtaggactt | atagtgttgg | tctgcagctc | tatgcttata | 11160 |
| aacacacgta | gatgactgag | cgcggacact | gacatagcgg | taaaaactcg | atgtacttcc | 11220 |
| gaggaagcgt | ggtgcataat | gccacgcgcc | gcttgacact | aaaactcgat | gtatttccga | 11280 |
| ggaagcacag | tgcataatgc | tgtgcagtgt | cacattaatc | gcatatcaca | ctatatatta | 11340 |
| acaacactat | atcactttta | taagactcac | tatgggtctc | taatatacac | tacacatatt | 11400 |
| ttacttaaaa | acactataca | cactttataa | gttctttat | aatttttctt | ttgttttat | 11460 |
| tttgttttta | aaattt | | | | | 11476 |

<210> SEQ ID NO 20
<211> LENGTH: 1236
<212> TYPE: PRT
<213> ORGANISM: Western equine encephalitis virus

<400> SEQUENCE: 20

```
Met Phe Pro Tyr Pro Gln Leu Asn Phe Pro Pro Val Tyr Pro Thr Asn
1               5                   10                  15

Pro Met Ala Tyr Arg Asp Pro Asn Pro Arg Arg Arg Trp Arg Pro
        20                  25                  30

Phe Arg Pro Pro Leu Ala Ala Gln Ile Glu Asp Leu Arg Arg Ser Ile
        35                  40                  45

Ala Asn Leu Thr Phe Lys Gln Arg Ser Pro Asn Pro Pro Gly Pro
50                  55                  60

Pro Pro Lys Lys Lys Lys Ser Ala Pro Lys Pro Lys Pro Thr Gln Pro
65              70                  75                  80

Lys Lys Lys Lys Gln Gln Ala Lys Arg Thr Lys Arg Lys Pro Lys Pro
            85                  90                  95

Gly Lys Arg Gln Arg Met Cys Met Lys Leu Glu Ser Asp Lys Thr Phe
            100                 105                 110

Pro Ile Met Leu Asn Gly Gln Val Asn Gly Tyr Ala Cys Val Val Gly
            115                 120                 125

Gly Arg Leu Met Lys Pro Leu His Val Glu Gly Lys Ile Asp Asn Glu
        130                 135                 140

Gln Leu Ala Ala Val Lys Leu Lys Lys Ala Ser Lys Tyr Asp Leu Glu
145                 150                 155                 160

Tyr Gly Asp Val Pro Gln Asn Met Lys Ser Asp Thr Leu Gln Tyr Thr
                165                 170                 175

Ser Asp Lys Pro Pro Gly Phe Tyr Asn Trp His His Gly Ala Val Gln
            180                 185                 190

Tyr Glu Asn Gly Arg Phe Thr Val Pro Arg Gly Val Gly Gly Lys Gly
            195                 200                 205

Asp Ser Gly Arg Pro Ile Leu Asp Asn Arg Gly Arg Val Val Ala Ile
        210                 215                 220

Val Leu Gly Gly Ala Asn Glu Gly Thr Arg Thr Ala Leu Ser Val Val
225                 230                 235                 240

Thr Trp Asn Gln Lys Gly Val Thr Val Trp Asp Pro Glu Gly Ser
            245                 250                 255

Glu Pro Trp Ser Leu Val Thr Ala Leu Cys Val Leu Ser Asn Val Thr
            260                 265                 270

Phe Pro Cys Asp Lys Pro Pro Val Cys Tyr Ser Leu Ala Pro Glu Arg
        275                 280                 285

Thr Leu Asp Val Leu Glu Glu Asn Val Asp Asn Pro Asn Tyr Asp Thr
    290                 295                 300

Leu Leu Glu Asn Val Leu Lys Cys Pro Ser His Arg Pro Lys Arg Ser
305                 310                 315                 320

Ile Thr Asp Asp Phe Thr Leu Thr Ser Pro Tyr Leu Gly Phe Cys Pro
                325                 330                 335

Tyr Cys Arg His Ser Thr Pro Cys Phe Ser Pro Ile Lys Ile Glu Asn
            340                 345                 350

Val Trp Asp Glu Ser Asp Asp Gly Ser Ile Arg Ile Gln Val Ser Ala
            355                 360                 365

Gln Phe Gly Tyr Asn Gln Ala Gly Thr Ala Asp Val Thr Lys Phe Arg
    370                 375                 380

Tyr Met Ser Phe Asp His Asp His Asp Ile Lys Glu Asp Ser Met Glu
385                 390                 395                 400

Lys Ile Ala Ile Ser Thr Ser Gly Pro Cys Arg Arg Leu Gly His Lys
                405                 410                 415
```

```
Gly Tyr Phe Leu Leu Ala Gln Cys Pro Pro Gly Asp Ser Val Thr Val
            420                 425                 430

Ser Ile Thr Ser Gly Thr Ala Glu Asn Ser Cys Thr Val Glu Arg Lys
        435                 440                 445

Ile Arg Arg Lys Phe Val Gly Arg Glu Glu Tyr Leu Leu Pro Pro Ile
    450                 455                 460

His Gly Lys Gln Val Lys Cys His Val Tyr Asp His Leu Lys Glu Thr
465                 470                 475                 480

Ser Ala Gly Tyr Ile Thr Met His Arg Pro Gly Pro His Ala Tyr Lys
                485                 490                 495

Ser Tyr Leu Glu Glu Ala Ser Gly Glu Val Tyr Ile Lys Pro Pro Ser
            500                 505                 510

Gly Lys Asn Val Thr Tyr Glu Cys Lys Cys Gly Asp Tyr Ser Thr Gly
        515                 520                 525

Ile Val Ser Thr Arg Thr Lys Ile Asn Gly Cys Thr Lys Ala Lys Gln
    530                 535                 540

Cys Ile Ala Tyr Lys Ser Asp Gln Thr Lys Trp Val Phe Asn Ser Pro
545                 550                 555                 560

Asp Leu Ile Arg His Thr Asp His Ser Val Gln Gly Lys Leu His Ile
                565                 570                 575

Pro Phe Arg Leu Thr Pro Thr Val Cys Pro Val Pro Leu Ala His Thr
            580                 585                 590

Pro Thr Val Met Lys Trp Phe Lys Gly Ile Thr Leu His Leu Thr Ala
        595                 600                 605

Thr Arg Pro Thr Leu Leu Thr Thr Arg Lys Leu Gly Leu Arg Ala Asp
    610                 615                 620

Ala Thr Ala Glu Trp Ile Thr Gly Thr Thr Ser Arg Asn Phe Ser Val
625                 630                 635                 640

Gly Arg Glu Gly Leu Glu Tyr Val Trp Gly Asn His Glu Pro Val Arg
                645                 650                 655

Val Trp Ala Gln Glu Ser Ala Pro Gly Asp Pro His Gly Trp Pro His
            660                 665                 670

Glu Ile Ile Ile His Tyr Tyr His Arg His Pro Val Tyr Thr Val Ile
        675                 680                 685

Val Leu Cys Gly Val Ala Leu Ala Ile Leu Val Gly Thr Ala Ser Ser
    690                 695                 700

Ala Ala Cys Ile Ser Lys Ala Arg Arg Asp Cys Leu Thr Pro Tyr Ala
705                 710                 715                 720

Leu Ala Pro Asn Ala Thr Val Pro Thr Ala Leu Val Val Leu Cys Cys
                725                 730                 735

Ile Arg Pro Thr Asn Ala Glu Thr Leu Gly Glu Thr Leu Asn His Leu
            740                 745                 750

Trp Phe Asn Asn Gln Pro Phe Leu Trp Ala Gln Leu Cys Ile Pro Leu
        755                 760                 765

Ala Ala Leu Ile Ile Leu Phe Arg Cys Phe Ser Cys Cys Met Pro Phe
    770                 775                 780

Leu Leu Val Ala Gly Val Cys Leu Gly Lys Val Asp Ala Phe Glu His
785                 790                 795                 800

Ala Thr Thr Val Pro Asn Val Pro Gly Ile Pro Tyr Lys Ala Leu Val
                805                 810                 815

Glu Arg Ala Gly Tyr Ala Pro Leu Asn Leu Glu Ile Thr Val Val Ser
            820                 825                 830

Ser Glu Leu Thr Pro Ser Thr Asn Lys Glu Tyr Val Thr Cys Lys Phe
```

-continued

His Thr Val Ile Pro Ser Pro Gln Val Lys Cys Cys Gly Ser Leu Glu
835                 840                 845
                    850                 855                 860

Cys Lys Ala Ser Ser Arg Ala Asp Tyr Thr Cys Arg Val Phe Gly Gly
865                 870                 875                 880

Val Tyr Pro Phe Met Trp Gly Gly Ala Gln Cys Phe Cys Asp Ser Glu
                885                 890                 895

Asn Thr Gln Leu Ser Glu Ala Tyr Val Glu Phe Ala Pro Asp Cys Thr
                900                 905                 910

Ile Asp His Ala Val Ala Leu Lys Val His Thr Ala Ala Leu Lys Val
                915                 920                 925

Gly Leu Arg Ile Val Tyr Gly Asn Thr Thr Ala His Leu Asp Thr Phe
                930                 935                 940

Val Asn Gly Val Thr Pro Gly Ser Ser Arg Asp Leu Lys Val Ile Ala
945                 950                 955                 960

Gly Pro Ile Ser Ala Ala Phe Ser Pro Phe Asp His Lys Val Val Ile
                965                 970                 975

Arg Lys Gly Phe Val Tyr Asn Tyr Asp Phe Pro Glu Tyr Gly Ala Met
                980                 985                 990

Lys Pro Gly Ala Phe Gly Asp Ile Gln Ala Ser Ser Leu Asp Ala Thr
                995                 1000                1005

Asp Ile Val Ala Arg Thr Asp Ile Arg Leu Leu Lys Pro Ser Val
1010                1015                1020

Lys Asn Ile His Val Pro Tyr Thr Gln Ala Val Ser Gly Tyr Glu
1025                1030                1035

Met Trp Lys Asn Asn Ser Gly Arg Pro Leu Gln Glu Thr Ala Pro
1040                1045                1050

Phe Gly Cys Lys Ile Glu Val Glu Pro Leu Arg Ala Ser Asn Cys
1055                1060                1065

Ala Tyr Gly His Ile Pro Ile Ser Ile Asp Ile Pro Asp Ala Ala
1070                1075                1080

Phe Val Arg Ser Ser Glu Ser Pro Thr Ile Leu Glu Val Ser Cys
1085                1090                1095

Thr Val Ala Asp Cys Ile Tyr Ser Ala Asp Phe Gly Gly Ser Leu
1100                1105                1110

Thr Leu Gln Tyr Lys Ala Asp Arg Glu Gly His Cys Pro Val His
1115                1120                1125

Ser His Ser Thr Thr Ala Val Leu Lys Glu Ala Thr Thr His Val
1130                1135                1140

Thr Ala Val Gly Ser Ile Thr Leu His Phe Ser Thr Ser Ser Pro
1145                1150                1155

Gln Ala Asn Phe Ile Val Ser Leu Cys Gly Lys Lys Ser Thr Cys
1160                1165                1170

Asn Ala Glu Cys Lys Pro Pro Ala Asp His Ile Ile Gly Glu Pro
1175                1180                1185

His Lys Val Asp Gln Glu Phe Gln Ala Ala Val Ser Thr Thr Ser
1190                1195                1200

Trp Asn Trp Leu Leu Ala Leu Phe Gly Gly Ala Ser Ser Leu Ile
1205                1210                1215

Val Val Gly Leu Ile Val Leu Val Cys Ser Ser Met Leu Ile Asn
1220                1225                1230

Thr Arg Arg
1235

<210> SEQ ID NO 21
<211> LENGTH: 2466
<212> TYPE: PRT
<213> ORGANISM: Western equine encephalitis virus

<400> SEQUENCE: 21

```
Met Glu Arg Ile His Val Asp Leu Asp Ala Asp Ser Pro Tyr Val Lys
1               5                   10                  15

Ser Leu Gln Arg Ser Phe Pro Gln Phe Glu Ile Glu Ala Arg Gln Val
            20                  25                  30

Thr Asp Asn Asp His Ala Asn Ala Arg Ala Phe Ser His Val Ala Thr
        35                  40                  45

Lys Leu Ile Glu Ser Glu Val Asp Arg Asp Gln Val Ile Leu Asp Ile
    50                  55                  60

Gly Ser Ala Pro Val Arg His Ala His Ser Asn His Arg Tyr His Cys
65                  70                  75                  80

Ile Cys Pro Met Ile Ser Ala Glu Asp Pro Asp Arg Leu Gln Arg Tyr
                85                  90                  95

Ala Glu Arg Leu Lys Lys Ser Asp Ile Thr Asp Lys Asn Ile Ala Ser
            100                 105                 110

Lys Ala Ala Asp Leu Leu Glu Val Met Ser Thr Pro Asp Ala Glu Thr
        115                 120                 125

Pro Ser Leu Cys Met His Thr Asp Ala Thr Cys Arg Tyr Phe Gly Ser
    130                 135                 140

Val Ala Val Tyr Gln Asp Val Tyr Ala Val His Ala Pro Thr Ser Ile
145                 150                 155                 160

Tyr His Gln Ala Leu Lys Gly Val Arg Thr Ile Tyr Trp Ile Gly Phe
                165                 170                 175

Asp Thr Thr Pro Phe Met Tyr Lys Asn Met Ala Gly Ser Tyr Pro Thr
            180                 185                 190

Tyr Asn Thr Asn Trp Ala Asp Glu Arg Val Leu Glu Ala Arg Asn Ile
        195                 200                 205

Gly Leu Gly Asn Ser Asp Leu Gln Glu Ser Arg Leu Gly Asn Leu Ser
    210                 215                 220

Ile Leu Arg Lys Lys Arg Leu Gln Pro Thr Asn Lys Ile Ile Phe Ser
225                 230                 235                 240

Val Gly Ser Thr Ile Tyr Thr Glu Asp Arg Ser Leu Leu Arg Ser Trp
                245                 250                 255

His Leu Pro Asn Val Phe His Leu Lys Gly Lys Ser Asn Phe Thr Gly
            260                 265                 270

Arg Cys Gly Thr Ile Val Ser Cys Glu Gly Tyr Val Ile Lys Lys Ile
        275                 280                 285

Thr Ile Ser Pro Gly Leu Tyr Gly Lys Val Glu Asn Leu Ala Ser Thr
    290                 295                 300

Met His Arg Glu Gly Phe Leu Ser Cys Lys Val Thr Asp Thr Leu Arg
305                 310                 315                 320

Gly Glu Arg Val Ser Phe Ala Val Cys Thr Tyr Val Pro Ala Thr Leu
                325                 330                 335

Cys Asp Gln Met Thr Gly Ile Leu Ala Thr Asp Val Ser Val Asp Asp
            340                 345                 350

Ala Gln Lys Leu Leu Val Gly Leu Asn Gln Arg Ile Val Val Asn Gly
        355                 360                 365

Arg Thr Gln Arg Asn Thr Asn Thr Met Gln Asn Tyr Leu Leu Pro Val
```

```
              370                 375                 380
Val Ala Gln Ala Phe Ser Arg Trp Ala Arg Glu His Arg Ala Asp Leu
385                 390                 395                 400

Asp Asp Glu Lys Glu Leu Gly Val Arg Glu Arg Thr Leu Thr Met Gly
                    405                 410                 415

Cys Cys Trp Ala Phe Lys Thr Gln Lys Ile Thr Ser Ile Tyr Lys Lys
                420                 425                 430

Pro Gly Thr Gln Thr Ile Lys Lys Val Pro Ala Val Phe Asp Ser Phe
            435                 440                 445

Val Phe Pro Arg Leu Thr Ser His Gly Leu Asp Met Gly Phe Arg Arg
450                 455                 460

Arg Leu Lys Leu Leu Leu Glu Pro Thr Val Lys Pro Ala Pro Ala Ile
465                 470                 475                 480

Thr Met Ala Asp Val Glu His Leu Arg Gly Leu Gln Gln Glu Ala Glu
                    485                 490                 495

Glu Val Ala Ala Ala Glu Glu Ile Arg Glu Ala Leu Pro Pro Leu Leu
                500                 505                 510

Pro Glu Ile Glu Lys Glu Thr Val Glu Ala Glu Val Asp Leu Ile Met
            515                 520                 525

Gln Glu Ala Gly Ala Gly Ser Val Glu Thr Pro Arg Gly His Ile Arg
530                 535                 540

Val Thr Ser Tyr Pro Gly Glu Glu Lys Ile Gly Ser Tyr Ala Val Leu
545                 550                 555                 560

Ser Pro Gln Ala Val Leu Asn Ser Glu Lys Leu Ala Cys Ile His Pro
                565                 570                 575

Leu Ala Glu Gln Val Leu Val Met Thr His Lys Gly Arg Ala Gly Arg
                580                 585                 590

Tyr Lys Val Glu Pro Tyr His Gly Lys Val Ile Val Pro Glu Gly Thr
            595                 600                 605

Ala Val Pro Val Gln Asp Phe Gln Ala Leu Ser Glu Ser Ala Thr Ile
610                 615                 620

Val Phe Asn Glu Arg Glu Phe Val Asn Arg Tyr Leu His His Ile Ala
625                 630                 635                 640

Ile Asn Gly Gly Ala Leu Asn Thr Asp Glu Glu Tyr Tyr Lys Thr Val
                645                 650                 655

Lys Thr Gln Asp Thr Asp Ser Glu Tyr Val Phe Asp Val Asp Ala Arg
                660                 665                 670

Lys Cys Val Lys Arg Glu Asp Ala Gly Pro Leu Cys Leu Thr Gly Asp
            675                 680                 685

Leu Val Asp Pro Pro Phe His Glu Phe Ala Tyr Glu Ser Leu Arg Thr
690                 695                 700

Arg Pro Ala Ala Pro His Lys Val Pro Thr Ile Gly Val Tyr Gly Val
705                 710                 715                 720

Pro Gly Ser Gly Lys Ser Gly Ile Ile Lys Ser Ala Val Thr Lys Lys
                725                 730                 735

Asp Leu Val Val Ser Ala Lys Lys Glu Asn Cys Ala Glu Ile Ile Arg
                740                 745                 750

Asp Val Arg Arg Met Arg Cys Met Asp Val Ala Ala Arg Thr Val Asp
            755                 760                 765

Ser Val Leu Leu Asn Gly Val Lys His Pro Val Asn Thr Leu Tyr Ile
770                 775                 780

Asp Glu Ala Phe Ala Cys His Ala Gly Thr Leu Leu Ala Leu Ile Ala
785                 790                 795                 800
```

```
Ile Val Lys Pro Lys Lys Val Leu Cys Gly Asp Pro Gln Cys
                805                 810                 815

Gly Phe Phe Asn Met Met Cys Leu Lys Val His Phe Asn His Asp Ile
            820                 825                 830

Cys Thr Glu Val Tyr His Lys Ser Ile Ser Arg Arg Cys Thr Gln Thr
            835                 840                 845

Val Thr Ala Ile Val Ser Thr Leu Phe Tyr Asp Lys Arg Met Lys Thr
850                 855                 860

Val Asn Pro Cys Ala Asp Lys Ile Ile Ile Asp Thr Thr Gly Thr Thr
865                 870                 875                 880

Lys Pro His Lys Asp Asp Leu Ile Leu Thr Cys Phe Arg Gly Trp Val
            885                 890                 895

Lys Gln Leu Gln Ile Asp Tyr Lys Asn His Glu Ile Met Thr Ala Ala
            900                 905                 910

Ala Ser Gln Gly Leu Thr Arg Lys Gly Val Tyr Ala Val Arg Tyr Lys
            915                 920                 925

Val Asn Glu Asn Pro Leu Tyr Ser Gln Thr Ser Glu His Val Asn Val
930                 935                 940

Leu Leu Thr Arg Thr Glu Lys Arg Ile Val Trp Lys Thr Leu Ala Gly
945                 950                 955                 960

Asp Pro Trp Ile Lys Ile Leu Thr Ala Lys Tyr Ser Gly Asp Phe Thr
            965                 970                 975

Ala Ser Leu Asp Asp Trp Gln Arg Glu His Asp Ala Ile Met Ala Arg
            980                 985                 990

Val Leu Asp Lys Pro Gln Thr Ala Asp Val Phe Gln Asn Lys Val Asn
            995                 1000                1005

Val Cys Trp Ala Lys Ala Leu Glu Pro Val Leu Ala Thr Ala Asn
    1010                1015                1020

Ile Val Leu Thr Arg Gln Gln Trp Glu Thr Leu His Pro Phe Lys
    1025                1030                1035

His Asp Arg Ala Tyr Ser Pro Glu Met Ala Leu Asn Phe Phe Cys
    1040                1045                1050

Thr Arg Phe Phe Gly Val Asp Leu Asp Ser Gly Leu Phe Ser Ala
    1055                1060                1065

Pro Thr Val Ala Leu Thr Tyr Arg Asp Gln His Trp Asp Asn Ser
    1070                1075                1080

Pro Gly Lys Asn Met Tyr Gly Leu Asn Arg Glu Val Ala Lys Glu
    1085                1090                1095

Leu Ser Arg Arg Tyr Pro Cys Ile Thr Lys Ala Val Asp Thr Gly
    1100                1105                1110

Arg Val Ala Asp Ile Arg Asn Asn Thr Ile Lys Asp Tyr Ser Pro
    1115                1120                1125

Thr Ile Asn Val Val Pro Leu Asn Arg Arg Leu Pro His Ser Leu
    1130                1135                1140

Ile Val Asp His Lys Gly Gln Gly Thr Thr Asp His Ser Gly Phe
    1145                1150                1155

Leu Ser Lys Met Lys Gly Lys Ser Val Leu Val Ile Gly Asp Pro
    1160                1165                1170

Ile Ser Ile Pro Gly Lys Lys Val Glu Ser Met Gly Pro Leu Pro
    1175                1180                1185

Thr Asn Thr Ile Arg Cys Asp Leu Asp Leu Gly Ile Pro Ser His
    1190                1195                1200
```

```
Val Gly Lys Tyr Asp Ile Ile Phe Val Asn Val Arg Thr Pro Tyr
    1205                1210                1215

Lys Asn His His Tyr Gln Gln Cys Glu Asp His Ala Ile His His
    1220                1225                1230

Ser Met Leu Thr Cys Lys Ala Val His His Leu Asn Thr Gly Gly
    1235                1240                1245

Thr Cys Val Ala Ile Gly Tyr Gly Leu Ala Asp Arg Ala Thr Glu
    1250                1255                1260

Asn Ile Ile Thr Ala Val Ala Arg Ser Phe Arg Phe Thr Arg Val
    1265                1270                1275

Cys Gln Pro Lys Asn Thr Ala Glu Asn Thr Glu Val Leu Phe Val
    1280                1285                1290

Phe Phe Gly Lys Asp Asn Gly Asn His Thr His Asp Gln Asp Arg
    1295                1300                1305

Leu Ala Val Val Leu Asp Asn Ile Tyr Gln Gly Ser Thr Arg Tyr
    1310                1315                1320

Glu Ala Gly Arg Ala Pro Ala Tyr Arg Val Ile Arg Gly Asp Ile
    1325                1330                1335

Ser Lys Ser Ala Asp Gln Ala Ile Val Asn Ala Ala Asn Ser Lys
    1340                1345                1350

Gly Gln Pro Gly Ser Gly Val Cys Gly Ala Leu Tyr Arg Lys Trp
    1355                1360                1365

Pro Ala Ala Phe Asp Arg Gln Pro Ile Ala Val Gly Thr Ala Arg
    1370                1375                1380

Leu Val Lys His Glu Pro Leu Ile Ile His Ala Val Gly Pro Asn
    1385                1390                1395

Phe Ser Lys Met Pro Glu Pro Glu Gly Asp Leu Lys Leu Ala Ala
    1400                1405                1410

Ala Tyr Met Ser Ile Ala Ser Ile Val Asn Ala Glu Arg Ile Thr
    1415                1420                1425

Lys Ile Ser Val Pro Leu Leu Ser Thr Gly Ile Tyr Ser Gly Gly
    1430                1435                1440

Lys Asp Arg Val Met Gln Ser Leu His His Leu Phe Thr Ala Phe
    1445                1450                1455

Asp Thr Thr Asp Ala Asp Val Thr Ile Tyr Cys Leu Asp Lys Gln
    1460                1465                1470

Trp Glu Thr Arg Ile Ile Glu Ala Ile His Arg Lys Glu Ser Val
    1475                1480                1485

Glu Ile Leu Asp Asp Asp Lys Pro Val Asp Ile Asp Leu Val Arg
    1490                1495                1500

Val His Pro Asn Ser Ala Leu Ala Gly Arg Pro Gly Tyr Ser Val
    1505                1510                1515

Asn Glu Gly Lys Leu Tyr Ser Tyr Leu Glu Gly Thr Arg Phe His
    1520                1525                1530

Gln Thr Ala Lys Asp Ile Ala Glu Ile His Ala Met Trp Pro Asn
    1535                1540                1545

Lys Ser Glu Ala Asn Glu Gln Ile Cys Leu Tyr Ile Leu Gly Glu
    1550                1555                1560

Ser Met Ser Ser Ile Arg Ser Lys Cys Pro Val Glu Glu Ser Glu
    1565                1570                1575

Ala Ser Ala Pro Pro His Thr Leu Pro Cys Leu Cys Asn Tyr Ala
    1580                1585                1590

Met Thr Ala Glu Arg Val Tyr Arg Leu Arg Ser Ala Lys Lys Glu
```

-continued

|  |  |  |  |  |  |  |  |  |  |
|---|---|---|---|---|---|---|---|---|---|
|  |  | 1595 |  |  | 1600 |  |  | 1605 |  |
| Gln | Phe 1610 | Ala | Val | Cys | Ser 1615 | Ser | Phe | Leu | Leu 1620 | Pro | Lys | Tyr | Arg | Ile |
| Thr | Gly 1625 | Val | Gln | Lys | Leu 1630 | Gln | Cys | Ser | Lys 1635 | Pro | Val | Leu | Phe | Ser |
| Gly | Val 1640 | Val | Pro | Pro | Ala 1645 | Val | His | Pro | Arg 1650 | Lys | Tyr | Ala | Glu | Ile |
| Ile | Leu 1655 | Glu | Thr | Pro | Pro 1660 | Pro | Val | Thr | Thr 1665 | Thr | Val | Ile | Cys |
| Glu | Pro 1670 | Thr | Val | Pro | Glu 1675 | Arg | Ile | Pro | Ser 1680 | Pro | Ala | Ile | Ser | Arg |
| Ala | Pro 1685 | Ser | Ala | Glu | Ser 1690 | Leu | Leu | Ser | Phe 1695 | Ser | Gly | Val | Ser | Phe |
| Ser | Ser 1700 | Ser | Ala | Thr | Arg 1705 | Ser | Ser | Thr | Ala 1710 | Trp | Ser | Asp | Tyr | Asp |
| Arg | Arg 1715 | Phe | Val | Val | Thr 1720 | Ala | Asp | Val | His 1725 | Gln | Ala | Asn | Ile | Ser |
| Thr | Trp 1730 | Ser | Ile | Pro | Ser 1735 | Ala | Pro | Gly | Leu 1740 | Asp | Val | Gln | Ile | Pro |
| Ser | Asp 1745 | Val | Ser | Asp | Ser 1750 | His | Trp | Ser | Val 1755 | Pro | Ser | Ala | Ser | Gly |
| Phe | Glu 1760 | Val | Arg | Thr | Pro 1765 | Ser | Val | Gln | Asp 1770 | Leu | Thr | Ala | Glu | Cys |
| Ala | Lys 1775 | Pro | Arg | Gly | Leu 1780 | Ala | Glu | Ile | Met 1785 | Gln | Asp | Phe | Asn | Thr |
| Ala | Pro 1790 | Phe | Gln | Phe | Leu 1795 | Ser | Asp | His | Arg 1800 | Pro | Val | Pro | Ala | Pro |
| Arg | Arg 1805 | Arg | Pro | Ile | Pro 1810 | Ser | Pro | Arg | Ser 1815 | Thr | Val | Ser | Ala | Pro |
| Pro | Val 1820 | Pro | Lys | Pro | Arg 1825 | Arg | Thr | Lys | Tyr 1830 | Gln | Gln | Pro | Pro | Gly |
| Val | Ala 1835 | Arg | Ala | Ile | Ser 1840 | Glu | Ala | Glu | Leu 1845 | Asp | Glu | Tyr | Ile | Arg |
| Gln | His 1850 | Ser | Asn | Arg | Tyr 1855 | Glu | Ala | Gly | Ala 1860 | Tyr | Ile | Phe | Ser | Ser |
| Glu | Thr 1865 | Gly | Gln | Gly | His 1870 | Leu | Gln | Gln | Lys 1875 | Ser | Val | Arg | Gln | Cys |
| Lys | Leu 1880 | Gln | Glu | Pro | Ile 1885 | Leu | Asp | Arg | Ala 1890 | Val | His | Glu | Lys | Tyr |
| Tyr | Ala 1895 | Pro | Arg | Leu | Asp 1900 | Leu | Glu | Arg | Glu 1905 | Lys | Met | Leu | Gln | Lys |
| Lys | Leu 1910 | Gln | Leu | Cys | Ala 1915 | Ser | Glu | Gly | Asn 1920 | Arg | Ser | Arg | Tyr | Gln |
| Ser | Arg 1925 | Lys | Val | Glu | Asn 1930 | Met | Lys | Ala | Ile 1935 | Thr | Ala | Glu | Arg | Leu |
| Ile | Ser 1940 | Gly | Leu | Gly | Thr 1945 | Tyr | Leu | Ser | Ser 1950 | Glu | Val | Asn | Pro | Val |
| Glu | Cys 1955 | Tyr | Arg | Val | Asn 1960 | Tyr | Pro | Val | Pro 1965 | Ile | Tyr | Ser | Ser | Thr |
| Val | Ile 1970 | Asn | Arg | Phe | Thr 1975 | Ser | Ala | Glu | Val 1980 | Ala | Val | Lys | Thr | Cys |
| Asn | Leu 1985 | Val | Ile | Gln | Glu 1990 | Asn | Tyr | Pro | Thr 1995 | Val | Ala | Ser | Tyr | Cys |

```
Ile Thr Asp Glu Tyr Asp Ala Tyr Leu Asp Met Val Asp Gly Ala
2000                2005                2010

Ser Cys Cys Leu Asp Thr Ala Thr Phe Cys Pro Ala Lys Leu Arg
2015                2020                2025

Ser Tyr Pro Lys Lys His Ser Tyr Leu Gln Pro Glu Ile Arg Ser
2030                2035                2040

Ala Val Pro Ser Pro Ile Gln Asn Thr Leu Gln Asn Val Leu Ala
2045                2050                2055

Ala Ala Thr Lys Arg Asn Cys Asn Val Thr Gln Met Arg Glu Leu
2060                2065                2070

Pro Val Leu Asp Ser Ala Ala Phe Asn Val Asp Cys Phe Lys Lys
2075                2080                2085

Tyr Ala Cys Asn Asp Glu Tyr Trp Asp Thr Phe Arg Asp Asn Pro
2090                2095                2100

Ile Arg Leu Thr Thr Glu Asn Val Thr Gln Tyr Val Thr Lys Leu
2105                2110                2115

Lys Gly Pro Lys Ala Ala Ala Leu Phe Ala Lys Thr His Asn Leu
2120                2125                2130

Lys Pro Leu Gln Glu Ile Pro Met Asp Gln Phe Val Met Asp Leu
2135                2140                2145

Lys Arg Asp Val Lys Val Thr Pro Gly Thr Lys His Thr Glu Glu
2150                2155                2160

Arg Pro Lys Val Gln Val Ile Gln Ala Ala Asp Pro Leu Ala Thr
2165                2170                2175

Ala Tyr Leu Cys Gly Ile His Arg Glu Leu Val Arg Arg Leu Asn
2180                2185                2190

Ala Val Leu Leu Pro Asn Ile His Thr Leu Phe Asp Met Ser Ala
2195                2200                2205

Glu Asp Phe Asp Ala Ile Ile Ala Gly His Phe His His Gly Asp
2210                2215                2220

Pro Val Leu Glu Thr Asp Ile Ala Ser Phe Asp Lys Ser Glu Asp
2225                2230                2235

Asp Ala Ile Ala Ile Ser Ala Met Met Ile Leu Glu Asp Leu Gly
2240                2245                2250

Val Asp Gln Pro Leu Leu Asp Leu Ile Glu Ala Ala Phe Gly Asn
2255                2260                2265

Ile Thr Ser Val His Leu Pro Thr Gly Thr Arg Phe Lys Phe Gly
2270                2275                2280

Ala Met Met Lys Ser Gly Met Phe Leu Thr Leu Phe Val Asn Thr
2285                2290                2295

Leu Val Asn Ile Met Ile Ala Ser Arg Val Leu Arg Glu Arg Leu
2300                2305                2310

Thr Thr Ser Ala Cys Ala Ala Phe Ile Gly Asp Asp Asn Ile Val
2315                2320                2325

His Gly Val Val Ser Asp Thr Leu Met Ala Glu Arg Cys Ala Thr
2330                2335                2340

Trp Leu Asn Met Glu Val Lys Ile Ile Asp Ala Val Ile Gly Ile
2345                2350                2355

Lys Ala Pro Tyr Phe Cys Gly Gly Phe Ile Leu Val Asp Gln Ile
2360                2365                2370

Thr Gly Thr Ala Cys Arg Val Ala Asp Pro Leu Lys Arg Leu Phe
2375                2380                2385
```

```
Lys Leu Gly Lys Pro Leu Ser Val Glu Asp Thr Gln Asp Cys Asp
    2390            2395                2400

Arg Arg Arg Ala Leu His Asp Glu Ala Met Arg Trp Asn Arg Ile
    2405            2410                2415

Gly Ile Thr Asp Glu Leu Val Lys Ala Val Glu Ser Arg Tyr Glu
    2420            2425                2430

Ile Ile Leu Ala Gly Leu Ile Ile Thr Ser Leu Ser Thr Leu Ala
    2435            2440                2445

Glu Ser Val Lys Asn Phe Lys Ser Ile Arg Gly Ser Pro Ile Thr
    2450            2455                2460

Leu Tyr Gly
    2465

<210> SEQ ID NO 22
<211> LENGTH: 132
<212> TYPE: PRT
<213> ORGANISM: Mycobacterium tuberculosis

<400> SEQUENCE: 22

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Arg Ser
                20                  25                  30

Gly Gly Gly Ser Pro Thr Val His Ile Gly Pro Thr Ala Phe Leu Gly
            35                  40                  45

Leu Gly Val Val Asp Asn Asn Gly Asn Gly Ala Arg Val Gln Arg Val
        50                  55                  60

Val Gly Ser Ala Pro Ala Ala Ser Leu Gly Ile Ser Thr Gly Asp Val
65                  70                  75                  80

Ile Thr Ala Val Asp Gly Ala Pro Ile Asn Ser Ala Thr Ala Met Ala
                85                  90                  95

Asp Ala Leu Asn Gly His His Pro Gly Asp Val Ile Ser Val Thr Trp
                100                 105                 110

Gln Thr Lys Ser Gly Gly Thr Arg Thr Gly Asn Val Thr Leu Ala Glu
            115                 120                 125

Gly Pro Pro Ala
        130

<210> SEQ ID NO 23
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Met His His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
                20                  25                  30

Ile Ala Gly Gln Ile Arg Ser Gly Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80
```

```
Gly Ile Ser Thr Gly Asp Val Ile Thr Ala Val Asp Gly Ala Pro Ile
            85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Asp Asp Asp
            130                 135                 140

Asp Lys Asp Pro Pro Asp Pro His Gln Pro Asp Met Thr Lys Gly Tyr
145                 150                 155                 160

Cys Pro Gly Gly Arg Trp Gly Phe Gly Asp Leu Ala Val Cys Asp Gly
                165                 170                 175

Glu Lys Tyr Pro Asp Gly Ser Phe Trp His Gln Trp Met Gln Thr Trp
            180                 185                 190

Phe Thr Gly Pro Gln Phe Tyr Phe Asp Cys Val Ser Gly Gly Glu Pro
            195                 200                 205

Leu Pro Gly Pro Pro Pro Gly Gly Cys Gly Gly Ala Ile Pro Ser
            210                 215                 220

Glu Gln Pro Asn Ala Pro
225                 230

<210> SEQ ID NO 24
<211> LENGTH: 578
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
            35                  40                  45

Gly Pro Thr Ala Phe Leu Gly Leu Gly Val Val Asp Asn Asn Gly Asn
        50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
            85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
            115                 120                 125

Gly Asn Val Thr Leu Ala Glu Gly Pro Pro Ala Glu Phe Pro Leu Val
            130                 135                 140

Pro Arg Gly Ser Pro Met Gly Ser Asp Val Arg Asp Leu Asn Ala Leu
145                 150                 155                 160

Leu Pro Ala Val Pro Ser Leu Gly Gly Gly Gly Cys Ala Leu Pro
                165                 170                 175

Val Ser Gly Ala Ala Gln Trp Ala Pro Val Leu Asp Phe Ala Pro Pro
            180                 185                 190

Gly Ala Ser Ala Tyr Gly Ser Leu Gly Gly Pro Ala Pro Pro Ala
            195                 200                 205
```

Pro Pro Pro Pro Pro Pro Pro Pro His Ser Phe Ile Lys Gln Glu
    210                 215                 220

Pro Ser Trp Gly Gly Ala Glu Pro His Glu Glu Gln Cys Leu Ser Ala
225                 230                 235                 240

Phe Thr Val His Phe Ser Gly Gln Phe Thr Gly Thr Ala Gly Ala Cys
                245                 250                 255

Arg Tyr Gly Pro Phe Gly Pro Pro Pro Ser Gln Ala Ser Ser Gly
            260                 265                 270

Gln Ala Arg Met Phe Pro Asn Ala Pro Tyr Leu Pro Ser Cys Leu Glu
        275                 280                 285

Ser Gln Pro Ala Ile Arg Asn Gln Gly Tyr Ser Thr Val Thr Phe Asp
290                 295                 300

Gly Thr Pro Ser Tyr Gly His Thr Pro Ser His His Ala Ala Gln Phe
305                 310                 315                 320

Pro Asn His Ser Phe Lys His Glu Asp Pro Met Gly Gln Gln Gly Ser
            325                 330                 335

Leu Gly Glu Gln Gln Tyr Ser Val Pro Pro Val Tyr Gly Cys His
            340                 345                 350

Thr Pro Thr Asp Ser Cys Thr Gly Ser Gln Ala Leu Leu Leu Arg Thr
            355                 360                 365

Pro Tyr Ser Ser Asp Asn Leu Tyr Gln Met Thr Ser Gln Leu Glu Cys
370                 375                 380

Met Thr Trp Asn Gln Met Asn Leu Gly Ala Thr Leu Lys Gly His Ser
385                 390                 395                 400

Thr Gly Tyr Glu Ser Asp Asn His Thr Thr Pro Ile Leu Cys Gly Ala
                405                 410                 415

Gln Tyr Arg Ile His Thr His Gly Val Phe Arg Gly Ile Gln Asp Val
            420                 425                 430

Arg Arg Val Pro Gly Val Ala Pro Thr Leu Val Arg Ser Ala Ser Glu
        435                 440                 445

Thr Ser Glu Lys Arg Pro Phe Met Cys Ala Tyr Ser Gly Cys Asn Lys
450                 455                 460

Arg Tyr Phe Lys Leu Ser His Leu Gln Met His Ser Arg Lys His Thr
465                 470                 475                 480

Gly Glu Lys Pro Tyr Gln Cys Asp Phe Lys Asp Cys Glu Arg Arg Phe
                485                 490                 495

Phe Arg Ser Asp Gln Leu Lys Arg His Gln Arg Arg His Thr Gly Val
            500                 505                 510

Lys Pro Phe Gln Cys Lys Thr Cys Gln Arg Lys Phe Ser Arg Ser Asp
        515                 520                 525

His Leu Lys Thr His Thr Arg Thr His Thr Gly Glu Lys Pro Phe Ser
530                 535                 540

Cys Arg Trp Pro Ser Cys Gln Lys Lys Phe Ala Arg Ser Asp Glu Leu
545                 550                 555                 560

Val Arg His His Asn Met His Gln Arg Asn Met Thr Lys Leu Gln Leu
                565                 570                 575

Ala Leu

<210> SEQ ID NO 25
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 25

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr
        115                 120                 125

Gly Asn Val Thr Leu Ala Glu Gly Pro Pro Ala Glu Phe Ile Glu Gly
    130                 135                 140

Arg Gly Ser Gly Cys Pro Leu Leu Glu Asn Val Ile Ser Lys Thr Ile
145                 150                 155                 160

Asn Pro Gln Val Ser Lys Thr Glu Tyr Lys Glu Leu Leu Gln Glu Phe
                165                 170                 175

Ile Asp Asp Asn Ala Thr Thr Asn Ala Ile Asp Glu Leu Lys Glu Cys
            180                 185                 190

Phe Leu Asn Gln Thr Asp Glu Thr Leu Ser Asn Val Glu Val Phe Met
        195                 200                 205

Gln Leu Ile Tyr Asp Ser Ser Leu Cys Asp Leu Phe
    210                 215                 220

<210> SEQ ID NO 26
<211> LENGTH: 729
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Met His His His His His Thr Ala Ala Ser Asp Asn Phe Gln Leu
1               5                   10                  15

Ser Gln Gly Gly Gln Gly Phe Ala Ile Pro Ile Gly Gln Ala Met Ala
            20                  25                  30

Ile Ala Gly Gln Ile Arg Ser Gly Gly Ser Pro Thr Val His Ile
        35                  40                  45

Gly Pro Thr Ala Phe Leu Gly Leu Gly Val Val Asp Asn Asn Gly Asn
    50                  55                  60

Gly Ala Arg Val Gln Arg Val Val Gly Ser Ala Pro Ala Ala Ser Leu
65                  70                  75                  80

Gly Ile Ser Thr Gly Asp Val Ile Thr Ala Val Asp Gly Ala Pro Ile
                85                  90                  95

Asn Ser Ala Thr Ala Met Ala Asp Ala Leu Asn Gly His His Pro Gly
            100                 105                 110

Asp Val Ile Ser Val Thr Trp Gln Thr Lys Ser Gly Gly Thr Arg Thr

-continued

```
            115                 120                 125
Gly Asn Val Thr Leu Ala Glu Gly Pro Pro Ala Glu Phe Met Val Asp
        130                 135                 140
Phe Gly Ala Leu Pro Pro Glu Ile Asn Ser Ala Arg Met Tyr Ala Gly
145                 150                 155                 160
Pro Gly Ser Ala Ser Leu Val Ala Ala Gln Met Trp Asp Ser Val
                165                 170                 175
Ala Ser Asp Leu Phe Ser Ala Ser Ala Phe Gln Ser Val Val Trp
            180                 185                 190
Gly Leu Thr Val Gly Ser Trp Ile Gly Ser Ser Ala Gly Leu Met Val
        195                 200                 205
Ala Ala Ala Ser Pro Tyr Val Ala Trp Met Ser Val Thr Ala Gly Gln
    210                 215                 220
Ala Glu Leu Thr Ala Ala Gln Val Arg Val Ala Ala Ala Tyr Glu
225                 230                 235                 240
Thr Ala Tyr Gly Leu Thr Val Pro Pro Val Ile Ala Glu Asn Arg
                245                 250                 255
Ala Glu Leu Met Ile Leu Ile Ala Thr Asn Leu Leu Gly Gln Asn Thr
            260                 265                 270
Pro Ala Ile Ala Val Asn Glu Ala Glu Tyr Gly Glu Met Trp Ala Gln
        275                 280                 285
Asp Ala Ala Met Phe Gly Tyr Ala Ala Ala Thr Ala Thr Ala Thr
290                 295                 300
Ala Thr Leu Leu Pro Phe Glu Glu Ala Pro Glu Met Thr Ser Ala Gly
305                 310                 315                 320
Gly Leu Leu Glu Gln Ala Ala Ala Val Glu Glu Ala Ser Asp Thr Ala
                325                 330                 335
Ala Ala Asn Gln Leu Met Asn Asn Val Pro Gln Ala Leu Gln Gln Leu
            340                 345                 350
Ala Gln Pro Thr Gln Gly Thr Thr Pro Ser Ser Lys Leu Gly Gly Leu
        355                 360                 365
Trp Lys Thr Val Ser Pro His Arg Ser Pro Ile Ser Asn Met Val Ser
    370                 375                 380
Met Ala Asn Asn His Met Ser Met Thr Asn Ser Gly Val Ser Met Thr
385                 390                 395                 400
Asn Thr Leu Ser Ser Met Leu Lys Gly Phe Ala Pro Ala Ala Ala
                405                 410                 415
Gln Ala Val Gln Thr Ala Ala Gln Asn Gly Val Arg Ala Met Ser Ser
            420                 425                 430
Leu Gly Ser Ser Leu Gly Ser Ser Gly Leu Gly Gly Val Ala Ala
        435                 440                 445
Asn Leu Gly Arg Ala Ala Ser Val Gly Ser Leu Ser Val Pro Gln Ala
    450                 455                 460
Trp Ala Ala Ala Asn Gln Ala Val Thr Pro Ala Ala Arg Ala Leu Pro
465                 470                 475                 480
Leu Thr Ser Leu Thr Ser Ala Ala Glu Arg Gly Pro Gly Gln Met Leu
                485                 490                 495
Gly Gly Leu Pro Val Gly Gln Met Gly Ala Arg Ala Gly Gly Gly Leu
            500                 505                 510
Ser Gly Val Leu Arg Val Pro Pro Arg Pro Tyr Val Met Pro His Ser
        515                 520                 525
Pro Ala Ala Gly Asp Ile Ala Pro Pro Ala Leu Ser Gln Asp Arg Phe
    530                 535                 540
```

```
Ala Asp Phe Pro Ala Leu Pro Leu Asp Pro Ser Ala Met Val Ala Gln
545                 550                 555                 560

Val Gly Pro Gln Val Val Asn Ile Asn Thr Lys Leu Gly Tyr Asn Asn
            565                 570                 575

Ala Val Gly Ala Gly Thr Gly Ile Val Ile Asp Pro Asn Gly Val Val
        580                 585                 590

Leu Thr Asn Asn His Val Ile Ala Gly Ala Thr Asp Ile Asn Ala Phe
        595                 600                 605

Ser Val Gly Ser Gly Gln Thr Tyr Gly Val Asp Val Val Gly Tyr Asp
    610                 615                 620

Arg Thr Gln Asp Val Ala Val Leu Gln Leu Arg Gly Ala Gly Gly Leu
625                 630                 635                 640

Pro Ser Ala Ala Ile Gly Gly Gly Val Ala Val Gly Glu Pro Val Val
                645                 650                 655

Ala Met Gly Asn Ser Gly Gly Gln Gly Gly Thr Pro Arg Ala Val Pro
            660                 665                 670

Gly Arg Val Val Ala Leu Gly Gln Thr Val Gln Ala Ser Asp Ser Leu
            675                 680                 685

Thr Gly Ala Glu Glu Thr Leu Asn Gly Leu Ile Gln Phe Asp Ala Ala
        690                 695                 700

Ile Gln Pro Gly Asp Ser Gly Gly Pro Val Val Asn Gly Leu Gly Gln
705                 710                 715                 720

Val Val Gly Met Asn Thr Ala Ala Ser
                725

<210> SEQ ID NO 27
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile
            20                  25                  30

<210> SEQ ID NO 28
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Thr Ala Ala Ser Asp Asn Phe Gln Leu Ser Gln Gly Gly Gln Gly Phe
1               5                   10                  15

Ala Ile Pro Ile Gly Gln Ala Met Ala Ile Ala Gly Gln Ile Lys Leu
            20                  25                  30

Pro Thr Val His Ile Gly Pro Thr Ala Phe Leu Gly Leu Gly Val Val
        35                  40                  45

Asp Asn Asn Gly Asn Gly Ala Arg Val Gln Arg Val Val Gly Ser Ala
    50                  55                  60

Pro Ala Ala Ser Leu Gly Ile Ser Thr Gly Asp Val Ile Thr Ala Val
65                  70                  75                  80
```

Asp Gly Ala Pro Ile Asn Ser Ala Thr Ala Met Ala Asp Ala Leu Asn
85 90 95

Gly His His Pro Gly Asp Val Ile Ser Val Thr Trp Gln Thr Lys Ser
100 105 110

Gly Gly Thr Arg Thr Gly Asn Val Thr Leu Ala Glu Gly Pro Pro Ala
115 120 125

<210> SEQ ID NO 29
<211> LENGTH: 128
<212> TYPE: PRT
<213> ORGANISM: Mycobacterium tuberculosis

<400> SEQUENCE: 29

Thr Ala Ala Ser Asp Asn Phe Gln Leu Ser Gln Gly Gly Gln Gly Phe
1 5 10 15

Ala Ile Pro Ile Gly Gln Ala Met Ala Ile Ala Gly Gln Ile Arg Ser
20 25 30

Gly Gly Gly Ser Pro Thr Val His Ile Gly Pro Thr Ala Phe Leu Gly
35 40 45

Leu Gly Val Val Asp Asn Asn Gly Asn Gly Ala Arg Val Gln Arg Val
50 55 60

Val Gly Ser Ala Pro Ala Ala Ser Leu Gly Ile Ser Thr Gly Asp Val
65 70 75 80

Ile Thr Ala Val Asp Gly Ala Pro Ile Asn Ser Ala Thr Ala Met Ala
85 90 95

Asp Ala Leu Asn Gly His His Pro Gly Asp Val Ile Ser Val Thr Trp
100 105 110

Gln Thr Lys Ser Gly Gly Thr Arg Thr Gly Asn Val Thr Leu Ala Glu
115 120 125

<210> SEQ ID NO 30
<211> LENGTH: 355
<212> TYPE: PRT
<213> ORGANISM: Mycobacterium tuberculosis

<400> SEQUENCE: 30

Met Ser Asn Ser Arg Arg Arg Ser Leu Arg Trp Ser Trp Leu Leu Ser
1 5 10 15

Val Leu Ala Ala Val Gly Leu Gly Leu Ala Thr Ala Pro Ala Gln Ala
20 25 30

Ala Pro Pro Ala Leu Ser Gln Asp Arg Phe Ala Asp Phe Pro Ala Leu
35 40 45

Pro Leu Asp Pro Ser Ala Met Val Ala Gln Val Gly Pro Gln Val Val
50 55 60

Asn Ile Asn Thr Lys Leu Gly Tyr Asn Asn Ala Val Gly Ala Gly Thr
65 70 75 80

Gly Ile Val Ile Asp Pro Asn Gly Val Val Leu Thr Asn Asn His Val
85 90 95

Ile Ala Gly Ala Thr Asp Ile Asn Ala Phe Ser Val Gly Ser Gly Gln
100 105 110

Thr Tyr Gly Val Asp Val Val Gly Tyr Asp Arg Thr Gln Asp Val Ala
115 120 125

Val Leu Gln Leu Arg Gly Ala Gly Gly Leu Pro Ser Ala Ala Ile Gly
130 135 140

Gly Gly Val Ala Val Gly Glu Pro Val Val Ala Met Gly Asn Ser Gly
145 150 155 160

Gly Gln Gly Gly Thr Pro Arg Ala Val Pro Gly Arg Val Val Ala Leu
            165                 170                 175

Gly Gln Thr Val Gln Ala Ser Asp Ser Leu Thr Gly Ala Glu Glu Thr
            180                 185                 190

Leu Asn Gly Leu Ile Gln Phe Asp Ala Ala Ile Gln Pro Gly Asp Ser
            195                 200                 205

Gly Gly Pro Val Val Asn Gly Leu Gln Val Val Gly Met Asn Thr
210                 215                 220

Ala Ala Ser Asp Asn Phe Gln Leu Ser Gln Gly Gln Gly Phe Ala
225                 230                 235                 240

Ile Pro Ile Gly Gln Ala Met Ala Ile Ala Gly Gln Ile Arg Ser Gly
            245                 250                 255

Gly Gly Ser Pro Thr Val His Ile Gly Pro Thr Ala Phe Leu Gly Leu
            260                 265                 270

Gly Val Val Asp Asn Asn Gly Asn Gly Ala Arg Val Gln Arg Val Val
            275                 280                 285

Gly Ser Ala Pro Ala Ala Ser Leu Gly Ile Ser Thr Gly Asp Val Ile
            290                 295                 300

Thr Ala Val Asp Gly Ala Pro Ile Asn Ser Ala Thr Ala Met Ala Asp
305                 310                 315                 320

Ala Leu Asn Gly His His Pro Gly Asp Val Ile Ser Val Thr Trp Gln
            325                 330                 335

Thr Lys Ser Gly Gly Thr Arg Thr Gly Asn Val Thr Leu Ala Glu Gly
            340                 345                 350

Pro Pro Ala
        355

<210> SEQ ID NO 31
<211> LENGTH: 364
<212> TYPE: PRT
<213> ORGANISM: Haemophilus influenzae

<400> SEQUENCE: 31

Met Lys Leu Lys Thr Leu Ala Leu Ser Leu Leu Ala Ala Gly Val Leu
1               5                   10                  15

Ala Gly Cys Ser Ser His Ser Ser Asn Met Ala Asn Thr Gln Met Lys
            20                  25                  30

Ser Asp Lys Ile Ile Ile Ala His Arg Gly Ala Ser Gly Tyr Leu Pro
            35                  40                  45

Glu His Thr Leu Glu Ser Lys Ala Leu Ala Phe Ala Gln Gln Ala Asp
        50                  55                  60

Tyr Leu Glu Gln Asp Leu Ala Met Thr Lys Asp Gly Arg Leu Val Val
65                  70                  75                  80

Ile His Asp His Phe Leu Asp Gly Leu Thr Asp Val Ala Lys Lys Phe
                85                  90                  95

Pro His Arg His Arg Lys Asp Gly Arg Tyr Tyr Val Ile Asp Phe Thr
            100                 105                 110

Leu Lys Glu Ile Gln Ser Leu Glu Met Thr Glu Asn Phe Glu Thr Lys
            115                 120                 125

Asp Gly Lys Gln Ala Gln Val Tyr Pro Asn Arg Phe Pro Leu Trp Lys
        130                 135                 140

Ser His Phe Arg Ile His Thr Phe Glu Asp Glu Ile Glu Phe Ile Gln
145                 150                 155                 160

Gly Leu Glu Lys Ser Thr Gly Lys Lys Val Gly Ile Tyr Pro Glu Ile

```
                165                 170                 175
Lys Ala Pro Trp Phe His His Gln Asn Gly Lys Asp Ile Ala Ala Glu
            180                 185                 190

Thr Leu Lys Val Leu Lys Lys Tyr Gly Tyr Asp Lys Thr Asp Met
            195                 200                 205

Val Tyr Leu Gln Thr Phe Asp Phe Asn Glu Leu Lys Arg Ile Lys Thr
210                 215                 220

Glu Leu Leu Pro Gln Met Gly Met Asp Leu Lys Leu Val Gln Leu Ile
225                 230                 235                 240

Ala Tyr Thr Asp Trp Lys Glu Thr Gln Glu Lys Asp Pro Lys Gly Tyr
            245                 250                 255

Trp Val Asn Tyr Asn Tyr Asp Trp Met Phe Lys Pro Gly Ala Met Ala
            260                 265                 270

Glu Val Val Lys Tyr Ala Asp Gly Val Gly Pro Gly Trp Tyr Met Leu
            275                 280                 285

Val Asn Lys Glu Glu Ser Lys Pro Asp Asn Ile Val Tyr Thr Pro Leu
            290                 295                 300

Val Lys Glu Leu Ala Gln Tyr Asn Val Glu Val His Pro Tyr Thr Val
305                 310                 315                 320

Arg Lys Asp Ala Leu Pro Ala Phe Phe Thr Asp Val Asn Gln Met Tyr
                325                 330                 335

Asp Val Leu Leu Asn Lys Ser Gly Ala Thr Gly Val Phe Thr Asp Phe
            340                 345                 350

Pro Asp Thr Gly Val Glu Phe Leu Lys Gly Ile Lys
            355                 360

<210> SEQ ID NO 32
<211> LENGTH: 313
<212> TYPE: PRT
<213> ORGANISM: Streptococcus pneumonae

<400> SEQUENCE: 32

Met Glu Ile Asn Val Ser Lys Leu Arg Thr Asp Leu Pro Gln Val Gly
1               5                   10                  15

Val Gln Pro Tyr Arg Gln Val His Ala His Ser Thr Gly Asn Pro His
            20                  25                  30

Ser Thr Val Gln Asn Glu Ala Asp Tyr His Trp Arg Lys Asp Pro Glu
        35                  40                  45

Leu Gly Phe Phe Ser His Ile Val Gly Asn Gly Cys Ile Met Gln Val
    50                  55                  60

Gly Pro Val Asp Asn Gly Ala Trp Asp Val Gly Gly Trp Asn Ala
65                  70                  75                  80

Glu Thr Tyr Ala Ala Val Glu Leu Ile Glu Ser His Ser Thr Lys Glu
            85                  90                  95

Glu Phe Met Thr Asp Tyr Arg Leu Tyr Ile Glu Leu Leu Arg Asn Leu
            100                 105                 110

Ala Asp Glu Ala Gly Leu Pro Lys Thr Leu Asp Thr Gly Ser Leu Ala
        115                 120                 125

Gly Ile Lys Thr His Glu Tyr Cys Thr Asn Asn Gln Pro Asn Asn His
    130                 135                 140

Ser Asp His Val Asp Pro Tyr Pro Tyr Leu Ala Lys Trp Gly Ile Ser
145                 150                 155                 160

Arg Glu Gln Phe Lys His Asp Ile Glu Asn Gly Leu Thr Ile Glu Thr
                165                 170                 175
```

Gly Trp Gln Lys Asn Asp Thr Gly Tyr Trp Tyr Val His Ser Asp Gly
            180                 185                 190

Ser Tyr Pro Lys Asp Lys Phe Glu Lys Ile Asn Gly Thr Trp Tyr Tyr
        195                 200                 205

Phe Asp Ser Ser Gly Tyr Met Leu Ala Asp Arg Trp Arg Lys His Thr
210                 215                 220

Asp Gly Asn Trp Tyr Trp Phe Asp Asn Ser Gly Glu Met Ala Thr Gly
225                 230                 235                 240

Trp Lys Lys Ile Ala Asp Lys Trp Tyr Tyr Phe Asn Glu Glu Gly Ala
                245                 250                 255

Met Lys Thr Gly Trp Val Lys Tyr Lys Asp Thr Trp Tyr Tyr Leu Asp
            260                 265                 270

Ala Lys Glu Gly Ala Met Val Ser Asn Ala Phe Ile Gln Ser Ala Asp
        275                 280                 285

Gly Thr Gly Trp Tyr Tyr Leu Lys Pro Asp Gly Thr Leu Ala Asp Arg
    290                 295                 300

Pro Glu Phe Arg Met Ser Gln Met Ala
305                 310

<210> SEQ ID NO 33
<211> LENGTH: 166
<212> TYPE: PRT
<213> ORGANISM: Homo sapiens

<400> SEQUENCE: 33

Met Lys Tyr Thr Ser Tyr Ile Leu Ala Phe Gln Leu Cys Ile Val Leu
1               5                   10                  15

Gly Ser Leu Gly Cys Tyr Cys Gln Asp Pro Tyr Val Lys Glu Ala Glu
            20                  25                  30

Asn Leu Lys Lys Tyr Phe Asn Ala Gly His Ser Asp Val Ala Asp Asn
        35                  40                  45

Gly Thr Leu Phe Leu Gly Ile Leu Lys Asn Trp Lys Glu Glu Ser Asp
    50                  55                  60

Arg Lys Ile Met Gln Ser Gln Ile Val Ser Phe Tyr Phe Lys Leu Phe
65                  70                  75                  80

Lys Asn Phe Lys Asp Asp Gln Ser Ile Gln Lys Ser Val Glu Thr Ile
                85                  90                  95

Lys Glu Asp Met Asn Val Lys Phe Phe Asn Ser Asn Lys Lys Lys Arg
            100                 105                 110

Asp Asp Phe Glu Lys Leu Thr Asn Tyr Ser Val Thr Asp Leu Asn Val
        115                 120                 125

Gln Arg Lys Ala Ile His Glu Leu Ile Gln Val Met Ala Glu Leu Ser
    130                 135                 140

Pro Ala Ala Lys Thr Gly Lys Arg Lys Arg Ser Gln Met Leu Phe Arg
145                 150                 155                 160

Gly Arg Arg Ala Ser Gln
                165

<210> SEQ ID NO 34
<211> LENGTH: 233
<212> TYPE: PRT
<213> ORGANISM: Homo sapiens

<400> SEQUENCE: 34

Met Ser Thr Glu Ser Met Ile Arg Asp Val Glu Leu Ala Glu Glu Ala
1               5                   10                  15

```
Leu Pro Lys Lys Thr Gly Gly Pro Gln Gly Ser Arg Arg Cys Leu Phe
            20                  25                  30

Leu Ser Leu Phe Ser Phe Leu Ile Val Ala Gly Ala Thr Thr Leu Phe
        35                  40                  45

Cys Leu Leu His Phe Gly Val Ile Gly Pro Gln Arg Glu Glu Phe Pro
    50                  55                  60

Arg Asp Leu Ser Leu Ile Ser Pro Leu Ala Gln Ala Val Arg Ser Ser
65                  70                  75                  80

Ser Arg Thr Pro Ser Asp Lys Pro Val Ala His Val Val Ala Asn Pro
                85                  90                  95

Gln Ala Glu Gly Gln Leu Gln Trp Leu Asn Arg Arg Ala Asn Ala Leu
            100                 105                 110

Leu Ala Asn Gly Val Glu Leu Arg Asp Asn Gln Leu Val Val Pro Ser
        115                 120                 125

Glu Gly Leu Tyr Leu Ile Tyr Ser Gln Val Leu Phe Lys Gly Gln Gly
    130                 135                 140

Cys Pro Ser Thr His Val Leu Leu Thr His Thr Ile Ser Arg Ile Ala
145                 150                 155                 160

Val Ser Tyr Gln Thr Lys Val Asn Leu Leu Ser Ala Ile Lys Ser Pro
                165                 170                 175

Cys Gln Arg Glu Thr Pro Glu Gly Ala Glu Ala Lys Pro Trp Tyr Glu
            180                 185                 190

Pro Ile Tyr Leu Gly Gly Val Phe Gln Leu Glu Lys Gly Asp Arg Leu
        195                 200                 205

Ser Ala Glu Ile Asn Arg Pro Asp Tyr Leu Asp Phe Ala Glu Ser Gly
    210                 215                 220

Gln Val Tyr Phe Gly Ile Ile Ala Leu
225                 230

<210> SEQ ID NO 35
<211> LENGTH: 153
<212> TYPE: PRT
<213> ORGANISM: Homo sapiens

<400> SEQUENCE: 35

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30

Gln Leu Glu His Leu Leu Leu Asp Leu Gln Met Ile Leu Asn Gly Ile
        35                  40                  45

Asn Asn Tyr Lys Asn Pro Lys Leu Thr Arg Met Leu Thr Phe Lys Phe
    50                  55                  60

Tyr Met Pro Lys Lys Ala Thr Glu Leu Lys His Leu Gln Cys Leu Glu
65                  70                  75                  80

Glu Glu Leu Lys Pro Leu Glu Glu Val Leu Asn Leu Ala Gln Ser Lys
                85                  90                  95

Asn Phe His Leu Arg Pro Arg Asp Leu Ile Ser Asn Ile Asn Val Ile
            100                 105                 110

Val Leu Glu Leu Lys Gly Ser Glu Thr Thr Phe Met Cys Glu Tyr Ala
        115                 120                 125

Asp Glu Thr Ala Thr Ile Val Glu Phe Leu Asn Arg Trp Ile Thr Phe
    130                 135                 140

Cys Gln Ser Ile Ile Ser Thr Leu Thr
145                 150
```

<210> SEQ ID NO 36
<211> LENGTH: 99
<212> TYPE: PRT
<213> ORGANISM: Homo sapiens

<400> SEQUENCE: 36

```
Met Thr Ser Lys Leu Ala Val Ala Leu Leu Ala Ala Phe Leu Ile Ser
1               5                   10                  15

Ala Ala Leu Cys Glu Gly Ala Val Leu Pro Arg Ser Ala Lys Glu Leu
            20                  25                  30

Arg Cys Gln Cys Ile Lys Thr Tyr Ser Lys Pro Phe His Pro Lys Phe
        35                  40                  45

Ile Lys Glu Leu Arg Val Ile Glu Ser Gly Pro His Cys Ala Asn Thr
    50                  55                  60

Glu Ile Ile Val Lys Leu Ser Asp Gly Arg Glu Leu Cys Leu Asp Pro
65                  70                  75                  80

Lys Glu Asn Trp Val Gln Arg Val Val Glu Lys Phe Leu Lys Arg Ala
                85                  90                  95

Glu Asn Ser
```

<210> SEQ ID NO 37
<211> LENGTH: 662
<212> TYPE: PRT
<213> ORGANISM: Homo sapiens

<400> SEQUENCE: 37

```
Met Glu Pro Leu Val Thr Trp Val Val Pro Leu Leu Phe Leu Phe Leu
1               5                   10                  15

Leu Ser Arg Gln Gly Ala Ala Cys Arg Thr Ser Glu Cys Cys Phe Gln
            20                  25                  30

Asp Pro Pro Tyr Pro Asp Ala Asp Ser Gly Ser Ala Ser Gly Pro Arg
        35                  40                  45

Asp Leu Arg Cys Tyr Arg Ile Ser Ser Asp Arg Tyr Glu Cys Ser Trp
    50                  55                  60

Gln Tyr Glu Gly Pro Thr Ala Gly Val Ser His Phe Leu Arg Cys Cys
65                  70                  75                  80

Leu Ser Ser Gly Arg Cys Cys Tyr Phe Ala Ala Gly Ser Ala Thr Arg
                85                  90                  95

Leu Gln Phe Ser Asp Gln Ala Gly Val Ser Val Leu Tyr Thr Val Thr
            100                 105                 110

Leu Trp Val Glu Ser Trp Ala Arg Asn Gln Thr Glu Lys Ser Pro Glu
        115                 120                 125

Val Thr Leu Gln Leu Tyr Asn Ser Val Lys Tyr Glu Pro Pro Leu Gly
    130                 135                 140

Asp Ile Lys Val Ser Lys Leu Ala Gly Gln Leu Arg Met Glu Trp Glu
145                 150                 155                 160

Thr Pro Asp Asn Gln Val Gly Ala Glu Val Gln Phe Arg His Arg Thr
                165                 170                 175

Pro Ser Ser Pro Trp Lys Leu Gly Asp Cys Gly Pro Gln Asp Asp Asp
            180                 185                 190

Thr Glu Ser Cys Leu Cys Pro Leu Glu Met Asn Val Ala Gln Glu Phe
        195                 200                 205

Gln Leu Arg Arg Arg Gln Leu Gly Ser Gln Gly Ser Ser Trp Ser Lys
    210                 215                 220
```

```
Trp Ser Ser Pro Val Cys Val Pro Pro Glu Asn Pro Pro Gln Pro Gln
225                 230                 235                 240

Val Arg Phe Ser Val Glu Gln Leu Gly Gln Asp Gly Arg Arg Arg Leu
            245                 250                 255

Thr Leu Lys Glu Gln Pro Thr Gln Leu Glu Leu Pro Glu Gly Cys Gln
        260                 265                 270

Gly Leu Ala Pro Gly Thr Glu Val Thr Tyr Arg Leu Gln Leu His Met
            275                 280                 285

Leu Ser Cys Pro Cys Lys Ala Lys Ala Thr Arg Thr Leu His Leu Gly
290                 295                 300

Lys Met Pro Tyr Leu Ser Gly Ala Ala Tyr Asn Val Ala Val Ile Ser
305                 310                 315                 320

Ser Asn Gln Phe Gly Pro Gly Leu Asn Gln Thr Trp His Ile Pro Ala
                325                 330                 335

Asp Thr His Thr Glu Pro Val Ala Leu Asn Ile Ser Val Gly Thr Asn
            340                 345                 350

Gly Thr Thr Met Tyr Trp Pro Ala Arg Ala Gln Ser Met Thr Tyr Cys
        355                 360                 365

Ile Glu Trp Gln Pro Val Gly Gln Asp Gly Gly Leu Ala Thr Cys Ser
370                 375                 380

Leu Thr Ala Pro Gln Asp Pro Asp Pro Ala Gly Met Ala Thr Tyr Ser
385                 390                 395                 400

Trp Ser Arg Glu Ser Gly Ala Met Gly Gln Glu Lys Cys Tyr Tyr Ile
                405                 410                 415

Thr Ile Phe Ala Ser Ala His Pro Glu Lys Leu Thr Leu Trp Ser Thr
            420                 425                 430

Val Leu Ser Thr Tyr His Phe Gly Gly Asn Ala Ser Ala Ala Gly Thr
        435                 440                 445

Pro His His Val Ser Val Lys Asn His Ser Leu Asp Ser Val Ser Val
        450                 455                 460

Asp Trp Ala Pro Ser Leu Leu Ser Thr Cys Pro Gly Val Leu Lys Glu
465                 470                 475                 480

Tyr Val Val Arg Cys Arg Asp Glu Asp Ser Lys Gln Val Ser Glu His
                485                 490                 495

Pro Val Gln Pro Thr Glu Thr Gln Val Thr Leu Ser Gly Leu Arg Ala
                500                 505                 510

Gly Val Ala Tyr Thr Val Gln Val Arg Ala Asp Thr Ala Trp Leu Arg
            515                 520                 525

Gly Val Trp Ser Gln Pro Gln Arg Phe Ser Ile Glu Val Gln Val Ser
        530                 535                 540

Asp Trp Leu Ile Phe Phe Ala Ser Leu Gly Ser Phe Leu Ser Ile Leu
545                 550                 555                 560

Leu Val Gly Val Leu Gly Tyr Leu Gly Leu Asn Arg Ala Ala Arg His
                565                 570                 575

Leu Cys Pro Pro Leu Pro Thr Pro Cys Ala Ser Ser Ala Ile Glu Phe
            580                 585                 590

Pro Gly Gly Lys Glu Thr Trp Gln Trp Ile Asn Pro Val Asp Phe Gln
        595                 600                 605

Glu Glu Ala Ser Leu Gln Glu Ala Leu Val Val Glu Met Ser Trp Asp
610                 615                 620

Lys Gly Glu Arg Thr Glu Pro Leu Glu Lys Thr Glu Leu Pro Glu Gly
625                 630                 635                 640

Ala Pro Glu Leu Ala Leu Asp Thr Glu Leu Ser Leu Glu Asp Gly Asp
```

-continued

```
                    645                 650                 655
Arg Cys Lys Ala Lys Met
                660

<210> SEQ ID NO 38
<211> LENGTH: 193
<212> TYPE: PRT
<213> ORGANISM: Homo sapiens

<400> SEQUENCE: 38

Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
                20                  25                  30

Leu Glu Ser Asp Tyr Phe Gly Lys Leu Glu Ser Lys Leu Ser Val Ile
            35                  40                  45

Arg Asn Leu Asn Asp Gln Val Leu Phe Ile Asp Gln Gly Asn Arg Pro
        50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Thr Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp

<210> SEQ ID NO 39
<211> LENGTH: 177
<212> TYPE: PRT
<213> ORGANISM: Homo sapiens

<400> SEQUENCE: 39

Met Phe His Val Ser Phe Arg Tyr Ile Phe Gly Leu Pro Pro Leu Ile
1               5                   10                  15

Leu Val Leu Leu Pro Val Ala Ser Ser Asp Cys Asp Ile Glu Gly Lys
                20                  25                  30

Asp Gly Lys Gln Tyr Glu Ser Val Leu Met Val Ser Ile Asp Gln Leu
            35                  40                  45

Leu Asp Ser Met Lys Glu Ile Gly Ser Asn Cys Leu Asn Asn Glu Phe
        50                  55                  60

Asn Phe Phe Lys Arg His Ile Cys Asp Ala Asn Lys Glu Gly Met Phe
65                  70                  75                  80

Leu Phe Arg Ala Ala Arg Lys Leu Arg Gln Phe Leu Lys Met Asn Ser
                85                  90                  95

Thr Gly Asp Phe Asp Leu His Leu Leu Lys Val Ser Glu Gly Thr Thr
            100                 105                 110
```

```
Ile Leu Leu Asn Cys Thr Gly Gln Val Lys Gly Arg Lys Pro Ala Ala
            115                 120                 125

Leu Gly Glu Ala Gln Pro Thr Lys Ser Leu Glu Glu Asn Lys Ser Leu
    130                 135                 140

Lys Glu Gln Lys Lys Leu Asn Asp Leu Cys Phe Leu Lys Arg Leu Leu
145                 150                 155                 160

Gln Glu Ile Lys Thr Cys Trp Asn Lys Ile Leu Met Gly Thr Lys Glu
                165                 170                 175

His
```

```
<210> SEQ ID NO 40
<211> LENGTH: 152
<212> TYPE: PRT
<213> ORGANISM: Homo sapiens

<400> SEQUENCE: 40

Met Ser Arg Leu Pro Val Leu Leu Leu Gln Leu Leu Val Arg Pro
1               5                   10                  15

Gly Leu Gln Ala Pro Met Thr Gln Thr Thr Ser Leu Lys Thr Ser Trp
            20                  25                  30

Val Asn Cys Ser Asn Met Ile Asp Glu Ile Ile Thr His Leu Lys Gln
        35                  40                  45

Pro Pro Leu Pro Leu Leu Asp Phe Asn Asn Leu Asn Gly Glu Asp Gln
50                  55                  60

Asp Ile Leu Met Glu Asn Asn Leu Arg Arg Pro Asn Leu Glu Ala Phe
65                  70                  75                  80

Asn Arg Ala Val Lys Ser Leu Gln Asn Ala Ser Ala Ile Glu Ser Ile
                85                  90                  95

Leu Lys Asn Leu Leu Pro Cys Leu Pro Leu Ala Thr Ala Ala Pro Thr
            100                 105                 110

Arg His Pro Ile His Ile Lys Asp Gly Asp Trp Asn Glu Phe Arg Arg
        115                 120                 125

Lys Leu Thr Phe Tyr Leu Lys Thr Leu Glu Asn Ala Gln Ala Gln Gln
    130                 135                 140

Thr Thr Leu Ser Leu Ala Ile Phe
145                 150
```

```
<210> SEQ ID NO 41
<211> LENGTH: 153
<212> TYPE: PRT
<213> ORGANISM: Homo sapiens

<400> SEQUENCE: 41

Met Gly Leu Thr Ser Gln Leu Leu Pro Pro Leu Phe Phe Leu Leu Ala
1               5                   10                  15

Cys Ala Gly Asn Phe Val His Gly His Lys Cys Asp Ile Thr Leu Gln
            20                  25                  30

Glu Ile Ile Lys Thr Leu Asn Ser Leu Thr Glu Gln Lys Thr Leu Cys
        35                  40                  45

Thr Glu Leu Thr Val Thr Asp Ile Phe Ala Ala Ser Lys Asn Thr Thr
50                  55                  60

Glu Lys Glu Thr Phe Cys Arg Ala Ala Thr Val Leu Arg Gln Phe Tyr
65                  70                  75                  80

Ser His His Glu Lys Asp Thr Arg Cys Leu Gly Ala Thr Ala Gln Gln
                85                  90                  95
```

```
Phe His Arg His Lys Gln Leu Ile Arg Phe Leu Lys Arg Leu Asp Arg
                100                 105                 110

Asn Leu Trp Gly Leu Ala Gly Leu Asn Ser Cys Pro Val Lys Glu Ala
            115                 120                 125

Asn Gln Ser Thr Leu Glu Asn Phe Leu Glu Arg Leu Lys Thr Ile Met
        130                 135                 140

Arg Glu Lys Tyr Ser Lys Cys Ser Ser
145                 150
```

<210> SEQ ID NO 42
<211> LENGTH: 134
<212> TYPE: PRT
<213> ORGANISM: Homo sapiens

<400> SEQUENCE: 42

```
Met Arg Met Leu Leu His Leu Ser Leu Leu Ala Leu Gly Ala Ala Tyr
1               5                   10                  15

Val Tyr Ala Ile Pro Thr Glu Ile Pro Thr Ser Ala Leu Val Lys Glu
            20                  25                  30

Thr Leu Ala Leu Leu Ser Thr His Arg Thr Leu Leu Ile Ala Asn Glu
        35                  40                  45

Thr Leu Arg Ile Pro Val Pro Val His Lys Asn His Gln Leu Cys Thr
    50                  55                  60

Glu Glu Ile Phe Gln Gly Ile Gly Thr Leu Glu Ser Gln Thr Val Gln
65                  70                  75                  80

Gly Gly Thr Val Glu Arg Leu Phe Lys Asn Leu Ser Leu Ile Lys Lys
                85                  90                  95

Tyr Ile Asp Gly Gln Lys Lys Lys Cys Gly Glu Glu Arg Arg Arg Val
            100                 105                 110

Asn Gln Phe Leu Asp Tyr Leu Gln Glu Phe Leu Gly Val Met Asn Thr
        115                 120                 125

Glu Trp Ile Ile Glu Ser
    130
```

<210> SEQ ID NO 43
<211> LENGTH: 212
<212> TYPE: PRT
<213> ORGANISM: Homo sapiens

<400> SEQUENCE: 43

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125
```

Leu Gln Asn Arg Phe Glu Ser Ser Glu Gln Ala Arg Ala Val Gln
130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210

<210> SEQ ID NO 44
<211> LENGTH: 140
<212> TYPE: PRT
<213> ORGANISM: Homo sapiens

<400> SEQUENCE: 44

Met Val Leu Thr Ser Ala Leu Leu Cys Ser Val Ala Gly Gln Gly
1               5                   10                  15

Cys Pro Thr Leu Ala Gly Ile Leu Asp Ile Asn Phe Leu Ile Asn Lys
                20                  25                  30

Met Gln Glu Asp Pro Ala Ser Lys Cys His Cys Ser Ala Asn Val Thr
            35                  40                  45

Ser Cys Leu Cys Leu Gly Ile Pro Ser Asp Asn Cys Thr Arg Pro Cys
50                  55                  60

Phe Ser Glu Arg Leu Ser Gln Met Thr Asn Thr Thr Met Gln Thr Arg
65                  70                  75                  80

Tyr Pro Leu Ile Phe Ser Arg Val Lys Lys Ser Val Glu Val Leu Lys
                85                  90                  95

Asn Asn Lys Cys Pro Tyr Phe Ser Cys Glu Gln Pro Cys Asn Gln Thr
            100                 105                 110

Thr Ala Gly Asn Ala Leu Thr Phe Leu Lys Ser Leu Leu Glu Ile Phe
        115                 120                 125

Gln Lys Glu Lys Met Arg Gly Met Arg Gly Lys Ile
    130                 135                 140

<210> SEQ ID NO 45
<211> LENGTH: 178
<212> TYPE: PRT
<213> ORGANISM: Homo sapiens

<400> SEQUENCE: 45

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
                20                  25                  30

Phe Pro Gly Asn Leu Pro Asn Met Leu Arg Asp Leu Arg Asp Ala Phe
            35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

```
Gln Ala Glu Asn Gln Asp Pro Asp Ile Lys Ala His Val Asn Ser Leu
                100                 105                 110

Gly Glu Asn Leu Lys Thr Leu Arg Leu Arg Leu Arg Arg Cys His Arg
            115                 120                 125

Phe Leu Pro Cys Glu Asn Lys Ser Lys Ala Val Glu Gln Val Lys Asn
        130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

<210> SEQ ID NO 46
<211> LENGTH: 145
<212> TYPE: PRT
<213> ORGANISM: Homo sapiens

<400> SEQUENCE: 46

Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Gln Phe Asn Arg Asn Phe Glu Ser Ile Ile Ile Cys Arg Asp Arg
    130                 135                 140

Thr
145

<210> SEQ ID NO 47
<211> LENGTH: 136
<212> TYPE: PRT
<213> ORGANISM: Homo sapiens

<400> SEQUENCE: 47

Met Asp Phe Gln Val Gln Ile Phe Ser Phe Leu Leu Ile Ser Ala Ser
1               5                   10                  15

Val Ile Met Ser Arg Ala Asn Trp Val Asn Val Ile Ser Asp Leu Lys
            20                  25                  30

Lys Ile Glu Asp Leu Ile Gln Ser Met His Ile Asp Ala Thr Leu Tyr
        35                  40                  45

Thr Glu Ser Asp Val His Pro Ser Cys Lys Val Thr Ala Met Lys Cys
    50                  55                  60

Phe Leu Leu Glu Leu Gln Val Ile Ser Leu Glu Ser Gly Asp Ala Ser
65                  70                  75                  80

Ile His Asp Thr Val Glu Asn Leu Ile Ile Leu Ala Asn Asn Ser Leu
```

85                  90                  95

Ser Ser Asn Gly Asn Val Thr Glu Ser Gly Cys Lys Glu Cys Glu Glu
            100                 105                 110

Leu Glu Glu Lys Asn Ile Lys Glu Phe Leu Gln Ser Phe Val His Ile
            115                 120                 125

Val Gln Met Phe Ile Asn Thr Ser
            130                 135

<210> SEQ ID NO 48
<211> LENGTH: 656
<212> TYPE: PRT
<213> ORGANISM: Homo sapiens

<400> SEQUENCE: 48

Met Glu Gly Asp Gly Ser Asp Pro Glu Pro Pro Asp Ala Gly Glu Asp
1               5                   10                  15

Ser Lys Ser Glu Asn Gly Glu Asn Ala Pro Ile Tyr Cys Ile Cys Arg
            20                  25                  30

Lys Pro Asp Ile Asn Cys Phe Met Ile Gly Cys Asp Asn Cys Asn Glu
            35                  40                  45

Trp Phe His Gly Asp Cys Ile Arg Ile Thr Glu Lys Met Ala Lys Ala
50                  55                  60

Ile Arg Glu Trp Tyr Cys Arg Glu Cys Arg Glu Lys Asp Pro Lys Leu
65                  70                  75                  80

Glu Ile Arg Tyr Arg His Lys Lys Ser Arg Glu Arg Asp Gly Asn Glu
                85                  90                  95

Arg Asp Ser Ser Glu Pro Arg Asp Glu Gly Gly Arg Lys Arg Pro
            100                 105                 110

Val Pro Asp Pro Asn Leu Gln Arg Arg Ala Gly Ser Gly Thr Gly Val
            115                 120                 125

Gly Ala Met Leu Ala Arg Gly Ser Ala Ser Pro His Lys Ser Ser Pro
            130                 135                 140

Gln Pro Leu Val Ala Thr Pro Ser Gln His His Gln Gln Gln Gln Gln
145                 150                 155                 160

Gln Ile Lys Arg Ser Ala Arg Met Cys Gly Cys Glu Ala Cys Arg
            165                 170                 175

Arg Thr Glu Asp Cys Gly His Cys Asp Phe Cys Arg Asp Met Lys Lys
            180                 185                 190

Phe Gly Gly Pro Asn Lys Ile Arg Gln Lys Cys Arg Leu Arg Gln Cys
            195                 200                 205

Gln Leu Arg Ala Arg Glu Ser Tyr Lys Tyr Phe Pro Ser Ser Leu Ser
            210                 215                 220

Pro Val Thr Pro Ser Glu Ser Leu Pro Arg Pro Arg Arg Pro Leu Pro
225                 230                 235                 240

Thr Gln Gln Gln Pro Gln Pro Ser Gln Lys Leu Gly Arg Ile Arg Glu
            245                 250                 255

Asp Glu Gly Ala Val Ala Ser Ser Thr Val Lys Glu Pro Pro Glu Ala
            260                 265                 270

Thr Ala Thr Pro Glu Pro Leu Ser Asp Glu Asp Leu Pro Leu Asp Pro
            275                 280                 285

Asp Leu Tyr Gln Asp Phe Cys Ala Gly Ala Phe Asp Asp Asn Gly Leu
            290                 295                 300

Pro Trp Met Ser Asp Thr Glu Glu Ser Pro Phe Leu Asp Pro Ala Leu
305                 310                 315                 320

```
Arg Lys Arg Ala Val Lys Val Lys His Val Lys Arg Glu Lys Lys
            325                 330                 335

Ser Glu Lys Lys Glu Glu Arg Tyr Lys Arg His Arg Gln Lys Gln
        340                 345                 350

Lys His Lys Asp Lys Trp Lys His Pro Glu Arg Ala Asp Ala Lys Asp
    355                 360                 365

Pro Ala Ser Leu Pro Gln Cys Leu Gly Pro Gly Cys Val Arg Pro Ala
370                 375                 380

Gln Pro Ser Ser Lys Tyr Cys Ser Asp Asp Cys Gly Met Lys Leu Ala
385                 390                 395                 400

Ala Asn Arg Ile Tyr Glu Ile Leu Pro Gln Arg Ile Gln Gln Trp Gln
                405                 410                 415

Gln Ser Pro Cys Ile Ala Glu Glu His Gly Lys Lys Leu Leu Glu Arg
            420                 425                 430

Ile Arg Arg Glu Gln Gln Ser Ala Arg Thr Arg Leu Gln Glu Met Glu
        435                 440                 445

Arg Arg Phe His Glu Leu Glu Ala Ile Ile Leu Arg Ala Lys Gln Gln
    450                 455                 460

Ala Val Arg Glu Asp Glu Glu Ser Asn Glu Gly Asp Ser Asp Asp Thr
465                 470                 475                 480

Asp Leu Gln Ile Phe Cys Val Ser Cys Gly His Pro Ile Asn Pro Arg
                485                 490                 495

Val Ala Leu Arg His Met Glu Arg Cys Tyr Ala Lys Tyr Glu Ser Gln
            500                 505                 510

Thr Ser Phe Gly Ser Met Tyr Pro Thr Arg Ile Glu Gly Ala Thr Arg
        515                 520                 525

Leu Phe Cys Asp Val Tyr Asn Pro Gln Ser Lys Thr Tyr Cys Lys Arg
    530                 535                 540

Leu Gln Val Leu Cys Pro Glu His Ser Arg Asp Pro Lys Val Pro Ala
545                 550                 555                 560

Asp Glu Val Cys Gly Cys Pro Leu Val Arg Asp Val Phe Glu Leu Thr
                565                 570                 575

Gly Asp Phe Cys Arg Leu Pro Lys Arg Gln Cys Asn Arg His Tyr Cys
            580                 585                 590

Trp Glu Lys Leu Arg Arg Ala Glu Val Asp Leu Glu Arg Val Arg Val
        595                 600                 605

Trp Tyr Lys Leu Asp Glu Leu Phe Glu Gln Glu Arg Asn Val Arg Thr
    610                 615                 620

Ala Met Thr Asn Arg Ala Gly Leu Leu Ala Leu Met Leu His Gln Thr
625                 630                 635                 640

Ile Gln His Asp Pro Leu Thr Thr Asp Leu Arg Ser Ser Ala Asp Arg
                645                 650                 655

<210> SEQ ID NO 49
<211> LENGTH: 124
<212> TYPE: PRT
<213> ORGANISM: Vibrio cholerae

<400> SEQUENCE: 49

Met Ile Lys Leu Lys Phe Gly Val Phe Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile Tyr Thr Leu Asn Asp Lys Ile Phe Ser Tyr
        35                  40                  45
```

```
Thr Glu Ser Leu Ala Gly Lys Arg Glu Met Ala Ile Ile Thr Phe Lys
 50                  55                  60

Asn Gly Ala Ile Phe Gln Val Glu Val Pro Gly Ser Gln His Ile Asp
 65                  70                  75                  80

Ser Gln Lys Lys Ala Ile Glu Arg Met Lys Asp Thr Leu Arg Ile Ala
                 85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
            115                 120
```

<210> SEQ ID NO 50
<211> LENGTH: 258
<212> TYPE: PRT
<213> ORGANISM: Vibrio cholerae

<400> SEQUENCE: 50

```
Met Val Lys Ile Ile Phe Val Phe Phe Ile Phe Leu Ser Ser Phe Ser
  1               5                  10                  15

Tyr Ala Asn Asp Asp Lys Leu Tyr Arg Ala Asp Ser Arg Pro Pro Asp
                 20                  25                  30

Glu Ile Lys Gln Ser Gly Gly Leu Met Pro Arg Gly Gln Asn Glu Tyr
             35                  40                  45

Phe Asp Arg Gly Thr Gln Met Asn Ile Asn Leu Tyr Asp His Ala Arg
 50                  55                  60

Gly Thr Gln Thr Gly Phe Val Arg His Asp Asp Gly Tyr Val Ser Thr
 65                  70                  75                  80

Ser Ile Ser Leu Arg Ser Ala His Leu Val Gly Gln Thr Ile Leu Ser
                 85                  90                  95

Gly His Ser Thr Tyr Tyr Ile Tyr Val Ile Ala Thr Ala Pro Asn Met
            100                 105                 110

Phe Asn Val Asn Asp Val Leu Gly Ala Tyr Ser Pro His Pro Asp Glu
            115                 120                 125

Gln Glu Val Ser Ala Leu Gly Gly Ile Pro Tyr Ser Gln Ile Tyr Gly
            130                 135                 140

Trp Tyr Arg Val His Phe Gly Val Leu Asp Glu Gln Leu His Arg Asn
145                 150                 155                 160

Arg Gly Tyr Arg Asp Arg Tyr Tyr Ser Asn Leu Asp Ile Ala Pro Ala
                165                 170                 175

Ala Asp Gly Tyr Gly Leu Ala Gly Phe Pro Pro Glu His Arg Ala Trp
            180                 185                 190

Arg Glu Glu Pro Trp Ile His His Ala Pro Pro Gly Cys Gly Asn Ala
            195                 200                 205

Pro Arg Ser Ser Met Ser Asn Thr Cys Asp Glu Lys Thr Gln Ser Leu
            210                 215                 220

Gly Val Lys Phe Leu Asp Glu Tyr Gln Ser Lys Val Leu Arg Gln Ile
225                 230                 235                 240

Phe Ser Gly Tyr Gln Ser Asp Ile Asp Thr His Asn Arg Ile Lys Asp
                245                 250                 255

Glu Leu
```

<210> SEQ ID NO 51
<211> LENGTH: 124
<212> TYPE: PRT
<213> ORGANISM: Vibrio cholerae

```
<400> SEQUENCE: 51

Met Ile Lys Leu Lys Phe Gly Val Phe Thr Val Leu Leu Ser Ser
1               5                   10                  15

Ala Tyr Ala His Gly Thr Pro Gln Asn Ile Thr Asp Leu Cys Ala Glu
            20                  25                  30

Tyr His Asn Thr Gln Ile His Thr Leu Asn Asp Lys Ile Leu Ser Tyr
        35                  40                  45

Thr Glu Ser Leu Ala Gly Asn Arg Glu Met Ala Ile Ile Thr Phe Lys
    50                  55                  60

Asn Gly Ala Thr Phe Gln Val Glu Val Pro Gly Ser Gln His Ile Asp
65                  70                  75                  80

Ser Gln Lys Lys Ala Ile Glu Arg Met Lys Asp Thr Leu Arg Ile Ala
                85                  90                  95

Tyr Leu Thr Glu Ala Lys Val Glu Lys Leu Cys Val Trp Asn Asn Lys
            100                 105                 110

Thr Pro His Ala Ile Ala Ala Ile Ser Met Ala Asn
        115                 120

<210> SEQ ID NO 52
<211> LENGTH: 18
<212> TYPE: PRT
<213> ORGANISM: Homo sapiens

<400> SEQUENCE: 52

Asp Pro Asn Ala Pro Lys Arg Pro Pro Ser Ala Phe Phe Leu Phe Cys
1               5                   10                  15

Ser Glu

<210> SEQ ID NO 53
<211> LENGTH: 96
<212> TYPE: PRT
<213> ORGANISM: Homo sapiens

<400> SEQUENCE: 53

Met Cys Cys Thr Lys Ser Leu Leu Leu Ala Ala Leu Met Ser Val Leu
1               5                   10                  15

Leu Leu His Leu Cys Gly Glu Ser Glu Ala Ala Ser Asn Phe Asp Cys
            20                  25                  30

Cys Leu Gly Tyr Thr Asp Arg Ile Leu His Pro Lys Phe Ile Val Gly
        35                  40                  45

Phe Thr Arg Gln Leu Ala Asn Glu Gly Cys Asp Ile Asn Ala Ile Ile
    50                  55                  60

Phe His Thr Lys Lys Lys Leu Ser Val Cys Ala Asn Pro Lys Gln Thr
65                  70                  75                  80

Trp Val Lys Tyr Ile Val Arg Leu Leu Ser Lys Lys Val Lys Asn Met
                85                  90                  95

<210> SEQ ID NO 54
<211> LENGTH: 92
<212> TYPE: PRT
<213> ORGANISM: Homo sapiens

<400> SEQUENCE: 54

Met Gln Val Ser Thr Ala Ala Leu Ala Val Leu Leu Cys Thr Met Ala
1               5                   10                  15

Leu Cys Asn Gln Phe Ser Ala Ser Leu Ala Ala Asp Thr Pro Thr Ala
            20                  25                  30
```

-continued

```
Cys Cys Phe Ser Tyr Thr Ser Arg Gln Ile Pro Gln Asn Phe Ile Ala
            35                  40                  45

Asp Tyr Phe Glu Thr Ser Ser Gln Cys Ser Lys Pro Gly Val Ile Phe
 50                  55                  60

Leu Thr Lys Arg Ser Arg Gln Val Cys Ala Asp Pro Ser Glu Glu Trp
 65                  70                  75                  80

Val Gln Lys Tyr Val Ser Asp Leu Glu Leu Ser Ala
                 85                  90

<210> SEQ ID NO 55
<211> LENGTH: 144
<212> TYPE: PRT
<213> ORGANISM: Homo sapiens

<400> SEQUENCE: 55

Met Trp Leu Gln Ser Leu Leu Leu Leu Gly Thr Val Ala Cys Ser Ile
 1               5                  10                  15

Ser Ala Pro Ala Arg Ser Pro Ser Pro Ser Thr Gln Pro Trp Glu His
                 20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
 50                  55                  60

Asp Leu Gln Glu Pro Thr Cys Leu Gln Thr Arg Leu Glu Leu Tyr Lys
 65                  70                  75                  80

Gln Gly Leu Arg Gly Ser Leu Thr Lys Leu Lys Gly Pro Leu Thr Met
                 85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
            130                 135                 140

<210> SEQ ID NO 56
<211> LENGTH: 204
<212> TYPE: PRT
<213> ORGANISM: Homo sapiens

<400> SEQUENCE: 56

Met Ala Gly Pro Ala Thr Gln Ser Pro Met Lys Leu Met Ala Leu Gln
 1               5                  10                  15

Leu Leu Leu Trp His Ser Ala Leu Trp Thr Val Gln Glu Ala Thr Pro
                 20                  25                  30

Leu Gly Pro Ala Ser Ser Leu Pro Gln Ser Phe Leu Leu Lys Cys Leu
            35                  40                  45

Glu Gln Val Arg Lys Ile Gln Gly Asp Gly Ala Ala Leu Gln Glu Lys
 50                  55                  60

Leu Cys Ala Thr Tyr Lys Leu Cys His Pro Glu Glu Leu Val Leu Leu
 65                  70                  75                  80

Gly His Ser Leu Gly Ile Pro Trp Ala Pro Leu Ser Ser Cys Pro Ser
                 85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
            115                 120                 125
```

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200

<210> SEQ ID NO 57
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Gln Glu Ile Asn Ser Ser Tyr
1               5

<210> SEQ ID NO 58
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Ser His Pro Arg Leu Ser Ala
1               5

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Ser Met Pro Asn Pro Met Val
1               5

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Gly Leu Gln Gln Val Leu Leu
1               5

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 61

His Glu Leu Ser Val Leu Leu
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Tyr Ala Pro Gln Arg Leu Pro
1               5

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Thr Pro Arg Thr Leu Pro Thr
1               5

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Ala Pro Val His Ser Ser Ile
1               5

<210> SEQ ID NO 65
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Ala Pro Pro His Ala Leu Ser
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Thr Phe Ser Asn Arg Phe Ile
1               5

<210> SEQ ID NO 67

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Val Val Pro Thr Pro Pro Tyr
1               5

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Leu Ala Pro Asp Ser Pro
1               5

<210> SEQ ID NO 69
<211> LENGTH: 69
<212> TYPE: PRT
<213> ORGANISM: Shigella dysenteria 1

<400> SEQUENCE: 69

Thr Pro Asp Cys Val Thr Gly Lys Val Glu Tyr Thr Lys Tyr Asn Asp
1               5                   10                  15

Asp Asp Thr Phe Thr Val Lys Val Gly Asp Lys Glu Leu Phe Thr Asn
            20                  25                  30

Arg Trp Asn Leu Gln Ser Leu Leu Leu Ser Ala Gln Ile Thr Gly Met
        35                  40                  45

Thr Val Thr Ile Lys Gln Asn Ala Cys His Asn Gly Gly Phe Ser
    50                  55                  60

Glu Val Ile Phe Arg
65

<210> SEQ ID NO 70
<211> LENGTH: 560
<212> TYPE: PRT
<213> ORGANISM: Corynephage omega

<400> SEQUENCE: 70

Met Ser Arg Lys Leu Phe Ala Ser Ile Leu Ile Gly Ala Leu Leu Gly
1               5                   10                  15

Ile Gly Ala Pro Pro Ser Ala His Ala Gly Ala Asp Asp Val Val Asp
            20                  25                  30

Ser Ser Lys Ser Phe Val Met Glu Asn Phe Ser Ser Tyr His Gly Thr
        35                  40                  45

Lys Pro Gly Tyr Val Asp Ser Ile Gln Lys Gly Ile Gln Lys Pro Lys
    50                  55                  60

Ser Gly Thr Gln Gly Asn Tyr Asp Asp Asp Trp Lys Gly Phe Tyr Ser
65                  70                  75                  80

Thr Asp Asn Lys Tyr Asp Ala Ala Gly Tyr Ser Val Asp Asn Glu Asn
                85                  90                  95

Pro Leu Ser Gly Lys Ala Gly Gly Val Val Lys Val Thr Tyr Pro Gly
            100                 105                 110

Leu Thr Lys Val Leu Ala Leu Lys Val Asp Asn Ala Glu Thr Ile Lys
```

-continued

```
            115                 120                 125
Lys Glu Leu Gly Leu Ser Leu Thr Glu Pro Leu Met Glu Gln Val Gly
        130                 135                 140
Thr Glu Glu Phe Ile Lys Arg Phe Gly Asp Gly Ala Ser Arg Val Val
145                 150                 155                 160
Leu Ser Leu Pro Phe Ala Glu Gly Ser Ser Val Glu Tyr Ile Asn
                165                 170                 175
Asn Trp Glu Gln Ala Lys Ala Leu Ser Val Glu Leu Glu Ile Asn Phe
            180                 185                 190
Glu Thr Arg Gly Lys Arg Gly Gln Asp Ala Met Tyr Glu Tyr Met Ala
        195                 200                 205
Gln Ala Cys Ala Gly Asn Arg Val Arg Ser Val Gly Ser Ser Leu
    210                 215                 220
Ser Cys Ile Asn Leu Asp Trp Asp Val Ile Arg Asp Lys Thr Lys Thr
225                 230                 235                 240
Lys Ile Glu Ser Leu Lys Glu His Gly Pro Ile Lys Asn Lys Met Ser
                245                 250                 255
Glu Ser Pro Asn Lys Thr Val Ser Glu Glu Lys Ala Lys Gln Tyr Leu
            260                 265                 270
Glu Glu Phe His Gln Thr Ala Leu Glu His Pro Glu Leu Ser Glu Leu
        275                 280                 285
Lys Thr Val Thr Gly Thr Asn Pro Val Phe Ala Gly Ala Asn Tyr Ala
    290                 295                 300
Ala Trp Ala Val Asn Val Ala Gln Val Ile Asp Ser Glu Thr Ala Asp
305                 310                 315                 320
Asn Leu Glu Lys Thr Thr Ala Ala Leu Ser Ile Leu Pro Gly Ile Gly
                325                 330                 335
Ser Val Met Gly Ile Ala Asp Gly Ala Val His His Asn Thr Glu Glu
            340                 345                 350
Ile Val Ala Gln Ser Ile Ala Leu Ser Ser Leu Met Val Ala Gln Ala
        355                 360                 365
Ile Pro Leu Val Gly Glu Leu Val Asp Ile Gly Phe Ala Ala Tyr Asn
    370                 375                 380
Phe Val Glu Ser Ile Ile Asn Leu Phe Gln Val Val His Asn Ser Tyr
385                 390                 395                 400
Asn Arg Pro Ala Tyr Ser Pro Gly His Lys Thr Gln Pro Phe Leu His
                405                 410                 415
Asp Gly Tyr Ala Val Ser Trp Asn Thr Val Glu Asp Ser Ile Ile Arg
            420                 425                 430
Thr Gly Phe Gln Gly Glu Ser Gly His Asp Ile Lys Ile Thr Ala Glu
        435                 440                 445
Asn Thr Pro Leu Pro Ile Ala Gly Val Leu Leu Pro Thr Ile Pro Gly
    450                 455                 460
Lys Leu Asp Val Asn Lys Ser Lys Thr His Ile Ser Val Asn Gly Arg
465                 470                 475                 480
Lys Ile Arg Met Arg Cys Arg Ala Ile Asp Gly Asp Val Thr Phe Cys
                485                 490                 495
Arg Pro Lys Ser Pro Val Tyr Val Gly Asn Gly Val His Ala Asn Leu
            500                 505                 510
His Val Ala Phe His Arg Ser Ser Glu Lys Ile His Ser Asn Glu
        515                 520                 525
Ile Ser Ser Asp Ser Ile Gly Val Leu Gly Tyr Gln Lys Thr Val Asp
    530                 535                 540
```

His Thr Lys Val Asn Ser Lys Leu Ser Leu Phe Phe Glu Ile Lys Ser
545                 550                 555                 560

<210> SEQ ID NO 71
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asp Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 72
<211> LENGTH: 297
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Ile Thr Cys Pro Pro Pro Met Ser Val Glu His Ala Asp Ile Trp Val
1               5                   10                  15

Lys Ser Tyr Ser Leu Tyr Ser Arg Glu Arg Tyr Ile Cys Asn Ser Gly
            20                  25                  30

Phe Lys Arg Lys Ala Gly Thr Ser Ser Leu Thr Glu Cys Val Leu Asn
        35                  40                  45

Lys Ala Thr Asn Val Ala His Trp Thr Thr Pro Ser Leu Lys Cys Ile
    50                  55                  60

Arg Glu Pro Lys Ser Cys Asp Lys Thr His Thr Cys Pro Pro Cys Pro
65                  70                  75                  80

Ala Pro Glu Leu Leu Gly Gly Pro Ser Val Phe Leu Phe Pro Pro Lys
                85                  90                  95

Pro Lys Asp Thr Leu Met Ile Ser Arg Thr Pro Glu Val Thr Cys Val
            100                 105                 110

Val Val Asp Val Ser His Glu Asp Pro Glu Val Lys Phe Asn Trp Tyr
        115                 120                 125

Val Asp Gly Val Glu Val His Asn Ala Lys Thr Lys Pro Arg Glu Glu
    130                 135                 140

Gln Tyr Asn Ser Thr Tyr Arg Val Val Ser Val Leu Thr Val Leu His
145                 150                 155                 160

```
Gln Asp Trp Leu Asn Gly Lys Glu Tyr Lys Cys Lys Val Ser Asn Lys
                165                 170                 175

Ala Leu Pro Ala Pro Ile Glu Lys Thr Ile Ser Lys Ala Lys Gly Gln
            180                 185                 190

Pro Arg Glu Pro Gln Val Tyr Thr Leu Pro Pro Ser Arg Asp Glu Leu
        195                 200                 205

Thr Lys Asn Gln Val Ser Leu Thr Cys Leu Val Lys Gly Phe Tyr Pro
    210                 215                 220

Ser Asp Ile Ala Val Glu Trp Glu Ser Asn Gly Gln Pro Glu Asn Asn
225                 230                 235                 240

Tyr Lys Thr Thr Pro Pro Val Leu Asp Ser Asp Gly Ser Phe Phe Leu
                245                 250                 255

Tyr Ser Lys Leu Thr Val Asp Lys Ser Arg Trp Gln Gln Gly Asn Val
            260                 265                 270

Phe Ser Cys Ser Val Met His Glu Ala Leu His Asn His Tyr Thr Gln
        275                 280                 285

Lys Ser Leu Ser Leu Ser Pro Gly Lys
    290                 295

<210> SEQ ID NO 73
<211> LENGTH: 535
<212> TYPE: PRT
<213> ORGANISM: Corynebacterium diphtheriae

<400> SEQUENCE: 73

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240
```

-continued

```
Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400

Val Glu Asp Ser Ile Ile Arg Thr Gly Phe Gln Gly Glu Ser Gly His
                405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
        435                 440                 445

His Ile Ser Val Asn Gly Arg Lys Ile Arg Met Arg Cys Arg Ala Ile
    450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
        515                 520                 525

Leu Phe Phe Glu Ile Lys Ser
    530                 535

<210> SEQ ID NO 74
<211> LENGTH: 1331
<212> TYPE: PRT
<213> ORGANISM: Homo sapiens

<400> SEQUENCE: 74

Met Glu Ser His Ser Arg Ala Gly Lys Ser Arg Lys Ser Ala Lys Phe
1               5                   10                  15

Arg Ser Ile Ser Arg Ser Leu Met Leu Cys Asn Ala Lys Thr Ser Asp
            20                  25                  30

Asp Gly Ser Ser Pro Asp Glu Lys Tyr Pro Asp Pro Phe Glu Ile Ser
        35                  40                  45

Leu Ala Gln Gly Lys Glu Gly Ile Phe His Ser Ser Val Gln Leu Ala
    50                  55                  60

Asp Thr Ser Glu Ala Gly Pro Ser Ser Val Pro Asp Leu Ala Leu Ala
```

```
              65                  70                  75                  80
Ser Glu Ala Ala Gln Leu Gln Ala Ala Gly Asn Asp Arg Gly Lys Thr
                    85                  90                  95

Cys Arg Arg Ile Phe Phe Met Lys Glu Ser Thr Ala Ser Ser Arg
                100                 105                 110

Glu Lys Pro Gly Lys Leu Glu Ala Gln Ser Ser Asn Phe Leu Phe Pro
            115                 120                 125

Lys Ala Cys His Gln Arg Ala Arg Ser Asn Ser Thr Ser Val Asn Pro
        130                 135                 140

Tyr Cys Thr Arg Glu Ile Asp Phe Pro Met Thr Lys Lys Ser Ala Ala
145                 150                 155                 160

Pro Thr Asp Arg Gln Pro Tyr Ser Leu Cys Ser Asn Arg Lys Ser Leu
                165                 170                 175

Ser Gln Gln Leu Asp Cys Pro Ala Gly Lys Ala Gly Thr Ser Arg
            180                 185                 190

Pro Thr Arg Ser Leu Ser Thr Ala Gln Leu Val Gln Pro Ser Gly Gly
        195                 200                 205

Leu Gln Ala Ser Val Ile Ser Asn Ile Val Leu Met Lys Gly Gln Ala
        210                 215                 220

Lys Gly Leu Gly Phe Ser Ile Val Gly Gly Lys Asp Ser Ile Tyr Gly
225                 230                 235                 240

Pro Ile Gly Ile Tyr Val Lys Thr Ile Phe Ala Gly Gly Ala Ala Ala
                245                 250                 255

Ala Asp Gly Arg Leu Gln Glu Gly Asp Glu Ile Leu Glu Leu Asn Gly
            260                 265                 270

Glu Ser Met Ala Gly Leu Thr His Gln Asp Ala Leu Gln Lys Phe Lys
        275                 280                 285

Gln Ala Lys Lys Gly Leu Leu Thr Leu Thr Val Arg Thr Arg Leu Thr
        290                 295                 300

Ala Pro Pro Ser Leu Cys Ser His Leu Ser Pro Pro Leu Cys Arg Ser
305                 310                 315                 320

Leu Ser Ser Ser Thr Cys Ile Thr Lys Asp Ser Ser Ser Phe Ala Leu
                325                 330                 335

Glu Ser Pro Ser Ala Pro Ile Ser Thr Ala Lys Pro Asn Tyr Arg Ile
            340                 345                 350

Met Val Glu Val Ser Leu Gln Lys Glu Ala Gly Val Gly Leu Gly Ile
        355                 360                 365

Gly Leu Cys Ser Val Pro Tyr Phe Gln Cys Ile Ser Gly Ile Phe Val
        370                 375                 380

His Thr Leu Ser Pro Gly Ser Val Ala His Leu Asp Gly Arg Leu Arg
385                 390                 395                 400

Cys Gly Asp Glu Ile Val Glu Ile Ser Asp Ser Pro Val His Cys Leu
                405                 410                 415

Thr Leu Asn Glu Val Tyr Thr Ile Leu Ser Arg Cys Asp Pro Gly Pro
            420                 425                 430

Val Pro Ile Ile Val Ser Arg His Pro Asp Pro Gln Val Ser Glu Gln
        435                 440                 445

Gln Leu Lys Glu Ala Val Ala Gln Ala Val Glu Asn Thr Lys Phe Gly
        450                 455                 460

Lys Glu Arg His Gln Trp Ser Leu Glu Gly Val Lys Arg Leu Glu Ser
465                 470                 475                 480

Ser Trp His Gly Arg Pro Thr Leu Glu Lys Glu Arg Glu Lys Asn Ser
                485                 490                 495
```

```
Ala Pro Pro His Arg Ala Gln Lys Val Met Ile Arg Ser Ser Ser
            500                 505                 510

Asp Ser Ser Tyr Met Ser Gly Ser Pro Gly Gly Ser Pro Gly Ser Gly
            515                 520                 525

Ser Ala Glu Lys Pro Ser Ser Asp Val Asp Ile Ser Thr His Ser Pro
530                 535                 540

Ser Leu Pro Leu Ala Arg Glu Pro Val Val Leu Ser Ile Ala Ser Ser
545                 550                 555                 560

Arg Leu Pro Gln Glu Ser Pro Leu Pro Glu Ser Arg Asp Ser His
            565                 570                 575

Pro Pro Leu Arg Leu Lys Lys Ser Phe Glu Ile Leu Val Arg Lys Pro
            580                 585                 590

Met Ser Ser Lys Pro Lys Pro Pro Arg Lys Tyr Phe Lys Ser Asp
            595                 600                 605

Ser Asp Pro Gln Lys Ser Leu Glu Glu Arg Glu Asn Ser Ser Cys Ser
            610                 615                 620

Ser Gly His Thr Pro Thr Cys Gly Gln Glu Ala Arg Glu Leu Leu
625                 630                 635                 640

Pro Leu Leu Leu Pro Gln Glu Asp Thr Ala Gly Arg Ser Pro Ser Ala
                645                 650                 655

Ser Ala Gly Cys Pro Gly Pro Gly Ile Gly Pro Gln Thr Lys Ser Ser
            660                 665                 670

Thr Glu Gly Glu Pro Gly Trp Arg Arg Ala Ser Pro Val Thr Gln Thr
            675                 680                 685

Ser Pro Ile Lys His Pro Leu Lys Arg Gln Ala Arg Met Asp Tyr
            690                 695                 700

Ser Phe Asp Thr Thr Ala Glu Asp Pro Trp Val Arg Ile Ser Asp Cys
705                 710                 715                 720

Ile Lys Asn Leu Phe Ser Pro Ile Met Ser Glu Asn His Gly His Met
                725                 730                 735

Pro Leu Gln Pro Asn Ala Ser Leu Asn Glu Glu Glu Gly Thr Gln Gly
            740                 745                 750

His Pro Asp Gly Thr Pro Pro Lys Leu Asp Thr Ala Asn Gly Thr Pro
            755                 760                 765

Lys Val Tyr Lys Ser Ala Asp Ser Ser Thr Val Lys Lys Gly Pro Pro
770                 775                 780

Val Ala Pro Lys Pro Ala Trp Phe Arg Gln Ser Leu Lys Gly Leu Arg
785                 790                 795                 800

Asn Arg Ala Ser Asp Pro Arg Gly Leu Pro Asp Pro Ala Leu Ser Thr
            805                 810                 815

Gln Pro Ala Pro Ala Ser Arg Glu His Leu Gly Ser His Ile Arg Ala
            820                 825                 830

Ser Ser Ser Ser Ser Ser Ile Arg Gln Arg Ile Ser Ser Phe Glu Thr
            835                 840                 845

Phe Gly Ser Ser Gln Leu Pro Asp Lys Gly Ala Gln Arg Leu Ser Leu
            850                 855                 860

Gln Pro Ser Ser Gly Glu Ala Ala Lys Pro Leu Gly Lys His Glu Glu
865                 870                 875                 880

Gly Arg Phe Ser Gly Leu Leu Gly Arg Gly Ala Ala Pro Thr Leu Val
                885                 890                 895

Pro Gln Gln Pro Glu Gln Val Leu Ser Ser Gly Ser Pro Ala Ala Ser
            900                 905                 910
```

-continued

```
Glu Ala Arg Asp Pro Gly Val Ser Glu Ser Pro Pro Gly Arg Gln
            915                 920                 925
Pro Asn Gln Lys Thr Leu Pro Pro Gly Pro Asp Pro Leu Leu Arg Leu
    930                 935                 940
Leu Ser Thr Gln Ala Glu Glu Ser Gln Gly Pro Val Leu Lys Met Pro
945                 950                 955                 960
Ser Gln Arg Ala Arg Ser Phe Pro Leu Thr Arg Ser Gln Ser Cys Glu
            965                 970                 975
Thr Lys Leu Leu Asp Glu Lys Thr Ser Lys Leu Tyr Ser Ile Ser Ser
            980                 985                 990
Gln Val Ser Ser Ala Val Met Lys Ser Leu Leu Cys Leu Pro Ser Ser
            995                 1000                1005
Ile Ser Cys Ala Gln Thr Pro Cys Ile Pro Lys Glu Gly Ala Ser
    1010                1015                1020
Pro Thr Ser Ser Ser Asn Glu Asp Ser Ala Ala Asn Gly Ser Ala
    1025                1030                1035
Glu Thr Ser Ala Leu Asp Thr Gly Phe Ser Leu Asn Leu Ser Glu
    1040                1045                1050
Leu Arg Glu Tyr Thr Glu Gly Leu Thr Glu Ala Lys Glu Asp Asp
    1055                1060                1065
Asp Gly Asp His Ser Ser Leu Gln Ser Gly Gln Ser Val Ile Ser
    1070                1075                1080
Leu Leu Ser Ser Glu Glu Leu Lys Lys Leu Ile Glu Glu Val Lys
    1085                1090                1095
Val Leu Asp Glu Ala Thr Leu Lys Gln Leu Asp Gly Ile His Val
    1100                1105                1110
Thr Ile Leu His Lys Glu Glu Gly Ala Gly Leu Gly Phe Ser Leu
    1115                1120                1125
Ala Gly Gly Ala Asp Leu Glu Asn Lys Val Ile Thr Val His Arg
    1130                1135                1140
Val Phe Pro Asn Gly Leu Ala Ser Gln Glu Gly Thr Ile Gln Lys
    1145                1150                1155
Gly Asn Glu Val Leu Ser Ile Asn Gly Lys Ser Leu Lys Gly Thr
    1160                1165                1170
Thr His His Asp Ala Leu Ala Ile Leu Arg Gln Ala Arg Glu Pro
    1175                1180                1185
Arg Gln Ala Val Ile Val Thr Arg Lys Leu Thr Pro Glu Ala Met
    1190                1195                1200
Pro Asp Leu Asn Ser Ser Thr Asp Ser Ala Ala Ser Ala Ser Ala
    1205                1210                1215
Ala Ser Asp Val Ser Val Glu Ser Thr Glu Ala Thr Val Cys Thr
    1220                1225                1230
Val Thr Leu Glu Lys Met Ser Ala Gly Leu Gly Phe Ser Leu Glu
    1235                1240                1245
Gly Gly Lys Gly Ser Leu His Gly Asp Lys Pro Leu Thr Ile Asn
    1250                1255                1260
Arg Ile Phe Lys Gly Ala Ala Ser Glu Gln Ser Glu Thr Val Gln
    1265                1270                1275
Pro Gly Asp Glu Ile Leu Gln Leu Gly Gly Thr Ala Met Gln Gly
    1280                1285                1290
Leu Thr Arg Phe Glu Ala Trp Asn Ile Ile Lys Ala Leu Pro Asp
    1295                1300                1305
Gly Pro Val Thr Ile Val Ile Arg Arg Lys Ser Leu Gln Ser Lys
```

Glu Thr Thr Ala Ala Gly Asp Ser
     1325            1330

<210> SEQ ID NO 75
<211> LENGTH: 155
<212> TYPE: PRT
<213> ORGANISM: Homo sapiens

<400> SEQUENCE: 75

Met Thr Pro Gly Lys Thr Ser Leu Val Ser Leu Leu Leu Leu Ser
1               5                   10                  15

Leu Glu Ala Ile Val Lys Ala Gly Ile Thr Ile Pro Arg Asn Pro Gly
            20                  25                  30

Cys Pro Asn Ser Glu Asp Lys Asn Phe Pro Arg Thr Val Met Val Asn
        35                  40                  45

Leu Asn Ile His Asn Arg Asn Thr Asn Thr Pro Lys Arg Ser Ser
    50                  55                  60

Asp Tyr Tyr Asn Arg Ser Thr Ser Pro Trp Asn Leu His Arg Asn Glu
65                  70                  75                  80

Asp Pro Glu Arg Tyr Pro Ser Val Ile Trp Glu Ala Lys Cys Arg His
                85                  90                  95

Leu Gly Cys Ile Asn Ala Asp Gly Asn Val Asp Tyr His Met Asn Ser
            100                 105                 110

Val Pro Ile Gln Gln Glu Ile Leu Val Leu Arg Arg Glu Pro Pro His
        115                 120                 125

Cys Pro Asn Ser Phe Arg Leu Glu Lys Ile Leu Val Ser Val Gly Cys
    130                 135                 140

Thr Cys Val Thr Pro Ile Val His His Val Ala
145                 150                 155

<210> SEQ ID NO 76
<211> LENGTH: 476
<212> TYPE: PRT
<213> ORGANISM: Homo sapiens

<400> SEQUENCE: 76

Arg Ala Val Pro Gly Gly Ser Ser Pro Ala Trp Thr Gln Cys Gln Gln
1               5                   10                  15

Leu Ser Gln Lys Leu Cys Thr Leu Ala Trp Ser Ala His Pro Leu Val
            20                  25                  30

Gly His Met Asp Leu Arg Glu Glu Gly Asp Glu Glu Thr Thr Asn Asp
        35                  40                  45

Val Pro His Ile Gln Cys Gly Asp Gly Cys Asp Pro Gln Gly Leu Arg
    50                  55                  60

Asp Asn Ser Gln Phe Cys Leu Gln Arg Ile His Gln Gly Leu Ile Phe
65                  70                  75                  80

Tyr Glu Lys Leu Leu Gly Ser Asp Ile Phe Thr Gly Glu Pro Ser Leu
                85                  90                  95

Leu Pro Asp Ser Pro Val Gly Gln Leu His Ala Ser Leu Leu Gly Leu
            100                 105                 110

Ser Gln Leu Leu Gln Pro Glu Gly His His Trp Glu Thr Gln Gln Ile
        115                 120                 125

Pro Ser Leu Ser Pro Ser Gln Pro Trp Gln Arg Leu Leu Leu Arg Phe
    130                 135                 140

Lys Ile Leu Arg Ser Leu Gln Ala Phe Val Ala Val Ala Ala Arg Val

```
            145                 150                 155                 160

Phe Ala His Gly Ala Ala Thr Leu Ser Pro Ile Trp Glu Leu Lys Lys
                        165                 170                 175

Asp Val Tyr Val Val Glu Leu Asp Trp Tyr Pro Asp Ala Pro Gly Glu
                        180                 185                 190

Met Val Leu Thr Cys Asp Thr Pro Glu Glu Asp Gly Ile Thr Trp
                        195                 200                 205

Thr Leu Asp Gln Ser Ser Glu Val Leu Gly Ser Gly Lys Thr Leu Thr
                        210                 215                 220

Ile Gln Val Lys Glu Phe Gly Asp Ala Gly Gln Tyr Thr Cys His Lys
        225                 230                 235                 240

Gly Gly Glu Val Leu Ser His Ser Leu Leu Leu Leu His Lys Lys Glu
                        245                 250                 255

Asp Gly Ile Trp Ser Thr Asp Ile Leu Lys Asp Gln Lys Glu Pro Lys
                        260                 265                 270

Asn Lys Thr Phe Leu Arg Cys Glu Ala Lys Asn Tyr Ser Gly Arg Phe
                        275                 280                 285

Thr Cys Trp Trp Leu Thr Thr Ile Ser Thr Asp Leu Thr Phe Ser Val
                        290                 295                 300

Lys Ser Ser Arg Gly Ser Ser Asp Pro Gln Gly Val Thr Cys Gly Ala
        305                 310                 315                 320

Ala Thr Leu Ser Ala Glu Arg Val Arg Gly Asp Asn Lys Glu Tyr Glu
                        325                 330                 335

Tyr Ser Val Glu Cys Gln Glu Asp Ser Ala Cys Pro Ala Ala Glu Glu
                        340                 345                 350

Ser Leu Pro Ile Glu Val Met Val Asp Ala Val His Lys Leu Lys Tyr
                        355                 360                 365

Glu Asn Tyr Thr Ser Ser Phe Phe Ile Arg Asp Ile Ile Lys Pro Asp
                        370                 375                 380

Pro Pro Lys Asn Leu Gln Leu Lys Pro Leu Lys Asn Ser Arg Gln Val
        385                 390                 395                 400

Glu Val Ser Trp Glu Tyr Pro Asp Thr Trp Ser Thr Pro His Ser Tyr
                        405                 410                 415

Phe Ser Leu Thr Phe Cys Val Gln Val Gln Gly Lys Ser Lys Arg Glu
                        420                 425                 430

Lys Lys Asp Arg Val Phe Thr Asp Lys Thr Ser Ala Thr Val Ile Cys
                        435                 440                 445

Arg Lys Asn Ala Ser Ile Ser Val Arg Ala Gln Asp Arg Tyr Tyr Ser
        450                 455                 460

Ser Ser Trp Ser Glu Trp Ala Ser Val Pro Cys Ser
        465                 470                 475

<210> SEQ ID NO 77
<211> LENGTH: 234
<212> TYPE: PRT
<213> ORGANISM: Homo sapiens

<400> SEQUENCE: 77

Met Cys Phe Pro Lys Val Leu Ser Asp Asp Met Lys Lys Leu Lys Ala
        1               5                   10                  15

Arg Met Val Met Leu Leu Pro Thr Ser Ala Gln Gly Leu Gly Ala Trp
                        20                  25                  30

Val Ser Ala Cys Asp Thr Glu Asp Thr Val Gly His Leu Gly Pro Trp
                        35                  40                  45
```

```
Arg Asp Lys Asp Pro Ala Leu Trp Cys Gln Leu Cys Leu Ser Ser Gln
 50                  55                  60

His Gln Ala Ile Glu Arg Phe Tyr Asp Lys Met Gln Asn Ala Glu Ser
 65                  70                  75                  80

Gly Arg Gly Gln Val Met Ser Ser Leu Ala Glu Leu Glu Asp Asp Phe
                 85                  90                  95

Lys Glu Gly Tyr Leu Glu Thr Val Ala Ala Tyr Tyr Glu Glu Gln His
            100                 105                 110

Pro Glu Leu Thr Pro Leu Leu Glu Lys Glu Arg Asp Gly Leu Arg Cys
        115                 120                 125

Arg Gly Asn Arg Ser Pro Val Pro Asp Val Glu Asp Pro Ala Thr Glu
130                 135                 140

Glu Pro Gly Glu Ser Phe Cys Asp Lys Val Met Arg Trp Phe Gln Ala
145                 150                 155                 160

Met Leu Gln Arg Leu Gln Thr Trp Trp His Gly Val Leu Ala Trp Val
                165                 170                 175

Lys Glu Lys Val Val Ala Leu Val His Ala Val Gln Ala Leu Trp Lys
            180                 185                 190

Gln Phe Gln Ser Phe Cys Cys Ser Leu Ser Glu Leu Phe Met Ser Ser
        195                 200                 205

Phe Gln Ser Tyr Gly Ala Pro Arg Gly Asp Lys Glu Glu Leu Thr Pro
210                 215                 220

Gln Lys Cys Ser Glu Pro Gln Ser Ser Lys
225                 230

<210> SEQ ID NO 78
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Met Ala Val Pro Met Gln Leu Ser Cys Ser Arg
1               5                   10

<210> SEQ ID NO 79
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ser Thr Gly
1

<210> SEQ ID NO 80
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Thr Arg
1
```

```
<210> SEQ ID NO 81
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Arg Ser Gln
1

<210> SEQ ID NO 82
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Arg Ser Ala Gly Glu
1               5

<210> SEQ ID NO 83
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Arg Ser
1

<210> SEQ ID NO 84
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Gly Gly
1

<210> SEQ ID NO 85
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Gly Ser Gly Gly Ser Gly Gly Ser Gly
1               5

<210> SEQ ID NO 86
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86
```

```
Gly Gly Ser Gly Gly Ser Gly Gly Ser Gly Gly
1               5                   10

<210> SEQ ID NO 87
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Gly Gly Ser Gly Gly Ser Gly Gly Ser Gly Gly Ser Gly Gly
1               5                   10

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Gly Gly Ser Gly Gly Ser Gly Gly Ser Gly Gly Ser Gly Gly Ser Gly
1               5                   10                  15

Gly

<210> SEQ ID NO 89
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Gly Gly Ser Gly Gly Ser Gly Gly Ser Gly Gly Ser Gly Gly Ser Gly
1               5                   10                  15

Gly Ser Gly Gly
            20

<210> SEQ ID NO 90
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gly Gly Ser Gly Gly Ser Gly Gly Ser Gly Gly Ser Gly Gly Ser Gly
1               5                   10                  15

Gly Ser Gly Gly Ser Gly Gly
            20

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91
```

Gly Gly Ser Gly Gly Ser Gly Gly Ser Gly Gly Ser Gly Gly Ser Gly
1               5                   10                  15

<210> SEQ ID NO 92
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gly Ser Gly Gly Ser Gly Gly Ser Gly Gly Ser Gly Gly Ser Gly Gly
1               5                   10                  15

<210> SEQ ID NO 93
<211> LENGTH: 1872
<212> TYPE: DNA
<213> ORGANISM: Mycobacterium tuberculosis

<400> SEQUENCE: 93

| | |
|---|---:|
| gactacgttg gtgtagaaaa atcctgccgc ccggacccct aaggctggga caatttctga | 60 |
| tagctacccc gacacaggag gttacgggat gagcaattcg cgccgccgct cactcaggtg | 120 |
| gtcatggttg ctgagcgtgc tggctgccgt cgggctgggc ctggccacgg cgccggccca | 180 |
| ggcggcccecg ccggccttgt cgcaggaccg gttcgccgac ttccccgcgc tgccccctcga | 240 |
| cccgtccgcg atggtcgccc aagtggggcc acaggtggtc aacatcaaca ccaaactggg | 300 |
| ctacaacaac gccgtgggcg ccgggaccgg catcgtcatc gatcccaacg gtgtcgtgct | 360 |
| gaccaacaac cacgtgatcg cgggcgccac cgacatcaat gcgttcagcg tcggctccgg | 420 |
| ccaaacctac ggcgtcgatg tggtcgggta tgaccgcacc caggatgtcg cggtgctgca | 480 |
| gctgcgcggt gccggtggcc tgccgtcggc ggcgatcggt ggcggcgtcg cggttggtga | 540 |
| gcccgtcgtc gcgatgggca acagcggtgg cagggcgga acgccccgtg cggtgcctgg | 600 |
| cagggtggtc gcgctcggcc aaaccgtgca ggcgtcggat tcgctgaccg gtgccgaaga | 660 |
| gacattgaac gggttgatcc agttcgatgc cgcgatccag cccggtgatt cgggcgggcc | 720 |
| cgtcgtcaac ggcctaggac aggtggtcgg tatgaacacg gccgcgtccg ataacttcca | 780 |
| gctgtcccag ggtgggcagg gattcgccat tccgatcggg caggcgatgg cgatcgcggg | 840 |
| ccagatccga tcgggtgggg ggtcaccccac cgttcatatc gggcctaccg ccttcctcgg | 900 |
| cttgggtgtt gtcgacaaca acggcaacgg cgcacgagtc caacgcgtgg tcgggagcgc | 960 |
| tccggcggca agtctcggca tctccaccgg cgacgtgatc accgcggtcg acggcgctcc | 1020 |
| gatcaactcg gccaccgcga tggcggacgc gcttaacggg catcatcccg gtgacgtcat | 1080 |
| ctcggtgacc tggcaaacca agtcgggcgg cacgcgtaca gggaacgtga cattggccga | 1140 |
| gggaccccag gcctgatttc gtcgcggata ccacccgccg gccggccaat ggattggcg | 1200 |
| ccagccgtga ttgccgcgtg agcccccgag ttccgtctcc cgtgcgcgtg gcatcgtgga | 1260 |
| agcaatgaac gaggcagaac acagcgtcga gcaccctccc gtgcagggca gtcacgtcga | 1320 |
| aggcggtgtg gtcgagcatc cggatgccaa ggacttcggc agcgccgccg ccctgcccgc | 1380 |
| cgatccgacc tggtttaagc acgccgtctt ctacgaggtg ctggtccggg cgttcttcga | 1440 |
| cgccagcgcg gacggttccg gcgatctgcg tggactcatc gatcgcctcg actacctgca | 1500 |
| gtggcttggc atcgactgca tctggttgcc gccgttctac gactcgccgc tgcgcgacgg | 1560 |
| cggttacgac attcgcgact tctacaaggt gctgcccgaa ttcggcaccg tcgacgattt | 1620 |

```
cgtcgccctg gtcgacgccg ctcaccggcg aggtatccgc atcatcaccg acctggtgat      1680
gaatcacacc tcggagtcgc acccctggtt tcaggagtcc cgccgcgacc cagacggacc      1740
gtacggtgac tattacgtgt ggagcgacac cagcgagcgc tacaccgacg cccggatcat      1800
cttcgtcgac accgaagagt cgaactggtc attcgatcct gtccgccgac agttctactg      1860
gcaccgattc tt                                                          1872

<210> SEQ ID NO 94
<211> LENGTH: 396
<212> TYPE: DNA
<213> ORGANISM: Mycobacterium tuberculosis

<400> SEQUENCE: 94
acggccgcgt ccgataactt ccagctgtcc cagggtgggc agggattcgc cattccgatc        60
gggcaggcga tggcgatcgc gggccagatc cgatcgggtg gggggtcacc caccgttcat       120
atcgggccta ccgccttcct cggcttgggt gttgtcgaca caacggcaa cggcgcacga       180 gtccaacgcg tggtcgggag cgctccggcg caagtctcg gcatctccac cggcgacgtg       240
atcaccgcgg tcgacggcgc tccgatcaac tcggccaccg cgatggcgga cgcgcttaac       300
gggcatcatc ccggtgacgt catctcggtg acctggcaaa ccaagtcggg cggcacgcgt       360
acagggaacg tgacattggc cgagggaccc ccggcc                                 396

<210> SEQ ID NO 95
<211> LENGTH: 702
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 95
catatgcatc accatcacca tcacacggcc gcgtccgata acttccagct gtcccagggt        60
gggcagggat tcgccattcc gatcgggcag gcgatggcga tcgcgggcca gatccgatcg       120 ggtgggggt cacccaccgt tcatatcggg cctaccgcct tcctcggctt gggtgttgtc       180
gacaacaacg gcaacggcgc acgagtccaa cgcgtggtcg ggagcgctcc ggcggcaagt       240
ctcggcatct ccaccggcga cgtgatcacc gcggtcgacg gcgctccgat caactcggcc       300
accgcgatgg cggacgcgct taacgggcat catcccggtg acgtcatctc ggtgacctgg       360
caaaccaagt cgggcggcac gcgtacaggg aacgtgacat tggccgaggg acccccggcc       420
gaattcgacg acgacgacaa ggatccacct gacccgcatc agccggacat gacgaaaggc       480
tattgcccgg gtggccgatg gggttttggc gacttggccg tgtgcgacgg cgagaagtac       540 cccgacggc cgtttggca ccagtggatg caaacgtggt ttaccggccc acagttttac       600
ttcgattgtg tcagcggcgg tgagcccctc cccggcccgc cgccaccggg tggttgcggt       660
ggggcaattc cgtccgagca gcccaacgct ccctgagaat tc                          702

<210> SEQ ID NO 96
<211> LENGTH: 1746
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 96
catatgcatc accatcacca tcacacggcc gcgtccgata acttccagct gtcccagggt        60
```

```
gggcagggat tcgccattcc gatcgggcag gcgatggcga tcgcgggcca gatccgatcg    120 ggtgggggt  cacccaccgt tcatatcggg cctaccgcct tcctcggctt gggtgttgtc    180
gacaacaacg gcaacggcgc acgagtccaa cgcgtggtcg ggagcgctcc ggcggcaagt    240
ctcggcatct ccaccggcga cgtgatcacc gcggtcgacg gcgctccgat caactcggcc    300
accgcgatgg cggacgcgct taacgggcat catcccggtg acgtcatctc ggtgacctgg    360
caaaccaagt cgggcggcac gcgtacaggg aacgtgacat tggccgaggg acccccggcc    420
gaattcccgc tggtgccgcg cggcagcccg atgggctccg acgttcggga cctgaacgca    480
ctgctgccgg cagttccgtc cctgggtggt ggtggtggtt gcgcactgcc ggttagcggt    540
gcagcacagt gggctccggt tctggacttc gcaccgccgg gtgcatccgc atacggttcc    600
ctgggtggtc cggcaccgcc gccggcaccg ccgccgccgc cgccgccgcc gccgcactcc    660
ttcatcaaac aggaaccgag ctgggtggt  gcagaaccgc acgaagaaca gtgcctgagc    720
gcattcaccg ttcacttctc cggccagttc actggcacag ccggagcctg tcgctacggg    780
cccttcggtc ctcctccgcc cagccaggcg tcatccggcc aggccaggat gtttcctaac    840
gcgccctacc tgcccagctg cctcgagagc cagcccgcta ttcgcaatca gggttacagc    900
acggtcacct tcgacgggac gcccagctac ggtcacacgc cctcgcacca tgcggcgcag    960
ttccccaacc actcattcaa gcatgaggat cccatgggcc agcagggctc gctgggtgag    1020
cagcagtact cggtgccgcc cccggtctat ggctgccaca cccccaccga cagctgcacc    1080
ggcagccagg ctttgctgct gaggacgccc tacagcagtg acaatttata ccaaatgaca    1140
tcccagcttg aatgcatgac ctggaatcag atgaacttag gagccaccct aaagggccac    1200
agcacagggt acgagagcga taaccacaca acgcccatcc tctgcggagc caatacagga    1260
atacacacgc acggtgtctt cagaggcatt caggatgtgc gacgtgtgcc tggagtagcc    1320
ccgactcttg tacggtcggc atctgagacc agtgagaaac gccccttcat gtgtgcttac    1380
tcaggctgca ataagagata ttttaagctg tcccacttac agatgcacag caggaagcac    1440
actggtgaga aaccatacca gtgtgacttc aaggactgtg aacgaaggtt ttttcgttca    1500
gaccagctca aaagacacca aaggagacat acaggtgtga accattcca gtgtaaaact    1560 tgtcagcgaa agttctcccg gtccgaccac ctgaagaccc acaccaggac tcatacaggt    1620
gaaaagccct tcagctgtcg gtggccaagt tgtcagaaaa gtttgcccg gtcagatgaa    1680 ttagtccgcc atcacaacat gcatcagaga aacatgacca aactccagct ggcgctttga    1740
gaattc                                                              1746

<210> SEQ ID NO 97
<211> LENGTH: 672
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 97
catatgcatc accatcacca tcacacggcc gcgtccgata acttccagct gtcccagggt     60
gggcagggat tcgccattcc gatcgggcag gcgatggcga tcgcgggcca gatccgatcg    120 ggtgggggt  cacccaccgt tcatatcggg cctaccgcct tcctcggctt gggtgttgtc    180
gacaacaacg gcaacggcgc acgagtccaa cgcgtggtcg ggagcgctcc ggcggcaagt    240
ctcggcatct ccaccggcga cgtgatcacc gcggtcgacg gcgctccgat caactcggcc    300
```

```
accgcgatgg cggacgcgct taacgggcat catcccggtg acgtcatctc ggtgacctgg    360
caaaccaagt cgggcggcac gcgtacaggg aacgtgacat tggccgaggg accccggcc    420 gaattcatcg agggaagggg ctctggctgc cccttattgg agaatgtgat ttccaagaca    480
atcaatccac aagtgtctaa gactgaatac aagaacttc ttcaagagtt catagacgac     540
aatgccacta caaatgccat agatgaattg aaggaatgtt ttcttaacca aacggatgaa    600
actctgagca atgttgaggt gtttatgcaa ttaatatatg acagcagtct ttgtgattta    660
ttttaagaat tc                                                         672
```

<210> SEQ ID NO 98
<211> LENGTH: 2191
<212> TYPE: DNA
<213> ORGANISM: Artificial Sequence
<220> FEATURE:
<223> OTHER INFORMATION: Description of Artificial Sequence: Synthetic
      polynucleotide <400> SEQUENCE: 98

```
atgcatcacc atccaccatca cacggccgcg tccgataact tccagctgtc ccagggtggg    60
cagggattcg ccattccgat cgggcaggcg atggcgatcg cgggccagat ccgatcgggt   120 gggggtcac ccaccgttca tatcgggcct accgccttcc tcggcttggg tgttgtcgac    180
aacaacggca acggcgcacg agtccaacgc gtggtcggga cgctccggc ggcaagtctc     240 ggcatctcca ccggcgacgt gatcaccgcg gtcgacggcg ctccgatcaa ctcggccacc    300
gcgatggcga acgcgcttaa cgggcatcat cccggtgacg tcatctcggt gacctggcaa    360
accaagtcgg gcggcacgcg tacagggaac gtgacattgg ccgagggacc ccggccgaa    420 ttcatggtgt atttcggggc gttaccaccg gagatcaact ccgcgaggat gtacgccggc    480
ccgggttcgg cctcgctggt ggccgcggct cagatgtggg acagcgtggc gagtgacctg    540
ttttcggccg cgtcggcgtt tcagtcgtg gtctggggtc tgacggtggg gtcgtggata     600
ggttcgtcgg cgggtctgat ggtggcggcg gcctcgccgt atgtggcgtg gatgagcgtc    660
accgcggggc aggccgagct gaccgccgcc caggtccggg ttgctgcggc ggcctacgag    720
acggcgtatg ggctgacggt gccccgccg gtgatcgccg agaaccgtgc tgaactgatg     780
attctgatag cgaccaacct cttggggcaa acaccccgg cgatcgcggt caacgaggcc     840
gaatacggcg agatgtgggc caagacgcc gccgcgatgt ttggctacgc cgcggcgacg     900
gcgacggcga cggcgacgtt gctgccgttc gaggaggcgc cggagatgac cagcgcgggt    960
gggctcctcg agcaggccgc cgcggtcgag gaggcctccg acaccgccgc ggcgaaccag   1020
ttgatgaaca atgtgcccca ggcgctgcaa cagctggccc agcccacgca gggcaccacg   1080
ccttcttcca agctgggtgg cctgtggaag acggtctcgc cgcatcggtc gccgatcagc   1140
aacatggtgt cgatgccaa caaccacatg tcgatgacca actcgggtgt gtcgatgacc    1200
aacaccttga gctcgatgtt gaaggcgttt gctccggcgg cggccgccca ggccgtgcaa   1260
accgcggcgc aaaacggggt ccgggcgatg agctcgctgg gcagctcgct gggttcttcg    1320
ggtctgggcg gtggggtggc cgccaacttg ggtcggcgg cctcggtcgg ttcgttgtcg    1380
gtgccgcagg cctgggccgc ggccaaccag gcagtcaccc cggcggcgcg ggcgctgccg    1440
ctgaccagcc tgaccagcgc cgcggaaaga gggcccgggc agatgctggg cgggctgccg    1500 gtgggggcaga tgggcgccag ggccggtggt gggctcagtg gtgtgctgcg tgttccgccg    1560
cgaccctatg tgatgccgca ttctccggca gccggcgata tcgccccgcc ggccttgtcg    1620
```

```
caggaccggt tcgccgactt ccccgcgctg cccctcgacc cgtccgcgat ggtcgcccaa    1680
gtggggccac aggtggtcaa catcaacacc aaactgggct acaacaacgc cgtgggcgcc    1740
gggaccggca tcgtcatcga tcccaacggt gtcgtgctga ccaacaacca cgtgatcgcg    1800
ggcgccaccg acatcaatgc gttcagcgtc ggctccggcc aaacctacgg cgtcgatgtg    1860
gtcgggtatg accgcaccca ggatgtcgcg gtgctgcagc tgcgcggtgc cggtggcctg    1920
ccgtcggcgg cgatcggtgg cggcgtcgcg gttggtgagc ccgtcgtcgc gatgggcaac    1980
agcggtgggc agggcggaac gccccgtgcg gtgcctggca gggtggtcgc gctcggccaa    2040
accgtgcagg cgtcggattc gctgaccggt gccgaagaga cattgaacgg gttgatccag    2100
ttcgatgccg cgatccagcc cggtgattcg ggcgggcccg tcgtcaacgg cctaggacag    2160
gtggtcggta tgaacacggc cgcgtcctag g                                   2191

<210> SEQ ID NO 99
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 99
caattacata tgcatcacca tcaccatcac acggccgcgt ccgataactt c              51

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 100
ctaatcgaat tcggccgggg gtccctcggc caa                                  33

<210> SEQ ID NO 101
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 101
caattagaat tcgacgacga cgacaaggat ccacctgacc cgcatcag                  48

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 102
caattagaat tctcagggag cgttgggctg ctc                                  33

<210> SEQ ID NO 103
<211> LENGTH: 34
<212> TYPE: DNA
<213> ORGANISM: Artificial Sequence
<220> FEATURE:
```

<223> OTHER INFORMATION: Description of Artificial Sequence: Synthetic
      oligonucleotide

<400> SEQUENCE: 103
gcgaagctta tgaagttgct gatggtcctc atgc                               34

<210> SEQ ID NO 104
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 104
cggctcgagt taaataaat cacaaagact gctgtc                              36

<210> SEQ ID NO 105
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Met His His His His His His
1               5

<210> SEQ ID NO 106
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Asp Asp Asp Lys
1

<210> SEQ ID NO 107
<211> LENGTH: 95
<212> TYPE: PRT
<213> ORGANISM: Homo sapiens

<400> SEQUENCE: 107

Met Cys Cys Thr Lys Ser Leu Leu Ala Ala Leu Met Ser Val Leu
1               5                   10                  15

Leu Leu His Leu Cys Gly Glu Ser Glu Ala Ser Asn Phe Asp Cys Cys
                20                  25                  30

Leu Gly Tyr Thr Asp Arg Ile Leu His Pro Lys Phe Ile Val Gly Phe
            35                  40                  45

Thr Arg Gln Leu Ala Asn Glu Gly Cys Asp Ile Asn Ala Ile Ile Phe
        50                  55                  60

His Thr Lys Lys Lys Leu Ser Val Cys Ala Asn Pro Lys Gln Thr Trp
65                  70                  75                  80

Val Lys Tyr Ile Val Arg Leu Leu Ser Lys Lys Val Lys Asn Met
                85                  90                  95

<210> SEQ ID NO 108
<211> LENGTH: 20
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 108
ggggtcaacg ttgaggggggg                                              20

<210> SEQ ID NO 109
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gggggacgat cgtcggggggg                                              20

<210> SEQ ID NO 110
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
ggggacgacg tcgtgggggg g                                             21

<210> SEQ ID NO 111
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
tccatgacgt tcctgatgct                                               20

<210> SEQ ID NO 112
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
tccatgacgt tcctgacgtt                                               20

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
tcgtcgtttt gtcgttttgt cgtt                                          24

<210> SEQ ID NO 114
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      oligonucleotide

<400> SEQUENCE: 114
tcgtcgttgt cgttttgtcg tt                                              22

<210> SEQ ID NO 115
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
tcgacgttcg tcgttcgtcg ttc                                             23

<210> SEQ ID NO 116
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
tcgcgacgtt cgcccgacgt tcggta                                          26

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
tcgtcgtttt cggcgcgcgc cg                                              22

<210> SEQ ID NO 118
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 118
tcgtcgtcgt tcgaacgacg ttgat                                           25

<210> SEQ ID NO 119
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 119
tcgcgaacgt tcgccgcgtt cgaacgcgg                                       29
```